US010889812B2

(12) United States Patent
Mao et al.

(10) Patent No.: US 10,889,812 B2
(45) Date of Patent: Jan. 12, 2021

(54) SHORT NON-CODING PROTEIN REGULATORY RNAS (SPRRNAS) AND METHODS OF USE

(71) Applicant: University of Maryland, Baltimore, Baltimore, MD (US)

(72) Inventors: Li Mao, Clarksville, MD (US); Yuping Mei, Ellicott City, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 300 days.

(21) Appl. No.: 15/521,606

(22) PCT Filed: Oct. 24, 2015

(86) PCT No.: PCT/US2015/057259
§ 371 (c)(1),
(2) Date: Apr. 24, 2017

(87) PCT Pub. No.: WO2016/065349
PCT Pub. Date: Apr. 28, 2016

(65) Prior Publication Data

US 2018/0273941 A1 Sep. 27, 2018

Related U.S. Application Data

(60) Provisional application No. 62/068,106, filed on Oct. 24, 2014.

(51) Int. Cl.

| | |
|---|---|
| ***C12N 15/113*** | (2010.01) |
| ***A61K 31/7088*** | (2006.01) |
| ***C12Q 1/6886*** | (2018.01) |
| ***A61P 35/00*** | (2006.01) |
| ***A61K 48/00*** | (2006.01) |
| ***G01N 33/574*** | (2006.01) |
| ***G01N 33/96*** | (2006.01) |

(52) U.S. Cl.
CPC ........ *C12N 15/113* (2013.01); *A61K 31/7088* (2013.01); *A61K 48/0016* (2013.01); *A61P 35/00* (2018.01); *C12Q 1/6886* (2013.01); *G01N 33/57423* (2013.01); *G01N 33/96* (2013.01); *A61K 2300/00* (2013.01); *C12N 2310/113* (2013.01); *C12Q 2600/136* (2013.01); *C12Q 2600/178* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 7,250,496 B2 * | 7/2007 | Bentwich | ............... | G16B 20/00 536/23.1 |
| 2008/0113351 A1 | 5/2008 | Naito | | |
| 2011/0046209 A1 | 2/2011 | Anderson | | |
| 2016/0024575 A1 * | 1/2016 | Spindler | ............. | C12Q 1/6886 506/2 |

FOREIGN PATENT DOCUMENTS

| | | |
|---|---|---|
| WO | 2012087983 A1 | 6/2012 |
| WO | 2013090620 A1 | 6/2013 |
| WO | 2013095132 A1 | 6/2013 |

OTHER PUBLICATIONS

GenBank accession No. EH335278 Database [online] 2007 [retrieved on Aug. 16, 2019]. Retrieved from the Internet: <URL: https://www.ncbi.nlm.nih.gov/nuccore/EH335278>.*
GenBank accession No. EH334137 Database [online] [retrieved on Aug. 16, 2019]. Retrieved from the Internet: <URL: https://www.ncbi.nlm.nih.gov/nuccore/eh334137>.*
Official Communication form European Appl. No. 15851885.2, dated Aug. 20, 2018.
International Search Report from Appl. No. PCT/US2015/057259, dated May 20, 2016.
Gerstl et al., Prediction of Transcribed PIWI-interacting RNAs from CHO RNAseq Data, Journal of Biotechnology, 166:51-57 (2013).
Guffanti et al., A Transcriptional Sketch of a Primary Human Breast Cancer by 454 Deep Sequencing; BMC Genomics, 10:163 XP021047888.
Kim et al., The Transcriptome of Human CD34+ Hematopoietic Stem-progenitor Cells, PNAS, 106:8278-8283 (2009).
Girard et al., A Germline-specific Class of Small RNAs Binds Mammalian Piwi Proteins, Nature, 442:199-202 (2006).
Mei et al., Novel dimensions of piRNS in cancer, Cancer Letters, 336:46-52 (2013).
Siddiqi et al., Piwis and Piwi-Interanting RNAs in the Epigenetics of Cancer, Journal of Cellular Biochemistry, 113:373-380 (2012).
Ortogero et al., A Novel Class of Somatic Small RNAs Similar to Germ Cell Pachytene PIWI-interacting Small RNAs, Journal of Biological Chemistry, 289: 32824-32834 (2014).
Yan et al., Widespread Expression of PiRNA-like Molecules in Somatic Tissues; Nucleic Acids Research, 39:6596-6607 (2011).
Mei et al., A piRNA-like small RNA interacts with and modulates p-ERM proteins in human somatic cells, Nature Communications, 6:1-12 (2015).
Wang et al., A piRNA-like Small RNA Induces Chemoresistance to Cisplatin-Based Thereapy by Inhibiting Apoptosis in Lung Squamous Cell Carcinoma, Molecular Therapy Nucleic Acids, 6:269-278 (2017).
Brock et al., Protein Functional Effector sncRNAs (pfeRNAs) in lung cancer, Cancer Letters, 403:138-143 (2017).
EMBL Database, Accession No. AA758482 (1998).
NCBI, GeneBank Accession No. M31637, (1995).

(Continued)

*Primary Examiner* — Tracy Vivlemore
(74) *Attorney, Agent, or Firm* — Nevrivy Patent Law Group P.L.L.C.

(57) ABSTRACT

The present invention provides isolated nucleic acid molecules comprising short non-coding protein regulatory RNAs (sprRNA), variants, fragments and inhibitors thereof and compositions and methods of using the same.

10 Claims, 42 Drawing Sheets

Specification includes a Sequence Listing.

(56) References Cited

OTHER PUBLICATIONS

Maxwell et al., Deep-sequencing of human argonaute-associated small RNAs provides insight into miRNA sorting and reveals argonaute association with RNA fragments of diverse origin, RNA Biology, 8:158-177 (2011).

Koss et al., Ezrin/Radixin/Moesin Proteins Are Phosphorylated by TNF-α and Modulate Permeability Increases in Human Pulmonary Microvascular Endothlial Cells, The Journal of Immunology. 176: 1218-1227 (2006).

European Communication from European Appl. No. 15851885.2, dated Aug. 2, 2019.

* cited by examiner

FIG. 2a-b
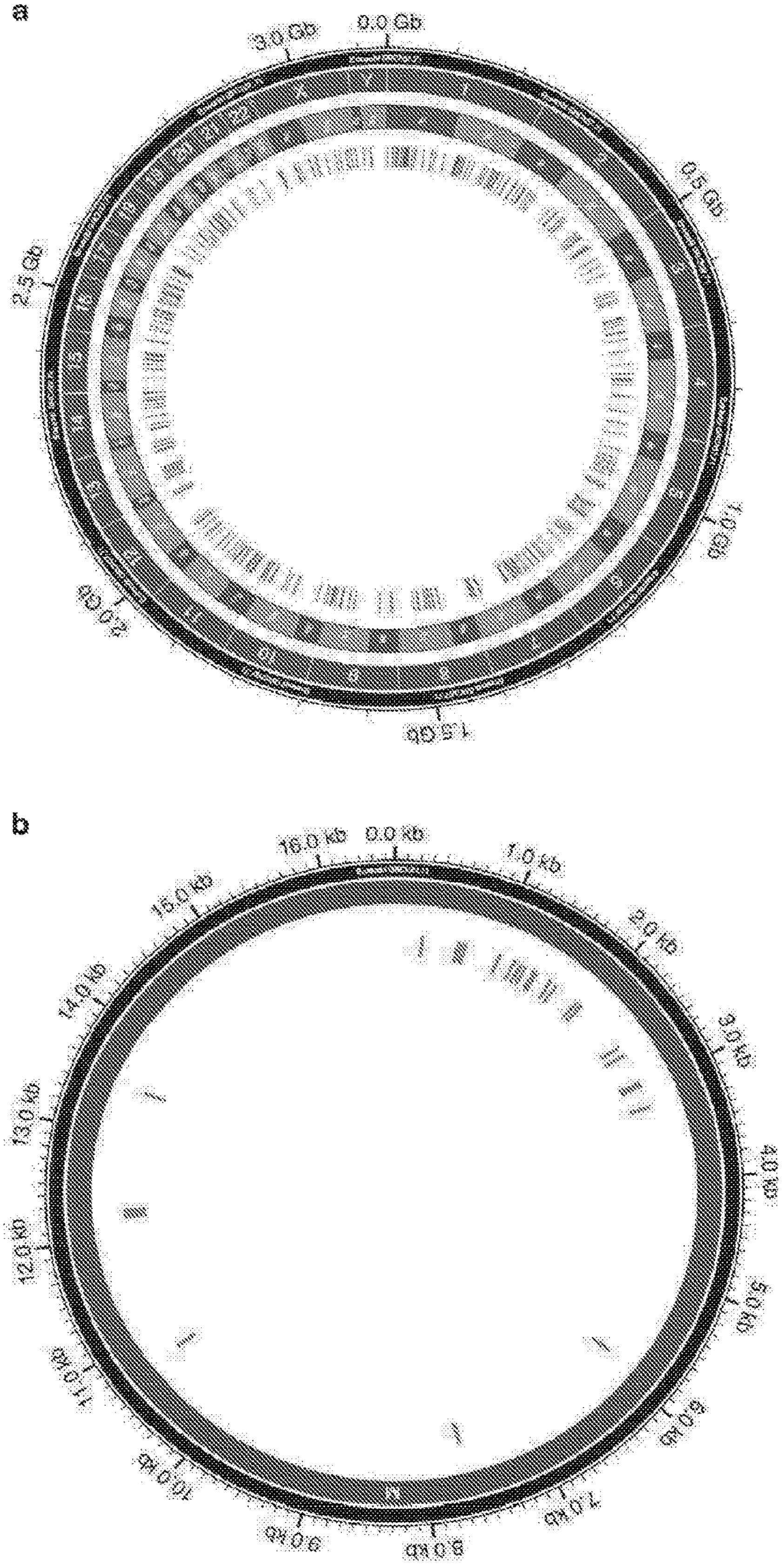

FIG. 2c-e
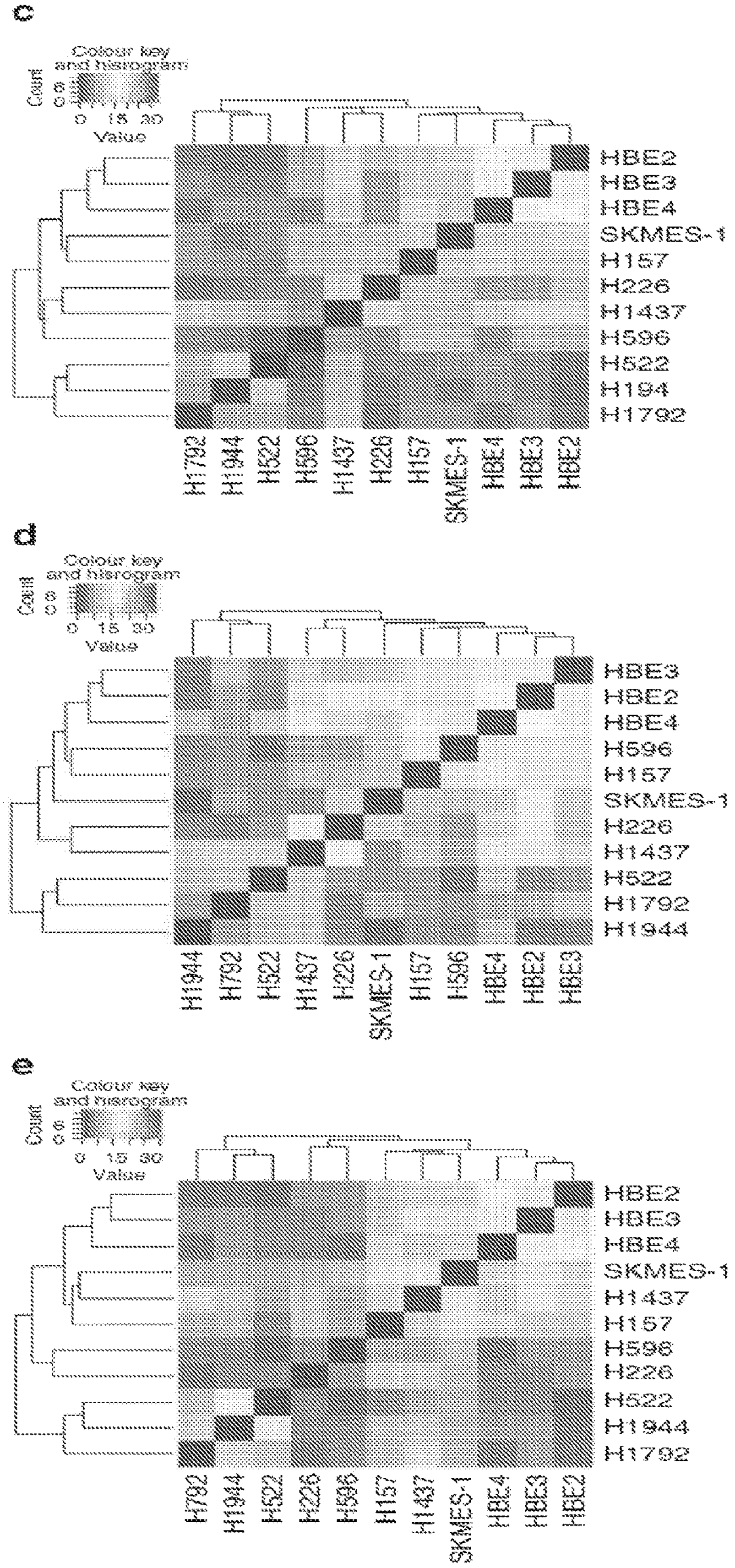

FIG. 7
a
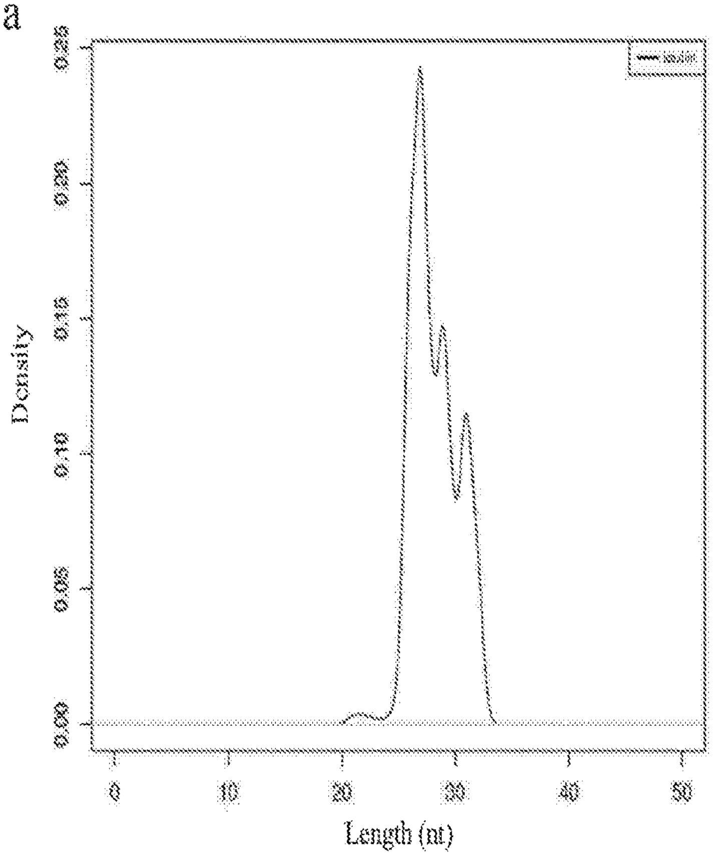
b
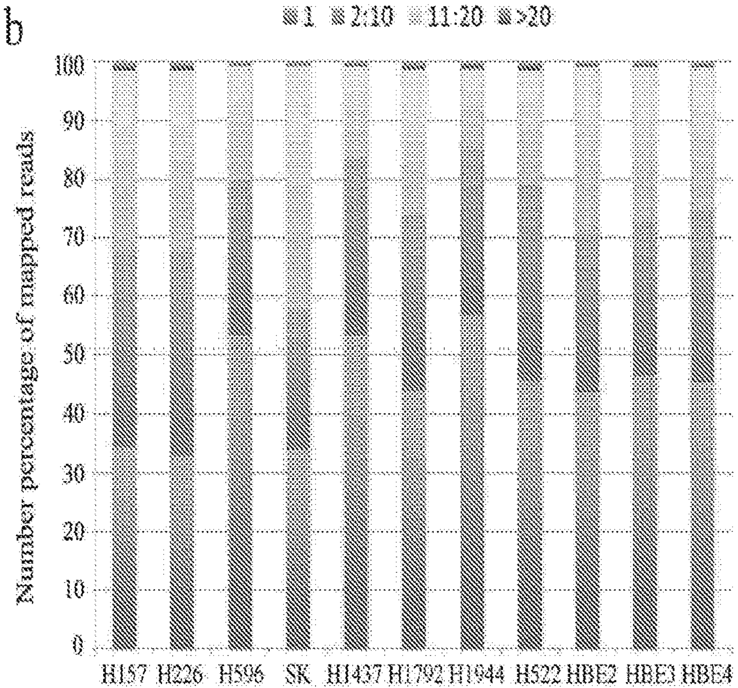

FIG. 8
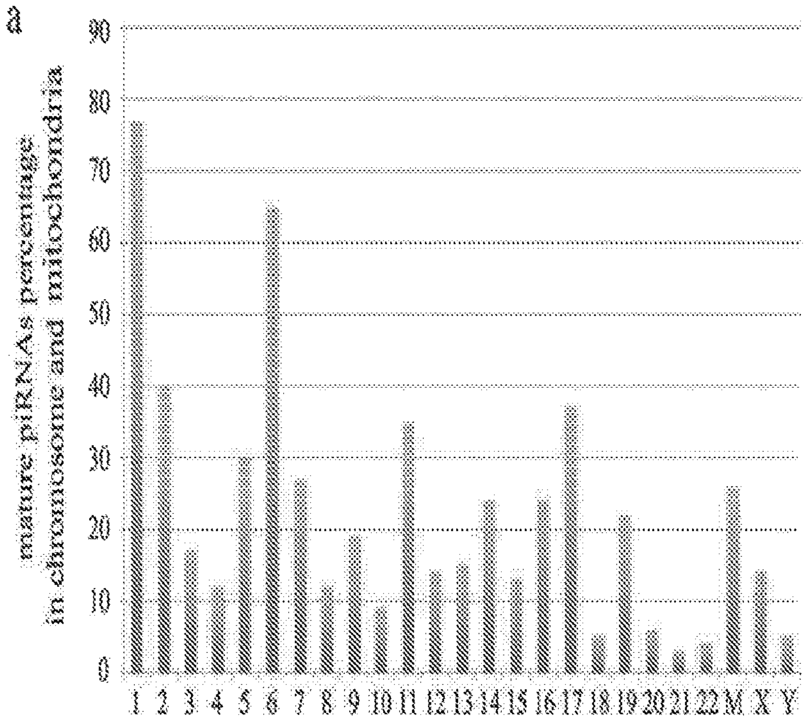
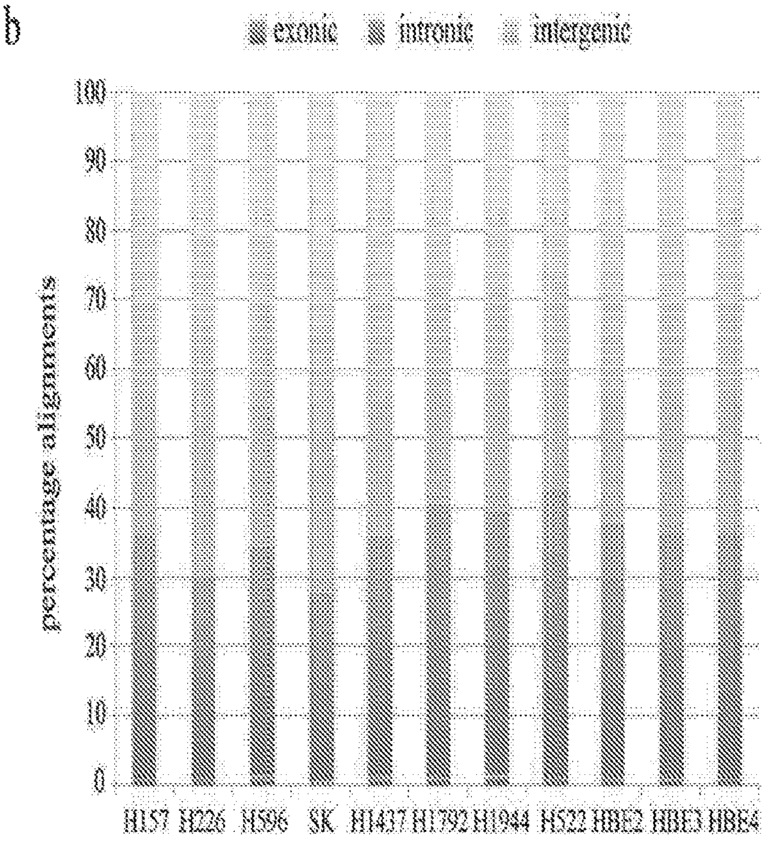

FIG. 12 a BindN: prediction of RNA-binding residues of Moesin

Figure 12:
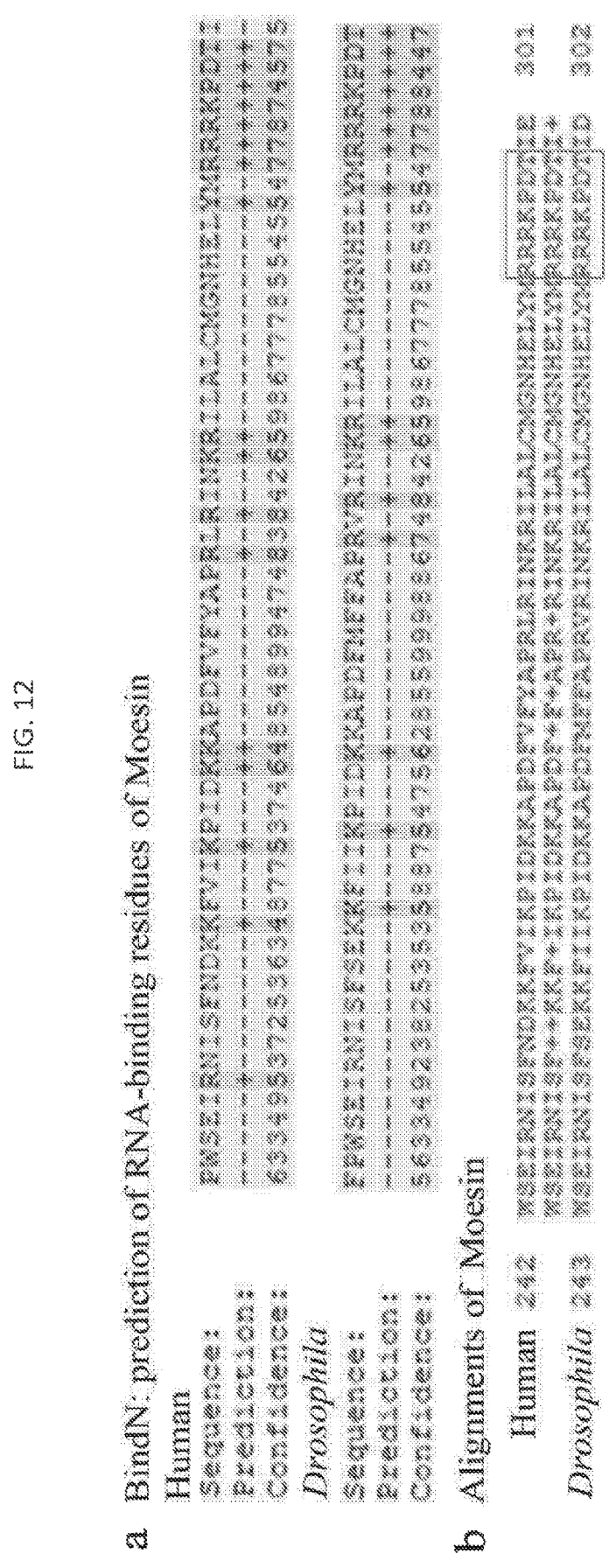

Human

```
Sequence:    FWSEIRNISFNDKKFVIKPIDKKAPDFVFYAPRLRINKRILALCMGNHELYMRRRKPDTI
Prediction:  -----+--------+---+---++---------+-+--++-------------+-++++++-
Confidence:  633495372536348775374648554599474838426598677785545547787457 5
```

*Drosophila*

```
Sequence:    FFWSEIRNISFSEKKFIIKPIDKKAPDFMFFAPRVRINKRILALCMGNHELYMRRRKPDT
Prediction:  -------------+---+----+---------+-+--++----------+-+++++++
Confidence:  563349238253535887547562855999886748426598677785545547788447
```

b Alignments of Moesin

```
Human      242  WSEIRNISFNDKKFVIKPIDKKAPDFVFYAPRLRINKRILALCMGNHELYMRRRKPDTIE  301
                WSEIRNISF++KKF+IKPIDKKAPDF+F+APR+RINKRILALCMGNHELYMRRRKPDTI+
Drosophila 243  WSEIRNISFSEKKFIIKPIDKKAPDFMFFAPRVRINKRILALCMGNHELYMRRRKPDTID  302
```

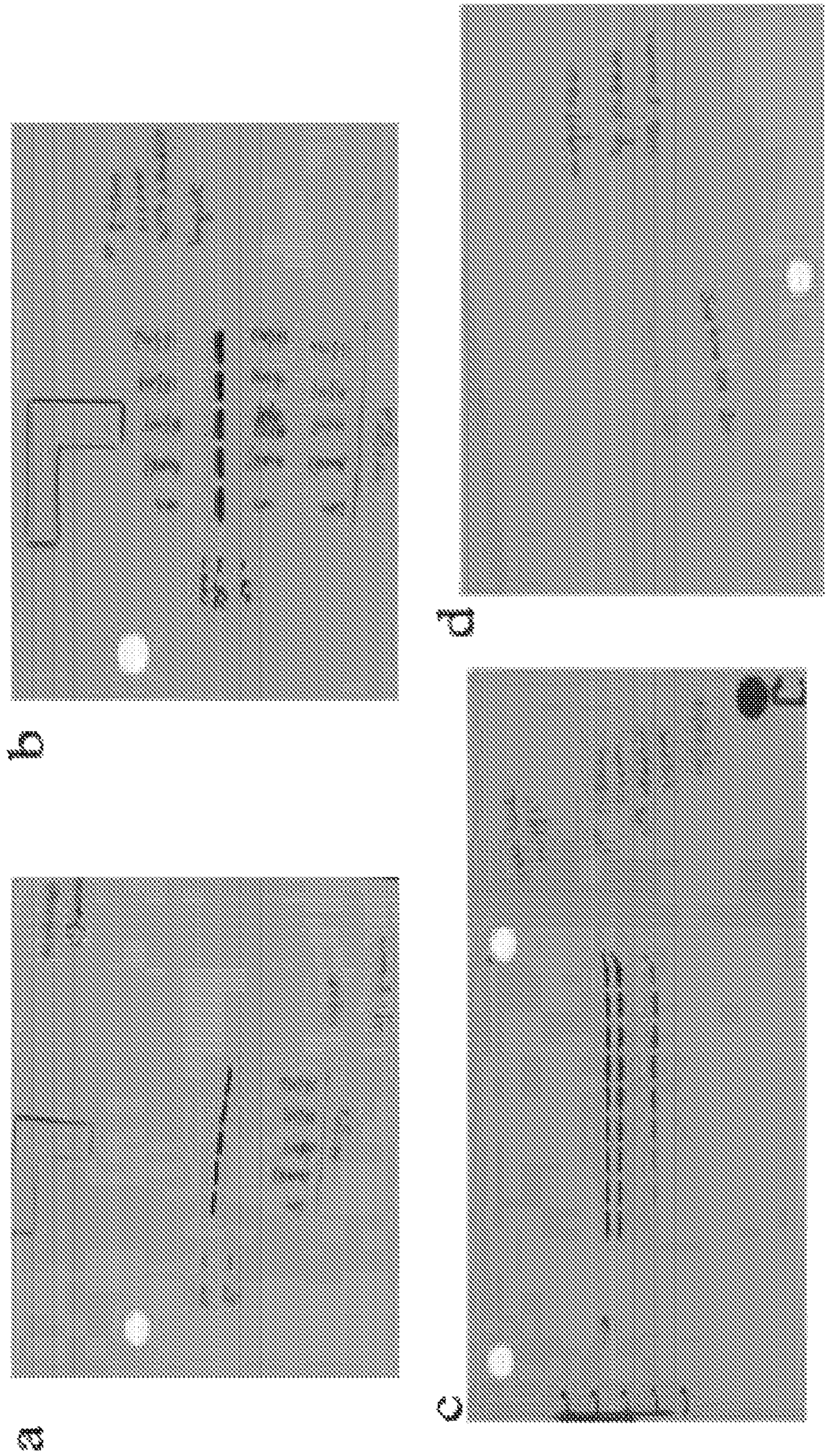
FIG. 13a-d

FIG. 13e-f
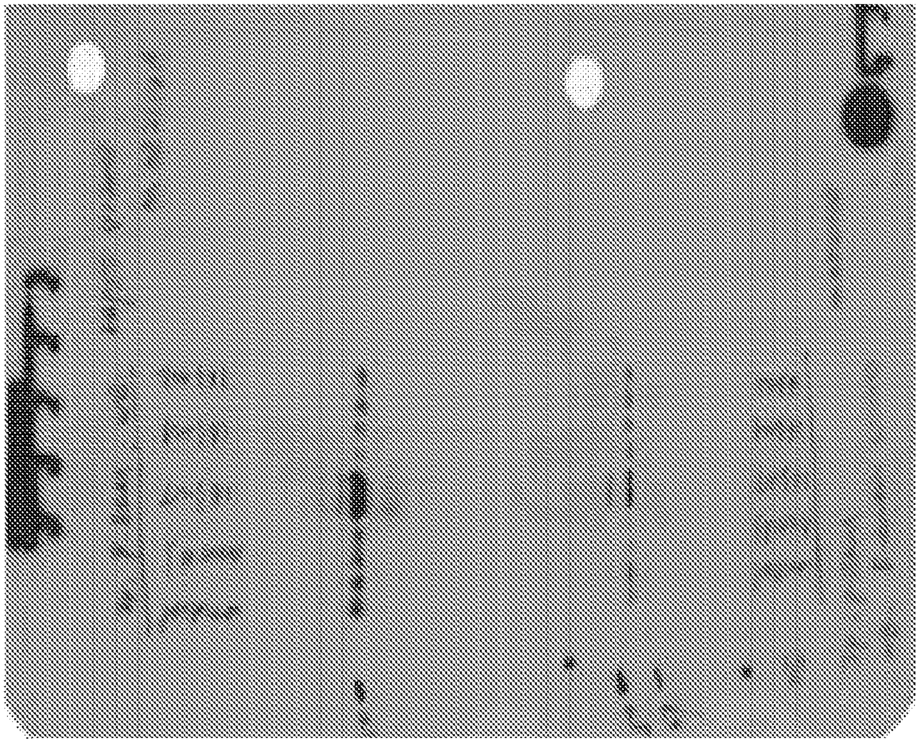
f
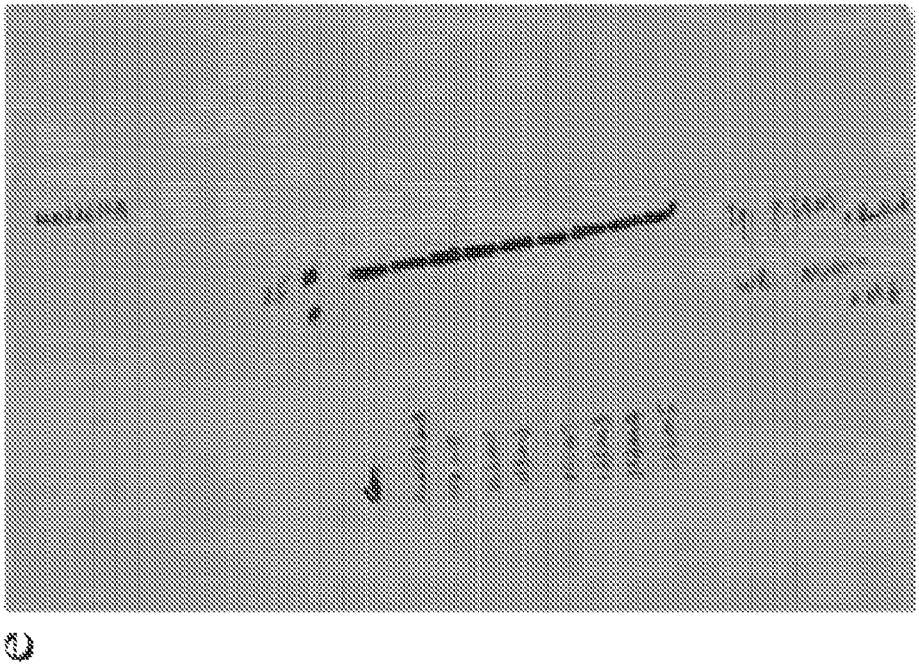
e

FIG. 13g-l
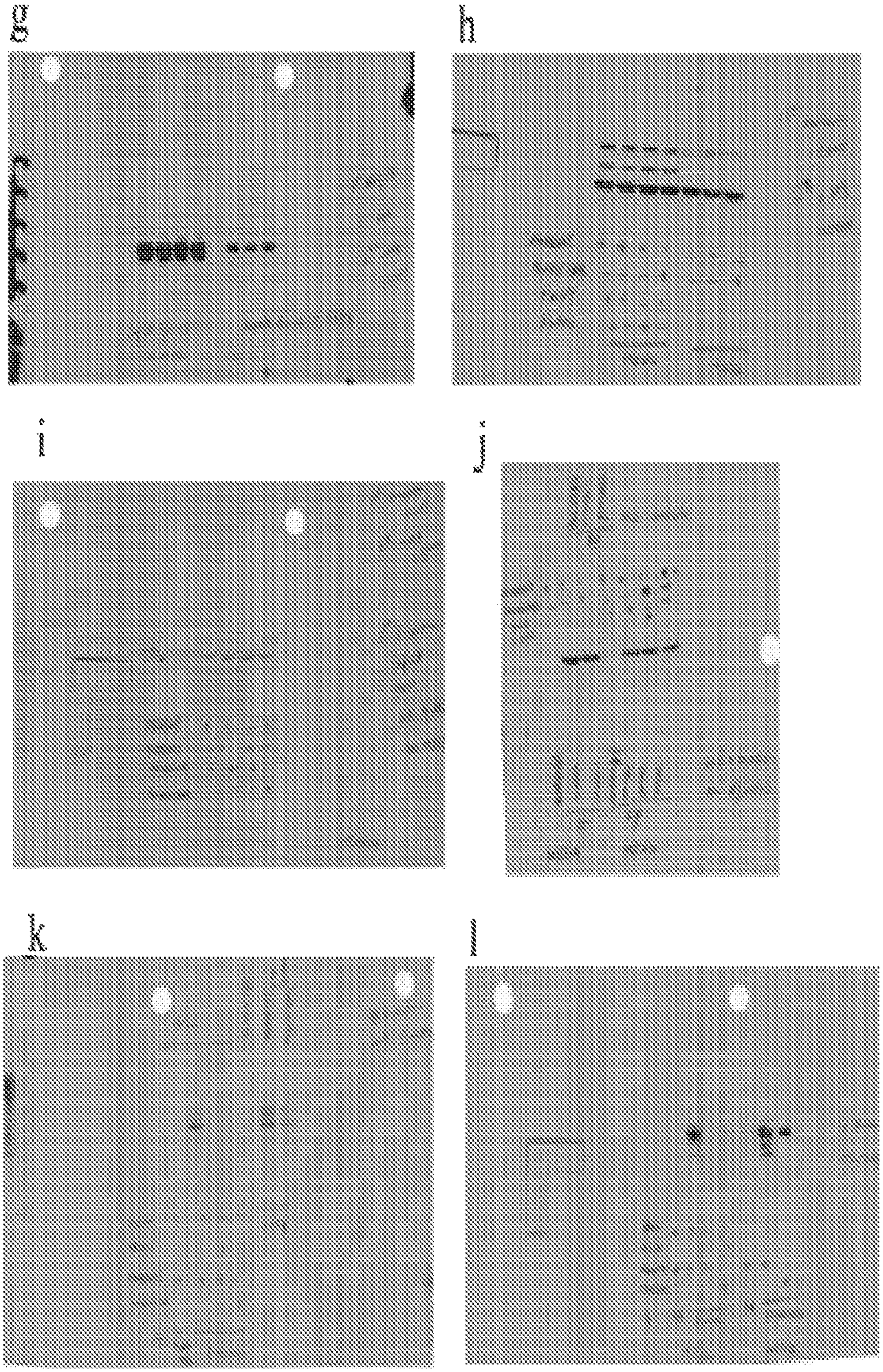

FIG. 14b-d
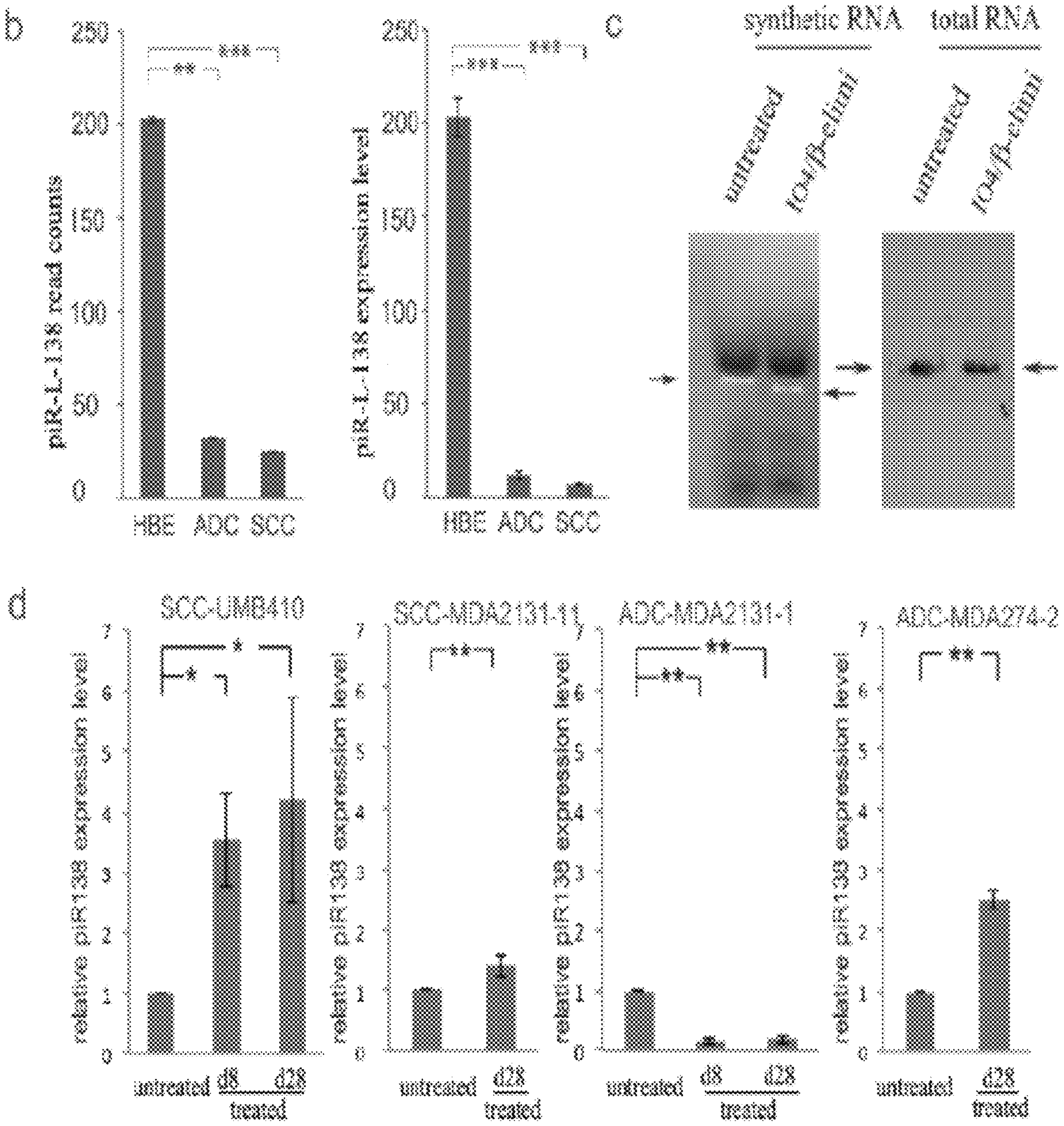

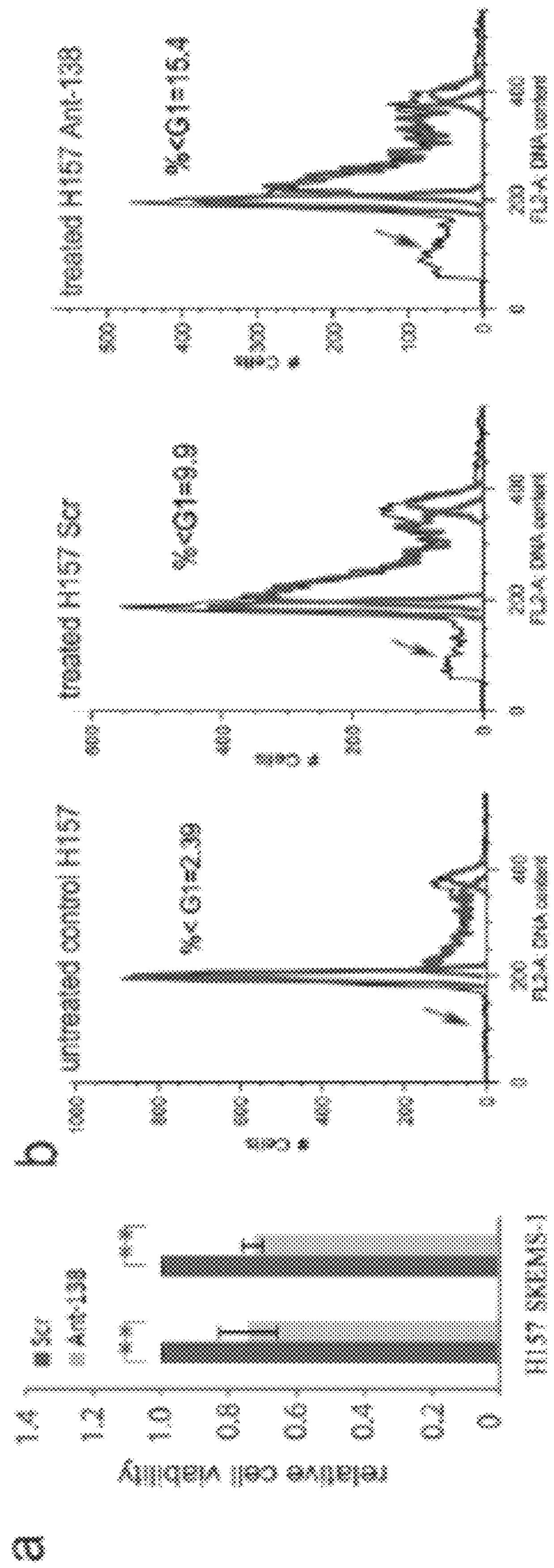
FIG. 15a-b

FIG. 15d-e
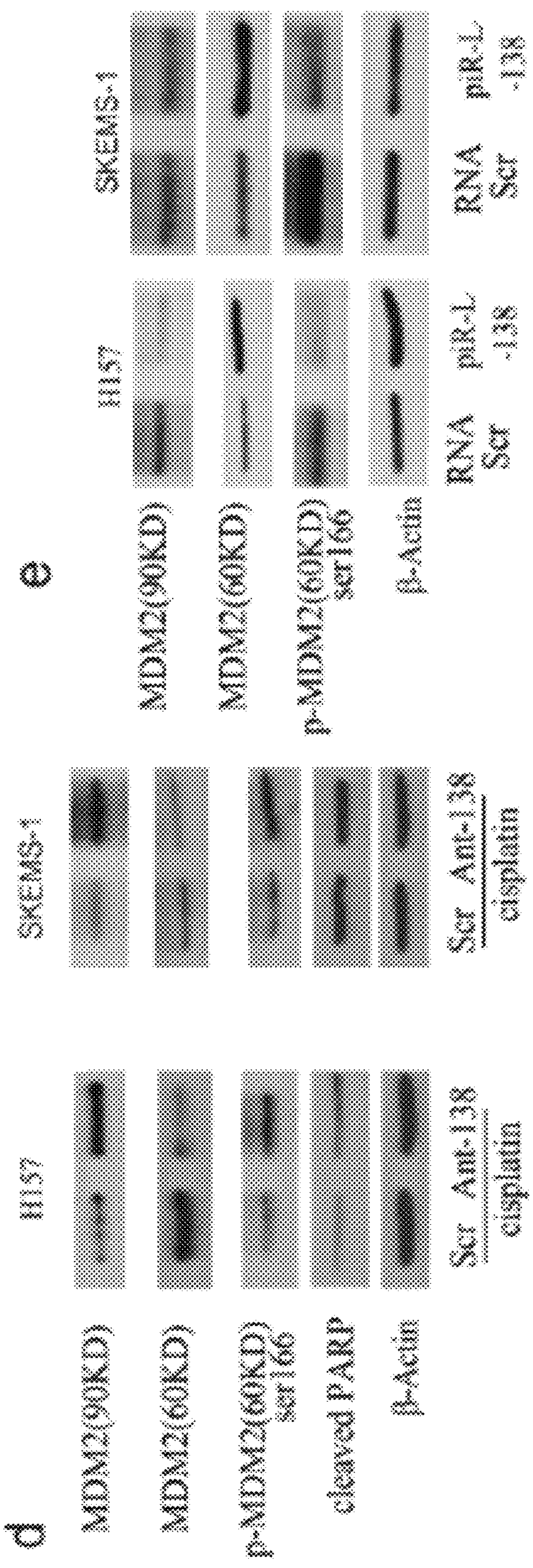

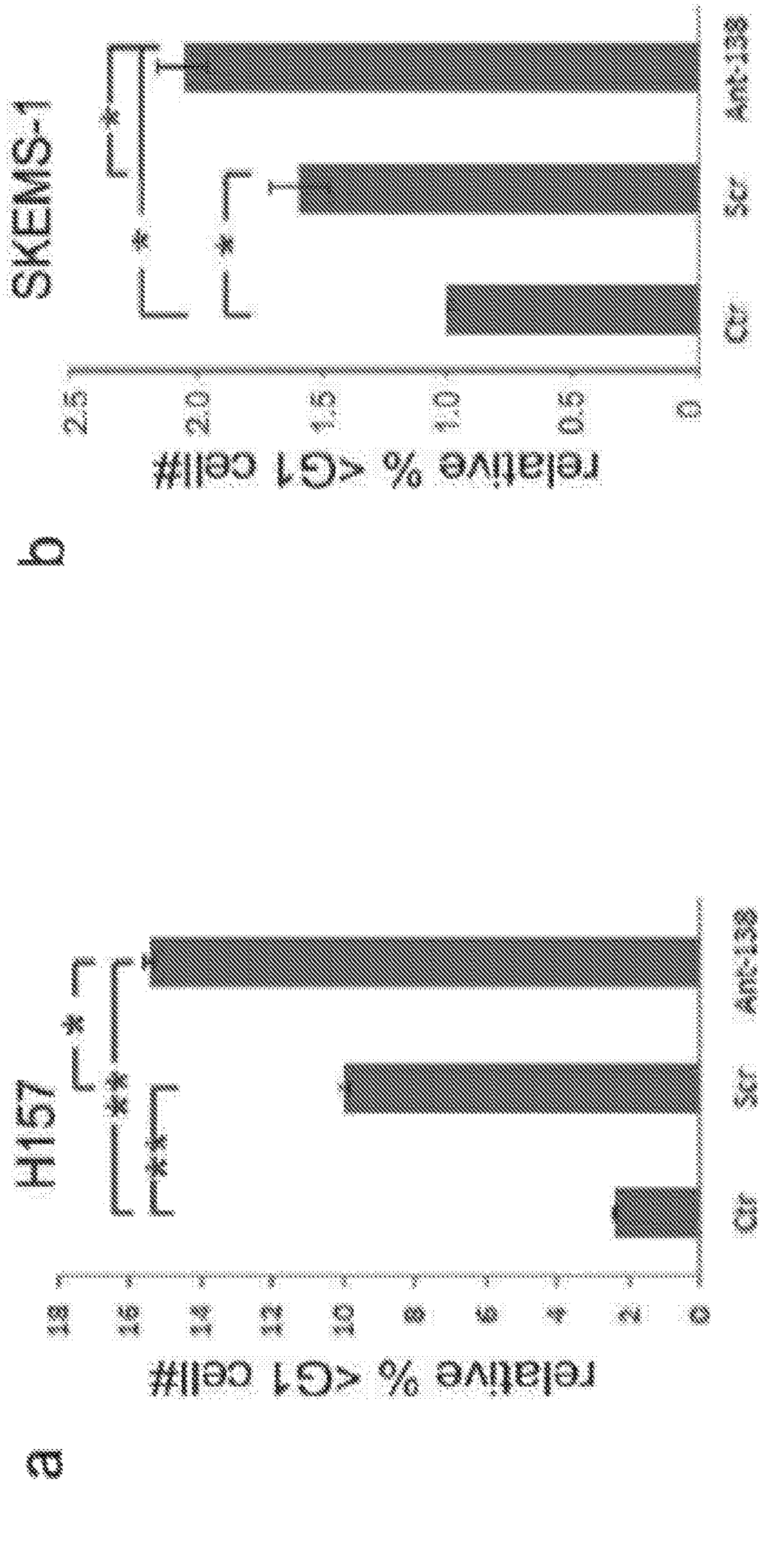
FIG. 20a-b

FIG. 20c-d
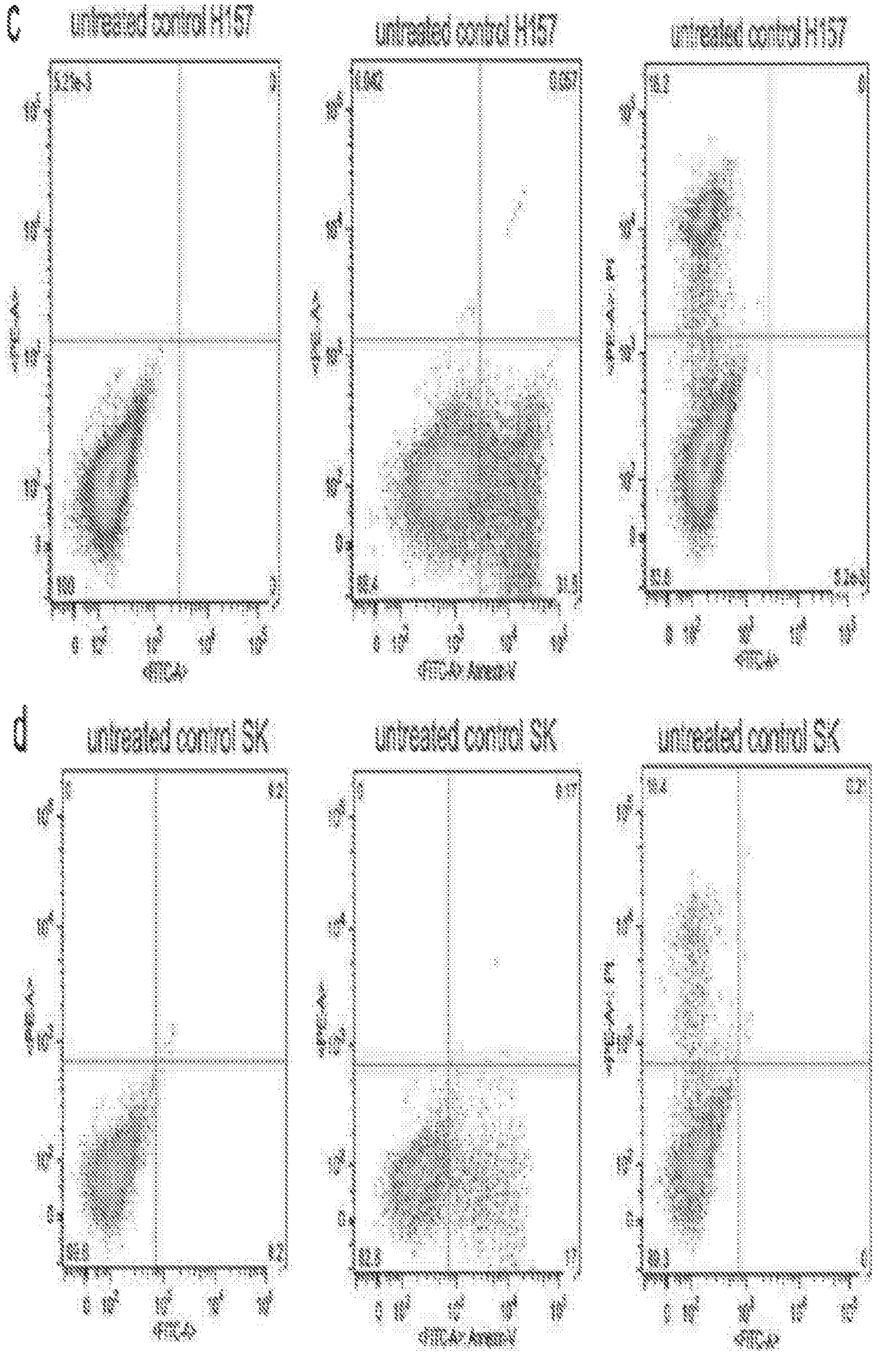

FIG. 24b-c
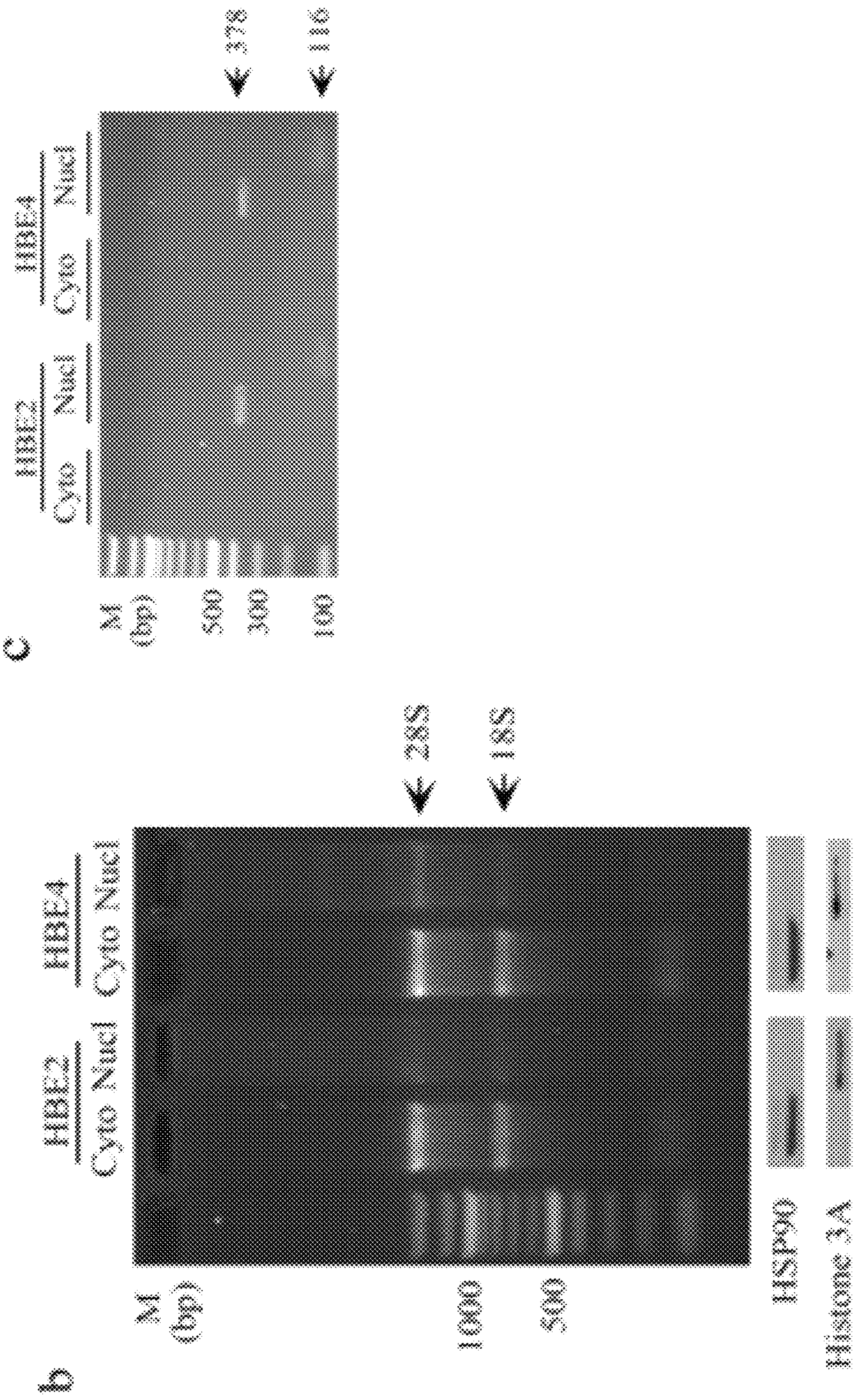

piRNA-138: 5' ACUUUAGCUCUAGAAUUACUCUGAGACCU 3': the structure is predicted by all the methods FIG. 28b-c
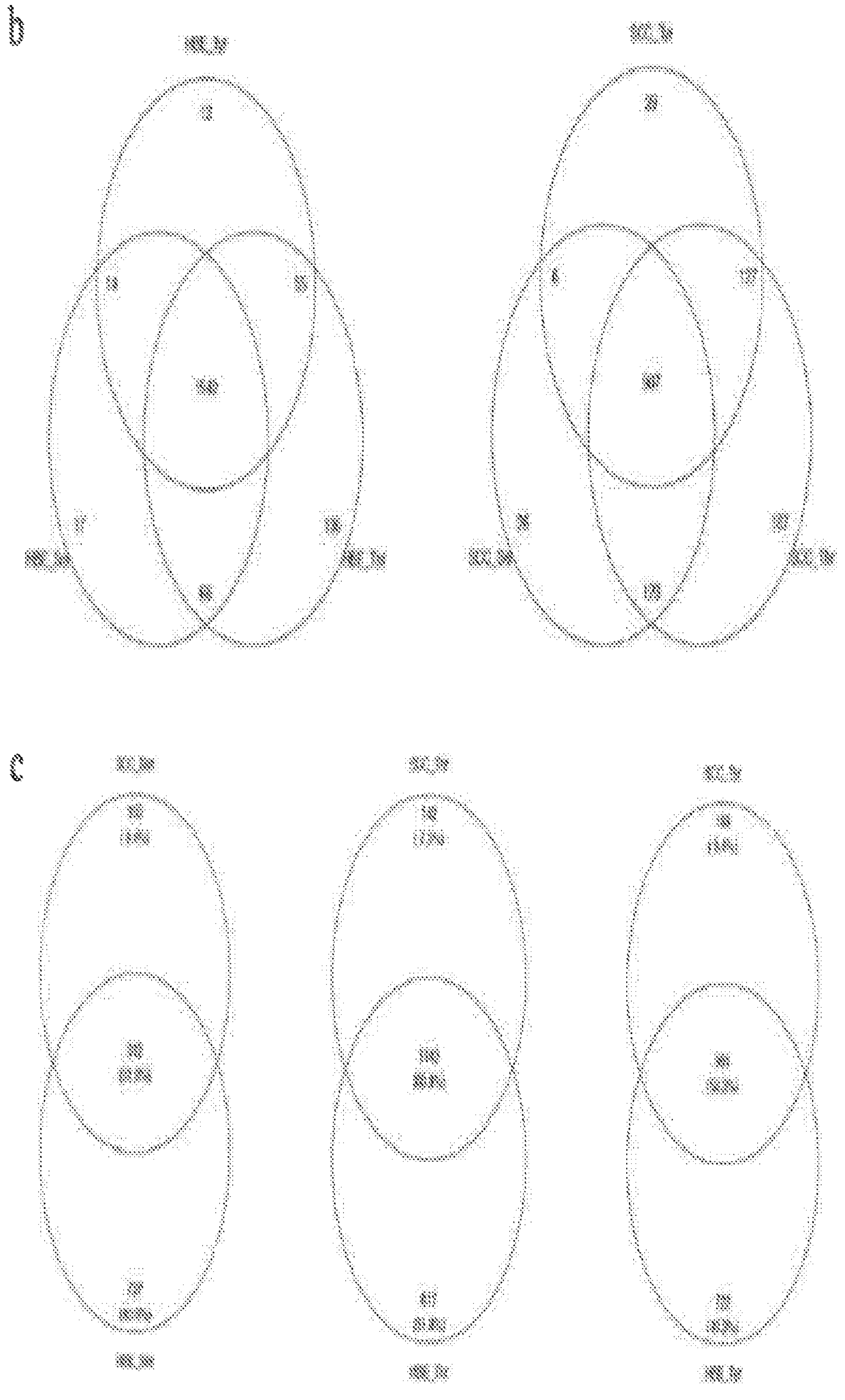

FIG. 29a-b
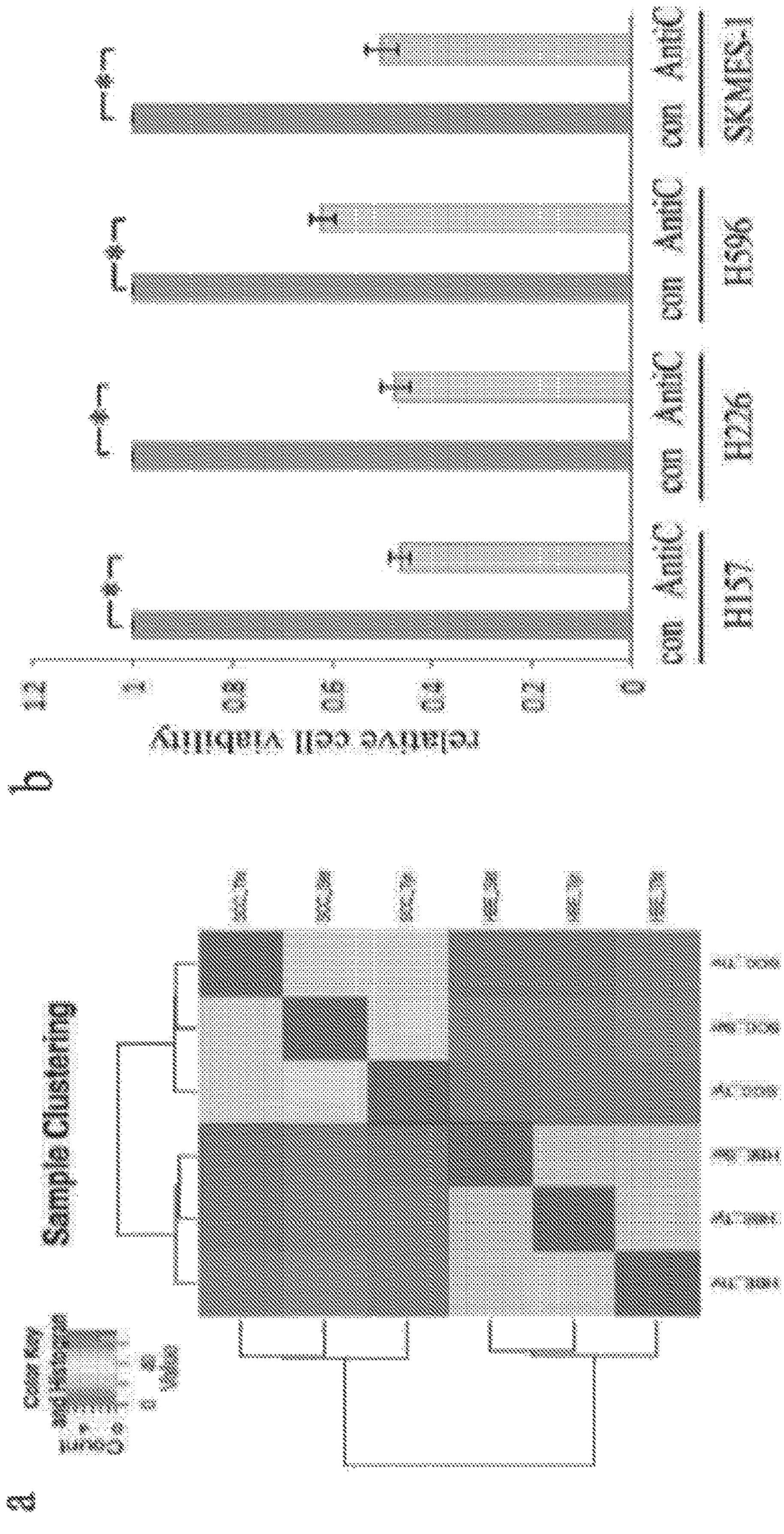

FIG. 29d-e
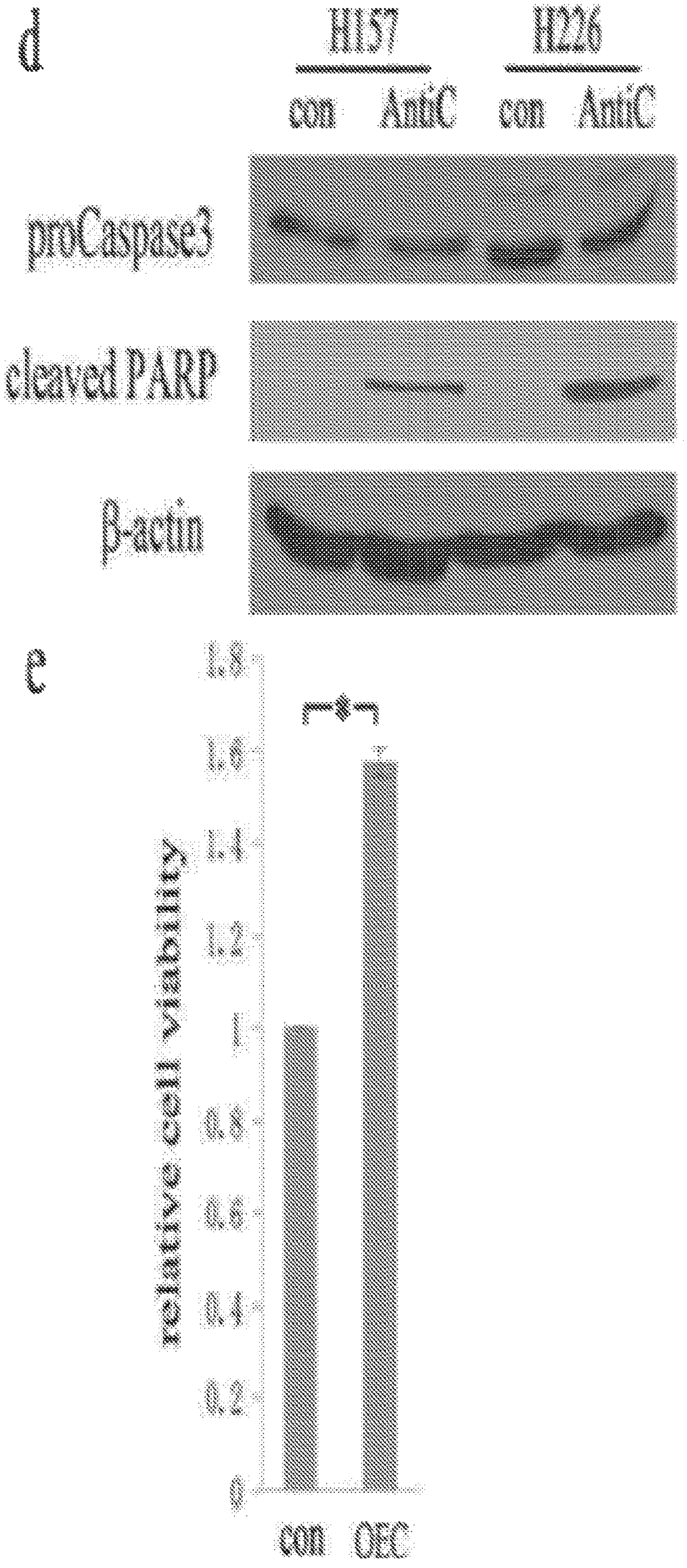

SEQUENCE LISTING

```
<160> NUMBER OF SEQ ID NOS: 2802

<210> SEQ ID NO 1
<211> LENGTH: 27
<212> TYPE: RNA
<213> ORGANISM: Homo sapiens

<400> SEQUENCE: 1

ugccaugaga caaaaguugg gccugga                                          27


<210> SEQ ID NO 2
<211> LENGTH: 27
<212> TYPE: RNA
<213> ORGANISM: Homo sapiens

<400> SEQUENCE: 2

ugguucagug guagaauucu cgccucc                                          27


<210> SEQ ID NO 3
<211> LENGTH: 31
<212> TYPE: RNA
<213> ORGANISM: Homo sapiens

<400> SEQUENCE: 3

ggcauuggug guucaguggu agaauucucg c                                     31


<210> SEQ ID NO 4
<211> LENGTH: 29
<212> TYPE: RNA
<213> ORGANISM: Homo sapiens

<400> SEQUENCE: 4

auuggugguu cagugguaga auucucgcc                                        29


<210> SEQ ID NO 5
<211> LENGTH: 29
<212> TYPE: RNA
<213> ORGANISM: Homo sapiens

<400> SEQUENCE: 5

uuggugguuc agugguagaa uucucgccu                                        29
```

-continued

<210> SEQ ID NO 6
<211> LENGTH: 32
<212> TYPE: RNA
<213> ORGANISM: Homo sapiens

<400> SEQUENCE: 6
guauauggca ugugggcuag uuucagacag gu 32

<210> SEQ ID NO 7
<211> LENGTH: 28
<212> TYPE: RNA
<213> ORGANISM: Homo sapiens

<400> SEQUENCE: 7
uuggaggaug aaacaaagga aucugacu 28

<210> SEQ ID NO 8
<211> LENGTH: 26
<212> TYPE: RNA
<213> ORGANISM: Homo sapiens

<400> SEQUENCE: 8
gucagggaca uuucugaagc gagcgu 26

<210> SEQ ID NO 9
<211> LENGTH: 32
<212> TYPE: RNA
<213> ORGANISM: Homo sapiens

<400> SEQUENCE: 9
uagagcauga gacucuuaau cucagggucg ug 32

<210> SEQ ID NO 10
<211> LENGTH: 31
<212> TYPE: RNA
<213> ORGANISM: Homo sapiens

<400> SEQUENCE: 10
uagagcauga gacucuuaau cucagggucg u 31

<210> SEQ ID NO 11
<211> LENGTH: 30
<212> TYPE: RNA
<213> ORGANISM: Homo sapiens

<400> SEQUENCE: 11
cggcuagcuc agucgguaga gcaugagacu 30

<210> SEQ ID NO 12
<211> LENGTH: 32
<212> TYPE: RNA
<213> ORGANISM: Homo sapiens

<400> SEQUENCE: 12
gcccggcuag cucagucggu agagcaugag ac 32

<210> SEQ ID NO 13
<211> LENGTH: 29
<212> TYPE: RNA
<213> ORGANISM: Homo sapiens

<400> SEQUENCE: 13

-continued ccggcuagcu cagucgguag agcaugaga 29

<210> SEQ ID NO 14
<211> LENGTH: 31
<212> TYPE: RNA
<213> ORGANISM: Homo sapiens

<400> SEQUENCE: 14
gcccggcuag cucagucggu agagcaugag a 31

<210> SEQ ID NO 15
<211> LENGTH: 30
<212> TYPE: RNA
<213> ORGANISM: Homo sapiens

<400> SEQUENCE: 15
gcccggcuag cucagucggu agagcaugag 30

<210> SEQ ID NO 16
<211> LENGTH: 29
<212> TYPE: RNA
<213> ORGANISM: Homo sapiens

<400> SEQUENCE: 16
gcccggcuag cucagucggu agagcauga 29

<210> SEQ ID NO 17
<211> LENGTH: 31
<212> TYPE: RNA
<213> ORGANISM: Homo sapiens

<400> SEQUENCE: 17
uucccuggug gucuaguggu uaggauucgg c 31

<210> SEQ ID NO 18
<211> LENGTH: 31
<212> TYPE: RNA
<213> ORGANISM: Homo sapiens

<400> SEQUENCE: 18
ucgccgugau cguauagugg uuaguacucu g 31

<210> SEQ ID NO 19
<211> LENGTH: 26
<212> TYPE: RNA
<213> ORGANISM: Homo sapiens

<400> SEQUENCE: 19
cggcuguuaa ccgaaagguu gguggu 26

<210> SEQ ID NO 20
<211> LENGTH: 30
<212> TYPE: RNA
<213> ORGANISM: Homo sapiens

<400> SEQUENCE: 20
guuaaccgaa agguuggugg uucgagccca 30

<210> SEQ ID NO 21
<211> LENGTH: 27
<212> TYPE: RNA
<213> ORGANISM: Homo sapiens

<400> SEQUENCE: 21

-continued uaaccgaaag guuggugguu cgagccc                                    27

<210> SEQ ID NO 22
<211> LENGTH: 29
<212> TYPE: RNA
<213> ORGANISM: Homo sapiens

<400> SEQUENCE: 22
uguuaaccga aagguuggug guucgagcc                                  29

<210> SEQ ID NO 23
<211> LENGTH: 26
<212> TYPE: RNA
<213> ORGANISM: Homo sapiens

<400> SEQUENCE: 23
uaaccgaaag guuggugguu cgagcc                                     26

<210> SEQ ID NO 24
<211> LENGTH: 28
<212> TYPE: RNA
<213> ORGANISM: Homo sapiens

<400> SEQUENCE: 24
uguuaaccga aagguuggug guucgagc                                   28

<210> SEQ ID NO 25
<211> LENGTH: 32
<212> TYPE: RNA
<213> ORGANISM: Homo sapiens

<400> SEQUENCE: 25
uccguagugu agugguuauc acguucgccu ca                              32

<210> SEQ ID NO 26
<211> LENGTH: 32
<212> TYPE: RNA
<213> ORGANISM: Homo sapiens

<400> SEQUENCE: 26
uuccguagug uagugguuau cacguucgcc uc                              32

<210> SEQ ID NO 27
<211> LENGTH: 30
<212> TYPE: RNA
<213> ORGANISM: Homo sapiens

<400> SEQUENCE: 27
uccguagugu agugguuauc acguucgccu                                 30

<210> SEQ ID NO 28
<211> LENGTH: 30
<212> TYPE: RNA
<213> ORGANISM: Homo sapiens

<400> SEQUENCE: 28
uuccguagug uagugguuau cacguucgcc                                 30

<210> SEQ ID NO 29
<211> LENGTH: 27
<212> TYPE: RNA
<213> ORGANISM: Homo sapiens

<400> SEQUENCE: 29
cguaguguag ugguuaucac guucgcc 27

<210> SEQ ID NO 30
<211> LENGTH: 28
<212> TYPE: RNA
<213> ORGANISM: Homo sapiens

<400> SEQUENCE: 30
ccguagugua gugguuauca cguucgcc 28

<210> SEQ ID NO 31
<211> LENGTH: 28
<212> TYPE: RNA
<213> ORGANISM: Homo sapiens

<400> SEQUENCE: 31
gcagaguggc gcagcggaag cgugcugg 28

<210> SEQ ID NO 32
<211> LENGTH: 32
<212> TYPE: RNA
<213> ORGANISM: Homo sapiens

<400> SEQUENCE: 32
gcagaguggc gcagcggaag cgugcugggc cc 32

<210> SEQ ID NO 33
<211> LENGTH: 28
<212> TYPE: RNA
<213> ORGANISM: Homo sapiens

<400> SEQUENCE: 33
cggaagcgug cugggcccau aacccaga 28

<210> SEQ ID NO 34
<211> LENGTH: 32
<212> TYPE: RNA
<213> ORGANISM: Homo sapiens

<400> SEQUENCE: 34
cgugcugggc ccauaaccca gaggucgaug ga 32

<210> SEQ ID NO 35
<211> LENGTH: 32
<212> TYPE: RNA
<213> ORGANISM: Homo sapiens

<400> SEQUENCE: 35
uuggugguuc agugguagaa uucucgccug cc 32

<210> SEQ ID NO 36
<211> LENGTH: 31
<212> TYPE: RNA
<213> ORGANISM: Homo sapiens

<400> SEQUENCE: 36
uuggugguuc agugguagaa uucucgccug c 31

<210> SEQ ID NO 37
<211> LENGTH: 29
<212> TYPE: RNA
<213> ORGANISM: Homo sapiens

<400> SEQUENCE: 37 cauuggugu ucagugguag aauucucgc 29

<210> SEQ ID NO 38
<211> LENGTH: 31
<212> TYPE: RNA
<213> ORGANISM: Homo sapiens

<400> SEQUENCE: 38
agcauuggug guucaguggu agaauucucg c 31

<210> SEQ ID NO 39
<211> LENGTH: 32
<212> TYPE: RNA
<213> ORGANISM: Homo sapiens

<400> SEQUENCE: 39
agccugagca acauagcgag accccgucuc ua 32

<210> SEQ ID NO 40
<211> LENGTH: 30
<212> TYPE: RNA
<213> ORGANISM: Homo sapiens

<400> SEQUENCE: 40
gcauuggugg uucaguggua gaauucucac 30

<210> SEQ ID NO 41
<211> LENGTH: 30
<212> TYPE: RNA
<213> ORGANISM: Homo sapiens

<400> SEQUENCE: 41
ggcgggagua acuaugacuc ucuuaaggua 30

<210> SEQ ID NO 42
<211> LENGTH: 30
<212> TYPE: RNA
<213> ORGANISM: Homo sapiens

<400> SEQUENCE: 42
guuaaccgaa agguuggugg uucgagccca 30

<210> SEQ ID NO 43
<211> LENGTH: 27
<212> TYPE: RNA
<213> ORGANISM: Homo sapiens

<400> SEQUENCE: 43
uaaccgaaag guuggugguu cgagccc 27

<210> SEQ ID NO 44
<211> LENGTH: 26
<212> TYPE: RNA
<213> ORGANISM: Homo sapiens

<400> SEQUENCE: 44
uaaccgaaag guuggugguu cgagcc 26

<210> SEQ ID NO 45
<211> LENGTH: 28
<212> TYPE: RNA

<213> ORGANISM: Homo sapiens

<400> SEQUENCE: 45
ccugggcaac auagcgagac cucgucuc 28

<210> SEQ ID NO 46
<211> LENGTH: 26
<212> TYPE: RNA
<213> ORGANISM: Homo sapiens

<400> SEQUENCE: 46
ggccgguuag cucaguuggu uagagc 26

<210> SEQ ID NO 47
<211> LENGTH: 29
<212> TYPE: RNA
<213> ORGANISM: Homo sapiens

<400> SEQUENCE: 47
uaagccucuc cacauccaaa uugaacagc 29

<210> SEQ ID NO 48
<211> LENGTH: 32
<212> TYPE: RNA
<213> ORGANISM: Homo sapiens

<400> SEQUENCE: 48
aucgaggcua gagucacgcu uggguaucgg cu 32

<210> SEQ ID NO 49
<211> LENGTH: 31
<212> TYPE: RNA
<213> ORGANISM: Homo sapiens

<400> SEQUENCE: 49
gcuaaaagag cacacccguc uauguagcaa a 31

<210> SEQ ID NO 50
<211> LENGTH: 31
<212> TYPE: RNA
<213> ORGANISM: Homo sapiens

<400> SEQUENCE: 50
cagaguguag cuuaacacaa agcacccaac u 31

<210> SEQ ID NO 51
<211> LENGTH: 32
<212> TYPE: RNA
<213> ORGANISM: Homo sapiens

<400> SEQUENCE: 51
auagguuugg uccuagccuu ucuauuagcu cu 32

<210> SEQ ID NO 52
<211> LENGTH: 26
<212> TYPE: RNA
<213> ORGANISM: Homo sapiens

<400> SEQUENCE: 52
auagguuugg uccuagccuu ucuauu 26

<210> SEQ ID NO 53
<211> LENGTH: 27

<212> TYPE: RNA
<213> ORGANISM: Homo sapiens

<400> SEQUENCE: 53
ugagagugau gaguugcaca cuggugg 27

<210> SEQ ID NO 54
<211> LENGTH: 26
<212> TYPE: RNA
<213> ORGANISM: Homo sapiens

<400> SEQUENCE: 54
gagagugaug aguugcacac uggugg 26

<210> SEQ ID NO 55
<211> LENGTH: 30
<212> TYPE: RNA
<213> ORGANISM: Homo sapiens

<400> SEQUENCE: 55
uucgaugaag agaugaugac gagucugacu 30

<210> SEQ ID NO 56
<211> LENGTH: 30
<212> TYPE: RNA
<213> ORGANISM: Homo sapiens

<400> SEQUENCE: 56
ggcucguugg ucuaggggua ugauucucgg 30

<210> SEQ ID NO 57
<211> LENGTH: 28
<212> TYPE: RNA
<213> ORGANISM: Homo sapiens

<400> SEQUENCE: 57
gaaugcagcc caaagcgggu gguaaacu 28

<210> SEQ ID NO 58
<211> LENGTH: 26
<212> TYPE: RNA
<213> ORGANISM: Homo sapiens

<400> SEQUENCE: 58
caacaaguac cguaagggaa aguuga 26

<210> SEQ ID NO 59
<211> LENGTH: 26
<212> TYPE: RNA
<213> ORGANISM: Homo sapiens

<400> SEQUENCE: 59
ggccgugauc guauaguggu uaguac 26

<210> SEQ ID NO 60
<211> LENGTH: 28
<212> TYPE: RNA
<213> ORGANISM: Homo sapiens

<400> SEQUENCE: 60
ggccgugauc guauaguggu uaguacuc 28

<210> SEQ ID NO 61

<211> LENGTH: 30
<212> TYPE: RNA
<213> ORGANISM: Homo sapiens

<400> SEQUENCE: 61
ggccgugauc guauaguggu uaguacucug 30

<210> SEQ ID NO 62
<211> LENGTH: 27
<212> TYPE: RNA
<213> ORGANISM: Homo sapiens

<400> SEQUENCE: 62
ggccgugauc guauaguggu uaguacu 27

<210> SEQ ID NO 63
<211> LENGTH: 27
<212> TYPE: RNA
<213> ORGANISM: Homo sapiens

<400> SEQUENCE: 63
ugacugugcu guccugauug uugcugc 27

<210> SEQ ID NO 64
<211> LENGTH: 28
<212> TYPE: RNA
<213> ORGANISM: Homo sapiens

<400> SEQUENCE: 64
gcauuggugg uauaguggua agcauagc 28

<210> SEQ ID NO 65
<211> LENGTH: 31
<212> TYPE: RNA
<213> ORGANISM: Homo sapiens

<400> SEQUENCE: 65
ggggauguag cucaguggua gagcgcaugc u 31

<210> SEQ ID NO 66
<211> LENGTH: 27
<212> TYPE: RNA
<213> ORGANISM: Homo sapiens

<400> SEQUENCE: 66
uucugggucg ggguuucgua cguagca 27

<210> SEQ ID NO 67
<211> LENGTH: 27
<212> TYPE: RNA
<213> ORGANISM: Homo sapiens

<400> SEQUENCE: 67
agccaauggg gcgaagcuac caucugu 27

<210> SEQ ID NO 68
<211> LENGTH: 26
<212> TYPE: RNA
<213> ORGANISM: Homo sapiens

<400> SEQUENCE: 68
gcauuggugg uauaguggug agcaua 26

<210> SEQ ID NO 69
<211> LENGTH: 27
<212> TYPE: RNA
<213> ORGANISM: Homo sapiens

<400> SEQUENCE: 69
uaaggugcau cuagugcaga uagugaa 27

<210> SEQ ID NO 70
<211> LENGTH: 30
<212> TYPE: RNA
<213> ORGANISM: Homo sapiens

<400> SEQUENCE: 70
uaaggugcau cuagugcaga uagugaagua 30

<210> SEQ ID NO 71
<211> LENGTH: 29
<212> TYPE: RNA
<213> ORGANISM: Homo sapiens

<400> SEQUENCE: 71
uaaggugcau cuagugcaga uagugaagu 29

<210> SEQ ID NO 72
<211> LENGTH: 27
<212> TYPE: RNA
<213> ORGANISM: Homo sapiens

<400> SEQUENCE: 72
ucgcgaguuc aaaucucgcu ggggccu 27

<210> SEQ ID NO 73
<211> LENGTH: 32
<212> TYPE: RNA
<213> ORGANISM: Homo sapiens

<400> SEQUENCE: 73
uccuuagguc gcugguucga uuccggcucg aa 32

<210> SEQ ID NO 74
<211> LENGTH: 26
<212> TYPE: RNA
<213> ORGANISM: Homo sapiens

<400> SEQUENCE: 74
cuuaggucgc ugguucgauu ccggcu 26

<210> SEQ ID NO 75
<211> LENGTH: 26
<212> TYPE: RNA
<213> ORGANISM: Homo sapiens

<400> SEQUENCE: 75
ccccccacug cuaaauuuga cugguu 26

<210> SEQ ID NO 76
<211> LENGTH: 28
<212> TYPE: RNA
<213> ORGANISM: Homo sapiens

<400> SEQUENCE: 76
ucagaagauu ccagguucga cuccuggc 28

<210> SEQ ID NO 77
<211> LENGTH: 27
<212> TYPE: RNA
<213> ORGANISM: Homo sapiens

<400> SEQUENCE: 77
ucggcaucaa uauggugacc ucccggg 27

<210> SEQ ID NO 78
<211> LENGTH: 28
<212> TYPE: RNA
<213> ORGANISM: Homo sapiens

<400> SEQUENCE: 78
uguagugcgc uaugccgauc gggugucc 28

<210> SEQ ID NO 79
<211> LENGTH: 28
<212> TYPE: RNA
<213> ORGANISM: Homo sapiens

<400> SEQUENCE: 79
gcauuggugg uauaguggug agcauagc 28

<210> SEQ ID NO 80
<211> LENGTH: 30
<212> TYPE: RNA
<213> ORGANISM: Homo sapiens

<400> SEQUENCE: 80
gaccaaugau gagauuggag ggugucugaa 30

<210> SEQ ID NO 81
<211> LENGTH: 31
<212> TYPE: RNA
<213> ORGANISM: Homo sapiens

<400> SEQUENCE: 81
gaccaaugau gagauuggag ggugucugaa u 31

<210> SEQ ID NO 82
<211> LENGTH: 26
<212> TYPE: RNA
<213> ORGANISM: Homo sapiens

<400> SEQUENCE: 82
accaaugaug agauuggagg gugucu 26

<210> SEQ ID NO 83
<211> LENGTH: 30
<212> TYPE: RNA
<213> ORGANISM: Homo sapiens

<400> SEQUENCE: 83
accaaugaug agauuggagg gugucugaau 30

<210> SEQ ID NO 84
<211> LENGTH: 29
<212> TYPE: RNA
<213> ORGANISM: Homo sapiens

<400> SEQUENCE: 84
uugcaagcaa cacucugugg cagaugauc 29

<210> SEQ ID NO 85
<211> LENGTH: 30
<212> TYPE: RNA
<213> ORGANISM: Homo sapiens

<400> SEQUENCE: 85
guucaugaug acacaggacc uugucugaac 30

<210> SEQ ID NO 86
<211> LENGTH: 27
<212> TYPE: RNA
<213> ORGANISM: Homo sapiens

<400> SEQUENCE: 86 gggggguauag cucagugggu agagcau 27

<210> SEQ ID NO 87
<211> LENGTH: 29
<212> TYPE: RNA
<213> ORGANISM: Homo sapiens

<400> SEQUENCE: 87
uggauaaggc gucugauucc ggaucagaa 29

<210> SEQ ID NO 88
<211> LENGTH: 28
<212> TYPE: RNA
<213> ORGANISM: Homo sapiens

<400> SEQUENCE: 88
aucagacccc agaaaaggug uugguuga 28

<210> SEQ ID NO 89
<211> LENGTH: 29
<212> TYPE: RNA
<213> ORGANISM: Homo sapiens

<400> SEQUENCE: 89
aucagacccc agaaaaggug uugguugau 29

<210> SEQ ID NO 90
<211> LENGTH: 31
<212> TYPE: RNA
<213> ORGANISM: Homo sapiens

<400> SEQUENCE: 90
auuggugguu cagugguaga auucucgccu g 31

<210> SEQ ID NO 91
<211> LENGTH: 30
<212> TYPE: RNA
<213> ORGANISM: Homo sapiens

<400> SEQUENCE: 91
uuggugguuc agugguagaa uucucgccug 30

<210> SEQ ID NO 92
<211> LENGTH: 27
<212> TYPE: RNA
<213> ORGANISM: Homo sapiens

<400> SEQUENCE: 92
uuggugguuc agugguagaa uucucgc 27

<210> SEQ ID NO 93
<211> LENGTH: 29
<212> TYPE: RNA
<213> ORGANISM: Homo sapiens

<400> SEQUENCE: 93
uggugguuca gugguagaau ucucgccug 29

<210> SEQ ID NO 94
<211> LENGTH: 29
<212> TYPE: RNA
<213> ORGANISM: Homo sapiens

<400> SEQUENCE: 94
ucacaaugcu gacacucaaa cugcugaca 29

<210> SEQ ID NO 95
<211> LENGTH: 29
<212> TYPE: RNA
<213> ORGANISM: Homo sapiens

<400> SEQUENCE: 95
gguuccaugg uguaaugguu agcacucug 29

<210> SEQ ID NO 96
<211> LENGTH: 30
<212> TYPE: RNA
<213> ORGANISM: Homo sapiens

<400> SEQUENCE: 96
auaacugacg aagacuacuc cugucugauu 30

<210> SEQ ID NO 97
<211> LENGTH: 29
<212> TYPE: RNA
<213> ORGANISM: Homo sapiens

<400> SEQUENCE: 97
agcaguugaa caugggucag ucgguccug 29

<210> SEQ ID NO 98
<211> LENGTH: 31
<212> TYPE: RNA
<213> ORGANISM: Homo sapiens

<400> SEQUENCE: 98
acuugugaug ucuucaaagg aaccacugau g 31

<210> SEQ ID NO 99
<211> LENGTH: 29
<212> TYPE: RNA
<213> ORGANISM: Homo sapiens

<400> SEQUENCE: 99
caaagugauu gguaccucgu ugucugaug 29

<210> SEQ ID NO 100
<211> LENGTH: 30
<212> TYPE: RNA
<213> ORGANISM: Homo sapiens

<400> SEQUENCE: 100

```
gggggu auag cucaguggua gagcauuuga                                    30

<210> SEQ ID NO 101
<211> LENGTH: 28
<212> TYPE: RNA
<213> ORGANISM: Homo sapiens

<400> SEQUENCE: 101

gggggu auag cucaguggua gagcauuu                                      28

<210> SEQ ID NO 102
<211> LENGTH: 29
<212> TYPE: RNA
<213> ORGANISM: Homo sapiens

<400> SEQUENCE: 102

gggggu auag cucaguggua gagcauuug                                     29

<210> SEQ ID NO 103
<211> LENGTH: 32
<212> TYPE: RNA
<213> ORGANISM: Homo sapiens

<400> SEQUENCE: 103

agccuaugau gguuaguuau cccugucuga aa                                  32

<210> SEQ ID NO 104
<211> LENGTH: 31
<212> TYPE: RNA
<213> ORGANISM: Homo sapiens

<400> SEQUENCE: 104

ugcgcgacau caaggagaag cugugcuacg u                                   31

<210> SEQ ID NO 105
<211> LENGTH: 28
<212> TYPE: RNA
<213> ORGANISM: Homo sapiens

<400> SEQUENCE: 105

ugcgcgacau caaggagaag cugugcua                                       28

<210> SEQ ID NO 106
<211> LENGTH: 26
<212> TYPE: RNA
<213> ORGANISM: Homo sapiens

<400> SEQUENCE: 106

ugcgcgacau caaggagaag cugugc                                         26

<210> SEQ ID NO 107
<211> LENGTH: 31
<212> TYPE: RNA
<213> ORGANISM: Homo sapiens

<400> SEQUENCE: 107

uugcugugau gacuaucuua ggacaccuuu g                                   31

<210> SEQ ID NO 108
<211> LENGTH: 32
<212> TYPE: RNA
<213> ORGANISM: Homo sapiens
```

<400> SEQUENCE: 108
cugcgaugau ggcauuucuu aggacaccuu ug 32

<210> SEQ ID NO 109
<211> LENGTH: 27
<212> TYPE: RNA
<213> ORGANISM: Homo sapiens

<400> SEQUENCE: 109
cagaccccag aaaaggugu gguugau 27

<210> SEQ ID NO 110
<211> LENGTH: 27
<212> TYPE: RNA
<213> ORGANISM: Homo sapiens

<400> SEQUENCE: 110
ggccagccug guccacaugg gucggaa 27

<210> SEQ ID NO 111
<211> LENGTH: 28
<212> TYPE: RNA
<213> ORGANISM: Homo sapiens

<400> SEQUENCE: 111
cguccaugau guuccgcaac uaccuaca 28

<210> SEQ ID NO 112
<211> LENGTH: 27
<212> TYPE: RNA
<213> ORGANISM: Homo sapiens

<400> SEQUENCE: 112
cguccaugau guuccgcaac uaccuac 27

<210> SEQ ID NO 113
<211> LENGTH: 30
<212> TYPE: RNA
<213> ORGANISM: Homo sapiens

<400> SEQUENCE: 113
gggggauuag cucaaauggu agagcgcucg 30

<210> SEQ ID NO 114
<211> LENGTH: 32
<212> TYPE: RNA
<213> ORGANISM: Homo sapiens

<400> SEQUENCE: 114
uccguagugu agugguuauc acguucgccu ga 32

<210> SEQ ID NO 115
<211> LENGTH: 31
<212> TYPE: RNA
<213> ORGANISM: Homo sapiens

<400> SEQUENCE: 115
uccguagugu agugguuauc acguucgccu g 31

<210> SEQ ID NO 116
<211> LENGTH: 28
<212> TYPE: RNA
<213> ORGANISM: Homo sapiens

<400> SEQUENCE: 116
auaggguuua cgaccucgau guuggauc 28

<210> SEQ ID NO 117
<211> LENGTH: 31
<212> TYPE: RNA
<213> ORGANISM: Homo sapiens

<400> SEQUENCE: 117
guuuagacgg gcucacauca ccccauaaac a 31

<210> SEQ ID NO 118
<211> LENGTH: 31
<212> TYPE: RNA
<213> ORGANISM: Homo sapiens

<400> SEQUENCE: 118
guuuagacgg gcucacauca ccccauaaac a 31

<210> SEQ ID NO 119
<211> LENGTH: 30
<212> TYPE: RNA
<213> ORGANISM: Homo sapiens

<400> SEQUENCE: 119
ccccuggugg ucuagugguu aggauucggc 30

<210> SEQ ID NO 120
<211> LENGTH: 30
<212> TYPE: RNA
<213> ORGANISM: Homo sapiens

<400> SEQUENCE: 120
aguucgugau ggauuugcuu uuuucugauu 30

<210> SEQ ID NO 121
<211> LENGTH: 29
<212> TYPE: RNA
<213> ORGANISM: Homo sapiens

<400> SEQUENCE: 121
ggucagucgg uccugagaga ugggcgagc 29

<210> SEQ ID NO 122
<211> LENGTH: 27
<212> TYPE: RNA
<213> ORGANISM: Homo sapiens

<400> SEQUENCE: 122
aggggcccgu gccuuggaaa gcgucgc 27

<210> SEQ ID NO 123
<211> LENGTH: 26
<212> TYPE: RNA
<213> ORGANISM: Homo sapiens

<400> SEQUENCE: 123
uggauaugau gacugauuac cugaga 26

<210> SEQ ID NO 124
<211> LENGTH: 30
<212> TYPE: RNA

<213> ORGANISM: Homo sapiens

<400> SEQUENCE: 124
uggcuaugau cugccuuguu caagcugaga 30

<210> SEQ ID NO 125
<211> LENGTH: 27
<212> TYPE: RNA
<213> ORGANISM: Homo sapiens

<400> SEQUENCE: 125
ggugcugaug acacccacug gcugaac 27

<210> SEQ ID NO 126
<211> LENGTH: 31
<212> TYPE: RNA
<213> ORGANISM: Homo sapiens

<400> SEQUENCE: 126
gcaaucacug augucuccau gucucugagc a 31

<210> SEQ ID NO 127
<211> LENGTH: 29
<212> TYPE: RNA
<213> ORGANISM: Homo sapiens

<400> SEQUENCE: 127
ucacaaagau gaguggugaa aaucugauc 29

<210> SEQ ID NO 128
<211> LENGTH: 28
<212> TYPE: RNA
<213> ORGANISM: Homo sapiens

<400> SEQUENCE: 128
cacaaagaug aguggugaaa aucugauc 28

<210> SEQ ID NO 129
<211> LENGTH: 26
<212> TYPE: RNA
<213> ORGANISM: Homo sapiens

<400> SEQUENCE: 129
caaagaugag uggugaaaau cugauc 26

<210> SEQ ID NO 130
<211> LENGTH: 30
<212> TYPE: RNA
<213> ORGANISM: Homo sapiens

<400> SEQUENCE: 130
cucacaaaga ugaguggaga aaaucugauc 30

<210> SEQ ID NO 131
<211> LENGTH: 32
<212> TYPE: RNA
<213> ORGANISM: Homo sapiens

<400> SEQUENCE: 131
ugagguagua gguuguaugg uuuagaguua ca 32

<210> SEQ ID NO 132
<211> LENGTH: 32

<212> TYPE: RNA
<213> ORGANISM: Homo sapiens

<400> SEQUENCE: 132
guucagugau gaggccugga augugcgcug gg 32

<210> SEQ ID NO 133
<211> LENGTH: 31
<212> TYPE: RNA
<213> ORGANISM: Homo sapiens

<400> SEQUENCE: 133
guucagugau gaggccugga augugcgcug g 31

<210> SEQ ID NO 134
<211> LENGTH: 30
<212> TYPE: RNA
<213> ORGANISM: Homo sapiens

<400> SEQUENCE: 134
guucagugau gaggccugga augugcgcug 30

<210> SEQ ID NO 135
<211> LENGTH: 29
<212> TYPE: RNA
<213> ORGANISM: Homo sapiens

<400> SEQUENCE: 135
guucagugau gaggccugga augugcgcu 29

<210> SEQ ID NO 136
<211> LENGTH: 28
<212> TYPE: RNA
<213> ORGANISM: Homo sapiens

<400> SEQUENCE: 136
acugugugcu gauugucacg uucugauu 28

<210> SEQ ID NO 137
<211> LENGTH: 31
<212> TYPE: RNA
<213> ORGANISM: Homo sapiens

<400> SEQUENCE: 137
ucccuggugg ucuagugguu aggauucggc a 31

<210> SEQ ID NO 138
<211> LENGTH: 32
<212> TYPE: RNA
<213> ORGANISM: Homo sapiens

<400> SEQUENCE: 138
ucccuggugg ucuagugguu aggauucggc ac 32

<210> SEQ ID NO 139
<211> LENGTH: 29
<212> TYPE: RNA
<213> ORGANISM: Homo sapiens

<400> SEQUENCE: 139
agagaggggc ccgugccuug gaaagcguc 29

<210> SEQ ID NO 140

```
<211> LENGTH: 26
<212> TYPE: RNA
<213> ORGANISM: Homo sapiens

<400> SEQUENCE: 140

caugauacug uaaacgcuuu cugaug                                          26

<210> SEQ ID NO 141
<211> LENGTH: 27
<212> TYPE: RNA
<213> ORGANISM: Homo sapiens

<400> SEQUENCE: 141

uggucguggu uguaguccgu gcgagaa                                         27

<210> SEQ ID NO 142
<211> LENGTH: 28
<212> TYPE: RNA
<213> ORGANISM: Homo sapiens

<400> SEQUENCE: 142

agaacgugug gaaaacuaau gacugagc                                        28

<210> SEQ ID NO 143
<211> LENGTH: 26
<212> TYPE: RNA
<213> ORGANISM: Homo sapiens

<400> SEQUENCE: 143

ucccuggugg ucuagugguu aggaua                                          26

<210> SEQ ID NO 144
<211> LENGTH: 28
<212> TYPE: RNA
<213> ORGANISM: Homo sapiens

<400> SEQUENCE: 144

cguaguguag uggucaucac guucgccu                                        28

<210> SEQ ID NO 145
<211> LENGTH: 32
<212> TYPE: RNA
<213> ORGANISM: Homo sapiens

<400> SEQUENCE: 145

guuuccguag uguagugguc aucacguucg cc                                   32

<210> SEQ ID NO 146
<211> LENGTH: 31
<212> TYPE: RNA
<213> ORGANISM: Homo sapiens

<400> SEQUENCE: 146

guuuccguag uguagugguc aucacguucg c                                    31

<210> SEQ ID NO 147
<211> LENGTH: 29
<212> TYPE: RNA
<213> ORGANISM: Homo sapiens

<400> SEQUENCE: 147

cugcaaugau gaaaauguag cuacugagc                                       29
```

<210> SEQ ID NO 148
<211> LENGTH: 31
<212> TYPE: RNA
<213> ORGANISM: Homo sapiens

<400> SEQUENCE: 148
ccgccuggga auaccgggug cuguaggcuu a 31

<210> SEQ ID NO 149
<211> LENGTH: 27
<212> TYPE: RNA
<213> ORGANISM: Homo sapiens

<400> SEQUENCE: 149
gcagaguggc gcagcggaag cgugcug 27

<210> SEQ ID NO 150
<211> LENGTH: 26
<212> TYPE: RNA
<213> ORGANISM: Homo sapiens

<400> SEQUENCE: 150
uguagucgug gccgaguggu uaaggc 26

<210> SEQ ID NO 151
<211> LENGTH: 31
<212> TYPE: RNA
<213> ORGANISM: Homo sapiens

<400> SEQUENCE: 151
agcccggcua gcucagucgg uagagcauga g 31

<210> SEQ ID NO 152
<211> LENGTH: 32
<212> TYPE: RNA
<213> ORGANISM: Homo sapiens

<400> SEQUENCE: 152
agcccggcua gcucagucgg uagagcauga ga 32

<210> SEQ ID NO 153
<211> LENGTH: 31
<212> TYPE: RNA
<213> ORGANISM: Homo sapiens

<400> SEQUENCE: 153
uccuuagguc gcugguucga auccggcucg a 31

<210> SEQ ID NO 154
<211> LENGTH: 32
<212> TYPE: RNA
<213> ORGANISM: Homo sapiens

<400> SEQUENCE: 154
uccuuagguc gcugguucga auccggcucg aa 32

<210> SEQ ID NO 155
<211> LENGTH: 28
<212> TYPE: RNA
<213> ORGANISM: Homo sapiens

<400> SEQUENCE: 155
ucgcugguuc gaauccggcu cggaggac 28

<210> SEQ ID NO 156
<211> LENGTH: 32
<212> TYPE: RNA
<213> ORGANISM: Homo sapiens

<400> SEQUENCE: 156
gccuggguag cucagucggu agagcaucag ac 32

<210> SEQ ID NO 157
<211> LENGTH: 31
<212> TYPE: RNA
<213> ORGANISM: Homo sapiens

<400> SEQUENCE: 157
gccuggguag cucagucggu agagcaucag a 31

<210> SEQ ID NO 158
<211> LENGTH: 30
<212> TYPE: RNA
<213> ORGANISM: Homo sapiens

<400> SEQUENCE: 158
gccuggguag cucagucggu agagcaucag 30

<210> SEQ ID NO 159
<211> LENGTH: 27
<212> TYPE: RNA
<213> ORGANISM: Homo sapiens

<400> SEQUENCE: 159
ggccccaugg uguaaugguc agcacuc 27

<210> SEQ ID NO 160
<211> LENGTH: 32
<212> TYPE: RNA
<213> ORGANISM: Homo sapiens

<400> SEQUENCE: 160 gggggguguag cucaguggua gagcgcgugc uu 32

<210> SEQ ID NO 161
<211> LENGTH: 29
<212> TYPE: RNA
<213> ORGANISM: Homo sapiens

<400> SEQUENCE: 161 gggggguguag cucaguggua gagcgcgug 29

<210> SEQ ID NO 162
<211> LENGTH: 31
<212> TYPE: RNA
<213> ORGANISM: Homo sapiens

<400> SEQUENCE: 162 gggggguguag cucaguggua gagcgcgugc u 31

<210> SEQ ID NO 163
<211> LENGTH: 30
<212> TYPE: RNA
<213> ORGANISM: Homo sapiens

<400> SEQUENCE: 163 gggggguguag cucaguggua gagcgcgugc 30

<210> SEQ ID NO 164
<211> LENGTH: 31
<212> TYPE: RNA
<213> ORGANISM: Homo sapiens

<400> SEQUENCE: 164
guguagcuca gugguagagc gcgugcuucg c 31

<210> SEQ ID NO 165
<211> LENGTH: 27
<212> TYPE: RNA
<213> ORGANISM: Homo sapiens

<400> SEQUENCE: 165
uaaaugcggu ggcaucgaca aaagaac 27

<210> SEQ ID NO 166
<211> LENGTH: 27
<212> TYPE: RNA
<213> ORGANISM: Homo sapiens

<400> SEQUENCE: 166
ccccccacug cuaaauuuga cuggcua 27

<210> SEQ ID NO 167
<211> LENGTH: 27
<212> TYPE: RNA
<213> ORGANISM: Homo sapiens

<400> SEQUENCE: 167
gcuaaaccua gccccaaacc cacucca 27

<210> SEQ ID NO 168
<211> LENGTH: 26
<212> TYPE: RNA
<213> ORGANISM: Homo sapiens

<400> SEQUENCE: 168
gcuaaaccua gccccaaacc cacucc 26

<210> SEQ ID NO 169
<211> LENGTH: 32
<212> TYPE: RNA
<213> ORGANISM: Homo sapiens

<400> SEQUENCE: 169
uggcgaugag gagguaccua uuguguugag ua 32

<210> SEQ ID NO 170
<211> LENGTH: 31
<212> TYPE: RNA
<213> ORGANISM: Homo sapiens

<400> SEQUENCE: 170
ugcccccaug ucuaacaaca uggcuuucuc a 31

<210> SEQ ID NO 171
<211> LENGTH: 27
<212> TYPE: RNA
<213> ORGANISM: Homo sapiens

<400> SEQUENCE: 171
ugaagcugca gaaccaacga gguggcc 27

<210> SEQ ID NO 172
<211> LENGTH: 30
<212> TYPE: RNA
<213> ORGANISM: Homo sapiens

<400> SEQUENCE: 172
ugagguagua gguuguauag uuuuagggu c 30

<210> SEQ ID NO 173
<211> LENGTH: 32
<212> TYPE: RNA
<213> ORGANISM: Homo sapiens

<400> SEQUENCE: 173
ugccaaugau gguuaagaau uucuucaccu ga 32

<210> SEQ ID NO 174
<211> LENGTH: 27
<212> TYPE: RNA
<213> ORGANISM: Homo sapiens

<400> SEQUENCE: 174
cacaugcaag caucccc guu ccaguga 27

<210> SEQ ID NO 175
<211> LENGTH: 31
<212> TYPE: RNA
<213> ORGANISM: Homo sapiens

<400> SEQUENCE: 175
cgccaucuuc agcaaacccu gaugaaggcu a 31

<210> SEQ ID NO 176
<211> LENGTH: 27
<212> TYPE: RNA
<213> ORGANISM: Homo sapiens

<400> SEQUENCE: 176
ucgaaggugg auuuagcagu aaacuga 27

<210> SEQ ID NO 177
<211> LENGTH: 29
<212> TYPE: RNA
<213> ORGANISM: Homo sapiens

<400> SEQUENCE: 177
ggcgacaaac cuaccgagcc uggugauag 29

<210> SEQ ID NO 178
<211> LENGTH: 31
<212> TYPE: RNA
<213> ORGANISM: Homo sapiens

<400> SEQUENCE: 178
caacaauagg guuuacgacc ucgauguugg a 31

<210> SEQ ID NO 179
<211> LENGTH: 29
<212> TYPE: RNA
<213> ORGANISM: Homo sapiens

<400> SEQUENCE: 179
gacaucccga uggugcagcc gcuauuaaa 29

<210> SEQ ID NO 180
<211> LENGTH: 31
<212> TYPE: RNA
<213> ORGANISM: Homo sapiens

<400> SEQUENCE: 180
guuaagaugg cagagcccgg uaaucgcaua a 31

<210> SEQ ID NO 181
<211> LENGTH: 32
<212> TYPE: RNA
<213> ORGANISM: Homo sapiens

<400> SEQUENCE: 181
gagggcguga ucaugaaagg ugauaagcuc uu 32

<210> SEQ ID NO 182
<211> LENGTH: 32
<212> TYPE: RNA
<213> ORGANISM: Homo sapiens

<400> SEQUENCE: 182
uacguacaua accuaaaccu acuccaaugc ua 32

<210> SEQ ID NO 183
<211> LENGTH: 32
<212> TYPE: RNA
<213> ORGANISM: Homo sapiens

<400> SEQUENCE: 183
ugaaucugac aacagaggcu uacgaccccu ua 32

<210> SEQ ID NO 184
<211> LENGTH: 30
<212> TYPE: RNA
<213> ORGANISM: Homo sapiens

<400> SEQUENCE: 184
gagaaagcuc acaagaacug cuaacucaug 30

<210> SEQ ID NO 185
<211> LENGTH: 31
<212> TYPE: RNA
<213> ORGANISM: Homo sapiens

<400> SEQUENCE: 185
gagaaagcuc acaagaacug cuaacucaug c 31

<210> SEQ ID NO 186
<211> LENGTH: 29
<212> TYPE: RNA
<213> ORGANISM: Homo sapiens

<400> SEQUENCE: 186
gagaaagcuc acaagaacug cuaacucau 29

<210> SEQ ID NO 187
<211> LENGTH: 31
<212> TYPE: RNA
<213> ORGANISM: Homo sapiens

<400> SEQUENCE: 187
ugcccccaug ucuaacaaca uggcuuucuc a 31

<210> SEQ ID NO 188
<211> LENGTH: 29
<212> TYPE: RNA
<213> ORGANISM: Homo sapiens

<400> SEQUENCE: 188
agguauuccu gcuaaugcua ggcugccaa 29

<210> SEQ ID NO 189
<211> LENGTH: 26
<212> TYPE: RNA
<213> ORGANISM: Homo sapiens

<400> SEQUENCE: 189
ucagacauuu gguguaugug cuuggc 26

<210> SEQ ID NO 190
<211> LENGTH: 30
<212> TYPE: RNA
<213> ORGANISM: Homo sapiens

<400> SEQUENCE: 190
cauugaucau cgacacuucg aacgcacuug 30

<210> SEQ ID NO 191
<211> LENGTH: 28
<212> TYPE: RNA
<213> ORGANISM: Homo sapiens

<400> SEQUENCE: 191
uccucauuag uauaguggug aguauccc 28

<210> SEQ ID NO 192
<211> LENGTH: 29
<212> TYPE: RNA
<213> ORGANISM: Homo sapiens

<400> SEQUENCE: 192
ucugcacagc cgcuuuccac acagacauc 29

<210> SEQ ID NO 193
<211> LENGTH: 29
<212> TYPE: RNA
<213> ORGANISM: Homo sapiens

<400> SEQUENCE: 193
aggaguucug ggcuguagug cgcuaugcc 29

<210> SEQ ID NO 194
<211> LENGTH: 27
<212> TYPE: RNA
<213> ORGANISM: Homo sapiens

<400> SEQUENCE: 194
agacuaguca agugcaguag ugagaag 27

<210> SEQ ID NO 195
<211> LENGTH: 29
<212> TYPE: RNA
<213> ORGANISM: Homo sapiens

<400> SEQUENCE: 195
cagagugcca accauuacac aauggaacc 29

<210> SEQ ID NO 196
<211> LENGTH: 26
<212> TYPE: RNA
<213> ORGANISM: Homo sapiens

<400> SEQUENCE: 196
uaaagacguu aggucaaggu guagcc 26

<210> SEQ ID NO 197
<211> LENGTH: 28
<212> TYPE: RNA
<213> ORGANISM: Homo sapiens

<400> SEQUENCE: 197
aggguucagc ugucucuuac uuuuaacc 28

<210> SEQ ID NO 198
<211> LENGTH: 26
<212> TYPE: RNA
<213> ORGANISM: Homo sapiens

<400> SEQUENCE: 198
gucaggaugg ccgagcgguc uaaggc 26

<210> SEQ ID NO 199
<211> LENGTH: 26
<212> TYPE: RNA
<213> ORGANISM: Homo sapiens

<400> SEQUENCE: 199
ugguucgucc aagugcacuu uccagu 26

<210> SEQ ID NO 200
<211> LENGTH: 29
<212> TYPE: RNA
<213> ORGANISM: Homo sapiens

<400> SEQUENCE: 200
gguuccaugg uguaauggua agcacucug 29

<210> SEQ ID NO 201
<211> LENGTH: 29
<212> TYPE: RNA
<213> ORGANISM: Homo sapiens

<400> SEQUENCE: 201
aagccggcuu cacgcucagg agaaaacgc 29

<210> SEQ ID NO 202
<211> LENGTH: 27
<212> TYPE: RNA
<213> ORGANISM: Homo sapiens

<400> SEQUENCE: 202
ugcucagaau uuauuaauuu ucacggu 27

<210> SEQ ID NO 203
<211> LENGTH: 30
<212> TYPE: RNA

<213> ORGANISM: Homo sapiens

<400> SEQUENCE: 203
aaauuguuca aggucuauca guggaugcag 30

<210> SEQ ID NO 204
<211> LENGTH: 29
<212> TYPE: RNA
<213> ORGANISM: Homo sapiens

<400> SEQUENCE: 204
ggcugaucug gcuggcuagg cggguguec 29

<210> SEQ ID NO 205
<211> LENGTH: 30
<212> TYPE: RNA
<213> ORGANISM: Homo sapiens

<400> SEQUENCE: 205
caggaauccu aaccgcuaga ccauauggga 30

<210> SEQ ID NO 206
<211> LENGTH: 29
<212> TYPE: RNA
<213> ORGANISM: Homo sapiens

<400> SEQUENCE: 206
uuuuaugagu gaaacauaag agucugaca 29

<210> SEQ ID NO 207
<211> LENGTH: 29
<212> TYPE: RNA
<213> ORGANISM: Homo sapiens

<400> SEQUENCE: 207
gccugggaau aacgggugcu guaggcuuu 29

<210> SEQ ID NO 208
<211> LENGTH: 27
<212> TYPE: RNA
<213> ORGANISM: Homo sapiens

<400> SEQUENCE: 208
ccuagggcuc agagcacugc agcagau 27

<210> SEQ ID NO 209
<211> LENGTH: 29
<212> TYPE: RNA
<213> ORGANISM: Homo sapiens

<400> SEQUENCE: 209
gguuccaugg uguaaugguu agcauucug 29

<210> SEQ ID NO 210
<211> LENGTH: 29
<212> TYPE: RNA
<213> ORGANISM: Homo sapiens

<400> SEQUENCE: 210
ugagaauucu gccacugaac cacccaugc 29

<210> SEQ ID NO 211
<211> LENGTH: 29

<212> TYPE: RNA
<213> ORGANISM: Homo sapiens

<400> SEQUENCE: 211
gguuccaugg uguaauggug agcacucug 29

<210> SEQ ID NO 212
<211> LENGTH: 31
<212> TYPE: RNA
<213> ORGANISM: Homo sapiens

<400> SEQUENCE: 212
gcccagcacg cuuccgcugc gccacucugc u 31

<210> SEQ ID NO 213
<211> LENGTH: 27
<212> TYPE: RNA
<213> ORGANISM: Homo sapiens

<400> SEQUENCE: 213
gcgugccugu agucccagcu acucggg 27

<210> SEQ ID NO 214
<211> LENGTH: 27
<212> TYPE: RNA
<213> ORGANISM: Homo sapiens

<400> SEQUENCE: 214
acccaggauc uccuguuuac gagacag 27

<210> SEQ ID NO 215
<211> LENGTH: 29
<212> TYPE: RNA
<213> ORGANISM: Homo sapiens

<400> SEQUENCE: 215
ucugauaacc cacuaccauc ggaccagcc 29

<210> SEQ ID NO 216
<211> LENGTH: 29
<212> TYPE: RNA
<213> ORGANISM: Homo sapiens

<400> SEQUENCE: 216
caugcgcucu accacugagc uacaucccc 29

<210> SEQ ID NO 217
<211> LENGTH: 26
<212> TYPE: RNA
<213> ORGANISM: Homo sapiens

<400> SEQUENCE: 217
uucucacuac ugcacuugac uagucu 26

<210> SEQ ID NO 218
<211> LENGTH: 29
<212> TYPE: RNA
<213> ORGANISM: Homo sapiens

<400> SEQUENCE: 218
cugaugcucu accaacugag cuauccagg 29

<210> SEQ ID NO 219

<211> LENGTH: 27
<212> TYPE: RNA
<213> ORGANISM: Homo sapiens

<400> SEQUENCE: 219
accucucaug ucucuucacc augccag 27

<210> SEQ ID NO 220
<211> LENGTH: 31
<212> TYPE: RNA
<213> ORGANISM: Homo sapiens

<400> SEQUENCE: 220
ucagggcccu guucaacuaa gcacucuacu c 31

<210> SEQ ID NO 221
<211> LENGTH: 27
<212> TYPE: RNA
<213> ORGANISM: Homo sapiens

<400> SEQUENCE: 221
guauuagagg caccgccugc ccaguga 27

<210> SEQ ID NO 222
<211> LENGTH: 27
<212> TYPE: RNA
<213> ORGANISM: Homo sapiens

<400> SEQUENCE: 222
aucugugaug ugaaccacaa ccugagu 27

<210> SEQ ID NO 223
<211> LENGTH: 29
<212> TYPE: RNA
<213> ORGANISM: Homo sapiens

<400> SEQUENCE: 223
uccuuuuuag uauaguggug aguaucccc 29

<210> SEQ ID NO 224
<211> LENGTH: 27
<212> TYPE: RNA
<213> ORGANISM: Homo sapiens

<400> SEQUENCE: 224
cagggucggg ccugguuagu acuugga 27

<210> SEQ ID NO 225
<211> LENGTH: 27
<212> TYPE: RNA
<213> ORGANISM: Homo sapiens

<400> SEQUENCE: 225
ugagccgaga ucacgccacu gcacucc 27

<210> SEQ ID NO 226
<211> LENGTH: 31
<212> TYPE: RNA
<213> ORGANISM: Homo sapiens

<400> SEQUENCE: 226
gcccagcacg cuuccgcugc gccacucugc u 31

<210> SEQ ID NO 227
<211> LENGTH: 28
<212> TYPE: RNA
<213> ORGANISM: Homo sapiens

<400> SEQUENCE: 227
aaagccuaca gcacccggua uucccagg 28

<210> SEQ ID NO 228
<211> LENGTH: 27
<212> TYPE: RNA
<213> ORGANISM: Homo sapiens

<400> SEQUENCE: 228
agacuaguca agugcaguag ugagaag 27

<210> SEQ ID NO 229
<211> LENGTH: 26
<212> TYPE: RNA
<213> ORGANISM: Homo sapiens

<400> SEQUENCE: 229
ggcuaagauc aaguguagua ucuguu 26

<210> SEQ ID NO 230
<211> LENGTH: 26
<212> TYPE: RNA
<213> ORGANISM: Homo sapiens

<400> SEQUENCE: 230
gucaggaugg ccgagcgguc uaaggc 26

<210> SEQ ID NO 231
<211> LENGTH: 26
<212> TYPE: RNA
<213> ORGANISM: Homo sapiens

<400> SEQUENCE: 231
cggacaggau ugacagauug auagcu 26

<210> SEQ ID NO 232
<211> LENGTH: 28
<212> TYPE: RNA
<213> ORGANISM: Homo sapiens

<400> SEQUENCE: 232
gcaugagugg uucugugcua gaauucuc 28

<210> SEQ ID NO 233
<211> LENGTH: 31
<212> TYPE: RNA
<213> ORGANISM: Homo sapiens

<400> SEQUENCE: 233
ugaucagagc ccagugcugg acaucauggg a 31

<210> SEQ ID NO 234
<211> LENGTH: 26
<212> TYPE: RNA
<213> ORGANISM: Homo sapiens

<400> SEQUENCE: 234
gucaggaugg ccgagcgguc uaaggc 26

<210> SEQ ID NO 235
<211> LENGTH: 32
<212> TYPE: RNA
<213> ORGANISM: Homo sapiens

<400> SEQUENCE: 235
ccuggacuca agcgauccuc cagccucagc cu 32

<210> SEQ ID NO 236
<211> LENGTH: 28
<212> TYPE: RNA
<213> ORGANISM: Homo sapiens

<400> SEQUENCE: 236
uggcugauuu gcguucaguu gaugcaga 28

<210> SEQ ID NO 237
<211> LENGTH: 29
<212> TYPE: RNA
<213> ORGANISM: Homo sapiens

<400> SEQUENCE: 237
cagagugcuc accauuacac cauggaacc 29

<210> SEQ ID NO 238
<211> LENGTH: 31
<212> TYPE: RNA
<213> ORGANISM: Homo sapiens

<400> SEQUENCE: 238
gcguuggugg uauaguggug agcauagcug c 31

<210> SEQ ID NO 239
<211> LENGTH: 30
<212> TYPE: RNA
<213> ORGANISM: Homo sapiens

<400> SEQUENCE: 239
gggucuuagc uauugugugu ucagauaugu 30

<210> SEQ ID NO 240
<211> LENGTH: 26
<212> TYPE: RNA
<213> ORGANISM: Homo sapiens

<400> SEQUENCE: 240
accacucaga ccgcguucuc ucccuc 26

<210> SEQ ID NO 241
<211> LENGTH: 29
<212> TYPE: RNA
<213> ORGANISM: Homo sapiens

<400> SEQUENCE: 241
gguuccaugg uguaaugguu agcacucug 29

<210> SEQ ID NO 242
<211> LENGTH: 29
<212> TYPE: RNA
<213> ORGANISM: Homo sapiens

<400> SEQUENCE: 242
gcauuggcgg uacaguggca gaauucucg 29

<210> SEQ ID NO 243
<211> LENGTH: 30
<212> TYPE: RNA
<213> ORGANISM: Homo sapiens

<400> SEQUENCE: 243
guccugcaau ucacauuaau ucucacagcu 30

<210> SEQ ID NO 244
<211> LENGTH: 26
<212> TYPE: RNA
<213> ORGANISM: Homo sapiens

<400> SEQUENCE: 244
ugggucuuag cuauugugug uucaga 26

<210> SEQ ID NO 245
<211> LENGTH: 29
<212> TYPE: RNA
<213> ORGANISM: Homo sapiens

<400> SEQUENCE: 245
cagugcucua accccugagc uauggagcc 29

<210> SEQ ID NO 246
<211> LENGTH: 29
<212> TYPE: RNA
<213> ORGANISM: Homo sapiens

<400> SEQUENCE: 246
uugagauacu gacuagucug guguuauuu 29

<210> SEQ ID NO 247
<211> LENGTH: 26
<212> TYPE: RNA
<213> ORGANISM: Homo sapiens

<400> SEQUENCE: 247
uaguggguua ucagaacuua uuaaca 26

<210> SEQ ID NO 248
<211> LENGTH: 29
<212> TYPE: RNA
<213> ORGANISM: Homo sapiens

<400> SEQUENCE: 248
uaacaggggc ccucucagcc cuccuaaug 29

<210> SEQ ID NO 249
<211> LENGTH: 31
<212> TYPE: RNA
<213> ORGANISM: Homo sapiens

<400> SEQUENCE: 249
uaccugaugc augaucucua caguucugag a 31

<210> SEQ ID NO 250
<211> LENGTH: 29
<212> TYPE: RNA
<213> ORGANISM: Homo sapiens

<400> SEQUENCE: 250
caagaauucu accacugaac aaccaaugc 29

<210> SEQ ID NO 251
<211> LENGTH: 27
<212> TYPE: RNA
<213> ORGANISM: Homo sapiens

<400> SEQUENCE: 251
uggcuuuagc ucagcgguua cuucgac 27

<210> SEQ ID NO 252
<211> LENGTH: 26
<212> TYPE: RNA
<213> ORGANISM: Homo sapiens

<400> SEQUENCE: 252
agggugguuc agugguagaa uucucg 26

<210> SEQ ID NO 253
<211> LENGTH: 29
<212> TYPE: RNA
<213> ORGANISM: Homo sapiens

<400> SEQUENCE: 253
cuuaaugaug acuguuuuuu uugauugcu 29

<210> SEQ ID NO 254
<211> LENGTH: 26
<212> TYPE: RNA
<213> ORGANISM: Homo sapiens

<400> SEQUENCE: 254
agccugguga uagcugguug uccaag 26

<210> SEQ ID NO 255
<211> LENGTH: 27
<212> TYPE: RNA
<213> ORGANISM: Homo sapiens

<400> SEQUENCE: 255
guuuggaggu ucuagcaggg gagcgca 27

<210> SEQ ID NO 256
<211> LENGTH: 31
<212> TYPE: RNA
<213> ORGANISM: Homo sapiens

<400> SEQUENCE: 256
agugacgcuc agacaggcau agcccuggga g 31

<210> SEQ ID NO 257
<211> LENGTH: 27
<212> TYPE: RNA
<213> ORGANISM: Homo sapiens

<400> SEQUENCE: 257
agacuaguca agugcaguag ugagaag 27

<210> SEQ ID NO 258
<211> LENGTH: 29
<212> TYPE: RNA
<213> ORGANISM: Homo sapiens

<400> SEQUENCE: 258
ucugaaacca auuuuuugag gccuugcgu 29

<210> SEQ ID NO 259
<211> LENGTH: 29
<212> TYPE: RNA
<213> ORGANISM: Homo sapiens

<400> SEQUENCE: 259
cagagugcua accauugcac cauagaacc 29

<210> SEQ ID NO 260
<211> LENGTH: 28
<212> TYPE: RNA
<213> ORGANISM: Homo sapiens

<400> SEQUENCE: 260
agccugguga uagcugguug uccaagau 28

<210> SEQ ID NO 261
<211> LENGTH: 31
<212> TYPE: RNA
<213> ORGANISM: Homo sapiens

<400> SEQUENCE: 261
uccuuggugg ucuagugguu aggauucggc u 31

<210> SEQ ID NO 262
<211> LENGTH: 31
<212> TYPE: RNA
<213> ORGANISM: Homo sapiens

<400> SEQUENCE: 262
cagauucaca aucugauguu uugguuaaac u 31

<210> SEQ ID NO 263
<211> LENGTH: 27
<212> TYPE: RNA
<213> ORGANISM: Homo sapiens

<400> SEQUENCE: 263
caugaaugga ugaacgagau ucccacu 27

<210> SEQ ID NO 264
<211> LENGTH: 29
<212> TYPE: RNA
<213> ORGANISM: Homo sapiens

<400> SEQUENCE: 264
cagagugcuc accauuacac cauggaacc 29

<210> SEQ ID NO 265
<211> LENGTH: 31
<212> TYPE: RNA
<213> ORGANISM: Homo sapiens

<400> SEQUENCE: 265
aguuguaaac accacugcac ucggaccagc c 31

<210> SEQ ID NO 266
<211> LENGTH: 31
<212> TYPE: RNA
<213> ORGANISM: Homo sapiens

<400> SEQUENCE: 266
aguuguaaac accacugcac ucggaccagc c 31

<210> SEQ ID NO 267
<211> LENGTH: 26
<212> TYPE: RNA
<213> ORGANISM: Homo sapiens

<400> SEQUENCE: 267
gguagugugg ccgagcgguc uaaggc 26

<210> SEQ ID NO 268
<211> LENGTH: 29
<212> TYPE: RNA
<213> ORGANISM: Homo sapiens

<400> SEQUENCE: 268
acuuuagcuc uagaauuacu cugagaccu 29

<210> SEQ ID NO 269
<211> LENGTH: 26
<212> TYPE: RNA
<213> ORGANISM: Homo sapiens

<400> SEQUENCE: 269
uucucacuac ugcacuugac uagucu 26

<210> SEQ ID NO 270
<211> LENGTH: 30
<212> TYPE: RNA
<213> ORGANISM: Homo sapiens

<400> SEQUENCE: 270
cugaaaugaa gagaauacuc auugcugauc 30

<210> SEQ ID NO 271
<211> LENGTH: 26
<212> TYPE: RNA
<213> ORGANISM: Homo sapiens

<400> SEQUENCE: 271
accacucaga ccgcguucuc ucccuc 26

<210> SEQ ID NO 272
<211> LENGTH: 27
<212> TYPE: RNA
<213> ORGANISM: Homo sapiens

<400> SEQUENCE: 272
uuuccuagug uccaaagagc uguuccu 27

<210> SEQ ID NO 273
<211> LENGTH: 26
<212> TYPE: RNA
<213> ORGANISM: Homo sapiens

<400> SEQUENCE: 273
ucagaacuuc cacaaaauca uuuguu 26

<210> SEQ ID NO 274
<211> LENGTH: 27
<212> TYPE: RNA
<213> ORGANISM: Homo sapiens

<400> SEQUENCE: 274
agccagccag aucagccgaa ucaaccc 27

<210> SEQ ID NO 275
<211> LENGTH: 26
<212> TYPE: RNA
<213> ORGANISM: Homo sapiens

<400> SEQUENCE: 275
agacuaguca agugcaguag ugagaa 26

<210> SEQ ID NO 276
<211> LENGTH: 27
<212> TYPE: RNA
<213> ORGANISM: Homo sapiens

<400> SEQUENCE: 276
ugagccgaga ucacgccacu gcacucc 27

<210> SEQ ID NO 277
<211> LENGTH: 27
<212> TYPE: RNA
<213> ORGANISM: Homo sapiens

<400> SEQUENCE: 277
agacuaguca agugcaguag ugagaag 27

<210> SEQ ID NO 278
<211> LENGTH: 26
<212> TYPE: RNA
<213> ORGANISM: Homo sapiens

<400> SEQUENCE: 278
acaauuccuu ggcugugucu gagcac 26

<210> SEQ ID NO 279
<211> LENGTH: 29
<212> TYPE: RNA
<213> ORGANISM: Homo sapiens

<400> SEQUENCE: 279
gcauuggugg uucaguagua gaauucucg 29

<210> SEQ ID NO 280
<211> LENGTH: 29
<212> TYPE: RNA
<213> ORGANISM: Homo sapiens

<400> SEQUENCE: 280
cauuuggcag aaucauuaca ucauugguu 29

<210> SEQ ID NO 281
<211> LENGTH: 26
<212> TYPE: RNA
<213> ORGANISM: Homo sapiens

<400> SEQUENCE: 281
cgggucuucc aggagucggg uugcuu 26

<210> SEQ ID NO 282
<211> LENGTH: 30
<212> TYPE: RNA

<213> ORGANISM: Homo sapiens

<400> SEQUENCE: 282
auaucaugau guuacuuuga uucucugacc 30

<210> SEQ ID NO 283
<211> LENGTH: 26
<212> TYPE: RNA
<213> ORGANISM: Homo sapiens

<400> SEQUENCE: 283
ugguucccug accgggaauu gaaccc 26

<210> SEQ ID NO 284
<211> LENGTH: 26
<212> TYPE: RNA
<213> ORGANISM: Homo sapiens

<400> SEQUENCE: 284
guuaauaagu ucugauaacc cacuac 26

<210> SEQ ID NO 285
<211> LENGTH: 27
<212> TYPE: RNA
<213> ORGANISM: Homo sapiens

<400> SEQUENCE: 285
aagccaguca aauuuagcag ugggggg 27

<210> SEQ ID NO 286
<211> LENGTH: 31
<212> TYPE: RNA
<213> ORGANISM: Homo sapiens

<400> SEQUENCE: 286
gcguuggugg uauaguggug agcauagcug c 31

<210> SEQ ID NO 287
<211> LENGTH: 28
<212> TYPE: RNA
<213> ORGANISM: Homo sapiens

<400> SEQUENCE: 287
gaugaugaug agaagccuuu ugcugagc 28

<210> SEQ ID NO 288
<211> LENGTH: 27
<212> TYPE: RNA
<213> ORGANISM: Homo sapiens

<400> SEQUENCE: 288
gcucuacacg uucagagaaa cuucucu 27

<210> SEQ ID NO 289
<211> LENGTH: 27
<212> TYPE: RNA
<213> ORGANISM: Homo sapiens

<400> SEQUENCE: 289
ccucagacgc aggcuuucuu caguaga 27

<210> SEQ ID NO 290
<211> LENGTH: 27

<212> TYPE: RNA
<213> ORGANISM: Homo sapiens

<400> SEQUENCE: 290
uaaaacucaa aggaccuggc ggugcuu 27

<210> SEQ ID NO 291
<211> LENGTH: 29
<212> TYPE: RNA
<213> ORGANISM: Homo sapiens

<400> SEQUENCE: 291
ccuggauagc ucaguuggua gagcaucag 29

<210> SEQ ID NO 292
<211> LENGTH: 29
<212> TYPE: RNA
<213> ORGANISM: Homo sapiens

<400> SEQUENCE: 292
gcaugggucg uucaguggua gaauucucu 29

<210> SEQ ID NO 293
<211> LENGTH: 29
<212> TYPE: RNA
<213> ORGANISM: Homo sapiens

<400> SEQUENCE: 293
agccugguga uagcugguug uccaagaua 29

<210> SEQ ID NO 294
<211> LENGTH: 28
<212> TYPE: RNA
<213> ORGANISM: Homo sapiens

<400> SEQUENCE: 294
aaguccuacg ugaucugagu ucagaccg 28

<210> SEQ ID NO 295
<211> LENGTH: 26
<212> TYPE: RNA
<213> ORGANISM: Homo sapiens

<400> SEQUENCE: 295
gucaggaugg ccgagcgguc uaaggc 26

<210> SEQ ID NO 296
<211> LENGTH: 28
<212> TYPE: RNA
<213> ORGANISM: Homo sapiens

<400> SEQUENCE: 296
aggaguucug ggcuguagug cgcuaugc 28

<210> SEQ ID NO 297
<211> LENGTH: 27
<212> TYPE: RNA
<213> ORGANISM: Homo sapiens

<400> SEQUENCE: 297
acccaggauc uccuguuuac aagacag 27

<210> SEQ ID NO 298

<211> LENGTH: 26
<212> TYPE: RNA
<213> ORGANISM: Homo sapiens

<400> SEQUENCE: 298
agcugcgcuc cccugcuaga accucc 26

<210> SEQ ID NO 299
<211> LENGTH: 27
<212> TYPE: RNA
<213> ORGANISM: Homo sapiens

<400> SEQUENCE: 299
cagggucggg ccugguuagu acuugga 27

<210> SEQ ID NO 300
<211> LENGTH: 29
<212> TYPE: RNA
<213> ORGANISM: Homo sapiens

<400> SEQUENCE: 300
gguuccaugg uguaauggua agcacucug 29

<210> SEQ ID NO 301
<211> LENGTH: 27
<212> TYPE: RNA
<213> ORGANISM: Homo sapiens

<400> SEQUENCE: 301
gagucagcua aauacuuuga cgccggu 27

<210> SEQ ID NO 302
<211> LENGTH: 27
<212> TYPE: RNA
<213> ORGANISM: Homo sapiens

<400> SEQUENCE: 302
uuggugguau aguggugagc auagcug 27

<210> SEQ ID NO 303
<211> LENGTH: 26
<212> TYPE: RNA
<213> ORGANISM: Homo sapiens

<400> SEQUENCE: 303
aggccaugau gacaguauuu cugagu 26

<210> SEQ ID NO 304
<211> LENGTH: 28
<212> TYPE: RNA
<213> ORGANISM: Homo sapiens

<400> SEQUENCE: 304
aaagccuaca gcacccggua uucccagg 28

<210> SEQ ID NO 305
<211> LENGTH: 29
<212> TYPE: RNA
<213> ORGANISM: Homo sapiens

<400> SEQUENCE: 305
caugcgcucu accacugagc uacaucccc 29

<210> SEQ ID NO 306
<211> LENGTH: 29
<212> TYPE: RNA
<213> ORGANISM: Homo sapiens

<400> SEQUENCE: 306
aucugugaug auagaaauug gaucugagg 29

<210> SEQ ID NO 307
<211> LENGTH: 32
<212> TYPE: RNA
<213> ORGANISM: Homo sapiens

<400> SEQUENCE: 307
ggcugguccg augguagcag guuaucagaa cu 32

<210> SEQ ID NO 308
<211> LENGTH: 28
<212> TYPE: RNA
<213> ORGANISM: Homo sapiens

<400> SEQUENCE: 308
uccaaguacu aaccaggccc gacccugc 28

<210> SEQ ID NO 309
<211> LENGTH: 26
<212> TYPE: RNA
<213> ORGANISM: Homo sapiens

<400> SEQUENCE: 309
agucucaguu uccucugcaa acaguu 26

<210> SEQ ID NO 310
<211> LENGTH: 29
<212> TYPE: RNA
<213> ORGANISM: Homo sapiens

<400> SEQUENCE: 310
ugucacccca uugaucgcca ggguugauu 29

<210> SEQ ID NO 311
<211> LENGTH: 30
<212> TYPE: RNA
<213> ORGANISM: Homo sapiens

<400> SEQUENCE: 311
ggucaaugau gaaugguaaa aggucugagu 30

<210> SEQ ID NO 312
<211> LENGTH: 27
<212> TYPE: RNA
<213> ORGANISM: Homo sapiens

<400> SEQUENCE: 312
uaucugaaca cacaauagcu aagaccc 27

<210> SEQ ID NO 313
<211> LENGTH: 27
<212> TYPE: RNA
<213> ORGANISM: Homo sapiens

<400> SEQUENCE: 313
auccagcggu ugucagcuau ccaggcu 27

<210> SEQ ID NO 314
<211> LENGTH: 29
<212> TYPE: RNA
<213> ORGANISM: Homo sapiens

<400> SEQUENCE: 314
gagcgcucua ccgccugagc uaauucccc 29

<210> SEQ ID NO 315
<211> LENGTH: 29
<212> TYPE: RNA
<213> ORGANISM: Homo sapiens

<400> SEQUENCE: 315
aggaguucug ggcuguagug cgcuaugcc 29

<210> SEQ ID NO 316
<211> LENGTH: 27
<212> TYPE: RNA
<213> ORGANISM: Homo sapiens

<400> SEQUENCE: 316
caugaaugga ugaacgagau ucccacu 27

<210> SEQ ID NO 317
<211> LENGTH: 28
<212> TYPE: RNA
<213> ORGANISM: Homo sapiens

<400> SEQUENCE: 317
caccagugug aguucuacca uugccaaa 28

<210> SEQ ID NO 318
<211> LENGTH: 26
<212> TYPE: RNA
<213> ORGANISM: Homo sapiens

<400> SEQUENCE: 318
ucacagugaa uucuaccagu gccaua 26

<210> SEQ ID NO 319
<211> LENGTH: 27
<212> TYPE: RNA
<213> ORGANISM: Homo sapiens

<400> SEQUENCE: 319
gugggccacu uuugguaagc agaacug 27

<210> SEQ ID NO 320
<211> LENGTH: 28
<212> TYPE: RNA
<213> ORGANISM: Homo sapiens

<400> SEQUENCE: 320
ucaugcucua ucgacugagc uagccggg 28

<210> SEQ ID NO 321
<211> LENGTH: 27
<212> TYPE: RNA
<213> ORGANISM: Homo sapiens

<400> SEQUENCE: 321
agacuaguca agugcaguag ugagaag 27

<210> SEQ ID NO 322
<211> LENGTH: 31
<212> TYPE: RNA
<213> ORGANISM: Homo sapiens

<400> SEQUENCE: 322
ggcugguccg agugcagugg uguuuacaac u 31

<210> SEQ ID NO 323
<211> LENGTH: 27
<212> TYPE: RNA
<213> ORGANISM: Homo sapiens

<400> SEQUENCE: 323
agacuaguca agugcaguag ugagaag 27

<210> SEQ ID NO 324
<211> LENGTH: 26
<212> TYPE: RNA
<213> ORGANISM: Homo sapiens

<400> SEQUENCE: 324 uagugguua ucagaacuua uuaaca 26

<210> SEQ ID NO 325
<211> LENGTH: 31
<212> TYPE: RNA
<213> ORGANISM: Homo sapiens

<400> SEQUENCE: 325
ucucagaacu guagagauca ugcaucaggu a 31

<210> SEQ ID NO 326
<211> LENGTH: 27
<212> TYPE: RNA
<213> ORGANISM: Homo sapiens

<400> SEQUENCE: 326
agacuaguca agugcaguag ugagaag 27

<210> SEQ ID NO 327
<211> LENGTH: 32
<212> TYPE: RNA
<213> ORGANISM: Homo sapiens

<400> SEQUENCE: 327
uacaguccaa ugcuucacuc agccauuuua cc 32

<210> SEQ ID NO 328
<211> LENGTH: 27
<212> TYPE: RNA
<213> ORGANISM: Homo sapiens

<400> SEQUENCE: 328
ugagccgaga ucacgccacu gcacucc 27

<210> SEQ ID NO 329
<211> LENGTH: 31
<212> TYPE: RNA
<213> ORGANISM: Homo sapiens

<400> SEQUENCE: 329
ugcugcaguu aaaaagcucc uaguuggauc u 31

<210> SEQ ID NO 330
<211> LENGTH: 29
<212> TYPE: RNA
<213> ORGANISM: Homo sapiens

<400> SEQUENCE: 330
ucuggugaug aaauggaacg uuucugaug 29

<210> SEQ ID NO 331
<211> LENGTH: 27
<212> TYPE: RNA
<213> ORGANISM: Homo sapiens

<400> SEQUENCE: 331
aagccaguca aauuuagcag ugggggg 27

<210> SEQ ID NO 332
<211> LENGTH: 31
<212> TYPE: RNA
<213> ORGANISM: Homo sapiens

<400> SEQUENCE: 332
aaguuucagc uuugcaacca uacucccuc g 31

<210> SEQ ID NO 333
<211> LENGTH: 28
<212> TYPE: RNA
<213> ORGANISM: Homo sapiens

<400> SEQUENCE: 333
uguugucaga uucacaaucu gauguuuu 28

<210> SEQ ID NO 334
<211> LENGTH: 26
<212> TYPE: RNA
<213> ORGANISM: Homo sapiens

<400> SEQUENCE: 334
gucaggaugg ccgagcgguc uaaggc 26

<210> SEQ ID NO 335
<211> LENGTH: 31
<212> TYPE: RNA
<213> ORGANISM: Homo sapiens

<400> SEQUENCE: 335
aguuguaaac accacugcac ucggaccagc c 31

<210> SEQ ID NO 336
<211> LENGTH: 31
<212> TYPE: RNA
<213> ORGANISM: Homo sapiens

<400> SEQUENCE: 336
gcccagcacg cuuccgcugc gccacucugc u 31

<210> SEQ ID NO 337
<211> LENGTH: 27
<212> TYPE: RNA
<213> ORGANISM: Homo sapiens

<400> SEQUENCE: 337

-continued acccaggauc uccuguuuac gagacag 27

<210> SEQ ID NO 338
<211> LENGTH: 28
<212> TYPE: RNA
<213> ORGANISM: Homo sapiens

<400> SEQUENCE: 338
aaggaugaug agacaggcua ugcugaag 28

<210> SEQ ID NO 339
<211> LENGTH: 27
<212> TYPE: RNA
<213> ORGANISM: Homo sapiens

<400> SEQUENCE: 339
uuggugguau aguggugagc auagcug 27

<210> SEQ ID NO 340
<211> LENGTH: 26
<212> TYPE: RNA
<213> ORGANISM: Homo sapiens

<400> SEQUENCE: 340
gucaggaugg ccgagcgguc uaaggc 26

<210> SEQ ID NO 341
<211> LENGTH: 26
<212> TYPE: RNA
<213> ORGANISM: Homo sapiens

<400> SEQUENCE: 341
aacauucauu gcugucggug gguuug 26

<210> SEQ ID NO 342
<211> LENGTH: 27
<212> TYPE: RNA
<213> ORGANISM: Homo sapiens

<400> SEQUENCE: 342
agacuaguca agugcaguag ugagaag 27

<210> SEQ ID NO 343
<211> LENGTH: 31
<212> TYPE: RNA
<213> ORGANISM: Homo sapiens

<400> SEQUENCE: 343
gcguuggugg uauaguggug agcauagcug c 31

<210> SEQ ID NO 344
<211> LENGTH: 29
<212> TYPE: RNA
<213> ORGANISM: Homo sapiens

<400> SEQUENCE: 344
acuuuagcuc uagaauuacu cugagaccu 29

<210> SEQ ID NO 345
<211> LENGTH: 26
<212> TYPE: RNA
<213> ORGANISM: Homo sapiens -continued

<400> SEQUENCE: 345
ugccaucaga acucuaacau gcuauu 26

<210> SEQ ID NO 346
<211> LENGTH: 30
<212> TYPE: RNA
<213> ORGANISM: Homo sapiens

<400> SEQUENCE: 346
uuccaucagc uuucuuugcc aucauuugga 30

<210> SEQ ID NO 347
<211> LENGTH: 30
<212> TYPE: RNA
<213> ORGANISM: Homo sapiens

<400> SEQUENCE: 347
uccaaguacu aaccaggccc gacccugcuu 30

<210> SEQ ID NO 348
<211> LENGTH: 32
<212> TYPE: RNA
<213> ORGANISM: Homo sapiens

<400> SEQUENCE: 348
aggcaugaug acuccaacug uggagacuga cu 32

<210> SEQ ID NO 349
<211> LENGTH: 31
<212> TYPE: RNA
<213> ORGANISM: Homo sapiens

<400> SEQUENCE: 349
gcccagcacg cuuccgcugc gccacucugc u 31

<210> SEQ ID NO 350
<211> LENGTH: 28
<212> TYPE: RNA
<213> ORGANISM: Homo sapiens

<400> SEQUENCE: 350
gcuuuggugg uucaguggua gaauucuc 28

<210> SEQ ID NO 351
<211> LENGTH: 27
<212> TYPE: RNA
<213> ORGANISM: Homo sapiens

<400> SEQUENCE: 351
agacuaguca agugcaguag ugagaag 27

<210> SEQ ID NO 352
<211> LENGTH: 30
<212> TYPE: RNA
<213> ORGANISM: Homo sapiens

<400> SEQUENCE: 352
uagaggagcc uguucuguaa ucgauaaacc 30

<210> SEQ ID NO 353
<211> LENGTH: 27
<212> TYPE: RNA
<213> ORGANISM: Homo sapiens

<400> SEQUENCE: 353
aacgagacuc uggcaugcua acuaguu 27

<210> SEQ ID NO 354
<211> LENGTH: 27
<212> TYPE: RNA
<213> ORGANISM: Homo sapiens

<400> SEQUENCE: 354
gcucuacacg uucagagaaa cuucucu 27

<210> SEQ ID NO 355
<211> LENGTH: 26
<212> TYPE: RNA
<213> ORGANISM: Homo sapiens

<400> SEQUENCE: 355
gucacucaga cauccaagga agguag 26

<210> SEQ ID NO 356
<211> LENGTH: 26
<212> TYPE: RNA
<213> ORGANISM: Homo sapiens

<400> SEQUENCE: 356
uucucacuac ugcacuugac uagucu 26

<210> SEQ ID NO 357
<211> LENGTH: 31
<212> TYPE: RNA
<213> ORGANISM: Homo sapiens

<400> SEQUENCE: 357
ugucagaagu caaagcaauu caucacagac u 31

<210> SEQ ID NO 358
<211> LENGTH: 26
<212> TYPE: RNA
<213> ORGANISM: Homo sapiens

<400> SEQUENCE: 358
uguaaacauc cuugacugga agcugu 26

<210> SEQ ID NO 359
<211> LENGTH: 29
<212> TYPE: RNA
<213> ORGANISM: Homo sapiens

<400> SEQUENCE: 359
aagccggcuu cacgcucagg agaaaacgc 29

<210> SEQ ID NO 360
<211> LENGTH: 29
<212> TYPE: RNA
<213> ORGANISM: Homo sapiens

<400> SEQUENCE: 360
cuggagugca guggcgugau cucggcuca 29

<210> SEQ ID NO 361
<211> LENGTH: 27
<212> TYPE: RNA

<213> ORGANISM: Homo sapiens

<400> SEQUENCE: 361
uuggcaguuc agugguagaa uucucgc 27

<210> SEQ ID NO 362
<211> LENGTH: 27
<212> TYPE: RNA
<213> ORGANISM: Homo sapiens

<400> SEQUENCE: 362
auaaaugaug aucagcagaa ucugagu 27

<210> SEQ ID NO 363
<211> LENGTH: 26
<212> TYPE: RNA
<213> ORGANISM: Homo sapiens

<400> SEQUENCE: 363
ucccuggugg ucuaguggcu aggauu 26

<210> SEQ ID NO 364
<211> LENGTH: 26
<212> TYPE: RNA
<213> ORGANISM: Homo sapiens

<400> SEQUENCE: 364
ugacaugaug agauuucacu cugaca 26

<210> SEQ ID NO 365
<211> LENGTH: 26
<212> TYPE: RNA
<213> ORGANISM: Homo sapiens

<400> SEQUENCE: 365
cagggcacgu guuaggaccu gaaaga 26

<210> SEQ ID NO 366
<211> LENGTH: 27
<212> TYPE: RNA
<213> ORGANISM: Homo sapiens

<400> SEQUENCE: 366
ugcgcucccc ugcuagaacc uccaaac 27

<210> SEQ ID NO 367
<211> LENGTH: 29
<212> TYPE: RNA
<213> ORGANISM: Homo sapiens

<400> SEQUENCE: 367
cagugcucua accccugagc uauggagcc 29

<210> SEQ ID NO 368
<211> LENGTH: 29
<212> TYPE: RNA
<213> ORGANISM: Homo sapiens

<400> SEQUENCE: 368
gucgaugaug auugguaaaa ggucugauu 29

<210> SEQ ID NO 369
<211> LENGTH: 26

-continued

<212> TYPE: RNA
<213> ORGANISM: Homo sapiens

<400> SEQUENCE: 369
gcugacacgc uguccucugg cgaccu 26

<210> SEQ ID NO 370
<211> LENGTH: 26
<212> TYPE: RNA
<213> ORGANISM: Homo sapiens

<400> SEQUENCE: 370
guuuggaggu ucuagcaggg gagcgc 26

<210> SEQ ID NO 371
<211> LENGTH: 26
<212> TYPE: RNA
<213> ORGANISM: Homo sapiens

<400> SEQUENCE: 371
gucaggaugg ccgagcgguc uaaggc 26

<210> SEQ ID NO 372
<211> LENGTH: 27
<212> TYPE: RNA
<213> ORGANISM: Homo sapiens

<400> SEQUENCE: 372
cccgaguagc ugggacuaca ggcacgc 27

<210> SEQ ID NO 373
<211> LENGTH: 26
<212> TYPE: RNA
<213> ORGANISM: Homo sapiens

<400> SEQUENCE: 373
ucgacuucca uggccaccgu ccugcu 26

<210> SEQ ID NO 374
<211> LENGTH: 31
<212> TYPE: RNA
<213> ORGANISM: Homo sapiens

<400> SEQUENCE: 374
gcguuggugg uauaguggug agcauagcug c 31

<210> SEQ ID NO 375
<211> LENGTH: 29
<212> TYPE: RNA
<213> ORGANISM: Homo sapiens

<400> SEQUENCE: 375
cacuuugaca uucagagcac ugggcagaa 29

<210> SEQ ID NO 376
<211> LENGTH: 28
<212> TYPE: RNA
<213> ORGANISM: Homo sapiens

<400> SEQUENCE: 376
aaagugaaug auuaaagguc uuggggcc 28

<210> SEQ ID NO 377

<211> LENGTH: 27
<212> TYPE: RNA
<213> ORGANISM: Homo sapiens

<400> SEQUENCE: 377
agacuaguca agugcaguag ugagaag 27

<210> SEQ ID NO 378
<211> LENGTH: 27
<212> TYPE: RNA
<213> ORGANISM: Homo sapiens

<400> SEQUENCE: 378
guucaccauc uuuggggucc uaacacg 27

<210> SEQ ID NO 379
<211> LENGTH: 27
<212> TYPE: RNA
<213> ORGANISM: Homo sapiens

<400> SEQUENCE: 379
uaucugaaca cacaauagcu aagaccc 27

<210> SEQ ID NO 380
<211> LENGTH: 27
<212> TYPE: RNA
<213> ORGANISM: Homo sapiens

<400> SEQUENCE: 380
agacuaguca agugcaguag ugagaag 27

<210> SEQ ID NO 381
<211> LENGTH: 27
<212> TYPE: RNA
<213> ORGANISM: Homo sapiens

<400> SEQUENCE: 381
uggguucgaa ucccauccuc gucggcc 27

<210> SEQ ID NO 382
<211> LENGTH: 26
<212> TYPE: RNA
<213> ORGANISM: Homo sapiens

<400> SEQUENCE: 382
ccggggaccu cuugaucugc agucaa 26

<210> SEQ ID NO 383
<211> LENGTH: 31
<212> TYPE: RNA
<213> ORGANISM: Homo sapiens

<400> SEQUENCE: 383
uggccaagga ugagaacucu aaucugauuu u 31

<210> SEQ ID NO 384
<211> LENGTH: 29
<212> TYPE: RNA
<213> ORGANISM: Homo sapiens

<400> SEQUENCE: 384
gaagagcuga cagccuagac uaacgacau 29

<210> SEQ ID NO 385
<211> LENGTH: 29
<212> TYPE: RNA
<213> ORGANISM: Homo sapiens

<400> SEQUENCE: 385
ggaaagaaga cccuguugag cuugacucu 29

<210> SEQ ID NO 386
<211> LENGTH: 29
<212> TYPE: RNA
<213> ORGANISM: Homo sapiens

<400> SEQUENCE: 386
gcucagaaaa uaccuuucag ucacacauu 29

<210> SEQ ID NO 387
<211> LENGTH: 30
<212> TYPE: RNA
<213> ORGANISM: Homo sapiens

<400> SEQUENCE: 387
aaagugaaga caugagaucc aacucugagc 30

<210> SEQ ID NO 388
<211> LENGTH: 27
<212> TYPE: RNA
<213> ORGANISM: Homo sapiens

<400> SEQUENCE: 388
gcucagaaca augcucucau cagugaa 27

<210> SEQ ID NO 389
<211> LENGTH: 27
<212> TYPE: RNA
<213> ORGANISM: Homo sapiens

<400> SEQUENCE: 389
cagggucggg ccugguuagu acuugga 27

<210> SEQ ID NO 390
<211> LENGTH: 27
<212> TYPE: RNA
<213> ORGANISM: Homo sapiens

<400> SEQUENCE: 390
cugucuagua aacaggagau ccugggu 27

<210> SEQ ID NO 391
<211> LENGTH: 26
<212> TYPE: RNA
<213> ORGANISM: Homo sapiens

<400> SEQUENCE: 391
aagccaguca aauuuagcag uggggg 26

<210> SEQ ID NO 392
<211> LENGTH: 27
<212> TYPE: RNA
<213> ORGANISM: Homo sapiens

<400> SEQUENCE: 392
guaagugaag auaaagugug ucugagg 27

<210> SEQ ID NO 393
<211> LENGTH: 29
<212> TYPE: RNA
<213> ORGANISM: Homo sapiens

<400> SEQUENCE: 393
cagagugcuc accauuacac uauggaacc 29

<210> SEQ ID NO 394
<211> LENGTH: 26
<212> TYPE: RNA
<213> ORGANISM: Homo sapiens

<400> SEQUENCE: 394
uagcucaguc gguagagcau gagacu 26

<210> SEQ ID NO 395
<211> LENGTH: 32
<212> TYPE: RNA
<213> ORGANISM: Homo sapiens

<400> SEQUENCE: 395
cuggacugag ggaaauaauc uauucugagg cu 32

<210> SEQ ID NO 396
<211> LENGTH: 27
<212> TYPE: RNA
<213> ORGANISM: Homo sapiens

<400> SEQUENCE: 396
uuggugguau agugguaagc auagcug 27

<210> SEQ ID NO 397
<211> LENGTH: 27
<212> TYPE: RNA
<213> ORGANISM: Homo sapiens

<400> SEQUENCE: 397
uccaaguacu aaccaggccc gacccug 27

<210> SEQ ID NO 398
<211> LENGTH: 27
<212> TYPE: RNA
<213> ORGANISM: Homo sapiens

<400> SEQUENCE: 398
cagggucggg ccugguuagu acuugga 27

<210> SEQ ID NO 399
<211> LENGTH: 28
<212> TYPE: RNA
<213> ORGANISM: Homo sapiens

<400> SEQUENCE: 399
uuugguguau gugcuuggcu gaggagcc 28

<210> SEQ ID NO 400
<211> LENGTH: 29
<212> TYPE: RNA
<213> ORGANISM: Homo sapiens

<400> SEQUENCE: 400
cagagugcuc accauuacac cauggaacc 29

<210> SEQ ID NO 401
<211> LENGTH: 30
<212> TYPE: RNA
<213> ORGANISM: Homo sapiens

<400> SEQUENCE: 401
caggaauccu aaccgcuaga ccauauggga 30

<210> SEQ ID NO 402
<211> LENGTH: 28
<212> TYPE: RNA
<213> ORGANISM: Homo sapiens

<400> SEQUENCE: 402
cucagaacca cacagagauu gcaucacu 28

<210> SEQ ID NO 403
<211> LENGTH: 28
<212> TYPE: RNA
<213> ORGANISM: Homo sapiens

<400> SEQUENCE: 403
ccugggaaua ccgggugcug uaggcuuu 28

<210> SEQ ID NO 404
<211> LENGTH: 27
<212> TYPE: RNA
<213> ORGANISM: Homo sapiens

<400> SEQUENCE: 404
ugagccgaga ucacgccacu gcacucc 27

<210> SEQ ID NO 405
<211> LENGTH: 26
<212> TYPE: RNA
<213> ORGANISM: Homo sapiens

<400> SEQUENCE: 405
accagaguuu ccucuggcuu ugcccu 26

<210> SEQ ID NO 406
<211> LENGTH: 27
<212> TYPE: RNA
<213> ORGANISM: Homo sapiens

<400> SEQUENCE: 406
guccaugaug auuucaaguu aucccug 27

<210> SEQ ID NO 407
<211> LENGTH: 30
<212> TYPE: RNA
<213> ORGANISM: Homo sapiens

<400> SEQUENCE: 407
gucaaugaug uauucuucuu ggaacugaau 30

<210> SEQ ID NO 408
<211> LENGTH: 30
<212> TYPE: RNA
<213> ORGANISM: Homo sapiens

<400> SEQUENCE: 408
ccucagaccc ccggguguca aaggucccgg                                    30

<210> SEQ ID NO 409
<211> LENGTH: 26
<212> TYPE: RNA
<213> ORGANISM: Homo sapiens

<400> SEQUENCE: 409
ugacauucag agcacugggc agaaau                                        26

<210> SEQ ID NO 410
<211> LENGTH: 28
<212> TYPE: RNA
<213> ORGANISM: Homo sapiens

<400> SEQUENCE: 410
cugaaaugaa gagaauacuc auugcuga                                      28

<210> SEQ ID NO 411
<211> LENGTH: 31
<212> TYPE: RNA
<213> ORGANISM: Homo sapiens

<400> SEQUENCE: 411
gcguuggugg uauaguggug agcauagcug c                                  31

<210> SEQ ID NO 412
<211> LENGTH: 26
<212> TYPE: RNA
<213> ORGANISM: Homo sapiens

<400> SEQUENCE: 412
gucagaaugg ucgagcgguc uaaggc                                        26

<210> SEQ ID NO 413
<211> LENGTH: 32
<212> TYPE: RNA
<213> ORGANISM: Homo sapiens

<400> SEQUENCE: 413
uacugugaug agcucagaug gggagacuga gg                                 32

<210> SEQ ID NO 414
<211> LENGTH: 27
<212> TYPE: RNA
<213> ORGANISM: Homo sapiens

<400> SEQUENCE: 414
gugacacaug uuuaacggcc gcgguac                                       27

<210> SEQ ID NO 415
<211> LENGTH: 31
<212> TYPE: RNA
<213> ORGANISM: Homo sapiens

<400> SEQUENCE: 415
acuuccuuua ccuacauugu uccaacaugc c                                  31

<210> SEQ ID NO 416
<211> LENGTH: 29
<212> TYPE: RNA
<213> ORGANISM: Homo sapiens

<400> SEQUENCE: 416
ucucagguaa acaggugggc aucacagcu 29

<210> SEQ ID NO 417
<211> LENGTH: 31
<212> TYPE: RNA
<213> ORGANISM: Homo sapiens

<400> SEQUENCE: 417
ggcugguccg agugcagugg uguuuacaac u 31

<210> SEQ ID NO 418
<211> LENGTH: 26
<212> TYPE: RNA
<213> ORGANISM: Homo sapiens

<400> SEQUENCE: 418
aacauucaac gcugucggug aguuug 26

<210> SEQ ID NO 419
<211> LENGTH: 29
<212> TYPE: RNA
<213> ORGANISM: Homo sapiens

<400> SEQUENCE: 419
cagugcucua accccugagc uauggagcc 29

<210> SEQ ID NO 420
<211> LENGTH: 31
<212> TYPE: RNA
<213> ORGANISM: Homo sapiens

<400> SEQUENCE: 420
uaaccaggcc cgacccugcu uagcuuccga g 31

<210> SEQ ID NO 421
<211> LENGTH: 27
<212> TYPE: RNA
<213> ORGANISM: Homo sapiens

<400> SEQUENCE: 421
gccagaucag ccgaaucaac ccuggcg 27

<210> SEQ ID NO 422
<211> LENGTH: 27
<212> TYPE: RNA
<213> ORGANISM: Homo sapiens

<400> SEQUENCE: 422
acccaggauc uccuguuuac uagacag 27

<210> SEQ ID NO 423
<211> LENGTH: 27
<212> TYPE: RNA
<213> ORGANISM: Homo sapiens

<400> SEQUENCE: 423
cgggucggag uuagcucaag cgguuac 27

<210> SEQ ID NO 424
<211> LENGTH: 26
<212> TYPE: RNA
<213> ORGANISM: Homo sapiens

<400> SEQUENCE: 424
accacucaga ccgcguucuc ucccuc 26

<210> SEQ ID NO 425
<211> LENGTH: 29
<212> TYPE: RNA
<213> ORGANISM: Homo sapiens

<400> SEQUENCE: 425
cagaaugcua accauuacac gauggaacc 29

<210> SEQ ID NO 426
<211> LENGTH: 31
<212> TYPE: RNA
<213> ORGANISM: Homo sapiens

<400> SEQUENCE: 426
gcccagcacg cuuccgcugc gccacucugc u 31

<210> SEQ ID NO 427
<211> LENGTH: 26
<212> TYPE: RNA
<213> ORGANISM: Homo sapiens

<400> SEQUENCE: 427
uggcaacaac acaucaacag uagggu 26

<210> SEQ ID NO 428
<211> LENGTH: 27
<212> TYPE: RNA
<213> ORGANISM: Homo sapiens

<400> SEQUENCE: 428
cagggucggg ccugguuagu acuugga 27

<210> SEQ ID NO 429
<211> LENGTH: 28
<212> TYPE: RNA
<213> ORGANISM: Homo sapiens

<400> SEQUENCE: 429
aggaguucug ggcuguagug cgcuaugc 28

<210> SEQ ID NO 430
<211> LENGTH: 32
<212> TYPE: RNA
<213> ORGANISM: Homo sapiens

<400> SEQUENCE: 430
guucauccca cagugccagu ucugcuuacc aa 32

<210> SEQ ID NO 431
<211> LENGTH: 29
<212> TYPE: RNA
<213> ORGANISM: Homo sapiens

<400> SEQUENCE: 431
caugcgcucu accacugagc uacaucccc 29

<210> SEQ ID NO 432
<211> LENGTH: 27
<212> TYPE: RNA
<213> ORGANISM: Homo sapiens

```
<400> SEQUENCE: 432

ggucugaacu cagaucacgu aggacuu                                      27

<210> SEQ ID NO 433
<211> LENGTH: 26
<212> TYPE: RNA
<213> ORGANISM: Homo sapiens

<400> SEQUENCE: 433

uucucacuac ugcacuugac uagucu                                       26

<210> SEQ ID NO 434
<211> LENGTH: 32
<212> TYPE: RNA
<213> ORGANISM: Homo sapiens

<400> SEQUENCE: 434

uacaguccaa ugcuucacuc agccauuuua cc                                32

<210> SEQ ID NO 435
<211> LENGTH: 28
<212> TYPE: RNA
<213> ORGANISM: Homo sapiens

<400> SEQUENCE: 435

guauuagagg caccgccugc ccagugac                                     28

<210> SEQ ID NO 436
<211> LENGTH: 26
<212> TYPE: RNA
<213> ORGANISM: Homo sapiens

<400> SEQUENCE: 436

ccaugggugg uucaguggua gaauuc                                       26

<210> SEQ ID NO 437
<211> LENGTH: 29
<212> TYPE: RNA
<213> ORGANISM: Homo sapiens

<400> SEQUENCE: 437

ggucccaugg uguaaugguu agcacucug                                    29

<210> SEQ ID NO 438
<211> LENGTH: 32
<212> TYPE: RNA
<213> ORGANISM: Homo sapiens

<400> SEQUENCE: 438

uacaguccaa ugcuucacuc agccauuuua cc                                32

<210> SEQ ID NO 439
<211> LENGTH: 26
<212> TYPE: RNA
<213> ORGANISM: Homo sapiens

<400> SEQUENCE: 439

uucucacuac ugcacuugac uagucu                                       26

<210> SEQ ID NO 440
<211> LENGTH: 26
<212> TYPE: RNA
```

<213> ORGANISM: Homo sapiens

<400> SEQUENCE: 440
gaugccuggg aguugcgauc ugcccg 26

<210> SEQ ID NO 441
<211> LENGTH: 27
<212> TYPE: RNA
<213> ORGANISM: Homo sapiens

<400> SEQUENCE: 441
ugagccgaga ucacgccacu gcacucc 27

<210> SEQ ID NO 442
<211> LENGTH: 29
<212> TYPE: RNA
<213> ORGANISM: Homo sapiens

<400> SEQUENCE: 442
ccgaauccua accaguagac uaccaggga 29

<210> SEQ ID NO 443
<211> LENGTH: 27
<212> TYPE: RNA
<213> ORGANISM: Homo sapiens

<400> SEQUENCE: 443
cacaaaaugu cugaaccugc gguuccu 27

<210> SEQ ID NO 444
<211> LENGTH: 26
<212> TYPE: RNA
<213> ORGANISM: Homo sapiens

<400> SEQUENCE: 444
gccuuagacu gcucggucau ccugac 26

<210> SEQ ID NO 445
<211> LENGTH: 28
<212> TYPE: RNA
<213> ORGANISM: Homo sapiens

<400> SEQUENCE: 445
ccggggaccu cuugaucugc agucaaau 28

<210> SEQ ID NO 446
<211> LENGTH: 31
<212> TYPE: RNA
<213> ORGANISM: Homo sapiens

<400> SEQUENCE: 446
acaacccccc acugcuaaau uugacuggcu u 31

<210> SEQ ID NO 447
<211> LENGTH: 31
<212> TYPE: RNA
<213> ORGANISM: Homo sapiens

<400> SEQUENCE: 447
gcccagcacg cuuccgcugc gccacucugc u 31

<210> SEQ ID NO 448
<211> LENGTH: 30

<212> TYPE: RNA
<213> ORGANISM: Homo sapiens

<400> SEQUENCE: 448
cagaugugau aaccacuaca cuauggaacc 30

<210> SEQ ID NO 449
<211> LENGTH: 26
<212> TYPE: RNA
<213> ORGANISM: Homo sapiens

<400> SEQUENCE: 449
agacuaguca agugcaguag ugagaa 26

<210> SEQ ID NO 450
<211> LENGTH: 26
<212> TYPE: RNA
<213> ORGANISM: Homo sapiens

<400> SEQUENCE: 450
agacuaguca agugcaguag ugagaa 26

<210> SEQ ID NO 451
<211> LENGTH: 32
<212> TYPE: RNA
<213> ORGANISM: Homo sapiens

<400> SEQUENCE: 451
ccuggacuca agcgauccuc cagccucagc cu 32

<210> SEQ ID NO 452
<211> LENGTH: 29
<212> TYPE: RNA
<213> ORGANISM: Homo sapiens

<400> SEQUENCE: 452
aucaaugaug aaacuagcca aaucugagc 29

<210> SEQ ID NO 453
<211> LENGTH: 31
<212> TYPE: RNA
<213> ORGANISM: Homo sapiens

<400> SEQUENCE: 453
uacuagagaa guuucucuga acguguagag c 31

<210> SEQ ID NO 454
<211> LENGTH: 27
<212> TYPE: RNA
<213> ORGANISM: Homo sapiens

<400> SEQUENCE: 454
uuggcaguuc agugguagaa uucucgc 27

<210> SEQ ID NO 455
<211> LENGTH: 27
<212> TYPE: RNA
<213> ORGANISM: Homo sapiens

<400> SEQUENCE: 455
ggcuaagauc aaguguagua ucuguuc 27

<210> SEQ ID NO 456

<211> LENGTH: 29
<212> TYPE: RNA
<213> ORGANISM: Homo sapiens

<400> SEQUENCE: 456
caccaugaug gaacugagga ucugaggaa 29

<210> SEQ ID NO 457
<211> LENGTH: 29
<212> TYPE: RNA
<213> ORGANISM: Homo sapiens

<400> SEQUENCE: 457
guucagaaag gccauuuuca uucagcccc 29

<210> SEQ ID NO 458
<211> LENGTH: 31
<212> TYPE: RNA
<213> ORGANISM: Homo sapiens

<400> SEQUENCE: 458
ucccuggugg ucuaguggcu aggauucggc a 31

<210> SEQ ID NO 459
<211> LENGTH: 26
<212> TYPE: RNA
<213> ORGANISM: Homo sapiens

<400> SEQUENCE: 459
gccuuagacc acucggccau ccugac 26

<210> SEQ ID NO 460
<211> LENGTH: 29
<212> TYPE: RNA
<213> ORGANISM: Homo sapiens

<400> SEQUENCE: 460
uuguaaacac cacugcacuc ggaccagcc 29

<210> SEQ ID NO 461
<211> LENGTH: 28
<212> TYPE: RNA
<213> ORGANISM: Homo sapiens

<400> SEQUENCE: 461
aaagccuaca gcacccggua uucccagg 28

<210> SEQ ID NO 462
<211> LENGTH: 29
<212> TYPE: RNA
<213> ORGANISM: Homo sapiens

<400> SEQUENCE: 462
uggaauccua accacuagac caccaggga 29

<210> SEQ ID NO 463
<211> LENGTH: 29
<212> TYPE: RNA
<213> ORGANISM: Homo sapiens

<400> SEQUENCE: 463 acccccacu gcuaaauuug acuggcuuu 29

<210> SEQ ID NO 464
<211> LENGTH: 28
<212> TYPE: RNA
<213> ORGANISM: Homo sapiens

<400> SEQUENCE: 464
cugaaugaug auaucccacu aacugagc 28

<210> SEQ ID NO 465
<211> LENGTH: 29
<212> TYPE: RNA
<213> ORGANISM: Homo sapiens

<400> SEQUENCE: 465
uggaggugau gaacugucug agccugacc 29

<210> SEQ ID NO 466
<211> LENGTH: 31
<212> TYPE: RNA
<213> ORGANISM: Homo sapiens

<400> SEQUENCE: 466
agggagauga agaggacagu gacugagaga c 31

<210> SEQ ID NO 467
<211> LENGTH: 27
<212> TYPE: RNA
<213> ORGANISM: Homo sapiens

<400> SEQUENCE: 467
aggaguucug ggcuguagug cgcuaug 27

<210> SEQ ID NO 468
<211> LENGTH: 29
<212> TYPE: RNA
<213> ORGANISM: Homo sapiens

<400> SEQUENCE: 468
ccggacaggg acaggauuga cagauugau 29

<210> SEQ ID NO 469
<211> LENGTH: 32
<212> TYPE: RNA
<213> ORGANISM: Homo sapiens

<400> SEQUENCE: 469
gccuuggugg ugcaguggua gaauucucgc cu 32

<210> SEQ ID NO 470
<211> LENGTH: 27
<212> TYPE: RNA
<213> ORGANISM: Homo sapiens

<400> SEQUENCE: 470
auggauaagg cacuggccuc cuaagcc 27

<210> SEQ ID NO 471
<211> LENGTH: 26
<212> TYPE: RNA
<213> ORGANISM: Homo sapiens

<400> SEQUENCE: 471
aggcugugau ggaccuggcu gagccu 26

<210> SEQ ID NO 472
<211> LENGTH: 27
<212> TYPE: RNA
<213> ORGANISM: Homo sapiens

<400> SEQUENCE: 472
aucagaacuu ccacaacauc auguguu 27

<210> SEQ ID NO 473
<211> LENGTH: 29
<212> TYPE: RNA
<213> ORGANISM: Homo sapiens

<400> SEQUENCE: 473
uaagaauucu accacugaac cacccaugc 29

<210> SEQ ID NO 474
<211> LENGTH: 30
<212> TYPE: RNA
<213> ORGANISM: Homo sapiens

<400> SEQUENCE: 474
uccaaguacu aaccaggccc gacccugcuu 30

<210> SEQ ID NO 475
<211> LENGTH: 27
<212> TYPE: RNA
<213> ORGANISM: Homo sapiens

<400> SEQUENCE: 475
ggcuuaggag gccagugccu uauccau 27

<210> SEQ ID NO 476
<211> LENGTH: 28
<212> TYPE: RNA
<213> ORGANISM: Homo sapiens

<400> SEQUENCE: 476
uccaaguacu aaccaggccc gacccugc 28

<210> SEQ ID NO 477
<211> LENGTH: 28
<212> TYPE: RNA
<213> ORGANISM: Homo sapiens

<400> SEQUENCE: 477
gaccaacuga cccauguuca acugcugu 28

<210> SEQ ID NO 478
<211> LENGTH: 29
<212> TYPE: RNA
<213> ORGANISM: Homo sapiens

<400> SEQUENCE: 478
aaucagauuu cagagucuca acagcaagu 29

<210> SEQ ID NO 479
<211> LENGTH: 27
<212> TYPE: RNA
<213> ORGANISM: Homo sapiens

<400> SEQUENCE: 479
aggaguucug ggcuguagug cgcuaug 27

<210> SEQ ID NO 480
<211> LENGTH: 28
<212> TYPE: RNA
<213> ORGANISM: Homo sapiens

<400> SEQUENCE: 480
cugccaugau gcuagacucc ugagcaga 28

<210> SEQ ID NO 481
<211> LENGTH: 31
<212> TYPE: RNA
<213> ORGANISM: Homo sapiens

<400> SEQUENCE: 481
agggagauga agaggacagu gacugagaga c 31

<210> SEQ ID NO 482
<211> LENGTH: 27
<212> TYPE: RNA
<213> ORGANISM: Homo sapiens

<400> SEQUENCE: 482
ucagaacauc cgagaaaauc auguggu 27

<210> SEQ ID NO 483
<211> LENGTH: 28
<212> TYPE: RNA
<213> ORGANISM: Homo sapiens

<400> SEQUENCE: 483
gaguagagug cuuaguugaa cagggccc 28

<210> SEQ ID NO 484
<211> LENGTH: 27
<212> TYPE: RNA
<213> ORGANISM: Homo sapiens

<400> SEQUENCE: 484
ugggaauacc gggugcugua ggcuuuu 27

<210> SEQ ID NO 485
<211> LENGTH: 29
<212> TYPE: RNA
<213> ORGANISM: Homo sapiens

<400> SEQUENCE: 485
ugaaaugaug gcaaucaucu uucgggacu 29

<210> SEQ ID NO 486
<211> LENGTH: 29
<212> TYPE: RNA
<213> ORGANISM: Homo sapiens

<400> SEQUENCE: 486
cuuucugugu ggaauuugaa uaucugaaa 29

<210> SEQ ID NO 487
<211> LENGTH: 11
<212> TYPE: RNA
<213> ORGANISM: Artificial Sequence
<220> FEATURE:
<223> OTHER INFORMATION: synthetic construct
<220> FEATURE:

<221> NAME/KEY: misc_feature
<222> LOCATION: (1)..(2)
<223> OTHER INFORMATION: n is a, c, g, or u
<220> FEATURE:
<221> NAME/KEY: misc_feature
<222> LOCATION: (5)..(6)
<223> OTHER INFORMATION: n is a, c, g, or u
<220> FEATURE:
<221> NAME/KEY: misc_feature
<222> LOCATION: (10)..(11)
<223> OTHER INFORMATION: n is a, c, g, or u

<400> SEQUENCE: 487
nnuunnuuun n 11

<210> SEQ ID NO 488
<211> LENGTH: 7
<212> TYPE: PRT
<213> ORGANISM: Artificial Sequence
<220> FEATURE:
<223> OTHER INFORMATION: synthetic construct

<400> SEQUENCE: 488

Arg Arg Arg Lys Pro Asp Thr
1 5

<210> SEQ ID NO 489
<211> LENGTH: 25
<212> TYPE: RNA
<213> ORGANISM: Artificial Sequence
<220> FEATURE:
<223> OTHER INFORMATION: synthetic construct

<400> SEQUENCE: 489
cucucaccgc cgcggcccgg guucg 25

<210> SEQ ID NO 490
<211> LENGTH: 43
<212> TYPE: RNA
<213> ORGANISM: Homo sapiens

<400> SEQUENCE: 490
cucucaccgc cgcggcccgg guucgauucc cggucaggga acc 43

<210> SEQ ID NO 491
<211> LENGTH: 42
<212> TYPE: RNA
<213> ORGANISM: Homo sapiens

<400> SEQUENCE: 491
cucucaccgc cgcggcccgg guucgauucc cggucaggga ac 42

<210> SEQ ID NO 492
<211> LENGTH: 44
<212> TYPE: RNA
<213> ORGANISM: Homo sapiens

<400> SEQUENCE: 492
cucucaccgc cgcggcccgg guucgauucc cggucaggga acca 44

<210> SEQ ID NO 493
<211> LENGTH: 43
<212> TYPE: RNA
<213> ORGANISM: Homo sapiens

<400> SEQUENCE: 493
cucucaccgc cgcggcccgg guucguuucc cggucaggga acc 43

<210> SEQ ID NO 494
<211> LENGTH: 44
<212> TYPE: RNA
<213> ORGANISM: Homo sapiens

<400> SEQUENCE: 494
cucucaccgc cgcggcccgg guucguuucc cggucaggga acca 44

<210> SEQ ID NO 495
<211> LENGTH: 11
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (3)..(4)
<223> OTHER INFORMATION: n is a, c, g, or u
<220> FEATURE:
<221> NAME/KEY: misc_feature
<222> LOCATION: (8)..(9)
<223> OTHER INFORMATION: n is a, c, g, or u

<400> SEQUENCE: 495
uunnuuunnu u 11

<210> SEQ ID NO 496
<211> LENGTH: 30
<212> TYPE: DNA
<213> ORGANISM: Artificial Sequence
<220> FEATURE:
<223> OTHER INFORMATION: synthetic construct

<400> SEQUENCE: 496
ggtcagagaa tcaaagtaac atcatgatat 30

<210> SEQ ID NO 497
<211> LENGTH: 30
<212> TYPE: RNA
<213> ORGANISM: Artificial Sequence
<220> FEATURE:
<223> OTHER INFORMATION: synthetic construct

<400> SEQUENCE: 497
ggucagagaa ucaaaguaac aucaugauau 30

<210> SEQ ID NO 498
<211> LENGTH: 30
<212> TYPE: DNA
<213> ORGANISM: Artificial Sequence
<220> FEATURE:
<223> OTHER INFORMATION: synthetic construct

<400> SEQUENCE: 498
ggtcagagaa tcaaagtaac atcatgatat 30

<210> SEQ ID NO 499
<211> LENGTH: 17
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: 5'-adenylation
<220> FEATURE:
<221> NAME/KEY: misc_feature
<222> LOCATION: (17)..(17)
<223> OTHER INFORMATION: 3'-dideoxy C

<400> SEQUENCE: 499
ctgtaggcac catcaat 17

<210> SEQ ID NO 500
<211> LENGTH: 38
<212> TYPE: DNA
<213> ORGANISM: Artificial Sequence
<220> FEATURE:
<223> OTHER INFORMATION: synthetic construct

<400> SEQUENCE: 500
caagcagaag acggcatacg aattgatggt gcctacag 38

<210> SEQ ID NO 501
<211> LENGTH: 21
<212> TYPE: DNA
<213> ORGANISM: Artificial Sequence
<220> FEATURE:
<223> OTHER INFORMATION: synthetic construct

<400> SEQUENCE: 501
caagcagaag acggcatacg a 21

<210> SEQ ID NO 502
<211> LENGTH: 30
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: biotin label
<220> FEATURE:
<221> NAME/KEY: misc_feature
<222> LOCATION: (30)..(30)
<223> OTHER INFORMATION: 2'-O-methylation

<400> SEQUENCE: 502
auaucaugau guuacuuuga uucucugacc 30

<210> SEQ ID NO 503
<211> LENGTH: 30
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: biotin label

<400> SEQUENCE: 503
gauaccaagg acauacgcuu augcaugcua 30

<210> SEQ ID NO 504
<211> LENGTH: 19
<212> TYPE: RNA
<213> ORGANISM: Artificial Sequence
<220> FEATURE:
<223> OTHER INFORMATION: synthetic construct

<400> SEQUENCE: 504
ccguuagcag gaagccuaa 19

<210> SEQ ID NO 505
<211> LENGTH: 21
<212> TYPE: RNA
<213> ORGANISM: Artificial Sequence
<220> FEATURE:
<223> OTHER INFORMATION: synthetic construct

<400> SEQUENCE: 505
gauaccaagg gacauacgcu u 21

<210> SEQ ID NO 506
<211> LENGTH: 29
<212> TYPE: DNA
<213> ORGANISM: Artificial Sequence
<220> FEATURE:
<223> OTHER INFORMATION: synthetic construct

<400> SEQUENCE: 506
gataccaggg acatacgctt gatcctagc 29

<210> SEQ ID NO 507
<211> LENGTH: 6
<212> TYPE: DNA
<213> ORGANISM: Artificial Sequence
<220> FEATURE:
<223> OTHER INFORMATION: synthetic construct

<400> SEQUENCE: 507 atcacg 6

<210> SEQ ID NO 508
<211> LENGTH: 6
<212> TYPE: DNA
<213> ORGANISM: Artificial Sequence
<220> FEATURE:
<223> OTHER INFORMATION: synthetic construct

<400> SEQUENCE: 508 cgatgt 6

<210> SEQ ID NO 509
<211> LENGTH: 6
<212> TYPE: DNA
<213> ORGANISM: Artificial Sequence
<220> FEATURE:
<223> OTHER INFORMATION: synthetic construct

<400> SEQUENCE: 509 ttaggc 6

<210> SEQ ID NO 510
<211> LENGTH: 6
<212> TYPE: DNA
<213> ORGANISM: Artificial Sequence
<220> FEATURE:
<223> OTHER INFORMATION: synthetic construct

<400> SEQUENCE: 510 tgacca 6

<210> SEQ ID NO 511
<211> LENGTH: 6
<212> TYPE: DNA
<213> ORGANISM: Artificial Sequence
<220> FEATURE:
<223> OTHER INFORMATION: synthetic construct

<400> SEQUENCE: 511 acagtg 6

<210> SEQ ID NO 512
<211> LENGTH: 6
<212> TYPE: DNA
<213> ORGANISM: Artificial Sequence
<220> FEATURE:
<223> OTHER INFORMATION: synthetic construct

<400> SEQUENCE: 512 gccaat 6

<210> SEQ ID NO 513
<211> LENGTH: 6
<212> TYPE: DNA
<213> ORGANISM: Artificial Sequence
<220> FEATURE:
<223> OTHER INFORMATION: synthetic construct

<400> SEQUENCE: 513 cagatc 6

<210> SEQ ID NO 514
<211> LENGTH: 6
<212> TYPE: DNA
<213> ORGANISM: Artificial Sequence
<220> FEATURE:
<223> OTHER INFORMATION: synthetic construct

<400> SEQUENCE: 514 acttga 6

<210> SEQ ID NO 515
<211> LENGTH: 6
<212> TYPE: DNA
<213> ORGANISM: Artificial Sequence
<220> FEATURE:
<223> OTHER INFORMATION: synthetic construct

<400> SEQUENCE: 515 tagctt 6

<210> SEQ ID NO 516
<211> LENGTH: 6
<212> TYPE: DNA
<213> ORGANISM: Artificial Sequence
<220> FEATURE:
<223> OTHER INFORMATION: synthetic construct

<400> SEQUENCE: 516 ggctac 6

<210> SEQ ID NO 517
<211> LENGTH: 6
<212> TYPE: DNA
<213> ORGANISM: Artificial Sequence
<220> FEATURE:
<223> OTHER INFORMATION: synthetic construct

<400> SEQUENCE: 517 cttgta 6

<210> SEQ ID NO 518
<211> LENGTH: 30
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (30)..(30)
<223> OTHER INFORMATION: 2'-O-methylation

<400> SEQUENCE: 518
auaucaugau guuacuuuga uucucugacc 30

<210> SEQ ID NO 519
<211> LENGTH: 30
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (30)..(30)
<223> OTHER INFORMATION: 2'-O-methylation

<400> SEQUENCE: 519
auaucaugau gacacgacga cacucugacc 30

<210> SEQ ID NO 520
<211> LENGTH: 30
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (30)..(30)
<223> OTHER INFORMATION: 2'-O-methylation

<400> SEQUENCE: 520
auaucaugau guuacgacga uucucugacc 30

<210> SEQ ID NO 521
<211> LENGTH: 30
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (30)..(30)
<223> OTHER INFORMATION: 2'-O-methylation

<400> SEQUENCE: 521
auaucaugau guuacgcuga uucucugacc 30

<210> SEQ ID NO 522
<211> LENGTH: 30
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (30)..(30)
<223> OTHER INFORMATION: 2'-O-methylation

<400> SEQUENCE: 522
auaucaugau guuacucuga uucucugacc 30

<210> SEQ ID NO 523
<211> LENGTH: 30
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (30)..(30)
<223> OTHER INFORMATION: 2'-O-methylation

<400> SEQUENCE: 523
auuucaugau guuacuuuga uucucugacc 30

<210> SEQ ID NO 524
<211> LENGTH: 30
<212> TYPE: RNA
<213> ORGANISM: Artificial Sequence
<220> FEATURE:
<223> OTHER INFORMATION: synthetic construct

<400> SEQUENCE: 524
gauaccaagg acauacgcuu augcaugcua 30

<210> SEQ ID NO 525
<211> LENGTH: 30
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: 5'-Digoxin

<400> SEQUENCE: 525
ggtcagagaa tcaaagtaac atcatgatat 30

<210> SEQ ID NO 526
<211> LENGTH: 26
<212> TYPE: DNA
<213> ORGANISM: Artificial Sequence
<220> FEATURE:
<223> OTHER INFORMATION: synthetic construct

<400> SEQUENCE: 526
atatcatgat gttactttga ttctct 26

<210> SEQ ID NO 527
<211> LENGTH: 20
<212> TYPE: DNA
<213> ORGANISM: Artificial Sequence
<220> FEATURE:
<223> OTHER INFORMATION: synthetic construct

<400> SEQUENCE: 527
atgacacgca aattcgtgaa 20

<210> SEQ ID NO 528
<211> LENGTH: 27
<212> TYPE: DNA
<213> ORGANISM: Artificial Sequence
<220> FEATURE:
<223> OTHER INFORMATION: synthetic construct

<400> SEQUENCE: 528
ggtcagagaa tcaaagtaac atcatga 27

<210> SEQ ID NO 529
<211> LENGTH: 22
<212> TYPE: DNA
<213> ORGANISM: Artificial Sequence
<220> FEATURE:
<223> OTHER INFORMATION: synthetic construct

<400> SEQUENCE: 529
atatcatgat gacacgacga ca 22

<210> SEQ ID NO 530
<211> LENGTH: 18
<212> TYPE: DNA
<213> ORGANISM: Artificial Sequence
<220> FEATURE:
<223> OTHER INFORMATION: synthetic construct

<400> SEQUENCE: 530
atatcatgat gttacgac 18

<210> SEQ ID NO 531
<211> LENGTH: 17
<212> TYPE: DNA
<213> ORGANISM: Artificial Sequence
<220> FEATURE:
<223> OTHER INFORMATION: synthetic construct

<400> SEQUENCE: 531
atatcatgat gttacgc 17

<210> SEQ ID NO 532
<211> LENGTH: 17
<212> TYPE: DNA
<213> ORGANISM: Artificial Sequence
<220> FEATURE:
<223> OTHER INFORMATION: synthetic construct

<400> SEQUENCE: 532
atatcatgat gttactc 17

<210> SEQ ID NO 533
<211> LENGTH: 22
<212> TYPE: DNA
<213> ORGANISM: Artificial Sequence
<220> FEATURE:
<223> OTHER INFORMATION: synthetic construct

<400> SEQUENCE: 533
atttcatgat gttactttga tt 22

<210> SEQ ID NO 534
<211> LENGTH: 26
<212> TYPE: DNA
<213> ORGANISM: Artificial Sequence
<220> FEATURE:
<223> OTHER INFORMATION: synthetic construct

<400> SEQUENCE: 534
agcaagctta tgcaaaacaa ccaaat 26

<210> SEQ ID NO 535
<211> LENGTH: 30
<212> TYPE: DNA
<213> ORGANISM: Artificial Sequence
<220> FEATURE:
<223> OTHER INFORMATION: synthetic construct

<400> SEQUENCE: 535
atctcgagtt acatagactc aaattcgtca 30

<210> SEQ ID NO 536
<211> LENGTH: 33
<212> TYPE: DNA
<213> ORGANISM: Artificial Sequence
<220> FEATURE:
<223> OTHER INFORMATION: synthetic construct

<400> SEQUENCE: 536
aactatacat gattgaggtg cagcagatga agg 33

<210> SEQ ID NO 537
<211> LENGTH: 35
<212> TYPE: DNA
<213> ORGANISM: Artificial Sequence
<220> FEATURE:
<223> OTHER INFORMATION: synthetic construct

<400> SEQUENCE: 537
gcacctcaat catgtatagt tcatggttcc ccatg 35

<210> SEQ ID NO 538
<211> LENGTH: 20
<212> TYPE: DNA
<213> ORGANISM: Artificial Sequence
<220> FEATURE:
<223> OTHER INFORMATION: synthetic construct

<400> SEQUENCE: 538
tgcaccacca actgcttagc 20

<210> SEQ ID NO 539
<211> LENGTH: 21
<212> TYPE: DNA
<213> ORGANISM: Artificial Sequence
<220> FEATURE:
<223> OTHER INFORMATION: synthetic construct

<400> SEQUENCE: 539
ggcatggact gtggtcatga g 21

<210> SEQ ID NO 540
<211> LENGTH: 20
<212> TYPE: DNA
<213> ORGANISM: Artificial Sequence
<220> FEATURE:
<223> OTHER INFORMATION: synthetic construct

<400> SEQUENCE: 540
gggaagcagc tatttgacca 20

<210> SEQ ID NO 541
<211> LENGTH: 20
<212> TYPE: DNA
<213> ORGANISM: Artificial Sequence
<220> FEATURE:
<223> OTHER INFORMATION: synthetic construct

<400> SEQUENCE: 541
cttaaagagc agggggcttt 20

<210> SEQ ID NO 542
<211> LENGTH: 21
<212> TYPE: RNA
<213> ORGANISM: Artificial Sequence
<220> FEATURE:
<223> OTHER INFORMATION: synthetic construct

<400> SEQUENCE: 542
ccguuagcag gaagccuaau u 21

<210> SEQ ID NO 543
<211> LENGTH: 21
<212> TYPE: RNA
<213> ORGANISM: Artificial Sequence
<220> FEATURE:
<223> OTHER INFORMATION: synthetic construct

<400> SEQUENCE: 543
uuaggcuucc ugcuaacggu u 21

<210> SEQ ID NO 544
<211> LENGTH: 21
<212> TYPE: RNA
<213> ORGANISM: Artificial Sequence
<220> FEATURE:
<223> OTHER INFORMATION: synthetic construct

<400> SEQUENCE: 544
gauaccaagg gacauacgcu u 21

<210> SEQ ID NO 545
<211> LENGTH: 21
<212> TYPE: RNA
<213> ORGANISM: Artificial Sequence
<220> FEATURE:
<223> OTHER INFORMATION: synthetic construct

<400> SEQUENCE: 545
gcguaugucc cuugguaucu u 21

<210> SEQ ID NO 546
<211> LENGTH: 19
<212> TYPE: DNA
<213> ORGANISM: Artificial Sequence
<220> FEATURE:
<223> OTHER INFORMATION: synthetic construct

<400> SEQUENCE: 546
gagccagagc cagaggaag 19

<210> SEQ ID NO 547
<211> LENGTH: 20
<212> TYPE: DNA
<213> ORGANISM: Artificial Sequence
<220> FEATURE:
<223> OTHER INFORMATION: synthetic construct

<400> SEQUENCE: 547
ataattcccc ctctgctggt 20

<210> SEQ ID NO 548
<211> LENGTH: 20
<212> TYPE: DNA
<213> ORGANISM: Artificial Sequence
<220> FEATURE:
<223> OTHER INFORMATION: synthetic construct

<400> SEQUENCE: 548
gtgggtttgg tctccatgtt 20

<210> SEQ ID NO 549
<211> LENGTH: 20
<212> TYPE: DNA
<213> ORGANISM: Artificial Sequence
<220> FEATURE:
<223> OTHER INFORMATION: synthetic construct

<400> SEQUENCE: 549
cctgtccttg cgtaccagat 20

<210> SEQ ID NO 550
<211> LENGTH: 20
<212> TYPE: DNA
<213> ORGANISM: Artificial Sequence
<220> FEATURE:
<223> OTHER INFORMATION: synthetic construct

<400> SEQUENCE: 550
gcagggagag ctaccaacaa 20

<210> SEQ ID NO 551
<211> LENGTH: 20
<212> TYPE: DNA
<213> ORGANISM: Artificial Sequence
<220> FEATURE:
<223> OTHER INFORMATION: synthetic construct

<400> SEQUENCE: 551
aaccactggg acttcctcct 20

<210> SEQ ID NO 552
<211> LENGTH: 20
<212> TYPE: DNA
<213> ORGANISM: Artificial Sequence
<220> FEATURE:
<223> OTHER INFORMATION: synthetic construct

<400> SEQUENCE: 552
accagagaaa aattggcaca 20

<210> SEQ ID NO 553
<211> LENGTH: 20
<212> TYPE: DNA
<213> ORGANISM: Artificial Sequence
<220> FEATURE:
<223> OTHER INFORMATION: synthetic construct

<400> SEQUENCE: 553
gccagtcttg gggaaaatct 20

<210> SEQ ID NO 554
<211> LENGTH: 19
<212> TYPE: DNA
<213> ORGANISM: Artificial Sequence
<220> FEATURE:
<223> OTHER INFORMATION: synthetic construct

<400> SEQUENCE: 554
ctacttcggg gacccattg 19

<210> SEQ ID NO 555

<211> LENGTH: 20
<212> TYPE: DNA
<213> ORGANISM: Artificial Sequence
<220> FEATURE:
<223> OTHER INFORMATION: synthetic construct

<400> SEQUENCE: 555
caaacacagg tgccatcact 20

<210> SEQ ID NO 556
<211> LENGTH: 29
<212> TYPE: DNA
<213> ORGANISM: Artificial Sequence
<220> FEATURE:
<223> OTHER INFORMATION: synthetic construct

<400> SEQUENCE: 556
aggtctcaga gtaattctag agctaaagt 29

<210> SEQ ID NO 557
<211> LENGTH: 29
<212> TYPE: RNA
<213> ORGANISM: Artificial Sequence
<220> FEATURE:
<223> OTHER INFORMATION: synthetic construct

<400> SEQUENCE: 557
aggucucaga guaauucuag agcuaaagu 29

<210> SEQ ID NO 558
<211> LENGTH: 24
<212> TYPE: DNA
<213> ORGANISM: Artificial Sequence
<220> FEATURE:
<223> OTHER INFORMATION: synthetic construct; anti-sense DNA

<400> SEQUENCE: 558
cgaacccggg ccgcggcggt gaga 24

<210> SEQ ID NO 559
<211> LENGTH: 24
<212> TYPE: RNA
<213> ORGANISM: Artificial Sequence
<220> FEATURE:
<223> OTHER INFORMATION: synthetic construct; anti-sense RNA

<400> SEQUENCE: 559
cgaacccggg ccgcggcggu gaga 24

<210> SEQ ID NO 560
<211> LENGTH: 50
<212> TYPE: RNA
<213> ORGANISM: Homo sapiens

<400> SEQUENCE: 560
ugaaaagaac uuugaagaga gaguucaaga gggcgugaaa ccguuaagag 50

<210> SEQ ID NO 561
<211> LENGTH: 46
<212> TYPE: RNA
<213> ORGANISM: Homo sapiens

<400> SEQUENCE: 561
gugguucgug cugaaggccu guauccuagg cuacacacug aggacu 46

<210> SEQ ID NO 562
<211> LENGTH: 48
<212> TYPE: RNA
<213> ORGANISM: Homo sapiens

<400> SEQUENCE: 562
aggacacauu gaucaucgac acuucgaacg cacuugcggc cccggguu 48

<210> SEQ ID NO 563
<211> LENGTH: 28
<212> TYPE: RNA
<213> ORGANISM: Homo sapiens

<400> SEQUENCE: 563
gcaugggugg uucaguggua gaauucuc 28

<210> SEQ ID NO 564
<211> LENGTH: 26
<212> TYPE: RNA
<213> ORGANISM: Homo sapiens

<400> SEQUENCE: 564
uuuggcaaug guagaacuca cacugg 26

<210> SEQ ID NO 565
<211> LENGTH: 49
<212> TYPE: RNA
<213> ORGANISM: Homo sapiens

<400> SEQUENCE: 565
acggcccugg cggagcgcug agaagacggu cgaacuugac uaucuagag 49

<210> SEQ ID NO 566
<211> LENGTH: 33
<212> TYPE: RNA
<213> ORGANISM: Homo sapiens

<400> SEQUENCE: 566
auuggucgug guuguagucc gugcgagaau acc 33

<210> SEQ ID NO 567
<211> LENGTH: 50
<212> TYPE: RNA
<213> ORGANISM: Homo sapiens

<400> SEQUENCE: 567
cuccuacuug gauaacugug guaauucuag agcuaauaca ugccgacggg 50

<210> SEQ ID NO 568
<211> LENGTH: 31
<212> TYPE: RNA
<213> ORGANISM: Homo sapiens

<400> SEQUENCE: 568
ccggcggcgu ccggugagcu cucgcuggcc c 31

<210> SEQ ID NO 569
<211> LENGTH: 39
<212> TYPE: RNA
<213> ORGANISM: Homo sapiens

<400> SEQUENCE: 569
gucuacggcc auaccacccu gaacgcgccc gaucucguc 39

<210> SEQ ID NO 570
<211> LENGTH: 34
<212> TYPE: RNA
<213> ORGANISM: Homo sapiens

<400> SEQUENCE: 570
cgcgaccuca gaucagacgu ggcgacccgc ugaa 34

<210> SEQ ID NO 571
<211> LENGTH: 34
<212> TYPE: RNA
<213> ORGANISM: Homo sapiens

<400> SEQUENCE: 571
gcaugggugg uucaguggua gaauucucgc cugc 34

<210> SEQ ID NO 572
<211> LENGTH: 50
<212> TYPE: RNA
<213> ORGANISM: Homo sapiens

<400> SEQUENCE: 572
ccuggaugau gauaagcaaa ugcugacuga acaugaaggu cuuaauuagc 50

<210> SEQ ID NO 573
<211> LENGTH: 45
<212> TYPE: RNA
<213> ORGANISM: Homo sapiens

<400> SEQUENCE: 573
acggcccugg cggagcgcug agaagacggu cgaacuugac uaucu 45

<210> SEQ ID NO 574
<211> LENGTH: 32
<212> TYPE: RNA
<213> ORGANISM: Homo sapiens

<400> SEQUENCE: 574
gccuuggugg uucaguggua gaauucucgc cu 32

<210> SEQ ID NO 575
<211> LENGTH: 49
<212> TYPE: RNA
<213> ORGANISM: Homo sapiens

<400> SEQUENCE: 575
acuugcggcc ccggguuccu cccggggcua cgccugucug agcgucgcu 49

<210> SEQ ID NO 576
<211> LENGTH: 27
<212> TYPE: RNA
<213> ORGANISM: Homo sapiens

<400> SEQUENCE: 576
uagcuuauca gacugauguu gacuguu 27

<210> SEQ ID NO 577
<211> LENGTH: 43
<212> TYPE: RNA
<213> ORGANISM: Homo sapiens

<400> SEQUENCE: 577
agcagccgac uuagaacugg ugcggaccag gggaauccga cug 43

<210> SEQ ID NO 578
<211> LENGTH: 32
<212> TYPE: RNA
<213> ORGANISM: Homo sapiens

<400> SEQUENCE: 578
gcaugggugg uucaguggua gaauucucgc ca 32

<210> SEQ ID NO 579
<211> LENGTH: 50
<212> TYPE: RNA
<213> ORGANISM: Homo sapiens

<400> SEQUENCE: 579
acauugauca ucgacacuuc gaacgcacuu gcggccccgg guuccucccg 50

<210> SEQ ID NO 580
<211> LENGTH: 36
<212> TYPE: RNA
<213> ORGANISM: Homo sapiens

<400> SEQUENCE: 580
cgcgaccuca gaucagacgu ggcgacccgc ugaauu 36

<210> SEQ ID NO 581
<211> LENGTH: 33
<212> TYPE: RNA
<213> ORGANISM: Homo sapiens

<400> SEQUENCE: 581
ucccuggugg ucuaguggcu aggauucggc gcu 33

<210> SEQ ID NO 582
<211> LENGTH: 26
<212> TYPE: RNA
<213> ORGANISM: Homo sapiens

<400> SEQUENCE: 582
uuuggcaaug guagaacuca cacuga 26

<210> SEQ ID NO 583
<211> LENGTH: 34
<212> TYPE: RNA
<213> ORGANISM: Homo sapiens

<400> SEQUENCE: 583
gcauuggugg uucaguggua gaauucucgc cugc 34

<210> SEQ ID NO 584
<211> LENGTH: 50
<212> TYPE: RNA
<213> ORGANISM: Homo sapiens

<400> SEQUENCE: 584
auugaucauc gacacuucga acgcacuugc ggccccgggu uccucccggg 50

<210> SEQ ID NO 585
<211> LENGTH: 47
<212> TYPE: RNA
<213> ORGANISM: Homo sapiens

<400> SEQUENCE: 585
gacucuuagc gguggaucac ucggcucgug cgucgaugaa gaacgca 47

<210> SEQ ID NO 586
<211> LENGTH: 50
<212> TYPE: RNA
<213> ORGANISM: Homo sapiens

<400> SEQUENCE: 586
aauguaggua agggaagucg gcaagccgga uccguaacuu cgggauaagg 50

<210> SEQ ID NO 587
<211> LENGTH: 31
<212> TYPE: RNA
<213> ORGANISM: Homo sapiens

<400> SEQUENCE: 587
gcaugggugg uucaguggua gaauucucgc c 31

<210> SEQ ID NO 588
<211> LENGTH: 34
<212> TYPE: RNA
<213> ORGANISM: Homo sapiens

<400> SEQUENCE: 588
uccccugugg ucuagugguu aggauucggc gcuc 34

<210> SEQ ID NO 589
<211> LENGTH: 33
<212> TYPE: RNA
<213> ORGANISM: Homo sapiens

<400> SEQUENCE: 589
gcauuggugg uucaguggua gaauucucgc cug 33

<210> SEQ ID NO 590
<211> LENGTH: 32
<212> TYPE: RNA
<213> ORGANISM: Homo sapiens

<400> SEQUENCE: 590
ucccuguggu cuaguggcua ggauucggcg cu 32

<210> SEQ ID NO 591
<211> LENGTH: 41
<212> TYPE: RNA
<213> ORGANISM: Homo sapiens

<400> SEQUENCE: 591
acgaacgaga cucuggcaug cuaacuaguu acgcgacccc c 41

<210> SEQ ID NO 592
<211> LENGTH: 50
<212> TYPE: RNA
<213> ORGANISM: Homo sapiens

<400> SEQUENCE: 592
cacuguaagg cuaacuuagc auuaaccuuu uaaguuaaag auuaagagaa 50

<210> SEQ ID NO 593
<211> LENGTH: 28
<212> TYPE: RNA
<213> ORGANISM: Homo sapiens

<400> SEQUENCE: 593
ucccuggugg ucuagugguu aggauucg 28

<210> SEQ ID NO 594
<211> LENGTH: 50
<212> TYPE: RNA
<213> ORGANISM: Homo sapiens

<400> SEQUENCE: 594
auucaaacga gaacuuugaa ggccgaagug gagaaggguu ccaugugaac 50

<210> SEQ ID NO 595
<211> LENGTH: 32
<212> TYPE: RNA
<213> ORGANISM: Homo sapiens

<400> SEQUENCE: 595
gcauuggugg uucaguggua gaauucucgc ca 32

<210> SEQ ID NO 596
<211> LENGTH: 32
<212> TYPE: RNA
<213> ORGANISM: Homo sapiens

<400> SEQUENCE: 596
gcccggcuag cucagucggu agagcauggg ac 32

<210> SEQ ID NO 597
<211> LENGTH: 50
<212> TYPE: RNA
<213> ORGANISM: Homo sapiens

<400> SEQUENCE: 597
cacuguaaug cuaacuuagc auuaaccuuu uaaguuaaag auuaagagaa 50

<210> SEQ ID NO 598
<211> LENGTH: 32
<212> TYPE: RNA
<213> ORGANISM: Homo sapiens

<400> SEQUENCE: 598
ucccuggugg ucuaguggau aggauucggc gc 32

<210> SEQ ID NO 599
<211> LENGTH: 34
<212> TYPE: RNA
<213> ORGANISM: Homo sapiens

<400> SEQUENCE: 599
guuuccguag uguagugguu aucacguucg ccuc 34

<210> SEQ ID NO 600
<211> LENGTH: 32
<212> TYPE: RNA
<213> ORGANISM: Homo sapiens

<400> SEQUENCE: 600
gcauuggugg uucaguggua gaauucucgc cc 32

<210> SEQ ID NO 601
<211> LENGTH: 50
<212> TYPE: RNA
<213> ORGANISM: Homo sapiens

<400> SEQUENCE: 601
ucccuggugg ucuagugguu aggauucggc gcucucaccg ccgcggcccg 50

<210> SEQ ID NO 602
<211> LENGTH: 33
<212> TYPE: RNA
<213> ORGANISM: Homo sapiens

<400> SEQUENCE: 602
ccagugcgcc ccgggcgggu cgcgccgucg ggc 33

<210> SEQ ID NO 603
<211> LENGTH: 47
<212> TYPE: RNA
<213> ORGANISM: Homo sapiens

<400> SEQUENCE: 603
acggcccugg cggagcgcug agaagacggu cgaacuugac uaucuag 47

<210> SEQ ID NO 604
<211> LENGTH: 30
<212> TYPE: RNA
<213> ORGANISM: Homo sapiens

<400> SEQUENCE: 604
ucccuggugg ucuagugguu aggauucggc 30

<210> SEQ ID NO 605
<211> LENGTH: 34
<212> TYPE: RNA
<213> ORGANISM: Homo sapiens

<400> SEQUENCE: 605
gcccggcuag cucagucggu agagcaugag acuc 34

<210> SEQ ID NO 606
<211> LENGTH: 41
<212> TYPE: RNA
<213> ORGANISM: Homo sapiens

<400> SEQUENCE: 606
aacgaacgag acucuggcau gcuaacuagu uacgcgaccc c 41

<210> SEQ ID NO 607
<211> LENGTH: 30
<212> TYPE: RNA
<213> ORGANISM: Homo sapiens

<400> SEQUENCE: 607
aguaagguca gcuaaauaag cuaucgggcc 30

<210> SEQ ID NO 608
<211> LENGTH: 26
<212> TYPE: RNA
<213> ORGANISM: Homo sapiens

<400> SEQUENCE: 608
uuuggcaaug guagaacuca cacugu 26

<210> SEQ ID NO 609
<211> LENGTH: 49
<212> TYPE: RNA
<213> ORGANISM: Homo sapiens

<400> SEQUENCE: 609
caggacggug gccauggaag ucggaauccg cuaaggagug uguaacaac         49

<210> SEQ ID NO 610
<211> LENGTH: 49
<212> TYPE: RNA
<213> ORGANISM: Homo sapiens

<400> SEQUENCE: 610
cuggaugaug auaagcaaau gcugacugaa caugaagguc uuaauuagc         49

<210> SEQ ID NO 611
<211> LENGTH: 32
<212> TYPE: RNA
<213> ORGANISM: Homo sapiens

<400> SEQUENCE: 611
gcaugagugg uucaguggua gaauucucgc cu                            32

<210> SEQ ID NO 612
<211> LENGTH: 50
<212> TYPE: RNA
<213> ORGANISM: Homo sapiens

<400> SEQUENCE: 612
cggcggcggc ggcgacucug gacgcgagcc gggcccuucc cguggaucgc         50

<210> SEQ ID NO 613
<211> LENGTH: 48
<212> TYPE: RNA
<213> ORGANISM: Homo sapiens

<400> SEQUENCE: 613
cuugcggccc cggguuccuc ccggggcuac gccugucuga gcgucgcu           48

<210> SEQ ID NO 614
<211> LENGTH: 33
<212> TYPE: RNA
<213> ORGANISM: Homo sapiens

<400> SEQUENCE: 614
aucauugguc gugguuguag uccgugcgag aau                           33

<210> SEQ ID NO 615
<211> LENGTH: 50
<212> TYPE: RNA
<213> ORGANISM: Homo sapiens

<400> SEQUENCE: 615
cucguacgac ucuuagcggu ggaucacucg gcucgugcgu cgaugaagaa         50

<210> SEQ ID NO 616
<211> LENGTH: 50
<212> TYPE: RNA
<213> ORGANISM: Homo sapiens

<400> SEQUENCE: 616
gaagggcagg gcgcccugga augggUucgc cccgagagag gggcccgugc         50

<210> SEQ ID NO 617
<211> LENGTH: 32
<212> TYPE: RNA

<213> ORGANISM: Homo sapiens

<400> SEQUENCE: 617
gcauuggcgg uucaguggua gaauucucgc cu 32

<210> SEQ ID NO 618
<211> LENGTH: 45
<212> TYPE: RNA
<213> ORGANISM: Homo sapiens

<400> SEQUENCE: 618
aagggaaagu ugaaaagaac uuugaagaga gaguucaaga gggcg 45

<210> SEQ ID NO 619
<211> LENGTH: 33
<212> TYPE: RNA
<213> ORGANISM: Homo sapiens

<400> SEQUENCE: 619
gcaugggugg uucaguggua gaauucucgc cug 33

<210> SEQ ID NO 620
<211> LENGTH: 48
<212> TYPE: RNA
<213> ORGANISM: Homo sapiens

<400> SEQUENCE: 620
ggcugguccg augguagugg guuaucagaa cuuauuaaca uuaguguc 48

<210> SEQ ID NO 621
<211> LENGTH: 32
<212> TYPE: RNA
<213> ORGANISM: Homo sapiens

<400> SEQUENCE: 621
auugaaaguc agcccucgac acaaggguuu gu 32

<210> SEQ ID NO 622
<211> LENGTH: 36
<212> TYPE: RNA
<213> ORGANISM: Homo sapiens

<400> SEQUENCE: 622
aucauugguc gugguuguag uccgugcgag aauacc 36

<210> SEQ ID NO 623
<211> LENGTH: 50
<212> TYPE: RNA
<213> ORGANISM: Homo sapiens

<400> SEQUENCE: 623
cugcugugau gacauuccaa uuaaagcacg uguuagacug cugacgcggg 50

<210> SEQ ID NO 624
<211> LENGTH: 40
<212> TYPE: RNA
<213> ORGANISM: Homo sapiens

<400> SEQUENCE: 624
acgaacgaga cucuggcaug cuaacuaguu acgcgacccc 40

<210> SEQ ID NO 625
<211> LENGTH: 49

<212> TYPE: RNA
<213> ORGANISM: Homo sapiens

<400> SEQUENCE: 625
gcagcucccu cgcugcgauc uauugaaagu cagcccucga cacaagggu 49

<210> SEQ ID NO 626
<211> LENGTH: 28
<212> TYPE: RNA
<213> ORGANISM: Homo sapiens

<400> SEQUENCE: 626
gcauuggugg uucaguggua gaauucuc 28

<210> SEQ ID NO 627
<211> LENGTH: 33
<212> TYPE: RNA
<213> ORGANISM: Homo sapiens

<400> SEQUENCE: 627
guuuccguag uguagugguu aucacguucg cca 33

<210> SEQ ID NO 628
<211> LENGTH: 50
<212> TYPE: RNA
<213> ORGANISM: Homo sapiens

<400> SEQUENCE: 628
acacauugau caucgacacu ucgaacgcac uugcggcccc ggguuccucc 50

<210> SEQ ID NO 629
<211> LENGTH: 41
<212> TYPE: RNA
<213> ORGANISM: Homo sapiens

<400> SEQUENCE: 629
agcagccgac uuagaacugg ugcggaccag gggaauccga c 41

<210> SEQ ID NO 630
<211> LENGTH: 33
<212> TYPE: RNA
<213> ORGANISM: Homo sapiens

<400> SEQUENCE: 630
guuuccguag uguagugguu aucacguucg ccu 33

<210> SEQ ID NO 631
<211> LENGTH: 50
<212> TYPE: RNA
<213> ORGANISM: Homo sapiens

<400> SEQUENCE: 631
ccuacuugga uaacuguggu aauucuagag cuaauacaug ccgacgggcg 50

<210> SEQ ID NO 632
<211> LENGTH: 40
<212> TYPE: RNA
<213> ORGANISM: Homo sapiens

<400> SEQUENCE: 632
cgcgaccuca gaucagacgu ggcgacccgc ugaauuuaag 40

<210> SEQ ID NO 633

<211> LENGTH: 32
<212> TYPE: RNA
<213> ORGANISM: Homo sapiens

<400> SEQUENCE: 633
ccccuguggu cuagugguua ggauucggcg cu 32

<210> SEQ ID NO 634
<211> LENGTH: 50
<212> TYPE: RNA
<213> ORGANISM: Homo sapiens

<400> SEQUENCE: 634
cacauugauc aucgacacuu cgaacgcacu ugcggccccg gguuccuccc 50

<210> SEQ ID NO 635
<211> LENGTH: 32
<212> TYPE: RNA
<213> ORGANISM: Homo sapiens

<400> SEQUENCE: 635
ggccgugauc guauaguggu uaguacucug cg 32

<210> SEQ ID NO 636
<211> LENGTH: 43
<212> TYPE: RNA
<213> ORGANISM: Homo sapiens

<400> SEQUENCE: 636
aagcaggguc gggccugguu aguacuugga ugggagaccg ccu 43

<210> SEQ ID NO 637
<211> LENGTH: 38
<212> TYPE: RNA
<213> ORGANISM: Homo sapiens

<400> SEQUENCE: 637
aagggcuggg ucggucgggc uggggcgcga agcggggc 38

<210> SEQ ID NO 638
<211> LENGTH: 33
<212> TYPE: RNA
<213> ORGANISM: Homo sapiens

<400> SEQUENCE: 638
gccgugaucg uauagugguu aguacucugc guu 33

<210> SEQ ID NO 639
<211> LENGTH: 33
<212> TYPE: RNA
<213> ORGANISM: Homo sapiens

<400> SEQUENCE: 639
gcccggcuag cucagucggu agagcaugag acu 33

<210> SEQ ID NO 640
<211> LENGTH: 50
<212> TYPE: RNA
<213> ORGANISM: Homo sapiens

<400> SEQUENCE: 640
cgacucuuag cgguggauca cucggcucgu gcgucgauga agaacgcagc 50

```
<210> SEQ ID NO 641
<211> LENGTH: 50
<212> TYPE: RNA
<213> ORGANISM: Homo sapiens

<400> SEQUENCE: 641

acgacucuua gcgguggauc acucggcucg ugcgucgaug aagaacgcag          50

<210> SEQ ID NO 642
<211> LENGTH: 39
<212> TYPE: RNA
<213> ORGANISM: Homo sapiens

<400> SEQUENCE: 642

cgcgaccuca gaucagacgu ggcgacccgc ugaauuuaa                      39

<210> SEQ ID NO 643
<211> LENGTH: 32
<212> TYPE: RNA
<213> ORGANISM: Homo sapiens

<400> SEQUENCE: 643

ggcugguccg augguagugg guuaucagaa cu                             32

<210> SEQ ID NO 644
<211> LENGTH: 34
<212> TYPE: RNA
<213> ORGANISM: Homo sapiens

<400> SEQUENCE: 644

gccgugaucg uauagugguu aguacucugc guug                           34

<210> SEQ ID NO 645
<211> LENGTH: 50
<212> TYPE: RNA
<213> ORGANISM: Homo sapiens

<400> SEQUENCE: 645

aggacacauu gaucaucgac acuucgaacg cacuugcggc cccggguucc          50

<210> SEQ ID NO 646
<211> LENGTH: 42
<212> TYPE: RNA
<213> ORGANISM: Homo sapiens

<400> SEQUENCE: 646

auagucggca cuggcaauuu uugacagucu cuacggagac ug                  42

<210> SEQ ID NO 647
<211> LENGTH: 33
<212> TYPE: RNA
<213> ORGANISM: Homo sapiens

<400> SEQUENCE: 647

gcauuugugg uucaguggua gaauucucgc cug                            33

<210> SEQ ID NO 648
<211> LENGTH: 46
<212> TYPE: RNA
<213> ORGANISM: Homo sapiens

<400> SEQUENCE: 648

ugcggccccg gguuccuccc ggggcuacgc cugucugagc gucgcu              46
```

<210> SEQ ID NO 649
<211> LENGTH: 32
<212> TYPE: RNA
<213> ORGANISM: Homo sapiens

<400> SEQUENCE: 649
gcaugggugg uucaguggua gaauucucgc cu 32

<210> SEQ ID NO 650
<211> LENGTH: 30
<212> TYPE: RNA
<213> ORGANISM: Homo sapiens

<400> SEQUENCE: 650
ggccgugauc guauaguggu uaguacucug 30

<210> SEQ ID NO 651
<211> LENGTH: 29
<212> TYPE: RNA
<213> ORGANISM: Homo sapiens

<400> SEQUENCE: 651
gccgugaucg uauagugguu aguacucug 29

<210> SEQ ID NO 652
<211> LENGTH: 33
<212> TYPE: RNA
<213> ORGANISM: Homo sapiens

<400> SEQUENCE: 652
gcauuugugg uucaguggua gaauucucgc cuc 33

<210> SEQ ID NO 653
<211> LENGTH: 50
<212> TYPE: RNA
<213> ORGANISM: Homo sapiens

<400> SEQUENCE: 653
aauuccgaua acgaacgaga cucuggcaug cuaacuaguu acgcgacccc 50

<210> SEQ ID NO 654
<211> LENGTH: 32
<212> TYPE: RNA
<213> ORGANISM: Homo sapiens

<400> SEQUENCE: 654
gcauuggugg uucaguggua gaauucucgc cu 32

<210> SEQ ID NO 655
<211> LENGTH: 50
<212> TYPE: RNA
<213> ORGANISM: Homo sapiens

<400> SEQUENCE: 655
gguuaauucc gauaacgaac gagacucugg caugcuaacu aguuacgcga 50

<210> SEQ ID NO 656
<211> LENGTH: 33
<212> TYPE: RNA
<213> ORGANISM: Homo sapiens

<400> SEQUENCE: 656
gcauuggugg uucaguggua gaauucucgc cuu 33

<210> SEQ ID NO 657
<211> LENGTH: 42
<212> TYPE: RNA
<213> ORGANISM: Homo sapiens

<400> SEQUENCE: 657
acggcccugg cggagcgcug agaagacggu cgaacuugac ua 42

<210> SEQ ID NO 658
<211> LENGTH: 29
<212> TYPE: RNA
<213> ORGANISM: Homo sapiens

<400> SEQUENCE: 658
gcauuggugg uucaguggua gaauucucg 29

<210> SEQ ID NO 659
<211> LENGTH: 30
<212> TYPE: RNA
<213> ORGANISM: Homo sapiens

<400> SEQUENCE: 659
auuggucgug guuguagucc gugcgagaau 30

<210> SEQ ID NO 660
<211> LENGTH: 30
<212> TYPE: RNA
<213> ORGANISM: Homo sapiens

<400> SEQUENCE: 660
gcaugggugg uucaguggua gaauucucgc 30

<210> SEQ ID NO 661
<211> LENGTH: 41
<212> TYPE: RNA
<213> ORGANISM: Homo sapiens

<400> SEQUENCE: 661
auugaucauc gacacuucga acgcacuugc ggccccgggu u 41

<210> SEQ ID NO 662
<211> LENGTH: 50
<212> TYPE: RNA
<213> ORGANISM: Homo sapiens

<400> SEQUENCE: 662
cgcacuugcg gccccggguu ccucccgggg cuacgccugu cugagcgucg 50

<210> SEQ ID NO 663
<211> LENGTH: 35
<212> TYPE: RNA
<213> ORGANISM: Homo sapiens

<400> SEQUENCE: 663
ucccuggugg ucuagugguu aggauucggc gcucu 35

<210> SEQ ID NO 664
<211> LENGTH: 35
<212> TYPE: RNA
<213> ORGANISM: Homo sapiens

<400> SEQUENCE: 664
agugacgcgc augaauggau gaacgagauu cccac 35

<210> SEQ ID NO 665
<211> LENGTH: 32
<212> TYPE: RNA
<213> ORGANISM: Homo sapiens

<400> SEQUENCE: 665
ucccuggugg ucuaguggcu aggauucggc gc 32

<210> SEQ ID NO 666
<211> LENGTH: 33
<212> TYPE: RNA
<213> ORGANISM: Homo sapiens

<400> SEQUENCE: 666
guuuccguag uguagugguc aucacguucg ccu 33

<210> SEQ ID NO 667
<211> LENGTH: 47
<212> TYPE: RNA
<213> ORGANISM: Homo sapiens

<400> SEQUENCE: 667
uugcggcccc ggguuccucc cggggcuacg ccugucugag cgucgcu 47

<210> SEQ ID NO 668
<211> LENGTH: 49
<212> TYPE: RNA
<213> ORGANISM: Homo sapiens

<400> SEQUENCE: 668
gacucuuagc gguggaucac ucggcucgug cgucgaugaa gaacgcagc 49

<210> SEQ ID NO 669
<211> LENGTH: 31
<212> TYPE: RNA
<213> ORGANISM: Homo sapiens

<400> SEQUENCE: 669
gcauuugugg uucaguggua gaauucucgc c 31

<210> SEQ ID NO 670
<211> LENGTH: 35
<212> TYPE: RNA
<213> ORGANISM: Homo sapiens

<400> SEQUENCE: 670
cgcgaccuca gaucagacgu ggcgacccgc ugaau 35

<210> SEQ ID NO 671
<211> LENGTH: 49
<212> TYPE: RNA
<213> ORGANISM: Homo sapiens

<400> SEQUENCE: 671
cuugcggccc cggguuccuc ccggggcuac gccugucuga gcgucgcuu 49

<210> SEQ ID NO 672
<211> LENGTH: 34
<212> TYPE: RNA
<213> ORGANISM: Homo sapiens

<400> SEQUENCE: 672
ggccgugauc guauaguggu uaguacucug cguu 34

<210> SEQ ID NO 673
<211> LENGTH: 50
<212> TYPE: RNA
<213> ORGANISM: Homo sapiens

<400> SEQUENCE: 673
augugaauug caggacacau ugaucaucga cacuucgaac gcacuugcgg 50

<210> SEQ ID NO 674
<211> LENGTH: 33
<212> TYPE: RNA
<213> ORGANISM: Homo sapiens

<400> SEQUENCE: 674
cgcgaccuca gaucagacgu ggcgacccgc uga 33

<210> SEQ ID NO 675
<211> LENGTH: 43
<212> TYPE: RNA
<213> ORGANISM: Homo sapiens

<400> SEQUENCE: 675
acauugauca ucgacacuuc gaacgcacuu gcggccccgg guu 43

<210> SEQ ID NO 676
<211> LENGTH: 30
<212> TYPE: RNA
<213> ORGANISM: Homo sapiens

<400> SEQUENCE: 676
gcauuggugg uucaguggua gaauucucgc 30

<210> SEQ ID NO 677
<211> LENGTH: 50
<212> TYPE: RNA
<213> ORGANISM: Homo sapiens

<400> SEQUENCE: 677
cuacuuggau aacuguggua auucuagagc uaauacaugc cgacgggcgc 50

<210> SEQ ID NO 678
<211> LENGTH: 32
<212> TYPE: RNA
<213> ORGANISM: Homo sapiens

<400> SEQUENCE: 678
gcaugggugg uucaguggua gaauucucgc cg 32

<210> SEQ ID NO 679
<211> LENGTH: 32
<212> TYPE: RNA
<213> ORGANISM: Homo sapiens

<400> SEQUENCE: 679
gcauuugugg uucaguggua gaauucucgc cu 32

<210> SEQ ID NO 680
<211> LENGTH: 34
<212> TYPE: RNA
<213> ORGANISM: Homo sapiens

<400> SEQUENCE: 680
ucccuggugg ucuagugguu aggauucggc gcuc 34

<210> SEQ ID NO 681
<211> LENGTH: 36
<212> TYPE: RNA
<213> ORGANISM: Homo sapiens

<400> SEQUENCE: 681
gcgggagacc gggguucgau uccccgacgg ggagcc 36

<210> SEQ ID NO 682
<211> LENGTH: 36
<212> TYPE: RNA
<213> ORGANISM: Homo sapiens

<400> SEQUENCE: 682
ugccgugauc guauaguggu uaguacucug cguugu 36

<210> SEQ ID NO 683
<211> LENGTH: 31
<212> TYPE: RNA
<213> ORGANISM: Homo sapiens

<400> SEQUENCE: 683
gcauuggugg uucaguggua gaauucucgc c 31

<210> SEQ ID NO 684
<211> LENGTH: 35
<212> TYPE: RNA
<213> ORGANISM: Homo sapiens

<400> SEQUENCE: 684
guuuccguag uguaguggu u aucacguucg ccuga 35

<210> SEQ ID NO 685
<211> LENGTH: 50
<212> TYPE: RNA
<213> ORGANISM: Homo sapiens

<400> SEQUENCE: 685
uacgacucuu agcgguggau cacucggcuc gugcgucgau gaagaacgca 50

<210> SEQ ID NO 686
<211> LENGTH: 33
<212> TYPE: RNA
<213> ORGANISM: Homo sapiens

<400> SEQUENCE: 686
ggcugguccg augguagugg guuaucagaa cuu 33

<210> SEQ ID NO 687
<211> LENGTH: 33
<212> TYPE: RNA
<213> ORGANISM: Homo sapiens

<400> SEQUENCE: 687
guuuccguag uguagugguu aucacauucg ccu 33

<210> SEQ ID NO 688
<211> LENGTH: 50
<212> TYPE: RNA
<213> ORGANISM: Homo sapiens

```
<400> SEQUENCE: 688

cauugaucau cgacacuucg aacgcacuug cggccccggg uuccucccgg            50

<210> SEQ ID NO 689
<211> LENGTH: 34
<212> TYPE: RNA
<213> ORGANISM: Homo sapiens

<400> SEQUENCE: 689

gcauuugugg uucaguggua gaauucucgc cugc                            34

<210> SEQ ID NO 690
<211> LENGTH: 41
<212> TYPE: RNA
<213> ORGANISM: Homo sapiens

<400> SEQUENCE: 690

cgcgaccuca gaucagacgu ggcgacccgc ugaauuuaag c                    41

<210> SEQ ID NO 691
<211> LENGTH: 37
<212> TYPE: RNA
<213> ORGANISM: Homo sapiens

<400> SEQUENCE: 691

gcgggagacc gggguucgau uccccgacgg ggagcca                         37

<210> SEQ ID NO 692
<211> LENGTH: 38
<212> TYPE: RNA
<213> ORGANISM: Homo sapiens

<400> SEQUENCE: 692

ucugaagguc gugaguucgu uccucacacg gggcacca                        38

<210> SEQ ID NO 693
<211> LENGTH: 45
<212> TYPE: RNA
<213> ORGANISM: Homo sapiens

<400> SEQUENCE: 693

gcggccccgg guuccucccg gggcuacgcc ugucgagcg ucgcu                 45

<210> SEQ ID NO 694
<211> LENGTH: 34
<212> TYPE: RNA
<213> ORGANISM: Homo sapiens

<400> SEQUENCE: 694

gcauuggugg uucaguggua gaauucucgc cuuc                            34

<210> SEQ ID NO 695
<211> LENGTH: 47
<212> TYPE: RNA
<213> ORGANISM: Homo sapiens

<400> SEQUENCE: 695

ggcugguccg augguagugg guuaucagaa cuuauuaaca uuagugu              47

<210> SEQ ID NO 696
<211> LENGTH: 36
<212> TYPE: RNA
```

<213> ORGANISM: Homo sapiens

<400> SEQUENCE: 696
ggccgugauc guauaguggu uaguacucug cguugu 36

<210> SEQ ID NO 697
<211> LENGTH: 41
<212> TYPE: RNA
<213> ORGANISM: Homo sapiens

<400> SEQUENCE: 697
cgguggauca cucggcucgu gcgucgauga agaacgcagc u 41

<210> SEQ ID NO 698
<211> LENGTH: 50
<212> TYPE: RNA
<213> ORGANISM: Homo sapiens

<400> SEQUENCE: 698
aaggauuggc ucuaagggcu gggucggucg ggcuggggcg cgaagcgggg 50

<210> SEQ ID NO 699
<211> LENGTH: 36
<212> TYPE: RNA
<213> ORGANISM: Homo sapiens

<400> SEQUENCE: 699
cgggagaccg ggguucgauu ccccgacggg gagcca 36

<210> SEQ ID NO 700
<211> LENGTH: 37
<212> TYPE: RNA
<213> ORGANISM: Homo sapiens

<400> SEQUENCE: 700
cgcgaccuca gaucagacgu ggcgacccgc ugaauuu 37

<210> SEQ ID NO 701
<211> LENGTH: 45
<212> TYPE: RNA
<213> ORGANISM: Homo sapiens

<400> SEQUENCE: 701
cucgcugcga ucuauugaaa gucagcccuc gacacaaggg uuugu 45

<210> SEQ ID NO 702
<211> LENGTH: 36
<212> TYPE: RNA
<213> ORGANISM: Homo sapiens

<400> SEQUENCE: 702
agugacgcgc augaauggau gaacgagauu cccacu 36

<210> SEQ ID NO 703
<211> LENGTH: 31
<212> TYPE: RNA
<213> ORGANISM: Homo sapiens

<400> SEQUENCE: 703
ucccuggugg ucuagugguu aggauucggc g 31

<210> SEQ ID NO 704
<211> LENGTH: 50

<212> TYPE: RNA
<213> ORGANISM: Homo sapiens

<400> SEQUENCE: 704
ucguacgacu cuuagcggug gaucacucgg cucgugcguc gaugaagaac 50

<210> SEQ ID NO 705
<211> LENGTH: 33
<212> TYPE: RNA
<213> ORGANISM: Homo sapiens

<400> SEQUENCE: 705
gcccggcuag cucagucggu agagcauggg acu 33

<210> SEQ ID NO 706
<211> LENGTH: 50
<212> TYPE: RNA
<213> ORGANISM: Homo sapiens

<400> SEQUENCE: 706
acggcccugg cggagcgcug agaagacggu cgaacuugac uaucuagagg 50

<210> SEQ ID NO 707
<211> LENGTH: 32
<212> TYPE: RNA
<213> ORGANISM: Homo sapiens

<400> SEQUENCE: 707
guuuccguag uguagugguu aucacguucg cc 32

<210> SEQ ID NO 708
<211> LENGTH: 33
<212> TYPE: RNA
<213> ORGANISM: Homo sapiens

<400> SEQUENCE: 708
uauugaaagu cagcccucga cacaaggguu ugu 33

<210> SEQ ID NO 709
<211> LENGTH: 33
<212> TYPE: RNA
<213> ORGANISM: Homo sapiens

<400> SEQUENCE: 709
gcauuggugg uucaguggua gaauucucgc cuc 33

<210> SEQ ID NO 710
<211> LENGTH: 33
<212> TYPE: RNA
<213> ORGANISM: Homo sapiens

<400> SEQUENCE: 710
guuuccguag uguagugguu aucacguucg ccg 33

<210> SEQ ID NO 711
<211> LENGTH: 35
<212> TYPE: RNA
<213> ORGANISM: Homo sapiens

<400> SEQUENCE: 711
gccgugaucg uauaguggaa aguacucugc guugu 35

<210> SEQ ID NO 712

<211> LENGTH: 32
<212> TYPE: RNA
<213> ORGANISM: Homo sapiens

<400> SEQUENCE: 712
gcaugugugg uucaguggua gaauucucgc cu 32

<210> SEQ ID NO 713
<211> LENGTH: 34
<212> TYPE: RNA
<213> ORGANISM: Homo sapiens

<400> SEQUENCE: 713
gcauuggugg uucaguggua gaauucucgc cucc 34

<210> SEQ ID NO 714
<211> LENGTH: 49
<212> TYPE: RNA
<213> ORGANISM: Homo sapiens

<400> SEQUENCE: 714
cacuugcggc cccggguucc ucccggggcu acgccugucu gagcgucgc 49

<210> SEQ ID NO 715
<211> LENGTH: 33
<212> TYPE: RNA
<213> ORGANISM: Homo sapiens

<400> SEQUENCE: 715
uccccugugg ucuagugguu aggauucggc gcu 33

<210> SEQ ID NO 716
<211> LENGTH: 50
<212> TYPE: RNA
<213> ORGANISM: Homo sapiens

<400> SEQUENCE: 716
cgguggauca cucggcucgu gcgucgauga agaacgcagc uagcugcgag 50

<210> SEQ ID NO 717
<211> LENGTH: 30
<212> TYPE: RNA
<213> ORGANISM: Homo sapiens

<400> SEQUENCE: 717
cggcuagcuc agucgguaga gcaugggacu 30

<210> SEQ ID NO 718
<211> LENGTH: 34
<212> TYPE: RNA
<213> ORGANISM: Homo sapiens

<400> SEQUENCE: 718
gcccggcuag cucagucggu agagcauggg acuc 34

<210> SEQ ID NO 719
<211> LENGTH: 50
<212> TYPE: RNA
<213> ORGANISM: Homo sapiens

<400> SEQUENCE: 719
guacgacucu uagcggugga ucacucggcu cgugcgucga ugaagaacgc 50

<210> SEQ ID NO 720
<211> LENGTH: 33
<212> TYPE: RNA
<213> ORGANISM: Homo sapiens

<400> SEQUENCE: 720
gcuucuguag uguaguggu uaucacguucg ccu                33

<210> SEQ ID NO 721
<211> LENGTH: 31
<212> TYPE: RNA
<213> ORGANISM: Homo sapiens

<400> SEQUENCE: 721
aguaagguca gcuaaauaag cuaucgggcc c                  31

<210> SEQ ID NO 722
<211> LENGTH: 32
<212> TYPE: RNA
<213> ORGANISM: Homo sapiens

<400> SEQUENCE: 722
gcauuggugg uucaguggua gaauucucgc cg                 32

<210> SEQ ID NO 723
<211> LENGTH: 50
<212> TYPE: RNA
<213> ORGANISM: Homo sapiens

<400> SEQUENCE: 723
cguacgacuc uuagcggugg aucacucggc ucgugcgucg augaagaacg      50

<210> SEQ ID NO 724
<211> LENGTH: 46
<212> TYPE: RNA
<213> ORGANISM: Homo sapiens

<400> SEQUENCE: 724
aguaagguca gcuaaauaag cuaucgggcc cauaccccga aaaugu          46

<210> SEQ ID NO 725
<211> LENGTH: 32
<212> TYPE: RNA
<213> ORGANISM: Homo sapiens

<400> SEQUENCE: 725
gccugggugg uucaguggua gaauucucgc cu                 32

<210> SEQ ID NO 726
<211> LENGTH: 35
<212> TYPE: RNA
<213> ORGANISM: Homo sapiens

<400> SEQUENCE: 726
ggccgugauc guauaguggu uaguacucug cguug              35

<210> SEQ ID NO 727
<211> LENGTH: 29
<212> TYPE: RNA
<213> ORGANISM: Homo sapiens

<400> SEQUENCE: 727
aguaagguca gcuaaauaag cuaucgggc                     29

```
<210> SEQ ID NO 728
<211> LENGTH: 33
<212> TYPE: RNA
<213> ORGANISM: Homo sapiens

<400> SEQUENCE: 728

ucccuggugg ucuagugguu aggauucggc gcu                              33

<210> SEQ ID NO 729
<211> LENGTH: 33
<212> TYPE: RNA
<213> ORGANISM: Homo sapiens

<400> SEQUENCE: 729

ggccgugauc guauaguggu uaguacucug cgu                              33

<210> SEQ ID NO 730
<211> LENGTH: 44
<212> TYPE: RNA
<213> ORGANISM: Homo sapiens

<400> SEQUENCE: 730

acggcccugg cggagcgcug agaagacggu cgaacuugac uauc                  44

<210> SEQ ID NO 731
<211> LENGTH: 32
<212> TYPE: RNA
<213> ORGANISM: Homo sapiens

<400> SEQUENCE: 731

gcauuagugg uucaguggua gaauucucgc cu                               32

<210> SEQ ID NO 732
<211> LENGTH: 42
<212> TYPE: RNA
<213> ORGANISM: Homo sapiens

<400> SEQUENCE: 732

cgcgaccuca gaucagacgu ggcgacccgc ugaauuuaag ca                    42

<210> SEQ ID NO 733
<211> LENGTH: 49
<212> TYPE: RNA
<213> ORGANISM: Homo sapiens

<400> SEQUENCE: 733

gcaggacaca uugaucaucg acacuucgaa cgcacuugcg gccccgggu             49

<210> SEQ ID NO 734
<211> LENGTH: 29
<212> TYPE: RNA
<213> ORGANISM: Homo sapiens

<400> SEQUENCE: 734

cggcgcgcgg cggcggcggc ggcggcggc                                   29

<210> SEQ ID NO 735
<211> LENGTH: 32
<212> TYPE: RNA
<213> ORGANISM: Homo sapiens

<400> SEQUENCE: 735

aucauugguc gugguuguag uccgugcgag aa                               32
```

<210> SEQ ID NO 736
<211> LENGTH: 36
<212> TYPE: RNA
<213> ORGANISM: Homo sapiens

<400> SEQUENCE: 736
gaacaugggu cagucggucc ugagagaugg gcgagc 36

<210> SEQ ID NO 737
<211> LENGTH: 34
<212> TYPE: RNA
<213> ORGANISM: Homo sapiens

<400> SEQUENCE: 737
ccagugcgcc ccgggcgggu cgcgccgucg ggcc 34

<210> SEQ ID NO 738
<211> LENGTH: 50
<212> TYPE: RNA
<213> ORGANISM: Homo sapiens

<400> SEQUENCE: 738
gcacuugcgg ccccggguuc cucccggggc uacgccuguc ugagcgucgc 50

<210> SEQ ID NO 739
<211> LENGTH: 32
<212> TYPE: RNA
<213> ORGANISM: Homo sapiens

<400> SEQUENCE: 739
gcauuggugg uucaguggua gaauucccgc cu 32

<210> SEQ ID NO 740
<211> LENGTH: 32
<212> TYPE: RNA
<213> ORGANISM: Homo sapiens

<400> SEQUENCE: 740
gcauuggagg uucaguggua gaauucucgc cu 32

<210> SEQ ID NO 741
<211> LENGTH: 50
<212> TYPE: RNA
<213> ORGANISM: Homo sapiens

<400> SEQUENCE: 741
acauugauca ucgacacuuc gaacgcacuu gcggccccgg guuccucccc 50

<210> SEQ ID NO 742
<211> LENGTH: 31
<212> TYPE: RNA
<213> ORGANISM: Homo sapiens

<400> SEQUENCE: 742
gccgugaucg uauagugguu aguacucugc g 31

<210> SEQ ID NO 743
<211> LENGTH: 50
<212> TYPE: RNA
<213> ORGANISM: Homo sapiens

<400> SEQUENCE: 743
ucgcgugaug acauucuccg gaaucgcugu acggccuuga ugaaagcaca 50

<210> SEQ ID NO 744
<211> LENGTH: 33
<212> TYPE: RNA
<213> ORGANISM: Homo sapiens

<400> SEQUENCE: 744
guuuccguag uguaguggu aucacuuucg ccu 33

<210> SEQ ID NO 745
<211> LENGTH: 49
<212> TYPE: RNA
<213> ORGANISM: Homo sapiens

<400> SEQUENCE: 745
uuaguacuug gaugggagac cgccugggaa uaccgggugc uguaggcuu 49

<210> SEQ ID NO 746
<211> LENGTH: 50
<212> TYPE: RNA
<213> ORGANISM: Homo sapiens

<400> SEQUENCE: 746
ucccacaugg ucuagcgguu aggauuccug guuuucaccc aggcggcccg 50

<210> SEQ ID NO 747
<211> LENGTH: 32
<212> TYPE: RNA
<213> ORGANISM: Homo sapiens

<400> SEQUENCE: 747
gcauuggugg uucaguggua gaauuaucgc cu 32

<210> SEQ ID NO 748
<211> LENGTH: 29
<212> TYPE: RNA
<213> ORGANISM: Homo sapiens

<400> SEQUENCE: 748
gcaugggugg uucaguggua gaauucucg 29

<210> SEQ ID NO 749
<211> LENGTH: 50
<212> TYPE: RNA
<213> ORGANISM: Homo sapiens

<400> SEQUENCE: 749
acauugauca ucgacacuuc gaacgcacuu gcggccccgg gcuccucccg 50

<210> SEQ ID NO 750
<211> LENGTH: 44
<212> TYPE: RNA
<213> ORGANISM: Homo sapiens

<400> SEQUENCE: 750
gguucgugcu gaaggccugu auccuaggcu acacacugag gacu 44

<210> SEQ ID NO 751
<211> LENGTH: 26
<212> TYPE: RNA
<213> ORGANISM: Homo sapiens

<400> SEQUENCE: 751
uagcucaguc gguagagcau gggacu 26

<210> SEQ ID NO 752
<211> LENGTH: 50
<212> TYPE: RNA
<213> ORGANISM: Homo sapiens

<400> SEQUENCE: 752
uaccugguug auccugccag uagcauaugc uugucucaaa gauuaagcca 50

<210> SEQ ID NO 753
<211> LENGTH: 43
<212> TYPE: RNA
<213> ORGANISM: Homo sapiens

<400> SEQUENCE: 753
ccagugcgcc ccgggcgggu cgcgccgucg ggcccggggg agg 43

<210> SEQ ID NO 754
<211> LENGTH: 35
<212> TYPE: RNA
<213> ORGANISM: Homo sapiens

<400> SEQUENCE: 754
cgggagaccg ggguucgauu ccccgacggg gagcc 35

<210> SEQ ID NO 755
<211> LENGTH: 26
<212> TYPE: RNA
<213> ORGANISM: Homo sapiens

<400> SEQUENCE: 755
gucaggaugg ccgagcgguc uaaggc 26

<210> SEQ ID NO 756
<211> LENGTH: 50
<212> TYPE: RNA
<213> ORGANISM: Homo sapiens

<400> SEQUENCE: 756
cacuguaaag cuaacuuagc auuaaccuuu uaaguuaaag auuaagagaa 50

<210> SEQ ID NO 757
<211> LENGTH: 49
<212> TYPE: RNA
<213> ORGANISM: Homo sapiens

<400> SEQUENCE: 757
uuccuaugau gaggaccuuu ucacagaccu guacugagcu ccgugagga 49

<210> SEQ ID NO 758
<211> LENGTH: 33
<212> TYPE: RNA
<213> ORGANISM: Homo sapiens

<400> SEQUENCE: 758
gccuuggugg uucaguggua gaauucucgc cuc 33

<210> SEQ ID NO 759
<211> LENGTH: 32
<212> TYPE: RNA
<213> ORGANISM: Homo sapiens

<400> SEQUENCE: 759
gcauuggugg uuuaguggua gaauucucgc cu 32

<210> SEQ ID NO 760
<211> LENGTH: 50
<212> TYPE: RNA
<213> ORGANISM: Homo sapiens

<400> SEQUENCE: 760
guuuauguag cuuaccuccu caaagcaaua cacugaaaau guuuagacgg 50

<210> SEQ ID NO 761
<211> LENGTH: 43
<212> TYPE: RNA
<213> ORGANISM: Homo sapiens

<400> SEQUENCE: 761
cgcgaccuca gaucagacgu ggcgacccgc ugaauuuaag cau 43

<210> SEQ ID NO 762
<211> LENGTH: 44
<212> TYPE: RNA
<213> ORGANISM: Homo sapiens

<400> SEQUENCE: 762
ccagugcgcc ccgggcgggu cgcgccgucg ggcccggggg aggu 44

<210> SEQ ID NO 763
<211> LENGTH: 50
<212> TYPE: RNA
<213> ORGANISM: Homo sapiens

<400> SEQUENCE: 763
aaugugaauu gcaggacaca uugaucaucg acacuucgaa cgcacuugcg 50

<210> SEQ ID NO 764
<211> LENGTH: 32
<212> TYPE: RNA
<213> ORGANISM: Homo sapiens

<400> SEQUENCE: 764
gcauuggugg cucaguggua gaauucucgc cu 32

<210> SEQ ID NO 765
<211> LENGTH: 31
<212> TYPE: RNA
<213> ORGANISM: Homo sapiens

<400> SEQUENCE: 765
agcagagugg cgcagcggaa gcgugcuggg c 31

<210> SEQ ID NO 766
<211> LENGTH: 32
<212> TYPE: RNA
<213> ORGANISM: Homo sapiens

<400> SEQUENCE: 766
gcaugggcgg uucaguggua gaauucucgc cu 32

<210> SEQ ID NO 767
<211> LENGTH: 28
<212> TYPE: RNA
<213> ORGANISM: Homo sapiens

```
<400> SEQUENCE: 767

agcagccgac uuagaacugg ugcggacc                                      28

<210> SEQ ID NO 768
<211> LENGTH: 50
<212> TYPE: RNA
<213> ORGANISM: Homo sapiens

<400> SEQUENCE: 768

auugaucauc gacacuucga acgcacuugc ggccccgggc uccucccggg              50

<210> SEQ ID NO 769
<211> LENGTH: 33
<212> TYPE: RNA
<213> ORGANISM: Homo sapiens

<400> SEQUENCE: 769

gcauuggugg uucaguggua gaauucucgc cua                                33

<210> SEQ ID NO 770
<211> LENGTH: 49
<212> TYPE: RNA
<213> ORGANISM: Homo sapiens

<400> SEQUENCE: 770

ugcaggacac auugaucauc gacacuucga acgcacuugc ggccccggg               49

<210> SEQ ID NO 771
<211> LENGTH: 36
<212> TYPE: RNA
<213> ORGANISM: Homo sapiens

<400> SEQUENCE: 771

ggcugguccg augguagugg guuaucagaa cuuauu                             36

<210> SEQ ID NO 772
<211> LENGTH: 35
<212> TYPE: RNA
<213> ORGANISM: Homo sapiens

<400> SEQUENCE: 772

gcauuggugg uucaguggua gaauucucgc cuccc                              35

<210> SEQ ID NO 773
<211> LENGTH: 35
<212> TYPE: RNA
<213> ORGANISM: Homo sapiens

<400> SEQUENCE: 773

ucccuggugg ucuaguggcu aggauucggc gcuuu                              35

<210> SEQ ID NO 774
<211> LENGTH: 36
<212> TYPE: RNA
<213> ORGANISM: Homo sapiens

<400> SEQUENCE: 774

guuuccguag uguagugguu aucacguucg ccugac                             36

<210> SEQ ID NO 775
<211> LENGTH: 48
<212> TYPE: RNA
```

<213> ORGANISM: Homo sapiens

<400> SEQUENCE: 775
acuuggauaa cugugguaau ucuagagcua auacaugccg acgggcgc 48

<210> SEQ ID NO 776
<211> LENGTH: 50
<212> TYPE: RNA
<213> ORGANISM: Homo sapiens

<400> SEQUENCE: 776
cuaucuagag gaaguaaaag ucguaacaag guuuccguag gugaaccugc 50

<210> SEQ ID NO 777
<211> LENGTH: 50
<212> TYPE: RNA
<213> ORGANISM: Homo sapiens

<400> SEQUENCE: 777
acgcacuugc ggccccgggu uccucccggg gcuacgccug ucugagcguc 50

<210> SEQ ID NO 778
<211> LENGTH: 32
<212> TYPE: RNA
<213> ORGANISM: Homo sapiens

<400> SEQUENCE: 778
augggucagu cgguccugag agaugggcga gc 32

<210> SEQ ID NO 779
<211> LENGTH: 48
<212> TYPE: RNA
<213> ORGANISM: Homo sapiens

<400> SEQUENCE: 779
acggcccugg cggagcgcug agaagacggu cgaacuugac uaucuaga 48

<210> SEQ ID NO 780
<211> LENGTH: 30
<212> TYPE: RNA
<213> ORGANISM: Homo sapiens

<400> SEQUENCE: 780
uuggucgugg uuguaguccg ugcgagaaua 30

<210> SEQ ID NO 781
<211> LENGTH: 50
<212> TYPE: RNA
<213> ORGANISM: Homo sapiens

<400> SEQUENCE: 781
aaugugagac gaauuuuuga gcggguaaag gucgcccuca aggugacccg 50

<210> SEQ ID NO 782
<211> LENGTH: 26
<212> TYPE: RNA
<213> ORGANISM: Homo sapiens

<400> SEQUENCE: 782
gagaaagcuc acaagaacug cuaacu 26

<210> SEQ ID NO 783
<211> LENGTH: 33

<212> TYPE: RNA
<213> ORGANISM: Homo sapiens

<400> SEQUENCE: 783
gcaugggugg uucaguggua gaauucucgc cuc                                33

<210> SEQ ID NO 784
<211> LENGTH: 49
<212> TYPE: RNA
<213> ORGANISM: Homo sapiens

<400> SEQUENCE: 784
aacuguggua auucuagagc uaauacaugc cgacgggcgc ugacccccu               49

<210> SEQ ID NO 785
<211> LENGTH: 32
<212> TYPE: RNA
<213> ORGANISM: Homo sapiens

<400> SEQUENCE: 785
gcccggcuag cucagucggu agagcaugag ac                                32

<210> SEQ ID NO 786
<211> LENGTH: 34
<212> TYPE: RNA
<213> ORGANISM: Homo sapiens

<400> SEQUENCE: 786
aguugguccg aguguugugg guuauuguua aguu                              34

<210> SEQ ID NO 787
<211> LENGTH: 33
<212> TYPE: RNA
<213> ORGANISM: Homo sapiens

<400> SEQUENCE: 787
gcauuagugg uucaguggua gaauucucgc cuc                               33

<210> SEQ ID NO 788
<211> LENGTH: 39
<212> TYPE: RNA
<213> ORGANISM: Homo sapiens

<400> SEQUENCE: 788
gaugggagac cgccugggaa uaccgggugc uguaggcuu                         39

<210> SEQ ID NO 789
<211> LENGTH: 50
<212> TYPE: RNA
<213> ORGANISM: Homo sapiens

<400> SEQUENCE: 789
cgcgaccuca gaucagacgu ggcgacccgc ugaauuuaag cauauuaguc              50

<210> SEQ ID NO 790
<211> LENGTH: 35
<212> TYPE: RNA
<213> ORGANISM: Homo sapiens

<400> SEQUENCE: 790
uccucguuag uauaguggug aguaucccg ccugu                              35

<210> SEQ ID NO 791

```
<211> LENGTH: 32
<212> TYPE: RNA
<213> ORGANISM: Homo sapiens

<400> SEQUENCE: 791

uuggucgugg uuguaguccg ugcgagaaua cc                                    32

<210> SEQ ID NO 792
<211> LENGTH: 48
<212> TYPE: RNA
<213> ORGANISM: Homo sapiens

<400> SEQUENCE: 792

cuugcggccc cggguuccuc ccggggcuac gccugucuga gcgucgcg                   48

<210> SEQ ID NO 793
<211> LENGTH: 32
<212> TYPE: RNA
<213> ORGANISM: Homo sapiens

<400> SEQUENCE: 793

gcaugggagg uucaguggua gaauucucgc cu                                    32

<210> SEQ ID NO 794
<211> LENGTH: 32
<212> TYPE: RNA
<213> ORGANISM: Homo sapiens

<400> SEQUENCE: 794

gcauuggugg uucaguggua gacuucucgc cu                                    32

<210> SEQ ID NO 795
<211> LENGTH: 32
<212> TYPE: RNA
<213> ORGANISM: Homo sapiens

<400> SEQUENCE: 795

gcacuggugg uucaguggua gaauucucgc cu                                    32

<210> SEQ ID NO 796
<211> LENGTH: 29
<212> TYPE: RNA
<213> ORGANISM: Homo sapiens

<400> SEQUENCE: 796

cgcgaccuca gaucagacgu ggcgacccg                                        29

<210> SEQ ID NO 797
<211> LENGTH: 29
<212> TYPE: RNA
<213> ORGANISM: Homo sapiens

<400> SEQUENCE: 797

acuuggauaa cugugguaau ucuagagcu                                        29

<210> SEQ ID NO 798
<211> LENGTH: 32
<212> TYPE: RNA
<213> ORGANISM: Homo sapiens

<400> SEQUENCE: 798

gcauuggugg uucaguggua gaauucuagc cu                                    32
```

<210> SEQ ID NO 799
<211> LENGTH: 31
<212> TYPE: RNA
<213> ORGANISM: Homo sapiens

<400> SEQUENCE: 799
ucccuguggu cuaguggcua ggauucggcg c 31

<210> SEQ ID NO 800
<211> LENGTH: 45
<212> TYPE: RNA
<213> ORGANISM: Homo sapiens

<400> SEQUENCE: 800
aauauagucg gcacuggcaa uuuuugacag ucucuacgga gacug 45

<210> SEQ ID NO 801
<211> LENGTH: 50
<212> TYPE: RNA
<213> ORGANISM: Homo sapiens

<400> SEQUENCE: 801
ccacuacucu gaucguuuuu ucacugaccc ggugaggcgg gggggcgagc 50

<210> SEQ ID NO 802
<211> LENGTH: 32
<212> TYPE: RNA
<213> ORGANISM: Homo sapiens

<400> SEQUENCE: 802
gcauuggugg uuccguggua gaauucucgc cu 32

<210> SEQ ID NO 803
<211> LENGTH: 50
<212> TYPE: RNA
<213> ORGANISM: Homo sapiens

<400> SEQUENCE: 803
acgaacgaga cucuggcaug cuaacuaguu acgcgacccc cgagcggucg 50

<210> SEQ ID NO 804
<211> LENGTH: 50
<212> TYPE: RNA
<213> ORGANISM: Homo sapiens

<400> SEQUENCE: 804
augggucagu cgguccugag agaugggcga gcgccguucc gaagggacgg 50

<210> SEQ ID NO 805
<211> LENGTH: 38
<212> TYPE: RNA
<213> ORGANISM: Homo sapiens

<400> SEQUENCE: 805
ucugaggguc cagguucag gucccuguuc gggcgcca 38

<210> SEQ ID NO 806
<211> LENGTH: 48
<212> TYPE: RNA
<213> ORGANISM: Homo sapiens

<400> SEQUENCE: 806
guaacaaggu uuccguaggu gaaccugcgg aaggaucauu aacggagc 48

<210> SEQ ID NO 807
<211> LENGTH: 49
<212> TYPE: RNA
<213> ORGANISM: Homo sapiens

<400> SEQUENCE: 807
aacgcacuug cggccccggg uuccucccgg ggcuacgccu gucugagcg 49

<210> SEQ ID NO 808
<211> LENGTH: 28
<212> TYPE: RNA
<213> ORGANISM: Homo sapiens

<400> SEQUENCE: 808
uaggaugggg ugugauaggu ggcacgga 28

<210> SEQ ID NO 809
<211> LENGTH: 50
<212> TYPE: RNA
<213> ORGANISM: Homo sapiens

<400> SEQUENCE: 809 agugguuac uagagaaguu ucucugaacg uguagagcac cgaaaaccac 50

<210> SEQ ID NO 810
<211> LENGTH: 30
<212> TYPE: RNA
<213> ORGANISM: Homo sapiens

<400> SEQUENCE: 810
ggccgugauc guauaguggc uaguacucug 30

<210> SEQ ID NO 811
<211> LENGTH: 31
<212> TYPE: RNA
<213> ORGANISM: Homo sapiens

<400> SEQUENCE: 811
ccaagcguug gauuguucac ccacuaauag g 31

<210> SEQ ID NO 812
<211> LENGTH: 32
<212> TYPE: RNA
<213> ORGANISM: Homo sapiens

<400> SEQUENCE: 812
gcauuggugg uucaguggua gaauucuccc cu 32

<210> SEQ ID NO 813
<211> LENGTH: 45
<212> TYPE: RNA
<213> ORGANISM: Homo sapiens

<400> SEQUENCE: 813
gcuaagcagg gucgggccug guuaguacuu ggaugggaga ccgcc 45

<210> SEQ ID NO 814
<211> LENGTH: 33
<212> TYPE: RNA
<213> ORGANISM: Homo sapiens

<400> SEQUENCE: 814
uaggaugggg ugugauaggu ggcacggaga auu 33

<210> SEQ ID NO 815
<211> LENGTH: 42
<212> TYPE: RNA
<213> ORGANISM: Homo sapiens

<400> SEQUENCE: 815
uuuuucauau cauuggucgu gguuguaguc cgugcgagaa ua 42

<210> SEQ ID NO 816
<211> LENGTH: 28
<212> TYPE: RNA
<213> ORGANISM: Homo sapiens

<400> SEQUENCE: 816
cgugaucgua uagugguuag uacucugc 28

<210> SEQ ID NO 817
<211> LENGTH: 37
<212> TYPE: RNA
<213> ORGANISM: Homo sapiens

<400> SEQUENCE: 817
ggcugguccg augguagugg guuaucagaa cuuauua 37

<210> SEQ ID NO 818
<211> LENGTH: 33
<212> TYPE: RNA
<213> ORGANISM: Homo sapiens

<400> SEQUENCE: 818
gucuacggcc auaccacccu gaacgcgccc gau 33

<210> SEQ ID NO 819
<211> LENGTH: 45
<212> TYPE: RNA
<213> ORGANISM: Homo sapiens

<400> SEQUENCE: 819
cacccggggg gccggcggcg gcggcgacuc uggacgcgag ccggg 45

<210> SEQ ID NO 820
<211> LENGTH: 31
<212> TYPE: RNA
<213> ORGANISM: Homo sapiens

<400> SEQUENCE: 820
guuuccguag uguagugguu aucacguucg c 31

<210> SEQ ID NO 821
<211> LENGTH: 43
<212> TYPE: RNA
<213> ORGANISM: Homo sapiens

<400> SEQUENCE: 821
cuuggauggg agaccgccug ggaauaccgg gugcuguagg cuu 43

<210> SEQ ID NO 822
<211> LENGTH: 27
<212> TYPE: RNA
<213> ORGANISM: Homo sapiens

<400> SEQUENCE: 822
cggccgggcg cgacccgcuc cggggac 27

<210> SEQ ID NO 823
<211> LENGTH: 39
<212> TYPE: RNA
<213> ORGANISM: Homo sapiens

<400> SEQUENCE: 823
cugccacgcg ggaggcccgg guucguuucc cggcccaug 39

<210> SEQ ID NO 824
<211> LENGTH: 27
<212> TYPE: RNA
<213> ORGANISM: Homo sapiens

<400> SEQUENCE: 824
gcaugggugg uucaguggua gaauucu 27

<210> SEQ ID NO 825
<211> LENGTH: 39
<212> TYPE: RNA
<213> ORGANISM: Homo sapiens

<400> SEQUENCE: 825
cucucaccgc cgcggcccgg guucgauucc cggucaggg 39

<210> SEQ ID NO 826
<211> LENGTH: 36
<212> TYPE: RNA
<213> ORGANISM: Homo sapiens

<400> SEQUENCE: 826
ucccuggugg ucuagugguu aggauucggc gcucuc 36

<210> SEQ ID NO 827
<211> LENGTH: 34
<212> TYPE: RNA
<213> ORGANISM: Homo sapiens

<400> SEQUENCE: 827
aucauugguc gugguuguag uccgugcgag aaua 34

<210> SEQ ID NO 828
<211> LENGTH: 32
<212> TYPE: RNA
<213> ORGANISM: Homo sapiens

<400> SEQUENCE: 828
auugugaauc ugacaacaga ggcuuacgac cc 32

<210> SEQ ID NO 829
<211> LENGTH: 29
<212> TYPE: RNA
<213> ORGANISM: Homo sapiens

<400> SEQUENCE: 829
gcccggcuag cucagucggu agagcaugg 29

<210> SEQ ID NO 830
<211> LENGTH: 42
<212> TYPE: RNA
<213> ORGANISM: Homo sapiens

<400> SEQUENCE: 830

-continued aagcaggguc gggccugguu aguacuugga ugggagaccg cc          42

<210> SEQ ID NO 831
<211> LENGTH: 30
<212> TYPE: RNA
<213> ORGANISM: Homo sapiens

<400> SEQUENCE: 831
gcguuggugg uauagugguu agcauagcug                        30

<210> SEQ ID NO 832
<211> LENGTH: 50
<212> TYPE: RNA
<213> ORGANISM: Homo sapiens

<400> SEQUENCE: 832
gcgggccgcc ggugaaauac cacuacucug aucguuuuuu cacugacccg  50

<210> SEQ ID NO 833
<211> LENGTH: 29
<212> TYPE: RNA
<213> ORGANISM: Homo sapiens

<400> SEQUENCE: 833
ccaagcguug gauuguucac ccacuaaua                         29

<210> SEQ ID NO 834
<211> LENGTH: 27
<212> TYPE: RNA
<213> ORGANISM: Homo sapiens

<400> SEQUENCE: 834
cgugaucgua uagugguuag uacucug                           27

<210> SEQ ID NO 835
<211> LENGTH: 26
<212> TYPE: RNA
<213> ORGANISM: Homo sapiens

<400> SEQUENCE: 835
cccuucccgu ggaucgcccc agcugc                            26

<210> SEQ ID NO 836
<211> LENGTH: 33
<212> TYPE: RNA
<213> ORGANISM: Homo sapiens

<400> SEQUENCE: 836
ucccuggugg ucuagugguu aggauucggc gcg                    33

<210> SEQ ID NO 837
<211> LENGTH: 32
<212> TYPE: RNA
<213> ORGANISM: Homo sapiens

<400> SEQUENCE: 837
gcauuggugg uucagugguu agauucucgu cu                     32

<210> SEQ ID NO 838
<211> LENGTH: 50
<212> TYPE: RNA
<213> ORGANISM: Homo sapiens

<400> SEQUENCE: 838
ccguggagag gaacgagugu gagucugaaa ccaauuuuuu gaggccuugc 50

<210> SEQ ID NO 839
<211> LENGTH: 27
<212> TYPE: RNA
<213> ORGANISM: Homo sapiens

<400> SEQUENCE: 839
ucccacaugg ucuagcgguu aggauuc 27

<210> SEQ ID NO 840
<211> LENGTH: 30
<212> TYPE: RNA
<213> ORGANISM: Homo sapiens

<400> SEQUENCE: 840
gcguuugugg uauaguggug agcauagcug 30

<210> SEQ ID NO 841
<211> LENGTH: 42
<212> TYPE: RNA
<213> ORGANISM: Homo sapiens

<400> SEQUENCE: 841
cucucaccgc cgcggcccgg guucguuucc cggucaggga ac 42

<210> SEQ ID NO 842
<211> LENGTH: 29
<212> TYPE: RNA
<213> ORGANISM: Homo sapiens

<400> SEQUENCE: 842
ugccgugauc guauaguggu uaguacucu 29

<210> SEQ ID NO 843
<211> LENGTH: 32
<212> TYPE: RNA
<213> ORGANISM: Homo sapiens

<400> SEQUENCE: 843
ggggguauag cucaguggua gagcauuuga cu 32

<210> SEQ ID NO 844
<211> LENGTH: 46
<212> TYPE: RNA
<213> ORGANISM: Homo sapiens

<400> SEQUENCE: 844
cgcucucacc gccgcggccc ggguucgauu cccggucagg gaacca 46

<210> SEQ ID NO 845
<211> LENGTH: 42
<212> TYPE: RNA
<213> ORGANISM: Homo sapiens

<400> SEQUENCE: 845
aacggagcag gucaaaacuc ccgugcugau caguaguggg au 42

<210> SEQ ID NO 846
<211> LENGTH: 29
<212> TYPE: RNA
<213> ORGANISM: Homo sapiens -continued

<400> SEQUENCE: 846
ccccuguggu cuagugguua ggauucggc 29

<210> SEQ ID NO 847
<211> LENGTH: 29
<212> TYPE: RNA
<213> ORGANISM: Homo sapiens

<400> SEQUENCE: 847
gcccggcuag cucagucggu agagcauga 29

<210> SEQ ID NO 848
<211> LENGTH: 50
<212> TYPE: RNA
<213> ORGANISM: Homo sapiens

<400> SEQUENCE: 848
ugguuaguac uuggauggga gaccgccugg gaauaccggg ugcuguaggc 50

<210> SEQ ID NO 849
<211> LENGTH: 38
<212> TYPE: RNA
<213> ORGANISM: Homo sapiens

<400> SEQUENCE: 849
augggagacc gccugggaau accgggugcu guaggcuu 38

<210> SEQ ID NO 850
<211> LENGTH: 32
<212> TYPE: RNA
<213> ORGANISM: Homo sapiens

<400> SEQUENCE: 850
ggccgugauc guauagugga uaguacucug cg 32

<210> SEQ ID NO 851
<211> LENGTH: 50
<212> TYPE: RNA
<213> ORGANISM: Homo sapiens

<400> SEQUENCE: 851
cauugugaag cagaauucac caagcguugg auuguucacc cacuaauagg 50

<210> SEQ ID NO 852
<211> LENGTH: 27
<212> TYPE: RNA
<213> ORGANISM: Homo sapiens

<400> SEQUENCE: 852
ucccuggugg ucuagugguu aggauuc 27

<210> SEQ ID NO 853
<211> LENGTH: 32
<212> TYPE: RNA
<213> ORGANISM: Homo sapiens

<400> SEQUENCE: 853
gcauuggugg uucagcggua gaauucucgc cu 32

<210> SEQ ID NO 854
<211> LENGTH: 49
<212> TYPE: RNA

<213> ORGANISM: Homo sapiens

<400> SEQUENCE: 854 cacccgggggg gccggcggcg gcggcgacuc uggacgcgag ccgggcccu    49

<210> SEQ ID NO 855
<211> LENGTH: 37
<212> TYPE: RNA
<213> ORGANISM: Homo sapiens

<400> SEQUENCE: 855
ucugaagguc gugaguucgu uccucacacg gggcacc    37

<210> SEQ ID NO 856
<211> LENGTH: 33
<212> TYPE: RNA
<213> ORGANISM: Homo sapiens

<400> SEQUENCE: 856
cggcggcggc ggcgacucug gacgcgagcc ggg    33

<210> SEQ ID NO 857
<211> LENGTH: 31
<212> TYPE: RNA
<213> ORGANISM: Homo sapiens

<400> SEQUENCE: 857
ucccuggagg ucuagugguu aggauucggc g    31

<210> SEQ ID NO 858
<211> LENGTH: 27
<212> TYPE: RNA
<213> ORGANISM: Homo sapiens

<400> SEQUENCE: 858
ccgugaucgu auagugguua guacucu    27

<210> SEQ ID NO 859
<211> LENGTH: 31
<212> TYPE: RNA
<213> ORGANISM: Homo sapiens

<400> SEQUENCE: 859
uccccugugg ucuagugguu aggauucggc g    31

<210> SEQ ID NO 860
<211> LENGTH: 30
<212> TYPE: RNA
<213> ORGANISM: Homo sapiens

<400> SEQUENCE: 860
ggccgcgauc guauagugguu aguacucug    30

<210> SEQ ID NO 861
<211> LENGTH: 28
<212> TYPE: RNA
<213> ORGANISM: Homo sapiens

<400> SEQUENCE: 861
gcccggcuag cucagucggu agagcaug    28

<210> SEQ ID NO 862
<211> LENGTH: 30

<212> TYPE: RNA
<213> ORGANISM: Homo sapiens

<400> SEQUENCE: 862
ucccauaugg ucuagcgguu aggauuccug 30

<210> SEQ ID NO 863
<211> LENGTH: 45
<212> TYPE: RNA
<213> ORGANISM: Homo sapiens

<400> SEQUENCE: 863
ccugucacgc gggagaccgg gguucgauuc cccgacgggg agcca 45

<210> SEQ ID NO 864
<211> LENGTH: 34
<212> TYPE: RNA
<213> ORGANISM: Homo sapiens

<400> SEQUENCE: 864
ucccuggugg ucuaguggcu aggauucggc gcuu 34

<210> SEQ ID NO 865
<211> LENGTH: 50
<212> TYPE: RNA
<213> ORGANISM: Homo sapiens

<400> SEQUENCE: 865
uguguuacua gagaaguuuc ucugaacgug uagagcaccg aaaaccacga 50

<210> SEQ ID NO 866
<211> LENGTH: 35
<212> TYPE: RNA
<213> ORGANISM: Homo sapiens

<400> SEQUENCE: 866
cauaucauug gucgugguug uaguccgugc gagaa 35

<210> SEQ ID NO 867
<211> LENGTH: 45
<212> TYPE: RNA
<213> ORGANISM: Homo sapiens

<400> SEQUENCE: 867
gauucccauu cuugcgaccc ggguucguuu cccgggcggc gcacc 45

<210> SEQ ID NO 868
<211> LENGTH: 50
<212> TYPE: RNA
<213> ORGANISM: Homo sapiens

<400> SEQUENCE: 868
cugcgaugau ggcauuucuu aggacaccuu uggauuaaua augaaaacaa 50

<210> SEQ ID NO 869
<211> LENGTH: 45
<212> TYPE: RNA
<213> ORGANISM: Homo sapiens

<400> SEQUENCE: 869
cgcucucacc gccgcggccc ggguucgauu cccggucagg gaacc 45

<210> SEQ ID NO 870

```
<211> LENGTH: 40
<212> TYPE: RNA
<213> ORGANISM: Homo sapiens

<400> SEQUENCE: 870

uuuuucauau cauuggucgu gguuguaguc cgugcgagaa                              40

<210> SEQ ID NO 871
<211> LENGTH: 40
<212> TYPE: RNA
<213> ORGANISM: Homo sapiens

<400> SEQUENCE: 871

auugugaauc ugacaacaga ggcuuacgac cccuuauuua                              40

<210> SEQ ID NO 872
<211> LENGTH: 27
<212> TYPE: RNA
<213> ORGANISM: Homo sapiens

<400> SEQUENCE: 872

cgguccccg cgaggggggc ccgggca                                             27

<210> SEQ ID NO 873
<211> LENGTH: 44
<212> TYPE: RNA
<213> ORGANISM: Homo sapiens

<400> SEQUENCE: 873

cugucacgcg ggagaccggg guucgauucc ccgacgggga gcca                         44

<210> SEQ ID NO 874
<211> LENGTH: 50
<212> TYPE: RNA
<213> ORGANISM: Homo sapiens

<400> SEQUENCE: 874

ucguacguag cagagcagcu cccucgcugc gaucuauuga aagucagccc                   50

<210> SEQ ID NO 875
<211> LENGTH: 31
<212> TYPE: RNA
<213> ORGANISM: Homo sapiens

<400> SEQUENCE: 875

caagcguugg auuguucacc cacuaauagg g                                       31

<210> SEQ ID NO 876
<211> LENGTH: 30
<212> TYPE: RNA
<213> ORGANISM: Homo sapiens

<400> SEQUENCE: 876

ggccguaauc guauaguggu uaguacucug                                         30

<210> SEQ ID NO 877
<211> LENGTH: 30
<212> TYPE: RNA
<213> ORGANISM: Homo sapiens

<400> SEQUENCE: 877

ggccgugcuc guauaguggu uaguacucug                                         30
```

```
<210> SEQ ID NO 878
<211> LENGTH: 28
<212> TYPE: RNA
<213> ORGANISM: Homo sapiens

<400> SEQUENCE: 878

ggcucguugg ucuaggggua ugauucuc                                28

<210> SEQ ID NO 879
<211> LENGTH: 26
<212> TYPE: RNA
<213> ORGANISM: Homo sapiens

<400> SEQUENCE: 879

ggccgugauc guauaguggu uaguac                                  26

<210> SEQ ID NO 880
<211> LENGTH: 34
<212> TYPE: RNA
<213> ORGANISM: Homo sapiens

<400> SEQUENCE: 880

uccucguuag uauaguggug aguauccccg ccug                         34

<210> SEQ ID NO 881
<211> LENGTH: 29
<212> TYPE: RNA
<213> ORGANISM: Homo sapiens

<400> SEQUENCE: 881

uaggaugggg ugugauagga ggcacggag                               29

<210> SEQ ID NO 882
<211> LENGTH: 50
<212> TYPE: RNA
<213> ORGANISM: Homo sapiens

<400> SEQUENCE: 882

cuucaaaccu guagcugucu agcgacagag ugguucauuu ccaccuuucg        50

<210> SEQ ID NO 883
<211> LENGTH: 33
<212> TYPE: RNA
<213> ORGANISM: Homo sapiens

<400> SEQUENCE: 883

ucacuggugg ucuagugguu aggauucggc gcu                          33

<210> SEQ ID NO 884
<211> LENGTH: 29
<212> TYPE: RNA
<213> ORGANISM: Homo sapiens

<400> SEQUENCE: 884

uaggaugggg ugugauaggu ggcacggcg                               29

<210> SEQ ID NO 885
<211> LENGTH: 28
<212> TYPE: RNA
<213> ORGANISM: Homo sapiens

<400> SEQUENCE: 885

gugaucguau agugguuagu acucugcg                                28
```

<210> SEQ ID NO 886
<211> LENGTH: 29
<212> TYPE: RNA
<213> ORGANISM: Homo sapiens

<400> SEQUENCE: 886
cgugaucgua uagugguuag uacucugcg 29

<210> SEQ ID NO 887
<211> LENGTH: 39
<212> TYPE: RNA
<213> ORGANISM: Homo sapiens

<400> SEQUENCE: 887
cuuuuugauc cuucgauguc ggcucuuccu aucauugug 39

<210> SEQ ID NO 888
<211> LENGTH: 29
<212> TYPE: RNA
<213> ORGANISM: Homo sapiens

<400> SEQUENCE: 888
ggcucguugg ucuaggggua ugauucucg 29

<210> SEQ ID NO 889
<211> LENGTH: 45
<212> TYPE: RNA
<213> ORGANISM: Homo sapiens

<400> SEQUENCE: 889
ccugucacgc gggagaccgg gguucguuuc cccgacgggg agcca 45

<210> SEQ ID NO 890
<211> LENGTH: 29
<212> TYPE: RNA
<213> ORGANISM: Homo sapiens

<400> SEQUENCE: 890
ucccauaugg ucuagcgguu aggauuccu 29

<210> SEQ ID NO 891
<211> LENGTH: 29
<212> TYPE: RNA
<213> ORGANISM: Homo sapiens

<400> SEQUENCE: 891
agccgugauc guauaguggu uaguacucu 29

<210> SEQ ID NO 892
<211> LENGTH: 26
<212> TYPE: RNA
<213> ORGANISM: Homo sapiens

<400> SEQUENCE: 892
gcauuggugg uucaguggua gaauuc 26

<210> SEQ ID NO 893
<211> LENGTH: 37
<212> TYPE: RNA
<213> ORGANISM: Homo sapiens

<400> SEQUENCE: 893
ucugaggguc caggguucag gucccuguuc gggcgcc 37

<210> SEQ ID NO 894
<211> LENGTH: 43
<212> TYPE: RNA
<213> ORGANISM: Homo sapiens

<400> SEQUENCE: 894 cccgggggc cggcggcggc ggcgacucug gacgcgagcc ggg 43

<210> SEQ ID NO 895
<211> LENGTH: 43
<212> TYPE: RNA
<213> ORGANISM: Homo sapiens

<400> SEQUENCE: 895
ccccggcggc gggggcacgg ucccccgcga ggggggcccg ggc 43

<210> SEQ ID NO 896
<211> LENGTH: 48
<212> TYPE: RNA
<213> ORGANISM: Homo sapiens

<400> SEQUENCE: 896
cagucggucc ugagagaugg gcgagcgccg uuccgaaggg acgggcga 48

<210> SEQ ID NO 897
<211> LENGTH: 49
<212> TYPE: RNA
<213> ORGANISM: Homo sapiens

<400> SEQUENCE: 897
ccuaaggagg ggugaaccgg cccaggucgg aaacggagca ggucaaaac 49

<210> SEQ ID NO 898
<211> LENGTH: 41
<212> TYPE: RNA
<213> ORGANISM: Homo sapiens

<400> SEQUENCE: 898
uugcaaauuc gaagaagcag cuucaaaccu gccggggcuu c 41

<210> SEQ ID NO 899
<211> LENGTH: 30
<212> TYPE: RNA
<213> ORGANISM: Homo sapiens

<400> SEQUENCE: 899
gcccggcuag cucagucggu agagcauggg 30

<210> SEQ ID NO 900
<211> LENGTH: 37
<212> TYPE: RNA
<213> ORGANISM: Homo sapiens

<400> SEQUENCE: 900
ucagaagauu gcagguucga guccugccgc ggucgcc 37

<210> SEQ ID NO 901
<211> LENGTH: 30
<212> TYPE: RNA
<213> ORGANISM: Homo sapiens

<400> SEQUENCE: 901

-continued ggccgugauc guauaguggu uaguacucuu 30

<210> SEQ ID NO 902
<211> LENGTH: 33
<212> TYPE: RNA
<213> ORGANISM: Homo sapiens

<400> SEQUENCE: 902
ucccuggugg ucuagugguu aggauucggc gcc 33

<210> SEQ ID NO 903
<211> LENGTH: 50
<212> TYPE: RNA
<213> ORGANISM: Homo sapiens

<400> SEQUENCE: 903
aaauacaacg augguuuuuc auaucauugg ucgugguugu aguccgugcg 50

<210> SEQ ID NO 904
<211> LENGTH: 29
<212> TYPE: RNA
<213> ORGANISM: Homo sapiens

<400> SEQUENCE: 904
uaggaugggg ugugauaggu ggcacggag 29

<210> SEQ ID NO 905
<211> LENGTH: 50
<212> TYPE: RNA
<213> ORGANISM: Homo sapiens

<400> SEQUENCE: 905
uguguuacua gagaaguuuc ucugaacgug uagagcacca aaaaccacga 50

<210> SEQ ID NO 906
<211> LENGTH: 50
<212> TYPE: RNA
<213> ORGANISM: Homo sapiens

<400> SEQUENCE: 906
ucgcgccugu gaauagccac ugcacuccag ccugggcaac auagcgagac 50

<210> SEQ ID NO 907
<211> LENGTH: 33
<212> TYPE: RNA
<213> ORGANISM: Homo sapiens

<400> SEQUENCE: 907
ccaagcguug gauuguucac ccacuaauag gga 33

<210> SEQ ID NO 908
<211> LENGTH: 42
<212> TYPE: RNA
<213> ORGANISM: Homo sapiens

<400> SEQUENCE: 908
cuuacacuua ggagauuuca acuuaacuug accgcucuga cc 42

<210> SEQ ID NO 909
<211> LENGTH: 33
<212> TYPE: RNA
<213> ORGANISM: Homo sapiens

<400> SEQUENCE: 909
gcaugggugg uucaguggua gaauucucgc cuu 33

<210> SEQ ID NO 910
<211> LENGTH: 26
<212> TYPE: RNA
<213> ORGANISM: Homo sapiens

<400> SEQUENCE: 910
ccaccccacg ucucgucgcg cgcgcg 26

<210> SEQ ID NO 911
<211> LENGTH: 39
<212> TYPE: RNA
<213> ORGANISM: Homo sapiens

<400> SEQUENCE: 911
auugaucauc gacacuucga acgcacuugc ggccccggg 39

<210> SEQ ID NO 912
<211> LENGTH: 26
<212> TYPE: RNA
<213> ORGANISM: Homo sapiens

<400> SEQUENCE: 912 cgguccccg cgagggggc ccgggc 26

<210> SEQ ID NO 913
<211> LENGTH: 50
<212> TYPE: RNA
<213> ORGANISM: Homo sapiens

<400> SEQUENCE: 913
aucgcgccug ugaauagcca cugcacucca gccugagcaa cauagcgaga 50

<210> SEQ ID NO 914
<211> LENGTH: 50
<212> TYPE: RNA
<213> ORGANISM: Homo sapiens

<400> SEQUENCE: 914
acgaugguuu uucauaucau uggucguggu uguaguccgu gcgagaauac 50

<210> SEQ ID NO 915
<211> LENGTH: 29
<212> TYPE: RNA
<213> ORGANISM: Homo sapiens

<400> SEQUENCE: 915 cacgguccc cgcgaggggg gcccgggca 29

<210> SEQ ID NO 916
<211> LENGTH: 50
<212> TYPE: RNA
<213> ORGANISM: Homo sapiens

<400> SEQUENCE: 916
ugaauugcag gacacauuga ucaucgacac uucgaacgca cuugcggccc 50

<210> SEQ ID NO 917
<211> LENGTH: 44
<212> TYPE: RNA
<213> ORGANISM: Homo sapiens

<400> SEQUENCE: 917
ccccggcggc gggggcacgg ucccccgcga ggggggcccg ggca 44

<210> SEQ ID NO 918
<211> LENGTH: 29
<212> TYPE: RNA
<213> ORGANISM: Homo sapiens

<400> SEQUENCE: 918
ucccuggugg ucuaguggcu aggauucgg 29

<210> SEQ ID NO 919
<211> LENGTH: 30
<212> TYPE: RNA
<213> ORGANISM: Homo sapiens

<400> SEQUENCE: 919
ccgugaucgu auagugguua guacucugcg 30

<210> SEQ ID NO 920
<211> LENGTH: 27
<212> TYPE: RNA
<213> ORGANISM: Homo sapiens

<400> SEQUENCE: 920
uaggaugggg ugugauaggu ggcacgg 27

<210> SEQ ID NO 921
<211> LENGTH: 44
<212> TYPE: RNA
<213> ORGANISM: Homo sapiens

<400> SEQUENCE: 921
cucucaccgc cgcggcccgg guucgauucc cggucaggga acca 44

<210> SEQ ID NO 922
<211> LENGTH: 45
<212> TYPE: RNA
<213> ORGANISM: Homo sapiens

<400> SEQUENCE: 922
guuuuucaua ucauuggucg ugguuguagu ccgugcgaga auacc 45

<210> SEQ ID NO 923
<211> LENGTH: 44
<212> TYPE: RNA
<213> ORGANISM: Homo sapiens

<400> SEQUENCE: 923
acccgggggg ccggcggcgg cggcgacucu ggacgcgagc cggg 44

<210> SEQ ID NO 924
<211> LENGTH: 30
<212> TYPE: RNA
<213> ORGANISM: Homo sapiens

<400> SEQUENCE: 924
gcguuggugg uauaguggua agcauagcug 30

<210> SEQ ID NO 925
<211> LENGTH: 30
<212> TYPE: RNA
<213> ORGANISM: Homo sapiens

```
<400> SEQUENCE: 925

gguuccauag uguagcgguu aucacgucug                              30

<210> SEQ ID NO 926
<211> LENGTH: 39
<212> TYPE: RNA
<213> ORGANISM: Homo sapiens

<400> SEQUENCE: 926

cugccacgcg ggaggcccgg guucguuucc cggccaaug                    39

<210> SEQ ID NO 927
<211> LENGTH: 33
<212> TYPE: RNA
<213> ORGANISM: Homo sapiens

<400> SEQUENCE: 927

ucccacaugg ucuagcgguu aggauuccug guu                          33

<210> SEQ ID NO 928
<211> LENGTH: 33
<212> TYPE: RNA
<213> ORGANISM: Homo sapiens

<400> SEQUENCE: 928

guuuccguag uguagugguu aucacgcucg ccu                          33

<210> SEQ ID NO 929
<211> LENGTH: 36
<212> TYPE: RNA
<213> ORGANISM: Homo sapiens

<400> SEQUENCE: 929

agccgugauc guauaguggu uaguacucug cguugu                       36

<210> SEQ ID NO 930
<211> LENGTH: 28
<212> TYPE: RNA
<213> ORGANISM: Homo sapiens

<400> SEQUENCE: 930

ggccgugauc guauaguggu uaguacuc                                28

<210> SEQ ID NO 931
<211> LENGTH: 42
<212> TYPE: RNA
<213> ORGANISM: Homo sapiens

<400> SEQUENCE: 931

uugugaaucu gacaacagag gcuuacgacc ccuuauuuac cc                42

<210> SEQ ID NO 932
<211> LENGTH: 30
<212> TYPE: RNA
<213> ORGANISM: Homo sapiens

<400> SEQUENCE: 932

ccccuguggu cuagugguua ggauucggcg                              30

<210> SEQ ID NO 933
<211> LENGTH: 30
<212> TYPE: RNA
```

<213> ORGANISM: Homo sapiens

<400> SEQUENCE: 933
agccgugauc guauaguggu uaguacucug                                    30

<210> SEQ ID NO 934
<211> LENGTH: 29
<212> TYPE: RNA
<213> ORGANISM: Homo sapiens

<400> SEQUENCE: 934
guuuccguag uguagugguc aucacguuc                                     29

<210> SEQ ID NO 935
<211> LENGTH: 50
<212> TYPE: RNA
<213> ORGANISM: Homo sapiens

<400> SEQUENCE: 935
ccguggagag aaacgagugu gagucugaaa ccaauuuuuu gaggccuugc              50

<210> SEQ ID NO 936
<211> LENGTH: 50
<212> TYPE: RNA
<213> ORGANISM: Homo sapiens

<400> SEQUENCE: 936
auacaacgau gguuuuucau aucauugguc gugguuguag uccgugcgag              50

<210> SEQ ID NO 937
<211> LENGTH: 28
<212> TYPE: RNA
<213> ORGANISM: Homo sapiens

<400> SEQUENCE: 937
gccgugaucg uauagugguu aguacucu                                      28

<210> SEQ ID NO 938
<211> LENGTH: 29
<212> TYPE: RNA
<213> ORGANISM: Homo sapiens

<400> SEQUENCE: 938
ggccgugauc guauaguggu uaguacucu                                     29

<210> SEQ ID NO 939
<211> LENGTH: 41
<212> TYPE: RNA
<213> ORGANISM: Homo sapiens

<400> SEQUENCE: 939
cugucacgcg ggagaccggg guucgauucc ccgacgggga g                       41

<210> SEQ ID NO 940
<211> LENGTH: 32
<212> TYPE: RNA
<213> ORGANISM: Homo sapiens

<400> SEQUENCE: 940
ccaagcguug gauuguucac ccacuaauag gg                                 32

<210> SEQ ID NO 941
<211> LENGTH: 50

<212> TYPE: RNA
<213> ORGANISM: Homo sapiens

<400> SEQUENCE: 941
ucuccuacuu ggauaacugu gguaauucua gagcuaauac augccgacgg 50

<210> SEQ ID NO 942
<211> LENGTH: 29
<212> TYPE: RNA
<213> ORGANISM: Homo sapiens

<400> SEQUENCE: 942
uaggauggcg ugugauaggu ggcacggag 29

<210> SEQ ID NO 943
<211> LENGTH: 29
<212> TYPE: RNA
<213> ORGANISM: Homo sapiens

<400> SEQUENCE: 943
uccugugguc uagugguuag gauucggcg 29

<210> SEQ ID NO 944
<211> LENGTH: 50
<212> TYPE: RNA
<213> ORGANISM: Homo sapiens

<400> SEQUENCE: 944
uccuacuugg auaacugugg uaauucuaga gcuaauacau gccgacgggc 50

<210> SEQ ID NO 945
<211> LENGTH: 35
<212> TYPE: RNA
<213> ORGANISM: Homo sapiens

<400> SEQUENCE: 945
agcagccgac uuagaacugg ugcggaccag gggaa 35

<210> SEQ ID NO 946
<211> LENGTH: 42
<212> TYPE: RNA
<213> ORGANISM: Homo sapiens

<400> SEQUENCE: 946
cugucacgcg ggagaccggg guucgauucc ccgacgggga gc 42

<210> SEQ ID NO 947
<211> LENGTH: 26
<212> TYPE: RNA
<213> ORGANISM: Homo sapiens

<400> SEQUENCE: 947
ucccuguggu cuagugguua ggauuc 26

<210> SEQ ID NO 948
<211> LENGTH: 35
<212> TYPE: RNA
<213> ORGANISM: Homo sapiens

<400> SEQUENCE: 948
uaggaugggg ugugauaggu ggcacggaga auuuu 35

<210> SEQ ID NO 949

<211> LENGTH: 32
<212> TYPE: RNA
<213> ORGANISM: Homo sapiens

<400> SEQUENCE: 949
agccgugauc guauaguggu uaguacucug cg 32

<210> SEQ ID NO 950
<211> LENGTH: 30
<212> TYPE: RNA
<213> ORGANISM: Homo sapiens

<400> SEQUENCE: 950
ggccgugauc guauaguggu uagcacucug 30

<210> SEQ ID NO 951
<211> LENGTH: 30
<212> TYPE: RNA
<213> ORGANISM: Homo sapiens

<400> SEQUENCE: 951
ggccgugauc guauaguagu uaguacucug 30

<210> SEQ ID NO 952
<211> LENGTH: 26
<212> TYPE: RNA
<213> ORGANISM: Homo sapiens

<400> SEQUENCE: 952
gccgugaucg uauagugguu aguacu 26

<210> SEQ ID NO 953
<211> LENGTH: 50
<212> TYPE: RNA
<213> ORGANISM: Homo sapiens

<400> SEQUENCE: 953
cgacucuuag cgguggauca cucggcucgu gcgucgcuga agaacgcagc 50

<210> SEQ ID NO 954
<211> LENGTH: 30
<212> TYPE: RNA
<213> ORGANISM: Homo sapiens

<400> SEQUENCE: 954
ggacgugauc guauaguggu uaguacucug 30

<210> SEQ ID NO 955
<211> LENGTH: 36
<212> TYPE: RNA
<213> ORGANISM: Homo sapiens

<400> SEQUENCE: 955
cauaucauug gucgugguug uaguccgugc gagaau 36

<210> SEQ ID NO 956
<211> LENGTH: 30
<212> TYPE: RNA
<213> ORGANISM: Homo sapiens

<400> SEQUENCE: 956
ccaagcguug gauuguucac ccacuaauag 30

<210> SEQ ID NO 957
<211> LENGTH: 34
<212> TYPE: RNA
<213> ORGANISM: Homo sapiens

<400> SEQUENCE: 957
ccccuguggu cuagugguua ggauucggcg cucu 34

<210> SEQ ID NO 958
<211> LENGTH: 37
<212> TYPE: RNA
<213> ORGANISM: Homo sapiens

<400> SEQUENCE: 958
ucagaagauu gaggguucgu gucccuucgu ggucgcc 37

<210> SEQ ID NO 959
<211> LENGTH: 50
<212> TYPE: RNA
<213> ORGANISM: Homo sapiens

<400> SEQUENCE: 959
cucuccuacu uggauaacug ugguaauucu agagcuaaua caugccgacg 50

<210> SEQ ID NO 960
<211> LENGTH: 31
<212> TYPE: RNA
<213> ORGANISM: Homo sapiens

<400> SEQUENCE: 960
ucccuggcgg ucuagugguu aggauucggc g 31

<210> SEQ ID NO 961
<211> LENGTH: 30
<212> TYPE: RNA
<213> ORGANISM: Homo sapiens

<400> SEQUENCE: 961
cggcuagcuc agucgguaga gcaugagacu 30

<210> SEQ ID NO 962
<211> LENGTH: 31
<212> TYPE: RNA
<213> ORGANISM: Homo sapiens

<400> SEQUENCE: 962
ggccgugauc guauaguggu uaguacucug c 31

<210> SEQ ID NO 963
<211> LENGTH: 26
<212> TYPE: RNA
<213> ORGANISM: Homo sapiens

<400> SEQUENCE: 963
cgugaucgua uagugguuag uacucu 26

<210> SEQ ID NO 964
<211> LENGTH: 30
<212> TYPE: RNA
<213> ORGANISM: Homo sapiens

<400> SEQUENCE: 964
ggccgugauc gcauaguggu uaguacucug 30

<210> SEQ ID NO 965
<211> LENGTH: 49
<212> TYPE: RNA
<213> ORGANISM: Homo sapiens

<400> SEQUENCE: 965
ggacacauug aucaucgaca cuucgaacgc acuugcggcc ccggguucc 49

<210> SEQ ID NO 966
<211> LENGTH: 50
<212> TYPE: RNA
<213> ORGANISM: Homo sapiens

<400> SEQUENCE: 966
cgcgccugug aauagccacu gcacuccagc cugagcaaca uagcgagacc 50

<210> SEQ ID NO 967
<211> LENGTH: 30
<212> TYPE: RNA
<213> ORGANISM: Homo sapiens

<400> SEQUENCE: 967
uccucguuag uauaguggug aguauccccg 30

<210> SEQ ID NO 968
<211> LENGTH: 49
<212> TYPE: RNA
<213> ORGANISM: Homo sapiens

<400> SEQUENCE: 968
uacuuggaua acugugguaa uucuagagcu aauacaugcc gacgggcgc 49

<210> SEQ ID NO 969
<211> LENGTH: 30
<212> TYPE: RNA
<213> ORGANISM: Homo sapiens

<400> SEQUENCE: 969
ggccgugauc guauaguggu uagaacucug 30

<210> SEQ ID NO 970
<211> LENGTH: 29
<212> TYPE: RNA
<213> ORGANISM: Homo sapiens

<400> SEQUENCE: 970
gcauuugugg uucaguggua gaauucucg 29

<210> SEQ ID NO 971
<211> LENGTH: 30
<212> TYPE: RNA
<213> ORGANISM: Homo sapiens

<400> SEQUENCE: 971
aacgcgcccg aucucgucug aucucggaag 30

<210> SEQ ID NO 972
<211> LENGTH: 26
<212> TYPE: RNA
<213> ORGANISM: Homo sapiens

<400> SEQUENCE: 972
gugaucguau agugguuagu acucug 26

<210> SEQ ID NO 973
<211> LENGTH: 31
<212> TYPE: RNA
<213> ORGANISM: Homo sapiens

<400> SEQUENCE: 973
ggccgugauc gcauaguggu uaguacucug c 31

<210> SEQ ID NO 974
<211> LENGTH: 36
<212> TYPE: RNA
<213> ORGANISM: Homo sapiens

<400> SEQUENCE: 974
cccgcgaggg gggucucccc cgcgggggcg cgccgg 36

<210> SEQ ID NO 975
<211> LENGTH: 43
<212> TYPE: RNA
<213> ORGANISM: Homo sapiens

<400> SEQUENCE: 975
auugugaauc ugacaacaga ggcuuacgac cccuuauuua ccc 43

<210> SEQ ID NO 976
<211> LENGTH: 35
<212> TYPE: RNA
<213> ORGANISM: Homo sapiens

<400> SEQUENCE: 976
cgguuccggc ggcguccggu gagcucucgc uggcc 35

<210> SEQ ID NO 977
<211> LENGTH: 40
<212> TYPE: RNA
<213> ORGANISM: Homo sapiens

<400> SEQUENCE: 977
gaugggagac cgccugggaa uaccgggugc uguaggcuuu 40

<210> SEQ ID NO 978
<211> LENGTH: 50
<212> TYPE: RNA
<213> ORGANISM: Homo sapiens

<400> SEQUENCE: 978
uggauaacug ugguaauucu agagcuaaua caugccgacg ggcgcugacc 50

<210> SEQ ID NO 979
<211> LENGTH: 50
<212> TYPE: RNA
<213> ORGANISM: Homo sapiens

<400> SEQUENCE: 979
acgagaguga gucugaaacc aauuuuuuga ggccuugcgu uucuuagcag 50

<210> SEQ ID NO 980
<211> LENGTH: 27
<212> TYPE: RNA
<213> ORGANISM: Homo sapiens

<400> SEQUENCE: 980
ugccgugauc guauaguggu uaguacu 27

<210> SEQ ID NO 981
<211> LENGTH: 27
<212> TYPE: RNA
<213> ORGANISM: Homo sapiens

<400> SEQUENCE: 981
cggauagcuc agucgguaga gcaucag 27

<210> SEQ ID NO 982
<211> LENGTH: 30
<212> TYPE: RNA
<213> ORGANISM: Homo sapiens

<400> SEQUENCE: 982
uaggauggag ugugauaggu ggcacggaga 30

<210> SEQ ID NO 983
<211> LENGTH: 49
<212> TYPE: RNA
<213> ORGANISM: Homo sapiens

<400> SEQUENCE: 983
acccacuccc gacccgggga gguagugacg aaaaauaaca auacaggac 49

<210> SEQ ID NO 984
<211> LENGTH: 50
<212> TYPE: RNA
<213> ORGANISM: Homo sapiens

<400> SEQUENCE: 984
ccggcggcgg cggcgacucu ggacgcgagc cgggcccuuc ccguggaucg 50

<210> SEQ ID NO 985
<211> LENGTH: 30
<212> TYPE: RNA
<213> ORGANISM: Homo sapiens

<400> SEQUENCE: 985
ccggcggcgu ccggugagcu cucgcuggcc 30

<210> SEQ ID NO 986
<211> LENGTH: 39
<212> TYPE: RNA
<213> ORGANISM: Homo sapiens

<400> SEQUENCE: 986
cauaucauug gucgugguug uaguccgugc gagaauacc 39

<210> SEQ ID NO 987
<211> LENGTH: 28
<212> TYPE: RNA
<213> ORGANISM: Homo sapiens

<400> SEQUENCE: 987
ucccacaugg ucuagcgguu aggauucc 28

<210> SEQ ID NO 988
<211> LENGTH: 27
<212> TYPE: RNA
<213> ORGANISM: Homo sapiens

<400> SEQUENCE: 988
ggcucguugg ucuaggggua ugauucu 27

<210> SEQ ID NO 989
<211> LENGTH: 40
<212> TYPE: RNA
<213> ORGANISM: Homo sapiens

<400> SEQUENCE: 989
agcagccgac uuagaacugg ugcggaccag gggaauccga 40

<210> SEQ ID NO 990
<211> LENGTH: 34
<212> TYPE: RNA
<213> ORGANISM: Homo sapiens

<400> SEQUENCE: 990
gcauuggcgg uucaguggua gaauucucgc cugc 34

<210> SEQ ID NO 991
<211> LENGTH: 33
<212> TYPE: RNA
<213> ORGANISM: Homo sapiens

<400> SEQUENCE: 991
ccccuguggu cuagugguua ggauucggcg cuc 33

<210> SEQ ID NO 992
<211> LENGTH: 30
<212> TYPE: RNA
<213> ORGANISM: Homo sapiens

<400> SEQUENCE: 992
gcccggauag cucagucggu agagcaucag 30

<210> SEQ ID NO 993
<211> LENGTH: 29
<212> TYPE: RNA
<213> ORGANISM: Homo sapiens

<400> SEQUENCE: 993
uaggauggug ugugauaggu ggcacggag 29

<210> SEQ ID NO 994
<211> LENGTH: 36
<212> TYPE: RNA
<213> ORGANISM: Homo sapiens

<400> SEQUENCE: 994
agcagccgac uuagaacugg ugcggaccag gggaau 36

<210> SEQ ID NO 995
<211> LENGTH: 32
<212> TYPE: RNA
<213> ORGANISM: Homo sapiens

<400> SEQUENCE: 995
gcauuggugg uucaguggua gaauucucgc uu 32

<210> SEQ ID NO 996
<211> LENGTH: 34
<212> TYPE: RNA
<213> ORGANISM: Homo sapiens

<400> SEQUENCE: 996
aucgacacuu cgaacgcacu ugcggccccg gguu 34

<210> SEQ ID NO 997
<211> LENGTH: 35
<212> TYPE: RNA
<213> ORGANISM: Homo sapiens

<400> SEQUENCE: 997
agccgugauc guauaguggu uaguacucug cguug 35

<210> SEQ ID NO 998
<211> LENGTH: 46
<212> TYPE: RNA
<213> ORGANISM: Homo sapiens

<400> SEQUENCE: 998
aggacacauu gaucaucgac acuucgaacg cacuugcggc cccggg 46

<210> SEQ ID NO 999
<211> LENGTH: 34
<212> TYPE: RNA
<213> ORGANISM: Homo sapiens

<400> SEQUENCE: 999
gcauuggugg uucaguggua gaauucucgc cugg 34

<210> SEQ ID NO 1000
<211> LENGTH: 28
<212> TYPE: RNA
<213> ORGANISM: Homo sapiens

<400> SEQUENCE: 1000
agccgugauc guauaguggu uaguacuc 28

<210> SEQ ID NO 1001
<211> LENGTH: 47
<212> TYPE: RNA
<213> ORGANISM: Homo sapiens

<400> SEQUENCE: 1001
aguacuugga ugggagaccg ccugggaaua ccgggugcug uaggcuu 47

<210> SEQ ID NO 1002
<211> LENGTH: 44
<212> TYPE: RNA
<213> ORGANISM: Homo sapiens

<400> SEQUENCE: 1002
guuuucaccc aggcggcccg gguucgacuc ccggugugg aacc 44

<210> SEQ ID NO 1003
<211> LENGTH: 29
<212> TYPE: RNA
<213> ORGANISM: Homo sapiens

<400> SEQUENCE: 1003
gguuccaugg uguaaugguu agcacucug 29

<210> SEQ ID NO 1004
<211> LENGTH: 49
<212> TYPE: RNA
<213> ORGANISM: Homo sapiens

<400> SEQUENCE: 1004
ucagucgguc cugagagaug ggcgagcgcc guuccgaagg gacgggcga 49

<210> SEQ ID NO 1005
<211> LENGTH: 50
<212> TYPE: RNA
<213> ORGANISM: Homo sapiens

<400> SEQUENCE: 1005
aucgcgccug ugaauagcca cugcacucca gccugggcaa cauagcgaga 50

<210> SEQ ID NO 1006
<211> LENGTH: 28
<212> TYPE: RNA
<213> ORGANISM: Homo sapiens

<400> SEQUENCE: 1006
auucaaacga gaacuuugaa ggccgaag 28

<210> SEQ ID NO 1007
<211> LENGTH: 43
<212> TYPE: RNA
<213> ORGANISM: Homo sapiens

<400> SEQUENCE: 1007
cugucacgcg ggagaccggg guucgauucc ccgacgggga gcc 43

<210> SEQ ID NO 1008
<211> LENGTH: 27
<212> TYPE: RNA
<213> ORGANISM: Homo sapiens

<400> SEQUENCE: 1008
gcauuggugg uucagugrua gaauucu 27

<210> SEQ ID NO 1009
<211> LENGTH: 27
<212> TYPE: RNA
<213> ORGANISM: Homo sapiens

<400> SEQUENCE: 1009
gugaucguau agugguuagu acucugc 27

<210> SEQ ID NO 1010
<211> LENGTH: 29
<212> TYPE: RNA
<213> ORGANISM: Homo sapiens

<400> SEQUENCE: 1010
gcuucuguag uguagugguu aucacguuc 29

<210> SEQ ID NO 1011
<211> LENGTH: 42
<212> TYPE: RNA
<213> ORGANISM: Homo sapiens

<400> SEQUENCE: 1011
cuuugggugc uaauggugga guuaaagacu uuuucucuga cc 42

<210> SEQ ID NO 1012
<211> LENGTH: 37
<212> TYPE: RNA

<213> ORGANISM: Homo sapiens

<400> SEQUENCE: 1012
ucagaagauu gaggguucgg gucccuucgu ggucgcc 37

<210> SEQ ID NO 1013
<211> LENGTH: 39
<212> TYPE: RNA
<213> ORGANISM: Homo sapiens

<400> SEQUENCE: 1013
ggcugguccg augguagugg guuaucagaa cuuauuaac 39

<210> SEQ ID NO 1014
<211> LENGTH: 38
<212> TYPE: RNA
<213> ORGANISM: Homo sapiens

<400> SEQUENCE: 1014
aaaucggucg uccgaccugg guauaggggc gaaagacu 38

<210> SEQ ID NO 1015
<211> LENGTH: 38
<212> TYPE: RNA
<213> ORGANISM: Homo sapiens

<400> SEQUENCE: 1015
ucagaagauu gaggguucga gucccuucgu ggucgcca 38

<210> SEQ ID NO 1016
<211> LENGTH: 27
<212> TYPE: RNA
<213> ORGANISM: Homo sapiens

<400> SEQUENCE: 1016
ggccgugauc guauaguggu uaguacu 27

<210> SEQ ID NO 1017
<211> LENGTH: 44
<212> TYPE: RNA
<213> ORGANISM: Homo sapiens

<400> SEQUENCE: 1017
ccuuccaagc aguugacccg gguucguuuc ccggccaacg cacc 44

<210> SEQ ID NO 1018
<211> LENGTH: 45
<212> TYPE: RNA
<213> ORGANISM: Homo sapiens

<400> SEQUENCE: 1018 cccgggggc cggcggcggc ggcgacucug gacgcgagcc gggcc 45

<210> SEQ ID NO 1019
<211> LENGTH: 30
<212> TYPE: RNA
<213> ORGANISM: Homo sapiens

<400> SEQUENCE: 1019
ggccgugauc gucuaguggu uaguacucug 30

<210> SEQ ID NO 1020
<211> LENGTH: 32

<212> TYPE: RNA
<213> ORGANISM: Homo sapiens

<400> SEQUENCE: 1020
cucgccguga ucguauagug guuaguacuc ug 32

<210> SEQ ID NO 1021
<211> LENGTH: 43
<212> TYPE: RNA
<213> ORGANISM: Homo sapiens

<400> SEQUENCE: 1021
uugugaaucu gacaacagag gcuuacgacc ccuuauuuac ccc 43

<210> SEQ ID NO 1022
<211> LENGTH: 27
<212> TYPE: RNA
<213> ORGANISM: Homo sapiens

<400> SEQUENCE: 1022
gccgugaucg uauagugguu aguacuc 27

<210> SEQ ID NO 1023
<211> LENGTH: 28
<212> TYPE: RNA
<213> ORGANISM: Homo sapiens

<400> SEQUENCE: 1023
ucccuguggu cuagugguua ggauucgg 28

<210> SEQ ID NO 1024
<211> LENGTH: 46
<212> TYPE: RNA
<213> ORGANISM: Homo sapiens

<400> SEQUENCE: 1024
guucuuguug uugaaauaca acgaugguuu uucauaucau uggucg 46

<210> SEQ ID NO 1025
<211> LENGTH: 30
<212> TYPE: RNA
<213> ORGANISM: Homo sapiens

<400> SEQUENCE: 1025
uccccugugg ucuagugguu aggauucggc 30

<210> SEQ ID NO 1026
<211> LENGTH: 43
<212> TYPE: RNA
<213> ORGANISM: Homo sapiens

<400> SEQUENCE: 1026 cccgggggc cggcggcggc ggcgacucug gacgcgcgcc ggg 43

<210> SEQ ID NO 1027
<211> LENGTH: 29
<212> TYPE: RNA
<213> ORGANISM: Homo sapiens

<400> SEQUENCE: 1027
uaggauggag ugugauaggu ggcacggag 29

<210> SEQ ID NO 1028

<211> LENGTH: 31
<212> TYPE: RNA
<213> ORGANISM: Homo sapiens

<400> SEQUENCE: 1028
ucccuggugg ucuagugguu aggauucggc a 31

<210> SEQ ID NO 1029
<211> LENGTH: 48
<212> TYPE: RNA
<213> ORGANISM: Homo sapiens

<400> SEQUENCE: 1029
gacucuuagc gguggaucac ucggcucgug cgucgaugaa gaacgcag 48

<210> SEQ ID NO 1030
<211> LENGTH: 29
<212> TYPE: RNA
<213> ORGANISM: Homo sapiens

<400> SEQUENCE: 1030
ggcuagcuca gucgguagag caugagacu 29

<210> SEQ ID NO 1031
<211> LENGTH: 50
<212> TYPE: RNA
<213> ORGANISM: Homo sapiens

<400> SEQUENCE: 1031
ucgcgccugu gaauagccac ugcacuccag ccugagcaac auagcgagac 50

<210> SEQ ID NO 1032
<211> LENGTH: 43
<212> TYPE: RNA
<213> ORGANISM: Homo sapiens

<400> SEQUENCE: 1032
gcuuugggug cuaauggugg aguuaaagac uuuuucucug acc 43

<210> SEQ ID NO 1033
<211> LENGTH: 32
<212> TYPE: RNA
<213> ORGANISM: Homo sapiens

<400> SEQUENCE: 1033
gcauuggugg uucaguggua gcauucucgc cu 32

<210> SEQ ID NO 1034
<211> LENGTH: 50
<212> TYPE: RNA
<213> ORGANISM: Homo sapiens

<400> SEQUENCE: 1034
gaacaugggu cagucggucc ugagagaugg gcgagcgccg uuccgaaggg 50

<210> SEQ ID NO 1035
<211> LENGTH: 29
<212> TYPE: RNA
<213> ORGANISM: Homo sapiens

<400> SEQUENCE: 1035
aaugugugac ugaaagguau uuucugagc 29

```
<210> SEQ ID NO 1036
<211> LENGTH: 30
<212> TYPE: RNA
<213> ORGANISM: Homo sapiens

<400> SEQUENCE: 1036

ggccgugauc guauaguggu uaguacucgg                                    30

<210> SEQ ID NO 1037
<211> LENGTH: 38
<212> TYPE: RNA
<213> ORGANISM: Homo sapiens

<400> SEQUENCE: 1037

cccgggggc cggcggcggc ggcgacucug gacgcgag                            38

<210> SEQ ID NO 1038
<211> LENGTH: 50
<212> TYPE: RNA
<213> ORGANISM: Homo sapiens

<400> SEQUENCE: 1038

ggcugguccg augguagugg guuaucagaa cuuauuaaca uuagugucac              50

<210> SEQ ID NO 1039
<211> LENGTH: 50
<212> TYPE: RNA
<213> ORGANISM: Homo sapiens

<400> SEQUENCE: 1039

cgcgccugug aauagccacu gcacuccagc cugggcaaca uagcgagacc              50

<210> SEQ ID NO 1040
<211> LENGTH: 38
<212> TYPE: RNA
<213> ORGANISM: Homo sapiens

<400> SEQUENCE: 1040

ucugaggguc caggguucau gucccuguuc gggcgcca                           38

<210> SEQ ID NO 1041
<211> LENGTH: 31
<212> TYPE: RNA
<213> ORGANISM: Homo sapiens

<400> SEQUENCE: 1041

auuggucgug guuguagucc gugcgagaau a                                  31

<210> SEQ ID NO 1042
<211> LENGTH: 36
<212> TYPE: RNA
<213> ORGANISM: Homo sapiens

<400> SEQUENCE: 1042

guuuccguag uguagugguc aucacguucg ccugac                             36

<210> SEQ ID NO 1043
<211> LENGTH: 28
<212> TYPE: RNA
<213> ORGANISM: Homo sapiens

<400> SEQUENCE: 1043

ccgugaucgu auaguggua guacucug                                       28
```

<210> SEQ ID NO 1044
<211> LENGTH: 41
<212> TYPE: RNA
<213> ORGANISM: Homo sapiens

<400> SEQUENCE: 1044
cucucaccgc cgcggcccgg guucgauucc cggucaggga a 41

<210> SEQ ID NO 1045
<211> LENGTH: 30
<212> TYPE: RNA
<213> ORGANISM: Homo sapiens

<400> SEQUENCE: 1045
uaggaugggg ugugauaggu ggcacggaga 30

<210> SEQ ID NO 1046
<211> LENGTH: 37
<212> TYPE: RNA
<213> ORGANISM: Homo sapiens

<400> SEQUENCE: 1046
cauugugaag cagaauucac caagcguugg auuguuc 37

<210> SEQ ID NO 1047
<211> LENGTH: 40
<212> TYPE: RNA
<213> ORGANISM: Homo sapiens

<400> SEQUENCE: 1047
cacccggggg gccggcggcg gcggcgacuc uggacgcgag 40

<210> SEQ ID NO 1048
<211> LENGTH: 48
<212> TYPE: RNA
<213> ORGANISM: Homo sapiens

<400> SEQUENCE: 1048
acgaugguuu uucauaucau uggucguggu uguaguccgu gcgagaau 48

<210> SEQ ID NO 1049
<211> LENGTH: 29
<212> TYPE: RNA
<213> ORGANISM: Homo sapiens

<400> SEQUENCE: 1049
ucccuguggu cuaguggcua ggauucggc 29

<210> SEQ ID NO 1050
<211> LENGTH: 30
<212> TYPE: RNA
<213> ORGANISM: Homo sapiens

<400> SEQUENCE: 1050
ggccgugauc guauagcggu uaguacucug 30

<210> SEQ ID NO 1051
<211> LENGTH: 29
<212> TYPE: RNA
<213> ORGANISM: Homo sapiens

<400> SEQUENCE: 1051
ucccacaugg ucuagcgguu aggauuccu 29

<210> SEQ ID NO 1052
<211> LENGTH: 40
<212> TYPE: RNA
<213> ORGANISM: Homo sapiens

<400> SEQUENCE: 1052
cucucaccgc cgcggcccgg guucgauucc cggucaggga 40

<210> SEQ ID NO 1053
<211> LENGTH: 40
<212> TYPE: RNA
<213> ORGANISM: Homo sapiens

<400> SEQUENCE: 1053
guuuuucaua ucauuggucg ugguuguagu ccgugcgaga 40

<210> SEQ ID NO 1054
<211> LENGTH: 43
<212> TYPE: RNA
<213> ORGANISM: Homo sapiens

<400> SEQUENCE: 1054
ggcugguccg augguagugg guuaucagaa cuuauuaaca uua 43

<210> SEQ ID NO 1055
<211> LENGTH: 30
<212> TYPE: RNA
<213> ORGANISM: Homo sapiens

<400> SEQUENCE: 1055
ugccgugauc guauaguggu uaguacucug 30

<210> SEQ ID NO 1056
<211> LENGTH: 31
<212> TYPE: RNA
<213> ORGANISM: Homo sapiens

<400> SEQUENCE: 1056
ucccuggugg ucuaguggcu aggauucggc g 31

<210> SEQ ID NO 1057
<211> LENGTH: 42
<212> TYPE: RNA
<213> ORGANISM: Homo sapiens

<400> SEQUENCE: 1057
gugguaauuc uagagcuaau acaugccgac gggcgcugac cc 42

<210> SEQ ID NO 1058
<211> LENGTH: 28
<212> TYPE: RNA
<213> ORGANISM: Homo sapiens

<400> SEQUENCE: 1058
gcguuggugg uauaguggug agcauagc 28

<210> SEQ ID NO 1059
<211> LENGTH: 34
<212> TYPE: RNA
<213> ORGANISM: Homo sapiens

<400> SEQUENCE: 1059
gccuuggugg uucaguggua gaauucucgc cugc 34

<210> SEQ ID NO 1060
<211> LENGTH: 31
<212> TYPE: RNA
<213> ORGANISM: Homo sapiens

<400> SEQUENCE: 1060
ucccuagugg ucuagugguu aggauucggc g 31

<210> SEQ ID NO 1061
<211> LENGTH: 50
<212> TYPE: RNA
<213> ORGANISM: Homo sapiens

<400> SEQUENCE: 1061
agugacgcgc augaauggau gaacgagauu cccacugucc cuaccuacua 50

<210> SEQ ID NO 1062
<211> LENGTH: 27
<212> TYPE: RNA
<213> ORGANISM: Homo sapiens

<400> SEQUENCE: 1062
cguaacuucg ggauaaggau uggcucu 27

<210> SEQ ID NO 1063
<211> LENGTH: 27
<212> TYPE: RNA
<213> ORGANISM: Homo sapiens

<400> SEQUENCE: 1063
cggcuagcuc agucgguaga gcaugag 27

<210> SEQ ID NO 1064
<211> LENGTH: 31
<212> TYPE: RNA
<213> ORGANISM: Homo sapiens

<400> SEQUENCE: 1064
ucccuggugg ucuagugguu aggauucggc c 31

<210> SEQ ID NO 1065
<211> LENGTH: 50
<212> TYPE: RNA
<213> ORGANISM: Homo sapiens

<400> SEQUENCE: 1065
cccugcgggc cgccggugaa auaccacuac ucugaucguu uuuucacuga 50

<210> SEQ ID NO 1066
<211> LENGTH: 33
<212> TYPE: RNA
<213> ORGANISM: Homo sapiens

<400> SEQUENCE: 1066
cgggccuggu uaguacuugg augggagacc gcc 33

<210> SEQ ID NO 1067
<211> LENGTH: 31
<212> TYPE: RNA
<213> ORGANISM: Homo sapiens

<400> SEQUENCE: 1067
agccgugauc guauaguggu uaguacucug c 31

<210> SEQ ID NO 1068
<211> LENGTH: 37
<212> TYPE: RNA
<213> ORGANISM: Homo sapiens

<400> SEQUENCE: 1068
auugugaagc agaauucacc aagcguugga uuguuca 37

<210> SEQ ID NO 1069
<211> LENGTH: 28
<212> TYPE: RNA
<213> ORGANISM: Homo sapiens

<400> SEQUENCE: 1069
ugccgugauc guauaguggu uaguacuc 28

<210> SEQ ID NO 1070
<211> LENGTH: 49
<212> TYPE: RNA
<213> ORGANISM: Homo sapiens

<400> SEQUENCE: 1070
ccguggagag gaacaacucu gagucuuaag cuaauuuuuu gaggccuug 49

<210> SEQ ID NO 1071
<211> LENGTH: 42
<212> TYPE: RNA
<213> ORGANISM: Homo sapiens

<400> SEQUENCE: 1071
ccugucacgc gggagaccgg gguucgauuc cccgacgggg ag 42

<210> SEQ ID NO 1072
<211> LENGTH: 31
<212> TYPE: RNA
<213> ORGANISM: Homo sapiens

<400> SEQUENCE: 1072
ucccuggugg ucuagugguu aggacucggc g 31

<210> SEQ ID NO 1073
<211> LENGTH: 42
<212> TYPE: RNA
<213> ORGANISM: Homo sapiens

<400> SEQUENCE: 1073
auugugaauc ugacaacaga ggcuuacgac cccuuauuua cc 42

<210> SEQ ID NO 1074
<211> LENGTH: 44
<212> TYPE: RNA
<213> ORGANISM: Homo sapiens

<400> SEQUENCE: 1074
ccuuccaagc aguugacccg gguucgauuc ccggccaacg cacc 44

<210> SEQ ID NO 1075
<211> LENGTH: 42
<212> TYPE: RNA
<213> ORGANISM: Homo sapiens

<400> SEQUENCE: 1075
cucucaccgc cgcggcccgg guucgauucc cggucaggga ac 42

<210> SEQ ID NO 1076
<211> LENGTH: 30
<212> TYPE: RNA
<213> ORGANISM: Homo sapiens

<400> SEQUENCE: 1076
ucccuggugg ucuaguggcu aggauucggc 30

<210> SEQ ID NO 1077
<211> LENGTH: 32
<212> TYPE: RNA
<213> ORGANISM: Homo sapiens

<400> SEQUENCE: 1077
gcauuggugg uucaguggaa gaauucucgc cu 32

<210> SEQ ID NO 1078
<211> LENGTH: 30
<212> TYPE: RNA
<213> ORGANISM: Homo sapiens

<400> SEQUENCE: 1078
ggccgugauc guauaguggu uaguacuaug 30

<210> SEQ ID NO 1079
<211> LENGTH: 42
<212> TYPE: RNA
<213> ORGANISM: Homo sapiens

<400> SEQUENCE: 1079
gcuuugggug cuaauggugg aguuaaagac uuuuucucug ac 42

<210> SEQ ID NO 1080
<211> LENGTH: 50
<212> TYPE: RNA
<213> ORGANISM: Homo sapiens

<400> SEQUENCE: 1080
gaaaagaacu uugaagagag aguucaagag ggcgugaaac cguuaagagg 50

<210> SEQ ID NO 1081
<211> LENGTH: 49
<212> TYPE: RNA
<213> ORGANISM: Homo sapiens

<400> SEQUENCE: 1081
acgaugguuu uucauaucau uggucguggu uguaguccgu gcgagaaua 49

<210> SEQ ID NO 1082
<211> LENGTH: 46
<212> TYPE: RNA
<213> ORGANISM: Homo sapiens

<400> SEQUENCE: 1082
guucuuguag uugaaauaca acgaugguuu uucauaucau uggucg 46

<210> SEQ ID NO 1083
<211> LENGTH: 35
<212> TYPE: RNA
<213> ORGANISM: Homo sapiens

<400> SEQUENCE: 1083
gcccggcuag cucagucggu agagcauggg acucu 35

<210> SEQ ID NO 1084
<211> LENGTH: 49
<212> TYPE: RNA
<213> ORGANISM: Homo sapiens

<400> SEQUENCE: 1084
aaaagaacuu ugaagagaga guucaagagg gcgugaaacc guuaagagg 49

<210> SEQ ID NO 1085
<211> LENGTH: 31
<212> TYPE: RNA
<213> ORGANISM: Homo sapiens

<400> SEQUENCE: 1085
cuacuuggau aacuguggua auucuagagc u 31

<210> SEQ ID NO 1086
<211> LENGTH: 45
<212> TYPE: RNA
<213> ORGANISM: Homo sapiens

<400> SEQUENCE: 1086
auuccggauc agaagauuga ggguucgagu cccuucgugg ucgcc 45

<210> SEQ ID NO 1087
<211> LENGTH: 28
<212> TYPE: RNA
<213> ORGANISM: Homo sapiens

<400> SEQUENCE: 1087
ucccauaugg ucuagcgguu aggauucc 28

<210> SEQ ID NO 1088
<211> LENGTH: 30
<212> TYPE: RNA
<213> ORGANISM: Homo sapiens

<400> SEQUENCE: 1088
ggccgugauc guauagugga uaguacucug 30

<210> SEQ ID NO 1089
<211> LENGTH: 50
<212> TYPE: RNA
<213> ORGANISM: Homo sapiens

<400> SEQUENCE: 1089
ccgaaacccc ccccgagugu uacagccccc ccggcagcag cacucgccga 50

<210> SEQ ID NO 1090
<211> LENGTH: 50
<212> TYPE: RNA
<213> ORGANISM: Homo sapiens

<400> SEQUENCE: 1090
aauugcagga cacauugauc aucgacacuu cgaacgcacu ugcggccccg 50

<210> SEQ ID NO 1091
<211> LENGTH: 32
<212> TYPE: RNA

<213> ORGANISM: Homo sapiens

<400> SEQUENCE: 1091
ccaagcguug gauuguucac ccacucauag gg 32

<210> SEQ ID NO 1092
<211> LENGTH: 28
<212> TYPE: RNA
<213> ORGANISM: Homo sapiens

<400> SEQUENCE: 1092
gcauuugugg uucaguggua gaauucuc 28

<210> SEQ ID NO 1093
<211> LENGTH: 28
<212> TYPE: RNA
<213> ORGANISM: Homo sapiens

<400> SEQUENCE: 1093
agcagagugg cgcagcggaa gcgugcug 28

<210> SEQ ID NO 1094
<211> LENGTH: 44
<212> TYPE: RNA
<213> ORGANISM: Homo sapiens

<400> SEQUENCE: 1094
auucccauuc uugcgacccg gguucguuuc ccgggcggcg cacc 44

<210> SEQ ID NO 1095
<211> LENGTH: 28
<212> TYPE: RNA
<213> ORGANISM: Homo sapiens

<400> SEQUENCE: 1095 ucccugugggu cuaguggcua ggauucgg 28

<210> SEQ ID NO 1096
<211> LENGTH: 50
<212> TYPE: RNA
<213> ORGANISM: Homo sapiens

<400> SEQUENCE: 1096
caucgacacu ucgaacgcac uugcggcccc ggguuccucc cggggcuacg 50

<210> SEQ ID NO 1097
<211> LENGTH: 29
<212> TYPE: RNA
<213> ORGANISM: Homo sapiens

<400> SEQUENCE: 1097
ccgugaucgu auagugguua guacucugc 29

<210> SEQ ID NO 1098
<211> LENGTH: 37
<212> TYPE: RNA
<213> ORGANISM: Homo sapiens

<400> SEQUENCE: 1098
aaaucggucg uccgaccugg guauaggggc gaaagac 37

<210> SEQ ID NO 1099
<211> LENGTH: 45

<212> TYPE: RNA
<213> ORGANISM: Homo sapiens

<400> SEQUENCE: 1099
cuaagcaggg ucgggccugg uuaguacuug gaugggagac cgccu 45

<210> SEQ ID NO 1100
<211> LENGTH: 33
<212> TYPE: RNA
<213> ORGANISM: Homo sapiens

<400> SEQUENCE: 1100
ucccugguag ucuagugguu aggauucggc gcu 33

<210> SEQ ID NO 1101
<211> LENGTH: 43
<212> TYPE: RNA
<213> ORGANISM: Homo sapiens

<400> SEQUENCE: 1101
uaagcagggu cgggccuggu uaguacuugg augggagacc gcc 43

<210> SEQ ID NO 1102
<211> LENGTH: 41
<212> TYPE: RNA
<213> ORGANISM: Homo sapiens

<400> SEQUENCE: 1102
cucucaccgc cgcggcccgg guucguuucc cggucaggga a 41

<210> SEQ ID NO 1103
<211> LENGTH: 50
<212> TYPE: RNA
<213> ORGANISM: Homo sapiens

<400> SEQUENCE: 1103
aacgaacgag acucuggcau gcuaacuagu uacgcgaccc ccgagcgguc 50

<210> SEQ ID NO 1104
<211> LENGTH: 44
<212> TYPE: RNA
<213> ORGANISM: Homo sapiens

<400> SEQUENCE: 1104 cccgggggc cggcggcggc ggcgacucug gacgcgagcc gggc 44

<210> SEQ ID NO 1105
<211> LENGTH: 37
<212> TYPE: RNA
<213> ORGANISM: Homo sapiens

<400> SEQUENCE: 1105
ucagaagauu gaggguucga gucccuucgu ggucgcc 37

<210> SEQ ID NO 1106
<211> LENGTH: 44
<212> TYPE: RNA
<213> ORGANISM: Homo sapiens

<400> SEQUENCE: 1106
ccugucacgc gggagaccgg gguucgauuc cccgacgggg agcc 44

<210> SEQ ID NO 1107

<211> LENGTH: 30
<212> TYPE: RNA
<213> ORGANISM: Homo sapiens

<400> SEQUENCE: 1107
guuuccguag uguagugguu aucacguucg 30

<210> SEQ ID NO 1108
<211> LENGTH: 37
<212> TYPE: RNA
<213> ORGANISM: Homo sapiens

<400> SEQUENCE: 1108
ucucaggguc gugggguucgu gccccacguu gggcgcc 37

<210> SEQ ID NO 1109
<211> LENGTH: 49
<212> TYPE: RNA
<213> ORGANISM: Homo sapiens

<400> SEQUENCE: 1109
caagacucca gacacaucca aaugaggcgc ugcauguggc agucugccu 49

<210> SEQ ID NO 1110
<211> LENGTH: 32
<212> TYPE: RNA
<213> ORGANISM: Homo sapiens

<400> SEQUENCE: 1110
gcauuggugg uucaguggua gaauucucgc au 32

<210> SEQ ID NO 1111
<211> LENGTH: 32
<212> TYPE: RNA
<213> ORGANISM: Homo sapiens

<400> SEQUENCE: 1111
ggccguaauc guauaguggu uaguacucug cg 32

<210> SEQ ID NO 1112
<211> LENGTH: 40
<212> TYPE: RNA
<213> ORGANISM: Homo sapiens

<400> SEQUENCE: 1112
gcuuugggug cuaauggugg aguuaaagac uuuuucucug 40

<210> SEQ ID NO 1113
<211> LENGTH: 31
<212> TYPE: RNA
<213> ORGANISM: Homo sapiens

<400> SEQUENCE: 1113
uaggaugggg ugugauaggu ggcacggaga a 31

<210> SEQ ID NO 1114
<211> LENGTH: 50
<212> TYPE: RNA
<213> ORGANISM: Homo sapiens

<400> SEQUENCE: 1114
gcagagcagc ucccucgcug cgaucuauug aaagucagcc cucgacacaa 50

<210> SEQ ID NO 1115
<211> LENGTH: 44
<212> TYPE: RNA
<213> ORGANISM: Homo sapiens

<400> SEQUENCE: 1115
uuuuucauau cauuggucgu gguuguaguc cgugcgagaa uacc 44

<210> SEQ ID NO 1116
<211> LENGTH: 31
<212> TYPE: RNA
<213> ORGANISM: Homo sapiens

<400> SEQUENCE: 1116
uccccugugg ucuaguggcu aggauucggc g 31

<210> SEQ ID NO 1117
<211> LENGTH: 35
<212> TYPE: RNA
<213> ORGANISM: Homo sapiens

<400> SEQUENCE: 1117
uccccugugg ucuagugguu aggauucggc gcucu 35

<210> SEQ ID NO 1118
<211> LENGTH: 34
<212> TYPE: RNA
<213> ORGANISM: Homo sapiens

<400> SEQUENCE: 1118
ugccgugauc guauaguggu uaguacucug cguu 34

<210> SEQ ID NO 1119
<211> LENGTH: 49
<212> TYPE: RNA
<213> ORGANISM: Homo sapiens

<400> SEQUENCE: 1119
cgacucuuag cgguggauca cucggcucgu gcgucgauga agaacgcag 49

<210> SEQ ID NO 1120
<211> LENGTH: 50
<212> TYPE: RNA
<213> ORGANISM: Homo sapiens

<400> SEQUENCE: 1120
agcaguugaa caugggucag ucgguccuga gagaugggcg agcgccguuc 50

<210> SEQ ID NO 1121
<211> LENGTH: 30
<212> TYPE: RNA
<213> ORGANISM: Homo sapiens

<400> SEQUENCE: 1121
aaaucaguua ugguuccuuu ggucgcucgc 30

<210> SEQ ID NO 1122
<211> LENGTH: 28
<212> TYPE: RNA
<213> ORGANISM: Homo sapiens

<400> SEQUENCE: 1122
cguaacuucg ggauaaggau uggcucua 28

```
<210> SEQ ID NO 1123
<211> LENGTH: 26
<212> TYPE: RNA
<213> ORGANISM: Homo sapiens

<400> SEQUENCE: 1123

caccccacgu cucgucgcgc gcgcgu                                              26

<210> SEQ ID NO 1124
<211> LENGTH: 40
<212> TYPE: RNA
<213> ORGANISM: Homo sapiens

<400> SEQUENCE: 1124

ggcugguccg augguagugg guuaucagaa cuuauuaaca                               40

<210> SEQ ID NO 1125
<211> LENGTH: 42
<212> TYPE: RNA
<213> ORGANISM: Homo sapiens

<400> SEQUENCE: 1125

cuuucaccgc cgcggcccgg guucguuucc cggucaggga ac                            42

<210> SEQ ID NO 1126
<211> LENGTH: 38
<212> TYPE: RNA
<213> ORGANISM: Homo sapiens

<400> SEQUENCE: 1126

ucucaggguc guggguucgu gccccacguu gggcgcca                                 38

<210> SEQ ID NO 1127
<211> LENGTH: 30
<212> TYPE: RNA
<213> ORGANISM: Homo sapiens

<400> SEQUENCE: 1127

ggccgucauc guauaguggu uaguacucug                                          30

<210> SEQ ID NO 1128
<211> LENGTH: 42
<212> TYPE: RNA
<213> ORGANISM: Homo sapiens

<400> SEQUENCE: 1128

acauugauca ucgacacuuc gaacgcacuu gcggccccgg gu                            42

<210> SEQ ID NO 1129
<211> LENGTH: 34
<212> TYPE: RNA
<213> ORGANISM: Homo sapiens

<400> SEQUENCE: 1129

gcauuagugg uucaguggua gaauucucgc cugc                                     34

<210> SEQ ID NO 1130
<211> LENGTH: 31
<212> TYPE: RNA
<213> ORGANISM: Homo sapiens

<400> SEQUENCE: 1130

ggccgugauc guauaguggu uaguacucug u                                        31
```

<210> SEQ ID NO 1131
<211> LENGTH: 39
<212> TYPE: RNA
<213> ORGANISM: Homo sapiens

<400> SEQUENCE: 1131
auugugaauc ugacaacaga ggcuuacgac cccuuauuu 39

<210> SEQ ID NO 1132
<211> LENGTH: 43
<212> TYPE: RNA
<213> ORGANISM: Homo sapiens

<400> SEQUENCE: 1132
cgcugcgauc uauugaaagu cagcccucga cacaaggguu ugu 43

<210> SEQ ID NO 1133
<211> LENGTH: 42
<212> TYPE: RNA
<213> ORGANISM: Homo sapiens

<400> SEQUENCE: 1133
cauugaucau cgacacuucg aacgcacuug cggccccggg uu 42

<210> SEQ ID NO 1134
<211> LENGTH: 26
<212> TYPE: RNA
<213> ORGANISM: Homo sapiens

<400> SEQUENCE: 1134
ucccuggugg ucuagugguu aggauu 26

<210> SEQ ID NO 1135
<211> LENGTH: 29
<212> TYPE: RNA
<213> ORGANISM: Homo sapiens

<400> SEQUENCE: 1135
gcguuguggu auagugguga gcauagcug 29

<210> SEQ ID NO 1136
<211> LENGTH: 50
<212> TYPE: RNA
<213> ORGANISM: Homo sapiens

<400> SEQUENCE: 1136 cccgggggc cggcggcggc ggcgacucug gacgcgagcc gggcccuucc 50

<210> SEQ ID NO 1137
<211> LENGTH: 27
<212> TYPE: RNA
<213> ORGANISM: Homo sapiens

<400> SEQUENCE: 1137
aggcggcgga ggggccgcgg gccgguc 27

<210> SEQ ID NO 1138
<211> LENGTH: 31
<212> TYPE: RNA
<213> ORGANISM: Homo sapiens

<400> SEQUENCE: 1138
ucacuggugg ucuagugguu aggauucggc g 31

<210> SEQ ID NO 1139
<211> LENGTH: 37
<212> TYPE: RNA
<213> ORGANISM: Homo sapiens

<400> SEQUENCE: 1139
uuuugauccu ucgaugucgg cucuuccuau cauugug 37

<210> SEQ ID NO 1140
<211> LENGTH: 34
<212> TYPE: RNA
<213> ORGANISM: Homo sapiens

<400> SEQUENCE: 1140
agugacgcgc augaauggau gaacgagauu ccca 34

<210> SEQ ID NO 1141
<211> LENGTH: 40
<212> TYPE: RNA
<213> ORGANISM: Homo sapiens

<400> SEQUENCE: 1141
uuaaguuaaa gauuaagaga accaacaccu cuuuacagug 40

<210> SEQ ID NO 1142
<211> LENGTH: 49
<212> TYPE: RNA
<213> ORGANISM: Homo sapiens

<400> SEQUENCE: 1142
aaaacaaagc aucgcgaagg cccgcggcgg guguugacgc gaugugauu 49

<210> SEQ ID NO 1143
<211> LENGTH: 41
<212> TYPE: RNA
<213> ORGANISM: Homo sapiens

<400> SEQUENCE: 1143
uuuuucauau cauuggucgu gguuguaguc cgugcgagaa u 41

<210> SEQ ID NO 1144
<211> LENGTH: 39
<212> TYPE: RNA
<213> ORGANISM: Homo sapiens

<400> SEQUENCE: 1144
ggcugguccg aagguaguga guuaucucaa uugauuguu 39

<210> SEQ ID NO 1145
<211> LENGTH: 28
<212> TYPE: RNA
<213> ORGANISM: Homo sapiens

<400> SEQUENCE: 1145
cacggucccc cgcgaggggg gcccgggc 28

<210> SEQ ID NO 1146
<211> LENGTH: 26
<212> TYPE: RNA
<213> ORGANISM: Homo sapiens

<400> SEQUENCE: 1146
gugguuguag uccgugcgag aauacc 26

<210> SEQ ID NO 1147
<211> LENGTH: 46
<212> TYPE: RNA
<213> ORGANISM: Homo sapiens

<400> SEQUENCE: 1147
ggcuaaugau ggaaaaauca uuauuggaaa agaaugacau gaacaa 46

<210> SEQ ID NO 1148
<211> LENGTH: 26
<212> TYPE: RNA
<213> ORGANISM: Homo sapiens

<400> SEQUENCE: 1148
cggcggcguc cggugagcuc ucgcug 26

<210> SEQ ID NO 1149
<211> LENGTH: 31
<212> TYPE: RNA
<213> ORGANISM: Homo sapiens

<400> SEQUENCE: 1149
ucccuggugg ucuagugguu aggcuucggc g 31

<210> SEQ ID NO 1150
<211> LENGTH: 29
<212> TYPE: RNA
<213> ORGANISM: Homo sapiens

<400> SEQUENCE: 1150
guuuccguag uguagugguu aucacguuc 29

<210> SEQ ID NO 1151
<211> LENGTH: 27
<212> TYPE: RNA
<213> ORGANISM: Homo sapiens

<400> SEQUENCE: 1151
ccacuacucu gaucguuuuu ucacuga 27

<210> SEQ ID NO 1152
<211> LENGTH: 29
<212> TYPE: RNA
<213> ORGANISM: Homo sapiens

<400> SEQUENCE: 1152
ucccuggugg ucuagugguu aggauucgg 29

<210> SEQ ID NO 1153
<211> LENGTH: 35
<212> TYPE: RNA
<213> ORGANISM: Homo sapiens

<400> SEQUENCE: 1153
ugccgugauc guauaguggu uaguacucug cguug 35

<210> SEQ ID NO 1154
<211> LENGTH: 31
<212> TYPE: RNA
<213> ORGANISM: Homo sapiens

<400> SEQUENCE: 1154
ucccuggugg ucuagugguu aggauuccgc g 31

<210> SEQ ID NO 1155
<211> LENGTH: 32
<212> TYPE: RNA
<213> ORGANISM: Homo sapiens

<400> SEQUENCE: 1155
uccccugugg ucuagugguu aggauucggc gc 32

<210> SEQ ID NO 1156
<211> LENGTH: 36
<212> TYPE: RNA
<213> ORGANISM: Homo sapiens

<400> SEQUENCE: 1156
auugugaagc agaauucacc aagcguugga uuguuc 36

<210> SEQ ID NO 1157
<211> LENGTH: 50
<212> TYPE: RNA
<213> ORGANISM: Homo sapiens

<400> SEQUENCE: 1157
cuuuuugauc cuucgauguc ggcucuuccu aucauuguga agcagaauuc 50

<210> SEQ ID NO 1158
<211> LENGTH: 46
<212> TYPE: RNA
<213> ORGANISM: Homo sapiens

<400> SEQUENCE: 1158
gacucuuagc gguggaucac ucggcucgug cgucgaugaa gaacgc 46

<210> SEQ ID NO 1159
<211> LENGTH: 38
<212> TYPE: RNA
<213> ORGANISM: Homo sapiens

<400> SEQUENCE: 1159
cauugugaag cagaauucac caagcguugg auuguuca 38

<210> SEQ ID NO 1160
<211> LENGTH: 42
<212> TYPE: RNA
<213> ORGANISM: Homo sapiens

<400> SEQUENCE: 1160
guuuuucaua ucauuggucg ugguuguagu ccgugcgaga au 42

<210> SEQ ID NO 1161
<211> LENGTH: 36
<212> TYPE: RNA
<213> ORGANISM: Homo sapiens

<400> SEQUENCE: 1161
cagaagauug aggguucgug ucccuucgug gucgcc 36

<210> SEQ ID NO 1162
<211> LENGTH: 36
<212> TYPE: RNA
<213> ORGANISM: Homo sapiens

<400> SEQUENCE: 1162
cgccgcggcc cggguucgau ucccggucag ggaacc 36

<210> SEQ ID NO 1163
<211> LENGTH: 32
<212> TYPE: RNA
<213> ORGANISM: Homo sapiens

<400> SEQUENCE: 1163
gcauuggugg uucaguggua gaauucucuc cu 32

<210> SEQ ID NO 1164
<211> LENGTH: 26
<212> TYPE: RNA
<213> ORGANISM: Homo sapiens

<400> SEQUENCE: 1164
gcaugggugg uucaguggua gaauuc 26

<210> SEQ ID NO 1165
<211> LENGTH: 43
<212> TYPE: RNA
<213> ORGANISM: Homo sapiens

<400> SEQUENCE: 1165
ccugucacgc gggagaccgg gguucgauuc cccgacgggg agc 43

<210> SEQ ID NO 1166
<211> LENGTH: 29
<212> TYPE: RNA
<213> ORGANISM: Homo sapiens

<400> SEQUENCE: 1166
ggucccaugg uguaaugguu agcacucug 29

<210> SEQ ID NO 1167
<211> LENGTH: 28
<212> TYPE: RNA
<213> ORGANISM: Homo sapiens

<400> SEQUENCE: 1167
uccccugugg ucuagugguu aggauucg 28

<210> SEQ ID NO 1168
<211> LENGTH: 46
<212> TYPE: RNA
<213> ORGANISM: Homo sapiens

<400> SEQUENCE: 1168
agcuaagcag ggucgggccu gguuaguacu uggaugggag accgcc 46

<210> SEQ ID NO 1169
<211> LENGTH: 33
<212> TYPE: RNA
<213> ORGANISM: Homo sapiens

<400> SEQUENCE: 1169
ccacuacucu gaucguuuuu ucacugaccc ggu 33

<210> SEQ ID NO 1170
<211> LENGTH: 31
<212> TYPE: RNA

<213> ORGANISM: Homo sapiens

<400> SEQUENCE: 1170
ugccgugauc guauaguggu uaguacucug c 31

<210> SEQ ID NO 1171
<211> LENGTH: 49
<212> TYPE: RNA
<213> ORGANISM: Homo sapiens

<400> SEQUENCE: 1171
aaucuggcuu ggcggaauau cucuuugaca agcacacccu gggagacag 49

<210> SEQ ID NO 1172
<211> LENGTH: 32
<212> TYPE: RNA
<213> ORGANISM: Homo sapiens

<400> SEQUENCE: 1172
ugccgugauc guauaguggu uaguacucug cg 32

<210> SEQ ID NO 1173
<211> LENGTH: 30
<212> TYPE: RNA
<213> ORGANISM: Homo sapiens

<400> SEQUENCE: 1173
ggccgugauc guauaguggu uaguaaucug 30

<210> SEQ ID NO 1174
<211> LENGTH: 30
<212> TYPE: RNA
<213> ORGANISM: Homo sapiens

<400> SEQUENCE: 1174
cgccgugauc guauaguggu uaguacucug 30

<210> SEQ ID NO 1175
<211> LENGTH: 50
<212> TYPE: RNA
<213> ORGANISM: Homo sapiens

<400> SEQUENCE: 1175
aacgaugguu uuucauauca uuggucgugg uuguaguccg ugcgagaaua 50

<210> SEQ ID NO 1176
<211> LENGTH: 33
<212> TYPE: RNA
<213> ORGANISM: Homo sapiens

<400> SEQUENCE: 1176
ucagaagguu gcguguucag gucacgucgg ggu 33

<210> SEQ ID NO 1177
<211> LENGTH: 31
<212> TYPE: RNA
<213> ORGANISM: Homo sapiens

<400> SEQUENCE: 1177
ucccauaugg ucuagcgguu aggauuccug g 31

<210> SEQ ID NO 1178
<211> LENGTH: 50

<212> TYPE: RNA
<213> ORGANISM: Homo sapiens

<400> SEQUENCE: 1178
cgacucuuag cgguggauca cucggcucgu gcgucgaugc agaacgcagc 50

<210> SEQ ID NO 1179
<211> LENGTH: 30
<212> TYPE: RNA
<213> ORGANISM: Homo sapiens

<400> SEQUENCE: 1179
ucccuguggu cuaguggcua ggauucggcg 30

<210> SEQ ID NO 1180
<211> LENGTH: 30
<212> TYPE: RNA
<213> ORGANISM: Homo sapiens

<400> SEQUENCE: 1180
ggccgugauc guauaguggu uaguccucug 30

<210> SEQ ID NO 1181
<211> LENGTH: 29
<212> TYPE: RNA
<213> ORGANISM: Homo sapiens

<400> SEQUENCE: 1181
aacgcgcccg aucucgucug aucucggaa 29

<210> SEQ ID NO 1182
<211> LENGTH: 30
<212> TYPE: RNA
<213> ORGANISM: Homo sapiens

<400> SEQUENCE: 1182
ggccgugauc guauagaggu uaguacucug 30

<210> SEQ ID NO 1183
<211> LENGTH: 50
<212> TYPE: RNA
<213> ORGANISM: Homo sapiens

<400> SEQUENCE: 1183
cugcagugau gacuuucuua ggacaccuuu ggauuuaccg ugaaaauuaa 50

<210> SEQ ID NO 1184
<211> LENGTH: 40
<212> TYPE: RNA
<213> ORGANISM: Homo sapiens

<400> SEQUENCE: 1184
cucucaccgc cgcggcccgg guucguuucc cggucaggga 40

<210> SEQ ID NO 1185
<211> LENGTH: 45
<212> TYPE: RNA
<213> ORGANISM: Homo sapiens

<400> SEQUENCE: 1185
agcagccgac uuagaacugg ugcggaccag gggaauccga cuguu 45

<210> SEQ ID NO 1186

```
<211> LENGTH: 49
<212> TYPE: RNA
<213> ORGANISM: Homo sapiens

<400> SEQUENCE: 1186

cucccucgcu gcgaucuauu gaaagucagc ccucgacaca aggguuugu        49

<210> SEQ ID NO 1187
<211> LENGTH: 31
<212> TYPE: RNA
<213> ORGANISM: Homo sapiens

<400> SEQUENCE: 1187

ggccgugauc guauagugga uaguacucug c                          31

<210> SEQ ID NO 1188
<211> LENGTH: 46
<212> TYPE: RNA
<213> ORGANISM: Homo sapiens

<400> SEQUENCE: 1188

cucgucugau cucggaagcu aagcaggguc gggccugguu aguacu           46

<210> SEQ ID NO 1189
<211> LENGTH: 32
<212> TYPE: RNA
<213> ORGANISM: Homo sapiens

<400> SEQUENCE: 1189

ggccgugauc gcauaguggu uaguacucug cg                         32

<210> SEQ ID NO 1190
<211> LENGTH: 30
<212> TYPE: RNA
<213> ORGANISM: Homo sapiens

<400> SEQUENCE: 1190

uaggauggcg ugugauaggu ggcacggaga                            30

<210> SEQ ID NO 1191
<211> LENGTH: 34
<212> TYPE: RNA
<213> ORGANISM: Homo sapiens

<400> SEQUENCE: 1191

ggcugguccg augguagugg guuaucagaa cuua                       34

<210> SEQ ID NO 1192
<211> LENGTH: 30
<212> TYPE: RNA
<213> ORGANISM: Homo sapiens

<400> SEQUENCE: 1192

gguuccauag uguagugguu aucacgucug                            30

<210> SEQ ID NO 1193
<211> LENGTH: 30
<212> TYPE: RNA
<213> ORGANISM: Homo sapiens

<400> SEQUENCE: 1193

ucccacaugg ucuagcgguu aggauuccug                            30
```

<210> SEQ ID NO 1194
<211> LENGTH: 33
<212> TYPE: RNA
<213> ORGANISM: Homo sapiens

<400> SEQUENCE: 1194
gcuuccguag uguagugguu aucacguucg ccu 33

<210> SEQ ID NO 1195
<211> LENGTH: 30
<212> TYPE: RNA
<213> ORGANISM: Homo sapiens

<400> SEQUENCE: 1195
gcauuugugg uucaguggua gaauucucgc 30

<210> SEQ ID NO 1196
<211> LENGTH: 30
<212> TYPE: RNA
<213> ORGANISM: Homo sapiens

<400> SEQUENCE: 1196
gcguuggugg uauaguggug agcauagcug 30

<210> SEQ ID NO 1197
<211> LENGTH: 29
<212> TYPE: RNA
<213> ORGANISM: Homo sapiens

<400> SEQUENCE: 1197
uccccugugg ucuagugguu aggauucgg 29

<210> SEQ ID NO 1198
<211> LENGTH: 29
<212> TYPE: RNA
<213> ORGANISM: Homo sapiens

<400> SEQUENCE: 1198
gcguuggugg uauaguggug agcauagcu 29

<210> SEQ ID NO 1199
<211> LENGTH: 45
<212> TYPE: RNA
<213> ORGANISM: Homo sapiens

<400> SEQUENCE: 1199
auuccggauc agaagauuga ggguucgggu cccuucgugg ucgcc 45

<210> SEQ ID NO 1200
<211> LENGTH: 43
<212> TYPE: RNA
<213> ORGANISM: Homo sapiens

<400> SEQUENCE: 1200
cucucaccgc cgcggcccgg guucguuucc cggucaggga acc 43

<210> SEQ ID NO 1201
<211> LENGTH: 50
<212> TYPE: RNA
<213> ORGANISM: Homo sapiens

<400> SEQUENCE: 1201
ucggaagcua agcagggucg ggccugguua guacuuggau gggagaccgc 50

<210> SEQ ID NO 1202
<211> LENGTH: 40
<212> TYPE: RNA
<213> ORGANISM: Homo sapiens

<400> SEQUENCE: 1202
uugcaaauuc gaagaagcag cuucaaaccu gccggggcuu 40

<210> SEQ ID NO 1203
<211> LENGTH: 39
<212> TYPE: RNA
<213> ORGANISM: Homo sapiens

<400> SEQUENCE: 1203
cuuacacuua ggagauuuca acuuaacuug accgcucug 39

<210> SEQ ID NO 1204
<211> LENGTH: 28
<212> TYPE: RNA
<213> ORGANISM: Homo sapiens

<400> SEQUENCE: 1204
ucccuggugg ucuaguggcu aggauucg 28

<210> SEQ ID NO 1205
<211> LENGTH: 30
<212> TYPE: RNA
<213> ORGANISM: Homo sapiens

<400> SEQUENCE: 1205
ccccuguggu cuaguggcua ggauucggcg 30

<210> SEQ ID NO 1206
<211> LENGTH: 45
<212> TYPE: RNA
<213> ORGANISM: Homo sapiens

<400> SEQUENCE: 1206
ucgucugauc ucggaagcua agcagggucg ggccugguua guacu 45

<210> SEQ ID NO 1207
<211> LENGTH: 30
<212> TYPE: RNA
<213> ORGANISM: Homo sapiens

<400> SEQUENCE: 1207
ggccgugauc guauaguggu ucguacucug 30

<210> SEQ ID NO 1208
<211> LENGTH: 34
<212> TYPE: RNA
<213> ORGANISM: Homo sapiens

<400> SEQUENCE: 1208
agcagccgac uuagaacugg ugcggaccag ggga 34

<210> SEQ ID NO 1209
<211> LENGTH: 35
<212> TYPE: RNA
<213> ORGANISM: Homo sapiens

<400> SEQUENCE: 1209
uugugaagca gaauucacca agcguuggau uguuc 35

<210> SEQ ID NO 1210
<211> LENGTH: 34
<212> TYPE: RNA
<213> ORGANISM: Homo sapiens

<400> SEQUENCE: 1210
aggacacauu gaucaucgac acuucgaacg cacu 34

<210> SEQ ID NO 1211
<211> LENGTH: 37
<212> TYPE: RNA
<213> ORGANISM: Homo sapiens

<400> SEQUENCE: 1211
aggucuccaa ggugaacagc cucuggcaug uuggaac 37

<210> SEQ ID NO 1212
<211> LENGTH: 41
<212> TYPE: RNA
<213> ORGANISM: Homo sapiens

<400> SEQUENCE: 1212
guuuuucaua ucauuggucg ugguuguagu ccgugcgaga a 41

<210> SEQ ID NO 1213
<211> LENGTH: 40
<212> TYPE: RNA
<213> ORGANISM: Homo sapiens

<400> SEQUENCE: 1213
cauugugaag cagaauucac caagcguugg auuguucacc 40

<210> SEQ ID NO 1214
<211> LENGTH: 40
<212> TYPE: RNA
<213> ORGANISM: Homo sapiens

<400> SEQUENCE: 1214
acuuacacuu aggagauuuc aacuuaacuu gaccgcucug 40

<210> SEQ ID NO 1215
<211> LENGTH: 32
<212> TYPE: RNA
<213> ORGANISM: Homo sapiens

<400> SEQUENCE: 1215
gucuacggcc auaccacccu gaacgcgccc ga 32

<210> SEQ ID NO 1216
<211> LENGTH: 43
<212> TYPE: RNA
<213> ORGANISM: Homo sapiens

<400> SEQUENCE: 1216
guuuuucaua ucauuggucg ugguuguagu ccgugcgaga aua 43

<210> SEQ ID NO 1217
<211> LENGTH: 43
<212> TYPE: RNA
<213> ORGANISM: Homo sapiens

<400> SEQUENCE: 1217
cucucaccgc cgcggcccgg guucgauucc cggucaggga acc 43

<210> SEQ ID NO 1218
<211> LENGTH: 27
<212> TYPE: RNA
<213> ORGANISM: Homo sapiens

<400> SEQUENCE: 1218
ucccuguggu cuagugguua ggauucg 27

<210> SEQ ID NO 1219
<211> LENGTH: 29
<212> TYPE: RNA
<213> ORGANISM: Homo sapiens

<400> SEQUENCE: 1219
uuggucgugg uuguaguccg ugcgagaau 29

<210> SEQ ID NO 1220
<211> LENGTH: 45
<212> TYPE: RNA
<213> ORGANISM: Homo sapiens

<400> SEQUENCE: 1220
auuccggauc agaagauuga ggguucgugu cccuucgugg ucgcc 45

<210> SEQ ID NO 1221
<211> LENGTH: 45
<212> TYPE: RNA
<213> ORGANISM: Homo sapiens

<400> SEQUENCE: 1221
cuuuacacgc agaagguccu ggguucgagc cccaguggaa ccacc 45

<210> SEQ ID NO 1222
<211> LENGTH: 49
<212> TYPE: RNA
<213> ORGANISM: Homo sapiens

<400> SEQUENCE: 1222
acgacucuua gcgguggauc acucggcucg ugcgucgaug aagaacgca 49

<210> SEQ ID NO 1223
<211> LENGTH: 43
<212> TYPE: RNA
<213> ORGANISM: Homo sapiens

<400> SEQUENCE: 1223
uuuucaccca ggcggcccgg guucgacucc cggugugga acc 43

<210> SEQ ID NO 1224
<211> LENGTH: 44
<212> TYPE: RNA
<213> ORGANISM: Homo sapiens

<400> SEQUENCE: 1224
auugugaauc ugacaacaga ggcuuacgac cccuuauuua cccc 44

<210> SEQ ID NO 1225
<211> LENGTH: 26
<212> TYPE: RNA
<213> ORGANISM: Homo sapiens

<400> SEQUENCE: 1225
cguaacuucg ggauaaggau uggcuc 26

<210> SEQ ID NO 1226
<211> LENGTH: 43
<212> TYPE: RNA
<213> ORGANISM: Homo sapiens

<400> SEQUENCE: 1226
acggcccugg cggagcgcug agaagacggu cgaacuugac uau 43

<210> SEQ ID NO 1227
<211> LENGTH: 47
<212> TYPE: RNA
<213> ORGANISM: Homo sapiens

<400> SEQUENCE: 1227
aggacacauu gaucaucgac acuucgaacg cacuugcggc cccgggu 47

<210> SEQ ID NO 1228
<211> LENGTH: 50
<212> TYPE: RNA
<213> ORGANISM: Homo sapiens

<400> SEQUENCE: 1228
cgcgcgcgug uggugugcgu cggagggcgg cggcggcggc ggcggcgggg 50

<210> SEQ ID NO 1229
<211> LENGTH: 34
<212> TYPE: RNA
<213> ORGANISM: Homo sapiens

<400> SEQUENCE: 1229
uacagaacau gaucaagggu guuacacugg gcuu 34

<210> SEQ ID NO 1230
<211> LENGTH: 30
<212> TYPE: RNA
<213> ORGANISM: Homo sapiens

<400> SEQUENCE: 1230
gccgugaucg uauagugguu aguacucugc 30

<210> SEQ ID NO 1231
<211> LENGTH: 29
<212> TYPE: RNA
<213> ORGANISM: Homo sapiens

<400> SEQUENCE: 1231
auuggucgug guuguagucc gugcgagaa 29

<210> SEQ ID NO 1232
<211> LENGTH: 31
<212> TYPE: RNA
<213> ORGANISM: Homo sapiens

<400> SEQUENCE: 1232
ucccacaugg ucuagcgguu aggauuccug g 31

<210> SEQ ID NO 1233
<211> LENGTH: 37
<212> TYPE: RNA
<213> ORGANISM: Homo sapiens

<400> SEQUENCE: 1233
ucagaagauu gaggguucga aucccuucgu gguugcc 37

<210> SEQ ID NO 1234
<211> LENGTH: 30
<212> TYPE: RNA
<213> ORGANISM: Homo sapiens

<400> SEQUENCE: 1234
gcccggcuag cucagucggu agagcaugag 30

<210> SEQ ID NO 1235
<211> LENGTH: 28
<212> TYPE: RNA
<213> ORGANISM: Homo sapiens

<400> SEQUENCE: 1235
aacgcgcccg aucucgucug aucucgga 28

<210> SEQ ID NO 1236
<211> LENGTH: 45
<212> TYPE: RNA
<213> ORGANISM: Homo sapiens

<400> SEQUENCE: 1236
cugaucucgg aagcuaagca gggucgggcc ugguuaguac uugga 45

<210> SEQ ID NO 1237
<211> LENGTH: 36
<212> TYPE: RNA
<213> ORGANISM: Homo sapiens

<400> SEQUENCE: 1237
aucuauugaa agucagcccu cgacacaagg guuugu 36

<210> SEQ ID NO 1238
<211> LENGTH: 32
<212> TYPE: RNA
<213> ORGANISM: Homo sapiens

<400> SEQUENCE: 1238
cggcaggggc cggcggcggc ccgccgcggg gc 32

<210> SEQ ID NO 1239
<211> LENGTH: 34
<212> TYPE: RNA
<213> ORGANISM: Homo sapiens

<400> SEQUENCE: 1239
agccgugauc guauaguggu uaguacucug cguu 34

<210> SEQ ID NO 1240
<211> LENGTH: 30
<212> TYPE: RNA
<213> ORGANISM: Homo sapiens

<400> SEQUENCE: 1240
caagcguugg auuguucacc cacuaauagg 30

<210> SEQ ID NO 1241
<211> LENGTH: 32
<212> TYPE: RNA
<213> ORGANISM: Homo sapiens

<400> SEQUENCE: 1241
ggccgugauc guauagcggu uaguacucug cg 32

<210> SEQ ID NO 1242
<211> LENGTH: 32
<212> TYPE: RNA
<213> ORGANISM: Homo sapiens

<400> SEQUENCE: 1242
gcauuggugg uucaguggua gaauucucga cu 32

<210> SEQ ID NO 1243
<211> LENGTH: 28
<212> TYPE: RNA
<213> ORGANISM: Homo sapiens

<400> SEQUENCE: 1243
cucgucugau cucggaagcu aagcaggg 28

<210> SEQ ID NO 1244
<211> LENGTH: 33
<212> TYPE: RNA
<213> ORGANISM: Homo sapiens

<400> SEQUENCE: 1244
guuuccguag uguagugguu aucaccuucg ccu 33

<210> SEQ ID NO 1245
<211> LENGTH: 43
<212> TYPE: RNA
<213> ORGANISM: Homo sapiens

<400> SEQUENCE: 1245
aaacggagca ggucaaaacu cccgugcuga ucaguagugg gau 43

<210> SEQ ID NO 1246
<211> LENGTH: 49
<212> TYPE: RNA
<213> ORGANISM: Homo sapiens

<400> SEQUENCE: 1246
cuuggaaagc gucgcgguuc cggcggcguc cggugagcuc ucgcuggcc 49

<210> SEQ ID NO 1247
<211> LENGTH: 33
<212> TYPE: RNA
<213> ORGANISM: Homo sapiens

<400> SEQUENCE: 1247
agcagagugg cgcagcggaa gcgugcuggg ccc 33

<210> SEQ ID NO 1248
<211> LENGTH: 45
<212> TYPE: RNA
<213> ORGANISM: Homo sapiens

<400> SEQUENCE: 1248
acuucggauc agaagauuga ggguucgaau cccuucgugg uugcc 45

<210> SEQ ID NO 1249
<211> LENGTH: 30
<212> TYPE: RNA

<213> ORGANISM: Homo sapiens

<400> SEQUENCE: 1249
uaggauggug ugugauaggu ggcacggaga 30

<210> SEQ ID NO 1250
<211> LENGTH: 50
<212> TYPE: RNA
<213> ORGANISM: Homo sapiens

<400> SEQUENCE: 1250
gguccaggau gaaaccuaau uugaguggac auccauggau gagaaaugcg 50

<210> SEQ ID NO 1251
<211> LENGTH: 38
<212> TYPE: RNA
<213> ORGANISM: Homo sapiens

<400> SEQUENCE: 1251
acgcgggaga ccgggguucg auuccccgac ggggagcc 38

<210> SEQ ID NO 1252
<211> LENGTH: 38
<212> TYPE: RNA
<213> ORGANISM: Homo sapiens

<400> SEQUENCE: 1252
auaucauugg ucgugguugu aguccgugcg agaauacc 38

<210> SEQ ID NO 1253
<211> LENGTH: 31
<212> TYPE: RNA
<213> ORGANISM: Homo sapiens

<400> SEQUENCE: 1253
ucccuggugg ucuagugguu aggauucgcc g 31

<210> SEQ ID NO 1254
<211> LENGTH: 38
<212> TYPE: RNA
<213> ORGANISM: Homo sapiens

<400> SEQUENCE: 1254
ucucaggguc gugggguucgg gccccacguu gggcgcca 38

<210> SEQ ID NO 1255
<211> LENGTH: 26
<212> TYPE: RNA
<213> ORGANISM: Homo sapiens

<400> SEQUENCE: 1255
uagcucaguc gguagagcau gagacu 26

<210> SEQ ID NO 1256
<211> LENGTH: 31
<212> TYPE: RNA
<213> ORGANISM: Homo sapiens

<400> SEQUENCE: 1256
uccugugguc uagugguuag gauucggcgc u 31

<210> SEQ ID NO 1257
<211> LENGTH: 27

<212> TYPE: RNA
<213> ORGANISM: Homo sapiens

<400> SEQUENCE: 1257
ucccauaugg ucuagcgguu aggauuc 27

<210> SEQ ID NO 1258
<211> LENGTH: 32
<212> TYPE: RNA
<213> ORGANISM: Homo sapiens

<400> SEQUENCE: 1258
gccgugaucg uauagugguu aguacucugc gu 32

<210> SEQ ID NO 1259
<211> LENGTH: 30
<212> TYPE: RNA
<213> ORGANISM: Homo sapiens

<400> SEQUENCE: 1259
aguugguccg aguguugugg guuauuguua 30

<210> SEQ ID NO 1260
<211> LENGTH: 37
<212> TYPE: RNA
<213> ORGANISM: Homo sapiens

<400> SEQUENCE: 1260
uucaaagguu gugggguucgu gucccaccag agucgcc 37

<210> SEQ ID NO 1261
<211> LENGTH: 31
<212> TYPE: RNA
<213> ORGANISM: Homo sapiens

<400> SEQUENCE: 1261
ucccuggugg ucucgugguu aggauucggc g 31

<210> SEQ ID NO 1262
<211> LENGTH: 50
<212> TYPE: RNA
<213> ORGANISM: Homo sapiens

<400> SEQUENCE: 1262
cgacucuuag cggaggauca cucggcucgu gcgucgauga agaacgcagc 50

<210> SEQ ID NO 1263
<211> LENGTH: 35
<212> TYPE: RNA
<213> ORGANISM: Homo sapiens

<400> SEQUENCE: 1263
ccggcggcgg cggcgacucu ggacgcgagc cgggc 35

<210> SEQ ID NO 1264
<211> LENGTH: 43
<212> TYPE: RNA
<213> ORGANISM: Homo sapiens

<400> SEQUENCE: 1264
uuaaguuaaa gauuaagaga accaacaccu cuuuacagug acc 43

<210> SEQ ID NO 1265

<211> LENGTH: 50
<212> TYPE: RNA
<213> ORGANISM: Homo sapiens

<400> SEQUENCE: 1265
aaacgagaac uuugaaggcc gaaguggaga aggguuccau gugaacagca 50

<210> SEQ ID NO 1266
<211> LENGTH: 47
<212> TYPE: RNA
<213> ORGANISM: Homo sapiens

<400> SEQUENCE: 1266
aacgcgcccg aucucgucug aucucggaag cuaagcaggg ucgggcc 47

<210> SEQ ID NO 1267
<211> LENGTH: 50
<212> TYPE: RNA
<213> ORGANISM: Homo sapiens

<400> SEQUENCE: 1267
ccaugugaac agcaguugaa caugggucag ucgguccuga gagaugggcg 50

<210> SEQ ID NO 1268
<211> LENGTH: 33
<212> TYPE: RNA
<213> ORGANISM: Homo sapiens

<400> SEQUENCE: 1268
gcccggauag cucagucggu agagcaucag acu 33

<210> SEQ ID NO 1269
<211> LENGTH: 46
<212> TYPE: RNA
<213> ORGANISM: Homo sapiens

<400> SEQUENCE: 1269
guucuugugg uugaaauaca acgaugguuu uucauaucau uggucg 46

<210> SEQ ID NO 1270
<211> LENGTH: 29
<212> TYPE: RNA
<213> ORGANISM: Homo sapiens

<400> SEQUENCE: 1270
uaggaugggg cgugauaggu ggcacggag 29

<210> SEQ ID NO 1271
<211> LENGTH: 34
<212> TYPE: RNA
<213> ORGANISM: Homo sapiens

<400> SEQUENCE: 1271
ucgggccugg uuaguacuug gaugggagac cgcc 34

<210> SEQ ID NO 1272
<211> LENGTH: 44
<212> TYPE: RNA
<213> ORGANISM: Homo sapiens

<400> SEQUENCE: 1272
gcgggccgcc ggugaaauac cacuacucug aucguuuuuu cacu 44

<210> SEQ ID NO 1273
<211> LENGTH: 49
<212> TYPE: RNA
<213> ORGANISM: Homo sapiens

<400> SEQUENCE: 1273
cacagaugau gaacuuauug acgggcggac agaaacugug ugcugauug 49

<210> SEQ ID NO 1274
<211> LENGTH: 32
<212> TYPE: RNA
<213> ORGANISM: Homo sapiens

<400> SEQUENCE: 1274
ggccgugauc guauaguggu uagcacucug cg 32

<210> SEQ ID NO 1275
<211> LENGTH: 43
<212> TYPE: RNA
<213> ORGANISM: Homo sapiens

<400> SEQUENCE: 1275
gagcuugacu cuagucuggc acggugaaga gacaugagag gug 43

<210> SEQ ID NO 1276
<211> LENGTH: 50
<212> TYPE: RNA
<213> ORGANISM: Homo sapiens

<400> SEQUENCE: 1276
uugcaggaca cauugaucau cgacacuucg aacgcacuug cggccccggg 50

<210> SEQ ID NO 1277
<211> LENGTH: 31
<212> TYPE: RNA
<213> ORGANISM: Homo sapiens

<400> SEQUENCE: 1277
ccacuacucu gaucguuuuu ucacugaccc g 31

<210> SEQ ID NO 1278
<211> LENGTH: 50
<212> TYPE: RNA
<213> ORGANISM: Homo sapiens

<400> SEQUENCE: 1278
uccucuccua cuuggauaac ugugguaauu cuagagcuaa uacaugccga 50

<210> SEQ ID NO 1279
<211> LENGTH: 37
<212> TYPE: RNA
<213> ORGANISM: Homo sapiens

<400> SEQUENCE: 1279
ggccgugauc guauaguggu uaguacucug cguugua 37

<210> SEQ ID NO 1280
<211> LENGTH: 41
<212> TYPE: RNA
<213> ORGANISM: Homo sapiens

<400> SEQUENCE: 1280
uuuaaguuaa agauuaagag aaccaacacc ucuuuacagu g 41

<210> SEQ ID NO 1281
<211> LENGTH: 47
<212> TYPE: RNA
<213> ORGANISM: Homo sapiens

<400> SEQUENCE: 1281
auagggcgga gggaagcuca ucagugggc cacgagcuga gugcguc 47

<210> SEQ ID NO 1282
<211> LENGTH: 33
<212> TYPE: RNA
<213> ORGANISM: Homo sapiens

<400> SEQUENCE: 1282
ucccuagugg ucuagugguu aggauucggc gcu 33

<210> SEQ ID NO 1283
<211> LENGTH: 47
<212> TYPE: RNA
<213> ORGANISM: Homo sapiens

<400> SEQUENCE: 1283
uaacuguggu aauucuagag cuaauacaug ccgacgggcg cugaccc 47

<210> SEQ ID NO 1284
<211> LENGTH: 32
<212> TYPE: RNA
<213> ORGANISM: Homo sapiens

<400> SEQUENCE: 1284
cagugcgccc cgggcggguc gcgccgucgg gc 32

<210> SEQ ID NO 1285
<211> LENGTH: 33
<212> TYPE: RNA
<213> ORGANISM: Homo sapiens

<400> SEQUENCE: 1285
uccucguuag uauaguggug aguaucccg ccu 33

<210> SEQ ID NO 1286
<211> LENGTH: 50
<212> TYPE: RNA
<213> ORGANISM: Homo sapiens

<400> SEQUENCE: 1286
uaucugugau gaucuuaucc cgaaccugaa cuucuguuga aaaaaaaaaa 50

<210> SEQ ID NO 1287
<211> LENGTH: 41
<212> TYPE: RNA
<213> ORGANISM: Homo sapiens

<400> SEQUENCE: 1287
cucacaagaa cugcuaacuc augcccccau gucuaacaac a 41

<210> SEQ ID NO 1288
<211> LENGTH: 29
<212> TYPE: RNA
<213> ORGANISM: Homo sapiens

<400> SEQUENCE: 1288
gccguaaucg uauagugguu aguacucug 29

<210> SEQ ID NO 1289
<211> LENGTH: 50
<212> TYPE: RNA
<213> ORGANISM: Homo sapiens

<400> SEQUENCE: 1289
uccccugugg ucuagugguu aggauucggc gcucucaccg ccgcggcccg 50

<210> SEQ ID NO 1290
<211> LENGTH: 40
<212> TYPE: RNA
<213> ORGANISM: Homo sapiens

<400> SEQUENCE: 1290
auugaucauc gacacuucga acgcacuugc ggccccgggu 40

<210> SEQ ID NO 1291
<211> LENGTH: 34
<212> TYPE: RNA
<213> ORGANISM: Homo sapiens

<400> SEQUENCE: 1291
gcauuggagg uucaguggua gaauucucgc cugc 34

<210> SEQ ID NO 1292
<211> LENGTH: 45
<212> TYPE: RNA
<213> ORGANISM: Homo sapiens

<400> SEQUENCE: 1292
gacucuuagc gguggaucac ucggcucgug cgucgaugaa gaacg 45

<210> SEQ ID NO 1293
<211> LENGTH: 37
<212> TYPE: RNA
<213> ORGANISM: Homo sapiens

<400> SEQUENCE: 1293
ucugaagguc gugaguucga gccucacacg gggcacc 37

<210> SEQ ID NO 1294
<211> LENGTH: 30
<212> TYPE: RNA
<213> ORGANISM: Homo sapiens

<400> SEQUENCE: 1294
ugccguaauc guauaguggu uaguacucug 30

<210> SEQ ID NO 1295
<211> LENGTH: 28
<212> TYPE: RNA
<213> ORGANISM: Homo sapiens

<400> SEQUENCE: 1295
uccugugguc uagugguuag gauucggc 28

<210> SEQ ID NO 1296
<211> LENGTH: 37
<212> TYPE: RNA
<213> ORGANISM: Homo sapiens

<400> SEQUENCE: 1296
ccgggagacc gggguucgau uccccgacgg ggagcca 37

<210> SEQ ID NO 1297
<211> LENGTH: 32
<212> TYPE: RNA
<213> ORGANISM: Homo sapiens

<400> SEQUENCE: 1297
gcauuggugg uucaguggca gaauucucgc cu 32

<210> SEQ ID NO 1298
<211> LENGTH: 41
<212> TYPE: RNA
<213> ORGANISM: Homo sapiens

<400> SEQUENCE: 1298
auugcaaauu cgaagaagca gcuucaaacc ugccggggcu u 41

<210> SEQ ID NO 1299
<211> LENGTH: 43
<212> TYPE: RNA
<213> ORGANISM: Homo sapiens

<400> SEQUENCE: 1299
acuuacacuu aggagauuuc aacuuaacuu gaccgcucug acc 43

<210> SEQ ID NO 1300
<211> LENGTH: 40
<212> TYPE: RNA
<213> ORGANISM: Homo sapiens

<400> SEQUENCE: 1300
cacgcgggag accgggguuc gauuccccga cggggagcca 40

<210> SEQ ID NO 1301
<211> LENGTH: 37
<212> TYPE: RNA
<213> ORGANISM: Homo sapiens

<400> SEQUENCE: 1301
cgguggauca cucggcucgu gcgucgauga agaacgc 37

<210> SEQ ID NO 1302
<211> LENGTH: 37
<212> TYPE: RNA
<213> ORGANISM: Homo sapiens

<400> SEQUENCE: 1302
ucagaagguu gcguguucaa aucacgucgg ggucacc 37

<210> SEQ ID NO 1303
<211> LENGTH: 27
<212> TYPE: RNA
<213> ORGANISM: Homo sapiens

<400> SEQUENCE: 1303
ggugguucag ugguagaauu cucgccu 27

<210> SEQ ID NO 1304
<211> LENGTH: 34
<212> TYPE: RNA
<213> ORGANISM: Homo sapiens

<400> SEQUENCE: 1304
ucagaagguu gcguguucag gucacgucgg gguc 34

<210> SEQ ID NO 1305
<211> LENGTH: 33
<212> TYPE: RNA
<213> ORGANISM: Homo sapiens

<400> SEQUENCE: 1305
ucccauaugg ucuagcgguu aggauuccug guu 33

<210> SEQ ID NO 1306
<211> LENGTH: 39
<212> TYPE: RNA
<213> ORGANISM: Homo sapiens

<400> SEQUENCE: 1306
cucucaccgc cgcggcccgg guucguuucc cggucaggg 39

<210> SEQ ID NO 1307
<211> LENGTH: 48
<212> TYPE: RNA
<213> ORGANISM: Homo sapiens

<400> SEQUENCE: 1307
gagaacuuug aaggccgaag uggagaaggg uuccauguga acagcagu 48

<210> SEQ ID NO 1308
<211> LENGTH: 34
<212> TYPE: RNA
<213> ORGANISM: Homo sapiens

<400> SEQUENCE: 1308
guuuccguag uguaguggu aucacguucg ccug 34

<210> SEQ ID NO 1309
<211> LENGTH: 45
<212> TYPE: RNA
<213> ORGANISM: Homo sapiens

<400> SEQUENCE: 1309
aggacacauu gaucaucgac acuucgaacg cacuugcggc cccgg 45

<210> SEQ ID NO 1310
<211> LENGTH: 41
<212> TYPE: RNA
<213> ORGANISM: Homo sapiens

<400> SEQUENCE: 1310
uggaugggag accgccuggg aauaccgggu gcuguaggcu u 41

<210> SEQ ID NO 1311
<211> LENGTH: 32
<212> TYPE: RNA
<213> ORGANISM: Homo sapiens

<400> SEQUENCE: 1311
ggccgugauc guauaguggu uagaacucug cg 32

<210> SEQ ID NO 1312
<211> LENGTH: 36
<212> TYPE: RNA
<213> ORGANISM: Homo sapiens

<400> SEQUENCE: 1312
aaaucggucg uccgaccugg guauaggggc gaaaga 36

<210> SEQ ID NO 1313
<211> LENGTH: 31
<212> TYPE: RNA
<213> ORGANISM: Homo sapiens

<400> SEQUENCE: 1313
gaacgcgccc gaucucgucu gaucucggaa g 31

<210> SEQ ID NO 1314
<211> LENGTH: 39
<212> TYPE: RNA
<213> ORGANISM: Homo sapiens

<400> SEQUENCE: 1314
acgcgggaga ccgggguucg auucccccgac ggggagcca 39

<210> SEQ ID NO 1315
<211> LENGTH: 34
<212> TYPE: RNA
<213> ORGANISM: Homo sapiens

<400> SEQUENCE: 1315
agaacuggug cggaccaggg gaauccgacu guuu 34

<210> SEQ ID NO 1316
<211> LENGTH: 49
<212> TYPE: RNA
<213> ORGANISM: Homo sapiens

<400> SEQUENCE: 1316
aggacacauu gaucaucgac acuucgaacg cacuugcggc cccggguua 49

<210> SEQ ID NO 1317
<211> LENGTH: 50
<212> TYPE: RNA
<213> ORGANISM: Homo sapiens

<400> SEQUENCE: 1317
cccgccacgc aguuuuaucc gguaaagcga augauuagag gucuuggggc 50

<210> SEQ ID NO 1318
<211> LENGTH: 30
<212> TYPE: RNA
<213> ORGANISM: Homo sapiens

<400> SEQUENCE: 1318
ugccgugauc guauagugga uaguacucug 30

<210> SEQ ID NO 1319
<211> LENGTH: 32
<212> TYPE: RNA
<213> ORGANISM: Homo sapiens

<400> SEQUENCE: 1319
gcccggauag cucagucggu agagcaucag ac 32

<210> SEQ ID NO 1320
<211> LENGTH: 45
<212> TYPE: RNA
<213> ORGANISM: Homo sapiens

<400> SEQUENCE: 1320
gucuacggcc auaccacccu gaacgcgccc gaucucgucu gaucu 45

<210> SEQ ID NO 1321
<211> LENGTH: 32
<212> TYPE: RNA
<213> ORGANISM: Homo sapiens

<400> SEQUENCE: 1321
ccacuacucu gaucguuuuu ucacugaccc gg 32

<210> SEQ ID NO 1322
<211> LENGTH: 50
<212> TYPE: RNA
<213> ORGANISM: Homo sapiens

<400> SEQUENCE: 1322
agaauuaaug ugaauugcag gacacauuga ucaucgacac uucgaacgca 50

<210> SEQ ID NO 1323
<211> LENGTH: 26
<212> TYPE: RNA
<213> ORGANISM: Homo sapiens

<400> SEQUENCE: 1323
cuuuuaaguu aaagauuaag agaacc 26

<210> SEQ ID NO 1324
<211> LENGTH: 32
<212> TYPE: RNA
<213> ORGANISM: Homo sapiens

<400> SEQUENCE: 1324
cuagagguga aauucuugga ccggcgcaag ac 32

<210> SEQ ID NO 1325
<211> LENGTH: 36
<212> TYPE: RNA
<213> ORGANISM: Homo sapiens

<400> SEQUENCE: 1325
cagaagauug aggguucggg ucccuucgug gucgcc 36

<210> SEQ ID NO 1326
<211> LENGTH: 45
<212> TYPE: RNA
<213> ORGANISM: Homo sapiens

<400> SEQUENCE: 1326
ccagugcgcc ccgggcgggu cgcgccgucg ggcccggggg agguu 45

<210> SEQ ID NO 1327
<211> LENGTH: 36
<212> TYPE: RNA
<213> ORGANISM: Homo sapiens

<400> SEQUENCE: 1327
guggcucgcc gugaucguau agugguuagu acucug 36

<210> SEQ ID NO 1328
<211> LENGTH: 36
<212> TYPE: RNA

<213> ORGANISM: Homo sapiens

<400> SEQUENCE: 1328
cgggagaccg ggguucguuu ccccgacggg gagcca 36

<210> SEQ ID NO 1329
<211> LENGTH: 48
<212> TYPE: RNA
<213> ORGANISM: Homo sapiens

<400> SEQUENCE: 1329
cgacucuuag cgguggauca cucggcucgu gcgucgauga agaacgca 48

<210> SEQ ID NO 1330
<211> LENGTH: 32
<212> TYPE: RNA
<213> ORGANISM: Homo sapiens

<400> SEQUENCE: 1330
gcaugggugg uucaguggua gaauucucgc cc 32

<210> SEQ ID NO 1331
<211> LENGTH: 30
<212> TYPE: RNA
<213> ORGANISM: Homo sapiens

<400> SEQUENCE: 1331
ggccgugauc gaauaguggu uaguacucug 30

<210> SEQ ID NO 1332
<211> LENGTH: 50
<212> TYPE: RNA
<213> ORGANISM: Homo sapiens

<400> SEQUENCE: 1332
auugcaggac acauugauca ucgacacuuc gaacgcacuu gcggccccgg 50

<210> SEQ ID NO 1333
<211> LENGTH: 27
<212> TYPE: RNA
<213> ORGANISM: Homo sapiens

<400> SEQUENCE: 1333
guuccgcgcg gcgccucgcc ucggccg 27

<210> SEQ ID NO 1334
<211> LENGTH: 47
<212> TYPE: RNA
<213> ORGANISM: Homo sapiens

<400> SEQUENCE: 1334
cgaguucgag gccagccugg uccacauggg ucggaaaaaa ggauuuu 47

<210> SEQ ID NO 1335
<211> LENGTH: 34
<212> TYPE: RNA
<213> ORGANISM: Homo sapiens

<400> SEQUENCE: 1335
gcaugggugg uucaguggua gaauucucgc cuuc 34

<210> SEQ ID NO 1336
<211> LENGTH: 50

<212> TYPE: RNA
<213> ORGANISM: Homo sapiens

<400> SEQUENCE: 1336
ccguggagag gaacaacucu gagucuuaac ccaauuuuuu gaggccuugc 50

<210> SEQ ID NO 1337
<211> LENGTH: 47
<212> TYPE: RNA
<213> ORGANISM: Homo sapiens

<400> SEQUENCE: 1337
acgaugguuu uucauaucau uggucguggu uguaguccgu gcgagaa 47

<210> SEQ ID NO 1338
<211> LENGTH: 49
<212> TYPE: RNA
<213> ORGANISM: Homo sapiens

<400> SEQUENCE: 1338
aacgaugguu uuucauauca uuggucgugg uuguaguccg ugcgagaau 49

<210> SEQ ID NO 1339
<211> LENGTH: 33
<212> TYPE: RNA
<213> ORGANISM: Homo sapiens

<400> SEQUENCE: 1339
ucccuggcgg ucuagugguu aggauucggc gcu 33

<210> SEQ ID NO 1340
<211> LENGTH: 41
<212> TYPE: RNA
<213> ORGANISM: Homo sapiens

<400> SEQUENCE: 1340
acggcccugg cggagcgcug agaagacggu cgaacuugac u 41

<210> SEQ ID NO 1341
<211> LENGTH: 30
<212> TYPE: RNA
<213> ORGANISM: Homo sapiens

<400> SEQUENCE: 1341
gacccggguu cguuucccgg ccaacgcacc 30

<210> SEQ ID NO 1342
<211> LENGTH: 33
<212> TYPE: RNA
<213> ORGANISM: Homo sapiens

<400> SEQUENCE: 1342
cuagagguga aauucuugga ccggcgcaag acg 33

<210> SEQ ID NO 1343
<211> LENGTH: 33
<212> TYPE: RNA
<213> ORGANISM: Homo sapiens

<400> SEQUENCE: 1343
guuuccguag uguagugguu aucacguucg ccc 33

<210> SEQ ID NO 1344

```
<211> LENGTH: 31
<212> TYPE: RNA
<213> ORGANISM: Homo sapiens

<400> SEQUENCE: 1344

cgcgaccuca gaucagacgu ggcgacccgc u                            31

<210> SEQ ID NO 1345
<211> LENGTH: 36
<212> TYPE: RNA
<213> ORGANISM: Homo sapiens

<400> SEQUENCE: 1345

ucccuggugg ucuaguggcu aggauucggc gcuuuc                       36

<210> SEQ ID NO 1346
<211> LENGTH: 30
<212> TYPE: RNA
<213> ORGANISM: Homo sapiens

<400> SEQUENCE: 1346

ucccuggcgg ucuagugguu aggauucggc                              30

<210> SEQ ID NO 1347
<211> LENGTH: 36
<212> TYPE: RNA
<213> ORGANISM: Homo sapiens

<400> SEQUENCE: 1347

acgcgaccuc agaucagacg uggcgacccg cugaau                       36

<210> SEQ ID NO 1348
<211> LENGTH: 48
<212> TYPE: RNA
<213> ORGANISM: Homo sapiens

<400> SEQUENCE: 1348

cuacggggau gauuuuacga acugaacucu cucuuucuga uggauuag          48

<210> SEQ ID NO 1349
<211> LENGTH: 50
<212> TYPE: RNA
<213> ORGANISM: Homo sapiens

<400> SEQUENCE: 1349

caguaguggg aucgcgccug ugaauagcca cugcacucca gccugggcaa        50

<210> SEQ ID NO 1350
<211> LENGTH: 32
<212> TYPE: RNA
<213> ORGANISM: Homo sapiens

<400> SEQUENCE: 1350

gcauuugugg uucaguggua gaauucucgc cg                           32

<210> SEQ ID NO 1351
<211> LENGTH: 37
<212> TYPE: RNA
<213> ORGANISM: Homo sapiens

<400> SEQUENCE: 1351

ucugaggguc caggguucaa gucccuguuc gggcgcc                      37
```

```
<210> SEQ ID NO 1352
<211> LENGTH: 50
<212> TYPE: RNA
<213> ORGANISM: Homo sapiens

<400> SEQUENCE: 1352

caguaguggg aucgcgccug ugaauagcca cugcacucca gccugagcaa         50

<210> SEQ ID NO 1353
<211> LENGTH: 35
<212> TYPE: RNA
<213> ORGANISM: Homo sapiens

<400> SEQUENCE: 1353

guucuuguug uugaaauaca acgaugguuu uucau                         35

<210> SEQ ID NO 1354
<211> LENGTH: 28
<212> TYPE: RNA
<213> ORGANISM: Homo sapiens

<400> SEQUENCE: 1354

uuggucgugg uuguaguccg ugcgagaa                                 28

<210> SEQ ID NO 1355
<211> LENGTH: 31
<212> TYPE: RNA
<213> ORGANISM: Homo sapiens

<400> SEQUENCE: 1355

ggccgugauc guauaguggu uagcacucug c                             31

<210> SEQ ID NO 1356
<211> LENGTH: 27
<212> TYPE: RNA
<213> ORGANISM: Homo sapiens

<400> SEQUENCE: 1356

cggggcuacg ccugucugag cgucgcu                                  27

<210> SEQ ID NO 1357
<211> LENGTH: 31
<212> TYPE: RNA
<213> ORGANISM: Homo sapiens

<400> SEQUENCE: 1357

ucccuggugg ucuagugguu aggauucggc u                             31

<210> SEQ ID NO 1358
<211> LENGTH: 45
<212> TYPE: RNA
<213> ORGANISM: Homo sapiens

<400> SEQUENCE: 1358

cgaggacaau auauuaaaug gauuuuugga gcagggagau ggaau              45

<210> SEQ ID NO 1359
<211> LENGTH: 36
<212> TYPE: RNA
<213> ORGANISM: Homo sapiens

<400> SEQUENCE: 1359

cgccgcggcc cggguucguu ucccggucag ggaacc                        36
```

<210> SEQ ID NO 1360
<211> LENGTH: 28
<212> TYPE: RNA
<213> ORGANISM: Homo sapiens

<400> SEQUENCE: 1360
cccgguaauc gcauaaaacu uaaaacuu 28

<210> SEQ ID NO 1361
<211> LENGTH: 50
<212> TYPE: RNA
<213> ORGANISM: Homo sapiens

<400> SEQUENCE: 1361
gaccagagcg aaagcauuug ccaagaaugu uuucauuaau caagaacgaa 50

<210> SEQ ID NO 1362
<211> LENGTH: 35
<212> TYPE: RNA
<213> ORGANISM: Homo sapiens

<400> SEQUENCE: 1362
auugugaauc ugacaacaga ggcuuacgac cccuu 35

<210> SEQ ID NO 1363
<211> LENGTH: 42
<212> TYPE: RNA
<213> ORGANISM: Homo sapiens

<400> SEQUENCE: 1363
cuguuaacua aguguuugug gguuuaaguc ccauuggucu ag 42

<210> SEQ ID NO 1364
<211> LENGTH: 34
<212> TYPE: RNA
<213> ORGANISM: Homo sapiens

<400> SEQUENCE: 1364
ucccuagugg ucuagugguu aggauucggc gcuc 34

<210> SEQ ID NO 1365
<211> LENGTH: 46
<212> TYPE: RNA
<213> ORGANISM: Homo sapiens

<400> SEQUENCE: 1365
acuuuuaauc ugagggucca ggguucaggu cccuguucgg gcgcca 46

<210> SEQ ID NO 1366
<211> LENGTH: 44
<212> TYPE: RNA
<213> ORGANISM: Homo sapiens

<400> SEQUENCE: 1366
cucgcugcga ucuauugaaa gucagcccuc gacacaaggg uuug 44

<210> SEQ ID NO 1367
<211> LENGTH: 31
<212> TYPE: RNA
<213> ORGANISM: Homo sapiens

<400> SEQUENCE: 1367
agaacuggug cggaccaggg gaauccgacu g 31

<210> SEQ ID NO 1368
<211> LENGTH: 48
<212> TYPE: RNA
<213> ORGANISM: Homo sapiens

<400> SEQUENCE: 1368
auaacugugg uaauucuaga gcuaauacau gccgacgggc gcugaccc        48

<210> SEQ ID NO 1369
<211> LENGTH: 49
<212> TYPE: RNA
<213> ORGANISM: Homo sapiens

<400> SEQUENCE: 1369
cccgguaauc gcauaaaacu uaaaacuuua cagucagagg uucauuucc       49

<210> SEQ ID NO 1370
<211> LENGTH: 37
<212> TYPE: RNA
<213> ORGANISM: Homo sapiens

<400> SEQUENCE: 1370
uucaaagguu guggguucgg gucccaccag agucgcc                    37

<210> SEQ ID NO 1371
<211> LENGTH: 31
<212> TYPE: RNA
<213> ORGANISM: Homo sapiens

<400> SEQUENCE: 1371
cgcgcgcggg ucgggggggcg gggcggacug u                         31

<210> SEQ ID NO 1372
<211> LENGTH: 30
<212> TYPE: RNA
<213> ORGANISM: Homo sapiens

<400> SEQUENCE: 1372
uccccugugg ucuaguggcu aggauucggc                            30

<210> SEQ ID NO 1373
<211> LENGTH: 32
<212> TYPE: RNA
<213> ORGANISM: Homo sapiens

<400> SEQUENCE: 1373
uauugaaagu cagcccucga cacaaggguu ug                         32

<210> SEQ ID NO 1374
<211> LENGTH: 38
<212> TYPE: RNA
<213> ORGANISM: Homo sapiens

<400> SEQUENCE: 1374
cgcgaccuca gaucagacgu ggcgacccgc ugaauuua                   38

<210> SEQ ID NO 1375
<211> LENGTH: 43
<212> TYPE: RNA
<213> ORGANISM: Homo sapiens

<400> SEQUENCE: 1375
agcaguugaa caugggucag ucgguccuga gagaugggcg agc 43

<210> SEQ ID NO 1376
<211> LENGTH: 44
<212> TYPE: RNA
<213> ORGANISM: Homo sapiens

<400> SEQUENCE: 1376
acuuggaugg gagaccgccu gggaauaccg ggugcuguag gcuu 44

<210> SEQ ID NO 1377
<211> LENGTH: 29
<212> TYPE: RNA
<213> ORGANISM: Homo sapiens

<400> SEQUENCE: 1377
cgguggauca cucggcucgu gcgucgaug 29

<210> SEQ ID NO 1378
<211> LENGTH: 44
<212> TYPE: RNA
<213> ORGANISM: Homo sapiens

<400> SEQUENCE: 1378
ccuaaggagg ggugaaccgg cccaggucgg aaacggagca gguc 44

<210> SEQ ID NO 1379
<211> LENGTH: 34
<212> TYPE: RNA
<213> ORGANISM: Homo sapiens

<400> SEQUENCE: 1379
gcauuggugg uuuaguggua gaauucucgc cugc 34

<210> SEQ ID NO 1380
<211> LENGTH: 29
<212> TYPE: RNA
<213> ORGANISM: Homo sapiens

<400> SEQUENCE: 1380
gccgugaucg uauagugguu agaacucug 29

<210> SEQ ID NO 1381
<211> LENGTH: 50
<212> TYPE: RNA
<213> ORGANISM: Homo sapiens

<400> SEQUENCE: 1381
auuccgauaa cgaacgagac ucuggcaugc uaacuaguua cgcgaccccc 50

<210> SEQ ID NO 1382
<211> LENGTH: 43
<212> TYPE: RNA
<213> ORGANISM: Homo sapiens

<400> SEQUENCE: 1382
gggguuucgu acguagcaga gcagcucccu cgcugcgauc uau 43

<210> SEQ ID NO 1383
<211> LENGTH: 50
<212> TYPE: RNA
<213> ORGANISM: Homo sapiens

<400> SEQUENCE: 1383
ccucuccuac uuggauaacu gugguaauuc uagagcuaau acaugccgac 50

<210> SEQ ID NO 1384
<211> LENGTH: 44
<212> TYPE: RNA
<213> ORGANISM: Homo sapiens

<400> SEQUENCE: 1384
ggcugguccg augguagugg guuaucagaa cuuauuaaca uuag 44

<210> SEQ ID NO 1385
<211> LENGTH: 41
<212> TYPE: RNA
<213> ORGANISM: Homo sapiens

<400> SEQUENCE: 1385
aacggagcag gucaaaacuc ccgugcugau caguaguggg a 41

<210> SEQ ID NO 1386
<211> LENGTH: 32
<212> TYPE: RNA
<213> ORGANISM: Homo sapiens

<400> SEQUENCE: 1386
gcaugggugg cucaguggua gaauucucgc cu 32

<210> SEQ ID NO 1387
<211> LENGTH: 37
<212> TYPE: RNA
<213> ORGANISM: Homo sapiens

<400> SEQUENCE: 1387
cuuuuugauc cuucgauguc ggcucuuccu aucauug 37

<210> SEQ ID NO 1388
<211> LENGTH: 38
<212> TYPE: RNA
<213> ORGANISM: Homo sapiens

<400> SEQUENCE: 1388
ucucaggguc guggguucga gccccacguu gggcgcca 38

<210> SEQ ID NO 1389
<211> LENGTH: 44
<212> TYPE: RNA
<213> ORGANISM: Homo sapiens

<400> SEQUENCE: 1389
cugucacgcg ggagaccggg guucguuucc ccgacgggga gcca 44

<210> SEQ ID NO 1390
<211> LENGTH: 33
<212> TYPE: RNA
<213> ORGANISM: Homo sapiens

<400> SEQUENCE: 1390
cgguuccggc ggcguccggu gagcucucgc ugg 33

<210> SEQ ID NO 1391
<211> LENGTH: 37
<212> TYPE: RNA
<213> ORGANISM: Homo sapiens

<400> SEQUENCE: 1391
ucugaggguc cagggguucau gucccuguuc gggcgcc 37

<210> SEQ ID NO 1392
<211> LENGTH: 32
<212> TYPE: RNA
<213> ORGANISM: Homo sapiens

<400> SEQUENCE: 1392
gcauuugugg uucaguggua gaauucucgc ca 32

<210> SEQ ID NO 1393
<211> LENGTH: 50
<212> TYPE: RNA
<213> ORGANISM: Homo sapiens

<400> SEQUENCE: 1393
uaaugugaau ugcaggacac auugaucauc gacacuucga acgcacuugc 50

<210> SEQ ID NO 1394
<211> LENGTH: 49
<212> TYPE: RNA
<213> ORGANISM: Homo sapiens

<400> SEQUENCE: 1394
gugaagggca gggcgcccug gaaugggguuc gccccgagag aggggcccg 49

<210> SEQ ID NO 1395
<211> LENGTH: 30
<212> TYPE: RNA
<213> ORGANISM: Homo sapiens

<400> SEQUENCE: 1395
gccuuggugg uucaguggua gaauucucgc 30

<210> SEQ ID NO 1396
<211> LENGTH: 33
<212> TYPE: RNA
<213> ORGANISM: Homo sapiens

<400> SEQUENCE: 1396
guuuccguag ugcagugguu aucacguucg ccu 33

<210> SEQ ID NO 1397
<211> LENGTH: 30
<212> TYPE: RNA
<213> ORGANISM: Homo sapiens

<400> SEQUENCE: 1397
cuccccggag ggggcgggcu ccggcgggug 30

<210> SEQ ID NO 1398
<211> LENGTH: 50
<212> TYPE: RNA
<213> ORGANISM: Homo sapiens

<400> SEQUENCE: 1398
uuaauuccga uaacgaacga gacucuggca ugcuaacuag uuacgcgacc 50

<210> SEQ ID NO 1399
<211> LENGTH: 29
<212> TYPE: RNA
<213> ORGANISM: Homo sapiens

<400> SEQUENCE: 1399
aguugguccg aguguugugg guuauuguu 29

<210> SEQ ID NO 1400
<211> LENGTH: 26
<212> TYPE: RNA
<213> ORGANISM: Homo sapiens

<400> SEQUENCE: 1400
ggcuagcuca gucgguagag caugag 26

<210> SEQ ID NO 1401
<211> LENGTH: 31
<212> TYPE: RNA
<213> ORGANISM: Homo sapiens

<400> SEQUENCE: 1401
auugaaaguc agcccucgac acaaggguuu g 31

<210> SEQ ID NO 1402
<211> LENGTH: 32
<212> TYPE: RNA
<213> ORGANISM: Homo sapiens

<400> SEQUENCE: 1402
gcauuggugg uucaguggua gaauccucgc cu 32

<210> SEQ ID NO 1403
<211> LENGTH: 31
<212> TYPE: RNA
<213> ORGANISM: Homo sapiens

<400> SEQUENCE: 1403 caaccccca cugcuaaauu ugacuggcuu u 31

<210> SEQ ID NO 1404
<211> LENGTH: 34
<212> TYPE: RNA
<213> ORGANISM: Homo sapiens

<400> SEQUENCE: 1404
ccggcggcgg cggcgacucu ggacgcgagc cggg 34

<210> SEQ ID NO 1405
<211> LENGTH: 34
<212> TYPE: RNA
<213> ORGANISM: Homo sapiens

<400> SEQUENCE: 1405
gcuucuguag uguagugguu aucacguucg ccuc 34

<210> SEQ ID NO 1406
<211> LENGTH: 34
<212> TYPE: RNA
<213> ORGANISM: Homo sapiens

<400> SEQUENCE: 1406
gcauuggugg uucaguggua gacuucucgc cugc 34

<210> SEQ ID NO 1407
<211> LENGTH: 27
<212> TYPE: RNA

<213> ORGANISM: Homo sapiens

<400> SEQUENCE: 1407
auguagauuc ucuggucauu gagcaua 27

<210> SEQ ID NO 1408
<211> LENGTH: 45
<212> TYPE: RNA
<213> ORGANISM: Homo sapiens

<400> SEQUENCE: 1408
acacauugau caucgacacu ucgaacgcac uugcggcccc ggguu 45

<210> SEQ ID NO 1409
<211> LENGTH: 38
<212> TYPE: RNA
<213> ORGANISM: Homo sapiens

<400> SEQUENCE: 1409
ggcugguccg augguagugg guuaucagaa cuuauuaa 38

<210> SEQ ID NO 1410
<211> LENGTH: 32
<212> TYPE: RNA
<213> ORGANISM: Homo sapiens

<400> SEQUENCE: 1410
gcauuggugg uucagaggua gaauucucgc cu 32

<210> SEQ ID NO 1411
<211> LENGTH: 32
<212> TYPE: RNA
<213> ORGANISM: Homo sapiens

<400> SEQUENCE: 1411
agcagagugg cgcagcggaa gcgugcuggg cc 32

<210> SEQ ID NO 1412
<211> LENGTH: 50
<212> TYPE: RNA
<213> ORGANISM: Homo sapiens

<400> SEQUENCE: 1412
ggauaacugu gguaauucua gagcuaauac augccgacgg gcgcugaccc 50

<210> SEQ ID NO 1413
<211> LENGTH: 49
<212> TYPE: RNA
<213> ORGANISM: Homo sapiens

<400> SEQUENCE: 1413
aggacacauu gaucaucgac acuucgaacg cacuugcggc cccggguuc 49

<210> SEQ ID NO 1414
<211> LENGTH: 34
<212> TYPE: RNA
<213> ORGANISM: Homo sapiens

<400> SEQUENCE: 1414
cgggagaccg ggguucgauu ccccgacggg gagc 34

<210> SEQ ID NO 1415
<211> LENGTH: 32

<212> TYPE: RNA
<213> ORGANISM: Homo sapiens

<400> SEQUENCE: 1415
gcauuggugg uccaguggua gaauucucgc cu 32

<210> SEQ ID NO 1416
<211> LENGTH: 50
<212> TYPE: RNA
<213> ORGANISM: Homo sapiens

<400> SEQUENCE: 1416
caaacgagaa cuuugaaggc cgaaguggag aaggguucca ugugaacagc 50

<210> SEQ ID NO 1417
<211> LENGTH: 26
<212> TYPE: RNA
<213> ORGANISM: Homo sapiens

<400> SEQUENCE: 1417
ggggcuacgc cugucugagc gucgcu 26

<210> SEQ ID NO 1418
<211> LENGTH: 29
<212> TYPE: RNA
<213> ORGANISM: Homo sapiens

<400> SEQUENCE: 1418
augguggagu uaaagacuuu uucucugac 29

<210> SEQ ID NO 1419
<211> LENGTH: 40
<212> TYPE: RNA
<213> ORGANISM: Homo sapiens

<400> SEQUENCE: 1419
aacgaacgag acucuggcau gcuaacuagu uacgcgaccc 40

<210> SEQ ID NO 1420
<211> LENGTH: 42
<212> TYPE: RNA
<213> ORGANISM: Homo sapiens

<400> SEQUENCE: 1420
acgcgaccuc agaucagacg uggcgacccg cugaauuuaa gc 42

<210> SEQ ID NO 1421
<211> LENGTH: 34
<212> TYPE: RNA
<213> ORGANISM: Homo sapiens

<400> SEQUENCE: 1421
gcauuggugg uucaguggua gaauucucgc cuug 34

<210> SEQ ID NO 1422
<211> LENGTH: 30
<212> TYPE: RNA
<213> ORGANISM: Homo sapiens

<400> SEQUENCE: 1422
caacccccca cugcuaaauu ugacuggcuu 30

<210> SEQ ID NO 1423

<211> LENGTH: 32
<212> TYPE: RNA
<213> ORGANISM: Homo sapiens

<400> SEQUENCE: 1423
gcacgggugg uucaguggua gaauucucgc cu 32

<210> SEQ ID NO 1424
<211> LENGTH: 43
<212> TYPE: RNA
<213> ORGANISM: Homo sapiens

<400> SEQUENCE: 1424
cugccacgcg ggaggcccgg guucguuucc cggccaaugc acc 43

<210> SEQ ID NO 1425
<211> LENGTH: 47
<212> TYPE: RNA
<213> ORGANISM: Homo sapiens

<400> SEQUENCE: 1425
cguaacuucg ggauaaggau uggcucuaag ggcugggucg gucgggc 47

<210> SEQ ID NO 1426
<211> LENGTH: 32
<212> TYPE: RNA
<213> ORGANISM: Homo sapiens

<400> SEQUENCE: 1426
uuuuuuggcc uguuugaugu augugugaaa ca 32

<210> SEQ ID NO 1427
<211> LENGTH: 32
<212> TYPE: RNA
<213> ORGANISM: Homo sapiens

<400> SEQUENCE: 1427
gcaugggugg uuuaguggua gaauucucgc cu 32

<210> SEQ ID NO 1428
<211> LENGTH: 32
<212> TYPE: RNA
<213> ORGANISM: Homo sapiens

<400> SEQUENCE: 1428
gcaugggugg uucaguggua gaauucccgc cu 32

<210> SEQ ID NO 1429
<211> LENGTH: 42
<212> TYPE: RNA
<213> ORGANISM: Homo sapiens

<400> SEQUENCE: 1429
uuuucaccca ggcggcccgg guucgacucc cggugugggga ac 42

<210> SEQ ID NO 1430
<211> LENGTH: 40
<212> TYPE: RNA
<213> ORGANISM: Homo sapiens

<400> SEQUENCE: 1430
auucccauuc uugcgacccg gguucguuuc ccgggcggcg 40

<210> SEQ ID NO 1431
<211> LENGTH: 26
<212> TYPE: RNA
<213> ORGANISM: Homo sapiens

<400> SEQUENCE: 1431
ccccacgucu cgucgcgcgc gcgucc 26

<210> SEQ ID NO 1432
<211> LENGTH: 50
<212> TYPE: RNA
<213> ORGANISM: Homo sapiens

<400> SEQUENCE: 1432
acauugauca ucgacacuuc gaacgcacuu gcggcaccgg guuccucccg 50

<210> SEQ ID NO 1433
<211> LENGTH: 31
<212> TYPE: RNA
<213> ORGANISM: Homo sapiens

<400> SEQUENCE: 1433
ggccgugauc guauaguggu uagaacucug c 31

<210> SEQ ID NO 1434
<211> LENGTH: 29
<212> TYPE: RNA
<213> ORGANISM: Homo sapiens

<400> SEQUENCE: 1434
guuuccguag uguagcgguu aucacauuc 29

<210> SEQ ID NO 1435
<211> LENGTH: 37
<212> TYPE: RNA
<213> ORGANISM: Homo sapiens

<400> SEQUENCE: 1435
ucagaagguu gcguguucaa gucacgucgg ggucacc 37

<210> SEQ ID NO 1436
<211> LENGTH: 37
<212> TYPE: RNA
<213> ORGANISM: Homo sapiens

<400> SEQUENCE: 1436
acgcgaccuc agaucagacg uggcgacccg cugaauu 37

<210> SEQ ID NO 1437
<211> LENGTH: 28
<212> TYPE: RNA
<213> ORGANISM: Homo sapiens

<400> SEQUENCE: 1437
caccccacgu cucgucgcgc gcgcgucc 28

<210> SEQ ID NO 1438
<211> LENGTH: 34
<212> TYPE: RNA
<213> ORGANISM: Homo sapiens

<400> SEQUENCE: 1438
gcauuggugg uucaguggca gaauucucgc cugc 34

<210> SEQ ID NO 1439
<211> LENGTH: 30
<212> TYPE: RNA
<213> ORGANISM: Homo sapiens

<400> SEQUENCE: 1439
ggccgugauc guauaguggu uaguacccug 30

<210> SEQ ID NO 1440
<211> LENGTH: 38
<212> TYPE: RNA
<213> ORGANISM: Homo sapiens

<400> SEQUENCE: 1440
ccuagcagcc gacuuagaac uggugcggac caggggaa 38

<210> SEQ ID NO 1441
<211> LENGTH: 49
<212> TYPE: RNA
<213> ORGANISM: Homo sapiens

<400> SEQUENCE: 1441
cugaggcugg aggaucgcuu gaguccagga guucugggcu guagugcgc 49

<210> SEQ ID NO 1442
<211> LENGTH: 34
<212> TYPE: RNA
<213> ORGANISM: Homo sapiens

<400> SEQUENCE: 1442
gcauuggugg uucaguggua gaauucuccc cugc 34

<210> SEQ ID NO 1443
<211> LENGTH: 37
<212> TYPE: RNA
<213> ORGANISM: Homo sapiens

<400> SEQUENCE: 1443
agcagccgac uuagaacugg ugcggaccag gggaauc 37

<210> SEQ ID NO 1444
<211> LENGTH: 32
<212> TYPE: RNA
<213> ORGANISM: Homo sapiens

<400> SEQUENCE: 1444
gcauuggugg uuaaguggua gaauucucgc cu 32

<210> SEQ ID NO 1445
<211> LENGTH: 43
<212> TYPE: RNA
<213> ORGANISM: Homo sapiens

<400> SEQUENCE: 1445 guuucaccc aggcggcccg gguucgacuc ccggugu ggg aac 43

<210> SEQ ID NO 1446
<211> LENGTH: 50
<212> TYPE: RNA
<213> ORGANISM: Homo sapiens

<400> SEQUENCE: 1446
uuggauaacu gugguaauuc uagagcuaau acaugccgac gggcgcugac 50

```
<210> SEQ ID NO 1447
<211> LENGTH: 28
<212> TYPE: RNA
<213> ORGANISM: Homo sapiens

<400> SEQUENCE: 1447

auuggucgug guuguagucc gugcgaga                                         28

<210> SEQ ID NO 1448
<211> LENGTH: 38
<212> TYPE: RNA
<213> ORGANISM: Homo sapiens

<400> SEQUENCE: 1448

ucgaggguc caggguucaa gucccuguuc gggcgcca                              38

<210> SEQ ID NO 1449
<211> LENGTH: 30
<212> TYPE: RNA
<213> ORGANISM: Homo sapiens

<400> SEQUENCE: 1449

cuuuuugauc cuucgauguc ggcucuuccu                                      30

<210> SEQ ID NO 1450
<211> LENGTH: 50
<212> TYPE: RNA
<213> ORGANISM: Homo sapiens

<400> SEQUENCE: 1450

ugccaagaau guuuucauua aucaagaacg aaagucggag guucgaagac                50

<210> SEQ ID NO 1451
<211> LENGTH: 29
<212> TYPE: RNA
<213> ORGANISM: Homo sapiens

<400> SEQUENCE: 1451

gccgucaucg uauagugguu aguacucug                                       29

<210> SEQ ID NO 1452
<211> LENGTH: 50
<212> TYPE: RNA
<213> ORGANISM: Homo sapiens

<400> SEQUENCE: 1452

cagaguguag cuuaacacaa agcacccaac uuacacuuag gagauuucaa                50

<210> SEQ ID NO 1453
<211> LENGTH: 26
<212> TYPE: RNA
<213> ORGANISM: Homo sapiens

<400> SEQUENCE: 1453

cggcuagcuc agucgguaga gcauga                                          26

<210> SEQ ID NO 1454
<211> LENGTH: 42
<212> TYPE: RNA
<213> ORGANISM: Homo sapiens

<400> SEQUENCE: 1454
```

agcagggucg ggccugguua guacuuggau gggagaccgc cu 42

<210> SEQ ID NO 1455
<211> LENGTH: 50
<212> TYPE: RNA
<213> ORGANISM: Homo sapiens

<400> SEQUENCE: 1455
cugcgggccg ccggugaaau accacuacuc ugaucguuuu uucacugacc 50

<210> SEQ ID NO 1456
<211> LENGTH: 31
<212> TYPE: RNA
<213> ORGANISM: Homo sapiens

<400> SEQUENCE: 1456
cccuccccgg gggagcgccg cguggggggcg g 31

<210> SEQ ID NO 1457
<211> LENGTH: 38
<212> TYPE: RNA
<213> ORGANISM: Homo sapiens

<400> SEQUENCE: 1457
auugugaauc ugacaacaga ggcuuacgac cccuuauu 38

<210> SEQ ID NO 1458
<211> LENGTH: 33
<212> TYPE: RNA
<213> ORGANISM: Homo sapiens

<400> SEQUENCE: 1458
gcauuggugg uucaguggua gaauucucgc cgg 33

<210> SEQ ID NO 1459
<211> LENGTH: 39
<212> TYPE: RNA
<213> ORGANISM: Homo sapiens

<400> SEQUENCE: 1459
cacgcgggag accggggguuc gauuccccga cggggagcc 39

<210> SEQ ID NO 1460
<211> LENGTH: 32
<212> TYPE: RNA
<213> ORGANISM: Homo sapiens

<400> SEQUENCE: 1460
gcaugggugg uucaguggua gacuucucgc cu 32

<210> SEQ ID NO 1461
<211> LENGTH: 31
<212> TYPE: RNA
<213> ORGANISM: Homo sapiens

<400> SEQUENCE: 1461
gucuacggcc auaccacccu gaacgcgccc g 31

<210> SEQ ID NO 1462
<211> LENGTH: 37
<212> TYPE: RNA
<213> ORGANISM: Homo sapiens

<400> SEQUENCE: 1462
gcgggagacc gggguucguu uccccgacgg ggagcca 37

<210> SEQ ID NO 1463
<211> LENGTH: 27
<212> TYPE: RNA
<213> ORGANISM: Homo sapiens

<400> SEQUENCE: 1463
caccccacgu cucgucgcgc gcgcguc 27

<210> SEQ ID NO 1464
<211> LENGTH: 32
<212> TYPE: RNA
<213> ORGANISM: Homo sapiens

<400> SEQUENCE: 1464
ucccuggugg ucuagugguu aggauucggc gu 32

<210> SEQ ID NO 1465
<211> LENGTH: 28
<212> TYPE: RNA
<213> ORGANISM: Homo sapiens

<400> SEQUENCE: 1465
ccggcggcgu ccggugagcu cucgcugg 28

<210> SEQ ID NO 1466
<211> LENGTH: 27
<212> TYPE: RNA
<213> ORGANISM: Homo sapiens

<400> SEQUENCE: 1466
uuggucgugg uuguaguccg ugcgaga 27

<210> SEQ ID NO 1467
<211> LENGTH: 33
<212> TYPE: RNA
<213> ORGANISM: Homo sapiens

<400> SEQUENCE: 1467
gcauuggcgg uucaguggua gaauucucgc cuc 33

<210> SEQ ID NO 1468
<211> LENGTH: 32
<212> TYPE: RNA
<213> ORGANISM: Homo sapiens

<400> SEQUENCE: 1468
gcauucgugg uucaguggua gaauucucgc cu 32

<210> SEQ ID NO 1469
<211> LENGTH: 27
<212> TYPE: RNA
<213> ORGANISM: Homo sapiens

<400> SEQUENCE: 1469
ccccuguggu cuagugguua ggauucg 27

<210> SEQ ID NO 1470
<211> LENGTH: 31
<212> TYPE: RNA
<213> ORGANISM: Homo sapiens

<400> SEQUENCE: 1470
ccccuguggu cuagugguua ggauucggcg c 31

<210> SEQ ID NO 1471
<211> LENGTH: 37
<212> TYPE: RNA
<213> ORGANISM: Homo sapiens

<400> SEQUENCE: 1471
aauucuagag cuaauacaug ccgacgggcg cugaccc 37

<210> SEQ ID NO 1472
<211> LENGTH: 32
<212> TYPE: RNA
<213> ORGANISM: Homo sapiens

<400> SEQUENCE: 1472
gcgggccgcc ggugaaauac cacuacucug au 32

<210> SEQ ID NO 1473
<211> LENGTH: 38
<212> TYPE: RNA
<213> ORGANISM: Homo sapiens

<400> SEQUENCE: 1473
gucuacggcc auaccacccu gaacgcgccc gaucucgu 38

<210> SEQ ID NO 1474
<211> LENGTH: 50
<212> TYPE: RNA
<213> ORGANISM: Homo sapiens

<400> SEQUENCE: 1474
cuuuggucgc ucgcuccucu ccuacuugga uaacuguggu aauucuagag 50

<210> SEQ ID NO 1475
<211> LENGTH: 31
<212> TYPE: RNA
<213> ORGANISM: Homo sapiens

<400> SEQUENCE: 1475
auugugaauc ugacaacaga ggcuuacgac c 31

<210> SEQ ID NO 1476
<211> LENGTH: 35
<212> TYPE: RNA
<213> ORGANISM: Homo sapiens

<400> SEQUENCE: 1476
gcgggagacc gggguucgau uccccgacgg ggagc 35

<210> SEQ ID NO 1477
<211> LENGTH: 32
<212> TYPE: RNA
<213> ORGANISM: Homo sapiens

<400> SEQUENCE: 1477
cgguuccggc ggcguccggu gagcucucgc ug 32

<210> SEQ ID NO 1478
<211> LENGTH: 44
<212> TYPE: RNA
<213> ORGANISM: Homo sapiens

<400> SEQUENCE: 1478
acgcaguuuu auccgguaaa gcgaaugauu agaggucuug gggc 44

<210> SEQ ID NO 1479
<211> LENGTH: 50
<212> TYPE: RNA
<213> ORGANISM: Homo sapiens

<400> SEQUENCE: 1479
uaauuaguga cgcgcaugaa uggaugaacg agauucccac ugucccuacc 50

<210> SEQ ID NO 1480
<211> LENGTH: 28
<212> TYPE: RNA
<213> ORGANISM: Homo sapiens

<400> SEQUENCE: 1480
cccucggauc ggccccgccg gggucggc 28

<210> SEQ ID NO 1481
<211> LENGTH: 35
<212> TYPE: RNA
<213> ORGANISM: Homo sapiens

<400> SEQUENCE: 1481
aacgagaacu uugaaggccg aaguggagaa ggguu 35

<210> SEQ ID NO 1482
<211> LENGTH: 32
<212> TYPE: RNA
<213> ORGANISM: Homo sapiens

<400> SEQUENCE: 1482
gcauugguag uucaguggua gaauucucgc cu 32

<210> SEQ ID NO 1483
<211> LENGTH: 32
<212> TYPE: RNA
<213> ORGANISM: Homo sapiens

<400> SEQUENCE: 1483
gcauuggugg uucaguggua gaacucucgc cu 32

<210> SEQ ID NO 1484
<211> LENGTH: 28
<212> TYPE: RNA
<213> ORGANISM: Homo sapiens

<400> SEQUENCE: 1484
cgguggauca cucggcucgu gcgucgau 28

<210> SEQ ID NO 1485
<211> LENGTH: 33
<212> TYPE: RNA
<213> ORGANISM: Homo sapiens

<400> SEQUENCE: 1485
ucccuggugg ccuagugguu aggauucggc gcu 33

<210> SEQ ID NO 1486
<211> LENGTH: 33
<212> TYPE: RNA

<213> ORGANISM: Homo sapiens

<400> SEQUENCE: 1486
aggagauuuc aacuuaacuu gaccgcucug acc 33

<210> SEQ ID NO 1487
<211> LENGTH: 43
<212> TYPE: RNA
<213> ORGANISM: Homo sapiens

<400> SEQUENCE: 1487
augucggcuc uuccuaucau ugugaagcag aauucaccaa gcg 43

<210> SEQ ID NO 1488
<211> LENGTH: 43
<212> TYPE: RNA
<213> ORGANISM: Homo sapiens

<400> SEQUENCE: 1488
cugucacgcg ggagaccggg guucaauucc ccgacgggga gcc 43

<210> SEQ ID NO 1489
<211> LENGTH: 33
<212> TYPE: RNA
<213> ORGANISM: Homo sapiens

<400> SEQUENCE: 1489
ucagaagguu gcguguucau gucacgucgg ggu 33

<210> SEQ ID NO 1490
<211> LENGTH: 29
<212> TYPE: RNA
<213> ORGANISM: Homo sapiens

<400> SEQUENCE: 1490
acgguccccc gcgagggggg cccgggcac 29

<210> SEQ ID NO 1491
<211> LENGTH: 34
<212> TYPE: RNA
<213> ORGANISM: Homo sapiens

<400> SEQUENCE: 1491
gcauuggugg uucaguggua gaauucucgc uugc 34

<210> SEQ ID NO 1492
<211> LENGTH: 36
<212> TYPE: RNA
<213> ORGANISM: Homo sapiens

<400> SEQUENCE: 1492
agugacgcgc augaauggau gaacgagauu cccccu 36

<210> SEQ ID NO 1493
<211> LENGTH: 33
<212> TYPE: RNA
<213> ORGANISM: Homo sapiens

<400> SEQUENCE: 1493
gacccagugg ccuaauggau aaggcaucag ccu 33

<210> SEQ ID NO 1494
<211> LENGTH: 29

<212> TYPE: RNA
<213> ORGANISM: Homo sapiens

<400> SEQUENCE: 1494
aacuggugcg gaccagggga auccgacug 29

<210> SEQ ID NO 1495
<211> LENGTH: 41
<212> TYPE: RNA
<213> ORGANISM: Homo sapiens

<400> SEQUENCE: 1495
uugugaaucu gacaacagag gcuuacgacc ccuuauuuac c 41

<210> SEQ ID NO 1496
<211> LENGTH: 50
<212> TYPE: RNA
<213> ORGANISM: Homo sapiens

<400> SEQUENCE: 1496
ucccugguag ucuagugguu aggauucggc gcucucaccg ccgcggcccg 50

<210> SEQ ID NO 1497
<211> LENGTH: 33
<212> TYPE: RNA
<213> ORGANISM: Homo sapiens

<400> SEQUENCE: 1497
guuuccguag cguagugguu aucacguucg ccu 33

<210> SEQ ID NO 1498
<211> LENGTH: 29
<212> TYPE: RNA
<213> ORGANISM: Homo sapiens

<400> SEQUENCE: 1498
ucccugguag ucuagugguu aggauucgg 29

<210> SEQ ID NO 1499
<211> LENGTH: 41
<212> TYPE: RNA
<213> ORGANISM: Homo sapiens

<400> SEQUENCE: 1499
cgagaacuuu gaaggccgaa guggagaagg guuccaugug a 41

<210> SEQ ID NO 1500
<211> LENGTH: 49
<212> TYPE: RNA
<213> ORGANISM: Homo sapiens

<400> SEQUENCE: 1500
auucaaacga gaacuuugaa ggccgaagug gagaaggguu ccaugugaa 49

<210> SEQ ID NO 1501
<211> LENGTH: 45
<212> TYPE: RNA
<213> ORGANISM: Homo sapiens

<400> SEQUENCE: 1501
gcguauauua aaguugcugc aguuaaaaag cucguaguug gaucu 45

<210> SEQ ID NO 1502

<211> LENGTH: 50
<212> TYPE: RNA
<213> ORGANISM: Homo sapiens

<400> SEQUENCE: 1502
gugggaucgc gccugugaau agccacugca cuccagccug agcaacauag 50

<210> SEQ ID NO 1503
<211> LENGTH: 42
<212> TYPE: RNA
<213> ORGANISM: Homo sapiens

<400> SEQUENCE: 1503
ugcgucggag ggcggcggcg gcggcggcgg cgggggugug gg 42

<210> SEQ ID NO 1504
<211> LENGTH: 33
<212> TYPE: RNA
<213> ORGANISM: Homo sapiens

<400> SEQUENCE: 1504
cuggugcgga ccaggggaau ccgacuguuu aau 33

<210> SEQ ID NO 1505
<211> LENGTH: 48
<212> TYPE: RNA
<213> ORGANISM: Homo sapiens

<400> SEQUENCE: 1505
cgaguucgag gccagccugg uccacauggg ucggaaaaaa ggauuuuu 48

<210> SEQ ID NO 1506
<211> LENGTH: 49
<212> TYPE: RNA
<213> ORGANISM: Homo sapiens

<400> SEQUENCE: 1506
aaggauuugg auuuguaagc uuugaaaggc augaagaugc acagaaagc 49

<210> SEQ ID NO 1507
<211> LENGTH: 32
<212> TYPE: RNA
<213> ORGANISM: Homo sapiens

<400> SEQUENCE: 1507
ccccuguggu cuaguggcua ggauucggcg cu 32

<210> SEQ ID NO 1508
<211> LENGTH: 27
<212> TYPE: RNA
<213> ORGANISM: Homo sapiens

<400> SEQUENCE: 1508
cuagcucagu cgguagagca ugagacu 27

<210> SEQ ID NO 1509
<211> LENGTH: 46
<212> TYPE: RNA
<213> ORGANISM: Homo sapiens

<400> SEQUENCE: 1509
gccugucacg cgggagaccg ggguucgauu ccccgacggg gagcca 46

<210> SEQ ID NO 1510
<211> LENGTH: 50
<212> TYPE: RNA
<213> ORGANISM: Homo sapiens

<400> SEQUENCE: 1510
cgacucuuag cggcggauca cucggcucgu gcgucgauga agaacgcagc 50

<210> SEQ ID NO 1511
<211> LENGTH: 50
<212> TYPE: RNA
<213> ORGANISM: Homo sapiens

<400> SEQUENCE: 1511
ucccuggugg ucuagugguu aggauucggc gcucucaccg ccgcggcccc 50

<210> SEQ ID NO 1512
<211> LENGTH: 42
<212> TYPE: RNA
<213> ORGANISM: Homo sapiens

<400> SEQUENCE: 1512
augguuuagu gaggcccucg gaucggcccc gccggggucg gc 42

<210> SEQ ID NO 1513
<211> LENGTH: 49
<212> TYPE: RNA
<213> ORGANISM: Homo sapiens

<400> SEQUENCE: 1513
uaauuaaaac aaagcaucgc gaaggcccgc ggcggguguu gacgcgaug 49

<210> SEQ ID NO 1514
<211> LENGTH: 31
<212> TYPE: RNA
<213> ORGANISM: Homo sapiens

<400> SEQUENCE: 1514
ucccuggugg ucuagugguu aggauccggc g 31

<210> SEQ ID NO 1515
<211> LENGTH: 37
<212> TYPE: RNA
<213> ORGANISM: Homo sapiens

<400> SEQUENCE: 1515
acgcgggaga ccgggguucg auuccccgac ggggagc 37

<210> SEQ ID NO 1516
<211> LENGTH: 32
<212> TYPE: RNA
<213> ORGANISM: Homo sapiens

<400> SEQUENCE: 1516
acauuggugg uucaguggua gaauucucgc cu 32

<210> SEQ ID NO 1517
<211> LENGTH: 50
<212> TYPE: RNA
<213> ORGANISM: Homo sapiens

<400> SEQUENCE: 1517
acuacggauc agaagauucu agguucgacu ccuggcuggc ucgcgauguc 50

<210> SEQ ID NO 1518
<211> LENGTH: 50
<212> TYPE: RNA
<213> ORGANISM: Homo sapiens

<400> SEQUENCE: 1518
cucucucucu cucucccccg cuccccgucc uccccccucc ccgggggagc 50

<210> SEQ ID NO 1519
<211> LENGTH: 42
<212> TYPE: RNA
<213> ORGANISM: Homo sapiens

<400> SEQUENCE: 1519
gcuuugguug cuaauggugg aguuaaagac uuuuucucug ac 42

<210> SEQ ID NO 1520
<211> LENGTH: 28
<212> TYPE: RNA
<213> ORGANISM: Homo sapiens

<400> SEQUENCE: 1520
ccaagcguug gauuguucac ccacuaau 28

<210> SEQ ID NO 1521
<211> LENGTH: 27
<212> TYPE: RNA
<213> ORGANISM: Homo sapiens

<400> SEQUENCE: 1521
uuuggcaaug guagaacuca cacugga 27

<210> SEQ ID NO 1522
<211> LENGTH: 31
<212> TYPE: RNA
<213> ORGANISM: Homo sapiens

<400> SEQUENCE: 1522
aagaacgaaa gucggagguu cgaagacgau c 31

<210> SEQ ID NO 1523
<211> LENGTH: 34
<212> TYPE: RNA
<213> ORGANISM: Homo sapiens

<400> SEQUENCE: 1523
ucccuggugg ucuagugguu aggauucggc gcuu 34

<210> SEQ ID NO 1524
<211> LENGTH: 46
<212> TYPE: RNA
<213> ORGANISM: Homo sapiens

<400> SEQUENCE: 1524
cgaguucgag gccagccugg uccacauggg ucggaaaaaa ggauuu 46

<210> SEQ ID NO 1525
<211> LENGTH: 33
<212> TYPE: RNA
<213> ORGANISM: Homo sapiens

<400> SEQUENCE: 1525
uccauggugg ucuagugguu aggauucggc gcu 33

<210> SEQ ID NO 1526
<211> LENGTH: 49
<212> TYPE: RNA
<213> ORGANISM: Homo sapiens

<400> SEQUENCE: 1526
cauuaguguc acuaaaguug guauacaacc ccccacugcu aaauuugac            49

<210> SEQ ID NO 1527
<211> LENGTH: 34
<212> TYPE: RNA
<213> ORGANISM: Homo sapiens

<400> SEQUENCE: 1527
ucccuggugg ucuagugguu aggauucggc gcua                            34

<210> SEQ ID NO 1528
<211> LENGTH: 35
<212> TYPE: RNA
<213> ORGANISM: Homo sapiens

<400> SEQUENCE: 1528
uaauuaguga cgcgcaugaa uggaugaacg agauu                           35

<210> SEQ ID NO 1529
<211> LENGTH: 35
<212> TYPE: RNA
<213> ORGANISM: Homo sapiens

<400> SEQUENCE: 1529
guuuccguag uguagugguu aucacguucg ccuca                           35

<210> SEQ ID NO 1530
<211> LENGTH: 50
<212> TYPE: RNA
<213> ORGANISM: Homo sapiens

<400> SEQUENCE: 1530
cuuggaaagc gucgcgguuc cggcggcguc cggugagcuc ucgcuggccc           50

<210> SEQ ID NO 1531
<211> LENGTH: 32
<212> TYPE: RNA
<213> ORGANISM: Homo sapiens

<400> SEQUENCE: 1531
gcaguggugg uucaguggua gaauucucgc cu                              32

<210> SEQ ID NO 1532
<211> LENGTH: 27
<212> TYPE: RNA
<213> ORGANISM: Homo sapiens

<400> SEQUENCE: 1532
ccggcggcgu ccggugagcu cucgcug                                    27

<210> SEQ ID NO 1533
<211> LENGTH: 49
<212> TYPE: RNA
<213> ORGANISM: Homo sapiens

<400> SEQUENCE: 1533

```
aaguguagua ucuguucuua ucaguuuaau aucugauacg uccucuauc          49

<210> SEQ ID NO 1534
<211> LENGTH: 32
<212> TYPE: RNA
<213> ORGANISM: Homo sapiens

<400> SEQUENCE: 1534

uccggcggcg uccggugagc ucucgcuggc cc                            32

<210> SEQ ID NO 1535
<211> LENGTH: 33
<212> TYPE: RNA
<213> ORGANISM: Homo sapiens

<400> SEQUENCE: 1535

ucccuggugg ucuagugguu aggacucggc gcu                           33

<210> SEQ ID NO 1536
<211> LENGTH: 35
<212> TYPE: RNA
<213> ORGANISM: Homo sapiens

<400> SEQUENCE: 1536

ccaagcguug gauuguucac ccacuaauag ggaac                         35

<210> SEQ ID NO 1537
<211> LENGTH: 31
<212> TYPE: RNA
<213> ORGANISM: Homo sapiens

<400> SEQUENCE: 1537

ggccgugauc guauagugguu aguacucug a                             31

<210> SEQ ID NO 1538
<211> LENGTH: 50
<212> TYPE: RNA
<213> ORGANISM: Homo sapiens

<400> SEQUENCE: 1538

cuaggaauaa uggaauagga ccgcgguucu auuuguugg uuuucggaac          50

<210> SEQ ID NO 1539
<211> LENGTH: 26
<212> TYPE: RNA
<213> ORGANISM: Homo sapiens

<400> SEQUENCE: 1539

uaggaugggg ugugauaggu ggcacg                                   26

<210> SEQ ID NO 1540
<211> LENGTH: 33
<212> TYPE: RNA
<213> ORGANISM: Homo sapiens

<400> SEQUENCE: 1540

ucccuugugg ucuagugguu aggauucggc gcu                           33

<210> SEQ ID NO 1541
<211> LENGTH: 33
<212> TYPE: RNA
<213> ORGANISM: Homo sapiens

<400> SEQUENCE: 1541
```

ucccuggugg ucuaguggu aggauuuggc gcu 33

<210> SEQ ID NO 1542
<211> LENGTH: 32
<212> TYPE: RNA
<213> ORGANISM: Homo sapiens

<400> SEQUENCE: 1542
gcauuggugg uucaguggua gaauucucac cu 32

<210> SEQ ID NO 1543
<211> LENGTH: 38
<212> TYPE: RNA
<213> ORGANISM: Homo sapiens

<400> SEQUENCE: 1543
ucauugugaa gcagaauuca ccaagcguug gauuguuc 38

<210> SEQ ID NO 1544
<211> LENGTH: 32
<212> TYPE: RNA
<213> ORGANISM: Homo sapiens

<400> SEQUENCE: 1544
cgagaacuuu gaaggccgaa guggagaagg gu 32

<210> SEQ ID NO 1545
<211> LENGTH: 33
<212> TYPE: RNA
<213> ORGANISM: Homo sapiens

<400> SEQUENCE: 1545
uccucguuag uauaguggu aguaucccccg ccu 33

<210> SEQ ID NO 1546
<211> LENGTH: 32
<212> TYPE: RNA
<213> ORGANISM: Homo sapiens

<400> SEQUENCE: 1546
gcauggguga uucaguggua gaauucucgc cu 32

<210> SEQ ID NO 1547
<211> LENGTH: 35
<212> TYPE: RNA
<213> ORGANISM: Homo sapiens

<400> SEQUENCE: 1547
gcauuggugg uucaguggua gaauucucgc cugcc 35

<210> SEQ ID NO 1548
<211> LENGTH: 30
<212> TYPE: RNA
<213> ORGANISM: Homo sapiens

<400> SEQUENCE: 1548
uaggaugggg ugugauaggu ggcacggagc 30

<210> SEQ ID NO 1549
<211> LENGTH: 29
<212> TYPE: RNA
<213> ORGANISM: Homo sapiens

<400> SEQUENCE: 1549
ggcuagcuca gucgguagag caugggacu 29

<210> SEQ ID NO 1550
<211> LENGTH: 47
<212> TYPE: RNA
<213> ORGANISM: Homo sapiens

<400> SEQUENCE: 1550
uaacaagguu uccguaggug aaccugcgga aggaucauua acggagc 47

<210> SEQ ID NO 1551
<211> LENGTH: 30
<212> TYPE: RNA
<213> ORGANISM: Homo sapiens

<400> SEQUENCE: 1551
gugaucguau agugguuagu acucugcguu 30

<210> SEQ ID NO 1552
<211> LENGTH: 41
<212> TYPE: RNA
<213> ORGANISM: Homo sapiens

<400> SEQUENCE: 1552
acgagaacuu ugaaggccga aguggagaag gguuccaugu g 41

<210> SEQ ID NO 1553
<211> LENGTH: 50
<212> TYPE: RNA
<213> ORGANISM: Homo sapiens

<400> SEQUENCE: 1553
ucuggacgcg agccgggccc uucccgugga ucgccccagc ugcggcgggc 50

<210> SEQ ID NO 1554
<211> LENGTH: 28
<212> TYPE: RNA
<213> ORGANISM: Homo sapiens

<400> SEQUENCE: 1554
acuuggauaa cugugguaau ucuagagc 28

<210> SEQ ID NO 1555
<211> LENGTH: 32
<212> TYPE: RNA
<213> ORGANISM: Homo sapiens

<400> SEQUENCE: 1555
gcaugggugg uucaguggua gaauucuagc cu 32

<210> SEQ ID NO 1556
<211> LENGTH: 27
<212> TYPE: RNA
<213> ORGANISM: Homo sapiens

<400> SEQUENCE: 1556
ccccacgucu cgucgcgcgc gcguccg 27

<210> SEQ ID NO 1557
<211> LENGTH: 50
<212> TYPE: RNA
<213> ORGANISM: Homo sapiens

<400> SEQUENCE: 1557
ccuuggaaag cgucgcgguu ccggcggcgu ccggugagcu cucgcuggcc 50

<210> SEQ ID NO 1558
<211> LENGTH: 32
<212> TYPE: RNA
<213> ORGANISM: Homo sapiens

<400> SEQUENCE: 1558
gccuuugugg uucaguggua gaauucucgc cu 32

<210> SEQ ID NO 1559
<211> LENGTH: 31
<212> TYPE: RNA
<213> ORGANISM: Homo sapiens

<400> SEQUENCE: 1559
ucccuggugg ccuagugguu aggauucggc g 31

<210> SEQ ID NO 1560
<211> LENGTH: 41
<212> TYPE: RNA
<213> ORGANISM: Homo sapiens

<400> SEQUENCE: 1560
acggagcagg ucaaaacucc cgugcugauc aguaguggga u 41

<210> SEQ ID NO 1561
<211> LENGTH: 34
<212> TYPE: RNA
<213> ORGANISM: Homo sapiens

<400> SEQUENCE: 1561
gcauuggugg uucaguggua gaauucucuc cugc 34

<210> SEQ ID NO 1562
<211> LENGTH: 47
<212> TYPE: RNA
<213> ORGANISM: Homo sapiens

<400> SEQUENCE: 1562
cccgacccgg ggagguagug acgaaaaaua acaauacagg acucuuu 47

<210> SEQ ID NO 1563
<211> LENGTH: 31
<212> TYPE: RNA
<213> ORGANISM: Homo sapiens

<400> SEQUENCE: 1563
cccaccccac gucucgucgc gcgcgcgucc g 31

<210> SEQ ID NO 1564
<211> LENGTH: 44
<212> TYPE: RNA
<213> ORGANISM: Homo sapiens

<400> SEQUENCE: 1564
aaacgagaac uuugaaggcc gaaguggaga aggguuccau guga 44

<210> SEQ ID NO 1565
<211> LENGTH: 32
<212> TYPE: RNA

<213> ORGANISM: Homo sapiens

<400> SEQUENCE: 1565
ccaagcguug gauuguucac ccacuacuag gg 32

<210> SEQ ID NO 1566
<211> LENGTH: 34
<212> TYPE: RNA
<213> ORGANISM: Homo sapiens

<400> SEQUENCE: 1566
gcacuggugg uucaguggua gaauucucgc cugc 34

<210> SEQ ID NO 1567
<211> LENGTH: 31
<212> TYPE: RNA
<213> ORGANISM: Homo sapiens

<400> SEQUENCE: 1567
ccggcuagcu cagucgguag agcaugagac u 31

<210> SEQ ID NO 1568
<211> LENGTH: 48
<212> TYPE: RNA
<213> ORGANISM: Homo sapiens

<400> SEQUENCE: 1568
augguuuuuc auaucauugg ucgugguugu aguccgugcg agaauacc 48

<210> SEQ ID NO 1569
<211> LENGTH: 32
<212> TYPE: RNA
<213> ORGANISM: Homo sapiens

<400> SEQUENCE: 1569
gcauuggugg uucagugguc gaauucucgc cu 32

<210> SEQ ID NO 1570
<211> LENGTH: 32
<212> TYPE: RNA
<213> ORGANISM: Homo sapiens

<400> SEQUENCE: 1570
cgcgaccuca gaucagacgu ggcgacccgc ug 32

<210> SEQ ID NO 1571
<211> LENGTH: 32
<212> TYPE: RNA
<213> ORGANISM: Homo sapiens

<400> SEQUENCE: 1571
gcauuggggg uucaguggua gaauucucgc cu 32

<210> SEQ ID NO 1572
<211> LENGTH: 33
<212> TYPE: RNA
<213> ORGANISM: Homo sapiens

<400> SEQUENCE: 1572
guuuccguag uguagcgguu aucacauucg ccu 33

<210> SEQ ID NO 1573
<211> LENGTH: 50

<212> TYPE: RNA
<213> ORGANISM: Homo sapiens

<400> SEQUENCE: 1573
caauguaggu aagggaaguc ggcaagccgg auccguaacu ucgggauaag 50

<210> SEQ ID NO 1574
<211> LENGTH: 50
<212> TYPE: RNA
<213> ORGANISM: Homo sapiens

<400> SEQUENCE: 1574
aaaguugcug caguuaaaaa gcucguaguu ggaucuuggg agcgggcggg 50

<210> SEQ ID NO 1575
<211> LENGTH: 48
<212> TYPE: RNA
<213> ORGANISM: Homo sapiens

<400> SEQUENCE: 1575
aguugauuua acauugucuc cccccacaac cgcgcuugac uagcuugc 48

<210> SEQ ID NO 1576
<211> LENGTH: 27
<212> TYPE: RNA
<213> ORGANISM: Homo sapiens

<400> SEQUENCE: 1576
cgcgcgcgug uggugugcgu cggaggg 27

<210> SEQ ID NO 1577
<211> LENGTH: 46
<212> TYPE: RNA
<213> ORGANISM: Homo sapiens

<400> SEQUENCE: 1577
aacagcaguu gaacaugggu cagucggucc ugagagaugg gcgagc 46

<210> SEQ ID NO 1578
<211> LENGTH: 31
<212> TYPE: RNA
<213> ORGANISM: Homo sapiens

<400> SEQUENCE: 1578
ggcugguccg augguagugg guuaucagaa c 31

<210> SEQ ID NO 1579
<211> LENGTH: 42
<212> TYPE: RNA
<213> ORGANISM: Homo sapiens

<400> SEQUENCE: 1579
cgagaacuuu gaaggccgaa guggagaagg guuccaugug aa 42

<210> SEQ ID NO 1580
<211> LENGTH: 33
<212> TYPE: RNA
<213> ORGANISM: Homo sapiens

<400> SEQUENCE: 1580
guuuccguag uguagugguu cucacguucg ccu 33

<210> SEQ ID NO 1581

<211> LENGTH: 47
<212> TYPE: RNA
<213> ORGANISM: Homo sapiens

<400> SEQUENCE: 1581 cgugugugu gcgucggagg gcggcggcgg cggcggcggc gggggug 47

<210> SEQ ID NO 1582
<211> LENGTH: 26
<212> TYPE: RNA
<213> ORGANISM: Homo sapiens

<400> SEQUENCE: 1582
cagucggucc ugagagaugg gcgagc 26

<210> SEQ ID NO 1583
<211> LENGTH: 29
<212> TYPE: RNA
<213> ORGANISM: Homo sapiens

<400> SEQUENCE: 1583
gcagugaucg uauaguggu aguacucug 29

<210> SEQ ID NO 1584
<211> LENGTH: 49
<212> TYPE: RNA
<213> ORGANISM: Homo sapiens

<400> SEQUENCE: 1584
caacgauggu uuuucauauc auuggucgug guuguagucc gugcgagaa 49

<210> SEQ ID NO 1585
<211> LENGTH: 37
<212> TYPE: RNA
<213> ORGANISM: Homo sapiens

<400> SEQUENCE: 1585
ccuagcagcc gacuuagaac uggugcggac cagggga 37

<210> SEQ ID NO 1586
<211> LENGTH: 30
<212> TYPE: RNA
<213> ORGANISM: Homo sapiens

<400> SEQUENCE: 1586
aguaagguca gcuaaauaag cuaucgugcc 30

<210> SEQ ID NO 1587
<211> LENGTH: 42
<212> TYPE: RNA
<213> ORGANISM: Homo sapiens

<400> SEQUENCE: 1587
acgagaacuu ugaaggccga aguggagaag gguuccaugu ga 42

<210> SEQ ID NO 1588
<211> LENGTH: 33
<212> TYPE: RNA
<213> ORGANISM: Homo sapiens

<400> SEQUENCE: 1588
gacccaguug ccuaauggau aaggcaucag ccu 33

```
<210> SEQ ID NO 1589
<211> LENGTH: 37
<212> TYPE: RNA
<213> ORGANISM: Homo sapiens

<400> SEQUENCE: 1589

gcgggagacc gggguucaau uccccgacgg ggagcca                           37

<210> SEQ ID NO 1590
<211> LENGTH: 50
<212> TYPE: RNA
<213> ORGANISM: Homo sapiens

<400> SEQUENCE: 1590

aacgagaacu uugaaggccg aaguggagaa ggguuccaug ugaacagcag             50

<210> SEQ ID NO 1591
<211> LENGTH: 33
<212> TYPE: RNA
<213> ORGANISM: Homo sapiens

<400> SEQUENCE: 1591

guuuccauag uguagugguu aucacguucg ccu                              33

<210> SEQ ID NO 1592
<211> LENGTH: 34
<212> TYPE: RNA
<213> ORGANISM: Homo sapiens

<400> SEQUENCE: 1592

gcauuggugg uucagguggua gaauuaucgc cugc                             34

<210> SEQ ID NO 1593
<211> LENGTH: 50
<212> TYPE: RNA
<213> ORGANISM: Homo sapiens

<400> SEQUENCE: 1593

gaaauacaac gaugguuuuu cauaucauug gucgugguug uaguccgugc             50

<210> SEQ ID NO 1594
<211> LENGTH: 44
<212> TYPE: RNA
<213> ORGANISM: Homo sapiens

<400> SEQUENCE: 1594

ucgcugcgau cuauugaaag ucagcccucg acacaagggu uugu                   44

<210> SEQ ID NO 1595
<211> LENGTH: 49
<212> TYPE: RNA
<213> ORGANISM: Homo sapiens

<400> SEQUENCE: 1595

uaacuguggu aauucuagag cuaauacaug ccgacgggcg cugacccccc             49

<210> SEQ ID NO 1596
<211> LENGTH: 30
<212> TYPE: RNA
<213> ORGANISM: Homo sapiens

<400> SEQUENCE: 1596

uaggaugggg ugugauagga ggcacggaga                                   30
```

<210> SEQ ID NO 1597
<211> LENGTH: 36
<212> TYPE: RNA
<213> ORGANISM: Homo sapiens

<400> SEQUENCE: 1597
cgguuccggc ggcguccggu gagcucucgc uggccc                     36

<210> SEQ ID NO 1598
<211> LENGTH: 32
<212> TYPE: RNA
<213> ORGANISM: Homo sapiens

<400> SEQUENCE: 1598
gcauuggugg uucaguggua gaauuuucgc cu                         32

<210> SEQ ID NO 1599
<211> LENGTH: 32
<212> TYPE: RNA
<213> ORGANISM: Homo sapiens

<400> SEQUENCE: 1599
agcagaguug cgcagcggaa gcgugcuggg cc                         32

<210> SEQ ID NO 1600
<211> LENGTH: 33
<212> TYPE: RNA
<213> ORGANISM: Homo sapiens

<400> SEQUENCE: 1600
ucccuggugg ucuagugguu aggauucggc ccu                        33

<210> SEQ ID NO 1601
<211> LENGTH: 34
<212> TYPE: RNA
<213> ORGANISM: Homo sapiens

<400> SEQUENCE: 1601
ucccugguag ucuagugguu aggauucggc gcuc                       34

<210> SEQ ID NO 1602
<211> LENGTH: 32
<212> TYPE: RNA
<213> ORGANISM: Homo sapiens

<400> SEQUENCE: 1602
uuuggcaaug guagaacuca cacuggugag gu                         32

<210> SEQ ID NO 1603
<211> LENGTH: 30
<212> TYPE: RNA
<213> ORGANISM: Homo sapiens

<400> SEQUENCE: 1603
uagugacgaa aaauaacaau acaggacucu                            30

<210> SEQ ID NO 1604
<211> LENGTH: 32
<212> TYPE: RNA
<213> ORGANISM: Homo sapiens

<400> SEQUENCE: 1604
gaaugggugg uucaguggua gaauucgc cu                           32

<210> SEQ ID NO 1605
<211> LENGTH: 48
<212> TYPE: RNA
<213> ORGANISM: Homo sapiens

<400> SEQUENCE: 1605
cuugcggcca cggguuccuc ccggggcuac gccugucuga gcgucgcu 48

<210> SEQ ID NO 1606
<211> LENGTH: 45
<212> TYPE: RNA
<213> ORGANISM: Homo sapiens

<400> SEQUENCE: 1606
gacucugaau ccagcgaucc gaguucgagu cucgguggaa ccucc 45

<210> SEQ ID NO 1607
<211> LENGTH: 42
<212> TYPE: RNA
<213> ORGANISM: Homo sapiens

<400> SEQUENCE: 1607
cugucacgcg ggagaccggg guucguuucc ccgacgggga gc 42

<210> SEQ ID NO 1608
<211> LENGTH: 49
<212> TYPE: RNA
<213> ORGANISM: Homo sapiens

<400> SEQUENCE: 1608
cugggucggg guuucguacg uagcagagca gcucccucgc ugcgaucua 49

<210> SEQ ID NO 1609
<211> LENGTH: 26
<212> TYPE: RNA
<213> ORGANISM: Homo sapiens

<400> SEQUENCE: 1609
cccacgucuc gucgcgcgcg cguccg 26

<210> SEQ ID NO 1610
<211> LENGTH: 50
<212> TYPE: RNA
<213> ORGANISM: Homo sapiens

<400> SEQUENCE: 1610
uacccacucc cgacccgggg agguagugac gaaaaauaac aauacaggac 50

<210> SEQ ID NO 1611
<211> LENGTH: 36
<212> TYPE: RNA
<213> ORGANISM: Homo sapiens

<400> SEQUENCE: 1611
augucggcuc uuccuaucau ugugaagcag aauuca 36

<210> SEQ ID NO 1612
<211> LENGTH: 27
<212> TYPE: RNA
<213> ORGANISM: Homo sapiens

<400> SEQUENCE: 1612
ucccuguggu cuaguggcua ggauucg 27

<210> SEQ ID NO 1613
<211> LENGTH: 32
<212> TYPE: RNA
<213> ORGANISM: Homo sapiens

<400> SEQUENCE: 1613
uaggaugggg ugugauaggu ggcacggaga au 32

<210> SEQ ID NO 1614
<211> LENGTH: 32
<212> TYPE: RNA
<213> ORGANISM: Homo sapiens

<400> SEQUENCE: 1614
ggcugguccg augguagugg guuaucagaa ca 32

<210> SEQ ID NO 1615
<211> LENGTH: 36
<212> TYPE: RNA
<213> ORGANISM: Homo sapiens

<400> SEQUENCE: 1615
ucccugguag ucuagugguu aggauucggc gcucuc 36

<210> SEQ ID NO 1616
<211> LENGTH: 29
<212> TYPE: RNA
<213> ORGANISM: Homo sapiens

<400> SEQUENCE: 1616
uccucguuag uauaguggug aguaucccc 29

<210> SEQ ID NO 1617
<211> LENGTH: 29
<212> TYPE: RNA
<213> ORGANISM: Homo sapiens

<400> SEQUENCE: 1617
agcaagguca gcuaaauaag cuaucgggc 29

<210> SEQ ID NO 1618
<211> LENGTH: 30
<212> TYPE: RNA
<213> ORGANISM: Homo sapiens

<400> SEQUENCE: 1618
agugacgcgc augaauggau gaacgagauu 30

<210> SEQ ID NO 1619
<211> LENGTH: 44
<212> TYPE: RNA
<213> ORGANISM: Homo sapiens

<400> SEQUENCE: 1619
cuuggauggg agaccgccug ggaauaccgg gugcuguagg cuuu 44

<210> SEQ ID NO 1620
<211> LENGTH: 50
<212> TYPE: RNA
<213> ORGANISM: Homo sapiens

<400> SEQUENCE: 1620
ccuucgcggg ggggaugcgu gcauuuauca gaucaaaacc aacccgguca 50

<210> SEQ ID NO 1621
<211> LENGTH: 32
<212> TYPE: RNA
<213> ORGANISM: Homo sapiens

<400> SEQUENCE: 1621
gcauuggugg uucaguggua gaauucucgc gu 32

<210> SEQ ID NO 1622
<211> LENGTH: 33
<212> TYPE: RNA
<213> ORGANISM: Homo sapiens

<400> SEQUENCE: 1622
guuuccguag ugucgugguu aucacguucg ccu 33

<210> SEQ ID NO 1623
<211> LENGTH: 34
<212> TYPE: RNA
<213> ORGANISM: Homo sapiens

<400> SEQUENCE: 1623
augacccgcc gggcagcuuc cgggaaacca aagu 34

<210> SEQ ID NO 1624
<211> LENGTH: 26
<212> TYPE: RNA
<213> ORGANISM: Homo sapiens

<400> SEQUENCE: 1624
gucaggaugg ccgagugguc uaaggc 26

<210> SEQ ID NO 1625
<211> LENGTH: 28
<212> TYPE: RNA
<213> ORGANISM: Homo sapiens

<400> SEQUENCE: 1625
gguggucuag ugguuaggau ucggcgcu 28

<210> SEQ ID NO 1626
<211> LENGTH: 30
<212> TYPE: RNA
<213> ORGANISM: Homo sapiens

<400> SEQUENCE: 1626
ccaccccacg ucucgucgcg cgcgcguccg 30

<210> SEQ ID NO 1627
<211> LENGTH: 33
<212> TYPE: RNA
<213> ORGANISM: Homo sapiens

<400> SEQUENCE: 1627
ucccuggugg ucuagugguu aggauccggc gcu 33

<210> SEQ ID NO 1628
<211> LENGTH: 31
<212> TYPE: RNA
<213> ORGANISM: Homo sapiens

<400> SEQUENCE: 1628 cuccccggggc uacgccuguc ugagcgucgc u 31

<210> SEQ ID NO 1629
<211> LENGTH: 29
<212> TYPE: RNA
<213> ORGANISM: Homo sapiens

<400> SEQUENCE: 1629
caccccacgu cucgucgcgc gcgcguccg 29

<210> SEQ ID NO 1630
<211> LENGTH: 32
<212> TYPE: RNA
<213> ORGANISM: Homo sapiens

<400> SEQUENCE: 1630 gcauggugg uucaguggua gaauuaucgc cu 32

<210> SEQ ID NO 1631
<211> LENGTH: 42
<212> TYPE: RNA
<213> ORGANISM: Homo sapiens

<400> SEQUENCE: 1631
auugcaaauu cgaagaagca gcuucaaacc ugccggggcu uc 42

<210> SEQ ID NO 1632
<211> LENGTH: 32
<212> TYPE: RNA
<213> ORGANISM: Homo sapiens

<400> SEQUENCE: 1632
gcauuggugg uucaguggua aaauucucgc cu 32

<210> SEQ ID NO 1633
<211> LENGTH: 46
<212> TYPE: RNA
<213> ORGANISM: Homo sapiens

<400> SEQUENCE: 1633 aacaugggucagucgguccu gagagauggg cgagcgccgu uccgaa 46

<210> SEQ ID NO 1634
<211> LENGTH: 29
<212> TYPE: RNA
<213> ORGANISM: Homo sapiens

<400> SEQUENCE: 1634
agugacgcgc augaauggau gaacgagau 29

<210> SEQ ID NO 1635
<211> LENGTH: 28
<212> TYPE: RNA
<213> ORGANISM: Homo sapiens

<400> SEQUENCE: 1635
aggauagcug gcgcucucgc agacccga 28

<210> SEQ ID NO 1636
<211> LENGTH: 28
<212> TYPE: RNA
<213> ORGANISM: Homo sapiens

<400> SEQUENCE: 1636
ugaauugcag gacacauuga ucaucgac 28

<210> SEQ ID NO 1637
<211> LENGTH: 31
<212> TYPE: RNA
<213> ORGANISM: Homo sapiens

<400> SEQUENCE: 1637
uaggauggag ugugauaggu ggcacggaga a 31

<210> SEQ ID NO 1638
<211> LENGTH: 29
<212> TYPE: RNA
<213> ORGANISM: Homo sapiens

<400> SEQUENCE: 1638
gcugugguuc agugguagaa uucucgccu 29

<210> SEQ ID NO 1639
<211> LENGTH: 30
<212> TYPE: RNA
<213> ORGANISM: Homo sapiens

<400> SEQUENCE: 1639
ucccuagugg ucuagugguu aggauucggc 30

<210> SEQ ID NO 1640
<211> LENGTH: 49
<212> TYPE: RNA
<213> ORGANISM: Homo sapiens

<400> SEQUENCE: 1640
ugguuaggau ucggcgcucu caccgccgcg gcccggguuc gauucccgg 49

<210> SEQ ID NO 1641
<211> LENGTH: 37
<212> TYPE: RNA
<213> ORGANISM: Homo sapiens

<400> SEQUENCE: 1641
uuagugaggc ccucggaucg gccccgccgg ggucggc 37

<210> SEQ ID NO 1642
<211> LENGTH: 39
<212> TYPE: RNA
<213> ORGANISM: Homo sapiens

<400> SEQUENCE: 1642
caaguguagu aucuguucuu aucaguuuaa uaucugaua 39

<210> SEQ ID NO 1643
<211> LENGTH: 34
<212> TYPE: RNA
<213> ORGANISM: Homo sapiens

<400> SEQUENCE: 1643 gggggguguag cucaguggua gagcauuuga cugc 34

<210> SEQ ID NO 1644
<211> LENGTH: 35
<212> TYPE: RNA

<213> ORGANISM: Homo sapiens

<400> SEQUENCE: 1644
gcauuggugg uucaguggua gaauucucgc cugcu 35

<210> SEQ ID NO 1645
<211> LENGTH: 33
<212> TYPE: RNA
<213> ORGANISM: Homo sapiens

<400> SEQUENCE: 1645
guuuccguag uguagugguu aucacguucc ccu 33

<210> SEQ ID NO 1646
<211> LENGTH: 31
<212> TYPE: RNA
<213> ORGANISM: Homo sapiens

<400> SEQUENCE: 1646
ucccugguag ucuagugguu aggauucggc g 31

<210> SEQ ID NO 1647
<211> LENGTH: 36
<212> TYPE: RNA
<213> ORGANISM: Homo sapiens

<400> SEQUENCE: 1647
cgaaagguug gugguucgag cccacccagg gacgcc 36

<210> SEQ ID NO 1648
<211> LENGTH: 50
<212> TYPE: RNA
<213> ORGANISM: Homo sapiens

<400> SEQUENCE: 1648
cucccggagc gggaccgggu cggaggaugg acgagaauca cgagcgacgg 50

<210> SEQ ID NO 1649
<211> LENGTH: 30
<212> TYPE: RNA
<213> ORGANISM: Homo sapiens

<400> SEQUENCE: 1649
uaggaugggg ugugauaggc ggcacggaga 30

<210> SEQ ID NO 1650
<211> LENGTH: 27
<212> TYPE: RNA
<213> ORGANISM: Homo sapiens

<400> SEQUENCE: 1650
cggcuagcuc agucgguaga gcauggg 27

<210> SEQ ID NO 1651
<211> LENGTH: 33
<212> TYPE: RNA
<213> ORGANISM: Homo sapiens

<400> SEQUENCE: 1651
ucccuggugg ucuaguggua aggauucggc gcu 33

<210> SEQ ID NO 1652
<211> LENGTH: 33

<212> TYPE: RNA
<213> ORGANISM: Homo sapiens

<400> SEQUENCE: 1652
ucccuggugg ucuagcgguu aggauucggc gcu 33

<210> SEQ ID NO 1653
<211> LENGTH: 39
<212> TYPE: RNA
<213> ORGANISM: Homo sapiens

<400> SEQUENCE: 1653
cccgaggggc ucucgcuucu ggcgccaagc gcccggccg 39

<210> SEQ ID NO 1654
<211> LENGTH: 30
<212> TYPE: RNA
<213> ORGANISM: Homo sapiens

<400> SEQUENCE: 1654
gagccgccug gauaccgcag cuaggaauaa 30

<210> SEQ ID NO 1655
<211> LENGTH: 46
<212> TYPE: RNA
<213> ORGANISM: Homo sapiens

<400> SEQUENCE: 1655
cccgacccgg ggagguagug acgaaaaaua acaauacagg acucuu 46

<210> SEQ ID NO 1656
<211> LENGTH: 34
<212> TYPE: RNA
<213> ORGANISM: Homo sapiens

<400> SEQUENCE: 1656
gcauuggugg uucagcggua gaauucucgc cugc 34

<210> SEQ ID NO 1657
<211> LENGTH: 29
<212> TYPE: RNA
<213> ORGANISM: Homo sapiens

<400> SEQUENCE: 1657
uuaaguuaaa gauuaagaga accaacacc 29

<210> SEQ ID NO 1658
<211> LENGTH: 32
<212> TYPE: RNA
<213> ORGANISM: Homo sapiens

<400> SEQUENCE: 1658
gcaugggugg uucaguguua gaauucucgc cu 32

<210> SEQ ID NO 1659
<211> LENGTH: 32
<212> TYPE: RNA
<213> ORGANISM: Homo sapiens

<400> SEQUENCE: 1659
gcauuggugg uucaguggua gaauacucgc cu 32

<210> SEQ ID NO 1660

<211> LENGTH: 35
<212> TYPE: RNA
<213> ORGANISM: Homo sapiens

<400> SEQUENCE: 1660
cucaaagcaa uacacugaaa auguuuagac gggcu 35

<210> SEQ ID NO 1661
<211> LENGTH: 45
<212> TYPE: RNA
<213> ORGANISM: Homo sapiens

<400> SEQUENCE: 1661
cccgacccgg ggagguagug acgaaaaaua acaauacagg acucu 45

<210> SEQ ID NO 1662
<211> LENGTH: 31
<212> TYPE: RNA
<213> ORGANISM: Homo sapiens

<400> SEQUENCE: 1662
aguaagguca gcuaaauaag cuaucgggcc u 31

<210> SEQ ID NO 1663
<211> LENGTH: 32
<212> TYPE: RNA
<213> ORGANISM: Homo sapiens

<400> SEQUENCE: 1663
cgacacuucg aacgcacuug cggccccggg uu 32

<210> SEQ ID NO 1664
<211> LENGTH: 34
<212> TYPE: RNA
<213> ORGANISM: Homo sapiens

<400> SEQUENCE: 1664
gcauuggugg uucaguggua gaauucucgc cuac 34

<210> SEQ ID NO 1665
<211> LENGTH: 36
<212> TYPE: RNA
<213> ORGANISM: Homo sapiens

<400> SEQUENCE: 1665
ccacgcggga ggcccggguu cguuucccgg cccaug 36

<210> SEQ ID NO 1666
<211> LENGTH: 50
<212> TYPE: RNA
<213> ORGANISM: Homo sapiens

<400> SEQUENCE: 1666
aucacaacca guuacagauu ucuuuguucc uucuccacuc ccacugcuuc 50

<210> SEQ ID NO 1667
<211> LENGTH: 39
<212> TYPE: RNA
<213> ORGANISM: Homo sapiens

<400> SEQUENCE: 1667
cgaacgagac ucuggcaugc uaacuaguua cgcgacccc 39

<210> SEQ ID NO 1668
<211> LENGTH: 49
<212> TYPE: RNA
<213> ORGANISM: Homo sapiens

<400> SEQUENCE: 1668
uuucuaugau gaaucaaacu agcucacuau gaccgacagu gaaaauaca 49

<210> SEQ ID NO 1669
<211> LENGTH: 32
<212> TYPE: RNA
<213> ORGANISM: Homo sapiens

<400> SEQUENCE: 1669
gcaugggugg uucagcggua gaauucucgc cu 32

<210> SEQ ID NO 1670
<211> LENGTH: 34
<212> TYPE: RNA
<213> ORGANISM: Homo sapiens

<400> SEQUENCE: 1670
ggccgugauc guauagugga uaguacucug cguu 34

<210> SEQ ID NO 1671
<211> LENGTH: 42
<212> TYPE: RNA
<213> ORGANISM: Homo sapiens

<400> SEQUENCE: 1671
aaacggagca ggucaaaacu cccgugcuga ucaguagugg ga 42

<210> SEQ ID NO 1672
<211> LENGTH: 40
<212> TYPE: RNA
<213> ORGANISM: Homo sapiens

<400> SEQUENCE: 1672
cuaagggcug ggucggucgg gcuggggcgc gaagcggggc 40

<210> SEQ ID NO 1673
<211> LENGTH: 50
<212> TYPE: RNA
<213> ORGANISM: Homo sapiens

<400> SEQUENCE: 1673
ugaacagcag uugaacaugg gucagucggu ccugagagau gggcgagcgc 50

<210> SEQ ID NO 1674
<211> LENGTH: 31
<212> TYPE: RNA
<213> ORGANISM: Homo sapiens

<400> SEQUENCE: 1674
gguuccggcg gcguccggug agcucucgcu g 31

<210> SEQ ID NO 1675
<211> LENGTH: 32
<212> TYPE: RNA
<213> ORGANISM: Homo sapiens

<400> SEQUENCE: 1675
ccgugaucgu auagugguua guacucugcg uu 32

<210> SEQ ID NO 1676
<211> LENGTH: 49
<212> TYPE: RNA
<213> ORGANISM: Homo sapiens

<400> SEQUENCE: 1676
aauuagugac gcgcaugaau ggaugaacga gauucccacu gucccuacc 49

<210> SEQ ID NO 1677
<211> LENGTH: 33
<212> TYPE: RNA
<213> ORGANISM: Homo sapiens

<400> SEQUENCE: 1677
ucccuggugg ucuaguggu aggauucgcc gcu 33

<210> SEQ ID NO 1678
<211> LENGTH: 31
<212> TYPE: RNA
<213> ORGANISM: Homo sapiens

<400> SEQUENCE: 1678
cggcuagcuc agucgguaga gcaugagacu c 31

<210> SEQ ID NO 1679
<211> LENGTH: 34
<212> TYPE: RNA
<213> ORGANISM: Homo sapiens

<400> SEQUENCE: 1679
gcauuggugg cucaguggua gaauucucgc cugc 34

<210> SEQ ID NO 1680
<211> LENGTH: 42
<212> TYPE: RNA
<213> ORGANISM: Homo sapiens

<400> SEQUENCE: 1680
auugaucauc gacacuucga acgcacuugc ggccccgggu ua 42

<210> SEQ ID NO 1681
<211> LENGTH: 34
<212> TYPE: RNA
<213> ORGANISM: Homo sapiens

<400> SEQUENCE: 1681
gcauuggugg uucaguggua gaauucuagc cugc 34

<210> SEQ ID NO 1682
<211> LENGTH: 39
<212> TYPE: RNA
<213> ORGANISM: Homo sapiens

<400> SEQUENCE: 1682
cuaagggcug ggucggucgg gcuggggcgc gaagcgggg 39

<210> SEQ ID NO 1683
<211> LENGTH: 46
<212> TYPE: RNA
<213> ORGANISM: Homo sapiens

<400> SEQUENCE: 1683
ccuagcagcc gacuuagaac uggugcggac caggggaauc cgacug 46

<210> SEQ ID NO 1684
<211> LENGTH: 50
<212> TYPE: RNA
<213> ORGANISM: Homo sapiens

<400> SEQUENCE: 1684
acccgggggg ccggcggcgg cggcgacucu ggacgcgagc cgggcccuuc                50

<210> SEQ ID NO 1685
<211> LENGTH: 33
<212> TYPE: RNA
<213> ORGANISM: Homo sapiens

<400> SEQUENCE: 1685
ucccuggugg ucuaguggau aggauucggc gcu                                  33

<210> SEQ ID NO 1686
<211> LENGTH: 35
<212> TYPE: RNA
<213> ORGANISM: Homo sapiens

<400> SEQUENCE: 1686
cuaauuagug acgcgcauga auggaugaac gagau                                35

<210> SEQ ID NO 1687
<211> LENGTH: 34
<212> TYPE: RNA
<213> ORGANISM: Homo sapiens

<400> SEQUENCE: 1687
gcauuggugg uucaguggua gaauucuugc cugc                                 34

<210> SEQ ID NO 1688
<211> LENGTH: 32
<212> TYPE: RNA
<213> ORGANISM: Homo sapiens

<400> SEQUENCE: 1688
aagggucggg gcggcagggg ccggcggcgg cc                                   32

<210> SEQ ID NO 1689
<211> LENGTH: 38
<212> TYPE: RNA
<213> ORGANISM: Homo sapiens

<400> SEQUENCE: 1689
cgcgggagac cgggguucga uuccccgacg gggagcca                             38

<210> SEQ ID NO 1690
<211> LENGTH: 38
<212> TYPE: RNA
<213> ORGANISM: Homo sapiens

<400> SEQUENCE: 1690
cacgcgggag accgggguuc gauuccccga cggggagc                             38

<210> SEQ ID NO 1691
<211> LENGTH: 37
<212> TYPE: RNA
<213> ORGANISM: Homo sapiens

<400> SEQUENCE: 1691
gcagaagguc cuggguucga gccccagugg aaccacc 37

<210> SEQ ID NO 1692
<211> LENGTH: 30
<212> TYPE: RNA
<213> ORGANISM: Homo sapiens

<400> SEQUENCE: 1692
agauuucaac uuaacuugac cgcucugacc 30

<210> SEQ ID NO 1693
<211> LENGTH: 43
<212> TYPE: RNA
<213> ORGANISM: Homo sapiens

<400> SEQUENCE: 1693
cuuacacuua ggagauuuca acuuaacuug accgcucuga cca 43

<210> SEQ ID NO 1694
<211> LENGTH: 32
<212> TYPE: RNA
<213> ORGANISM: Homo sapiens

<400> SEQUENCE: 1694
cccugguggu cuagugguua ggauucggcg cu 32

<210> SEQ ID NO 1695
<211> LENGTH: 48
<212> TYPE: RNA
<213> ORGANISM: Homo sapiens

<400> SEQUENCE: 1695
uugacucuag ucuggcacgg ugaagagaca ugagaggugu agaauaag 48

<210> SEQ ID NO 1696
<211> LENGTH: 48
<212> TYPE: RNA
<213> ORGANISM: Homo sapiens

<400> SEQUENCE: 1696
auucaaacga gaacuuugaa ggccgaagug gagaaggguu ccauguga 48

<210> SEQ ID NO 1697
<211> LENGTH: 38
<212> TYPE: RNA
<213> ORGANISM: Homo sapiens

<400> SEQUENCE: 1697
ucucccccgc uccccguccu ccccccuccc cgggggag 38

<210> SEQ ID NO 1698
<211> LENGTH: 46
<212> TYPE: RNA
<213> ORGANISM: Homo sapiens

<400> SEQUENCE: 1698
ccucgcugcg aucuauugaa agucagcccu cgacacaagg guuugu 46

<210> SEQ ID NO 1699
<211> LENGTH: 48
<212> TYPE: RNA
<213> ORGANISM: Homo sapiens

<400> SEQUENCE: 1699
agccaccgcc cguccccgcc ccuugccucu cggcgccccc ucgaugcu 48

<210> SEQ ID NO 1700
<211> LENGTH: 33
<212> TYPE: RNA
<213> ORGANISM: Homo sapiens

<400> SEQUENCE: 1700
gccguaaucg uauagugguu aguacucugc guu 33

<210> SEQ ID NO 1701
<211> LENGTH: 36
<212> TYPE: RNA
<213> ORGANISM: Homo sapiens

<400> SEQUENCE: 1701
cauugugaag cagaauucac caagcguugg auuguu 36

<210> SEQ ID NO 1702
<211> LENGTH: 29
<212> TYPE: RNA
<213> ORGANISM: Homo sapiens

<400> SEQUENCE: 1702
guuuccguag uguagugguu aucacauuc 29

<210> SEQ ID NO 1703
<211> LENGTH: 29
<212> TYPE: RNA
<213> ORGANISM: Homo sapiens

<400> SEQUENCE: 1703
ucggaugggg ugugauaggu ggcacggag 29

<210> SEQ ID NO 1704
<211> LENGTH: 33
<212> TYPE: RNA
<213> ORGANISM: Homo sapiens

<400> SEQUENCE: 1704
gcccgacuag cucagucggu agagcauggg acu 33

<210> SEQ ID NO 1705
<211> LENGTH: 50
<212> TYPE: RNA
<213> ORGANISM: Homo sapiens

<400> SEQUENCE: 1705
ucuuagcggu ggaucacucg gcucgugcgu cgaugaagaa cgcagcuagc 50

<210> SEQ ID NO 1706
<211> LENGTH: 44
<212> TYPE: RNA
<213> ORGANISM: Homo sapiens

<400> SEQUENCE: 1706
cugucacgcg ggagaccggg guucaauucc ccgacgggga gcca 44

<210> SEQ ID NO 1707
<211> LENGTH: 50
<212> TYPE: RNA
<213> ORGANISM: Homo sapiens

<400> SEQUENCE: 1707
cugcuugagg cucuggacug cauccuacca ccaacucguc caacugacaa 50

<210> SEQ ID NO 1708
<211> LENGTH: 49
<212> TYPE: RNA
<213> ORGANISM: Homo sapiens

<400> SEQUENCE: 1708
cguguggugu gcgucggagg gcggcggcgg cggcggcggc gggggugug 49

<210> SEQ ID NO 1709
<211> LENGTH: 50
<212> TYPE: RNA
<213> ORGANISM: Homo sapiens

<400> SEQUENCE: 1709
gcuuagcugu uaacuaagug uuugugggu uaagucccau uggucuagcc 50

<210> SEQ ID NO 1710
<211> LENGTH: 33
<212> TYPE: RNA
<213> ORGANISM: Homo sapiens

<400> SEQUENCE: 1710
gcccggcuaa cucagucggu agagcauggg acu 33

<210> SEQ ID NO 1711
<211> LENGTH: 49
<212> TYPE: RNA
<213> ORGANISM: Homo sapiens

<400> SEQUENCE: 1711
cgagaacuuu gaaggccgaa guggagaagg guuccaugug aacagcagu 49

<210> SEQ ID NO 1712
<211> LENGTH: 38
<212> TYPE: RNA
<213> ORGANISM: Homo sapiens

<400> SEQUENCE: 1712
cgagaacuuu gaaggccgaa guggagaagg guuccaug 38

<210> SEQ ID NO 1713
<211> LENGTH: 46
<212> TYPE: RNA
<213> ORGANISM: Homo sapiens

<400> SEQUENCE: 1713
augguuuuuc auaucauugg ucgugguugu aguccgugcg agaaua 46

<210> SEQ ID NO 1714
<211> LENGTH: 39
<212> TYPE: RNA
<213> ORGANISM: Homo sapiens

<400> SEQUENCE: 1714
cacgcaucga ccugguauug caguaccucc aggaacggu 39

<210> SEQ ID NO 1715
<211> LENGTH: 50
<212> TYPE: RNA
<213> ORGANISM: Homo sapiens

<400> SEQUENCE: 1715
gauaaccucg ggccgaucgc acgccccccg uggcggcgac gacccauucg 50

<210> SEQ ID NO 1716
<211> LENGTH: 26
<212> TYPE: RNA
<213> ORGANISM: Homo sapiens

<400> SEQUENCE: 1716 cuccccucgcu gcgaucuauu gaaagu 26

<210> SEQ ID NO 1717
<211> LENGTH: 37
<212> TYPE: RNA
<213> ORGANISM: Homo sapiens

<400> SEQUENCE: 1717
ccgaaagguu ggugguucgu gcccacccag ggacgcc 37

<210> SEQ ID NO 1718
<211> LENGTH: 48
<212> TYPE: RNA
<213> ORGANISM: Homo sapiens

<400> SEQUENCE: 1718
ccuuggaaag cgucgcgguu ccggcggcgu ccggugagcu cucgcugg 48

<210> SEQ ID NO 1719
<211> LENGTH: 33
<212> TYPE: RNA
<213> ORGANISM: Homo sapiens

<400> SEQUENCE: 1719
gcccgacuag cucagucggu agagcaugag acu 33

<210> SEQ ID NO 1720
<211> LENGTH: 27
<212> TYPE: RNA
<213> ORGANISM: Homo sapiens

<400> SEQUENCE: 1720
cccggcuagc ucagucggua gagcaug 27

<210> SEQ ID NO 1721
<211> LENGTH: 32
<212> TYPE: RNA
<213> ORGANISM: Homo sapiens

<400> SEQUENCE: 1721
gcaugggugg uucaguggua gaauucucgu cu 32

<210> SEQ ID NO 1722
<211> LENGTH: 32
<212> TYPE: RNA
<213> ORGANISM: Homo sapiens

<400> SEQUENCE: 1722
gcuuuggugg uucaguggua gaauucucgc cu 32

<210> SEQ ID NO 1723
<211> LENGTH: 28
<212> TYPE: RNA

<213> ORGANISM: Homo sapiens

<400> SEQUENCE: 1723
gcuagcucag ucgguagagc augagacu 28

<210> SEQ ID NO 1724
<211> LENGTH: 45
<212> TYPE: RNA
<213> ORGANISM: Homo sapiens

<400> SEQUENCE: 1724
gcuaaugaug gaaaaaucau uauuggaaaa gaaugacaug aacaa 45

<210> SEQ ID NO 1725
<211> LENGTH: 31
<212> TYPE: RNA
<213> ORGANISM: Homo sapiens

<400> SEQUENCE: 1725
ucccuggugg ucuagcgguu aggauucggc g 31

<210> SEQ ID NO 1726
<211> LENGTH: 50
<212> TYPE: RNA
<213> ORGANISM: Homo sapiens

<400> SEQUENCE: 1726
ugguccagga ugaaaccuaa uuugagugga cauccaugga ugagaaaugc 50

<210> SEQ ID NO 1727
<211> LENGTH: 30
<212> TYPE: RNA
<213> ORGANISM: Homo sapiens

<400> SEQUENCE: 1727
ucacuggugg ucuagugguu aggauucggc 30

<210> SEQ ID NO 1728
<211> LENGTH: 37
<212> TYPE: RNA
<213> ORGANISM: Homo sapiens

<400> SEQUENCE: 1728
cggugugagg ccgguagcgg cccccggcgc gccgggc 37

<210> SEQ ID NO 1729
<211> LENGTH: 33
<212> TYPE: RNA
<213> ORGANISM: Homo sapiens

<400> SEQUENCE: 1729
ucccuggugg ucuagugguu aggauucggc ucu 33

<210> SEQ ID NO 1730
<211> LENGTH: 50
<212> TYPE: RNA
<213> ORGANISM: Homo sapiens

<400> SEQUENCE: 1730
cauugaucau cgacacuucg aacgcacuug cggccacggg uuccucccgg 50

<210> SEQ ID NO 1731
<211> LENGTH: 30

<212> TYPE: RNA
<213> ORGANISM: Homo sapiens

<400> SEQUENCE: 1731
aguaagguca gcuaaauaag cuaucggccc 30

<210> SEQ ID NO 1732
<211> LENGTH: 33
<212> TYPE: RNA
<213> ORGANISM: Homo sapiens

<400> SEQUENCE: 1732
ucccuggugg ucuagugguu aggauucggc guu 33

<210> SEQ ID NO 1733
<211> LENGTH: 45
<212> TYPE: RNA
<213> ORGANISM: Homo sapiens

<400> SEQUENCE: 1733
uuaugguucc uuuggucgcu cgcuccucuc cuacuuggau aacug 45

<210> SEQ ID NO 1734
<211> LENGTH: 42
<212> TYPE: RNA
<213> ORGANISM: Homo sapiens

<400> SEQUENCE: 1734
gggucggagu uagcucaagc gguuaccucc ucaugccgga cu 42

<210> SEQ ID NO 1735
<211> LENGTH: 33
<212> TYPE: RNA
<213> ORGANISM: Homo sapiens

<400> SEQUENCE: 1735
guuuccguag uguagugguu aucaaguucg ccu 33

<210> SEQ ID NO 1736
<211> LENGTH: 50
<212> TYPE: RNA
<213> ORGANISM: Homo sapiens

<400> SEQUENCE: 1736
agucuggcac ggugaagaga caugagaggu guagaauaag ugggaggccc 50

<210> SEQ ID NO 1737
<211> LENGTH: 46
<212> TYPE: RNA
<213> ORGANISM: Homo sapiens

<400> SEQUENCE: 1737
aaaagaacuu ugaagagaga guucaagagg gcgugaaacc guuaag 46

<210> SEQ ID NO 1738
<211> LENGTH: 40
<212> TYPE: RNA
<213> ORGANISM: Homo sapiens

<400> SEQUENCE: 1738
cuuucaccgc cgcggcccgg guucguuucc cggucaggga 40

<210> SEQ ID NO 1739

<211> LENGTH: 35
<212> TYPE: RNA
<213> ORGANISM: Homo sapiens

<400> SEQUENCE: 1739
ucccacaugg ucuagcgguu aggauuccug guuuu 35

<210> SEQ ID NO 1740
<211> LENGTH: 39
<212> TYPE: RNA
<213> ORGANISM: Homo sapiens

<400> SEQUENCE: 1740
cgacucuuag cgguggauca cucggcucgu gcgucgaug 39

<210> SEQ ID NO 1741
<211> LENGTH: 31
<212> TYPE: RNA
<213> ORGANISM: Homo sapiens

<400> SEQUENCE: 1741
uuuaaguuaa agauuaagag aaccaacacc u 31

<210> SEQ ID NO 1742
<211> LENGTH: 31
<212> TYPE: RNA
<213> ORGANISM: Homo sapiens

<400> SEQUENCE: 1742
uagugacgaa aaauaacaau acaggacucu u 31

<210> SEQ ID NO 1743
<211> LENGTH: 33
<212> TYPE: RNA
<213> ORGANISM: Homo sapiens

<400> SEQUENCE: 1743
ucccuggugg ucuagugguu aggauucguc gcu 33

<210> SEQ ID NO 1744
<211> LENGTH: 45
<212> TYPE: RNA
<213> ORGANISM: Homo sapiens

<400> SEQUENCE: 1744
acuuuuaauc ugagggucca ggguucaugu cccuguucgg gcgcc 45

<210> SEQ ID NO 1745
<211> LENGTH: 40
<212> TYPE: RNA
<213> ORGANISM: Homo sapiens

<400> SEQUENCE: 1745
cgagaacuuu gaaggccgaa guggagaagg guuccaugug 40

<210> SEQ ID NO 1746
<211> LENGTH: 34
<212> TYPE: RNA
<213> ORGANISM: Homo sapiens

<400> SEQUENCE: 1746
gccugggugg uucaguggua gaauucucgc cugc 34

<210> SEQ ID NO 1747
<211> LENGTH: 35
<212> TYPE: RNA
<213> ORGANISM: Homo sapiens

<400> SEQUENCE: 1747
ccguugcccu cggccgaucg aaagggaguc ggguu 35

<210> SEQ ID NO 1748
<211> LENGTH: 32
<212> TYPE: RNA
<213> ORGANISM: Homo sapiens

<400> SEQUENCE: 1748
gcauuggugg uucaguggua gaauucacgc cu 32

<210> SEQ ID NO 1749
<211> LENGTH: 50
<212> TYPE: RNA
<213> ORGANISM: Homo sapiens

<400> SEQUENCE: 1749
cuuggauaac ugugguaauu cuagagcuaa uacaugccga cgggcgcuga 50

<210> SEQ ID NO 1750
<211> LENGTH: 48
<212> TYPE: RNA
<213> ORGANISM: Homo sapiens

<400> SEQUENCE: 1750
ccuagcagcc gacuuagaac uggugcggac caggggaauc cgacuguu 48

<210> SEQ ID NO 1751
<211> LENGTH: 50
<212> TYPE: RNA
<213> ORGANISM: Homo sapiens

<400> SEQUENCE: 1751
ucaguagugg gaucgcgccu gugaauagcc acugcacucc agccugggca 50

<210> SEQ ID NO 1752
<211> LENGTH: 32
<212> TYPE: RNA
<213> ORGANISM: Homo sapiens

<400> SEQUENCE: 1752
gcauuggucg uucaguggua gaauucucgc cu 32

<210> SEQ ID NO 1753
<211> LENGTH: 49
<212> TYPE: RNA
<213> ORGANISM: Homo sapiens

<400> SEQUENCE: 1753
cgaguucgag gccagccugg uccacauggg ucggaaaaaa ggauuuuuu 49

<210> SEQ ID NO 1754
<211> LENGTH: 49
<212> TYPE: RNA
<213> ORGANISM: Homo sapiens

<400> SEQUENCE: 1754
gauaacugug guaauucuag agcuaauaca ugccgacggg cgcugaccc 49

<210> SEQ ID NO 1755
<211> LENGTH: 47
<212> TYPE: RNA
<213> ORGANISM: Homo sapiens

<400> SEQUENCE: 1755
aguuaugguu ccuuuggucg cucgcuccuc uccuacuugg auaacug 47

<210> SEQ ID NO 1756
<211> LENGTH: 26
<212> TYPE: RNA
<213> ORGANISM: Homo sapiens

<400> SEQUENCE: 1756
ccgugaucgu auagugguua guacuc 26

<210> SEQ ID NO 1757
<211> LENGTH: 35
<212> TYPE: RNA
<213> ORGANISM: Homo sapiens

<400> SEQUENCE: 1757
gcauuggugg uucaguggua gaauucucgc cugca 35

<210> SEQ ID NO 1758
<211> LENGTH: 31
<212> TYPE: RNA
<213> ORGANISM: Homo sapiens

<400> SEQUENCE: 1758
cucucucucu cucuccccccg cuccccgucc u 31

<210> SEQ ID NO 1759
<211> LENGTH: 36
<212> TYPE: RNA
<213> ORGANISM: Homo sapiens

<400> SEQUENCE: 1759
cagaagauug aggguucgag ucccuucgug gucgcc 36

<210> SEQ ID NO 1760
<211> LENGTH: 33
<212> TYPE: RNA
<213> ORGANISM: Homo sapiens

<400> SEQUENCE: 1760
ucccuggugg ucuagugguu aggcuucggc gcu 33

<210> SEQ ID NO 1761
<211> LENGTH: 37
<212> TYPE: RNA
<213> ORGANISM: Homo sapiens

<400> SEQUENCE: 1761
cuaagggcug ggucggucgg gcuggggcgc gaagcgg 37

<210> SEQ ID NO 1762
<211> LENGTH: 34
<212> TYPE: RNA
<213> ORGANISM: Homo sapiens

<400> SEQUENCE: 1762
gcauuggugg uucaguggua gaauucccgc cugc 34

<210> SEQ ID NO 1763
<211> LENGTH: 32
<212> TYPE: RNA
<213> ORGANISM: Homo sapiens

<400> SEQUENCE: 1763
gcaugggggg uucaguggua gaauucucgc cu 32

<210> SEQ ID NO 1764
<211> LENGTH: 34
<212> TYPE: RNA
<213> ORGANISM: Homo sapiens

<400> SEQUENCE: 1764
gcccggcuag cucagucggu agagcaugag acug 34

<210> SEQ ID NO 1765
<211> LENGTH: 32
<212> TYPE: RNA
<213> ORGANISM: Homo sapiens

<400> SEQUENCE: 1765
gcaugggugg uucaguggua gaauccucgc cu 32

<210> SEQ ID NO 1766
<211> LENGTH: 38
<212> TYPE: RNA
<213> ORGANISM: Homo sapiens

<400> SEQUENCE: 1766
auugaucauc gacacuucga acgcacuugc ggccccgg 38

<210> SEQ ID NO 1767
<211> LENGTH: 30
<212> TYPE: RNA
<213> ORGANISM: Homo sapiens

<400> SEQUENCE: 1767
uaggaugggg ugugauaggu ggcacggcga 30

<210> SEQ ID NO 1768
<211> LENGTH: 42
<212> TYPE: RNA
<213> ORGANISM: Homo sapiens

<400> SEQUENCE: 1768
ccaagcguug gauuguucac ccacuaauag ggaacgugag cu 42

<210> SEQ ID NO 1769
<211> LENGTH: 33
<212> TYPE: RNA
<213> ORGANISM: Homo sapiens

<400> SEQUENCE: 1769
ucccuggugg ucuaguaguu aggauucggc gcu 33

<210> SEQ ID NO 1770
<211> LENGTH: 32
<212> TYPE: RNA
<213> ORGANISM: Homo sapiens

<400> SEQUENCE: 1770
gcauugguug uucaguggua gaauucucgc cu 32

<210> SEQ ID NO 1771
<211> LENGTH: 33
<212> TYPE: RNA
<213> ORGANISM: Homo sapiens

<400> SEQUENCE: 1771
cgagaacuuu gaaggccgaa guggagaagg guu 33

<210> SEQ ID NO 1772
<211> LENGTH: 34
<212> TYPE: RNA
<213> ORGANISM: Homo sapiens

<400> SEQUENCE: 1772
gacccagugg ccuaauggau aaggcaucag ccuc 34

<210> SEQ ID NO 1773
<211> LENGTH: 34
<212> TYPE: RNA
<213> ORGANISM: Homo sapiens

<400> SEQUENCE: 1773
acgagaacuu ugaaggccga aguggagaag gguu 34

<210> SEQ ID NO 1774
<211> LENGTH: 32
<212> TYPE: RNA
<213> ORGANISM: Homo sapiens

<400> SEQUENCE: 1774
gcaugggugg uccaguggua gaauucucgc cu 32

<210> SEQ ID NO 1775
<211> LENGTH: 28
<212> TYPE: RNA
<213> ORGANISM: Homo sapiens

<400> SEQUENCE: 1775
ccccuguggu cuagugguua ggauucgg 28

<210> SEQ ID NO 1776
<211> LENGTH: 37
<212> TYPE: RNA
<213> ORGANISM: Homo sapiens

<400> SEQUENCE: 1776
ccgaaagguu ggugguucgg gcccacccag ggacgcc 37

<210> SEQ ID NO 1777
<211> LENGTH: 50
<212> TYPE: RNA
<213> ORGANISM: Homo sapiens

<400> SEQUENCE: 1777
agaaauaugu cugauaaaag aguuacuuug auagaguaaa uaauaggagc 50

<210> SEQ ID NO 1778
<211> LENGTH: 34
<212> TYPE: RNA
<213> ORGANISM: Homo sapiens

<400> SEQUENCE: 1778
gucuacggcc auaccacccu gaacgcgccc gauc         34

<210> SEQ ID NO 1779
<211> LENGTH: 49
<212> TYPE: RNA
<213> ORGANISM: Homo sapiens

<400> SEQUENCE: 1779
acagcaguug aacauggguc agucgguccu gagagauggg cgagcgccg         49

<210> SEQ ID NO 1780
<211> LENGTH: 29
<212> TYPE: RNA
<213> ORGANISM: Homo sapiens

<400> SEQUENCE: 1780
cuacuuggau aacuguggua auucuagag         29

<210> SEQ ID NO 1781
<211> LENGTH: 27
<212> TYPE: RNA
<213> ORGANISM: Homo sapiens

<400> SEQUENCE: 1781
ccucggaucg gccccgccgg ggucggc         27

<210> SEQ ID NO 1782
<211> LENGTH: 26
<212> TYPE: RNA
<213> ORGANISM: Homo sapiens

<400> SEQUENCE: 1782
cggcgcgcgg cggcggcggc ggcggc         26

<210> SEQ ID NO 1783
<211> LENGTH: 33
<212> TYPE: RNA
<213> ORGANISM: Homo sapiens

<400> SEQUENCE: 1783
guuuccguag uguagugguu auaacguucg ccu         33

<210> SEQ ID NO 1784
<211> LENGTH: 34
<212> TYPE: RNA
<213> ORGANISM: Homo sapiens

<400> SEQUENCE: 1784
cugggucggg guuucguacg uagcagagca gcuc         34

<210> SEQ ID NO 1785
<211> LENGTH: 46
<212> TYPE: RNA
<213> ORGANISM: Homo sapiens

<400> SEQUENCE: 1785
uucagaugau gaauuuaacu guucaacugc ugaaugauaa cgggca         46

<210> SEQ ID NO 1786
<211> LENGTH: 32
<212> TYPE: RNA
<213> ORGANISM: Homo sapiens

<400> SEQUENCE: 1786
gcauuggugg uucugugguu gaauucucgc cu 32

<210> SEQ ID NO 1787
<211> LENGTH: 30
<212> TYPE: RNA
<213> ORGANISM: Homo sapiens

<400> SEQUENCE: 1787
ugccgugauc gcauaguggu uaguacucug 30

<210> SEQ ID NO 1788
<211> LENGTH: 31
<212> TYPE: RNA
<213> ORGANISM: Homo sapiens

<400> SEQUENCE: 1788
gcaugguggu ucagugguag aauucucgcc u 31

<210> SEQ ID NO 1789
<211> LENGTH: 50
<212> TYPE: RNA
<213> ORGANISM: Homo sapiens

<400> SEQUENCE: 1789
gccgaauccc cgccccgcgg cggggcgcgg gacauguggc guacggaaga 50

<210> SEQ ID NO 1790
<211> LENGTH: 33
<212> TYPE: RNA
<213> ORGANISM: Homo sapiens

<400> SEQUENCE: 1790
guuuccgucg uguaguggu aucacguucg ccu 33

<210> SEQ ID NO 1791
<211> LENGTH: 32
<212> TYPE: RNA
<213> ORGANISM: Homo sapiens

<400> SEQUENCE: 1791
ggccgugauc guauaguggu uaguacucug ug 32

<210> SEQ ID NO 1792
<211> LENGTH: 42
<212> TYPE: RNA
<213> ORGANISM: Homo sapiens

<400> SEQUENCE: 1792
cagugcgccc cgggcggguc gcgccgucgg gcccggggga gg 42

<210> SEQ ID NO 1793
<211> LENGTH: 42
<212> TYPE: RNA
<213> ORGANISM: Homo sapiens

<400> SEQUENCE: 1793
ugugaaucug acaacagagg cuuacgaccc cuuauuuacc cc 42

<210> SEQ ID NO 1794
<211> LENGTH: 35
<212> TYPE: RNA
<213> ORGANISM: Homo sapiens

<400> SEQUENCE: 1794
uacagaacau gaucaagggu guuacacugg gcuuc 35

<210> SEQ ID NO 1795
<211> LENGTH: 40
<212> TYPE: RNA
<213> ORGANISM: Homo sapiens

<400> SEQUENCE: 1795
ccugccacgc gggaggcccg gguucguuuc ccggcccaug 40

<210> SEQ ID NO 1796
<211> LENGTH: 34
<212> TYPE: RNA
<213> ORGANISM: Homo sapiens

<400> SEQUENCE: 1796
gcaugggugg uucaguggua gaauucucgc cucc 34

<210> SEQ ID NO 1797
<211> LENGTH: 50
<212> TYPE: RNA
<213> ORGANISM: Homo sapiens

<400> SEQUENCE: 1797
aguaaugcug aacuuaaggg uuuagaugua gauucucugg ucauugagca 50

<210> SEQ ID NO 1798
<211> LENGTH: 35
<212> TYPE: RNA
<213> ORGANISM: Homo sapiens

<400> SEQUENCE: 1798
gugugaggcc gguagcggcc cccggcgcgc cgggc 35

<210> SEQ ID NO 1799
<211> LENGTH: 27
<212> TYPE: RNA
<213> ORGANISM: Homo sapiens

<400> SEQUENCE: 1799
agccgugauc guauaguggu uaguacu 27

<210> SEQ ID NO 1800
<211> LENGTH: 33
<212> TYPE: RNA
<213> ORGANISM: Homo sapiens

<400> SEQUENCE: 1800
ucccuggugg ucuagugguu aggaaucggc gcu 33

<210> SEQ ID NO 1801
<211> LENGTH: 43
<212> TYPE: RNA
<213> ORGANISM: Homo sapiens

<400> SEQUENCE: 1801
aacgagaacu uugaaggccg aaguggagaa ggguuccaug uga 43

<210> SEQ ID NO 1802
<211> LENGTH: 34
<212> TYPE: RNA

<213> ORGANISM: Homo sapiens

<400> SEQUENCE: 1802
gcaugagugg uucaguggua gaauucucgc cugc 34

<210> SEQ ID NO 1803
<211> LENGTH: 32
<212> TYPE: RNA
<213> ORGANISM: Homo sapiens

<400> SEQUENCE: 1803
guuugugggu uuaaguccca uuggucuagc ca 32

<210> SEQ ID NO 1804
<211> LENGTH: 31
<212> TYPE: RNA
<213> ORGANISM: Homo sapiens

<400> SEQUENCE: 1804
aaaucaguua ugguuccuuu ggucgcucgc u 31

<210> SEQ ID NO 1805
<211> LENGTH: 33
<212> TYPE: RNA
<213> ORGANISM: Homo sapiens

<400> SEQUENCE: 1805
gcguuggugg uauaguggug agcauagcug ccu 33

<210> SEQ ID NO 1806
<211> LENGTH: 33
<212> TYPE: RNA
<213> ORGANISM: Homo sapiens

<400> SEQUENCE: 1806
cuagagcuaa uacaugccga cgggcgcuga ccc 33

<210> SEQ ID NO 1807
<211> LENGTH: 33
<212> TYPE: RNA
<213> ORGANISM: Homo sapiens

<400> SEQUENCE: 1807
ugccgugauc guauaguggu uaguacucug cgu 33

<210> SEQ ID NO 1808
<211> LENGTH: 38
<212> TYPE: RNA
<213> ORGANISM: Homo sapiens

<400> SEQUENCE: 1808
auuaaucaag aacgaaaguc ggagguucga agacgauc 38

<210> SEQ ID NO 1809
<211> LENGTH: 50
<212> TYPE: RNA
<213> ORGANISM: Homo sapiens

<400> SEQUENCE: 1809
ucagaugaug aauuuaacug uucaacugcu gaaugauaac gggcaugaac 50

<210> SEQ ID NO 1810
<211> LENGTH: 50

```
<212> TYPE: RNA
<213> ORGANISM: Homo sapiens

<400> SEQUENCE: 1810

auacguccuc uauccgagga caauauauua aauggauuuu uggagcaggg        50

<210> SEQ ID NO 1811
<211> LENGTH: 29
<212> TYPE: RNA
<213> ORGANISM: Homo sapiens

<400> SEQUENCE: 1811

caagcguugg auuguucacc cacuaauag                               29

<210> SEQ ID NO 1812
<211> LENGTH: 36
<212> TYPE: RNA
<213> ORGANISM: Homo sapiens

<400> SEQUENCE: 1812

uccucguuag uauaguggug aguauccccg ccuguc                       36

<210> SEQ ID NO 1813
<211> LENGTH: 29
<212> TYPE: RNA
<213> ORGANISM: Homo sapiens

<400> SEQUENCE: 1813

gcgccgcugg uguaguggua ucaugcaag                               29

<210> SEQ ID NO 1814
<211> LENGTH: 34
<212> TYPE: RNA
<213> ORGANISM: Homo sapiens

<400> SEQUENCE: 1814

ggccgugauc gcauaguggu uaguacucug cguu                         34

<210> SEQ ID NO 1815
<211> LENGTH: 50
<212> TYPE: RNA
<213> ORGANISM: Homo sapiens

<400> SEQUENCE: 1815

cauugaucau cgacacuucg aacgcacuug cggccccggg cuccucccgg        50

<210> SEQ ID NO 1816
<211> LENGTH: 45
<212> TYPE: RNA
<213> ORGANISM: Homo sapiens

<400> SEQUENCE: 1816

acuuuuaauc ugagggucca ggguucaggu cccuguucgg gcgcc             45

<210> SEQ ID NO 1817
<211> LENGTH: 45
<212> TYPE: RNA
<213> ORGANISM: Homo sapiens

<400> SEQUENCE: 1817

auucaaacga gaacuuugaa ggccgaagug gagaaggguu ccaug             45

<210> SEQ ID NO 1818
```

<211> LENGTH: 37
<212> TYPE: RNA
<213> ORGANISM: Homo sapiens

<400> SEQUENCE: 1818
ccgaaagguu ggugguucga gcccacccag ggacgcc 37

<210> SEQ ID NO 1819
<211> LENGTH: 50
<212> TYPE: RNA
<213> ORGANISM: Homo sapiens

<400> SEQUENCE: 1819
cuuaaugaug acuguuuuuu uugauugcuu gaagcaaugu gaaaaacaca 50

<210> SEQ ID NO 1820
<211> LENGTH: 32
<212> TYPE: RNA
<213> ORGANISM: Homo sapiens

<400> SEQUENCE: 1820
gcaugggugg uuccguggua gaauucucgc cu 32

<210> SEQ ID NO 1821
<211> LENGTH: 43
<212> TYPE: RNA
<213> ORGANISM: Homo sapiens

<400> SEQUENCE: 1821
cagugcgccc cgggcggguc gcgccgucgg gcccggggga ggu 43

<210> SEQ ID NO 1822
<211> LENGTH: 35
<212> TYPE: RNA
<213> ORGANISM: Homo sapiens

<400> SEQUENCE: 1822
cgcgaccuca gaucagacgu ggcgacccgc ugaaa 35

<210> SEQ ID NO 1823
<211> LENGTH: 33
<212> TYPE: RNA
<213> ORGANISM: Homo sapiens

<400> SEQUENCE: 1823
uccccugugg ucuaguggcu aggauucggc gcu 33

<210> SEQ ID NO 1824
<211> LENGTH: 44
<212> TYPE: RNA
<213> ORGANISM: Homo sapiens

<400> SEQUENCE: 1824
gacucugaau ccagcgaucc gaguucgagu cucgguggaa ccuc 44

<210> SEQ ID NO 1825
<211> LENGTH: 33
<212> TYPE: RNA
<213> ORGANISM: Homo sapiens

<400> SEQUENCE: 1825
gcuucuguag uguagugguu aucacguucg ccg 33

```
<210> SEQ ID NO 1826
<211> LENGTH: 32
<212> TYPE: RNA
<213> ORGANISM: Homo sapiens

<400> SEQUENCE: 1826

gcauuggugg uucagucgua gaauucucgc cu                                    32

<210> SEQ ID NO 1827
<211> LENGTH: 50
<212> TYPE: RNA
<213> ORGANISM: Homo sapiens

<400> SEQUENCE: 1827

agggucgggc cugguuagua cuuggauggg agaccgccug ggaauaccgg                 50

<210> SEQ ID NO 1828
<211> LENGTH: 31
<212> TYPE: RNA
<213> ORGANISM: Homo sapiens

<400> SEQUENCE: 1828

ccaagcguug gauuguucac ccacucauag g                                     31

<210> SEQ ID NO 1829
<211> LENGTH: 41
<212> TYPE: RNA
<213> ORGANISM: Homo sapiens

<400> SEQUENCE: 1829

ggcugguccg augguagugg guuaucagaa cuuauuaaca u                          41

<210> SEQ ID NO 1830
<211> LENGTH: 32
<212> TYPE: RNA
<213> ORGANISM: Homo sapiens

<400> SEQUENCE: 1830

gcaugcgugg uucaguggua gaauucucgc cu                                    32

<210> SEQ ID NO 1831
<211> LENGTH: 46
<212> TYPE: RNA
<213> ORGANISM: Homo sapiens

<400> SEQUENCE: 1831

cucgcugcga ucuauugaaa gucagcccuc gacacaaggg uuuguc                     46

<210> SEQ ID NO 1832
<211> LENGTH: 46
<212> TYPE: RNA
<213> ORGANISM: Homo sapiens

<400> SEQUENCE: 1832

auagggcgga gggaagcuca ucaguggggc cacgagcuga gugcgu                     46

<210> SEQ ID NO 1833
<211> LENGTH: 32
<212> TYPE: RNA
<213> ORGANISM: Homo sapiens

<400> SEQUENCE: 1833

ggccgucauc guauaguggu uaguacucug cg                                    32
```

<210> SEQ ID NO 1834
<211> LENGTH: 34
<212> TYPE: RNA
<213> ORGANISM: Homo sapiens

<400> SEQUENCE: 1834
gcauuggugg uuccguggua gaauucucgc cugc 34

<210> SEQ ID NO 1835
<211> LENGTH: 50
<212> TYPE: RNA
<213> ORGANISM: Homo sapiens

<400> SEQUENCE: 1835
uacaacgaug guuuuucaua ucauuggucg ugguuguagu ccgugcgaga 50

<210> SEQ ID NO 1836
<211> LENGTH: 43
<212> TYPE: RNA
<213> ORGANISM: Homo sapiens

<400> SEQUENCE: 1836 augguucuu uggucgcucg cuccucuccu acuuggauaa cug 43

<210> SEQ ID NO 1837
<211> LENGTH: 30
<212> TYPE: RNA
<213> ORGANISM: Homo sapiens

<400> SEQUENCE: 1837
ucccuggugg ucucgugguu aggauucggc 30

<210> SEQ ID NO 1838
<211> LENGTH: 29
<212> TYPE: RNA
<213> ORGANISM: Homo sapiens

<400> SEQUENCE: 1838
ccccuguggu cuaguggcua ggauucggc 29

<210> SEQ ID NO 1839
<211> LENGTH: 30
<212> TYPE: RNA
<213> ORGANISM: Homo sapiens

<400> SEQUENCE: 1839
cccugguggu cuagugguua ggauucggcg 30

<210> SEQ ID NO 1840
<211> LENGTH: 32
<212> TYPE: RNA
<213> ORGANISM: Homo sapiens

<400> SEQUENCE: 1840
gcaucggugg uucaguggua gaauucucgc cu 32

<210> SEQ ID NO 1841
<211> LENGTH: 50
<212> TYPE: RNA
<213> ORGANISM: Homo sapiens

<400> SEQUENCE: 1841
aacagcaguu gaacaugggu cagucggucc ugagagaugg gcgagcgccg 50

<210> SEQ ID NO 1842
<211> LENGTH: 33
<212> TYPE: RNA
<213> ORGANISM: Homo sapiens

<400> SEQUENCE: 1842
uaccuggugg ucuagugguu aggauucggc gcu 33

<210> SEQ ID NO 1843
<211> LENGTH: 45
<212> TYPE: RNA
<213> ORGANISM: Homo sapiens

<400> SEQUENCE: 1843
ccaagcguug gauuguucac ccacuaauag ggaacgugag cuggg 45

<210> SEQ ID NO 1844
<211> LENGTH: 33
<212> TYPE: RNA
<213> ORGANISM: Homo sapiens

<400> SEQUENCE: 1844
uagauugagg ccaguugauu agggugcuua gcu 33

<210> SEQ ID NO 1845
<211> LENGTH: 37
<212> TYPE: RNA
<213> ORGANISM: Homo sapiens

<400> SEQUENCE: 1845
ugccgugauc guauaguggu uaguacucug cguugua 37

<210> SEQ ID NO 1846
<211> LENGTH: 41
<212> TYPE: RNA
<213> ORGANISM: Homo sapiens

<400> SEQUENCE: 1846
acauugauca ucgacacuuc gaacgcacuu gcggccccgg g 41

<210> SEQ ID NO 1847
<211> LENGTH: 48
<212> TYPE: RNA
<213> ORGANISM: Homo sapiens

<400> SEQUENCE: 1847
cuucgaacgc acuugcggcc ccggguuccu cccggggcua cgccuguc 48

<210> SEQ ID NO 1848
<211> LENGTH: 44
<212> TYPE: RNA
<213> ORGANISM: Homo sapiens

<400> SEQUENCE: 1848
ucugauacgu ccucuauccg aggacaauau auuaaaugga uuuu 44

<210> SEQ ID NO 1849
<211> LENGTH: 38
<212> TYPE: RNA
<213> ORGANISM: Homo sapiens

<400> SEQUENCE: 1849
ucugaagguc gugaguucga gccucacacg gggcacca 38

<210> SEQ ID NO 1850
<211> LENGTH: 34
<212> TYPE: RNA
<213> ORGANISM: Homo sapiens

<400> SEQUENCE: 1850
auuucauaac uuugucaaag uuaaauuaua ggcu 34

<210> SEQ ID NO 1851
<211> LENGTH: 29
<212> TYPE: RNA
<213> ORGANISM: Homo sapiens

<400> SEQUENCE: 1851
uaggaugggg ugcgauaggu ggcacggag 29

<210> SEQ ID NO 1852
<211> LENGTH: 34
<212> TYPE: RNA
<213> ORGANISM: Homo sapiens

<400> SEQUENCE: 1852
ccaagcguug gauuguucac ccacuaauag ggaa 34

<210> SEQ ID NO 1853
<211> LENGTH: 43
<212> TYPE: RNA
<213> ORGANISM: Homo sapiens

<400> SEQUENCE: 1853
aaacgagaac uuugaaggcc gaaguggaga aggguuccau gug 43

<210> SEQ ID NO 1854
<211> LENGTH: 34
<212> TYPE: RNA
<213> ORGANISM: Homo sapiens

<400> SEQUENCE: 1854
ucccuguggu cuaguggcua ggauucggcg cuuu 34

<210> SEQ ID NO 1855
<211> LENGTH: 32
<212> TYPE: RNA
<213> ORGANISM: Homo sapiens

<400> SEQUENCE: 1855
gcaugggugg uucaguggua gaauucuccc cu 32

<210> SEQ ID NO 1856
<211> LENGTH: 50
<212> TYPE: RNA
<213> ORGANISM: Homo sapiens

<400> SEQUENCE: 1856
cgaacgagac ucuggcaugc uaacuaguua cgcgaccccc gagcggucgg 50

<210> SEQ ID NO 1857
<211> LENGTH: 32
<212> TYPE: RNA
<213> ORGANISM: Homo sapiens

<400> SEQUENCE: 1857
uagugacgaa aaauaacaau acaggacucu uu 32

<210> SEQ ID NO 1858
<211> LENGTH: 40
<212> TYPE: RNA
<213> ORGANISM: Homo sapiens

<400> SEQUENCE: 1858
cugauaacgc caaggucgcg gguucguucc ccguacgggc 40

<210> SEQ ID NO 1859
<211> LENGTH: 33
<212> TYPE: RNA
<213> ORGANISM: Homo sapiens

<400> SEQUENCE: 1859
gcccggcuaa cucagucggu agagcaugag acu 33

<210> SEQ ID NO 1860
<211> LENGTH: 32
<212> TYPE: RNA
<213> ORGANISM: Homo sapiens

<400> SEQUENCE: 1860
aauauauuaa auggauuuuu ggagcaggga ga 32

<210> SEQ ID NO 1861
<211> LENGTH: 44
<212> TYPE: RNA
<213> ORGANISM: Homo sapiens

<400> SEQUENCE: 1861
caaguguagu aucuguucuu aucaguuuaa uaucugauac gucc 44

<210> SEQ ID NO 1862
<211> LENGTH: 32
<212> TYPE: RNA
<213> ORGANISM: Homo sapiens

<400> SEQUENCE: 1862
gcauuggugg uucaguagua gaauucucgc cu 32

<210> SEQ ID NO 1863
<211> LENGTH: 34
<212> TYPE: RNA
<213> ORGANISM: Homo sapiens

<400> SEQUENCE: 1863
uaauuaguga cgcgcaugaa uggaugaacg agau 34

<210> SEQ ID NO 1864
<211> LENGTH: 27
<212> TYPE: RNA
<213> ORGANISM: Homo sapiens

<400> SEQUENCE: 1864
ccaagcguug gauuguucac ccacuaa 27

<210> SEQ ID NO 1865
<211> LENGTH: 47
<212> TYPE: RNA
<213> ORGANISM: Homo sapiens

<400> SEQUENCE: 1865
auucaaacga gaacuuugaa ggccgaagug gagaaggguu ccaugug 47

<210> SEQ ID NO 1866
<211> LENGTH: 33
<212> TYPE: RNA
<213> ORGANISM: Homo sapiens

<400> SEQUENCE: 1866
guuuccguag uguagugguu aucacguccg ccu 33

<210> SEQ ID NO 1867
<211> LENGTH: 50
<212> TYPE: RNA
<213> ORGANISM: Homo sapiens

<400> SEQUENCE: 1867
gugaaaugau ggcaaucauc uuucgggacu gaccugaaau gaagagaaua 50

<210> SEQ ID NO 1868
<211> LENGTH: 50
<212> TYPE: RNA
<213> ORGANISM: Homo sapiens

<400> SEQUENCE: 1868
cgccuuuuac uaaagauuuc cguggagagg aacaacucug agucuuaacc 50

<210> SEQ ID NO 1869
<211> LENGTH: 29
<212> TYPE: RNA
<213> ORGANISM: Homo sapiens

<400> SEQUENCE: 1869
uaggaugggg ugugauaggc ggcacggag 29

<210> SEQ ID NO 1870
<211> LENGTH: 38
<212> TYPE: RNA
<213> ORGANISM: Homo sapiens

<400> SEQUENCE: 1870
ccgaaagguu ggugguucga gcccacccag ggacgcca 38

<210> SEQ ID NO 1871
<211> LENGTH: 36
<212> TYPE: RNA
<213> ORGANISM: Homo sapiens

<400> SEQUENCE: 1871
gccgugaucg uauagugguu aguacucugc guugua 36

<210> SEQ ID NO 1872
<211> LENGTH: 27
<212> TYPE: RNA
<213> ORGANISM: Homo sapiens

<400> SEQUENCE: 1872
cgagaacuuu gaaggccgaa guggaga 27

<210> SEQ ID NO 1873
<211> LENGTH: 31
<212> TYPE: RNA
<213> ORGANISM: Homo sapiens

<400> SEQUENCE: 1873
cggcggcguc cggugagcuc ucgcuggccc u                                  31

<210> SEQ ID NO 1874
<211> LENGTH: 50
<212> TYPE: RNA
<213> ORGANISM: Homo sapiens

<400> SEQUENCE: 1874
auugaucauc gacacuucga acgcacuugc ggccacgggu uccucccggg              50

<210> SEQ ID NO 1875
<211> LENGTH: 36
<212> TYPE: RNA
<213> ORGANISM: Homo sapiens

<400> SEQUENCE: 1875
agugacgcgc augaauggau gaacgagauu cccaca                             36

<210> SEQ ID NO 1876
<211> LENGTH: 40
<212> TYPE: RNA
<213> ORGANISM: Homo sapiens

<400> SEQUENCE: 1876
auugugaagc agaauucacc aagcguugga uuguucaccc                         40

<210> SEQ ID NO 1877
<211> LENGTH: 26
<212> TYPE: RNA
<213> ORGANISM: Homo sapiens

<400> SEQUENCE: 1877
cuuuuugauc cuucgauguc ggcucu                                        26

<210> SEQ ID NO 1878
<211> LENGTH: 49
<212> TYPE: RNA
<213> ORGANISM: Homo sapiens

<400> SEQUENCE: 1878
cagcaguuga caugggguca gucgguccug agagaugggc gagcgccgu               49

<210> SEQ ID NO 1879
<211> LENGTH: 49
<212> TYPE: RNA
<213> ORGANISM: Homo sapiens

<400> SEQUENCE: 1879
acgagaacuu ugaaggccga aguggagaag gguuccaugu gaacagcag               49

<210> SEQ ID NO 1880
<211> LENGTH: 28
<212> TYPE: RNA
<213> ORGANISM: Homo sapiens

<400> SEQUENCE: 1880
gcguuggugg uauagugguu agcauagc                                      28

<210> SEQ ID NO 1881
<211> LENGTH: 30
<212> TYPE: RNA

<213> ORGANISM: Homo sapiens

<400> SEQUENCE: 1881
aguaagguca gcuaaauaag cuaucgcgcc 30

<210> SEQ ID NO 1882
<211> LENGTH: 48
<212> TYPE: RNA
<213> ORGANISM: Homo sapiens

<400> SEQUENCE: 1882
uaguacuugg augggagacc gccugggaau accgggugcu guaggcuu 48

<210> SEQ ID NO 1883
<211> LENGTH: 41
<212> TYPE: RNA
<213> ORGANISM: Homo sapiens

<400> SEQUENCE: 1883
ugugaaucug acaacagagg cuuacgaccc cuuauuuacc c 41

<210> SEQ ID NO 1884
<211> LENGTH: 50
<212> TYPE: RNA
<213> ORGANISM: Homo sapiens

<400> SEQUENCE: 1884
acauugauca ucgacacuuc gaacgcacuu gcggccacgg guuccucccg 50

<210> SEQ ID NO 1885
<211> LENGTH: 34
<212> TYPE: RNA
<213> ORGANISM: Homo sapiens

<400> SEQUENCE: 1885
gcauuggugg uucaguggua gaauucucgc cuga 34

<210> SEQ ID NO 1886
<211> LENGTH: 33
<212> TYPE: RNA
<213> ORGANISM: Homo sapiens

<400> SEQUENCE: 1886
ucccuggugg ucuaguggcu aggauucggc gcg 33

<210> SEQ ID NO 1887
<211> LENGTH: 34
<212> TYPE: RNA
<213> ORGANISM: Homo sapiens

<400> SEQUENCE: 1887
cauuggucgu gguuguaguc cgugcgagaa uacc 34

<210> SEQ ID NO 1888
<211> LENGTH: 43
<212> TYPE: RNA
<213> ORGANISM: Homo sapiens

<400> SEQUENCE: 1888
aagcuaugau gaauuugauu gcauugaucg ucugacauga uaa 43

<210> SEQ ID NO 1889
<211> LENGTH: 41

<212> TYPE: RNA
<213> ORGANISM: Homo sapiens

<400> SEQUENCE: 1889
uucauaucau uggucguggu uguaguccgu gcgagaauac c 41

<210> SEQ ID NO 1890
<211> LENGTH: 50
<212> TYPE: RNA
<213> ORGANISM: Homo sapiens

<400> SEQUENCE: 1890
cuaauuagug acgcgcauga auggaugaac gagauuccca cugucccuac 50

<210> SEQ ID NO 1891
<211> LENGTH: 44
<212> TYPE: RNA
<213> ORGANISM: Homo sapiens

<400> SEQUENCE: 1891
ggcucuaagg gcugggucgg ucgggcuggg gcgcgaagcg gggc 44

<210> SEQ ID NO 1892
<211> LENGTH: 29
<212> TYPE: RNA
<213> ORGANISM: Homo sapiens

<400> SEQUENCE: 1892
ccaccccacg ucucgucgcg cgcgcgucc 29

<210> SEQ ID NO 1893
<211> LENGTH: 50
<212> TYPE: RNA
<213> ORGANISM: Homo sapiens

<400> SEQUENCE: 1893
cgacucuuag cgguggauca cucggcucgu gcgucgauga agaacgccgc 50

<210> SEQ ID NO 1894
<211> LENGTH: 33
<212> TYPE: RNA
<213> ORGANISM: Homo sapiens

<400> SEQUENCE: 1894
ucccuggugg ucuagagguu aggauucggc gcu 33

<210> SEQ ID NO 1895
<211> LENGTH: 45
<212> TYPE: RNA
<213> ORGANISM: Homo sapiens

<400> SEQUENCE: 1895
acugugguaa uucuagagcu aauacaugcc gacgggcgcu gaccc 45

<210> SEQ ID NO 1896
<211> LENGTH: 50
<212> TYPE: RNA
<213> ORGANISM: Homo sapiens

<400> SEQUENCE: 1896
guguguuacu agagaaguuu cucugaacgu guagagcacc gaaaaccacg 50

<210> SEQ ID NO 1897

-continued

<211> LENGTH: 31
<212> TYPE: RNA
<213> ORGANISM: Homo sapiens

<400> SEQUENCE: 1897
uaggauggcg ugugauaggu ggcacggaga a 31

<210> SEQ ID NO 1898
<211> LENGTH: 39
<212> TYPE: RNA
<213> ORGANISM: Homo sapiens

<400> SEQUENCE: 1898
cugucacgcg ggagaccggg guucgauucc ccgacgggg 39

<210> SEQ ID NO 1899
<211> LENGTH: 32
<212> TYPE: RNA
<213> ORGANISM: Homo sapiens

<400> SEQUENCE: 1899
gcaugggugg uucaguggca gaauucucgc cu 32

<210> SEQ ID NO 1900
<211> LENGTH: 29
<212> TYPE: RNA
<213> ORGANISM: Homo sapiens

<400> SEQUENCE: 1900
gccgugaucg uauaguggau aguacucug 29

<210> SEQ ID NO 1901
<211> LENGTH: 36
<212> TYPE: RNA
<213> ORGANISM: Homo sapiens

<400> SEQUENCE: 1901
cucucucucu cucccccgcu ccccguccuc cccccu 36

<210> SEQ ID NO 1902
<211> LENGTH: 35
<212> TYPE: RNA
<213> ORGANISM: Homo sapiens

<400> SEQUENCE: 1902
ucccauaugg ucuagcgguu aggauuccug guuuu 35

<210> SEQ ID NO 1903
<211> LENGTH: 27
<212> TYPE: RNA
<213> ORGANISM: Homo sapiens

<400> SEQUENCE: 1903
aagggcuuag cuuaauuaaa guggcug 27

<210> SEQ ID NO 1904
<211> LENGTH: 32
<212> TYPE: RNA
<213> ORGANISM: Homo sapiens

<400> SEQUENCE: 1904
gcaugggugg uucagugggua gaauucucuc cu 32

```
<210> SEQ ID NO 1905
<211> LENGTH: 33
<212> TYPE: RNA
<213> ORGANISM: Homo sapiens

<400> SEQUENCE: 1905

ucccuggugg ucucgugguu aggauucggc gcu                                    33

<210> SEQ ID NO 1906
<211> LENGTH: 43
<212> TYPE: RNA
<213> ORGANISM: Homo sapiens

<400> SEQUENCE: 1906

cuguuaacua aguguuugug gguuuaaguc ccauuggucu agc                         43

<210> SEQ ID NO 1907
<211> LENGTH: 45
<212> TYPE: RNA
<213> ORGANISM: Homo sapiens

<400> SEQUENCE: 1907

auuugccaag aauguuuuca uuaaucaaga acgaaagucg gaggu                       45

<210> SEQ ID NO 1908
<211> LENGTH: 38
<212> TYPE: RNA
<213> ORGANISM: Homo sapiens

<400> SEQUENCE: 1908

uuuuugaucc uucgaugucg gcucuuccua ucauugug                               38

<210> SEQ ID NO 1909
<211> LENGTH: 32
<212> TYPE: RNA
<213> ORGANISM: Homo sapiens

<400> SEQUENCE: 1909

gcauuggugg aucaguggua gaauucucgc cu                                     32

<210> SEQ ID NO 1910
<211> LENGTH: 33
<212> TYPE: RNA
<213> ORGANISM: Homo sapiens

<400> SEQUENCE: 1910

gcauuggagg uucaguggua gaauucucgc cuc                                    33

<210> SEQ ID NO 1911
<211> LENGTH: 32
<212> TYPE: RNA
<213> ORGANISM: Homo sapiens

<400> SEQUENCE: 1911

gcaugggugg uucaguggua gaauucucgc uu                                     32

<210> SEQ ID NO 1912
<211> LENGTH: 32
<212> TYPE: RNA
<213> ORGANISM: Homo sapiens

<400> SEQUENCE: 1912

gcauugaugg uucaguggua gaauucucgc cu                                     32
```

<210> SEQ ID NO 1913
<211> LENGTH: 32
<212> TYPE: RNA
<213> ORGANISM: Homo sapiens

<400> SEQUENCE: 1913
gcguuggugg uucaguggua gaauucucgc cu 32

<210> SEQ ID NO 1914
<211> LENGTH: 30
<212> TYPE: RNA
<213> ORGANISM: Homo sapiens

<400> SEQUENCE: 1914
gcccgugauc guauaguggu uaguacucug 30

<210> SEQ ID NO 1915
<211> LENGTH: 33
<212> TYPE: RNA
<213> ORGANISM: Homo sapiens

<400> SEQUENCE: 1915
gugaagcaga auucaccaag cguuggauug uuc 33

<210> SEQ ID NO 1916
<211> LENGTH: 33
<212> TYPE: RNA
<213> ORGANISM: Homo sapiens

<400> SEQUENCE: 1916
guuuccguag uguaguggau aucacguucg ccu 33

<210> SEQ ID NO 1917
<211> LENGTH: 29
<212> TYPE: RNA
<213> ORGANISM: Homo sapiens

<400> SEQUENCE: 1917
ggggguauag cucaguggua gagcauuug 29

<210> SEQ ID NO 1918
<211> LENGTH: 27
<212> TYPE: RNA
<213> ORGANISM: Homo sapiens

<400> SEQUENCE: 1918
auugaucauc gacacuucga acgcacu 27

<210> SEQ ID NO 1919
<211> LENGTH: 33
<212> TYPE: RNA
<213> ORGANISM: Homo sapiens

<400> SEQUENCE: 1919
ucccuggugg ucuagugguu agguuucggc gcu 33

<210> SEQ ID NO 1920
<211> LENGTH: 33
<212> TYPE: RNA
<213> ORGANISM: Homo sapiens

<400> SEQUENCE: 1920
uaggauggcg ugugauaggu ggcacggaga auu 33

<210> SEQ ID NO 1921
<211> LENGTH: 35
<212> TYPE: RNA
<213> ORGANISM: Homo sapiens

<400> SEQUENCE: 1921
auugugaagc agaauucacc aagcguugga uuguu 35

<210> SEQ ID NO 1922
<211> LENGTH: 29
<212> TYPE: RNA
<213> ORGANISM: Homo sapiens

<400> SEQUENCE: 1922
cuggugcgga ccaggggaau ccgacuguu 29

<210> SEQ ID NO 1923
<211> LENGTH: 34
<212> TYPE: RNA
<213> ORGANISM: Homo sapiens

<400> SEQUENCE: 1923
cauaucauug gucgugguug uaguccgugc gaga 34

<210> SEQ ID NO 1924
<211> LENGTH: 30
<212> TYPE: RNA
<213> ORGANISM: Homo sapiens

<400> SEQUENCE: 1924
cggcggcguc cggugagcuc ucgcuggccc 30

<210> SEQ ID NO 1925
<211> LENGTH: 36
<212> TYPE: RNA
<213> ORGANISM: Homo sapiens

<400> SEQUENCE: 1925
cccgaggggc ucucgcuucu ggcgccaagc gcccgg 36

<210> SEQ ID NO 1926
<211> LENGTH: 35
<212> TYPE: RNA
<213> ORGANISM: Homo sapiens

<400> SEQUENCE: 1926
ucccugguag ucuagugguu aggauucggc gcucu 35

<210> SEQ ID NO 1927
<211> LENGTH: 37
<212> TYPE: RNA
<213> ORGANISM: Homo sapiens

<400> SEQUENCE: 1927
ucagaagauu ccagguucga cuccuggcug gcucgcc 37

<210> SEQ ID NO 1928
<211> LENGTH: 32
<212> TYPE: RNA
<213> ORGANISM: Homo sapiens

<400> SEQUENCE: 1928
gcauuggugg uucaguggua gaaaucucgc cu 32

<210> SEQ ID NO 1929
<211> LENGTH: 30
<212> TYPE: RNA
<213> ORGANISM: Homo sapiens

<400> SEQUENCE: 1929
ucccuggagg ucuagugguu aggauucggc 30

<210> SEQ ID NO 1930
<211> LENGTH: 27
<212> TYPE: RNA
<213> ORGANISM: Homo sapiens

<400> SEQUENCE: 1930
cuccucggcg cgcggcggcg gcggcgg 27

<210> SEQ ID NO 1931
<211> LENGTH: 49
<212> TYPE: RNA
<213> ORGANISM: Homo sapiens

<400> SEQUENCE: 1931
agugucacua aaguugguau acaaccccc acugcuaaau uugacuggc 49

<210> SEQ ID NO 1932
<211> LENGTH: 30
<212> TYPE: RNA
<213> ORGANISM: Homo sapiens

<400> SEQUENCE: 1932
ucccuggugg ucuagugguu aggauucgcc 30

<210> SEQ ID NO 1933
<211> LENGTH: 44
<212> TYPE: RNA
<213> ORGANISM: Homo sapiens

<400> SEQUENCE: 1933
aacuuacacu uaggagauuu caacuuaacu ugaccgcucu gacc 44

<210> SEQ ID NO 1934
<211> LENGTH: 50
<212> TYPE: RNA
<213> ORGANISM: Homo sapiens

<400> SEQUENCE: 1934
aauacaacga ugguuuuuca uaucauuggu cgugguugua guccgugcga 50

<210> SEQ ID NO 1935
<211> LENGTH: 39
<212> TYPE: RNA
<213> ORGANISM: Homo sapiens

<400> SEQUENCE: 1935
ucccuggugg ucuagugguu aggauucggc gcucucacc 39

<210> SEQ ID NO 1936
<211> LENGTH: 29
<212> TYPE: RNA
<213> ORGANISM: Homo sapiens

<400> SEQUENCE: 1936
ggccgugauc guauagugga uaguacucu 29

<210> SEQ ID NO 1937
<211> LENGTH: 50
<212> TYPE: RNA
<213> ORGANISM: Homo sapiens

<400> SEQUENCE: 1937
cgacucuuag cgguggauca cucggcccgu gcgucgauga agaacgcagc 50

<210> SEQ ID NO 1938
<211> LENGTH: 50
<212> TYPE: RNA
<213> ORGANISM: Homo sapiens

<400> SEQUENCE: 1938
agaagacccu guugagcuug acucuagucu ggcacggua agagacauga 50

<210> SEQ ID NO 1939
<211> LENGTH: 26
<212> TYPE: RNA
<213> ORGANISM: Homo sapiens

<400> SEQUENCE: 1939
aauugcagga cacauugauc aucgac 26

<210> SEQ ID NO 1940
<211> LENGTH: 34
<212> TYPE: RNA
<213> ORGANISM: Homo sapiens

<400> SEQUENCE: 1940
gcaugggugg uucaguggua gaauucucgc cugg 34

<210> SEQ ID NO 1941
<211> LENGTH: 27
<212> TYPE: RNA
<213> ORGANISM: Homo sapiens

<400> SEQUENCE: 1941
uuuggcaaug guagaacuca cacuggu 27

<210> SEQ ID NO 1942
<211> LENGTH: 50
<212> TYPE: RNA
<213> ORGANISM: Homo sapiens

<400> SEQUENCE: 1942
cgggauaagg auuggcucua agggcugggu cggucgggcu ggggcgcgaa 50

<210> SEQ ID NO 1943
<211> LENGTH: 32
<212> TYPE: RNA
<213> ORGANISM: Homo sapiens

<400> SEQUENCE: 1943
gcauuggugg uucagugcua gaauucucgc cu 32

<210> SEQ ID NO 1944
<211> LENGTH: 32
<212> TYPE: RNA
<213> ORGANISM: Homo sapiens

<400> SEQUENCE: 1944
gcaugggugg uucaguggua gaauucuugc cu 32

<210> SEQ ID NO 1945
<211> LENGTH: 39
<212> TYPE: RNA
<213> ORGANISM: Homo sapiens

<400> SEQUENCE: 1945
acgagaacuu ugaaggccga aguggagaag gguuccaug 39

<210> SEQ ID NO 1946
<211> LENGTH: 50
<212> TYPE: RNA
<213> ORGANISM: Homo sapiens

<400> SEQUENCE: 1946
aauugcagga cacauugauc aucgacacuu cgaacgcacu ugcggccccc 50

<210> SEQ ID NO 1947
<211> LENGTH: 26
<212> TYPE: RNA
<213> ORGANISM: Homo sapiens

<400> SEQUENCE: 1947
ccaagcguug gauuguucac ccacua 26

<210> SEQ ID NO 1948
<211> LENGTH: 49
<212> TYPE: RNA
<213> ORGANISM: Homo sapiens

<400> SEQUENCE: 1948
cuagagguga aauucuugga ccggcgcaag acggaccaga gcgaaagca 49

<210> SEQ ID NO 1949
<211> LENGTH: 42
<212> TYPE: RNA
<213> ORGANISM: Homo sapiens

<400> SEQUENCE: 1949
acgaccugcu ucugggucgg gguuucguac guagcagagc ag 42

<210> SEQ ID NO 1950
<211> LENGTH: 36
<212> TYPE: RNA
<213> ORGANISM: Homo sapiens

<400> SEQUENCE: 1950
ucuugcgacc cggguucguu ucccgggcgg cgcacc 36

<210> SEQ ID NO 1951
<211> LENGTH: 29
<212> TYPE: RNA
<213> ORGANISM: Homo sapiens

<400> SEQUENCE: 1951
guuuccgugg uguagugguu aucacauuc 29

<210> SEQ ID NO 1952
<211> LENGTH: 33
<212> TYPE: RNA
<213> ORGANISM: Homo sapiens

<400> SEQUENCE: 1952
ucccuggugg ucuagugguu aggauuccgc gcu 33

<210> SEQ ID NO 1953
<211> LENGTH: 50
<212> TYPE: RNA
<213> ORGANISM: Homo sapiens

<400> SEQUENCE: 1953
ccccuguggu cuagugguua ggauucggcg cucucaccgc cgcggcccgg 50

<210> SEQ ID NO 1954
<211> LENGTH: 30
<212> TYPE: RNA
<213> ORGANISM: Homo sapiens

<400> SEQUENCE: 1954
cuggacgcga gccgggcccu ucccguggau 30

<210> SEQ ID NO 1955
<211> LENGTH: 44
<212> TYPE: RNA
<213> ORGANISM: Homo sapiens

<400> SEQUENCE: 1955
cguagcgguc cugacgugca aaucggucgu ccgaccuggg uaua 44

<210> SEQ ID NO 1956
<211> LENGTH: 26
<212> TYPE: RNA
<213> ORGANISM: Homo sapiens

<400> SEQUENCE: 1956
ggcucguugg ucuaggggua ugauuc 26

<210> SEQ ID NO 1957
<211> LENGTH: 49
<212> TYPE: RNA
<213> ORGANISM: Homo sapiens

<400> SEQUENCE: 1957
ugguuaggau ucggcgcucu caccgccgcg gcccggguuc guuucccgg 49

<210> SEQ ID NO 1958
<211> LENGTH: 32
<212> TYPE: RNA
<213> ORGANISM: Homo sapiens

<400> SEQUENCE: 1958
gcauuggugg uucaauggua gaauucucgc cu 32

<210> SEQ ID NO 1959
<211> LENGTH: 31
<212> TYPE: RNA
<213> ORGANISM: Homo sapiens

<400> SEQUENCE: 1959
cuagagguga aauucuugga ccggcgcaag a 31

<210> SEQ ID NO 1960
<211> LENGTH: 42
<212> TYPE: RNA

```
<213> ORGANISM: Homo sapiens

<400> SEQUENCE: 1960

cuccuacuug gauaacugug guaauucuag agcuaauaca ug                    42

<210> SEQ ID NO 1961
<211> LENGTH: 31
<212> TYPE: RNA
<213> ORGANISM: Homo sapiens

<400> SEQUENCE: 1961

ggccguaauc guauaguggu uaguacucug c                                31

<210> SEQ ID NO 1962
<211> LENGTH: 29
<212> TYPE: RNA
<213> ORGANISM: Homo sapiens

<400> SEQUENCE: 1962

cggcggcguc cggugagcuc ucgcuggcc                                   29

<210> SEQ ID NO 1963
<211> LENGTH: 50
<212> TYPE: RNA
<213> ORGANISM: Homo sapiens

<400> SEQUENCE: 1963

auugugaagc agaauucacc aagcguugga uuguucaccc acuaauaggg            50

<210> SEQ ID NO 1964
<211> LENGTH: 32
<212> TYPE: RNA
<213> ORGANISM: Homo sapiens

<400> SEQUENCE: 1964

gcaugggugg uucaguggua gaauucucga cu                               32

<210> SEQ ID NO 1965
<211> LENGTH: 34
<212> TYPE: RNA
<213> ORGANISM: Homo sapiens

<400> SEQUENCE: 1965

gcauuggugg uucaguggua gaauucucgc augc                             34

<210> SEQ ID NO 1966
<211> LENGTH: 34
<212> TYPE: RNA
<213> ORGANISM: Homo sapiens

<400> SEQUENCE: 1966

cuggugcgga ccaggggaau ccgacuguuu aauu                             34

<210> SEQ ID NO 1967
<211> LENGTH: 32
<212> TYPE: RNA
<213> ORGANISM: Homo sapiens

<400> SEQUENCE: 1967

gcauuggugg uucaguggua gaauucuugc cu                               32

<210> SEQ ID NO 1968
<211> LENGTH: 32
```

<212> TYPE: RNA
<213> ORGANISM: Homo sapiens

<400> SEQUENCE: 1968
gaauuggugg uucaguggua gaauucucgc cu 32

<210> SEQ ID NO 1969
<211> LENGTH: 33
<212> TYPE: RNA
<213> ORGANISM: Homo sapiens

<400> SEQUENCE: 1969
gcaugggugg uucaguggua gaauucucgc cua 33

<210> SEQ ID NO 1970
<211> LENGTH: 29
<212> TYPE: RNA
<213> ORGANISM: Homo sapiens

<400> SEQUENCE: 1970
gcguuggugg uauaguggguu agcauagcu 29

<210> SEQ ID NO 1971
<211> LENGTH: 33
<212> TYPE: RNA
<213> ORGANISM: Homo sapiens

<400> SEQUENCE: 1971
ucccuaguag ucuagugguu aggauucggc gcu 33

<210> SEQ ID NO 1972
<211> LENGTH: 50
<212> TYPE: RNA
<213> ORGANISM: Homo sapiens

<400> SEQUENCE: 1972
cgacucuuag cgguggauca cucggcucgu gcgucgauga agaacgcaga 50

<210> SEQ ID NO 1973
<211> LENGTH: 33
<212> TYPE: RNA
<213> ORGANISM: Homo sapiens

<400> SEQUENCE: 1973
ucccuggugg ucuagugguu aggauucggc gca 33

<210> SEQ ID NO 1974
<211> LENGTH: 31
<212> TYPE: RNA
<213> ORGANISM: Homo sapiens

<400> SEQUENCE: 1974
uagcuuauca gacugauguu gacuguugaa u 31

<210> SEQ ID NO 1975
<211> LENGTH: 30
<212> TYPE: RNA
<213> ORGANISM: Homo sapiens

<400> SEQUENCE: 1975
agcaagguca gcuaaauaag cuaucgggcc 30

<210> SEQ ID NO 1976

<211> LENGTH: 50
<212> TYPE: RNA
<213> ORGANISM: Homo sapiens

<400> SEQUENCE: 1976
gaacgcacuu gcggccccgg guuccucccg gggcuacgcc ugucugagcg 50

<210> SEQ ID NO 1977
<211> LENGTH: 40
<212> TYPE: RNA
<213> ORGANISM: Homo sapiens

<400> SEQUENCE: 1977 cccgggggc cggcggcggc ggcgacucug gacgcgagcc 40

<210> SEQ ID NO 1978
<211> LENGTH: 30
<212> TYPE: RNA
<213> ORGANISM: Homo sapiens

<400> SEQUENCE: 1978
uaggaugggg cgugauaggu ggcacggaga 30

<210> SEQ ID NO 1979
<211> LENGTH: 34
<212> TYPE: RNA
<213> ORGANISM: Homo sapiens

<400> SEQUENCE: 1979
gcauuggugg uucaguggaa gaauucucgc cugc 34

<210> SEQ ID NO 1980
<211> LENGTH: 50
<212> TYPE: RNA
<213> ORGANISM: Homo sapiens

<400> SEQUENCE: 1980
cgccucuuag cgguggauca cucggcucgu gcgucgauga agaacgcagc 50

<210> SEQ ID NO 1981
<211> LENGTH: 49
<212> TYPE: RNA
<213> ORGANISM: Homo sapiens

<400> SEQUENCE: 1981
gguaaaaugg cugagugaag cauuggacug uaaaucuaaa gacaggggu 49

<210> SEQ ID NO 1982
<211> LENGTH: 32
<212> TYPE: RNA
<213> ORGANISM: Homo sapiens

<400> SEQUENCE: 1982
gcaugggugg uucaguggaa gaauucucgc cu 32

<210> SEQ ID NO 1983
<211> LENGTH: 45
<212> TYPE: RNA
<213> ORGANISM: Homo sapiens

<400> SEQUENCE: 1983
ccugucacgc gggagaccgg gguucaauuc cccgacgggg agcca 45

<210> SEQ ID NO 1984
<211> LENGTH: 29
<212> TYPE: RNA
<213> ORGANISM: Homo sapiens

<400> SEQUENCE: 1984
ggccgugauc gcauaguggu uaguacucu 29

<210> SEQ ID NO 1985
<211> LENGTH: 29
<212> TYPE: RNA
<213> ORGANISM: Homo sapiens

<400> SEQUENCE: 1985
gguaaaaugg cugagugaag cauuggacu 29

<210> SEQ ID NO 1986
<211> LENGTH: 31
<212> TYPE: RNA
<213> ORGANISM: Homo sapiens

<400> SEQUENCE: 1986
cgugaucgua uagugguuag uacucugcgu u 31

<210> SEQ ID NO 1987
<211> LENGTH: 33
<212> TYPE: RNA
<213> ORGANISM: Homo sapiens

<400> SEQUENCE: 1987
ucccuggugg ucuagugguu aggauuaggc gcu 33

<210> SEQ ID NO 1988
<211> LENGTH: 43
<212> TYPE: RNA
<213> ORGANISM: Homo sapiens

<400> SEQUENCE: 1988
ccggcagauu gucucuggau cucgagauaa aaccaucaag cua 43

<210> SEQ ID NO 1989
<211> LENGTH: 26
<212> TYPE: RNA
<213> ORGANISM: Homo sapiens

<400> SEQUENCE: 1989
ccggcuagcu cagucgguag agcaug 26

<210> SEQ ID NO 1990
<211> LENGTH: 33
<212> TYPE: RNA
<213> ORGANISM: Homo sapiens

<400> SEQUENCE: 1990
guuuccguag uguagugguu aucacgaucg ccu 33

<210> SEQ ID NO 1991
<211> LENGTH: 32
<212> TYPE: RNA
<213> ORGANISM: Homo sapiens

<400> SEQUENCE: 1991
ccggcggcgu ccggugagcu cucgcuggcc cu 32

<210> SEQ ID NO 1992
<211> LENGTH: 33
<212> TYPE: RNA
<213> ORGANISM: Homo sapiens

<400> SEQUENCE: 1992
uacagaacau gaucaagggu guuacacugg gcu 33

<210> SEQ ID NO 1993
<211> LENGTH: 33
<212> TYPE: RNA
<213> ORGANISM: Homo sapiens

<400> SEQUENCE: 1993
ucccuggugg ucuagugguu aggauucggc gau 33

<210> SEQ ID NO 1994
<211> LENGTH: 38
<212> TYPE: RNA
<213> ORGANISM: Homo sapiens

<400> SEQUENCE: 1994
cacgcaucga ccugguauug caguaccucc aggaacgg 38

<210> SEQ ID NO 1995
<211> LENGTH: 39
<212> TYPE: RNA
<213> ORGANISM: Homo sapiens

<400> SEQUENCE: 1995
acggcccugg cggagcgcug agaagacggu cgaacuuga 39

<210> SEQ ID NO 1996
<211> LENGTH: 32
<212> TYPE: RNA
<213> ORGANISM: Homo sapiens

<400> SEQUENCE: 1996
gcauugguga uucaguggua gaauucucgc cu 32

<210> SEQ ID NO 1997
<211> LENGTH: 30
<212> TYPE: RNA
<213> ORGANISM: Homo sapiens

<400> SEQUENCE: 1997
aguaagguca gcuaaauaag cuaucgagcc 30

<210> SEQ ID NO 1998
<211> LENGTH: 26
<212> TYPE: RNA
<213> ORGANISM: Homo sapiens

<400> SEQUENCE: 1998
cucggaucgg ccccgccggg gucggc 26

<210> SEQ ID NO 1999
<211> LENGTH: 50
<212> TYPE: RNA
<213> ORGANISM: Homo sapiens

<400> SEQUENCE: 1999
aucgacacuu cgaacgcacu ugcggccccg gguuccuccc ggggcuacgc 50

<210> SEQ ID NO 2000
<211> LENGTH: 48
<212> TYPE: RNA
<213> ORGANISM: Homo sapiens

<400> SEQUENCE: 2000
aauuaaaaca aagcaucgcg aaggcccgcg gcggguguug acgcgaug 48

<210> SEQ ID NO 2001
<211> LENGTH: 32
<212> TYPE: RNA
<213> ORGANISM: Homo sapiens

<400> SEQUENCE: 2001
gcauuggugg uucaguguua gaauucucgc cu 32

<210> SEQ ID NO 2002
<211> LENGTH: 50
<212> TYPE: RNA
<213> ORGANISM: Homo sapiens

<400> SEQUENCE: 2002
acaacgaugg uuuuucauau cauuggucgu gguuguaguc cgugcgagaa 50

<210> SEQ ID NO 2003
<211> LENGTH: 32
<212> TYPE: RNA
<213> ORGANISM: Homo sapiens

<400> SEQUENCE: 2003
gcaugggugg uucaguggua gcauucucgc cu 32

<210> SEQ ID NO 2004
<211> LENGTH: 50
<212> TYPE: RNA
<213> ORGANISM: Homo sapiens

<400> SEQUENCE: 2004
aaggguucca ugugaacagc aguugaacau gggucagucg guccugagag 50

<210> SEQ ID NO 2005
<211> LENGTH: 32
<212> TYPE: RNA
<213> ORGANISM: Homo sapiens

<400> SEQUENCE: 2005
ucauuggugg uucaguggua gaauucucgc cu 32

<210> SEQ ID NO 2006
<211> LENGTH: 32
<212> TYPE: RNA
<213> ORGANISM: Homo sapiens

<400> SEQUENCE: 2006
ucccugguag ucuagugguu aggauucggc gc 32

<210> SEQ ID NO 2007
<211> LENGTH: 30
<212> TYPE: RNA
<213> ORGANISM: Homo sapiens

<400> SEQUENCE: 2007
ugccgucauc guauaguggu uaguacucug 30

<210> SEQ ID NO 2008
<211> LENGTH: 30
<212> TYPE: RNA
<213> ORGANISM: Homo sapiens

<400> SEQUENCE: 2008
ggccguuauc guauaguggu uaguacucug 30

<210> SEQ ID NO 2009
<211> LENGTH: 50
<212> TYPE: RNA
<213> ORGANISM: Homo sapiens

<400> SEQUENCE: 2009
cucccaugau guccagcacu gggcucugau caccccugag gacacagugc 50

<210> SEQ ID NO 2010
<211> LENGTH: 31
<212> TYPE: RNA
<213> ORGANISM: Homo sapiens

<400> SEQUENCE: 2010
ucgagagggg cugugcucgc aagguuucuu u 31

<210> SEQ ID NO 2011
<211> LENGTH: 39
<212> TYPE: RNA
<213> ORGANISM: Homo sapiens

<400> SEQUENCE: 2011
uugugaaucu gacaacagag gcuuacgacc ccuuauuua 39

<210> SEQ ID NO 2012
<211> LENGTH: 29
<212> TYPE: RNA
<213> ORGANISM: Homo sapiens

<400> SEQUENCE: 2012
gccgugaucg uauagugguu agcacucug 29

<210> SEQ ID NO 2013
<211> LENGTH: 44
<212> TYPE: RNA
<213> ORGANISM: Homo sapiens

<400> SEQUENCE: 2013
cuguuaacua aguguuugug gguuuaaguc ccauuggucu agcc 44

<210> SEQ ID NO 2014
<211> LENGTH: 49
<212> TYPE: RNA
<213> ORGANISM: Homo sapiens

<400> SEQUENCE: 2014
acuaccgauu ggaugguuua gugaggcccu cggaucggcc ccgccgggg 49

<210> SEQ ID NO 2015
<211> LENGTH: 33
<212> TYPE: RNA
<213> ORGANISM: Homo sapiens

<400> SEQUENCE: 2015
gcgccgcugg uguaguggua ucaugcaaga uuc 33

<210> SEQ ID NO 2016
<211> LENGTH: 34
<212> TYPE: RNA
<213> ORGANISM: Homo sapiens

<400> SEQUENCE: 2016
gcauuggugg uucaguggua gaauucucgc ccgc 34

<210> SEQ ID NO 2017
<211> LENGTH: 32
<212> TYPE: RNA
<213> ORGANISM: Homo sapiens

<400> SEQUENCE: 2017
gcauaggugg uucaguggua gaauucucgc cu 32

<210> SEQ ID NO 2018
<211> LENGTH: 42
<212> TYPE: RNA
<213> ORGANISM: Homo sapiens

<400> SEQUENCE: 2018
agcagccgac uuagaacugg ugcggaccag gggaauccga cu 42

<210> SEQ ID NO 2019
<211> LENGTH: 26
<212> TYPE: RNA
<213> ORGANISM: Homo sapiens

<400> SEQUENCE: 2019
gugguucagu gguagaauuc ucgccu 26

<210> SEQ ID NO 2020
<211> LENGTH: 41
<212> TYPE: RNA
<213> ORGANISM: Homo sapiens

<400> SEQUENCE: 2020
ggcuuuggug acucuagaua accucgggcc gaucgcacgc c 41

<210> SEQ ID NO 2021
<211> LENGTH: 45
<212> TYPE: RNA
<213> ORGANISM: Homo sapiens

<400> SEQUENCE: 2021
cgcucucacc gccgcggccc ggguucguuu cccggucagg gaacc 45

<210> SEQ ID NO 2022
<211> LENGTH: 50
<212> TYPE: RNA
<213> ORGANISM: Homo sapiens

<400> SEQUENCE: 2022
ccgugcugau caguaguggg aucgcgccug ugaauagcca cugcacucca 50

<210> SEQ ID NO 2023
<211> LENGTH: 30
<212> TYPE: RNA
<213> ORGANISM: Homo sapiens

<400> SEQUENCE: 2023
ucccugguag ucuagugguu aggauucggc 30

<210> SEQ ID NO 2024
<211> LENGTH: 27
<212> TYPE: RNA
<213> ORGANISM: Homo sapiens

<400> SEQUENCE: 2024
caagagggcg ugaaaccguu aagaggu 27

<210> SEQ ID NO 2025
<211> LENGTH: 28
<212> TYPE: RNA
<213> ORGANISM: Homo sapiens

<400> SEQUENCE: 2025
ucccugguag ucuagugguu aggauucg 28

<210> SEQ ID NO 2026
<211> LENGTH: 50
<212> TYPE: RNA
<213> ORGANISM: Homo sapiens

<400> SEQUENCE: 2026
ucugauacgu ccucuauccg aggacaauau auuaaaugga uuuuuggagc 50

<210> SEQ ID NO 2027
<211> LENGTH: 36
<212> TYPE: RNA
<213> ORGANISM: Homo sapiens

<400> SEQUENCE: 2027
aacuggugcg gaccagggga auccgacugu uuaauu 36

<210> SEQ ID NO 2028
<211> LENGTH: 33
<212> TYPE: RNA
<213> ORGANISM: Homo sapiens

<400> SEQUENCE: 2028
ucccuggggg ucuagugguu aggauucggc gcu 33

<210> SEQ ID NO 2029
<211> LENGTH: 34
<212> TYPE: RNA
<213> ORGANISM: Homo sapiens

<400> SEQUENCE: 2029
uaggaugggg ugugauaggu ggcacggaga auuu 34

<210> SEQ ID NO 2030
<211> LENGTH: 35
<212> TYPE: RNA
<213> ORGANISM: Homo sapiens

<400> SEQUENCE: 2030
gucuacggcc auaccacccu gaacgcgccc gaucu 35

<210> SEQ ID NO 2031
<211> LENGTH: 31
<212> TYPE: RNA
<213> ORGANISM: Homo sapiens

```
<400> SEQUENCE: 2031

ucccuggugg ucuagugguu cggauucggc g                                31

<210> SEQ ID NO 2032
<211> LENGTH: 46
<212> TYPE: RNA
<213> ORGANISM: Homo sapiens

<400> SEQUENCE: 2032

gcuuugcacg uaugaggccc cggguucaau ccccggcauc uccacc                46

<210> SEQ ID NO 2033
<211> LENGTH: 50
<212> TYPE: RNA
<213> ORGANISM: Homo sapiens

<400> SEQUENCE: 2033

ucaguagugg gaucgcgccu gugaauagcc acugcaucc agccgagca               50

<210> SEQ ID NO 2034
<211> LENGTH: 30
<212> TYPE: RNA
<213> ORGANISM: Homo sapiens

<400> SEQUENCE: 2034

augucggcuc uuccuaucau ugugaagcag                                  30

<210> SEQ ID NO 2035
<211> LENGTH: 27
<212> TYPE: RNA
<213> ORGANISM: Homo sapiens

<400> SEQUENCE: 2035

cucccucgcu gcgaucuauu gaaaguc                                     27

<210> SEQ ID NO 2036
<211> LENGTH: 29
<212> TYPE: RNA
<213> ORGANISM: Homo sapiens

<400> SEQUENCE: 2036

gccgugaucg ucuagugguu aguacucug                                   29

<210> SEQ ID NO 2037
<211> LENGTH: 33
<212> TYPE: RNA
<213> ORGANISM: Homo sapiens

<400> SEQUENCE: 2037

uccuuggugg ucuagugguu aggauucggc gcu                              33

<210> SEQ ID NO 2038
<211> LENGTH: 34
<212> TYPE: RNA
<213> ORGANISM: Homo sapiens

<400> SEQUENCE: 2038

gggggauag cucaguggua gagcauuuga cugc                              34

<210> SEQ ID NO 2039
<211> LENGTH: 31
<212> TYPE: RNA
```

<213> ORGANISM: Homo sapiens

<400> SEQUENCE: 2039
augucggcuc uuccuaucau ugugaagcag a 31

<210> SEQ ID NO 2040
<211> LENGTH: 50
<212> TYPE: RNA
<213> ORGANISM: Homo sapiens

<400> SEQUENCE: 2040
gccaagaaug uuuucauuaa ucaagaacga aagucggagg uucgaagacg 50

<210> SEQ ID NO 2041
<211> LENGTH: 49
<212> TYPE: RNA
<213> ORGANISM: Homo sapiens

<400> SEQUENCE: 2041
aauuaaugug aauugcagga cacauugauc aucgacacuu cgaacgcac 49

<210> SEQ ID NO 2042
<211> LENGTH: 38
<212> TYPE: RNA
<213> ORGANISM: Homo sapiens

<400> SEQUENCE: 2042
ccgaggggcu cucgcuucug gcgccaagcg cccggccg 38

<210> SEQ ID NO 2043
<211> LENGTH: 50
<212> TYPE: RNA
<213> ORGANISM: Homo sapiens

<400> SEQUENCE: 2043
guuaauuccg auaacgaacg agacucuggc augcuaacua guuacgcgac 50

<210> SEQ ID NO 2044
<211> LENGTH: 50
<212> TYPE: RNA
<213> ORGANISM: Homo sapiens

<400> SEQUENCE: 2044
aggacacauu gaucaucgac acuucgaacg cacuugcggc cccggguuaa 50

<210> SEQ ID NO 2045
<211> LENGTH: 33
<212> TYPE: RNA
<213> ORGANISM: Homo sapiens

<400> SEQUENCE: 2045
ucccuggagg ucuaguggu aggauucggc gcu 33

<210> SEQ ID NO 2046
<211> LENGTH: 46
<212> TYPE: RNA
<213> ORGANISM: Homo sapiens

<400> SEQUENCE: 2046
auaaccucgg gccgaucgca cgcccccgu ggcggcgacg acccau 46

<210> SEQ ID NO 2047
<211> LENGTH: 33

<212> TYPE: RNA
<213> ORGANISM: Homo sapiens

<400> SEQUENCE: 2047
ccggcggcgu ccggugagcu cucgcuggcc cuu 33

<210> SEQ ID NO 2048
<211> LENGTH: 50
<212> TYPE: RNA
<213> ORGANISM: Homo sapiens

<400> SEQUENCE: 2048
gcggcugaug acagcacuuc ugcugagacg cugugauugc ucuguccaaa 50

<210> SEQ ID NO 2049
<211> LENGTH: 35
<212> TYPE: RNA
<213> ORGANISM: Homo sapiens

<400> SEQUENCE: 2049
cggcggcggc ggcgacucug gacgcgagcc gggcc 35

<210> SEQ ID NO 2050
<211> LENGTH: 41
<212> TYPE: RNA
<213> ORGANISM: Homo sapiens

<400> SEQUENCE: 2050
auugaucauc gacacuucga acgcacuugc ggccccgggu a 41

<210> SEQ ID NO 2051
<211> LENGTH: 30
<212> TYPE: RNA
<213> ORGANISM: Homo sapiens

<400> SEQUENCE: 2051
uuaaguuaaa gauuaagaga accaacaccu 30

<210> SEQ ID NO 2052
<211> LENGTH: 32
<212> TYPE: RNA
<213> ORGANISM: Homo sapiens

<400> SEQUENCE: 2052
gcaugggugg uucaguggua gaauucucgc au 32

<210> SEQ ID NO 2053
<211> LENGTH: 33
<212> TYPE: RNA
<213> ORGANISM: Homo sapiens

<400> SEQUENCE: 2053
cagugcgccc cgggcggguc gcgccgucgg gcc 33

<210> SEQ ID NO 2054
<211> LENGTH: 42
<212> TYPE: RNA
<213> ORGANISM: Homo sapiens

<400> SEQUENCE: 2054
aacgagaacu uugaaggccg aaguggagaa ggguuccaug ug 42

<210> SEQ ID NO 2055

<211> LENGTH: 50
<212> TYPE: RNA
<213> ORGANISM: Homo sapiens

<400> SEQUENCE: 2055
cugguuagua cuuggauggg agaccgccug ggaauaccgg gugcuguagg 50

<210> SEQ ID NO 2056
<211> LENGTH: 41
<212> TYPE: RNA
<213> ORGANISM: Homo sapiens

<400> SEQUENCE: 2056
auugugaauc ugacaacaga ggcuuacgac cccuuauuua c 41

<210> SEQ ID NO 2057
<211> LENGTH: 31
<212> TYPE: RNA
<213> ORGANISM: Homo sapiens

<400> SEQUENCE: 2057
guuugugggu uuaaguccca uuggucuagc c 31

<210> SEQ ID NO 2058
<211> LENGTH: 50
<212> TYPE: RNA
<213> ORGANISM: Homo sapiens

<400> SEQUENCE: 2058
caugugaaca gcaguugaac augggucagu cgguccugag agaugggcga 50

<210> SEQ ID NO 2059
<211> LENGTH: 34
<212> TYPE: RNA
<213> ORGANISM: Homo sapiens

<400> SEQUENCE: 2059
gcauuggugg uucaguggua gaauucucgc cugu 34

<210> SEQ ID NO 2060
<211> LENGTH: 31
<212> TYPE: RNA
<213> ORGANISM: Homo sapiens

<400> SEQUENCE: 2060
uaggauggug ugugauaggu ggcacggaga a 31

<210> SEQ ID NO 2061
<211> LENGTH: 32
<212> TYPE: RNA
<213> ORGANISM: Homo sapiens

<400> SEQUENCE: 2061
gcaugggugg uucaguggua gaauuuucgc cu 32

<210> SEQ ID NO 2062
<211> LENGTH: 34
<212> TYPE: RNA
<213> ORGANISM: Homo sapiens

<400> SEQUENCE: 2062
ggccguaauc guauaguggu uaguacucug cguu 34

-continued

<210> SEQ ID NO 2063
<211> LENGTH: 36
<212> TYPE: RNA
<213> ORGANISM: Homo sapiens

<400> SEQUENCE: 2063
auuaaucaag aacgaaaguc ggagguucga agacga 36

<210> SEQ ID NO 2064
<211> LENGTH: 50
<212> TYPE: RNA
<213> ORGANISM: Homo sapiens

<400> SEQUENCE: 2064
agaacaugau gauuggagau gcaugaaacg ugauuaacgu cucugcguaa 50

<210> SEQ ID NO 2065
<211> LENGTH: 32
<212> TYPE: RNA
<213> ORGANISM: Homo sapiens

<400> SEQUENCE: 2065
cgccgugauc guauaguggu uaguacucug cg 32

<210> SEQ ID NO 2066
<211> LENGTH: 37
<212> TYPE: RNA
<213> ORGANISM: Homo sapiens

<400> SEQUENCE: 2066
cccgcgaggg gggucucccc cgcgggggcg cgccggc 37

<210> SEQ ID NO 2067
<211> LENGTH: 27
<212> TYPE: RNA
<213> ORGANISM: Homo sapiens

<400> SEQUENCE: 2067
aauugcagga cacauugauc aucgaca 27

<210> SEQ ID NO 2068
<211> LENGTH: 34
<212> TYPE: RNA
<213> ORGANISM: Homo sapiens

<400> SEQUENCE: 2068
aaguguuugu ggguuuaagu cccauugguc uagc 34

<210> SEQ ID NO 2069
<211> LENGTH: 40
<212> TYPE: RNA
<213> ORGANISM: Homo sapiens

<400> SEQUENCE: 2069
auuucgacuc auuaaauuau gauaaucaua uuuaccaacc 40

<210> SEQ ID NO 2070
<211> LENGTH: 30
<212> TYPE: RNA
<213> ORGANISM: Homo sapiens

<400> SEQUENCE: 2070
ucccuggugg ucuagugguu aggauuccgc 30

<210> SEQ ID NO 2071
<211> LENGTH: 48
<212> TYPE: RNA
<213> ORGANISM: Homo sapiens

<400> SEQUENCE: 2071
aggacacauu gaucaucgac acuucgaacg cacuugcggc cccgggua 48

<210> SEQ ID NO 2072
<211> LENGTH: 27
<212> TYPE: RNA
<213> ORGANISM: Homo sapiens

<400> SEQUENCE: 2072
agcagccgac uuagaacugg ugcggac 27

<210> SEQ ID NO 2073
<211> LENGTH: 47
<212> TYPE: RNA
<213> ORGANISM: Homo sapiens

<400> SEQUENCE: 2073
ggacacauug aucaucgaca cuucgaacgc acuugcggcc ccggguu 47

<210> SEQ ID NO 2074
<211> LENGTH: 27
<212> TYPE: RNA
<213> ORGANISM: Homo sapiens

<400> SEQUENCE: 2074
ucccugguag ucuagugguu aggauuc 27

<210> SEQ ID NO 2075
<211> LENGTH: 32
<212> TYPE: RNA
<213> ORGANISM: Homo sapiens

<400> SEQUENCE: 2075 gggggguguag cucaguggua gagcauuuga cu 32

<210> SEQ ID NO 2076
<211> LENGTH: 36
<212> TYPE: RNA
<213> ORGANISM: Homo sapiens

<400> SEQUENCE: 2076
ccacgcggga ggcccggguu cguuucccgg ccaaug 36

<210> SEQ ID NO 2077
<211> LENGTH: 35
<212> TYPE: RNA
<213> ORGANISM: Homo sapiens

<400> SEQUENCE: 2077
gcauuggugg uucaguggua gaauucucgc cuucc 35

<210> SEQ ID NO 2078
<211> LENGTH: 45
<212> TYPE: RNA
<213> ORGANISM: Homo sapiens

<400> SEQUENCE: 2078
ccagugcgcc ccgggcgggu cgcgccgucg ggcccggggg aggua 45

<210> SEQ ID NO 2079
<211> LENGTH: 45
<212> TYPE: RNA
<213> ORGANISM: Homo sapiens

<400> SEQUENCE: 2079
guuaagaugg cagagcccgg uaaucgcaua aaacuuaaaa cuuua 45

<210> SEQ ID NO 2080
<211> LENGTH: 40
<212> TYPE: RNA
<213> ORGANISM: Homo sapiens

<400> SEQUENCE: 2080
ucauaucauu ggucgugguu guaguccgug cgagaauacc 40

<210> SEQ ID NO 2081
<211> LENGTH: 34
<212> TYPE: RNA
<213> ORGANISM: Homo sapiens

<400> SEQUENCE: 2081
gcaugugugg uucaguggua gaauucucgc cugc 34

<210> SEQ ID NO 2082
<211> LENGTH: 26
<212> TYPE: RNA
<213> ORGANISM: Homo sapiens

<400> SEQUENCE: 2082
ugccgugauc guauaguggu uaguac 26

<210> SEQ ID NO 2083
<211> LENGTH: 37
<212> TYPE: RNA
<213> ORGANISM: Homo sapiens

<400> SEQUENCE: 2083
gaucuauuga aagucagccc ucgacacaag gguuugu 37

<210> SEQ ID NO 2084
<211> LENGTH: 30
<212> TYPE: RNA
<213> ORGANISM: Homo sapiens

<400> SEQUENCE: 2084
uaggaugggg ugcgauaggu ggcacggaga 30

<210> SEQ ID NO 2085
<211> LENGTH: 42
<212> TYPE: RNA
<213> ORGANISM: Homo sapiens

<400> SEQUENCE: 2085
uuaaguuaaa gauuaagaga accaacaccu cuuuacagug ac 42

<210> SEQ ID NO 2086
<211> LENGTH: 35
<212> TYPE: RNA
<213> ORGANISM: Homo sapiens

<400> SEQUENCE: 2086

-continued

```
gcaagccgga uccguaacuu cgggauaagg auugg                                    35

<210> SEQ ID NO 2087
<211> LENGTH: 36
<212> TYPE: RNA
<213> ORGANISM: Homo sapiens

<400> SEQUENCE: 2087

cgggagaccg ggguucaauu ccccgacggg gagcca                                   36

<210> SEQ ID NO 2088
<211> LENGTH: 38
<212> TYPE: RNA
<213> ORGANISM: Homo sapiens

<400> SEQUENCE: 2088

uuuggugacu cuagauaacc ucgggccgau cgcacgcc                                 38

<210> SEQ ID NO 2089
<211> LENGTH: 36
<212> TYPE: RNA
<213> ORGANISM: Homo sapiens

<400> SEQUENCE: 2089

ggcugguccg agugcagugg uguuuacaac uaauug                                   36

<210> SEQ ID NO 2090
<211> LENGTH: 30
<212> TYPE: RNA
<213> ORGANISM: Homo sapiens

<400> SEQUENCE: 2090

aguaagguca gcuaaauaag cuauccggcc                                          30

<210> SEQ ID NO 2091
<211> LENGTH: 29
<212> TYPE: RNA
<213> ORGANISM: Homo sapiens

<400> SEQUENCE: 2091

gccgugaucg uauagugguu aguacucgg                                           29

<210> SEQ ID NO 2092
<211> LENGTH: 35
<212> TYPE: RNA
<213> ORGANISM: Homo sapiens

<400> SEQUENCE: 2092

cgggagaccg ggguucguuu ccccgacggg gagcc                                    35

<210> SEQ ID NO 2093
<211> LENGTH: 33
<212> TYPE: RNA
<213> ORGANISM: Homo sapiens

<400> SEQUENCE: 2093

cugggucggg guuucguacg uagcagagca gcu                                      33

<210> SEQ ID NO 2094
<211> LENGTH: 43
<212> TYPE: RNA
<213> ORGANISM: Homo sapiens

<400> SEQUENCE: 2094
```

cccgggggc cggcggcggc ggcgccucug gacgcgagcc ggg 43

<210> SEQ ID NO 2095
<211> LENGTH: 31
<212> TYPE: RNA
<213> ORGANISM: Homo sapiens

<400> SEQUENCE: 2095
uuggucgugg uuguaguccg ugcgagaaua c 31

<210> SEQ ID NO 2096
<211> LENGTH: 33
<212> TYPE: RNA
<213> ORGANISM: Homo sapiens

<400> SEQUENCE: 2096
gcuucuguag uguagugguu aucacauucg ccu 33

<210> SEQ ID NO 2097
<211> LENGTH: 41
<212> TYPE: RNA
<213> ORGANISM: Homo sapiens

<400> SEQUENCE: 2097
acgcgaccuc agaucagacg uggcgacccg cugaauuuaa g 41

<210> SEQ ID NO 2098
<211> LENGTH: 29
<212> TYPE: RNA
<213> ORGANISM: Homo sapiens

<400> SEQUENCE: 2098
gccgugaucg uauaguaguu aguacucug 29

<210> SEQ ID NO 2099
<211> LENGTH: 30
<212> TYPE: RNA
<213> ORGANISM: Homo sapiens

<400> SEQUENCE: 2099
cuagagguga aauucuugga ccggcgcaag 30

<210> SEQ ID NO 2100
<211> LENGTH: 30
<212> TYPE: RNA
<213> ORGANISM: Homo sapiens

<400> SEQUENCE: 2100
cuggugcgga ccaggggaau ccgacuguuu 30

<210> SEQ ID NO 2101
<211> LENGTH: 32
<212> TYPE: RNA
<213> ORGANISM: Homo sapiens

<400> SEQUENCE: 2101
gcauuggugg uucaguggua caauucucgc cu 32

<210> SEQ ID NO 2102
<211> LENGTH: 50
<212> TYPE: RNA
<213> ORGANISM: Homo sapiens

<400> SEQUENCE: 2102
aaauuaccca cucccgaccc ggggagguag ugacgaaaaa uaacaauaca 50

<210> SEQ ID NO 2103
<211> LENGTH: 26
<212> TYPE: RNA
<213> ORGANISM: Homo sapiens

<400> SEQUENCE: 2103
ccauaccacc cugaacgcgc ccgauc 26

<210> SEQ ID NO 2104
<211> LENGTH: 32
<212> TYPE: RNA
<213> ORGANISM: Homo sapiens

<400> SEQUENCE: 2104
gcaugggugg uucagguggua gaauucacgc cu 32

<210> SEQ ID NO 2105
<211> LENGTH: 45
<212> TYPE: RNA
<213> ORGANISM: Homo sapiens

<400> SEQUENCE: 2105
acuucggauc agaagauuga ggguucgagu cccuucgugg ucgcc 45

<210> SEQ ID NO 2106
<211> LENGTH: 42
<212> TYPE: RNA
<213> ORGANISM: Homo sapiens

<400> SEQUENCE: 2106
auagucggca uuggcaauuu uugacagucu cuacggagac ug 42

<210> SEQ ID NO 2107
<211> LENGTH: 28
<212> TYPE: RNA
<213> ORGANISM: Homo sapiens

<400> SEQUENCE: 2107
gcguuguggu auagugguga gcauagcu 28

<210> SEQ ID NO 2108
<211> LENGTH: 47
<212> TYPE: RNA
<213> ORGANISM: Homo sapiens

<400> SEQUENCE: 2108
cacccggggg gccggcggcg gcggcgacuc uggacgcgag ccgggcc 47

<210> SEQ ID NO 2109
<211> LENGTH: 26
<212> TYPE: RNA
<213> ORGANISM: Homo sapiens

<400> SEQUENCE: 2109
uaauacaugc cgacgggcgc ugaccc 26

<210> SEQ ID NO 2110
<211> LENGTH: 31
<212> TYPE: RNA
<213> ORGANISM: Homo sapiens

<400> SEQUENCE: 2110
aguaagguca gcuaaauaag cuaucggccc c                                   31

<210> SEQ ID NO 2111
<211> LENGTH: 38
<212> TYPE: RNA
<213> ORGANISM: Homo sapiens

<400> SEQUENCE: 2111
acgcgaccuc agaucagacg uggcgacccg cugaauuu                            38

<210> SEQ ID NO 2112
<211> LENGTH: 50
<212> TYPE: RNA
<213> ORGANISM: Homo sapiens

<400> SEQUENCE: 2112
aguucugggc uguagugcgc uaugccgauc ggguguccgc acuaaguucg               50

<210> SEQ ID NO 2113
<211> LENGTH: 50
<212> TYPE: RNA
<213> ORGANISM: Homo sapiens

<400> SEQUENCE: 2113
cuccucuccu acuuggauaa cugugguaau ucuagagcua auacaugccg               50

<210> SEQ ID NO 2114
<211> LENGTH: 33
<212> TYPE: RNA
<213> ORGANISM: Homo sapiens

<400> SEQUENCE: 2114
guuuccgcag uguagugguu aucacguucg ccu                                 33

<210> SEQ ID NO 2115
<211> LENGTH: 34
<212> TYPE: RNA
<213> ORGANISM: Homo sapiens

<400> SEQUENCE: 2115
ucccuggcgg ucuagugguu aggauucggc gcuc                                34

<210> SEQ ID NO 2116
<211> LENGTH: 40
<212> TYPE: RNA
<213> ORGANISM: Homo sapiens

<400> SEQUENCE: 2116
acggcccugg cggagcgcug agaagacggu cgaacuugac                          40

<210> SEQ ID NO 2117
<211> LENGTH: 26
<212> TYPE: RNA
<213> ORGANISM: Homo sapiens

<400> SEQUENCE: 2117
cgcgcgcgug uggugugcgu cggagg                                         26

<210> SEQ ID NO 2118
<211> LENGTH: 32
<212> TYPE: RNA

<213> ORGANISM: Homo sapiens

<400> SEQUENCE: 2118
gcaugggugg uucaguggua gaacucucgc cu 32

<210> SEQ ID NO 2119
<211> LENGTH: 32
<212> TYPE: RNA
<213> ORGANISM: Homo sapiens

<400> SEQUENCE: 2119
ccaagcguug gauuguucac ccacuaauag gc 32

<210> SEQ ID NO 2120
<211> LENGTH: 35
<212> TYPE: RNA
<213> ORGANISM: Homo sapiens

<400> SEQUENCE: 2120
acuggugcgg accaggggaa uccgacuguu uaauu 35

<210> SEQ ID NO 2121
<211> LENGTH: 33
<212> TYPE: RNA
<213> ORGANISM: Homo sapiens

<400> SEQUENCE: 2121
ucucuggugg ucuagugguu aggauucggc gcu 33

<210> SEQ ID NO 2122
<211> LENGTH: 50
<212> TYPE: RNA
<213> ORGANISM: Homo sapiens

<400> SEQUENCE: 2122
auugaucauc gacacuucga acgcacuugc ggccccggga uccucccggg 50

<210> SEQ ID NO 2123
<211> LENGTH: 46
<212> TYPE: RNA
<213> ORGANISM: Homo sapiens

<400> SEQUENCE: 2123
agugacgcgc augaauggau gaacgagauu cccacugucc cuaccu 46

<210> SEQ ID NO 2124
<211> LENGTH: 31
<212> TYPE: RNA
<213> ORGANISM: Homo sapiens

<400> SEQUENCE: 2124
aguaagguca gcuaaauaag cuaucgggcc a 31

<210> SEQ ID NO 2125
<211> LENGTH: 30
<212> TYPE: RNA
<213> ORGANISM: Homo sapiens

<400> SEQUENCE: 2125
ccuacuugga uaacuguggu aauucuagag 30

<210> SEQ ID NO 2126
<211> LENGTH: 40

<212> TYPE: RNA
<213> ORGANISM: Homo sapiens

<400> SEQUENCE: 2126
auuuuggauu cucagggaug gguucgauuc ucauaguccu 40

<210> SEQ ID NO 2127
<211> LENGTH: 27
<212> TYPE: RNA
<213> ORGANISM: Homo sapiens

<400> SEQUENCE: 2127
acgaaaaaua acaauacagg acucuuu 27

<210> SEQ ID NO 2128
<211> LENGTH: 46
<212> TYPE: RNA
<213> ORGANISM: Homo sapiens

<400> SEQUENCE: 2128
cucucucucu cucucucccc cgcuccccgu ccucccccu ccccgg 46

<210> SEQ ID NO 2129
<211> LENGTH: 40
<212> TYPE: RNA
<213> ORGANISM: Homo sapiens

<400> SEQUENCE: 2129
ggaugggaga ccgccuggga auaccgggug cuguaggcuu 40

<210> SEQ ID NO 2130
<211> LENGTH: 50
<212> TYPE: RNA
<213> ORGANISM: Homo sapiens

<400> SEQUENCE: 2130
cccgugcuga ucaguagugg gaucgcgccu gugaauagcc acugcacucc 50

<210> SEQ ID NO 2131
<211> LENGTH: 31
<212> TYPE: RNA
<213> ORGANISM: Homo sapiens

<400> SEQUENCE: 2131
agauuucaac uuaacuugac cgcucugacc a 31

<210> SEQ ID NO 2132
<211> LENGTH: 31
<212> TYPE: RNA
<213> ORGANISM: Homo sapiens

<400> SEQUENCE: 2132
ucccuggugg ucuagugguu agguuucggc g 31

<210> SEQ ID NO 2133
<211> LENGTH: 50
<212> TYPE: RNA
<213> ORGANISM: Homo sapiens

<400> SEQUENCE: 2133
auaacugugg uaauucuaga gcuaauacau gccgacgggc gcugaccccc 50

<210> SEQ ID NO 2134

<211> LENGTH: 29
<212> TYPE: RNA
<213> ORGANISM: Homo sapiens

<400> SEQUENCE: 2134
aauacaugcc gacgggcgcu gacccccuu 29

<210> SEQ ID NO 2135
<211> LENGTH: 27
<212> TYPE: RNA
<213> ORGANISM: Homo sapiens

<400> SEQUENCE: 2135
acuuggauaa cugugguaau ucuagag 27

<210> SEQ ID NO 2136
<211> LENGTH: 29
<212> TYPE: RNA
<213> ORGANISM: Homo sapiens

<400> SEQUENCE: 2136
cccgguaauc gcauaaaacu uaaaacuuu 29

<210> SEQ ID NO 2137
<211> LENGTH: 29
<212> TYPE: RNA
<213> ORGANISM: Homo sapiens

<400> SEQUENCE: 2137
gccgugaucg uaucgugguu aguacucug 29

<210> SEQ ID NO 2138
<211> LENGTH: 33
<212> TYPE: RNA
<213> ORGANISM: Homo sapiens

<400> SEQUENCE: 2138
gcccggcuag cucagucgga agagcauggg acu 33

<210> SEQ ID NO 2139
<211> LENGTH: 26
<212> TYPE: RNA
<213> ORGANISM: Homo sapiens

<400> SEQUENCE: 2139
cccaaaugug ggaaacucga cugcau 26

<210> SEQ ID NO 2140
<211> LENGTH: 44
<212> TYPE: RNA
<213> ORGANISM: Homo sapiens

<400> SEQUENCE: 2140 guuuucaua ucauuggucg ugguuguagu ccgugcgaga auac 44

<210> SEQ ID NO 2141
<211> LENGTH: 30
<212> TYPE: RNA
<213> ORGANISM: Homo sapiens

<400> SEQUENCE: 2141
gcauuagugg uucaguggua gaauucucgc 30

<210> SEQ ID NO 2142
<211> LENGTH: 41
<212> TYPE: RNA
<213> ORGANISM: Homo sapiens

<400> SEQUENCE: 2142
cugucacgcg ggagaccggg guucguuucc ccgacgggga g 41

<210> SEQ ID NO 2143
<211> LENGTH: 46
<212> TYPE: RNA
<213> ORGANISM: Homo sapiens

<400> SEQUENCE: 2143
cgcgcggcgc cucgccucgg ccggcgccua gcagccgacu uagaac 46

<210> SEQ ID NO 2144
<211> LENGTH: 34
<212> TYPE: RNA
<213> ORGANISM: Homo sapiens

<400> SEQUENCE: 2144
gggggauaug cucaggggua gagcauuuga cugc 34

<210> SEQ ID NO 2145
<211> LENGTH: 39
<212> TYPE: RNA
<213> ORGANISM: Homo sapiens

<400> SEQUENCE: 2145
cuuugggugc uaauggugga guuaaagacu uuuucucug 39

<210> SEQ ID NO 2146
<211> LENGTH: 47
<212> TYPE: RNA
<213> ORGANISM: Homo sapiens

<400> SEQUENCE: 2146
uguggugugc gucggagggc ggcggcggcg gcggcggcgg gggugug 47

<210> SEQ ID NO 2147
<211> LENGTH: 44
<212> TYPE: RNA
<213> ORGANISM: Homo sapiens

<400> SEQUENCE: 2147
guuaagaugg cagagcccgg uaaucgcaua aaacuuaaaa cuuu 44

<210> SEQ ID NO 2148
<211> LENGTH: 50
<212> TYPE: RNA
<213> ORGANISM: Homo sapiens

<400> SEQUENCE: 2148
gugggcagag uggugcagcg gaagcgugcu gggcccguaa cccagagguc 50

<210> SEQ ID NO 2149
<211> LENGTH: 30
<212> TYPE: RNA
<213> ORGANISM: Homo sapiens

<400> SEQUENCE: 2149
ucccuggugg ucuagugguu aggacucggc 30

<210> SEQ ID NO 2150
<211> LENGTH: 37
<212> TYPE: RNA
<213> ORGANISM: Homo sapiens

<400> SEQUENCE: 2150
ucagaagauu cuagguucga cuccuggcug gcucgcc 37

<210> SEQ ID NO 2151
<211> LENGTH: 50
<212> TYPE: RNA
<213> ORGANISM: Homo sapiens

<400> SEQUENCE: 2151
acucuuagcg guggaucacu cggcucgugc gucgaugaag aacgcagcua 50

<210> SEQ ID NO 2152
<211> LENGTH: 50
<212> TYPE: RNA
<213> ORGANISM: Homo sapiens

<400> SEQUENCE: 2152
gugggaucgc gccugugaau agccacugca cuccagccug ggcaacauag 50

<210> SEQ ID NO 2153
<211> LENGTH: 47
<212> TYPE: RNA
<213> ORGANISM: Homo sapiens

<400> SEQUENCE: 2153
uuagugucac uaaaguuggu auacaacccc ccacugcuaa auuugac 47

<210> SEQ ID NO 2154
<211> LENGTH: 35
<212> TYPE: RNA
<213> ORGANISM: Homo sapiens

<400> SEQUENCE: 2154
ccgaggggcu cucgcuucug gcgccaagcg cccgg 35

<210> SEQ ID NO 2155
<211> LENGTH: 48
<212> TYPE: RNA
<213> ORGANISM: Homo sapiens

<400> SEQUENCE: 2155
gcggcgacuc uggacgcgag ccgggcccuu cccguggauc gccccagc 48

<210> SEQ ID NO 2156
<211> LENGTH: 34
<212> TYPE: RNA
<213> ORGANISM: Homo sapiens

<400> SEQUENCE: 2156
ccgaggggcu cucgcuucug gcgccaagcg cccg 34

<210> SEQ ID NO 2157
<211> LENGTH: 50
<212> TYPE: RNA
<213> ORGANISM: Homo sapiens

<400> SEQUENCE: 2157
accucgggcc gaucgcacgc cccccguggc ggcgacgacc cauucgaacg 50

<210> SEQ ID NO 2158
<211> LENGTH: 50
<212> TYPE: RNA
<213> ORGANISM: Homo sapiens

<400> SEQUENCE: 2158 cuucggguc ggguuucgu acguagcaga gcagcucccu cgcugcgauc                50

<210> SEQ ID NO 2159
<211> LENGTH: 28
<212> TYPE: RNA
<213> ORGANISM: Homo sapiens

<400> SEQUENCE: 2159
ccauaugguc uagcgguuag gauuccug                                      28

<210> SEQ ID NO 2160
<211> LENGTH: 40
<212> TYPE: RNA
<213> ORGANISM: Homo sapiens

<400> SEQUENCE: 2160
ccuacuugga uaacuguggu aauucuagag cuaauacaug                         40

<210> SEQ ID NO 2161
<211> LENGTH: 39
<212> TYPE: RNA
<213> ORGANISM: Homo sapiens

<400> SEQUENCE: 2161
cauuaaucaa gaacgaaagu cggagguucg aagacgauc                          39

<210> SEQ ID NO 2162
<211> LENGTH: 34
<212> TYPE: RNA
<213> ORGANISM: Homo sapiens

<400> SEQUENCE: 2162 gcauggugg uucaguggua gaauucucgc cuug                                34

<210> SEQ ID NO 2163
<211> LENGTH: 46
<212> TYPE: RNA
<213> ORGANISM: Homo sapiens

<400> SEQUENCE: 2163
auuccggauc agaagauuga ggguucgagu cccuucgugg ucgcca                  46

<210> SEQ ID NO 2164
<211> LENGTH: 43
<212> TYPE: RNA
<213> ORGANISM: Homo sapiens

<400> SEQUENCE: 2164
uuuucauauc auuggucgug guuguagucc gugcgagaau acc                     43

<210> SEQ ID NO 2165
<211> LENGTH: 34
<212> TYPE: RNA
<213> ORGANISM: Homo sapiens

<400> SEQUENCE: 2165

```
gggggcauag cucaguggua gagcauuuga cugc                         34

<210> SEQ ID NO 2166
<211> LENGTH: 27
<212> TYPE: RNA
<213> ORGANISM: Homo sapiens

<400> SEQUENCE: 2166

cccaaaugug ggaaacucga cugcaua                                 27

<210> SEQ ID NO 2167
<211> LENGTH: 30
<212> TYPE: RNA
<213> ORGANISM: Homo sapiens

<400> SEQUENCE: 2167

cccaccccac gucucgucgc gcgcgcgucc                              30

<210> SEQ ID NO 2168
<211> LENGTH: 50
<212> TYPE: RNA
<213> ORGANISM: Homo sapiens

<400> SEQUENCE: 2168

auugaucauc gacacuucgc acgcacuugc ggccccgggu uccucccggg        50

<210> SEQ ID NO 2169
<211> LENGTH: 27
<212> TYPE: RNA
<213> ORGANISM: Homo sapiens

<400> SEQUENCE: 2169

gcguuguggu auagugguga gcauagc                                 27

<210> SEQ ID NO 2170
<211> LENGTH: 49
<212> TYPE: RNA
<213> ORGANISM: Homo sapiens

<400> SEQUENCE: 2170

aauugcagga cacauugauc aucgacacuu cgaacgcacu ugcggcccc         49

<210> SEQ ID NO 2171
<211> LENGTH: 31
<212> TYPE: RNA
<213> ORGANISM: Homo sapiens

<400> SEQUENCE: 2171

ggccgucauc guauaguggu uaguacucug c                            31

<210> SEQ ID NO 2172
<211> LENGTH: 32
<212> TYPE: RNA
<213> ORGANISM: Homo sapiens

<400> SEQUENCE: 2172

gcauuggugg uacaguggua gaauucucgc cu                           32

<210> SEQ ID NO 2173
<211> LENGTH: 37
<212> TYPE: RNA
<213> ORGANISM: Homo sapiens

<400> SEQUENCE: 2173
```

ugggagaccg ccugggaaua ccgggugcug uaggcuu 37

<210> SEQ ID NO 2174
<211> LENGTH: 44
<212> TYPE: RNA
<213> ORGANISM: Homo sapiens

<400> SEQUENCE: 2174
cagagaauag uuuaaauuag aaucuuagcu uugggugcua augg 44

<210> SEQ ID NO 2175
<211> LENGTH: 29
<212> TYPE: RNA
<213> ORGANISM: Homo sapiens

<400> SEQUENCE: 2175
gguuccaugg uguaauggug agcacucug 29

<210> SEQ ID NO 2176
<211> LENGTH: 28
<212> TYPE: RNA
<213> ORGANISM: Homo sapiens

<400> SEQUENCE: 2176
cuuuuugauc cuucgauguc ggcucuuc 28

<210> SEQ ID NO 2177
<211> LENGTH: 42
<212> TYPE: RNA
<213> ORGANISM: Homo sapiens

<400> SEQUENCE: 2177
ccauaccacc cugaacgcgc ccgaucucgu cugaucucgg aa 42

<210> SEQ ID NO 2178
<211> LENGTH: 32
<212> TYPE: RNA
<213> ORGANISM: Homo sapiens

<400> SEQUENCE: 2178
aaaucaguua ugguuccuuu ggucgcucgc uc 32

<210> SEQ ID NO 2179
<211> LENGTH: 44
<212> TYPE: RNA
<213> ORGANISM: Homo sapiens

<400> SEQUENCE: 2179
acuuacacuu aggagauuuc aacuuaacuu gaccgcucug acca 44

<210> SEQ ID NO 2180
<211> LENGTH: 45
<212> TYPE: RNA
<213> ORGANISM: Homo sapiens

<400> SEQUENCE: 2180
acagcaguug aacaugggucagucggucccu gagagauggg cgagc 45

<210> SEQ ID NO 2181
<211> LENGTH: 41
<212> TYPE: RNA
<213> ORGANISM: Homo sapiens

<400> SEQUENCE: 2181
uucauuaauc aagaacgaaa gucggagguu cgaagacgau c 41

<210> SEQ ID NO 2182
<211> LENGTH: 49
<212> TYPE: RNA
<213> ORGANISM: Homo sapiens

<400> SEQUENCE: 2182
cgauuugucu gguuaauucc gauaacgaac gagacucugg caugcuaac 49

<210> SEQ ID NO 2183
<211> LENGTH: 29
<212> TYPE: RNA
<213> ORGANISM: Homo sapiens

<400> SEQUENCE: 2183
ccguaacuuc gggauaagga uuggcucua 29

<210> SEQ ID NO 2184
<211> LENGTH: 39
<212> TYPE: RNA
<213> ORGANISM: Homo sapiens

<400> SEQUENCE: 2184
guuuuucaua ucauuggucg ugguuguagu ccgugcgag 39

<210> SEQ ID NO 2185
<211> LENGTH: 41
<212> TYPE: RNA
<213> ORGANISM: Homo sapiens

<400> SEQUENCE: 2185
aacuuacacu uaggagauuu caacuuaacu ugaccgcucu g 41

<210> SEQ ID NO 2186
<211> LENGTH: 32
<212> TYPE: RNA
<213> ORGANISM: Homo sapiens

<400> SEQUENCE: 2186
gcaugggugg aucaguggua gaauucucgc cu 32

<210> SEQ ID NO 2187
<211> LENGTH: 36
<212> TYPE: RNA
<213> ORGANISM: Homo sapiens

<400> SEQUENCE: 2187
ccuagcagcc gacuuagaac uggugcggac cagggg 36

<210> SEQ ID NO 2188
<211> LENGTH: 50
<212> TYPE: RNA
<213> ORGANISM: Homo sapiens

<400> SEQUENCE: 2188
agugugaguc ugaaaccaau uuuuugaggc cuugcguuuc uuagcagggc 50

<210> SEQ ID NO 2189
<211> LENGTH: 38
<212> TYPE: RNA
<213> ORGANISM: Homo sapiens

```
<400> SEQUENCE: 2189

ucugaggguc caggguucag gucccugucc aggcgcca                              38

<210> SEQ ID NO 2190
<211> LENGTH: 44
<212> TYPE: RNA
<213> ORGANISM: Homo sapiens

<400> SEQUENCE: 2190

uaccugguug auccugccag uagcauaugc uugucucaaa gauu                      44

<210> SEQ ID NO 2191
<211> LENGTH: 27
<212> TYPE: RNA
<213> ORGANISM: Homo sapiens

<400> SEQUENCE: 2191

cuggugcgga ccaggggaau ccgacug                                         27

<210> SEQ ID NO 2192
<211> LENGTH: 34
<212> TYPE: RNA
<213> ORGANISM: Homo sapiens

<400> SEQUENCE: 2192

acggcccugg cggagcgcug agaagacggu cgaa                                 34

<210> SEQ ID NO 2193
<211> LENGTH: 27
<212> TYPE: RNA
<213> ORGANISM: Homo sapiens

<400> SEQUENCE: 2193

cgccccgggc gggucgcgcc gucgggc                                         27

<210> SEQ ID NO 2194
<211> LENGTH: 43
<212> TYPE: RNA
<213> ORGANISM: Homo sapiens

<400> SEQUENCE: 2194

cuuucaccgc cgcggcccgg guucgauucc cggucaggga acc                       43

<210> SEQ ID NO 2195
<211> LENGTH: 50
<212> TYPE: RNA
<213> ORGANISM: Homo sapiens

<400> SEQUENCE: 2195

aucaguagug ggaucgcgcc ugugaauagc cacugcacuc cagccugagc                50

<210> SEQ ID NO 2196
<211> LENGTH: 36
<212> TYPE: RNA
<213> ORGANISM: Homo sapiens

<400> SEQUENCE: 2196

ccgggagacc gggguucgau uccccgacgg ggagcc                               36

<210> SEQ ID NO 2197
<211> LENGTH: 39
<212> TYPE: RNA
```

<213> ORGANISM: Homo sapiens

<400> SEQUENCE: 2197
cugccacgcg ggaggcccgg guucgauucc cggcccaug 39

<210> SEQ ID NO 2198
<211> LENGTH: 33
<212> TYPE: RNA
<213> ORGANISM: Homo sapiens

<400> SEQUENCE: 2198
agcagccgac uuagaacugg ugcggaccag ggg 33

<210> SEQ ID NO 2199
<211> LENGTH: 33
<212> TYPE: RNA
<213> ORGANISM: Homo sapiens

<400> SEQUENCE: 2199
gcuucucuag uguagugguu aucacguucg ccu 33

<210> SEQ ID NO 2200
<211> LENGTH: 34
<212> TYPE: RNA
<213> ORGANISM: Homo sapiens

<400> SEQUENCE: 2200
gcaugggagg uucaguggua gaauucucgc cugc 34

<210> SEQ ID NO 2201
<211> LENGTH: 32
<212> TYPE: RNA
<213> ORGANISM: Homo sapiens

<400> SEQUENCE: 2201
ccaagcguug gauuguucac ccacuaauag cg 32

<210> SEQ ID NO 2202
<211> LENGTH: 44
<212> TYPE: RNA
<213> ORGANISM: Homo sapiens

<400> SEQUENCE: 2202
acuuuuaauc ugagggucca ggguucaggu cccuguucgg gcgc 44

<210> SEQ ID NO 2203
<211> LENGTH: 46
<212> TYPE: RNA
<213> ORGANISM: Homo sapiens

<400> SEQUENCE: 2203
caccagugau gaguugaaua ccgccccagu cugaucaaug ugugac 46

<210> SEQ ID NO 2204
<211> LENGTH: 29
<212> TYPE: RNA
<213> ORGANISM: Homo sapiens

<400> SEQUENCE: 2204
ugguggaguu aaagacuuuu ucucugacc 29

<210> SEQ ID NO 2205
<211> LENGTH: 36

<212> TYPE: RNA
<213> ORGANISM: Homo sapiens

<400> SEQUENCE: 2205
cccugcgggc cgccggugaa auaccacuac ucugau 36

<210> SEQ ID NO 2206
<211> LENGTH: 50
<212> TYPE: RNA
<213> ORGANISM: Homo sapiens

<400> SEQUENCE: 2206
gggcggugau gaccccaaca ugccaucuga gugucggugc ugaaauccag 50

<210> SEQ ID NO 2207
<211> LENGTH: 33
<212> TYPE: RNA
<213> ORGANISM: Homo sapiens

<400> SEQUENCE: 2207
ucccuggucg ucuaguggau aggauucggc gcu 33

<210> SEQ ID NO 2208
<211> LENGTH: 50
<212> TYPE: RNA
<213> ORGANISM: Homo sapiens

<400> SEQUENCE: 2208
cgacucuuag cgguggauca cucggcucgc gcgucgauga agaacgcagc 50

<210> SEQ ID NO 2209
<211> LENGTH: 27
<212> TYPE: RNA
<213> ORGANISM: Homo sapiens

<400> SEQUENCE: 2209
aggaggggug aaccggccca ggucgga 27

<210> SEQ ID NO 2210
<211> LENGTH: 30
<212> TYPE: RNA
<213> ORGANISM: Homo sapiens

<400> SEQUENCE: 2210
ucccuggugg ucuaguggau aggcuucggc 30

<210> SEQ ID NO 2211
<211> LENGTH: 46
<212> TYPE: RNA
<213> ORGANISM: Homo sapiens

<400> SEQUENCE: 2211
cuuuacacgc agaagguccu ggguucgagc cccaguggaa ccacca 46

<210> SEQ ID NO 2212
<211> LENGTH: 27
<212> TYPE: RNA
<213> ORGANISM: Homo sapiens

<400> SEQUENCE: 2212
cuacuuggau aacuguggua auucuag 27

<210> SEQ ID NO 2213

<211> LENGTH: 32
<212> TYPE: RNA
<213> ORGANISM: Homo sapiens

<400> SEQUENCE: 2213
gcaggggugg uucaguggua gaauucucgc cu 32

<210> SEQ ID NO 2214
<211> LENGTH: 45
<212> TYPE: RNA
<213> ORGANISM: Homo sapiens

<400> SEQUENCE: 2214
acuuuuaauc ugagggucca ggguucaagu cccuguucgg gcgcc 45

<210> SEQ ID NO 2215
<211> LENGTH: 50
<212> TYPE: RNA
<213> ORGANISM: Homo sapiens

<400> SEQUENCE: 2215
cgacucuuag cgguggauca cucggcucgu gcgucgauga cgaacgcagc 50

<210> SEQ ID NO 2216
<211> LENGTH: 35
<212> TYPE: RNA
<213> ORGANISM: Homo sapiens

<400> SEQUENCE: 2216
cgggagaccg ggguucaauu ccccgacggg gagcc 35

<210> SEQ ID NO 2217
<211> LENGTH: 46
<212> TYPE: RNA
<213> ORGANISM: Homo sapiens

<400> SEQUENCE: 2217
cgacucuuag cgguggauca cucggcucgu gcgucgauga agaacg 46

<210> SEQ ID NO 2218
<211> LENGTH: 48
<212> TYPE: RNA
<213> ORGANISM: Homo sapiens

<400> SEQUENCE: 2218
aggacacauu gaucaucgac acuucgaacg cacuugcggc cccgggcu 48

<210> SEQ ID NO 2219
<211> LENGTH: 26
<212> TYPE: RNA
<213> ORGANISM: Homo sapiens

<400> SEQUENCE: 2219
cucggccgau cgaaagggag ucgggu 26

<210> SEQ ID NO 2220
<211> LENGTH: 36
<212> TYPE: RNA
<213> ORGANISM: Homo sapiens

<400> SEQUENCE: 2220
gcgggagacc gggguucguu uccccgacgg ggagcc 36

```
<210> SEQ ID NO 2221
<211> LENGTH: 36
<212> TYPE: RNA
<213> ORGANISM: Homo sapiens

<400> SEQUENCE: 2221

ucugauacgu ccucuauccg aggacaauau auuaaa                              36

<210> SEQ ID NO 2222
<211> LENGTH: 47
<212> TYPE: RNA
<213> ORGANISM: Homo sapiens

<400> SEQUENCE: 2222

cguagacgac cugcuucugg gucgggguuu cguacguagc agagcag                  47

<210> SEQ ID NO 2223
<211> LENGTH: 33
<212> TYPE: RNA
<213> ORGANISM: Homo sapiens

<400> SEQUENCE: 2223

guuucccuag uguagugguu aucacguucg ccu                                 33

<210> SEQ ID NO 2224
<211> LENGTH: 39
<212> TYPE: RNA
<213> ORGANISM: Homo sapiens

<400> SEQUENCE: 2224

auuauugaag uagauccuga cacuaaggaa augcugaag                           39

<210> SEQ ID NO 2225
<211> LENGTH: 50
<212> TYPE: RNA
<213> ORGANISM: Homo sapiens

<400> SEQUENCE: 2225

uuggugacuc uagauaaccu cgggccgauc gcacgccccc cguggcggcg               50

<210> SEQ ID NO 2226
<211> LENGTH: 29
<212> TYPE: RNA
<213> ORGANISM: Homo sapiens

<400> SEQUENCE: 2226

gccgugaucg uauagugguu aguaaucug                                      29

<210> SEQ ID NO 2227
<211> LENGTH: 28
<212> TYPE: RNA
<213> ORGANISM: Homo sapiens

<400> SEQUENCE: 2227

gcuaauacau gccgacgggc gcugaccc                                       28

<210> SEQ ID NO 2228
<211> LENGTH: 49
<212> TYPE: RNA
<213> ORGANISM: Homo sapiens

<400> SEQUENCE: 2228

gaaacgaucu caaccuauuc ucaaacuuua aaugggguaag aagcccggc               49
```

<210> SEQ ID NO 2229
<211> LENGTH: 50
<212> TYPE: RNA
<213> ORGANISM: Homo sapiens

<400> SEQUENCE: 2229
uuccgauaac gaacgagacu cuggcaugcu aacuaguuac gcgacccccg 50

<210> SEQ ID NO 2230
<211> LENGTH: 48
<212> TYPE: RNA
<213> ORGANISM: Homo sapiens

<400> SEQUENCE: 2230
cucucucucu cucuccccg cuccccgucc uccccccucc ccgggga 48

<210> SEQ ID NO 2231
<211> LENGTH: 43
<212> TYPE: RNA
<213> ORGANISM: Homo sapiens

<400> SEQUENCE: 2231
uaugugcuug gcugaggagc caaugggcg aagcuaccau cug 43

<210> SEQ ID NO 2232
<211> LENGTH: 34
<212> TYPE: RNA
<213> ORGANISM: Homo sapiens

<400> SEQUENCE: 2232
guuuccguag uguagugguu aucacauucg ccuc 34

<210> SEQ ID NO 2233
<211> LENGTH: 43
<212> TYPE: RNA
<213> ORGANISM: Homo sapiens

<400> SEQUENCE: 2233
aaguguagua ucuguucuua ucaguuuaau aucugauacg ucc 43

<210> SEQ ID NO 2234
<211> LENGTH: 32
<212> TYPE: RNA
<213> ORGANISM: Homo sapiens

<400> SEQUENCE: 2234
uuaaguuaaa gauuaagaga accaacaccu cu 32

<210> SEQ ID NO 2235
<211> LENGTH: 46
<212> TYPE: RNA
<213> ORGANISM: Homo sapiens

<400> SEQUENCE: 2235
cgcgaccuca gaucagacgu ggcgacccgc ugaauuuaag cauauu 46

<210> SEQ ID NO 2236
<211> LENGTH: 35
<212> TYPE: RNA
<213> ORGANISM: Homo sapiens

<400> SEQUENCE: 2236
aaucaagaac gaaagucgga gguucgaaga cgauc 35

<210> SEQ ID NO 2237
<211> LENGTH: 50
<212> TYPE: RNA
<213> ORGANISM: Homo sapiens

<400> SEQUENCE: 2237
cgagugugag ucugaaacca auuuuuugag gccuugcguu ucuuagcagg 50

<210> SEQ ID NO 2238
<211> LENGTH: 30
<212> TYPE: RNA
<213> ORGANISM: Homo sapiens

<400> SEQUENCE: 2238
uaggaugggg ugugauaggu ggcacggagg 30

<210> SEQ ID NO 2239
<211> LENGTH: 28
<212> TYPE: RNA
<213> ORGANISM: Homo sapiens

<400> SEQUENCE: 2239
uuuugauccu ucgaugucgg cucuuccu 28

<210> SEQ ID NO 2240
<211> LENGTH: 43
<212> TYPE: RNA
<213> ORGANISM: Homo sapiens

<400> SEQUENCE: 2240
cgggucggag uuagcucaag cgguuaccuc cucaugccgg acu 43

<210> SEQ ID NO 2241
<211> LENGTH: 32
<212> TYPE: RNA
<213> ORGANISM: Homo sapiens

<400> SEQUENCE: 2241
gcaugggugg uucagugcua gaauucucgc cu 32

<210> SEQ ID NO 2242
<211> LENGTH: 42
<212> TYPE: RNA
<213> ORGANISM: Homo sapiens

<400> SEQUENCE: 2242
cccggcggcg ggggcacggu cccccgcgag gggggcccgg gc 42

<210> SEQ ID NO 2243
<211> LENGTH: 45
<212> TYPE: RNA
<213> ORGANISM: Homo sapiens

<400> SEQUENCE: 2243
acgcaguuuu auccgguaaa gcgaaugauu agaggucuug gggcc 45

<210> SEQ ID NO 2244
<211> LENGTH: 49
<212> TYPE: RNA
<213> ORGANISM: Homo sapiens

<400> SEQUENCE: 2244

```
guaacaaggu uuccguaggu gaaccugcgg aaggaucauu aacggagcc              49

<210> SEQ ID NO 2245
<211> LENGTH: 50
<212> TYPE: RNA
<213> ORGANISM: Homo sapiens

<400> SEQUENCE: 2245

caagaacugc uaacucaugc ccccaugucu aacaacaugg cuuucucacc            50

<210> SEQ ID NO 2246
<211> LENGTH: 40
<212> TYPE: RNA
<213> ORGANISM: Homo sapiens

<400> SEQUENCE: 2246

cuguuaacua aguguuugug gguuuaaguc ccauuggucu                       40

<210> SEQ ID NO 2247
<211> LENGTH: 42
<212> TYPE: RNA
<213> ORGANISM: Homo sapiens

<400> SEQUENCE: 2247

aacgaacgag acucuggcau gcuaacuagu uacgcgaccc cc                    42

<210> SEQ ID NO 2248
<211> LENGTH: 34
<212> TYPE: RNA
<213> ORGANISM: Homo sapiens

<400> SEQUENCE: 2248

ucacuggugg ucuagugguu aggauucggc gcuc                             34

<210> SEQ ID NO 2249
<211> LENGTH: 50
<212> TYPE: RNA
<213> ORGANISM: Homo sapiens

<400> SEQUENCE: 2249

ccauugauga ucguucuucu cuccguauug gggagugaga gggagagaac            50

<210> SEQ ID NO 2250
<211> LENGTH: 32
<212> TYPE: RNA
<213> ORGANISM: Homo sapiens

<400> SEQUENCE: 2250

aagccggauc cguaacuucg ggauaaggau ug                               32

<210> SEQ ID NO 2251
<211> LENGTH: 41
<212> TYPE: RNA
<213> ORGANISM: Homo sapiens

<400> SEQUENCE: 2251

ccaagcguug gauuguucac ccacuaauag ggaacgugag c                     41

<210> SEQ ID NO 2252
<211> LENGTH: 34
<212> TYPE: RNA
<213> ORGANISM: Homo sapiens

<400> SEQUENCE: 2252
```

cggucguccg accugguau aggggcgaaa gacu 34

<210> SEQ ID NO 2253
<211> LENGTH: 49
<212> TYPE: RNA
<213> ORGANISM: Homo sapiens

<400> SEQUENCE: 2253
gugucacuaa aguugguaua caacccccca cugcuaaauu ugacuggcu 49

<210> SEQ ID NO 2254
<211> LENGTH: 39
<212> TYPE: RNA
<213> ORGANISM: Homo sapiens

<400> SEQUENCE: 2254
aauuagugac gcgcaugaau ggaugaacga gauucccac 39

<210> SEQ ID NO 2255
<211> LENGTH: 46
<212> TYPE: RNA
<213> ORGANISM: Homo sapiens

<400> SEQUENCE: 2255
acugcggauc agaagauucu agguucgacu ccuggcuggc ucgcca 46

<210> SEQ ID NO 2256
<211> LENGTH: 33
<212> TYPE: RNA
<213> ORGANISM: Homo sapiens

<400> SEQUENCE: 2256
gcccggcuag cucagucgga agagcaugag acu 33

<210> SEQ ID NO 2257
<211> LENGTH: 34
<212> TYPE: RNA
<213> ORGANISM: Homo sapiens

<400> SEQUENCE: 2257
ucccuggugg ucuagugguu aggauucggc gcug 34

<210> SEQ ID NO 2258
<211> LENGTH: 50
<212> TYPE: RNA
<213> ORGANISM: Homo sapiens

<400> SEQUENCE: 2258
cugauacguc cucuauccga ggacaauaua uuaaauggau uuuuggagca 50

<210> SEQ ID NO 2259
<211> LENGTH: 35
<212> TYPE: RNA
<213> ORGANISM: Homo sapiens

<400> SEQUENCE: 2259
cacgcgggag gcccggguuc guuucccggc ccaug 35

<210> SEQ ID NO 2260
<211> LENGTH: 32
<212> TYPE: RNA
<213> ORGANISM: Homo sapiens

<400> SEQUENCE: 2260
ggcucguugg ucuaggggua ugauucucgc uu 32

<210> SEQ ID NO 2261
<211> LENGTH: 50
<212> TYPE: RNA
<213> ORGANISM: Homo sapiens

<400> SEQUENCE: 2261
cucuuagcgg uggaucacuc ggcucgugcg ucgaugaaga acgcagcuag 50

<210> SEQ ID NO 2262
<211> LENGTH: 31
<212> TYPE: RNA
<213> ORGANISM: Homo sapiens

<400> SEQUENCE: 2262
aguaagguca gcuaaauaag cuaucgcgcc c 31

<210> SEQ ID NO 2263
<211> LENGTH: 38
<212> TYPE: RNA
<213> ORGANISM: Homo sapiens

<400> SEQUENCE: 2263
uucaaagguu gugguucga gucccaccag agucgcca 38

<210> SEQ ID NO 2264
<211> LENGTH: 50
<212> TYPE: RNA
<213> ORGANISM: Homo sapiens

<400> SEQUENCE: 2264
cacggcccug gcggagcgcu gagaagacgg ucgaacuuga cuaucuagag 50

<210> SEQ ID NO 2265
<211> LENGTH: 50
<212> TYPE: RNA
<213> ORGANISM: Homo sapiens

<400> SEQUENCE: 2265
cucgggccga ucgcacgccc cccguggcgg cgacgaccca uucgaacguc 50

<210> SEQ ID NO 2266
<211> LENGTH: 34
<212> TYPE: RNA
<213> ORGANISM: Homo sapiens

<400> SEQUENCE: 2266
caagcguugg auuguucacc cacuaauagg gaac 34

<210> SEQ ID NO 2267
<211> LENGTH: 50
<212> TYPE: RNA
<213> ORGANISM: Homo sapiens

<400> SEQUENCE: 2267
aguugauuag ggugcuuagc uguuaacuaa guguuugugg guuuaagucc 50

<210> SEQ ID NO 2268
<211> LENGTH: 32
<212> TYPE: RNA
<213> ORGANISM: Homo sapiens

<400> SEQUENCE: 2268
gcuugggugg uucaguggua gaauucucgc cu 32

<210> SEQ ID NO 2269
<211> LENGTH: 50
<212> TYPE: RNA
<213> ORGANISM: Homo sapiens

<400> SEQUENCE: 2269
uagugguuag gauucggcgc ucucaccgcc gcggcccggg uucgauuccc 50

<210> SEQ ID NO 2270
<211> LENGTH: 39
<212> TYPE: RNA
<213> ORGANISM: Homo sapiens

<400> SEQUENCE: 2270
auugugaagc agaauucacc aagcguugga uuguucacc 39

<210> SEQ ID NO 2271
<211> LENGTH: 36
<212> TYPE: RNA
<213> ORGANISM: Homo sapiens

<400> SEQUENCE: 2271
cuaauuagug acgcgcauga auggaugaac gagauu 36

<210> SEQ ID NO 2272
<211> LENGTH: 38
<212> TYPE: RNA
<213> ORGANISM: Homo sapiens

<400> SEQUENCE: 2272
ccgaaagguu ggugguucgu gcccacccag ggacgcca 38

<210> SEQ ID NO 2273
<211> LENGTH: 50
<212> TYPE: RNA
<213> ORGANISM: Homo sapiens

<400> SEQUENCE: 2273
ccucguacga cucuuagcgg uggaucacuc ggcucgugcg ucgaugaaga 50

<210> SEQ ID NO 2274
<211> LENGTH: 48
<212> TYPE: RNA
<213> ORGANISM: Homo sapiens

<400> SEQUENCE: 2274
aagaagaccc uguugagcuu gacucuaguc uggcacggug aagagaca 48

<210> SEQ ID NO 2275
<211> LENGTH: 50
<212> TYPE: RNA
<213> ORGANISM: Homo sapiens

<400> SEQUENCE: 2275
aauugcagga cacauugauc aucgacacuu cgaacgcacu ugcggcaccg 50

<210> SEQ ID NO 2276
<211> LENGTH: 44
<212> TYPE: RNA

<213> ORGANISM: Homo sapiens

<400> SEQUENCE: 2276
cacauugauc aucgacacuu cgaacgcacu ugcggccccg gguu 44

<210> SEQ ID NO 2277
<211> LENGTH: 33
<212> TYPE: RNA
<213> ORGANISM: Homo sapiens

<400> SEQUENCE: 2277
uaggauggag ugugauaggu ggcacggaga auu 33

<210> SEQ ID NO 2278
<211> LENGTH: 37
<212> TYPE: RNA
<213> ORGANISM: Homo sapiens

<400> SEQUENCE: 2278
agccgugauc guauaguggu uaguacucug cguugua 37

<210> SEQ ID NO 2279
<211> LENGTH: 36
<212> TYPE: RNA
<213> ORGANISM: Homo sapiens

<400> SEQUENCE: 2279
uaggaugggg ugugauaggu ggcacggaga auuuug 36

<210> SEQ ID NO 2280
<211> LENGTH: 30
<212> TYPE: RNA
<213> ORGANISM: Homo sapiens

<400> SEQUENCE: 2280
auuggugguu caguggauaga auucucgccu 30

<210> SEQ ID NO 2281
<211> LENGTH: 29
<212> TYPE: RNA
<213> ORGANISM: Homo sapiens

<400> SEQUENCE: 2281
uaggcugggg ugugauaggu ggcacggag 29

<210> SEQ ID NO 2282
<211> LENGTH: 43
<212> TYPE: RNA
<213> ORGANISM: Homo sapiens

<400> SEQUENCE: 2282
cugucacgcg ggagaccggg guucguuucc ccgacgggga gcc 43

<210> SEQ ID NO 2283
<211> LENGTH: 32
<212> TYPE: RNA
<213> ORGANISM: Homo sapiens

<400> SEQUENCE: 2283
gcauuggugg uucagugaua gaauucucgc cu 32

<210> SEQ ID NO 2284
<211> LENGTH: 44

```
<212> TYPE: RNA
<213> ORGANISM: Homo sapiens

<400> SEQUENCE: 2284

cugccacgcg ggaggcccgg guucguuucc cggccaaugc acca                44

<210> SEQ ID NO 2285
<211> LENGTH: 36
<212> TYPE: RNA
<213> ORGANISM: Homo sapiens

<400> SEQUENCE: 2285

acggcccugg cggagcgcug agaagacggu cgaacu                         36

<210> SEQ ID NO 2286
<211> LENGTH: 45
<212> TYPE: RNA
<213> ORGANISM: Homo sapiens

<400> SEQUENCE: 2286

cucccucgcu gcgaucuauu gaaagucagc ccucgacaca agggu               45

<210> SEQ ID NO 2287
<211> LENGTH: 50
<212> TYPE: RNA
<213> ORGANISM: Homo sapiens

<400> SEQUENCE: 2287

ccaagcguug gauuguucac ccacuaauag ggaacgugag cuggguuuag          50

<210> SEQ ID NO 2288
<211> LENGTH: 38
<212> TYPE: RNA
<213> ORGANISM: Homo sapiens

<400> SEQUENCE: 2288

cucucccccg cuccccgucc ucccccucc ccggggga                        38

<210> SEQ ID NO 2289
<211> LENGTH: 31
<212> TYPE: RNA
<213> ORGANISM: Homo sapiens

<400> SEQUENCE: 2289

ucccuggugg ucuaguggau aggauucggc g                              31

<210> SEQ ID NO 2290
<211> LENGTH: 31
<212> TYPE: RNA
<213> ORGANISM: Homo sapiens

<400> SEQUENCE: 2290

uccuuggugg ucuagugguu aggauucggc g                              31

<210> SEQ ID NO 2291
<211> LENGTH: 43
<212> TYPE: RNA
<213> ORGANISM: Homo sapiens

<400> SEQUENCE: 2291

ggccccgggu uccucccggg gcuacgccug ucugagcguc gcu                 43

<210> SEQ ID NO 2292
```

<211> LENGTH: 32
<212> TYPE: RNA
<213> ORGANISM: Homo sapiens

<400> SEQUENCE: 2292
gcauuggugg uucaguggua gaauucucgg cu 32

<210> SEQ ID NO 2293
<211> LENGTH: 31
<212> TYPE: RNA
<213> ORGANISM: Homo sapiens

<400> SEQUENCE: 2293
cucggcgcgc ggcggcggcg gcggcggcgg c 31

<210> SEQ ID NO 2294
<211> LENGTH: 31
<212> TYPE: RNA
<213> ORGANISM: Homo sapiens

<400> SEQUENCE: 2294
uaggaugggg ugugauagga ggcacggaga a 31

<210> SEQ ID NO 2295
<211> LENGTH: 50
<212> TYPE: RNA
<213> ORGANISM: Homo sapiens

<400> SEQUENCE: 2295
ugcgggccgc cggugaaaua ccacuacucu gaucguuuuu ucacugaccc 50

<210> SEQ ID NO 2296
<211> LENGTH: 50
<212> TYPE: RNA
<213> ORGANISM: Homo sapiens

<400> SEQUENCE: 2296
uaacuaugac ucucuuaagg uagccaaaug ccucgucauc uaauuaguga 50

<210> SEQ ID NO 2297
<211> LENGTH: 33
<212> TYPE: RNA
<213> ORGANISM: Homo sapiens

<400> SEQUENCE: 2297
guuuccguag uguaguggcu aucacguucg ccu 33

<210> SEQ ID NO 2298
<211> LENGTH: 43
<212> TYPE: RNA
<213> ORGANISM: Homo sapiens

<400> SEQUENCE: 2298
auugugaauc ugacaacagc ggcuuacgac cccuuauuua ccc 43

<210> SEQ ID NO 2299
<211> LENGTH: 34
<212> TYPE: RNA
<213> ORGANISM: Homo sapiens

<400> SEQUENCE: 2299
gguagugacg aaaaauaaca auacaggacu cuuu 34

<210> SEQ ID NO 2300
<211> LENGTH: 40
<212> TYPE: RNA
<213> ORGANISM: Homo sapiens

<400> SEQUENCE: 2300
aacgagaacu uugaaggccg aaguggagaa ggguuccaug 40

<210> SEQ ID NO 2301
<211> LENGTH: 36
<212> TYPE: RNA
<213> ORGANISM: Homo sapiens

<400> SEQUENCE: 2301
cgguggauca cucggcucgu gcgucgauga agaacg 36

<210> SEQ ID NO 2302
<211> LENGTH: 30
<212> TYPE: RNA
<213> ORGANISM: Homo sapiens

<400> SEQUENCE: 2302
gaccgcgugg ccuaauggau aaggcgucug 30

<210> SEQ ID NO 2303
<211> LENGTH: 45
<212> TYPE: RNA
<213> ORGANISM: Homo sapiens

<400> SEQUENCE: 2303
aaacgagaac uuugaaggcc gaaguggaga aggguuccau gugaa 45

<210> SEQ ID NO 2304
<211> LENGTH: 26
<212> TYPE: RNA
<213> ORGANISM: Homo sapiens

<400> SEQUENCE: 2304
gggguucgau uccccgacgg ggagcc 26

<210> SEQ ID NO 2305
<211> LENGTH: 39
<212> TYPE: RNA
<213> ORGANISM: Homo sapiens

<400> SEQUENCE: 2305
cuguuaacua aguguuugug gguuuaaguc ccauugguc 39

<210> SEQ ID NO 2306
<211> LENGTH: 29
<212> TYPE: RNA
<213> ORGANISM: Homo sapiens

<400> SEQUENCE: 2306
gcuuccguag uguaguggu aucacguuc 29

<210> SEQ ID NO 2307
<211> LENGTH: 38
<212> TYPE: RNA
<213> ORGANISM: Homo sapiens

<400> SEQUENCE: 2307
cuuuuugauc cuucgauguc ggcucuuccu aucauugu 38

<210> SEQ ID NO 2308
<211> LENGTH: 37
<212> TYPE: RNA
<213> ORGANISM: Homo sapiens

<400> SEQUENCE: 2308
cauuaaucaa gaacgaaagu cggagguucg aagacga 37

<210> SEQ ID NO 2309
<211> LENGTH: 50
<212> TYPE: RNA
<213> ORGANISM: Homo sapiens

<400> SEQUENCE: 2309
uucaaacgag aacuuugaag gccgaagugg agaaggguuc caugugaaca 50

<210> SEQ ID NO 2310
<211> LENGTH: 32
<212> TYPE: RNA
<213> ORGANISM: Homo sapiens

<400> SEQUENCE: 2310
gcauuggugu uucaguggua gaauucucgc cu 32

<210> SEQ ID NO 2311
<211> LENGTH: 28
<212> TYPE: RNA
<213> ORGANISM: Homo sapiens

<400> SEQUENCE: 2311
uaggauggcg ugugauaggu ggcacgga 28

<210> SEQ ID NO 2312
<211> LENGTH: 27
<212> TYPE: RNA
<213> ORGANISM: Homo sapiens

<400> SEQUENCE: 2312
ccaccccacg ucucgucgcg cgcgcgu 27

<210> SEQ ID NO 2313
<211> LENGTH: 33
<212> TYPE: RNA
<213> ORGANISM: Homo sapiens

<400> SEQUENCE: 2313
agaacuggug cggaccaggg gaauccgacu guu 33

<210> SEQ ID NO 2314
<211> LENGTH: 45
<212> TYPE: RNA
<213> ORGANISM: Homo sapiens

<400> SEQUENCE: 2314
ccucggccgg cgccuagcag ccgacuuaga acuggugcgg accag 45

<210> SEQ ID NO 2315
<211> LENGTH: 30
<212> TYPE: RNA
<213> ORGANISM: Homo sapiens

<400> SEQUENCE: 2315
ucccauaugg ucuagcgguu aggauuccuc 30

<210> SEQ ID NO 2316
<211> LENGTH: 30
<212> TYPE: RNA
<213> ORGANISM: Homo sapiens

<400> SEQUENCE: 2316
augguggagu uaaagacuuu uucucugacc 30

<210> SEQ ID NO 2317
<211> LENGTH: 50
<212> TYPE: RNA
<213> ORGANISM: Homo sapiens

<400> SEQUENCE: 2317
cuucgugauc gaugugguga cgucgugcuc ucccgggccg gguccgagcc 50

<210> SEQ ID NO 2318
<211> LENGTH: 49
<212> TYPE: RNA
<213> ORGANISM: Homo sapiens

<400> SEQUENCE: 2318
acacuucgaa cgcacuugcg gccccggguu ccuccccgggg cuacgccug 49

<210> SEQ ID NO 2319
<211> LENGTH: 27
<212> TYPE: RNA
<213> ORGANISM: Homo sapiens

<400> SEQUENCE: 2319
cccaccccac gucucgucgc gcgcgcg 27

<210> SEQ ID NO 2320
<211> LENGTH: 50
<212> TYPE: RNA
<213> ORGANISM: Homo sapiens

<400> SEQUENCE: 2320
ucuaauuagu gacgcgcaug aauggaugaa cgagauuccc acugucccua 50

<210> SEQ ID NO 2321
<211> LENGTH: 35
<212> TYPE: RNA
<213> ORGANISM: Homo sapiens

<400> SEQUENCE: 2321
guuuccguag uguagugguc aucacguucg ccuga 35

<210> SEQ ID NO 2322
<211> LENGTH: 45
<212> TYPE: RNA
<213> ORGANISM: Homo sapiens

<400> SEQUENCE: 2322
acuuggaugg gagaccgccu gggaauaccg ggugcuguag gcuuu 45

<210> SEQ ID NO 2323
<211> LENGTH: 39
<212> TYPE: RNA
<213> ORGANISM: Homo sapiens

<400> SEQUENCE: 2323
cucucccccg cuccccgucc uccccccucc ccggggggag 39

<210> SEQ ID NO 2324
<211> LENGTH: 36
<212> TYPE: RNA
<213> ORGANISM: Homo sapiens

<400> SEQUENCE: 2324
gcgggagacc gggguucaau uccccgacgg ggagcc 36

<210> SEQ ID NO 2325
<211> LENGTH: 30
<212> TYPE: RNA
<213> ORGANISM: Homo sapiens

<400> SEQUENCE: 2325
aguaagguca gcuaaauaag cuaucgggcu 30

<210> SEQ ID NO 2326
<211> LENGTH: 29
<212> TYPE: RNA
<213> ORGANISM: Homo sapiens

<400> SEQUENCE: 2326
cuccccgggg gagcgccgcg ugggggcgg 29

<210> SEQ ID NO 2327
<211> LENGTH: 42
<212> TYPE: RNA
<213> ORGANISM: Homo sapiens

<400> SEQUENCE: 2327
cugucacgcg ggagaccggg guucaauucc ccgacgggga gc 42

<210> SEQ ID NO 2328
<211> LENGTH: 45
<212> TYPE: RNA
<213> ORGANISM: Homo sapiens

<400> SEQUENCE: 2328
acugcggauc agaagauucu agguucgacu ccuggcuggc ucgcc 45

<210> SEQ ID NO 2329
<211> LENGTH: 29
<212> TYPE: RNA
<213> ORGANISM: Homo sapiens

<400> SEQUENCE: 2329
guuuccguag uguagugguu aucaccuuc 29

<210> SEQ ID NO 2330
<211> LENGTH: 35
<212> TYPE: RNA
<213> ORGANISM: Homo sapiens

<400> SEQUENCE: 2330
gggagaccgg gguucgauuc cccgacgggg agcca 35

<210> SEQ ID NO 2331
<211> LENGTH: 40
<212> TYPE: RNA
<213> ORGANISM: Homo sapiens

<400> SEQUENCE: 2331
ccuagcagcc gacuuagaac uggugcggac caggggaauc 40

<210> SEQ ID NO 2332
<211> LENGTH: 50
<212> TYPE: RNA
<213> ORGANISM: Homo sapiens

<400> SEQUENCE: 2332
ccaagcguug gauuguucac ccacuaauag ggaacgugag cugggauuag 50

<210> SEQ ID NO 2333
<211> LENGTH: 31
<212> TYPE: RNA
<213> ORGANISM: Homo sapiens

<400> SEQUENCE: 2333
ccggcuagcu cagucgguag agcaugggac u 31

<210> SEQ ID NO 2334
<211> LENGTH: 37
<212> TYPE: RNA
<213> ORGANISM: Homo sapiens

<400> SEQUENCE: 2334
aucaucgaca cuucgaacgc acuugcggcc ccggguu 37

<210> SEQ ID NO 2335
<211> LENGTH: 45
<212> TYPE: RNA
<213> ORGANISM: Homo sapiens

<400> SEQUENCE: 2335
uacuuggaug ggagaccgcc ugggaauacc gggugcugua ggcuu 45

<210> SEQ ID NO 2336
<211> LENGTH: 28
<212> TYPE: RNA
<213> ORGANISM: Homo sapiens

<400> SEQUENCE: 2336
acgagaacuu ugaaggccga aguggaga 28

<210> SEQ ID NO 2337
<211> LENGTH: 42
<212> TYPE: RNA
<213> ORGANISM: Homo sapiens

<400> SEQUENCE: 2337
gcugguccga ugguaguggg uuaucagaac uuauuaacau ua 42

<210> SEQ ID NO 2338
<211> LENGTH: 27
<212> TYPE: RNA
<213> ORGANISM: Homo sapiens

<400> SEQUENCE: 2338
aaacgagaac uuugaaggcc gaagugg 27

<210> SEQ ID NO 2339
<211> LENGTH: 50
<212> TYPE: RNA
<213> ORGANISM: Homo sapiens

<400> SEQUENCE: 2339
acagaugaug aacuuauuga cgggcggaca gaaacugugu gcugauuguc 50

<210> SEQ ID NO 2340
<211> LENGTH: 35
<212> TYPE: RNA
<213> ORGANISM: Homo sapiens

<400> SEQUENCE: 2340
agugacgcgc augaauggau gaacgagauu ccccc 35

<210> SEQ ID NO 2341
<211> LENGTH: 48
<212> TYPE: RNA
<213> ORGANISM: Homo sapiens

<400> SEQUENCE: 2341
cgucugaucu cggaagcuaa gcagggucgg gccugguuag uacuugga 48

<210> SEQ ID NO 2342
<211> LENGTH: 35
<212> TYPE: RNA
<213> ORGANISM: Homo sapiens

<400> SEQUENCE: 2342
caugacccgc cgggcagcuu ccgggaaacc aaagu 35

<210> SEQ ID NO 2343
<211> LENGTH: 49
<212> TYPE: RNA
<213> ORGANISM: Homo sapiens

<400> SEQUENCE: 2343
guuaguacuu ggaugggaga ccgccuggga auaccgggug cuguaggcu 49

<210> SEQ ID NO 2344
<211> LENGTH: 50
<212> TYPE: RNA
<213> ORGANISM: Homo sapiens

<400> SEQUENCE: 2344
gauuugucug guuaauuccg auaacgaacg agacucuggc augcuaacua 50

<210> SEQ ID NO 2345
<211> LENGTH: 38
<212> TYPE: RNA
<213> ORGANISM: Homo sapiens

<400> SEQUENCE: 2345
ucugaagguc gugaguucga uccucacacg gggcacca 38

<210> SEQ ID NO 2346
<211> LENGTH: 42
<212> TYPE: RNA
<213> ORGANISM: Homo sapiens

<400> SEQUENCE: 2346
agguuuccgu aggugaaccu gcggaaggau cauuaacgga gc 42

<210> SEQ ID NO 2347
<211> LENGTH: 49
<212> TYPE: RNA
<213> ORGANISM: Homo sapiens

```
<400> SEQUENCE: 2347

cacucccgac ccggggaggu agugacgaaa aauaacaaua caggacucu            49

<210> SEQ ID NO 2348
<211> LENGTH: 33
<212> TYPE: RNA
<213> ORGANISM: Homo sapiens

<400> SEQUENCE: 2348

ucccuggugg ucuagugguu aggauucgac gcu                            33

<210> SEQ ID NO 2349
<211> LENGTH: 35
<212> TYPE: RNA
<213> ORGANISM: Homo sapiens

<400> SEQUENCE: 2349

gucaggaugg ccgagcgguc uaaggcgcug cguuc                          35

<210> SEQ ID NO 2350
<211> LENGTH: 26
<212> TYPE: RNA
<213> ORGANISM: Homo sapiens

<400> SEQUENCE: 2350

uaaugguuag cacucuggac ucugaa                                    26

<210> SEQ ID NO 2351
<211> LENGTH: 27
<212> TYPE: RNA
<213> ORGANISM: Homo sapiens

<400> SEQUENCE: 2351

cuuuuugauc cuucgauguc ggcucuu                                   27

<210> SEQ ID NO 2352
<211> LENGTH: 32
<212> TYPE: RNA
<213> ORGANISM: Homo sapiens

<400> SEQUENCE: 2352

gcauuggugg uucaguugua gaauucucgc cu                             32

<210> SEQ ID NO 2353
<211> LENGTH: 48
<212> TYPE: RNA
<213> ORGANISM: Homo sapiens

<400> SEQUENCE: 2353

cugaucagua gugggaucgc gccugugaau agccacugca cuccagcc            48

<210> SEQ ID NO 2354
<211> LENGTH: 49
<212> TYPE: RNA
<213> ORGANISM: Homo sapiens

<400> SEQUENCE: 2354

auugcaggac acauugauca ucgacacuuc gaacgcacuu gcggcccccg          49

<210> SEQ ID NO 2355
<211> LENGTH: 48
<212> TYPE: RNA
```

<213> ORGANISM: Homo sapiens

<400> SEQUENCE: 2355
aauugcagga cacauugauc aucgacacuu cgaacgcacu ugcggccc 48

<210> SEQ ID NO 2356
<211> LENGTH: 45
<212> TYPE: RNA
<213> ORGANISM: Homo sapiens

<400> SEQUENCE: 2356
uggcucuaag ggcugggucg gucgggcugg ggcgcgaagc ggggc 45

<210> SEQ ID NO 2357
<211> LENGTH: 49
<212> TYPE: RNA
<213> ORGANISM: Homo sapiens

<400> SEQUENCE: 2357
aucuaauuag ugacgcgcau gaauggauga acgagauucc cacugucc 49

<210> SEQ ID NO 2358
<211> LENGTH: 48
<212> TYPE: RNA
<213> ORGANISM: Homo sapiens

<400> SEQUENCE: 2358
aacgaugguu uuucauauca uuggucgugg uuguaguccg ugcgagaa 48

<210> SEQ ID NO 2359
<211> LENGTH: 32
<212> TYPE: RNA
<213> ORGANISM: Homo sapiens

<400> SEQUENCE: 2359
gcgugggugg uucaguggua gaauucucgc cu 32

<210> SEQ ID NO 2360
<211> LENGTH: 32
<212> TYPE: RNA
<213> ORGANISM: Homo sapiens

<400> SEQUENCE: 2360
gcaauggugg uucaguggua gaauucucgc cu 32

<210> SEQ ID NO 2361
<211> LENGTH: 37
<212> TYPE: RNA
<213> ORGANISM: Homo sapiens

<400> SEQUENCE: 2361
uaucauuggu cgugguugua guccgugcga gaauacc 37

<210> SEQ ID NO 2362
<211> LENGTH: 42
<212> TYPE: RNA
<213> ORGANISM: Homo sapiens

<400> SEQUENCE: 2362
gcugcgaucu auugaaaguc agcccucgac acaaggguuu gu 42

<210> SEQ ID NO 2363
<211> LENGTH: 30

<212> TYPE: RNA
<213> ORGANISM: Homo sapiens

<400> SEQUENCE: 2363
guuuccguag uguaguggguc aucacguucg 30

<210> SEQ ID NO 2364
<211> LENGTH: 49
<212> TYPE: RNA
<213> ORGANISM: Homo sapiens

<400> SEQUENCE: 2364
cucucucucu cucucccccg cuccccgucc uccccccucc ccgggggag 49

<210> SEQ ID NO 2365
<211> LENGTH: 31
<212> TYPE: RNA
<213> ORGANISM: Homo sapiens

<400> SEQUENCE: 2365
aacgaacgag acucuggcau gcuaacuagu u 31

<210> SEQ ID NO 2366
<211> LENGTH: 29
<212> TYPE: RNA
<213> ORGANISM: Homo sapiens

<400> SEQUENCE: 2366
cccugugguc uagugguuag gauucggcg 29

<210> SEQ ID NO 2367
<211> LENGTH: 31
<212> TYPE: RNA
<213> ORGANISM: Homo sapiens

<400> SEQUENCE: 2367
aucauugguc gugguuguag uccgugcgag a 31

<210> SEQ ID NO 2368
<211> LENGTH: 43
<212> TYPE: RNA
<213> ORGANISM: Homo sapiens

<400> SEQUENCE: 2368
cagccgacuu agaacuggug cggaccaggg gaauccgacu guu 43

<210> SEQ ID NO 2369
<211> LENGTH: 33
<212> TYPE: RNA
<213> ORGANISM: Homo sapiens

<400> SEQUENCE: 2369
ucccuggugg ucuagugguu cggauucggc gcu 33

<210> SEQ ID NO 2370
<211> LENGTH: 50
<212> TYPE: RNA
<213> ORGANISM: Homo sapiens

<400> SEQUENCE: 2370
aucaucgaca cuucgaacgc acuugcggcc ccggguuccu cccggggcua 50

<210> SEQ ID NO 2371

<211> LENGTH: 32
<212> TYPE: RNA
<213> ORGANISM: Homo sapiens

<400> SEQUENCE: 2371
gcaugggugg uucaguggua gaauucucgc gu 32

<210> SEQ ID NO 2372
<211> LENGTH: 31
<212> TYPE: RNA
<213> ORGANISM: Homo sapiens

<400> SEQUENCE: 2372
agugacgaaa aauaacaaua caggacucuu u 31

<210> SEQ ID NO 2373
<211> LENGTH: 40
<212> TYPE: RNA
<213> ORGANISM: Homo sapiens

<400> SEQUENCE: 2373
cacgcaucga ccugguauug caguaccucc aggaacggug 40

<210> SEQ ID NO 2374
<211> LENGTH: 49
<212> TYPE: RNA
<213> ORGANISM: Homo sapiens

<400> SEQUENCE: 2374
cgugcgcgag ucgggggcuc gcacgaaagc cgccguggcg caaugaagg 49

<210> SEQ ID NO 2375
<211> LENGTH: 29
<212> TYPE: RNA
<213> ORGANISM: Homo sapiens

<400> SEQUENCE: 2375
ggccguaauc guauaguggu uaguacucu 29

<210> SEQ ID NO 2376
<211> LENGTH: 33
<212> TYPE: RNA
<213> ORGANISM: Homo sapiens

<400> SEQUENCE: 2376
gacccagucg ccuaauggau aaggcaucag ccu 33

<210> SEQ ID NO 2377
<211> LENGTH: 45
<212> TYPE: RNA
<213> ORGANISM: Homo sapiens

<400> SEQUENCE: 2377
acaagguuuc cguaggugaa ccugcggaag gaucauuaac ggagc 45

<210> SEQ ID NO 2378
<211> LENGTH: 30
<212> TYPE: RNA
<213> ORGANISM: Homo sapiens

<400> SEQUENCE: 2378
ucggaugggg ugugauaggu ggcacggaga 30

-continued

```
<210> SEQ ID NO 2379
<211> LENGTH: 44
<212> TYPE: RNA
<213> ORGANISM: Homo sapiens

<400> SEQUENCE: 2379

uuuucaccca ggcggcccgg guucgacucc cgguguggga acca            44

<210> SEQ ID NO 2380
<211> LENGTH: 37
<212> TYPE: RNA
<213> ORGANISM: Homo sapiens

<400> SEQUENCE: 2380

cugaaggucg ugaguucguu ccucacacgg ggcacca                   37

<210> SEQ ID NO 2381
<211> LENGTH: 34
<212> TYPE: RNA
<213> ORGANISM: Homo sapiens

<400> SEQUENCE: 2381

gcauuggugg uucaguggua gcauucucgc cugc                      34

<210> SEQ ID NO 2382
<211> LENGTH: 50
<212> TYPE: RNA
<213> ORGANISM: Homo sapiens

<400> SEQUENCE: 2382

gcugcgggau gaaccgaacg ccggguuaag gcgcccgaug ccgacgcuca      50

<210> SEQ ID NO 2383
<211> LENGTH: 29
<212> TYPE: RNA
<213> ORGANISM: Homo sapiens

<400> SEQUENCE: 2383

gccgugaucg uauagugguu cguacucug                            29

<210> SEQ ID NO 2384
<211> LENGTH: 43
<212> TYPE: RNA
<213> ORGANISM: Homo sapiens

<400> SEQUENCE: 2384

cugccacgcg ggaggcccgg guucguuucc cggcccaugc acc             43

<210> SEQ ID NO 2385
<211> LENGTH: 50
<212> TYPE: RNA
<213> ORGANISM: Homo sapiens

<400> SEQUENCE: 2385

gguuccaugg uguaaugguu agcacucugg acucugaauc cagcgauccg      50

<210> SEQ ID NO 2386
<211> LENGTH: 28
<212> TYPE: RNA
<213> ORGANISM: Homo sapiens

<400> SEQUENCE: 2386

ccaccccacg ucucgucgcg cgcgcguc                             28
```

<210> SEQ ID NO 2387
<211> LENGTH: 50
<212> TYPE: RNA
<213> ORGANISM: Homo sapiens

<400> SEQUENCE: 2387
uugcagugau gacuugcgaa ucaaaucugu caaucccug agugcaauca 50

<210> SEQ ID NO 2388
<211> LENGTH: 35
<212> TYPE: RNA
<213> ORGANISM: Homo sapiens

<400> SEQUENCE: 2388
caucgacacu ucgaacgcac uugcggcccc ggguu 35

<210> SEQ ID NO 2389
<211> LENGTH: 39
<212> TYPE: RNA
<213> ORGANISM: Homo sapiens

<400> SEQUENCE: 2389
aacgaacgag acucuggcau gcuaacuagu uacgcgacc 39

<210> SEQ ID NO 2390
<211> LENGTH: 33
<212> TYPE: RNA
<213> ORGANISM: Homo sapiens

<400> SEQUENCE: 2390
aggacacauu gaucaucgac acuucgaacg cac 33

<210> SEQ ID NO 2391
<211> LENGTH: 39
<212> TYPE: RNA
<213> ORGANISM: Homo sapiens

<400> SEQUENCE: 2391
accgccgcgg cccggguucg auucccgguc agggaacca 39

<210> SEQ ID NO 2392
<211> LENGTH: 32
<212> TYPE: RNA
<213> ORGANISM: Homo sapiens

<400> SEQUENCE: 2392
gcauuggugg uucaguggua gaauucuggc cu 32

<210> SEQ ID NO 2393
<211> LENGTH: 41
<212> TYPE: RNA
<213> ORGANISM: Homo sapiens

<400> SEQUENCE: 2393
aaacgagaac uuugaaggcc gaaguggaga aggguuccau g 41

<210> SEQ ID NO 2394
<211> LENGTH: 50
<212> TYPE: RNA
<213> ORGANISM: Homo sapiens

<400> SEQUENCE: 2394
cagggucggg ccugguuagu acuuggaugg gagaccgccu gggaauaccg 50

<210> SEQ ID NO 2395
<211> LENGTH: 27
<212> TYPE: RNA
<213> ORGANISM: Homo sapiens

<400> SEQUENCE: 2395
ccugggaaua ccgggugcug uaggcuu 27

<210> SEQ ID NO 2396
<211> LENGTH: 32
<212> TYPE: RNA
<213> ORGANISM: Homo sapiens

<400> SEQUENCE: 2396
ccauuggugg uucaguggua gaauucucgc cu 32

<210> SEQ ID NO 2397
<211> LENGTH: 49
<212> TYPE: RNA
<213> ORGANISM: Homo sapiens

<400> SEQUENCE: 2397
uaaguucggc aucaauaugg ugaccucccg ggagcggggg accaccagg 49

<210> SEQ ID NO 2398
<211> LENGTH: 36
<212> TYPE: RNA
<213> ORGANISM: Homo sapiens

<400> SEQUENCE: 2398
aaacgagaac uuugaaggcc gaaguggaga aggguu 36

<210> SEQ ID NO 2399
<211> LENGTH: 50
<212> TYPE: RNA
<213> ORGANISM: Homo sapiens

<400> SEQUENCE: 2399
cugguuaauu ccgauaacga acgagacucu ggcaugcuaa cuaguuacgc 50

<210> SEQ ID NO 2400
<211> LENGTH: 27
<212> TYPE: RNA
<213> ORGANISM: Homo sapiens

<400> SEQUENCE: 2400
cuuugauaga guaaauaaua ggagcuu 27

<210> SEQ ID NO 2401
<211> LENGTH: 27
<212> TYPE: RNA
<213> ORGANISM: Homo sapiens

<400> SEQUENCE: 2401
ccuuuuaagu uaaagauuaa gagaacc 27

<210> SEQ ID NO 2402
<211> LENGTH: 27
<212> TYPE: RNA
<213> ORGANISM: Homo sapiens

<400> SEQUENCE: 2402 ucgugggguuc gugccccacg uugggcg 27

<210> SEQ ID NO 2403
<211> LENGTH: 38
<212> TYPE: RNA
<213> ORGANISM: Homo sapiens

<400> SEQUENCE: 2403
ggcuuuggug acucuagaua accucgggcc gaucgcac 38

<210> SEQ ID NO 2404
<211> LENGTH: 46
<212> TYPE: RNA
<213> ORGANISM: Homo sapiens

<400> SEQUENCE: 2404
aacuguggua auucuagagc uaauacaugc cgacgggcgc ugaccc 46

<210> SEQ ID NO 2405
<211> LENGTH: 37
<212> TYPE: RNA
<213> ORGANISM: Homo sapiens

<400> SEQUENCE: 2405
auugaucauc gacacuucga acgcacuugc ggccccg 37

<210> SEQ ID NO 2406
<211> LENGTH: 35
<212> TYPE: RNA
<213> ORGANISM: Homo sapiens

<400> SEQUENCE: 2406
acgcgaccuc agaucagacg uggcgacccg cugaa 35

<210> SEQ ID NO 2407
<211> LENGTH: 46
<212> TYPE: RNA
<213> ORGANISM: Homo sapiens

<400> SEQUENCE: 2407
gcgggccgcc ggugaaauac cacuacucug aucguuuuuu cacuga 46

<210> SEQ ID NO 2408
<211> LENGTH: 28
<212> TYPE: RNA
<213> ORGANISM: Homo sapiens

<400> SEQUENCE: 2408
cguaggugaa ccugcggaag gaucauua 28

<210> SEQ ID NO 2409
<211> LENGTH: 43
<212> TYPE: RNA
<213> ORGANISM: Homo sapiens

<400> SEQUENCE: 2409
acgcaguuuu auccgguaaa gcgaaugauu agaggucuug ggg 43

<210> SEQ ID NO 2410
<211> LENGTH: 29
<212> TYPE: RNA
<213> ORGANISM: Homo sapiens

<400> SEQUENCE: 2410
gccgugcucg uauaguggui aguacucug 29

<210> SEQ ID NO 2411
<211> LENGTH: 49
<212> TYPE: RNA
<213> ORGANISM: Homo sapiens

<400> SEQUENCE: 2411
ggcugguccg aagguaguga guuaucucaa uugauuguuc acagucagu 49

<210> SEQ ID NO 2412
<211> LENGTH: 50
<212> TYPE: RNA
<213> ORGANISM: Homo sapiens

<400> SEQUENCE: 2412
ucaaacgaga acuuugaagg ccgaagugga gaaggguucc augugaacag 50

<210> SEQ ID NO 2413
<211> LENGTH: 35
<212> TYPE: RNA
<213> ORGANISM: Homo sapiens

<400> SEQUENCE: 2413
auuaaucaag aacgaaaguc ggagguucga agacg 35

<210> SEQ ID NO 2414
<211> LENGTH: 31
<212> TYPE: RNA
<213> ORGANISM: Homo sapiens

<400> SEQUENCE: 2414
ucccuggugg ucuagugguu aggauucguc g 31

<210> SEQ ID NO 2415
<211> LENGTH: 46
<212> TYPE: RNA
<213> ORGANISM: Homo sapiens

<400> SEQUENCE: 2415
acucuuaauc ucagggucgu ggguucgggc cccacguugg gcgcca 46

<210> SEQ ID NO 2416
<211> LENGTH: 32
<212> TYPE: RNA
<213> ORGANISM: Homo sapiens

<400> SEQUENCE: 2416
gcauuggugg uucaguggua uaauucucgc cu 32

<210> SEQ ID NO 2417
<211> LENGTH: 37
<212> TYPE: RNA
<213> ORGANISM: Homo sapiens

<400> SEQUENCE: 2417
cgcgggagac cgggguucga uuccccgacg gggagcc 37

<210> SEQ ID NO 2418
<211> LENGTH: 43
<212> TYPE: RNA
<213> ORGANISM: Homo sapiens

<400> SEQUENCE: 2418
auugugaagc agaauucacc aagcguugga uuguucaccc acu 43

<210> SEQ ID NO 2419
<211> LENGTH: 42
<212> TYPE: RNA
<213> ORGANISM: Homo sapiens

<400> SEQUENCE: 2419
uuuauccggu aaagcgaaug auuagagguc uuggggccga aa 42

<210> SEQ ID NO 2420
<211> LENGTH: 33
<212> TYPE: RNA
<213> ORGANISM: Homo sapiens

<400> SEQUENCE: 2420
gccgcgaucg uauagugguu aguacucugc guu 33

<210> SEQ ID NO 2421
<211> LENGTH: 33
<212> TYPE: RNA
<213> ORGANISM: Homo sapiens

<400> SEQUENCE: 2421
gccgucaucg uauagugguu aguacucugc guu 33

<210> SEQ ID NO 2422
<211> LENGTH: 30
<212> TYPE: RNA
<213> ORGANISM: Homo sapiens

<400> SEQUENCE: 2422
aguaaggaca gcuaaauaag cuaucgggcc 30

<210> SEQ ID NO 2423
<211> LENGTH: 27
<212> TYPE: RNA
<213> ORGANISM: Homo sapiens

<400> SEQUENCE: 2423
aagaacgaaa gucggagguu cgaagac 27

<210> SEQ ID NO 2424
<211> LENGTH: 50
<212> TYPE: RNA
<213> ORGANISM: Homo sapiens

<400> SEQUENCE: 2424
uuucguacgu agcagagcag cucccucgcu gcgaucuauu gaaagucagc 50

<210> SEQ ID NO 2425
<211> LENGTH: 50
<212> TYPE: RNA
<213> ORGANISM: Homo sapiens

<400> SEQUENCE: 2425
gguuaggauu cggcgcucuc accgccgcgg cccggguucg auucccgguc 50

<210> SEQ ID NO 2426
<211> LENGTH: 39
<212> TYPE: RNA
<213> ORGANISM: Homo sapiens

<400> SEQUENCE: 2426
cuuuaacgag gauccauugg agggcaaguc uggugccag 39

<210> SEQ ID NO 2427
<211> LENGTH: 44
<212> TYPE: RNA
<213> ORGANISM: Homo sapiens

<400> SEQUENCE: 2427
aguucgaggc cagccugguc cacauggguc ggaaaaaagg auuu 44

<210> SEQ ID NO 2428
<211> LENGTH: 29
<212> TYPE: RNA
<213> ORGANISM: Homo sapiens

<400> SEQUENCE: 2428
guuuccguag uguagugguu aucacgcuc 29

<210> SEQ ID NO 2429
<211> LENGTH: 44
<212> TYPE: RNA
<213> ORGANISM: Homo sapiens

<400> SEQUENCE: 2429
ccugccacgc gggaggcccg gguucguuuc ccggcccaug cacc 44

<210> SEQ ID NO 2430
<211> LENGTH: 34
<212> TYPE: RNA
<213> ORGANISM: Homo sapiens

<400> SEQUENCE: 2430
ggccgcgauc guauaguggu uaguacucug cguu 34

<210> SEQ ID NO 2431
<211> LENGTH: 31
<212> TYPE: RNA
<213> ORGANISM: Homo sapiens

<400> SEQUENCE: 2431
ccuaaggagg ggugaaccgg cccaggucgg a 31

<210> SEQ ID NO 2432
<211> LENGTH: 50
<212> TYPE: RNA
<213> ORGANISM: Homo sapiens

<400> SEQUENCE: 2432
aaacgaucuc aaccuauucu caaacuuuaa augguaaaga agcccggcuc 50

<210> SEQ ID NO 2433
<211> LENGTH: 46
<212> TYPE: RNA
<213> ORGANISM: Homo sapiens

<400> SEQUENCE: 2433 cccgggggc cggcggcggc ggcgacucug gacgcgagcc gggccc 46

<210> SEQ ID NO 2434
<211> LENGTH: 39
<212> TYPE: RNA

<213> ORGANISM: Homo sapiens

<400> SEQUENCE: 2434
cuuucaccgc cgcggcccgg guucguuucc cggucaggg 39

<210> SEQ ID NO 2435
<211> LENGTH: 29
<212> TYPE: RNA
<213> ORGANISM: Homo sapiens

<400> SEQUENCE: 2435
gccgcgaucg uauaguggu aguacucug 29

<210> SEQ ID NO 2436
<211> LENGTH: 39
<212> TYPE: RNA
<213> ORGANISM: Homo sapiens

<400> SEQUENCE: 2436
aucaagugua guaucuguuc uuaucaguuu aauaucuga 39

<210> SEQ ID NO 2437
<211> LENGTH: 34
<212> TYPE: RNA
<213> ORGANISM: Homo sapiens

<400> SEQUENCE: 2437
ggccgucauc guauaguggu uaguacucug cguu 34

<210> SEQ ID NO 2438
<211> LENGTH: 43
<212> TYPE: RNA
<213> ORGANISM: Homo sapiens

<400> SEQUENCE: 2438
aagguuuccg uaggugaacc ugcggaagga ucauuaacgg agc 43

<210> SEQ ID NO 2439
<211> LENGTH: 46
<212> TYPE: RNA
<213> ORGANISM: Homo sapiens

<400> SEQUENCE: 2439
ucucauaauc ugaaggucgu gaguucguuc cucacacggg gcacca 46

<210> SEQ ID NO 2440
<211> LENGTH: 33
<212> TYPE: RNA
<213> ORGANISM: Homo sapiens

<400> SEQUENCE: 2440
gcaugggugg uucaguggua gaauucucgc cgg 33

<210> SEQ ID NO 2441
<211> LENGTH: 50
<212> TYPE: RNA
<213> ORGANISM: Homo sapiens

<400> SEQUENCE: 2441
acauugauca ucgacacuuc gaacgcacuu gcgcccccgg guuccucccg 50

<210> SEQ ID NO 2442
<211> LENGTH: 32

```
<212> TYPE: RNA
<213> ORGANISM: Homo sapiens

<400> SEQUENCE: 2442

agauugaggg uucguguccc uucguggucg cc                              32

<210> SEQ ID NO 2443
<211> LENGTH: 31
<212> TYPE: RNA
<213> ORGANISM: Homo sapiens

<400> SEQUENCE: 2443

cuuuuugauc cuucgauguc ggcucuuccu a                               31

<210> SEQ ID NO 2444
<211> LENGTH: 34
<212> TYPE: RNA
<213> ORGANISM: Homo sapiens

<400> SEQUENCE: 2444

aagaugguca guaggacaga agguaacauu gaug                            34

<210> SEQ ID NO 2445
<211> LENGTH: 28
<212> TYPE: RNA
<213> ORGANISM: Homo sapiens

<400> SEQUENCE: 2445

cgccgcgugg gggcggcggc gggggag                                    28

<210> SEQ ID NO 2446
<211> LENGTH: 34
<212> TYPE: RNA
<213> ORGANISM: Homo sapiens

<400> SEQUENCE: 2446

gcaagccgga uccguaacuu cgggauaagg auug                            34

<210> SEQ ID NO 2447
<211> LENGTH: 36
<212> TYPE: RNA
<213> ORGANISM: Homo sapiens

<400> SEQUENCE: 2447

uagauugagg ccaguugauu agggugcuua gcuguu                          36

<210> SEQ ID NO 2448
<211> LENGTH: 37
<212> TYPE: RNA
<213> ORGANISM: Homo sapiens

<400> SEQUENCE: 2448

ccggcggcgg cggcgacucu ggacgcgagc cgggccc                         37

<210> SEQ ID NO 2449
<211> LENGTH: 50
<212> TYPE: RNA
<213> ORGANISM: Homo sapiens

<400> SEQUENCE: 2449

cgaccugcuu cugggucggg guuucguacg uagcagagca gcucccucgc           50

<210> SEQ ID NO 2450
```

<211> LENGTH: 31
<212> TYPE: RNA
<213> ORGANISM: Homo sapiens

<400> SEQUENCE: 2450
gccuuggugg uucaguggua gaauucucgc c 31

<210> SEQ ID NO 2451
<211> LENGTH: 26
<212> TYPE: RNA
<213> ORGANISM: Homo sapiens

<400> SEQUENCE: 2451
acagcuaucc auuggucuua gccccc 26

<210> SEQ ID NO 2452
<211> LENGTH: 33
<212> TYPE: RNA
<213> ORGANISM: Homo sapiens

<400> SEQUENCE: 2452
gcccggcuag cucagucggu agagcauggg ccu 33

<210> SEQ ID NO 2453
<211> LENGTH: 44
<212> TYPE: RNA
<213> ORGANISM: Homo sapiens

<400> SEQUENCE: 2453
cagugcgccc cgggcggguc gcgccgucgg gcccggggga gguu 44

<210> SEQ ID NO 2454
<211> LENGTH: 33
<212> TYPE: RNA
<213> ORGANISM: Homo sapiens

<400> SEQUENCE: 2454
cugguauugc aguaccucca ggaacggugc acc 33

<210> SEQ ID NO 2455
<211> LENGTH: 27
<212> TYPE: RNA
<213> ORGANISM: Homo sapiens

<400> SEQUENCE: 2455
cgaauagcuc agucgguaga gcaucag 27

<210> SEQ ID NO 2456
<211> LENGTH: 33
<212> TYPE: RNA
<213> ORGANISM: Homo sapiens

<400> SEQUENCE: 2456
gcccggcuag cucagucggu agagcaucag acu 33

<210> SEQ ID NO 2457
<211> LENGTH: 38
<212> TYPE: RNA
<213> ORGANISM: Homo sapiens

<400> SEQUENCE: 2457
ccgaaagguu ggugguucgg gcccacccag ggacgcca 38

<210> SEQ ID NO 2458
<211> LENGTH: 50
<212> TYPE: RNA
<213> ORGANISM: Homo sapiens

<400> SEQUENCE: 2458
acauugauca ucgacacuuc gaacgcacuu ccggccccgg guuccucccg 50

<210> SEQ ID NO 2459
<211> LENGTH: 29
<212> TYPE: RNA
<213> ORGANISM: Homo sapiens

<400> SEQUENCE: 2459
ggugguucag ugguagaauu cucgccugc 29

<210> SEQ ID NO 2460
<211> LENGTH: 27
<212> TYPE: RNA
<213> ORGANISM: Homo sapiens

<400> SEQUENCE: 2460
aguuaugguu ccuuuggucg cucgcuc 27

<210> SEQ ID NO 2461
<211> LENGTH: 34
<212> TYPE: RNA
<213> ORGANISM: Homo sapiens

<400> SEQUENCE: 2461
gcauuggugg uccaguggua gaauucucgc cugc 34

<210> SEQ ID NO 2462
<211> LENGTH: 45
<212> TYPE: RNA
<213> ORGANISM: Homo sapiens

<400> SEQUENCE: 2462
ugccaagaau guuuucauua aucaagaacg aaagucggag guucg 45

<210> SEQ ID NO 2463
<211> LENGTH: 35
<212> TYPE: RNA
<213> ORGANISM: Homo sapiens

<400> SEQUENCE: 2463
aacuuuggua ucguggaagg acucaugacc acagu 35

<210> SEQ ID NO 2464
<211> LENGTH: 40
<212> TYPE: RNA
<213> ORGANISM: Homo sapiens

<400> SEQUENCE: 2464
ccccgagggg cucucgcuuc uggcgccaag cgcccggccg 40

<210> SEQ ID NO 2465
<211> LENGTH: 47
<212> TYPE: RNA
<213> ORGANISM: Homo sapiens

<400> SEQUENCE: 2465
gcggcgacuc uggacgcgag ccgggcccuu cccguggauc gccccag 47

<210> SEQ ID NO 2466
<211> LENGTH: 43
<212> TYPE: RNA
<213> ORGANISM: Homo sapiens

<400> SEQUENCE: 2466 auaaacgaacg agacucuggc augcuaacua guuacgcgac ccc 43

<210> SEQ ID NO 2467
<211> LENGTH: 38
<212> TYPE: RNA
<213> ORGANISM: Homo sapiens

<400> SEQUENCE: 2467
ugccacgcgg gaggcccggg uucguuuccc ggccaaug 38

<210> SEQ ID NO 2468
<211> LENGTH: 32
<212> TYPE: RNA
<213> ORGANISM: Homo sapiens

<400> SEQUENCE: 2468
uccccugugg ucuaguggcu aggauucggc gc 32

<210> SEQ ID NO 2469
<211> LENGTH: 32
<212> TYPE: RNA
<213> ORGANISM: Homo sapiens

<400> SEQUENCE: 2469
gcauuggugg uucauuggua gaauucucgc cu 32

<210> SEQ ID NO 2470
<211> LENGTH: 45
<212> TYPE: RNA
<213> ORGANISM: Homo sapiens

<400> SEQUENCE: 2470
augguuuuuc auaucauugg ucgugguugu aguccgugcg agaau 45

<210> SEQ ID NO 2471
<211> LENGTH: 37
<212> TYPE: RNA
<213> ORGANISM: Homo sapiens

<400> SEQUENCE: 2471
auagcgacgu cgcuuuuuga uccuucgaug ucggcuc 37

<210> SEQ ID NO 2472
<211> LENGTH: 33
<212> TYPE: RNA
<213> ORGANISM: Homo sapiens

<400> SEQUENCE: 2472 gggggguauag cucaguggua gagcauuuga cug 33

<210> SEQ ID NO 2473
<211> LENGTH: 46
<212> TYPE: RNA
<213> ORGANISM: Homo sapiens

<400> SEQUENCE: 2473
cucgcugcga ucuauugaaa gucagcccuc gacacaaggg uuugua 46

<210> SEQ ID NO 2474
<211> LENGTH: 26
<212> TYPE: RNA
<213> ORGANISM: Homo sapiens

<400> SEQUENCE: 2474
ccuuuuucua ugaaauaaug ugaaug 26

<210> SEQ ID NO 2475
<211> LENGTH: 27
<212> TYPE: RNA
<213> ORGANISM: Homo sapiens

<400> SEQUENCE: 2475
uuggauaacu gugguaauuc uagagcu 27

<210> SEQ ID NO 2476
<211> LENGTH: 45
<212> TYPE: RNA
<213> ORGANISM: Homo sapiens

<400> SEQUENCE: 2476
ccugccacgc gggaggcccg gguucguuuc ccggccaaug cacca 45

<210> SEQ ID NO 2477
<211> LENGTH: 50
<212> TYPE: RNA
<213> ORGANISM: Homo sapiens

<400> SEQUENCE: 2477
auggccuccg uugcccucgg ccgaucgaaa gggagucggg uucagauccc 50

<210> SEQ ID NO 2478
<211> LENGTH: 28
<212> TYPE: RNA
<213> ORGANISM: Homo sapiens

<400> SEQUENCE: 2478
accccacguc ucgucgcgcg cgcguccg 28

<210> SEQ ID NO 2479
<211> LENGTH: 50
<212> TYPE: RNA
<213> ORGANISM: Homo sapiens

<400> SEQUENCE: 2479
aacagccucu ggcauguugg aacaauguag guaagggaag ucggcaagcc 50

<210> SEQ ID NO 2480
<211> LENGTH: 50
<212> TYPE: RNA
<213> ORGANISM: Homo sapiens

<400> SEQUENCE: 2480
aacuuuggua ucguggaagg acucaugacc acaguccaug ccaucacugc 50

<210> SEQ ID NO 2481
<211> LENGTH: 32
<212> TYPE: RNA
<213> ORGANISM: Homo sapiens

<400> SEQUENCE: 2481
gcaugggugg uucagugguc gaauucucgc cu 32

<210> SEQ ID NO 2482
<211> LENGTH: 33
<212> TYPE: RNA
<213> ORGANISM: Homo sapiens

<400> SEQUENCE: 2482
cgggcggguc gcgccgucgg gcccggggga ggu 33

<210> SEQ ID NO 2483
<211> LENGTH: 44
<212> TYPE: RNA
<213> ORGANISM: Homo sapiens

<400> SEQUENCE: 2483
uuuaaguuaa agauuaagag aaccaacacc ucuuuacagu gacc 44

<210> SEQ ID NO 2484
<211> LENGTH: 28
<212> TYPE: RNA
<213> ORGANISM: Homo sapiens

<400> SEQUENCE: 2484
gaucguauag ugguuaguac ucugcguu 28

<210> SEQ ID NO 2485
<211> LENGTH: 29
<212> TYPE: RNA
<213> ORGANISM: Homo sapiens

<400> SEQUENCE: 2485
uagauugagg ccaguugauu agggugcuu 29

<210> SEQ ID NO 2486
<211> LENGTH: 29
<212> TYPE: RNA
<213> ORGANISM: Homo sapiens

<400> SEQUENCE: 2486
uaggaugggg ugagauaggu ggcacggag 29

<210> SEQ ID NO 2487
<211> LENGTH: 31
<212> TYPE: RNA
<213> ORGANISM: Homo sapiens

<400> SEQUENCE: 2487
aacuggugcg gaccagggga auccgacugu u 31

<210> SEQ ID NO 2488
<211> LENGTH: 28
<212> TYPE: RNA
<213> ORGANISM: Homo sapiens

<400> SEQUENCE: 2488
ccacuacucu gaucguuuuu ucacugac 28

<210> SEQ ID NO 2489
<211> LENGTH: 38
<212> TYPE: RNA
<213> ORGANISM: Homo sapiens

<400> SEQUENCE: 2489
aauugcagga cacauugauc aucgacacuu cgaacgca 38

<210> SEQ ID NO 2490
<211> LENGTH: 48
<212> TYPE: RNA
<213> ORGANISM: Homo sapiens

<400> SEQUENCE: 2490
auacaugaug aucucaaucc aacuugaacu cucucacuga uuacuuga 48

<210> SEQ ID NO 2491
<211> LENGTH: 45
<212> TYPE: RNA
<213> ORGANISM: Homo sapiens

<400> SEQUENCE: 2491
cccguaagga uggcaaugcc aguggaacca cgcugcuuga ggcuc 45

<210> SEQ ID NO 2492
<211> LENGTH: 31
<212> TYPE: RNA
<213> ORGANISM: Homo sapiens

<400> SEQUENCE: 2492
ucccuggugg ucuagugguu aggauuuggc g 31

<210> SEQ ID NO 2493
<211> LENGTH: 43
<212> TYPE: RNA
<213> ORGANISM: Homo sapiens

<400> SEQUENCE: 2493
cgcauuuaua uagaggagac aagucguaac augguaagug uac 43

<210> SEQ ID NO 2494
<211> LENGTH: 33
<212> TYPE: RNA
<213> ORGANISM: Homo sapiens

<400> SEQUENCE: 2494
gcccggcuag cucagucggu agagcaugag ccu 33

<210> SEQ ID NO 2495
<211> LENGTH: 31
<212> TYPE: RNA
<213> ORGANISM: Homo sapiens

<400> SEQUENCE: 2495
ucucuggugg ucuagugguu aggauucggc g 31

<210> SEQ ID NO 2496
<211> LENGTH: 50
<212> TYPE: RNA
<213> ORGANISM: Homo sapiens

<400> SEQUENCE: 2496
cgacucuuag cgguggauca cucggcucgu gcgccgauga agaacgcagc 50

<210> SEQ ID NO 2497
<211> LENGTH: 50
<212> TYPE: RNA
<213> ORGANISM: Homo sapiens

<400> SEQUENCE: 2497
ucccuggugg ucuaguggu aggauucggc gcucucaccg ccgcgccccg 50

<210> SEQ ID NO 2498
<211> LENGTH: 50
<212> TYPE: RNA
<213> ORGANISM: Homo sapiens

<400> SEQUENCE: 2498
gucagucggu ccugagagau gggcgagcgc cguuccgaag ggacgggcga 50

<210> SEQ ID NO 2499
<211> LENGTH: 34
<212> TYPE: RNA
<213> ORGANISM: Homo sapiens

<400> SEQUENCE: 2499
uuucgauggu agucgccgug ccuaccaugg ugac 34

<210> SEQ ID NO 2500
<211> LENGTH: 50
<212> TYPE: RNA
<213> ORGANISM: Homo sapiens

<400> SEQUENCE: 2500
cacuaaguuc ggcaucaaua uggugaccuc ccgggagcgg gggaccacca 50

<210> SEQ ID NO 2501
<211> LENGTH: 31
<212> TYPE: RNA
<213> ORGANISM: Homo sapiens

<400> SEQUENCE: 2501
gagauuucaa cuuaacuuga ccgcucugac c 31

<210> SEQ ID NO 2502
<211> LENGTH: 28
<212> TYPE: RNA
<213> ORGANISM: Homo sapiens

<400> SEQUENCE: 2502
cugguggucu agugguuagg auucggcg 28

<210> SEQ ID NO 2503
<211> LENGTH: 37
<212> TYPE: RNA
<213> ORGANISM: Homo sapiens

<400> SEQUENCE: 2503
caauggaggc gugggguucga aucccacuuc ugacacc 37

<210> SEQ ID NO 2504
<211> LENGTH: 48
<212> TYPE: RNA
<213> ORGANISM: Homo sapiens

<400> SEQUENCE: 2504
gauuggaugg uuuagugagg cccucggauc ggccccgccg gggucggc 48

<210> SEQ ID NO 2505
<211> LENGTH: 33
<212> TYPE: RNA
<213> ORGANISM: Homo sapiens

<400> SEQUENCE: 2505
uaggauggug ugugauaggu ggcacggaga auu 33

<210> SEQ ID NO 2506
<211> LENGTH: 50
<212> TYPE: RNA
<213> ORGANISM: Homo sapiens

<400> SEQUENCE: 2506
auacguccuc uauccgagga caauauauua aauggauuuu uggaaauagg 50

<210> SEQ ID NO 2507
<211> LENGTH: 29
<212> TYPE: RNA
<213> ORGANISM: Homo sapiens

<400> SEQUENCE: 2507
cacuucgaac gcacuugcgg ccccggguu 29

<210> SEQ ID NO 2508
<211> LENGTH: 39
<212> TYPE: RNA
<213> ORGANISM: Homo sapiens

<400> SEQUENCE: 2508
gcgaucuauu gaaagucagc ccucgacaca aggguuugu 39

<210> SEQ ID NO 2509
<211> LENGTH: 30
<212> TYPE: RNA
<213> ORGANISM: Homo sapiens

<400> SEQUENCE: 2509
agaacuggug cggaccaggg gaauccgacu 30

<210> SEQ ID NO 2510
<211> LENGTH: 28
<212> TYPE: RNA
<213> ORGANISM: Homo sapiens

<400> SEQUENCE: 2510
ucccaugguc uagcgguuag gauuccug 28

<210> SEQ ID NO 2511
<211> LENGTH: 30
<212> TYPE: RNA
<213> ORGANISM: Homo sapiens

<400> SEQUENCE: 2511
cauuaaucaa gaacgaaagu cggagguucg 30

<210> SEQ ID NO 2512
<211> LENGTH: 30
<212> TYPE: RNA
<213> ORGANISM: Homo sapiens

<400> SEQUENCE: 2512
cauaccaccc ugaacgcgcc cgaucucguc 30

<210> SEQ ID NO 2513
<211> LENGTH: 50
<212> TYPE: RNA

-continued

<213> ORGANISM: Homo sapiens

<400> SEQUENCE: 2513
caugagaggu guagaauaag ugggaggccc ccggcgcccc cccggugucc 50

<210> SEQ ID NO 2514
<211> LENGTH: 32
<212> TYPE: RNA
<213> ORGANISM: Homo sapiens

<400> SEQUENCE: 2514
ggccgugauc guauagaggu uaguacucug cg 32

<210> SEQ ID NO 2515
<211> LENGTH: 37
<212> TYPE: RNA
<213> ORGANISM: Homo sapiens

<400> SEQUENCE: 2515
uucaaagguu gugguucga gucccaccag agucgcc 37

<210> SEQ ID NO 2516
<211> LENGTH: 34
<212> TYPE: RNA
<213> ORGANISM: Homo sapiens

<400> SEQUENCE: 2516
ggccgugauc guauaguggu uagaacucug cguu 34

<210> SEQ ID NO 2517
<211> LENGTH: 38
<212> TYPE: RNA
<213> ORGANISM: Homo sapiens

<400> SEQUENCE: 2517
ucguacgacu cuuagcggug gaucacucgg cucgugcg 38

<210> SEQ ID NO 2518
<211> LENGTH: 48
<212> TYPE: RNA
<213> ORGANISM: Homo sapiens

<400> SEQUENCE: 2518
ugaaauacaa cgaugguuuu ucauaucauu ggucgugguu guaguccg 48

<210> SEQ ID NO 2519
<211> LENGTH: 30
<212> TYPE: RNA
<213> ORGANISM: Homo sapiens

<400> SEQUENCE: 2519
uaggaugggg ugugauaggu agcacggaga 30

<210> SEQ ID NO 2520
<211> LENGTH: 30
<212> TYPE: RNA
<213> ORGANISM: Homo sapiens

<400> SEQUENCE: 2520
ucccauaugg ucuagcgguu aggauucaug 30

<210> SEQ ID NO 2521
<211> LENGTH: 50

<212> TYPE: RNA
<213> ORGANISM: Homo sapiens

<400> SEQUENCE: 2521
auucgugaug acugaucauu ucuucacuuu gaccagaugu cuacugaaga 50

<210> SEQ ID NO 2522
<211> LENGTH: 50
<212> TYPE: RNA
<213> ORGANISM: Homo sapiens

<400> SEQUENCE: 2522
auuugucugg uuaauuccga uaacgaacga gacucuggca ugcuaacuag 50

<210> SEQ ID NO 2523
<211> LENGTH: 50
<212> TYPE: RNA
<213> ORGANISM: Homo sapiens

<400> SEQUENCE: 2523
gacucuuagc gguggaucac ucggcucgug cgucgaugaa gaacgcagcc 50

<210> SEQ ID NO 2524
<211> LENGTH: 31
<212> TYPE: RNA
<213> ORGANISM: Homo sapiens

<400> SEQUENCE: 2524
uccauggugg ucuagugguu aggauucggc g 31

<210> SEQ ID NO 2525
<211> LENGTH: 31
<212> TYPE: RNA
<213> ORGANISM: Homo sapiens

<400> SEQUENCE: 2525
agcagaguug cgcagcggaa gcgugcuggg c 31

<210> SEQ ID NO 2526
<211> LENGTH: 35
<212> TYPE: RNA
<213> ORGANISM: Homo sapiens

<400> SEQUENCE: 2526
accuuuuaag uuaaagauua agagaaccaa caccu 35

<210> SEQ ID NO 2527
<211> LENGTH: 32
<212> TYPE: RNA
<213> ORGANISM: Homo sapiens

<400> SEQUENCE: 2527
ggacgugauc guauaguggu uaguacucug cg 32

<210> SEQ ID NO 2528
<211> LENGTH: 30
<212> TYPE: RNA
<213> ORGANISM: Homo sapiens

<400> SEQUENCE: 2528
cgcgaccuca gaucagacgu ggcgacccgc 30

<210> SEQ ID NO 2529

<211> LENGTH: 39
<212> TYPE: RNA
<213> ORGANISM: Homo sapiens

<400> SEQUENCE: 2529
agaaucuuag cuuugggugc uaauggugga guuaaagac 39

<210> SEQ ID NO 2530
<211> LENGTH: 27
<212> TYPE: RNA
<213> ORGANISM: Homo sapiens

<400> SEQUENCE: 2530
cggcggcguc cggugagcuc ucgcugg 27

<210> SEQ ID NO 2531
<211> LENGTH: 47
<212> TYPE: RNA
<213> ORGANISM: Homo sapiens

<400> SEQUENCE: 2531
ugcggccccg gguuccuccc ggggcuacgc cugucugagc gucgcuu 47

<210> SEQ ID NO 2532
<211> LENGTH: 31
<212> TYPE: RNA
<213> ORGANISM: Homo sapiens

<400> SEQUENCE: 2532
uaccuggugg ucuagugguu aggauucggc g 31

<210> SEQ ID NO 2533
<211> LENGTH: 41
<212> TYPE: RNA
<213> ORGANISM: Homo sapiens

<400> SEQUENCE: 2533
auugaucauc gacacuucga acgcacuugc ggccccgggc u 41

<210> SEQ ID NO 2534
<211> LENGTH: 33
<212> TYPE: RNA
<213> ORGANISM: Homo sapiens

<400> SEQUENCE: 2534
ucugaggguc cagggaucau gucccuguuc ggg 33

<210> SEQ ID NO 2535
<211> LENGTH: 33
<212> TYPE: RNA
<213> ORGANISM: Homo sapiens

<400> SEQUENCE: 2535
gccgggaucg uauagugguu aguacucugc guu 33

<210> SEQ ID NO 2536
<211> LENGTH: 31
<212> TYPE: RNA
<213> ORGANISM: Homo sapiens

<400> SEQUENCE: 2536
ucccuggugg ucuaguggua aggauucggc g 31

<210> SEQ ID NO 2537
<211> LENGTH: 31
<212> TYPE: RNA
<213> ORGANISM: Homo sapiens

<400> SEQUENCE: 2537
cgggaggccc ggguucguuu cccggcccau g 31

<210> SEQ ID NO 2538
<211> LENGTH: 50
<212> TYPE: RNA
<213> ORGANISM: Homo sapiens

<400> SEQUENCE: 2538
cagaguguug cuuaacacaa agcacccaac uuacacuuag gagauuucaa 50

<210> SEQ ID NO 2539
<211> LENGTH: 33
<212> TYPE: RNA
<213> ORGANISM: Homo sapiens

<400> SEQUENCE: 2539
guuuccguag ugaagugguu aucacguucg ccu 33

<210> SEQ ID NO 2540
<211> LENGTH: 50
<212> TYPE: RNA
<213> ORGANISM: Homo sapiens

<400> SEQUENCE: 2540
gcgacucugg acgcgagccg ggcccuuccc guggaucgcc ccagcugcgg 50

<210> SEQ ID NO 2541
<211> LENGTH: 34
<212> TYPE: RNA
<213> ORGANISM: Homo sapiens

<400> SEQUENCE: 2541
guuuccguag uguagugguc aucacguucg ccug 34

<210> SEQ ID NO 2542
<211> LENGTH: 47
<212> TYPE: RNA
<213> ORGANISM: Homo sapiens

<400> SEQUENCE: 2542
agccgacuua gaacuggugc ggaccagggg aauccgacug uuuaauu 47

<210> SEQ ID NO 2543
<211> LENGTH: 48
<212> TYPE: RNA
<213> ORGANISM: Homo sapiens

<400> SEQUENCE: 2543
uccguggaga ggaacgagug ugagucugaa accaauuuuu ugaggccu 48

<210> SEQ ID NO 2544
<211> LENGTH: 31
<212> TYPE: RNA
<213> ORGANISM: Homo sapiens

<400> SEQUENCE: 2544
aauauucaaa cgagaacuuu gaaggccgaa g 31

<210> SEQ ID NO 2545
<211> LENGTH: 33
<212> TYPE: RNA
<213> ORGANISM: Homo sapiens

<400> SEQUENCE: 2545
guuuccguag uguagugguu aucccguucg ccu 33

<210> SEQ ID NO 2546
<211> LENGTH: 41
<212> TYPE: RNA
<213> ORGANISM: Homo sapiens

<400> SEQUENCE: 2546
cuuucaccgc cgcggcccgg guucguuucc cggucaggga a 41

<210> SEQ ID NO 2547
<211> LENGTH: 44
<212> TYPE: RNA
<213> ORGANISM: Homo sapiens

<400> SEQUENCE: 2547
gaaacggagc aggucaaaac ucccgugcug aucaguagug ggau 44

<210> SEQ ID NO 2548
<211> LENGTH: 50
<212> TYPE: RNA
<213> ORGANISM: Homo sapiens

<400> SEQUENCE: 2548
ucuacuacuu ggauaacugu gguaauucua gagcuaauac augccgacgg 50

<210> SEQ ID NO 2549
<211> LENGTH: 33
<212> TYPE: RNA
<213> ORGANISM: Homo sapiens

<400> SEQUENCE: 2549
guuuccguag uguagugguu aucacguucg acu 33

<210> SEQ ID NO 2550
<211> LENGTH: 29
<212> TYPE: RNA
<213> ORGANISM: Homo sapiens

<400> SEQUENCE: 2550
auuaaucaag aacgaaaguc ggagguucg 29

<210> SEQ ID NO 2551
<211> LENGTH: 34
<212> TYPE: RNA
<213> ORGANISM: Homo sapiens

<400> SEQUENCE: 2551
guuuccguag uguagcgguu aucacauucg ccuc 34

<210> SEQ ID NO 2552
<211> LENGTH: 31
<212> TYPE: RNA
<213> ORGANISM: Homo sapiens

<400> SEQUENCE: 2552
gaauuguggu ucagugguag aauucucgcc u 31

<210> SEQ ID NO 2553
<211> LENGTH: 38
<212> TYPE: RNA
<213> ORGANISM: Homo sapiens

<400> SEQUENCE: 2553
aaguguagua ucuguucuua ucaguuuaau aucugaua 38

<210> SEQ ID NO 2554
<211> LENGTH: 45
<212> TYPE: RNA
<213> ORGANISM: Homo sapiens

<400> SEQUENCE: 2554
gcuaagcagg gucgggucug guuaguacuu ggaugggaga ccgcc 45

<210> SEQ ID NO 2555
<211> LENGTH: 32
<212> TYPE: RNA
<213> ORGANISM: Homo sapiens

<400> SEQUENCE: 2555
gcauuggugg uucgguggua gaauucucgc cu 32

<210> SEQ ID NO 2556
<211> LENGTH: 46
<212> TYPE: RNA
<213> ORGANISM: Homo sapiens

<400> SEQUENCE: 2556
gcggccccgg guuccucccg gggcuacgcc ugucugagcg ucgcuu 46

<210> SEQ ID NO 2557
<211> LENGTH: 27
<212> TYPE: RNA
<213> ORGANISM: Homo sapiens

<400> SEQUENCE: 2557 cuccccggggc uacgccuguc ugagcgu 27

<210> SEQ ID NO 2558
<211> LENGTH: 39
<212> TYPE: RNA
<213> ORGANISM: Homo sapiens

<400> SEQUENCE: 2558
cuaauuagug acgcgcauga auggaugaac gagauuccc 39

<210> SEQ ID NO 2559
<211> LENGTH: 50
<212> TYPE: RNA
<213> ORGANISM: Homo sapiens

<400> SEQUENCE: 2559
acaauguagg uaagggaagu cggcaagccg gauccguaac uucgggauaa 50

<210> SEQ ID NO 2560
<211> LENGTH: 50
<212> TYPE: RNA
<213> ORGANISM: Homo sapiens

<400> SEQUENCE: 2560
cucacugaug aguacguucu gacuuucguu cuucugaguu ugcugaagcc 50

<210> SEQ ID NO 2561
<211> LENGTH: 32
<212> TYPE: RNA
<213> ORGANISM: Homo sapiens

<400> SEQUENCE: 2561
gcauuggugg uucaguggua gaguucucgc cu 32

<210> SEQ ID NO 2562
<211> LENGTH: 37
<212> TYPE: RNA
<213> ORGANISM: Homo sapiens

<400> SEQUENCE: 2562
ucugaagguc gugaguucga uccucacacg gggcacc 37

<210> SEQ ID NO 2563
<211> LENGTH: 31
<212> TYPE: RNA
<213> ORGANISM: Homo sapiens

<400> SEQUENCE: 2563
uuuuuuggcc uguuugaugu augugugaaa c 31

<210> SEQ ID NO 2564
<211> LENGTH: 50
<212> TYPE: RNA
<213> ORGANISM: Homo sapiens

<400> SEQUENCE: 2564
ccgaggggcu cucgcuucug gcgccaagcg cccggccgcg cgccggccgg 50

<210> SEQ ID NO 2565
<211> LENGTH: 32
<212> TYPE: RNA
<213> ORGANISM: Homo sapiens

<400> SEQUENCE: 2565
gcauugcugg uucaguggua gaauucucgc cu 32

<210> SEQ ID NO 2566
<211> LENGTH: 33
<212> TYPE: RNA
<213> ORGANISM: Homo sapiens

<400> SEQUENCE: 2566
guucccguag uguagugguu aucacguucg ccu 33

<210> SEQ ID NO 2567
<211> LENGTH: 34
<212> TYPE: RNA
<213> ORGANISM: Homo sapiens

<400> SEQUENCE: 2567
gcauuugugg uucaguggua gaauucucgc cuuc 34

<210> SEQ ID NO 2568
<211> LENGTH: 33
<212> TYPE: RNA
<213> ORGANISM: Homo sapiens

<400> SEQUENCE: 2568
gguuccaugg uguaaugguu agcacucugg acu 33

<210> SEQ ID NO 2569
<211> LENGTH: 35
<212> TYPE: RNA
<213> ORGANISM: Homo sapiens

<400> SEQUENCE: 2569
uuuugauccu ucgaugucgg cucuuccuau cauug 35

<210> SEQ ID NO 2570
<211> LENGTH: 29
<212> TYPE: RNA
<213> ORGANISM: Homo sapiens

<400> SEQUENCE: 2570
uaggaugggg agugauaggu ggcacggag 29

<210> SEQ ID NO 2571
<211> LENGTH: 33
<212> TYPE: RNA
<213> ORGANISM: Homo sapiens

<400> SEQUENCE: 2571
ucccuggugg uauaguggguu aggauucggc gcu 33

<210> SEQ ID NO 2572
<211> LENGTH: 33
<212> TYPE: RNA
<213> ORGANISM: Homo sapiens

<400> SEQUENCE: 2572
gcccggcuag cucagucggu agagcaugcg acu 33

<210> SEQ ID NO 2573
<211> LENGTH: 31
<212> TYPE: RNA
<213> ORGANISM: Homo sapiens

<400> SEQUENCE: 2573
ucccuggugg ucuaguggguu aggauuaggc g 31

<210> SEQ ID NO 2574
<211> LENGTH: 33
<212> TYPE: RNA
<213> ORGANISM: Homo sapiens

<400> SEQUENCE: 2574
cgcgggaggc ccggguucgu uucccggcca aug 33

<210> SEQ ID NO 2575
<211> LENGTH: 32
<212> TYPE: RNA
<213> ORGANISM: Homo sapiens

<400> SEQUENCE: 2575
gcaugggugg uucaguggua gaauucucac cu 32

<210> SEQ ID NO 2576
<211> LENGTH: 50
<212> TYPE: RNA
<213> ORGANISM: Homo sapiens

```
<400> SEQUENCE: 2576

cccuugaaaa uccgggggag agggguguaaa ucucgcgccg ggccguaccc          50

<210> SEQ ID NO 2577
<211> LENGTH: 34
<212> TYPE: RNA
<213> ORGANISM: Homo sapiens

<400> SEQUENCE: 2577

ggccgugauc guauaguggu uagcacucug cguu                           34

<210> SEQ ID NO 2578
<211> LENGTH: 35
<212> TYPE: RNA
<213> ORGANISM: Homo sapiens

<400> SEQUENCE: 2578

guucuugugg uugaaauaca acgaugguuu uucau                          35

<210> SEQ ID NO 2579
<211> LENGTH: 27
<212> TYPE: RNA
<213> ORGANISM: Homo sapiens

<400> SEQUENCE: 2579

ggugcggacc aggggaaucc gacuguu                                   27

<210> SEQ ID NO 2580
<211> LENGTH: 30
<212> TYPE: RNA
<213> ORGANISM: Homo sapiens

<400> SEQUENCE: 2580

aucauugguc gugguuguag uccgugcgag                                30

<210> SEQ ID NO 2581
<211> LENGTH: 38
<212> TYPE: RNA
<213> ORGANISM: Homo sapiens

<400> SEQUENCE: 2581

uucauaucau uggucguggu uguaguccgu gcgagaau                       38

<210> SEQ ID NO 2582
<211> LENGTH: 35
<212> TYPE: RNA
<213> ORGANISM: Homo sapiens

<400> SEQUENCE: 2582

gcaugggugg uucaguggua gaauucucgc cugcc                          35

<210> SEQ ID NO 2583
<211> LENGTH: 27
<212> TYPE: RNA
<213> ORGANISM: Homo sapiens

<400> SEQUENCE: 2583

gcgccgcugg uguaguggua ucaugca                                   27

<210> SEQ ID NO 2584
<211> LENGTH: 49
<212> TYPE: RNA
<213> ORGANISM: Homo sapiens
```

<400> SEQUENCE: 2584
cguaacaagg uuuccguagg ugaaccugcg gaaggaucau uaacggagc 49

<210> SEQ ID NO 2585
<211> LENGTH: 26
<212> TYPE: RNA
<213> ORGANISM: Homo sapiens

<400> SEQUENCE: 2585
ccacccugaa cgcgcccgau cucguc 26

<210> SEQ ID NO 2586
<211> LENGTH: 31
<212> TYPE: RNA
<213> ORGANISM: Homo sapiens

<400> SEQUENCE: 2586
uccugugguc uaguggcuag gauucggcgc u 31

<210> SEQ ID NO 2587
<211> LENGTH: 34
<212> TYPE: RNA
<213> ORGANISM: Homo sapiens

<400> SEQUENCE: 2587
ucccuggugg ucuagugguu aggauucggc gccu 34

<210> SEQ ID NO 2588
<211> LENGTH: 32
<212> TYPE: RNA
<213> ORGANISM: Homo sapiens

<400> SEQUENCE: 2588
ggccgcgauc guauaguggu uaguacucug cg 32

<210> SEQ ID NO 2589
<211> LENGTH: 49
<212> TYPE: RNA
<213> ORGANISM: Homo sapiens

<400> SEQUENCE: 2589
aauacaugau gaucucaauc caacuugaac ucucucacug auuacuuga 49

<210> SEQ ID NO 2590
<211> LENGTH: 50
<212> TYPE: RNA
<213> ORGANISM: Homo sapiens

<400> SEQUENCE: 2590
auuaaugaug agauauaacc uugacugaag cugaugauga guuuguauaa 50

<210> SEQ ID NO 2591
<211> LENGTH: 50
<212> TYPE: RNA
<213> ORGANISM: Homo sapiens

<400> SEQUENCE: 2591
cacuucgaac gcacuugcgg ccccggguuc cuccoggggc uacgccuguc 50

<210> SEQ ID NO 2592
<211> LENGTH: 50
<212> TYPE: RNA

```
<213> ORGANISM: Homo sapiens

<400> SEQUENCE: 2592

gauaacugug guaauucuag agcuaauaca ugccgacggg cgcugacccc                50

<210> SEQ ID NO 2593
<211> LENGTH: 28
<212> TYPE: RNA
<213> ORGANISM: Homo sapiens

<400> SEQUENCE: 2593

gcuagcucag ucgguagagc augggacu                                       28

<210> SEQ ID NO 2594
<211> LENGTH: 46
<212> TYPE: RNA
<213> ORGANISM: Homo sapiens

<400> SEQUENCE: 2594

cucccucgcu gcgaucuauu gaaagucagc ccucgacaca aggguu                    46

<210> SEQ ID NO 2595
<211> LENGTH: 28
<212> TYPE: RNA
<213> ORGANISM: Homo sapiens

<400> SEQUENCE: 2595

cagaguguag cuuaacacaa agcaccca                                       28

<210> SEQ ID NO 2596
<211> LENGTH: 50
<212> TYPE: RNA
<213> ORGANISM: Homo sapiens

<400> SEQUENCE: 2596

ucuggucgg gguuucguac guagcagagc agcucccucg cugcgaucua                 50

<210> SEQ ID NO 2597
<211> LENGTH: 33
<212> TYPE: RNA
<213> ORGANISM: Homo sapiens

<400> SEQUENCE: 2597

aagccggauc cguaacuucg ggauaaggau ugg                                 33

<210> SEQ ID NO 2598
<211> LENGTH: 50
<212> TYPE: RNA
<213> ORGANISM: Homo sapiens

<400> SEQUENCE: 2598

uugccaagaa uguuucauu aaucaagaac gaaagucgga gguucgaaga                 50

<210> SEQ ID NO 2599
<211> LENGTH: 50
<212> TYPE: RNA
<213> ORGANISM: Homo sapiens

<400> SEQUENCE: 2599

auugaucauc gacacuucga acgcacuugc ggcaccgggu uccucccggg                50

<210> SEQ ID NO 2600
<211> LENGTH: 49
```

```
<212> TYPE: RNA
<213> ORGANISM: Homo sapiens

<400> SEQUENCE: 2600

ccaagacucc agacacaucc aaaugaggcg cugcaugugg cagucugcc        49

<210> SEQ ID NO 2601
<211> LENGTH: 31
<212> TYPE: RNA
<213> ORGANISM: Homo sapiens

<400> SEQUENCE: 2601

cgccgugauc guauaguggu uaguacucug c                           31

<210> SEQ ID NO 2602
<211> LENGTH: 34
<212> TYPE: RNA
<213> ORGANISM: Homo sapiens

<400> SEQUENCE: 2602

ggccgugauc guauaguggu uaguacucug cgua                        34

<210> SEQ ID NO 2603
<211> LENGTH: 29
<212> TYPE: RNA
<213> ORGANISM: Homo sapiens

<400> SEQUENCE: 2603

gccgugaucg uauagugguu aguccucug                              29

<210> SEQ ID NO 2604
<211> LENGTH: 28
<212> TYPE: RNA
<213> ORGANISM: Homo sapiens

<400> SEQUENCE: 2604

ggugcggacc aggggaaucc gacuguuu                               28

<210> SEQ ID NO 2605
<211> LENGTH: 35
<212> TYPE: RNA
<213> ORGANISM: Homo sapiens

<400> SEQUENCE: 2605

gcauuggugg uucagugguA gaauucuccc cugcc                       35

<210> SEQ ID NO 2606
<211> LENGTH: 29
<212> TYPE: RNA
<213> ORGANISM: Homo sapiens

<400> SEQUENCE: 2606

gccgugaucg cauagugguu aguacucug                              29

<210> SEQ ID NO 2607
<211> LENGTH: 32
<212> TYPE: RNA
<213> ORGANISM: Homo sapiens

<400> SEQUENCE: 2607

gcaugggugg uucagugguA aaauucucgc cu                          32

<210> SEQ ID NO 2608
```

<211> LENGTH: 36
<212> TYPE: RNA
<213> ORGANISM: Homo sapiens

<400> SEQUENCE: 2608
auugaaguag auccugacac uaaggaaaug cugaag 36

<210> SEQ ID NO 2609
<211> LENGTH: 45
<212> TYPE: RNA
<213> ORGANISM: Homo sapiens

<400> SEQUENCE: 2609
gcuguuaacu aaguguuugu ggguuuaagu cccauugguc uagcc 45

<210> SEQ ID NO 2610
<211> LENGTH: 29
<212> TYPE: RNA
<213> ORGANISM: Homo sapiens

<400> SEQUENCE: 2610
cccggggcua cgccugucug agcgucgcu 29

<210> SEQ ID NO 2611
<211> LENGTH: 33
<212> TYPE: RNA
<213> ORGANISM: Homo sapiens

<400> SEQUENCE: 2611
cuuuuugauc cuucgauguc ggcucuuccu auc 33

<210> SEQ ID NO 2612
<211> LENGTH: 50
<212> TYPE: RNA
<213> ORGANISM: Homo sapiens

<400> SEQUENCE: 2612
uagugguuag gauucggcgc ucucaccgcc gcggcccggg uucguuuccc 50

<210> SEQ ID NO 2613
<211> LENGTH: 30
<212> TYPE: RNA
<213> ORGANISM: Homo sapiens

<400> SEQUENCE: 2613
uaggaugggg ugugauaggu ggcacggagu 30

<210> SEQ ID NO 2614
<211> LENGTH: 38
<212> TYPE: RNA
<213> ORGANISM: Homo sapiens

<400> SEQUENCE: 2614
cacccggggg gccggcggcg gcggcgacuc uggacgcg 38

<210> SEQ ID NO 2615
<211> LENGTH: 35
<212> TYPE: RNA
<213> ORGANISM: Homo sapiens

<400> SEQUENCE: 2615
aaaccauucg uagacgaccu gcuucugggu cgggg 35

```
<210> SEQ ID NO 2616
<211> LENGTH: 44
<212> TYPE: RNA
<213> ORGANISM: Homo sapiens

<400> SEQUENCE: 2616

auugugaauc ugacaacaga ggcuuacgac cccuuauuua ccac       44

<210> SEQ ID NO 2617
<211> LENGTH: 34
<212> TYPE: RNA
<213> ORGANISM: Homo sapiens

<400> SEQUENCE: 2617

gccgugaucg uauagugguu aguacucugc guua                 34

<210> SEQ ID NO 2618
<211> LENGTH: 34
<212> TYPE: RNA
<213> ORGANISM: Homo sapiens

<400> SEQUENCE: 2618

cuauugaaag ucagcccucg acacaagggu uugu                 34

<210> SEQ ID NO 2619
<211> LENGTH: 29
<212> TYPE: RNA
<213> ORGANISM: Homo sapiens

<400> SEQUENCE: 2619

gcccggauag cucagucggu agagcauca                       29

<210> SEQ ID NO 2620
<211> LENGTH: 43
<212> TYPE: RNA
<213> ORGANISM: Homo sapiens

<400> SEQUENCE: 2620

cauaaucuga aggucgugag uucguuccuc acacggggca cca        43

<210> SEQ ID NO 2621
<211> LENGTH: 45
<212> TYPE: RNA
<213> ORGANISM: Homo sapiens

<400> SEQUENCE: 2621

ccugccacgc gggaggcccg gguucguuuc ccggcccaug cacca      45

<210> SEQ ID NO 2622
<211> LENGTH: 29
<212> TYPE: RNA
<213> ORGANISM: Homo sapiens

<400> SEQUENCE: 2622

ggcggcgucc ggugagcucu cgcuggccc                       29

<210> SEQ ID NO 2623
<211> LENGTH: 33
<212> TYPE: RNA
<213> ORGANISM: Homo sapiens

<400> SEQUENCE: 2623

guuuccgaag uguagugguu aucacguucg ccu                  33
```

<210> SEQ ID NO 2624
<211> LENGTH: 48
<212> TYPE: RNA
<213> ORGANISM: Homo sapiens

<400> SEQUENCE: 2624
cuugcggccc cggguuccuc ccggggcuac gccugucuga gcgucgcc 48

<210> SEQ ID NO 2625
<211> LENGTH: 34
<212> TYPE: RNA
<213> ORGANISM: Homo sapiens

<400> SEQUENCE: 2625
uauugaaagu cagcccucga cacaaggguu ugua 34

<210> SEQ ID NO 2626
<211> LENGTH: 46
<212> TYPE: RNA
<213> ORGANISM: Homo sapiens

<400> SEQUENCE: 2626
cucuauccga ggacaauaua uuaaauggau uuuuggagca gggaga 46

<210> SEQ ID NO 2627
<211> LENGTH: 31
<212> TYPE: RNA
<213> ORGANISM: Homo sapiens

<400> SEQUENCE: 2627
uaggaugggg ugugauaggu ggcacggcga a 31

<210> SEQ ID NO 2628
<211> LENGTH: 50
<212> TYPE: RNA
<213> ORGANISM: Homo sapiens

<400> SEQUENCE: 2628
uccaagacuc cagacacauc caaaugaggc gcugcaugug gcagucugcc 50

<210> SEQ ID NO 2629
<211> LENGTH: 50
<212> TYPE: RNA
<213> ORGANISM: Homo sapiens

<400> SEQUENCE: 2629
acguccucua uccgaggaca auauauuaaa uggauuuuug gagcagggag 50

<210> SEQ ID NO 2630
<211> LENGTH: 26
<212> TYPE: RNA
<213> ORGANISM: Homo sapiens

<400> SEQUENCE: 2630
cagagaauag uuuaaauuag aaucuu 26

<210> SEQ ID NO 2631
<211> LENGTH: 50
<212> TYPE: RNA
<213> ORGANISM: Homo sapiens

<400> SEQUENCE: 2631
ugcggcugau gacagcacuu cugcugagac gcugugauug cucuguccaa 50

<210> SEQ ID NO 2632
<211> LENGTH: 46
<212> TYPE: RNA
<213> ORGANISM: Homo sapiens

<400> SEQUENCE: 2632
acucuuaauc ucagggucgu ggguucgugc cccacguugg gcgcca 46

<210> SEQ ID NO 2633
<211> LENGTH: 37
<212> TYPE: RNA
<213> ORGANISM: Homo sapiens

<400> SEQUENCE: 2633
ucaaagguug uggguucgag ucccaccaga gucgcca 37

<210> SEQ ID NO 2634
<211> LENGTH: 34
<212> TYPE: RNA
<213> ORGANISM: Homo sapiens

<400> SEQUENCE: 2634
aucaagugua guaucuguuc uuaucaguuu aaua 34

<210> SEQ ID NO 2635
<211> LENGTH: 30
<212> TYPE: RNA
<213> ORGANISM: Homo sapiens

<400> SEQUENCE: 2635
aaauggauuu uuggagcagg gagauggaau 30

<210> SEQ ID NO 2636
<211> LENGTH: 46
<212> TYPE: RNA
<213> ORGANISM: Homo sapiens

<400> SEQUENCE: 2636
cuacgcauuu auauagagga gacaagucgu aacaugguaa guguac 46

<210> SEQ ID NO 2637
<211> LENGTH: 28
<212> TYPE: RNA
<213> ORGANISM: Homo sapiens

<400> SEQUENCE: 2637
acuucgaacg cacuugcggc cccggguu 28

<210> SEQ ID NO 2638
<211> LENGTH: 31
<212> TYPE: RNA
<213> ORGANISM: Homo sapiens

<400> SEQUENCE: 2638
ggccgugauc guauagcggu uaguacucug c 31

<210> SEQ ID NO 2639
<211> LENGTH: 28
<212> TYPE: RNA
<213> ORGANISM: Homo sapiens

<400> SEQUENCE: 2639
cccggggggc cggcggcggc ggcgacuc 28

<210> SEQ ID NO 2640
<211> LENGTH: 31
<212> TYPE: RNA
<213> ORGANISM: Homo sapiens

<400> SEQUENCE: 2640
cgagaacuuu gaaggccgaa guggagaagg g 31

<210> SEQ ID NO 2641
<211> LENGTH: 33
<212> TYPE: RNA
<213> ORGANISM: Homo sapiens

<400> SEQUENCE: 2641
ucccuggugg ucuaguggcu aggauuccgc gcu 33

<210> SEQ ID NO 2642
<211> LENGTH: 50
<212> TYPE: RNA
<213> ORGANISM: Homo sapiens

<400> SEQUENCE: 2642
aacagcuaag gacugcaaaa ccccacucug caucaacuga acgcaaauca 50

<210> SEQ ID NO 2643
<211> LENGTH: 48
<212> TYPE: RNA
<213> ORGANISM: Homo sapiens

<400> SEQUENCE: 2643
cuugcggccc cggguuccuc ccggggcuac gccugucugc gcgucgcu 48

<210> SEQ ID NO 2644
<211> LENGTH: 50
<212> TYPE: RNA
<213> ORGANISM: Homo sapiens

<400> SEQUENCE: 2644
cuggcacggu gaagagacau gagaggugua gaauaagugg gaggcccccg 50

<210> SEQ ID NO 2645
<211> LENGTH: 49
<212> TYPE: RNA
<213> ORGANISM: Homo sapiens

<400> SEQUENCE: 2645
uuccguggag aggaacgagu gugagucuga aaccaauuuu uugaggccu 49

<210> SEQ ID NO 2646
<211> LENGTH: 43
<212> TYPE: RNA
<213> ORGANISM: Homo sapiens

<400> SEQUENCE: 2646
gcucuaaggg cugggucggu cgggcugggg cgcgaagcgg ggc 43

<210> SEQ ID NO 2647
<211> LENGTH: 43
<212> TYPE: RNA
<213> ORGANISM: Homo sapiens

<400> SEQUENCE: 2647
uuuaaguuaa agauuaagag aaccaacacc ucuuuacagu gac 43

<210> SEQ ID NO 2648
<211> LENGTH: 26
<212> TYPE: RNA
<213> ORGANISM: Homo sapiens

<400> SEQUENCE: 2648
cccgguaauc gcauaaaacu uaaaac 26

<210> SEQ ID NO 2649
<211> LENGTH: 50
<212> TYPE: RNA
<213> ORGANISM: Homo sapiens

<400> SEQUENCE: 2649
aauugcagga cacauugauc aucgccacuu cgaacgcacu ugcggccccg 50

<210> SEQ ID NO 2650
<211> LENGTH: 43
<212> TYPE: RNA
<213> ORGANISM: Homo sapiens

<400> SEQUENCE: 2650 cccgggggc cggcggcggc ggcgacucug gacgcgagcc ggc 43

<210> SEQ ID NO 2651
<211> LENGTH: 50
<212> TYPE: RNA
<213> ORGANISM: Homo sapiens

<400> SEQUENCE: 2651
ucauugugaa gcagaauuca ccaagcguug gauuguucac ccacuaauag 50

<210> SEQ ID NO 2652
<211> LENGTH: 32
<212> TYPE: RNA
<213> ORGANISM: Homo sapiens

<400> SEQUENCE: 2652
ggccgugauc guauaguggc uaguacucug cg 32

<210> SEQ ID NO 2653
<211> LENGTH: 50
<212> TYPE: RNA
<213> ORGANISM: Homo sapiens

<400> SEQUENCE: 2653
ucuccuacuu ggauaacugu gguaauucua gagcuaauac augccgccgg 50

<210> SEQ ID NO 2654
<211> LENGTH: 38
<212> TYPE: RNA
<213> ORGANISM: Homo sapiens

<400> SEQUENCE: 2654
cacgcaucga ccugguauug caguacuucc aggaacgg 38

<210> SEQ ID NO 2655
<211> LENGTH: 50
<212> TYPE: RNA
<213> ORGANISM: Homo sapiens

<400> SEQUENCE: 2655
aguaguggga ucgcgccugu gaauagccac ugcacuccag ccugagcaac 50

<210> SEQ ID NO 2656
<211> LENGTH: 32
<212> TYPE: RNA
<213> ORGANISM: Homo sapiens

<400> SEQUENCE: 2656
gcaugggugg uucaauggua gaauucucgc cu 32

<210> SEQ ID NO 2657
<211> LENGTH: 33
<212> TYPE: RNA
<213> ORGANISM: Homo sapiens

<400> SEQUENCE: 2657
guuuccguag uguagcgguu aucacguucg ccu 33

<210> SEQ ID NO 2658
<211> LENGTH: 32
<212> TYPE: RNA
<213> ORGANISM: Homo sapiens

<400> SEQUENCE: 2658
ggccgugauc gucuaguggu uaguacucug cg 32

<210> SEQ ID NO 2659
<211> LENGTH: 36
<212> TYPE: RNA
<213> ORGANISM: Homo sapiens

<400> SEQUENCE: 2659
ucaaagguug uggguucgug ucccaccaga gucgcc 36

<210> SEQ ID NO 2660
<211> LENGTH: 29
<212> TYPE: RNA
<213> ORGANISM: Homo sapiens

<400> SEQUENCE: 2660
cccaccccac gucucgucgc gcgcgcguc 29

<210> SEQ ID NO 2661
<211> LENGTH: 35
<212> TYPE: RNA
<213> ORGANISM: Homo sapiens

<400> SEQUENCE: 2661
ggccgugauc guauaguggu uaguacucug cguua 35

<210> SEQ ID NO 2662
<211> LENGTH: 43
<212> TYPE: RNA
<213> ORGANISM: Homo sapiens

<400> SEQUENCE: 2662
cagucggucc ugagagaugg gcgagcgccg uuccgaaggg acg 43

<210> SEQ ID NO 2663
<211> LENGTH: 32
<212> TYPE: RNA
<213> ORGANISM: Homo sapiens

<400> SEQUENCE: 2663
guuaagaugg cagagcccgg uaaucgcaua aa 32

<210> SEQ ID NO 2664
<211> LENGTH: 50
<212> TYPE: RNA
<213> ORGANISM: Homo sapiens

<400> SEQUENCE: 2664
acauugauca ucgacacuuc gaacgcacuu gcggccccgc guuccucccg 50

<210> SEQ ID NO 2665
<211> LENGTH: 44
<212> TYPE: RNA
<213> ORGANISM: Homo sapiens

<400> SEQUENCE: 2665
cgcucucacc gccgcggccc ggguucgauu cccggucagg gaac 44

<210> SEQ ID NO 2666
<211> LENGTH: 50
<212> TYPE: RNA
<213> ORGANISM: Homo sapiens

<400> SEQUENCE: 2666
aucaagugua guaucuguuc uuaucaguuu aauaucugau acguccucua 50

<210> SEQ ID NO 2667
<211> LENGTH: 34
<212> TYPE: RNA
<213> ORGANISM: Homo sapiens

<400> SEQUENCE: 2667
ugccgcgauc guauaguggu uaguacucug cguu 34

<210> SEQ ID NO 2668
<211> LENGTH: 32
<212> TYPE: RNA
<213> ORGANISM: Homo sapiens

<400> SEQUENCE: 2668
gcaugggugg uucagaggua gaauucucgc cu 32

<210> SEQ ID NO 2669
<211> LENGTH: 40
<212> TYPE: RNA
<213> ORGANISM: Homo sapiens

<400> SEQUENCE: 2669
auugcaaauu cgaagaagca gcuucaaacc ugccggggcu 40

<210> SEQ ID NO 2670
<211> LENGTH: 33
<212> TYPE: RNA
<213> ORGANISM: Homo sapiens

<400> SEQUENCE: 2670
gcauuggugg uucaguggua gacuucucgc cuc 33

<210> SEQ ID NO 2671
<211> LENGTH: 47
<212> TYPE: RNA

<213> ORGANISM: Homo sapiens

<400> SEQUENCE: 2671
gcgggccgcc ggugaaauac cacuacucug aucguuuuuu cacugac 47

<210> SEQ ID NO 2672
<211> LENGTH: 32
<212> TYPE: RNA
<213> ORGANISM: Homo sapiens

<400> SEQUENCE: 2672
auuggucgug guuguagucc gugcgagaau ac 32

<210> SEQ ID NO 2673
<211> LENGTH: 45
<212> TYPE: RNA
<213> ORGANISM: Homo sapiens

<400> SEQUENCE: 2673
aacuuacacu uaggagauuu caacuuaacu ugaccgcucu gacca 45

<210> SEQ ID NO 2674
<211> LENGTH: 28
<212> TYPE: RNA
<213> ORGANISM: Homo sapiens

<400> SEQUENCE: 2674
ggcucguugg ucuaguggua ugauucuc 28

<210> SEQ ID NO 2675
<211> LENGTH: 33
<212> TYPE: RNA
<213> ORGANISM: Homo sapiens

<400> SEQUENCE: 2675
gcauuggugg uucaguggaa gaauucucgc cuc 33

<210> SEQ ID NO 2676
<211> LENGTH: 33
<212> TYPE: RNA
<213> ORGANISM: Homo sapiens

<400> SEQUENCE: 2676
gcauuggugg uuuaguggua gaauucucgc cuc 33

<210> SEQ ID NO 2677
<211> LENGTH: 50
<212> TYPE: RNA
<213> ORGANISM: Homo sapiens

<400> SEQUENCE: 2677
agagcgaaag cauuugccaa gaauguuuuc auuaaucaag aacgaaaguc 50

<210> SEQ ID NO 2678
<211> LENGTH: 31
<212> TYPE: RNA
<213> ORGANISM: Homo sapiens

<400> SEQUENCE: 2678
uccucguuag uauaguggug aguaucccg c 31

<210> SEQ ID NO 2679
<211> LENGTH: 34

<212> TYPE: RNA
<213> ORGANISM: Homo sapiens

<400> SEQUENCE: 2679
ggccgugauc guauaguggu uaguacucug cggu 34

<210> SEQ ID NO 2680
<211> LENGTH: 33
<212> TYPE: RNA
<213> ORGANISM: Homo sapiens

<400> SEQUENCE: 2680
gcacggcuag cucagucggu agagcaugag acu 33

<210> SEQ ID NO 2681
<211> LENGTH: 26
<212> TYPE: RNA
<213> ORGANISM: Homo sapiens

<400> SEQUENCE: 2681
cgguaaucgc auaaaacuua aaacuu 26

<210> SEQ ID NO 2682
<211> LENGTH: 32
<212> TYPE: RNA
<213> ORGANISM: Homo sapiens

<400> SEQUENCE: 2682
ccacgcguug gauuguucac ccacuaauag gg 32

<210> SEQ ID NO 2683
<211> LENGTH: 50
<212> TYPE: RNA
<213> ORGANISM: Homo sapiens

<400> SEQUENCE: 2683
ccggggggcc ggcggcggcg gcgacucugg acgcgagccg ggcccuuccc 50

<210> SEQ ID NO 2684
<211> LENGTH: 29
<212> TYPE: RNA
<213> ORGANISM: Homo sapiens

<400> SEQUENCE: 2684
gccgugaucg uauagugguu aguacuaug 29

<210> SEQ ID NO 2685
<211> LENGTH: 29
<212> TYPE: RNA
<213> ORGANISM: Homo sapiens

<400> SEQUENCE: 2685
guuuccguag uguagugguu aucacuuuc 29

<210> SEQ ID NO 2686
<211> LENGTH: 50
<212> TYPE: RNA
<213> ORGANISM: Homo sapiens

<400> SEQUENCE: 2686
gugguuagga uucggcgcuc ucaccgccgc ggcccggguu cgauucccgg 50

<210> SEQ ID NO 2687

```
<211> LENGTH: 29
<212> TYPE: RNA
<213> ORGANISM: Homo sapiens

<400> SEQUENCE: 2687

cauugguggu ucagugguag aauucucgc                                             29

<210> SEQ ID NO 2688
<211> LENGTH: 48
<212> TYPE: RNA
<213> ORGANISM: Homo sapiens

<400> SEQUENCE: 2688

uugcaggaca cauugaucau cgacacuucg aacgcacuug cggccccg                        48

<210> SEQ ID NO 2689
<211> LENGTH: 46
<212> TYPE: RNA
<213> ORGANISM: Homo sapiens

<400> SEQUENCE: 2689

agcagccgac uuagaacugg ugcggaccag gggaauccga cuguuu                          46

<210> SEQ ID NO 2690
<211> LENGTH: 39
<212> TYPE: RNA
<213> ORGANISM: Homo sapiens

<400> SEQUENCE: 2690

ggcugguccg agugcagugg uguuuacaac uaauugauc                                  39

<210> SEQ ID NO 2691
<211> LENGTH: 45
<212> TYPE: RNA
<213> ORGANISM: Homo sapiens

<400> SEQUENCE: 2691

ccagugcgcc ccgggcgggu cgcgccgucg ggcccggggg aggug                           45

<210> SEQ ID NO 2692
<211> LENGTH: 50
<212> TYPE: RNA
<213> ORGANISM: Homo sapiens

<400> SEQUENCE: 2692

caggacggug gccauggaag ucggaauccg cuaaggagug uguaacaacc                      50

<210> SEQ ID NO 2693
<211> LENGTH: 33
<212> TYPE: RNA
<213> ORGANISM: Homo sapiens

<400> SEQUENCE: 2693

gccgagaucg uauagugguu aguacucugc guu                                        33

<210> SEQ ID NO 2694
<211> LENGTH: 29
<212> TYPE: RNA
<213> ORGANISM: Homo sapiens

<400> SEQUENCE: 2694

ccggcggcgu ccggugagcu cucgcuggc                                             29
```

<210> SEQ ID NO 2695
<211> LENGTH: 30
<212> TYPE: RNA
<213> ORGANISM: Homo sapiens

<400> SEQUENCE: 2695
agaaagguca gcuaaauaag cuaucgggcc 30

<210> SEQ ID NO 2696
<211> LENGTH: 45
<212> TYPE: RNA
<213> ORGANISM: Homo sapiens

<400> SEQUENCE: 2696
gccugucacg cgggagaccg ggguucgauu ccccgacggg gagcc 45

<210> SEQ ID NO 2697
<211> LENGTH: 34
<212> TYPE: RNA
<213> ORGANISM: Homo sapiens

<400> SEQUENCE: 2697
gcauuggugg uucaguggua gaauucucac cugc 34

<210> SEQ ID NO 2698
<211> LENGTH: 45
<212> TYPE: RNA
<213> ORGANISM: Homo sapiens

<400> SEQUENCE: 2698
ccgacuuaga acuggugcgg accaggggaa uccgacuguu uaauu 45

<210> SEQ ID NO 2699
<211> LENGTH: 31
<212> TYPE: RNA
<213> ORGANISM: Homo sapiens

<400> SEQUENCE: 2699
agcaagguca gcuaaauaag cuaucgggcc c 31

<210> SEQ ID NO 2700
<211> LENGTH: 50
<212> TYPE: RNA
<213> ORGANISM: Homo sapiens

<400> SEQUENCE: 2700
cacauugauc aucgacacuu cgaacgcacu ugcggccacg gguuccuccc 50

<210> SEQ ID NO 2701
<211> LENGTH: 40
<212> TYPE: RNA
<213> ORGANISM: Homo sapiens

<400> SEQUENCE: 2701
aauugcagga cacauugauc aucgacacuu cgaacgcacu 40

<210> SEQ ID NO 2702
<211> LENGTH: 34
<212> TYPE: RNA
<213> ORGANISM: Homo sapiens

<400> SEQUENCE: 2702
gcaugggcgg uucaguggua gaauucucgc cugc 34

<210> SEQ ID NO 2703
<211> LENGTH: 39
<212> TYPE: RNA
<213> ORGANISM: Homo sapiens

<400> SEQUENCE: 2703
uuucgacuca uuaaauuaug auaaucauau uuaccaacc 39

<210> SEQ ID NO 2704
<211> LENGTH: 49
<212> TYPE: RNA
<213> ORGANISM: Homo sapiens

<400> SEQUENCE: 2704
cauguuggaa caauguaggu aagggaaguc ggcaagccgg auccguaac 49

<210> SEQ ID NO 2705
<211> LENGTH: 33
<212> TYPE: RNA
<213> ORGANISM: Homo sapiens

<400> SEQUENCE: 2705
ucccuggugg ucuaguggcu aggauucggc gcc 33

<210> SEQ ID NO 2706
<211> LENGTH: 29
<212> TYPE: RNA
<213> ORGANISM: Homo sapiens

<400> SEQUENCE: 2706
gccgugaucg uauaguggcu aguacucug 29

<210> SEQ ID NO 2707
<211> LENGTH: 32
<212> TYPE: RNA
<213> ORGANISM: Homo sapiens

<400> SEQUENCE: 2707
guauuggugg uucaguggua gaauucucgc cu 32

<210> SEQ ID NO 2708
<211> LENGTH: 31
<212> TYPE: RNA
<213> ORGANISM: Homo sapiens

<400> SEQUENCE: 2708
uaggaugggg ugugauaggu ggcacggaga c 31

<210> SEQ ID NO 2709
<211> LENGTH: 30
<212> TYPE: RNA
<213> ORGANISM: Homo sapiens

<400> SEQUENCE: 2709
ucacauaugg ucuagcgguu aggauuccug 30

<210> SEQ ID NO 2710
<211> LENGTH: 50
<212> TYPE: RNA
<213> ORGANISM: Homo sapiens

<400> SEQUENCE: 2710
caagcuucca agacuccaga cacauccaaa ugaggcgcug cauguggcag 50

<210> SEQ ID NO 2711
<211> LENGTH: 38
<212> TYPE: RNA
<213> ORGANISM: Homo sapiens

<400> SEQUENCE: 2711 ucugagggu c cagguucau gucccugucc aggcgcca 38

<210> SEQ ID NO 2712
<211> LENGTH: 50
<212> TYPE: RNA
<213> ORGANISM: Homo sapiens

<400> SEQUENCE: 2712
cgcgcgcgcg uguggugugc gucggagggc ggcggcggcg gcggcggcgg 50

<210> SEQ ID NO 2713
<211> LENGTH: 26
<212> TYPE: RNA
<213> ORGANISM: Homo sapiens

<400> SEQUENCE: 2713
cgagaacuuu gaaggccgaa guggag 26

<210> SEQ ID NO 2714
<211> LENGTH: 48
<212> TYPE: RNA
<213> ORGANISM: Homo sapiens

<400> SEQUENCE: 2714
aacggagcag gucaaaacuc ccgugcugau caguaguggg aucgcgcc 48

<210> SEQ ID NO 2715
<211> LENGTH: 50
<212> TYPE: RNA
<213> ORGANISM: Homo sapiens

<400> SEQUENCE: 2715 cggggguuucg uacguagcag agcagcuccc ucgcugcgau cuauugaaag 50

<210> SEQ ID NO 2716
<211> LENGTH: 30
<212> TYPE: RNA
<213> ORGANISM: Homo sapiens

<400> SEQUENCE: 2716
gcguuugugg uauaguggua agcauagcug 30

<210> SEQ ID NO 2717
<211> LENGTH: 36
<212> TYPE: RNA
<213> ORGANISM: Homo sapiens

<400> SEQUENCE: 2717
cagaagauug aggguucgaa ucccuucgug guugcc 36

<210> SEQ ID NO 2718
<211> LENGTH: 30
<212> TYPE: RNA
<213> ORGANISM: Homo sapiens

<400> SEQUENCE: 2718
cccgguaauc gcauaaaacu uaaaacuuua                                              30

<210> SEQ ID NO 2719
<211> LENGTH: 34
<212> TYPE: RNA
<213> ORGANISM: Homo sapiens

<400> SEQUENCE: 2719
ccacuacucu gaucguuuuu ucacugaccc ggua                                         34

<210> SEQ ID NO 2720
<211> LENGTH: 34
<212> TYPE: RNA
<213> ORGANISM: Homo sapiens

<400> SEQUENCE: 2720
gggggauaug cuuagcggua gagcauuuga cugc                                         34

<210> SEQ ID NO 2721
<211> LENGTH: 28
<212> TYPE: RNA
<213> ORGANISM: Homo sapiens

<400> SEQUENCE: 2721
cuccgggggc uacgccuguc ugagcguc                                                28

<210> SEQ ID NO 2722
<211> LENGTH: 42
<212> TYPE: RNA
<213> ORGANISM: Homo sapiens

<400> SEQUENCE: 2722
gcuuuggaug cuaauggugg aguuaaagac uuuuucucug ac                                42

<210> SEQ ID NO 2723
<211> LENGTH: 50
<212> TYPE: RNA
<213> ORGANISM: Homo sapiens

<400> SEQUENCE: 2723
cuuuucuuug ugaagggcag ggcgcccugg aauggguucg ccccgagaga                        50

<210> SEQ ID NO 2724
<211> LENGTH: 36
<212> TYPE: RNA
<213> ORGANISM: Homo sapiens

<400> SEQUENCE: 2724
ggccgugauc guauaguggu uaguacucug cguuga                                       36

<210> SEQ ID NO 2725
<211> LENGTH: 36
<212> TYPE: RNA
<213> ORGANISM: Homo sapiens

<400> SEQUENCE: 2725
ggccgcgauc guauaguggu uaguacucug cguugu                                       36

<210> SEQ ID NO 2726
<211> LENGTH: 30
<212> TYPE: RNA
<213> ORGANISM: Homo sapiens

<400> SEQUENCE: 2726
ucccuggugg ucuaguggu aggauucgac 30

<210> SEQ ID NO 2727
<211> LENGTH: 49
<212> TYPE: RNA
<213> ORGANISM: Homo sapiens

<400> SEQUENCE: 2727
gacucuuagc gguggaucac ucggcucgug cgucgcugaa gaacgcagc 49

<210> SEQ ID NO 2728
<211> LENGTH: 29
<212> TYPE: RNA
<213> ORGANISM: Homo sapiens

<400> SEQUENCE: 2728
aauugcagga cacauugauc aucgacacu 29

<210> SEQ ID NO 2729
<211> LENGTH: 45
<212> TYPE: RNA
<213> ORGANISM: Homo sapiens

<400> SEQUENCE: 2729
cgaggacaau auauuaaaug gauuuuugga aauaggagau ggaau 45

<210> SEQ ID NO 2730
<211> LENGTH: 47
<212> TYPE: RNA
<213> ORGANISM: Homo sapiens

<400> SEQUENCE: 2730
ucuuagcggu ggaucacucg gcucgugcgu cgaugaagaa cgcagcu 47

<210> SEQ ID NO 2731
<211> LENGTH: 27
<212> TYPE: RNA
<213> ORGANISM: Homo sapiens

<400> SEQUENCE: 2731
acgguccccc gcgagggggg cccgggc 27

<210> SEQ ID NO 2732
<211> LENGTH: 49
<212> TYPE: RNA
<213> ORGANISM: Homo sapiens

<400> SEQUENCE: 2732
ggaagcuaag cagggucggg ccugguuagu acuuggaugg gagaccgcc 49

<210> SEQ ID NO 2733
<211> LENGTH: 43
<212> TYPE: RNA
<213> ORGANISM: Homo sapiens

<400> SEQUENCE: 2733
ugucacgcgg gagaccgggg uucgauuccc cgacggggag cca 43

<210> SEQ ID NO 2734
<211> LENGTH: 35
<212> TYPE: RNA
<213> ORGANISM: Homo sapiens

<400> SEQUENCE: 2734
gcaugggugg uucaguggua gaauucucgc cuucc 35

<210> SEQ ID NO 2735
<211> LENGTH: 26
<212> TYPE: RNA
<213> ORGANISM: Homo sapiens

<400> SEQUENCE: 2735
guuuuucaua ucauuggucg ugguug 26

<210> SEQ ID NO 2736
<211> LENGTH: 31
<212> TYPE: RNA
<213> ORGANISM: Homo sapiens

<400> SEQUENCE: 2736
gcccggcuag cucagucggu agagcaugag a 31

<210> SEQ ID NO 2737
<211> LENGTH: 32
<212> TYPE: RNA
<213> ORGANISM: Homo sapiens

<400> SEQUENCE: 2737
cccagcguug gauuguucac ccacuaauag gg 32

<210> SEQ ID NO 2738
<211> LENGTH: 50
<212> TYPE: RNA
<213> ORGANISM: Homo sapiens

<400> SEQUENCE: 2738
cggggggccg gcggcggcgg cgacucugga cgcgagccgg gcccuucccg 50

<210> SEQ ID NO 2739
<211> LENGTH: 46
<212> TYPE: RNA
<213> ORGANISM: Homo sapiens

<400> SEQUENCE: 2739
ucccuggugg ucuaguggu aggauucggc gcucucaccg ccgcgg 46

<210> SEQ ID NO 2740
<211> LENGTH: 40
<212> TYPE: RNA
<213> ORGANISM: Homo sapiens

<400> SEQUENCE: 2740
ugugaaucug acaacagagg cuuacgaccc cuuauuuacc 40

<210> SEQ ID NO 2741
<211> LENGTH: 50
<212> TYPE: RNA
<213> ORGANISM: Homo sapiens

<400> SEQUENCE: 2741
auugaucauc gacacuucga acgcacuugc ggccccgggu uccucccgcg 50

<210> SEQ ID NO 2742
<211> LENGTH: 40
<212> TYPE: RNA
<213> ORGANISM: Homo sapiens

<400> SEQUENCE: 2742
cugauaacgc caaggucgcg gguucgaucc ccguacgggc 40

<210> SEQ ID NO 2743
<211> LENGTH: 50
<212> TYPE: RNA
<213> ORGANISM: Homo sapiens

<400> SEQUENCE: 2743
aggacacauu gaucaucgac acuucgaacg cacuugcggc cccgggcucc 50

<210> SEQ ID NO 2744
<211> LENGTH: 44
<212> TYPE: RNA
<213> ORGANISM: Homo sapiens

<400> SEQUENCE: 2744
cuauccgagg acaauauauu aaauggauuu uuggagcagg gaga 44

<210> SEQ ID NO 2745
<211> LENGTH: 49
<212> TYPE: RNA
<213> ORGANISM: Homo sapiens

<400> SEQUENCE: 2745
gcgccuagca gccgacuuag aacuggugcg gaccagggga auccgacug 49

<210> SEQ ID NO 2746
<211> LENGTH: 35
<212> TYPE: RNA
<213> ORGANISM: Homo sapiens

<400> SEQUENCE: 2746
cccugcgggc cgccggugaa auaccacuac ucuga 35

<210> SEQ ID NO 2747
<211> LENGTH: 32
<212> TYPE: RNA
<213> ORGANISM: Homo sapiens

<400> SEQUENCE: 2747
gcauuguugg uucaguggua gaauucucgc cu 32

<210> SEQ ID NO 2748
<211> LENGTH: 35
<212> TYPE: RNA
<213> ORGANISM: Homo sapiens

<400> SEQUENCE: 2748
auggccuccg uugcccucgg ccgaucgaaa gggag 35

<210> SEQ ID NO 2749
<211> LENGTH: 33
<212> TYPE: RNA
<213> ORGANISM: Homo sapiens

<400> SEQUENCE: 2749
ucccugguag ucuagugguu aggauucggc gcg 33

<210> SEQ ID NO 2750
<211> LENGTH: 33
<212> TYPE: RNA

<213> ORGANISM: Homo sapiens

<400> SEQUENCE: 2750
cuaauggugg aguuaaagac uuuuucucug acc 33

<210> SEQ ID NO 2751
<211> LENGTH: 49
<212> TYPE: RNA
<213> ORGANISM: Homo sapiens

<400> SEQUENCE: 2751
uagauugagg ccaguugauu agggugcuua gcuguuaacu aaguguuug 49

<210> SEQ ID NO 2752
<211> LENGTH: 44
<212> TYPE: RNA
<213> ORGANISM: Homo sapiens

<400> SEQUENCE: 2752
aaguguagua ucuguucuua ucaguuuaau aucugauacg uccu 44

<210> SEQ ID NO 2753
<211> LENGTH: 30
<212> TYPE: RNA
<213> ORGANISM: Homo sapiens

<400> SEQUENCE: 2753 guuuguggguu uuaaguccca uuggucuagc 30

<210> SEQ ID NO 2754
<211> LENGTH: 33
<212> TYPE: RNA
<213> ORGANISM: Homo sapiens

<400> SEQUENCE: 2754
ucccuguggu cuaguggcua ggauucggcg cuu 33

<210> SEQ ID NO 2755
<211> LENGTH: 35
<212> TYPE: RNA
<213> ORGANISM: Homo sapiens

<400> SEQUENCE: 2755
ggcugguccg augguagugg guuaucagaa cuuau 35

<210> SEQ ID NO 2756
<211> LENGTH: 50
<212> TYPE: RNA
<213> ORGANISM: Homo sapiens

<400> SEQUENCE: 2756
uacaaugaug auaacauagu ucagcagacu aacgcugaug agcaauauua 50

<210> SEQ ID NO 2757
<211> LENGTH: 31
<212> TYPE: RNA
<213> ORGANISM: Homo sapiens

<400> SEQUENCE: 2757
ucccuggugg ucuaguggcu aggauuccgc g 31

<210> SEQ ID NO 2758
<211> LENGTH: 45

```
<212> TYPE: RNA
<213> ORGANISM: Homo sapiens

<400> SEQUENCE: 2758

cuuggaaagc gucgcgguuc cggcggcguc cggugagcuc ucgcu          45

<210> SEQ ID NO 2759
<211> LENGTH: 37
<212> TYPE: RNA
<213> ORGANISM: Homo sapiens

<400> SEQUENCE: 2759

ucucaggguc guggguucga gccccacguu gggcgcc                    37

<210> SEQ ID NO 2760
<211> LENGTH: 50
<212> TYPE: RNA
<213> ORGANISM: Homo sapiens

<400> SEQUENCE: 2760

aucaguagug ggaucgcgcc ugugaauagc cacugcacuc cagccugggc      50

<210> SEQ ID NO 2761
<211> LENGTH: 50
<212> TYPE: RNA
<213> ORGANISM: Homo sapiens

<400> SEQUENCE: 2761

agugggaucg cgccugugaa uagccacugc acuccagccu gagcaacaua      50

<210> SEQ ID NO 2762
<211> LENGTH: 50
<212> TYPE: RNA
<213> ORGANISM: Homo sapiens

<400> SEQUENCE: 2762

caaguguagu aucuguucuu aucaguuuaa uaucugauac guccucuauc      50

<210> SEQ ID NO 2763
<211> LENGTH: 50
<212> TYPE: RNA
<213> ORGANISM: Homo sapiens

<400> SEQUENCE: 2763

ucccuggugg ucuagugguu aggauucggc gcucucaccg ccgccgcccg      50

<210> SEQ ID NO 2764
<211> LENGTH: 46
<212> TYPE: RNA
<213> ORGANISM: Homo sapiens

<400> SEQUENCE: 2764

ccgauaacga acgagacucu ggcaugcuaa cuaguuacgc gacccc          46

<210> SEQ ID NO 2765
<211> LENGTH: 30
<212> TYPE: RNA
<213> ORGANISM: Homo sapiens

<400> SEQUENCE: 2765

ggccgugauc guauaguggu uaguacuccg                            30

<210> SEQ ID NO 2766
```

<211> LENGTH: 34
<212> TYPE: RNA
<213> ORGANISM: Homo sapiens

<400> SEQUENCE: 2766
gcgccgcugg uguaguggua ucaugcaaga uucc 34

<210> SEQ ID NO 2767
<211> LENGTH: 39
<212> TYPE: RNA
<213> ORGANISM: Homo sapiens

<400> SEQUENCE: 2767
ccuagcagcc gacuuagaac uggugcggac caggggaau 39

<210> SEQ ID NO 2768
<211> LENGTH: 42
<212> TYPE: RNA
<213> ORGANISM: Homo sapiens

<400> SEQUENCE: 2768
auugaucauc gacacuucga acgcacuugc ggccccgggu uc 42

<210> SEQ ID NO 2769
<211> LENGTH: 31
<212> TYPE: RNA
<213> ORGANISM: Homo sapiens

<400> SEQUENCE: 2769
ccauaccacc cugaacgcgc ccgaucucgu c 31

<210> SEQ ID NO 2770
<211> LENGTH: 48
<212> TYPE: RNA
<213> ORGANISM: Homo sapiens

<400> SEQUENCE: 2770
cucccucgcu gcgaucuauu gaaagucagc ccucgacaca aggguuug 48

<210> SEQ ID NO 2771
<211> LENGTH: 32
<212> TYPE: RNA
<213> ORGANISM: Homo sapiens

<400> SEQUENCE: 2771
gcauuggugc uucaguggua gaauucucgc cu 32

<210> SEQ ID NO 2772
<211> LENGTH: 31
<212> TYPE: RNA
<213> ORGANISM: Homo sapiens

<400> SEQUENCE: 2772
ucccuugugg ucuagugguu aggauucggc g 31

<210> SEQ ID NO 2773
<211> LENGTH: 49
<212> TYPE: RNA
<213> ORGANISM: Homo sapiens

<400> SEQUENCE: 2773
uuccguggag aggaacaacu cugagucuua acccaauuuu uugaggccu 49

<210> SEQ ID NO 2774
<211> LENGTH: 46
<212> TYPE: RNA
<213> ORGANISM: Homo sapiens

<400> SEQUENCE: 2774
guucuuguug uugaaauaca acgauggcuu uucauaucau uggucg 46

<210> SEQ ID NO 2775
<211> LENGTH: 44
<212> TYPE: RNA
<213> ORGANISM: Homo sapiens

<400> SEQUENCE: 2775
cagugcgccc cgggcggguc gcgccgucgg gcccggggga ggua 44

<210> SEQ ID NO 2776
<211> LENGTH: 34
<212> TYPE: RNA
<213> ORGANISM: Homo sapiens

<400> SEQUENCE: 2776
ggccgagauc guauaguggu uaguacucug cguu 34

<210> SEQ ID NO 2777
<211> LENGTH: 50
<212> TYPE: RNA
<213> ORGANISM: Homo sapiens

<400> SEQUENCE: 2777
cgacucuuag cgguggauca cucggcucgu gcgucgauga agaacccagc 50

<210> SEQ ID NO 2778
<211> LENGTH: 30
<212> TYPE: RNA
<213> ORGANISM: Homo sapiens

<400> SEQUENCE: 2778
cugguggucu agugguuagg auucggcgcu 30

<210> SEQ ID NO 2779
<211> LENGTH: 43
<212> TYPE: RNA
<213> ORGANISM: Homo sapiens

<400> SEQUENCE: 2779
ccugucacgc gggagaccgg gguucguuuc cccgacgggg agc 43

<210> SEQ ID NO 2780
<211> LENGTH: 37
<212> TYPE: RNA
<213> ORGANISM: Homo sapiens

<400> SEQUENCE: 2780
ucucaggguc gugggguucgg gccccacguu gggcgcc 37

<210> SEQ ID NO 2781
<211> LENGTH: 33
<212> TYPE: RNA
<213> ORGANISM: Homo sapiens

<400> SEQUENCE: 2781
agauggucag uaggacagaa gguaacauug aug 33

<210> SEQ ID NO 2782
<211> LENGTH: 45
<212> TYPE: RNA
<213> ORGANISM: Homo sapiens

<400> SEQUENCE: 2782
ggucaaugau guguuggcau guauuaucug aaucuauugc ugaug 45

<210> SEQ ID NO 2783
<211> LENGTH: 32
<212> TYPE: RNA
<213> ORGANISM: Homo sapiens

<400> SEQUENCE: 2783
gcaugggugg uuaaguggua gaauucucgc cu 32

<210> SEQ ID NO 2784
<211> LENGTH: 38
<212> TYPE: RNA
<213> ORGANISM: Homo sapiens

<400> SEQUENCE: 2784
ucauuaauca agaacgaaag ucggagguuc gaagacga 38

<210> SEQ ID NO 2785
<211> LENGTH: 37
<212> TYPE: RNA
<213> ORGANISM: Homo sapiens

<400> SEQUENCE: 2785
ggcugguccg augguagugg guuaucagca cuuauua 37

<210> SEQ ID NO 2786
<211> LENGTH: 29
<212> TYPE: RNA
<213> ORGANISM: Homo sapiens

<400> SEQUENCE: 2786
gccgugaucg uauagugguu aguacccug 29

<210> SEQ ID NO 2787
<211> LENGTH: 34
<212> TYPE: RNA
<213> ORGANISM: Homo sapiens

<400> SEQUENCE: 2787
ggccgggauc guauaguggu uaguacucug cguu 34

<210> SEQ ID NO 2788
<211> LENGTH: 45
<212> TYPE: RNA
<213> ORGANISM: Homo sapiens

<400> SEQUENCE: 2788
cccugcgggc cgccggugaa auaccacuac ucugaucguu uuuuc 45

<210> SEQ ID NO 2789
<211> LENGTH: 35
<212> TYPE: RNA
<213> ORGANISM: Homo sapiens

<400> SEQUENCE: 2789
auaucauugg ucgugguugu aguccgugcg agaau 35

<210> SEQ ID NO 2790
<211> LENGTH: 42
<212> TYPE: RNA
<213> ORGANISM: Homo sapiens

<400> SEQUENCE: 2790
ccccggcggc gggggcacgg ucccccgcga ggggggcccg gg 42

<210> SEQ ID NO 2791
<211> LENGTH: 50
<212> TYPE: RNA
<213> ORGANISM: Homo sapiens

<400> SEQUENCE: 2791
aacuccauca ugaaguguga cguggacauc cgcaaagacc uguacgccaa 50

<210> SEQ ID NO 2792
<211> LENGTH: 31
<212> TYPE: RNA
<213> ORGANISM: Homo sapiens

<400> SEQUENCE: 2792
cgggaggccc ggguucguuu cccggccaau g 31

<210> SEQ ID NO 2793
<211> LENGTH: 31
<212> TYPE: RNA
<213> ORGANISM: Homo sapiens

<400> SEQUENCE: 2793
cccugugguc uagugguuag gauucggcgc u 31

<210> SEQ ID NO 2794
<211> LENGTH: 42
<212> TYPE: RNA
<213> ORGANISM: Homo sapiens

<400> SEQUENCE: 2794
augugcuugg cugaggagcc aaugggggcga agcuaccauc ug 42

<210> SEQ ID NO 2795
<211> LENGTH: 27
<212> TYPE: RNA
<213> ORGANISM: Homo sapiens

<400> SEQUENCE: 2795
gcauuugugg uucaguggua gaauucu 27

<210> SEQ ID NO 2796
<211> LENGTH: 30
<212> TYPE: RNA
<213> ORGANISM: Homo sapiens

<400> SEQUENCE: 2796
aacgaacgag acucuggcau gcuaacuagu 30

<210> SEQ ID NO 2797
<211> LENGTH: 50
<212> TYPE: RNA
<213> ORGANISM: Homo sapiens

<400> SEQUENCE: 2797

```
ccacuacucu gaucguuuuu ucacugaccc ggugaggcgg gggggcgagg            50

<210> SEQ ID NO 2798
<211> LENGTH: 49
<212> TYPE: RNA
<213> ORGANISM: Homo sapiens

<400> SEQUENCE: 2798

uaaaagucgu aacaagguuu ccguagguga accugcggaa ggaucauua             49

<210> SEQ ID NO 2799
<211> LENGTH: 50
<212> TYPE: RNA
<213> ORGANISM: Homo sapiens

<400> SEQUENCE: 2799

aaauacaaca augguuuuuc auaucauugg ucgugguugu aguccgugcg            50

<210> SEQ ID NO 2800
<211> LENGTH: 29
<212> TYPE: RNA
<213> ORGANISM: Homo sapiens

<400> SEQUENCE: 2800

cucgucugau cucggaagcu aagcagggu                                  29

<210> SEQ ID NO 2801
<211> LENGTH: 32
<212> TYPE: RNA
<213> ORGANISM: Homo sapiens

<400> SEQUENCE: 2801

cucucucucc cccgcucccc guccucccc cu                               32

<210> SEQ ID NO 2802
<211> LENGTH: 36
<212> TYPE: RNA
<213> ORGANISM: Homo sapiens

<400> SEQUENCE: 2802

cgaaagguug gugguucgug cccacccagg gacgcc                          36
```

SHORT NON-CODING PROTEIN REGULATORY RNAS (SPRRNAS) AND METHODS OF USE

CROSS-REFERENCE TO RELATED APPLICATIONS

This application claims the benefit of U.S. Provisional Appl. No. 62/068,106, filed Oct. 24, 2014. The content of the aforementioned application is relied upon and is incorporated by reference in its entirety.

INCORPORATION-BY-REFERENCE OF MATERIAL SUBMITTED ELECTRONICALLY

Incorporated by reference in its entirety herein is a computer-readable sequence listing submitted concurrently herewith and identified as follows: One 428,242 Byte ASCII (Text) file named "Sequence_listing.txt," created on Oct. 24, 2015.

FIELD OF THE INVENTION

The present invention generally relates at least to the fields of medicine, molecular biology and cancer therapeutics.

BACKGROUND OF THE INVENTION

The concept of the "RNA World," referring to a period of time in primitive earth's history when the primary living substance was RNA or something chemically similar, is gaining support by research data (Higgs P G, Lehman N. The RNA World: molecular cooperation at the origins of life. *Nat Rev Genet.* 6(1):7-17, 2015. PMID: 25385129). These molecules are believed to carry out most of the information processing and metabolic transformations necessary for life, supporting the functional importance of RNA molecules without translation. New discoveries have expanded roles of non-coding RNAs (ncRNAs) in physiological and disease processes in organisms including humans, which improved our understanding of the molecular basis of life and redefined rules for RNAs (Cech T R, Steitz J A. The noncoding RNA revolution-trashing old rules to forge new ones. *Cell.* 157:77-94, 2014.). With tens of thousands functionally uncharacterized ncRNAs expressed in mammalian cells, it is not unreasonable to anticipate that new functions or rules of RNAs may further emerge to better understand RNA biology in addition to the basic DNA-RNA-proteins rule in today's life.

While ncRNAs don't translate into proteins or peptides, they are functional RNA molecules. Many ncRNAs are highly abundant in mammalian cells and functionally important, such as tRNAs, rRNAs, snoRNAs, and more recently characterized long ncRNAs (lncRNAs) and short ncRNAs (sncRNAs) which include microRNAs, siRNAs and piRNAs (Cech T R, Steitz J A. The noncoding RNA revolution-trashing old rules to forge new ones. *Cell.* 157:77-94, 2014.). The functions of ncRNAs are very broad from enzymatic activities of rRNAs and snRNAs, to mRNA expression targeting of siRNAs, to mRNA translation targeting of miRNAs, to transposon suppression of piRNAs in both physiological and pathological conditions (Gomes A Q, Nolasco S, Soares H. Non-coding RNAs: multi-tasking molecules in the cell. *Int J Mol Sci.* 14(8):16010-39, 2013.). However, the biological functions of most newly identified ncRNAs have not been tested or validated. Therefore, the roles of these ncRNAs in cellular biology require further investigation.

The biogenesis processes of miRNAs and siRNAs are under tight temporal and spatial control and have been well established. In mammals, both miRNAs and siRNAs are processed similarly by two RNase III proteins (Drosha and Dicer) in the nucleus and cytoplasm, respectively, followed by modifications through RNA editing, Argonaute loading and RNA decay, although the differences of the origin and precursors (Meister G, Tuschl T. Mechanisms of gene silencing by double-stranded RNA. *Nature* 431:343-349, 2004; Ha M, Kim N. Regulation of microRNA biogenesis. *Nat Rev Mol Cell Biol* 15(8):509-24, 2014; Carthew R W, Sonttheimer E J. Origins and mechanisms of miRNAs and siRNAs. Cell 136:642-655, 2009). Mature piRNA sequences are surprisingly diverse between different organisms, even between closely related species. piRNA biogenesis pathways in different organisms also appear to be diverse, and are distinct from those of miRNAs or siRNAs (Das P P, Bagijn M P, Goldstein L D, Woolford J R, Lehrbach N J, Sapetschnig A, Buhecha H R, Gilchrist M J, Howe K L, Stark R et al. Piwi and piRNAs act upstream of an endogenous siRNA pathway to suppress Tc3 transposon mobility in the *Caenorhabditis elegans* germline. *Mol Cell* 31:79-90, 2008; Houwing S, Kamminga LM, Berezikov E, Cronembold D, Girard A, van den Elst H, Filippov D V, Blaser H, Raz E, Moens C B et al. A role for piwi and piRNAs in germ cell maintenance and transposon silencing in Zebrafish. *Cell* 129:69-82, 2007; Vagin V V, Sigova A, Li C, Seitz H, Gvozdev V, Zamore P D. A distinct small RNA pathway silences selfish genetic elements in the germline *Science* 313:320-324, 2006.). piRNAs are predominantly expressed in germline cells or tissues but recent studies have shown their expression in somatic cells or tissues, suggesting unrecognized functionalities of these molecules in adult tissues. While the biogenesis of human piRNAs is poorly understood, its complexity is expected based on studies of other species. The mouse genome encodes 3 piwi proteins whereas 4 are found in human (Carmell M A, Girard A, van de Kant H J G, Bourc'his D, Bestor T H, de Rooij D G, Hannon G J. MIWI2 is essential for spermatogenesis and repression of transposons in the mouse male germline. *Dev Cell* 12:503-514, 2007; Deng W, Lin H. miwi, a murine homolog of piwi, encodes a cytoplasmic protein essential for spermatogenesis. *Dev Cell* 2:819-830, 2002; Kuramochi-Miyagawa S, Kimura T, Ijiri T W, Isobe T, Asada N, Fujita Y, Ikawa M, Iwai N, Okabe M, Deng W et al. Mili, a mammalian member of piwi family gene, is essential for spermatogenesis. *Development* 131:839-849, 2004.). These proteins express at different stages in development and associate with distinguishable subsets of piRNAs (Aravin A A, Sachidanandam R, Bourc'his D, Schaefer C, Pezic D, Toth K F, Bestor T, Hannon G J. A piRNA pathway primed by individual transposons is linked to de novo DNA methylation in Mice Mol Cell 31:785-799, 2008; Aravin A, Gaidatzis D, Pfeffer S, Lagos-Quintana M, Landgraf P, Iovino N, Morris P, Brownstein M J, Kuramochi-Miyagawa S, Nakano T et al. A novel class of small RNAs bind to MILI protein in mouse testes. *Nature* 442:203-207, 2006; Girard A, Sachidanandam R, Hannon G J, Carmell M A. A germline-specific class of small RNAs binds mammalian Piwi proteins. *Nature* 442:199-202, 2006) and may participate in different biogenesis. For example, pachytene piRNAs originate from distinct intergenic loci and associate with MILI and MIWI, transcription factor A-MYB, POL II and PLD6 (19. Aravin A A, Sachidanandam R, Bourc'his D, Schaefer C, Pezic D, Toth K F, Bestor T, Hannon G J. A piRNA pathway primed by individual transposons is linked to de novo DNA methylation in Mice, *Mol Cell* 31:785-799, 2008; Li X Z, Roy C K, Dong X, Bolcun-Filas E, Wang J, Han B W, Xu J, Moore M J, Schimenti J C, Weng Z et al. An ancient transcription factor initiates the burst of piRNA production during early meiosis in mouse testes. *Mol Cell* 50:67-81, 2013). The mouse MIWI- and MILI-associated sequence tags showed an association with 3' end extended sequences (Vourekas A, Zheng Q, Alexiou P, Maragkakis M, Kirino Y, Gregory B D, Mourelatos Z. Mili and Miwi target RNA repertoire reveals piRNA biogenesis and function of Miwi in spermiogenesis. *Nat Struct Mol Biol* 19:773-781, 2012), indicating that 5' end processing and incorporation of the 5' U into the MID domain of the Piwi protein occur first. This is likely followed by 3' end trimming by an unidentified exonuclease, by 3' end 2'-O-methylation of the piRNA by the mouse homolog of HEN1 and, finally, by binding of the 3' end by the PAZ domain of the Piwi protein (Kirino Y, Mourelatos Z. The mouse homolog of HEN1 is a potential methylase for Piwi-interacting RNAs. *RNA* 13:1397-1401, 2007; Kirino Y, Mourelatos Z. Mouse Piwi-interacting RNAs are 2"-Omethylated at their 3" termini *Nat Struct Mol Biol* 14:347-348, 2007). Tudor domain protein, TDRKH, which interacts with di-methylated MIWI and MIWI2 in mitochondria, has also been implicated in the final 3' precursor maturation step (Saxe J P, Chen M, Zhao H, Lin H. Tdrkh is essential for spermatogenesis and participates in primary piRNA biogenesis in the germline. *EMBO J* 32:1869-1885, 2013).

A number of ncRNAs have been shown to exhibit abnormal expression patterns in pathological conditions such as cancerous tissues where specific changes of miRNAs and lncRNAs have been documented to play critical functional roles in the disease processes (Mraz, M.; Pospisilova, S., "MicroRNAs in chronic lymphocytic leukemia: From causality to associations and back," *Expert Review of Hematology* 5 (6): 579-581, 2012; Pibouin L, Villaudy J, Ferbus D, Muleris M, Prospéri M T, Remvikos Y, Goubin G., "Cloning of the mRNA of overexpression in colon carcinoma-1: a sequence overexpressed in a subset of colon carcinomas," *Cancer Genet Cytogenet* 133 (1): 55-60, 2002; Fu X, Ravindranath L, Tran N, Petrovics G, Srivastava S. "Regulation of apoptosis by a prostate-specific and prostate cancer-associated noncoding gene, PCGEM1*," DNA Cell Biol* 25 (3): 135-41, 2006). For example, miRNAs involved in the large scale regulation of protein-coding genes and are extensively studied in recent years for their potential implications in human diseases such as cancer (Farh K K, Grimson A, Jan C, Lewis B P, Johnston W K, Lim LP, Burge C B, Bartel D P. "The widespread impact of mammalian MicroRNAs on mRNA repression and evolution," *Science* 310 (5755): 1817-21, 2005; Lim L P, Lau N C, Garrett-Engele P, Grimson A, Schelter J M, Castle J, Bartel D P, Linsley P S, Johnson J M. "Microarray analysis shows that some microRNAs downregulate large numbers of target mRNAs," *Nature* 433 (7027): 769-73, 2005). Recently, an increased attention has been devoted to lncRNAs. Although the biological functions and mechanisms of lncRNAs are less clear in part due to their length, IncRNAs likely possess multiple functions within a cell or in different cell types. Given the presence of tens of thousands ncRNAs in the human genome alone, it would not be surprising that ncRNAs have many not yet recognized biological functions. If RNAs possess various unrecognized chemical and biological functions in early life, it is also possible that cells might hijack these mechanisms to bypass limits of canonical pathways to achieve survival in physiological and pathological conditions.

Human cancer is a highly diverse disease with more than 100 different forms and is the second leading cause of death in the United States with 576,691 cancer-related deaths in 2011. Lung cancer is the leading cause of cancer-related death both in men and women. Although the national efforts in tobacco control has resulted in a reduced overall lung cancer incidence, the 42 million current smokers and 45 million former smokers in the United States make lung cancer a major healthcare challenge in the decades to come. Genetic and other molecular alterations caused by chronic exposure to tobacco smoke can last for years after smoking cessation. In the United States alone, it is estimated that 224,210 lung cancer patients will be diagnosed with 50% coming from former smokers and 159,260 will die from the disease this year. The number of deaths caused by lung cancer is more than the deaths from prostate, breast and colorectal cancers combined. The 5-year survival rate for patients diagnosed with lung cancer currently stands at a dismal 17% in the United States but much lower in other parts of the world such as <10% in the United Kingdom.

Lung cancer can be classified morphologically into small cell lung cancer (SCLC) and non-small cell lung cancer (NSCLC) subtypes with approximately 85% as NSCLC. Most NSCLC are either squamous cell carcinoma (SCC) or adenocarcinoma (ADC) and less common forms such as large cell and bronchial alveolar carcinoma based on histology. The histological classification reflects certain degrees of biologic features of the tumors and is clinically valuable in selecting treatment options. However, each histological subtype consists of a number of distinct subclasses with different underlying biological features which cannot be distinguished morphologically. Conversely, tumors with different histology may have similar underlying molecular features which may classify them biologically to benefit from molecular-based therapies. Therefore, molecular-based classification systems based on underlying biological features of the tumors will certainly provide more accurate and clinically powerful guide for treatment selections.

Clinically, lung patients can be classified into four stages based on conditions of the primary tumors, regional nodal involvement and the presence of distant metastasis. For NSCLC, if patients are diagnosed at earlier stages of the disease, surgery (sometimes radiation) may be effective treatment option. These patients, if successfully treated with surgery or radiation, can expect 50% chance of 5-year survival. Unfortunately, less than 50% of the patients with NSCLC are diagnosed at these earlier stages. Furthermore, many of the patients at these earlier stages may not be suitable for surgery due to locations of the tumors or poor pulmonary/cardiovascular functions. Patients diagnosed at later stages of the disease are rarely curable and have extremely poor survival expectations. Strategies to identify the disease early may improve cure rate and survival. Unfortunately, many of these patients remain vulnerable to develop recurrent or metastatic disease which will require systemic treatment. Current systemic treatment for patients with advanced stage NSCLC or recurrences consists of combinational chemotherapy, radiotherapy (for locally advanced or symptom controls) and molecular targeted therapy.

The benefits of conventional chemotherapy and chemoradiotherapy therapies have reached a plateau for the patient population. Substantial advances have been made to develop novel strategies targeting key abnormalities in lung cancer based on new knowledge obtained in the past decades. Unfortunately, survival rates of the patients with advanced stage NSCLC have improved only marginally.

Accordingly, what is needed are new therapeutic approaches in the treatment of cancer to improve patient survival, particularly for lung cancer.

This background information is provided for informational purposes only. No admission is necessarily intended, nor should it be construed, that any of the preceding information constitutes prior art against the present invention.

SUMMARY OF THE INVENTION

It is to be understood that both the foregoing general description of the embodiments and the following detailed description are exemplary, and thus do not restrict the scope of the embodiments.

In some aspects, the invention relates to short non-coding protein regulatory RNAs (sprRNAs), variants, fragments and inhibitors thereof and their uses as markers in certain disease states such as cancer, in particular lung cancer. In some embodiments, the sprRNAs, variants, fragments and inhibitors thereof are useful as therapeutic molecules in the treatment of diseases or conditions in subjects.

In one aspect, the present invention provides an isolated nucleic acid molecule comprising an sprRNA, variants, fragments and inhibitors thereof. In some embodiments, the sprRNA is at least 90% identical to any one of SEQ ID NOS:1-486, 489-494, or 560-2802. In some embodiments, the sprRNA is at least 90% identical to any one of SEQ ID NOS:192-486. In some embodiments, the sprRNA is piR-L-163 (SEQ ID NO:282). In some embodiments, the sprRNA is piR-L-138 (SEQ ID NO:268). In some embodiments, the sprRNA is SEQ ID NO:489. In some embodiments, the sprRNA comprises an sprRNA selected from the group consisting of:

i) sprRNA12600 (SEQ ID NO:490);
ii) sprRNA11568 (SEQ ID NO:491);
iii) sprRNA7410 (SEQ ID NO:492);
iv) sprRNA9378 (SEQ ID NO:493); and
v) sprRNA10698 (SEQ ID NO:494).

In another aspect, the invention provides an isolated nucleic acid molecule comprising cDNA of sprRNA, variants, and fragments thereof. In some embodiments, the sprRNA is at least 90% identical to any one of SEQ ID NOS:1-486, 489-494, or 560-2802. In some embodiments, the sprRNA is at least 90% identical to any one of SEQ ID NOS: 192-486 or 560-2802. In some embodiments, the cDNA encodes the sprRNA sequence comprising piR-L-163 (SEQ ID NO:282). In some embodiments, the cDNA encodes the sprRNA sequence comprising piR-L-138 (SEQ ID NO:268). In some embodiments, the cDNA encodes the sprRNA sequence comprising SEQ ID NO:489. In some embodiments, the cDNA encodes an sprRNA sequence selected from the group consisting of:

i) sprRNA12600 (SEQ ID NO:490);
ii) sprRNA11568 (SEQ ID NO:491);
iii) sprRNA7410 (SEQ ID NO:492);
iv) sprRNA9378 (SEQ ID NO:493); and
v) sprRNA10698 (SEQ ID NO:494).

In another aspect, the invention provides an isolated probe or primer comprising a nucleic acid sequence that hybridizes to the sprRNAs or cDNAs of the invention. In one embodiment, the invention provides an isolated probe or primer comprising a nucleic acid sequence that hybridizes to an isolated nucleic acid molecule comprising a sprRNA that is at least 90% identical to any one of SEQ ID NOS:1-486, 489-494, or 560-2802. In one embodiment, the invention provides an isolated probe or primer comprising a nucleic acid sequence that hybridizes to an isolated nucleic acid molecule comprising a sprRNA that is at least 90% identical to any one of SEQ ID NOS:192-486 or 560-2802.

In another aspect, the invention provides a nucleic acid molecule comprising a sequence that is antisense to an sprRNA of the invention. In some embodiments, the invention provides a nucleic acid molecule comprising a sequence that is antisense to a sprRNA that is at least 90% identical to any one of SEQ ID NOS:1-486, 489-494, or 560-2802. In some embodiments, the invention provides a nucleic acid molecule comprising a sequence that is antisense to a sprRNA that is at least 90% identical to any one of SEQ ID NOS:192-486 or 560-2802. In some embodiments, the nucleic acid molecule comprises Ant-138 (SEQ ID NO:556). In some embodiments, the nucleic acid molecule comprises Ant-163 (SEQ ID NO:496). In some embodiments, the nucleic acid molecule comprises AntiC (SEQ ID NO:558).

In another aspect, the invention provides a pharmaceutical composition comprising an sprRNA, variant, fragment or inhibitor thereof and a pharmaceutically acceptable carrier.

In another aspect, the invention provides a method of treating a disease or condition in a subject in need of treatment comprising administering to the subject a composition comprising an effective amount of a nucleic acid comprising an sprRNA, variant, fragment or inhibitor thereof. In some embodiments, the sprRNA is at least 90% identical to any one of SEQ ID NOS:1-486, 489-494, or 560-2802. In some embodiments, the sprRNA is piR-L-138 (SEQ ID NO:268). In some embodiments, the sprRNA is piR-L-163 (SEQ ID NO:282). In some embodiments, the sprRNA comprises SEQ ID NO:489. In some embodiments, the sprRNA is selected from the group consisting of:

i) sprRNA12600 (SEQ ID NO:490);
ii) sprRNA11568 (SEQ ID NO:491);
iii) sprRNA7410 (SEQ ID NO:492);
iv) sprRNA9378 (SEQ ID NO:493); and
v) sprRNA10698 (SEQ ID NO:494).

In some embodiments, the disease is cancer selected from the group consisting of breast cancer, prostate cancer, lung cancer, bladder cancer, pancreatic cancer, brain cancer, liver cancer, testicular cancer, skin cancer, colon cancer, ovarian cancer, cervical cancer, and uterine cancer. In some embodiments, the sprRNA or an inhibitor thereof is administered in combination with one or more additional therapies. In some embodiments, the inhibitor is Ant-138 (SEQ ID NO:556) and the one or more additional therapies are selected from the group consisting of cisplatin, gemcitabine (GEM), docetaxel and combinations thereof. In some embodiments, the inhibitor is AntiC (SEQ ID NO:558). In some embodiments, the condition to be treated is wound healing or tissue degeneration and the inhibitor administered is Ant-163 (SEQ ID NO:496).

In another aspect, the invention provides a method for diagnosing cancer or tumorigenesis in a subject comprising measuring the levels of one or more sprRNAs according to any one of SEQ ID NOS:1-486, 489-494, or 560-2802 in a subject's sample and comparing it to a control sample.

In another aspect, the invention provides a method of detecting the presence or absence of one or more sprRNAs according to SEQ ID NOS:1-486, 489-494, or 560-2802 in a sample from a patient comprising contacting the sample with a probe comprising a polynucleotide that hybridizes to one or more of SEQ ID NOS:1-486, 489-494, or 560-2802.

In another embodiment, the invention provides a method of detecting the presence or absence of one or more sprRNAs according to SEQ ID NOS:1-486, 489-494, or 560-2802 in a sample from a patient comprising isolating the sprRNAs from the patient, making complementary DNA from the sprRNAs, and detecting the complementary DNA.

In another embodiment, the invention provides a method of detecting sprRNA, comprising i) contacting a cell lysate with an antibody that binds one or more proteins;

ii) isolating the components from the cell lysate that bind the antibody; and iii) detecting the sprRNA from the isolated components.

In some embodiments, the antibody binds phosphor-serine, phosphor-threonine or phosphor-tyrosine proteins. In some embodiments, the sprRNA is any one of SEQ ID NOS:1-486, 489-494, or 560-2802.

In another aspect, the invention provides a method of preventing the binding of a sprRNA to a protein target, comprising contacting the sprRNA and protein target with an inhibitor whereby the inhibitor prevents binding of the sprRNA and protein target. In some embodiments the sprRNA corresponds to one or more of SEQ ID NOS:1-486, 489-494, or 560-2802. In some embodiments, the sprRNA is piR-L-163 (SEQ ID NO:282), the protein is an ERM protein and the inhibitor is Ant-163 (SEQ ID NO:496). In some embodiments, the sprRNA is piR-L-138 (SEQ ID NO:268), the protein is an MDM2 protein and the inhibitor is Ant-138 (SEQ ID NO:556). In some embodiments, the sprRNA is selected from the group consisting of: SEQ ID NO:489; sprRNA12600 (SEQ ID NO:490); sprRNA11568 (SEQ ID NO:491); sprRNA7410 (SEQ ID NO:492); sprRNA9378 (SEQ ID NO:493); and sprRNA10698 (SEQ ID NO:494), the protein is a nucleolin protein and the inhibitor is AntiC (SEQ ID NO:558).

In another aspect, the invention provides a method for identifying agonists or inhibitors that modulate binding of sprRNA to a protein target or modulate the biological activity of the sprRNA-protein interaction, comprising contacting the sprRNA and protein with the inhibitor or agonist and detecting whether the inhibitor or agonist affect binding and/or activity of the sprRNA and protein. In some embodiments, the sprRNA corresponds to one or more of SEQ ID NOS:1-486, 489-494, or 560-2802. In some embodiments, the inhibitor is an antisense nucleic acid to the sprRNA, variant or fragment thereof.

In another embodiment the present invention relates to a method for diagnosing cancer or tumorigenesis in a patient comprising measuring the levels of piRNA-L-163 in a patient sample such as blood plasma, serum saliva, sputum or urine compared to a matched sample from a noncancerous patient.

In another embodiment the present invention relates to a method for diagnosing lung cancer or metastasis in a patient comprising measuring the upregulated levels of piRNA-L-163 in a patient sample such as blood plasma, serum saliva, sputum or urine compared to a matched sample from a noncancerous patient.

In another embodiment the present invention relates to a method of detecting the presence or absence of one or more piRNA-L-163 sequences in a sample from the genome of a patient or subject with cancer comprising contacting the sample with a probe comprising a polynucleotide that hybridizes to piRNA-L-163.

In another embodiment the present invention relates to a probe comprising a polynucleotide that hybridizes to piRNA-L-163.

In another embodiment the present invention relates to a method of detecting the presence or absence of one or more piRNA-L-163 sequences in a sample from the genome of a patient or subject with lung cancer comprising contacting the sample with a probe comprising a polynucleotide that hybridizes to piRNA-L-163.

In another embodiment the present invention relates to a screening method for identifying inhibitors of cell proliferation in human bronchial epithelial cells comprising identifying molecule(s) which bind piRNA-L-163 and inhibit their function.

In another embodiment the present invention relates to a method for treating cancer or tumorigenesis in a patient comprising introducing into the patients cells an inhibitor molecule which prevents binding of piRNA-L-163 to ERM proteins.

In another embodiment the present invention relates to a kit for diagnosing lung cancer in a human subject comprising a probe comprising a polynucleotide that hybridizes to piRNA-163.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The skilled artisan will understand that the drawings, described below, are for illustration purposes only. The drawings are not intended to limit the scope of the present teachings in any way.

FIG. 2. Genome distribution and clustering analysis of piRNAs and piRNA-Ls expressed in HBE and NSCLC cells. (a) Distribution of piRNAs and piRNA-Ls in chromosomes. (b) Distribution of piRNAs and piRNA-Ls in mitochondria genome. Clustering based on piRNA and piRNA-L expression patterns in HBE2-4, ADC (SKMES-1, H157, H226 and H1437) and SCC (H596, H522, H194 and H1792); (c) entire piRNA and piRNA-L expressed, (d) piRNAs only, (e) piRNA-Ls only.

FIG. 7. Lengths of reads obtained in RNA-seq and human genome distributions of the reads. (a) Length distribution of all the reads. (b) Numbers of genomic loci mapped for the reads observed in each cell line (percentages of the reads).

FIG. 8. Chromosomes and mitochondria genome distributions of the reads. (a) Distribution of all the reads. (b) Percentages of the reads mapped to exonic, intronic, and intergentic regions, respectively for each cell line.

FIG. 12. Regions in moesin potentially critical for piR-L-163 and p-ERM interaction. (a) Predicted RNA binding element in human and *drosophila* moesin. (b) Alignment of human and *drosophila* moesin.

FIG. 13. Uncropped scans of critical Western blots presented in FIG. 5. (a-c) Protein levels in lysates obtained from H1792 cells transfected with different oligos. (d-f) p-ERM, F-actin and EBPSO levels in proteins pulled down by p-ERM. (g-h) EBPSO and F-actin levels in lysates of HBE4 and H522 cells with various treatment conditions. (i-l) F-actin, EBPSO and Moesin levels in proteins pulled down by$_P$-ERM.

Figure 18:
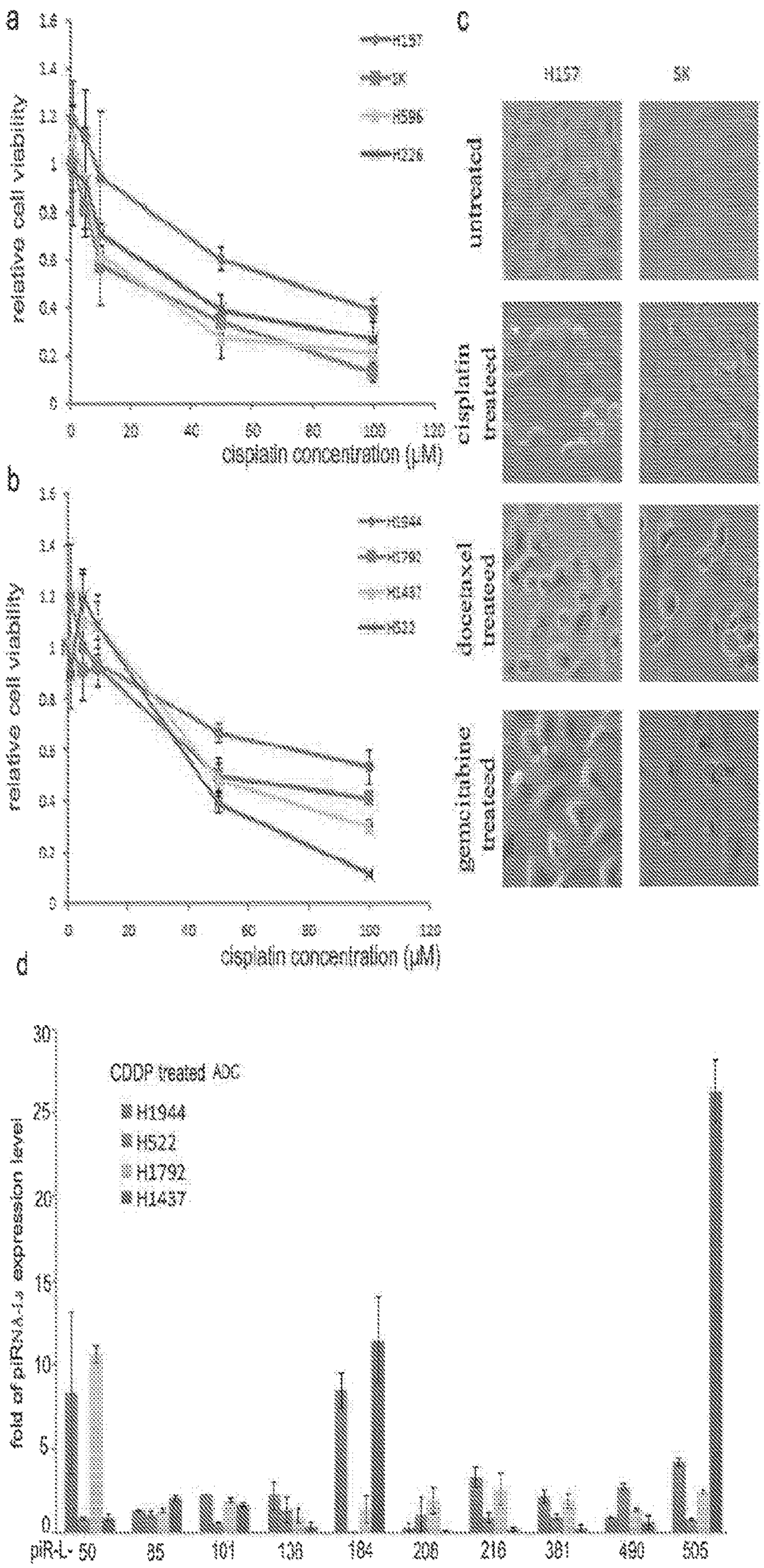

FIG. 18. Responses of NSCLC cell lines to CDDP and the impact of CDDP to expression level of selected piRNA-Ls in ADC cell lines. (a) Response curves of SCC cell lines to different concentrations of CDDP. (b) Response curves of ADC cell lines to different concentrations of CDDP. (c) Morphological changes of H157 and SKEMS-1 (SK) cells after treatment with different chemotherapeutic agents (IC25 doses). (d) Changes of piRNA-L expression (selected piRNA-Ls) in ADC cells after CDDP treatment. Values are averages of three independent replicates, error bars represent mean s.d.

Figure 19:
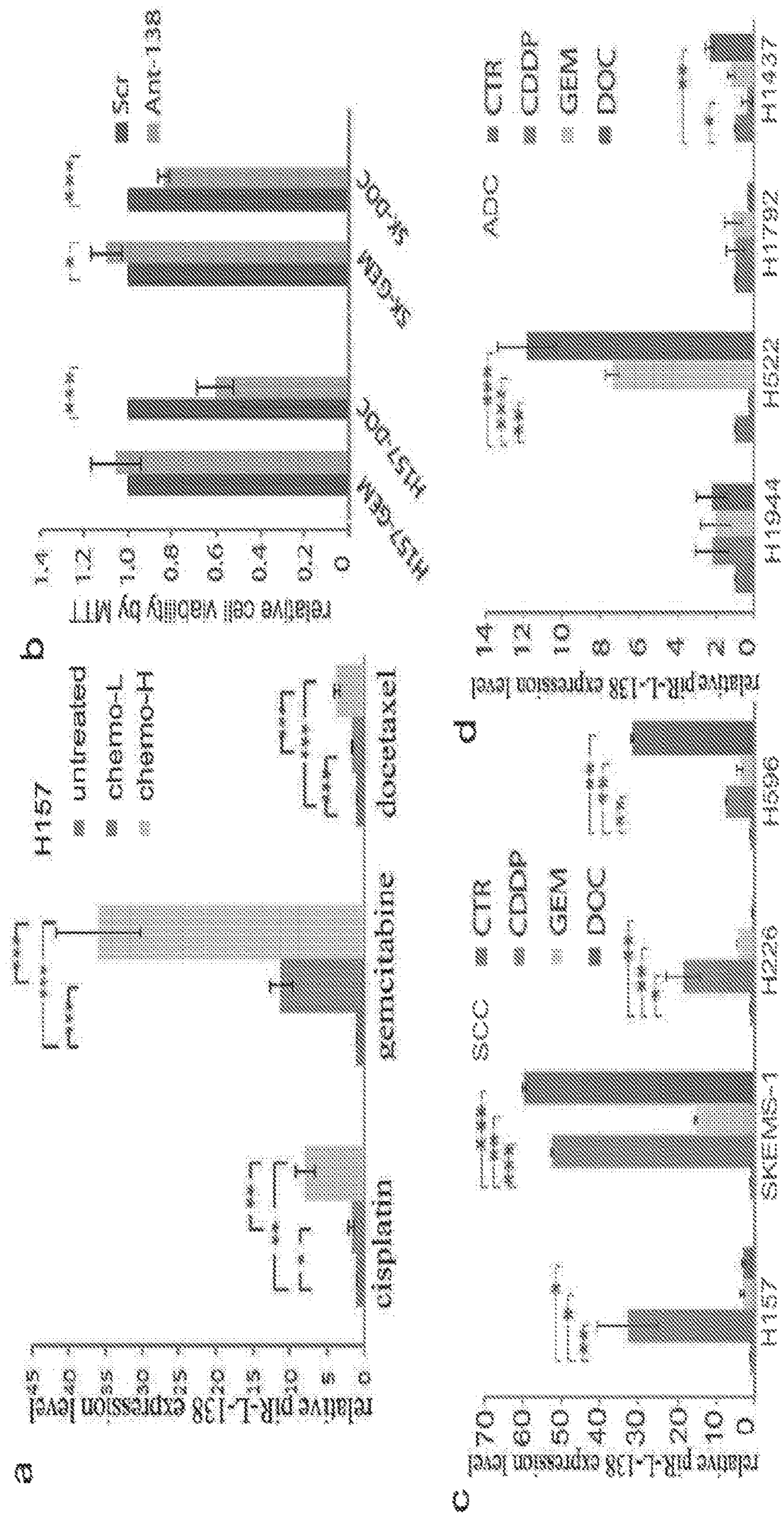

FIG. 19. Impact of chemotherapeutic agents to piR-L-138 expression in NSCLC cells and the effect of Ant-138 on SCC cell growth. (a) Impact of drug concentrations (H, LC25 doses; L, LC10 doses) to piR-L-138 expression levels in H157. (b) Viability of H157 and SKEMS-1 (SK) cells treated with gemcitabine (GEM) or docetaxel (DOC) and the impact of Ant-138 (compared to control Scr). (c) Changes of piR-L-138 expression level in SCC cell lines after treatment with different chemotherapeutic agents. (d) Changes of piR-L-138 expression level in ADC cell lines after treatment with different chemotherapeutic agents. Values are averages of three independent replicates; error bars represent mean s.d.; * $p<0.05$,  $p<0.01$, * $p<0.001$.

FIG. 20. Impact of Ant-138 in apoptosis of SCC cells following CDDP treatment. (a) Sub-G1 fractions of SCC cells transfected with either Scr or Ant-138 6 h after CDDP treatment. (b) Untreated controls of SCC cells in FITC annexin V experiments for FIG. 15*c*.

Figure 21:
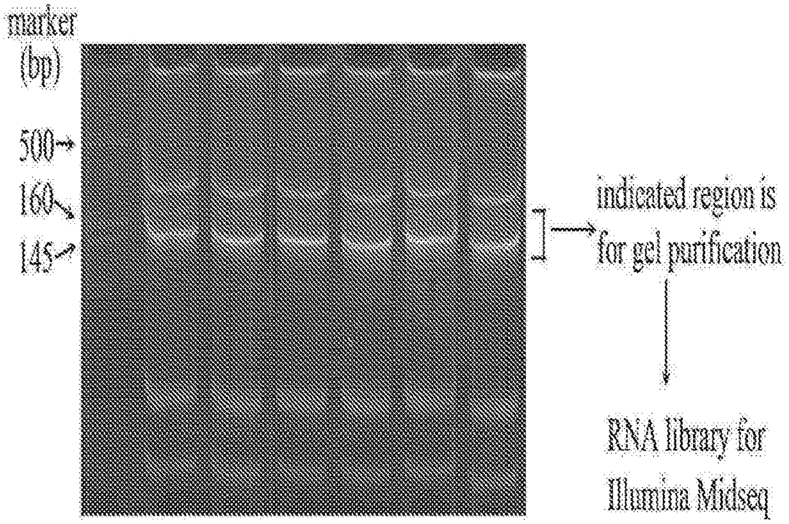

FIG. 21. Amplified bands of RNAs extracted from IP products of pooled HBE and SCC cell lines.

Figure 22:
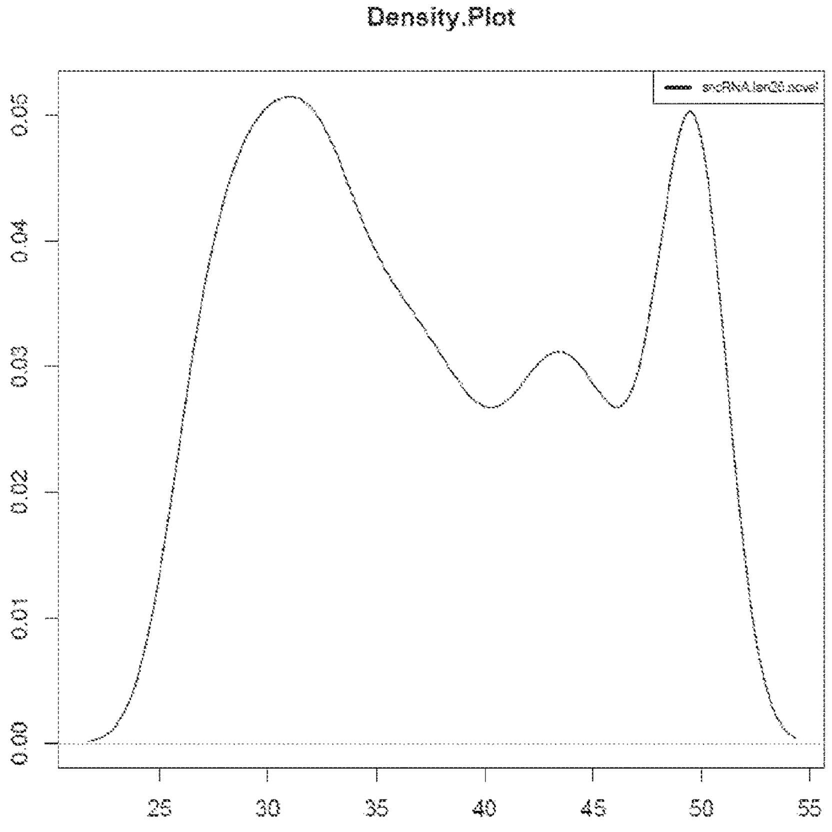

FIG. 22. Size distribution of identified unique phosphor-protein binding sncRNAs.

Figure 23:
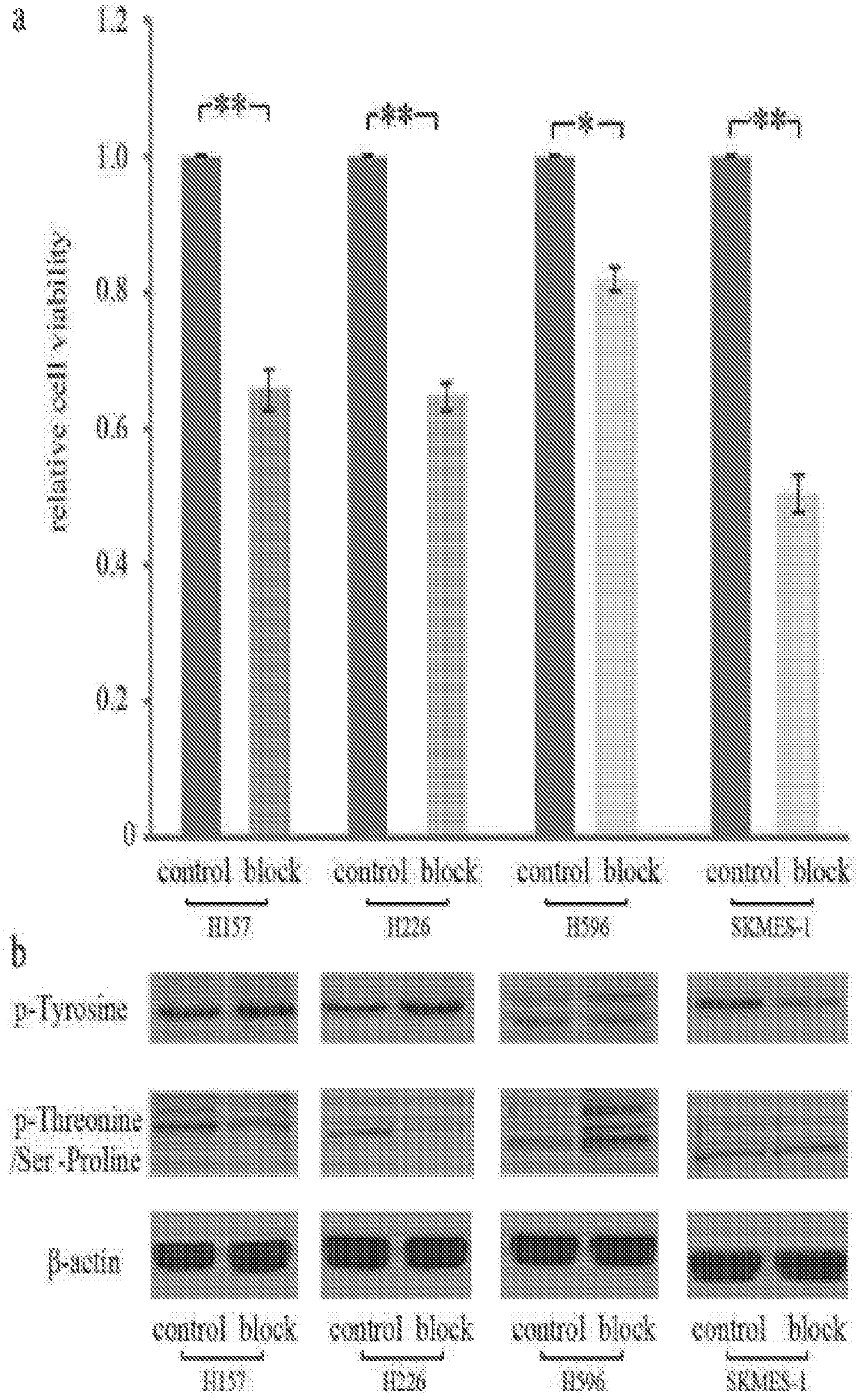

FIG. 23. Inhibiting proliferation (a) and altering levels of certain phosphor proteins (b) 24 h after the complementary DNA oligo treatment in lung SCC cells.

FIG. 24. Primers designed to amplify presumable pri- and pre-sprRNAs (piR-L-163 and piR-L-138) as colored (a). RNAs extracted from each subcellular components and the purity are verified by the presence or absence of HSP90 and Histone 3A (b). RT-PCR results of the pri- and pre-sprRNAs in each subcellular component (c).

Figure 25:
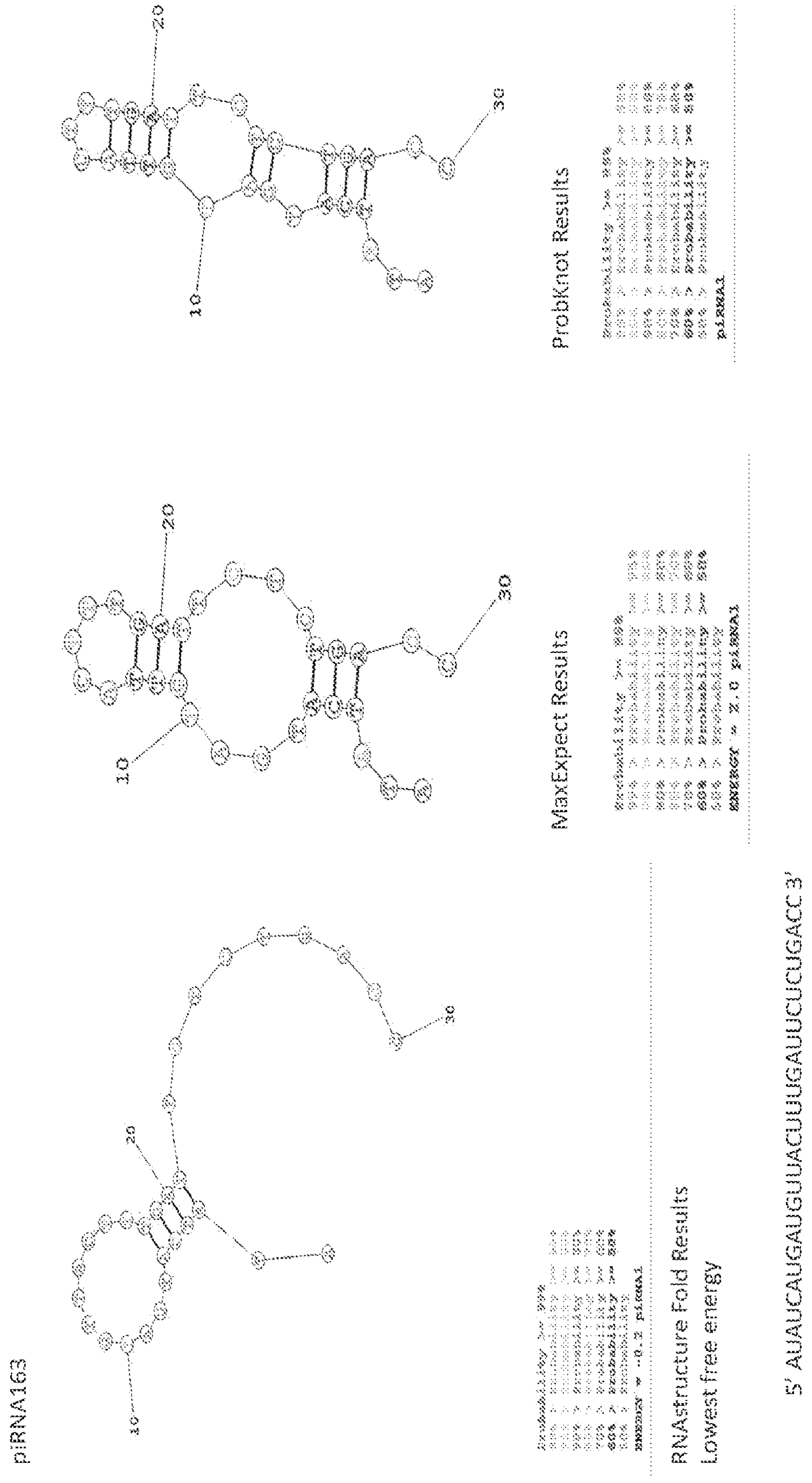

FIG. 25. Secondary structure prediction of piR-L-163.

Figure 26:
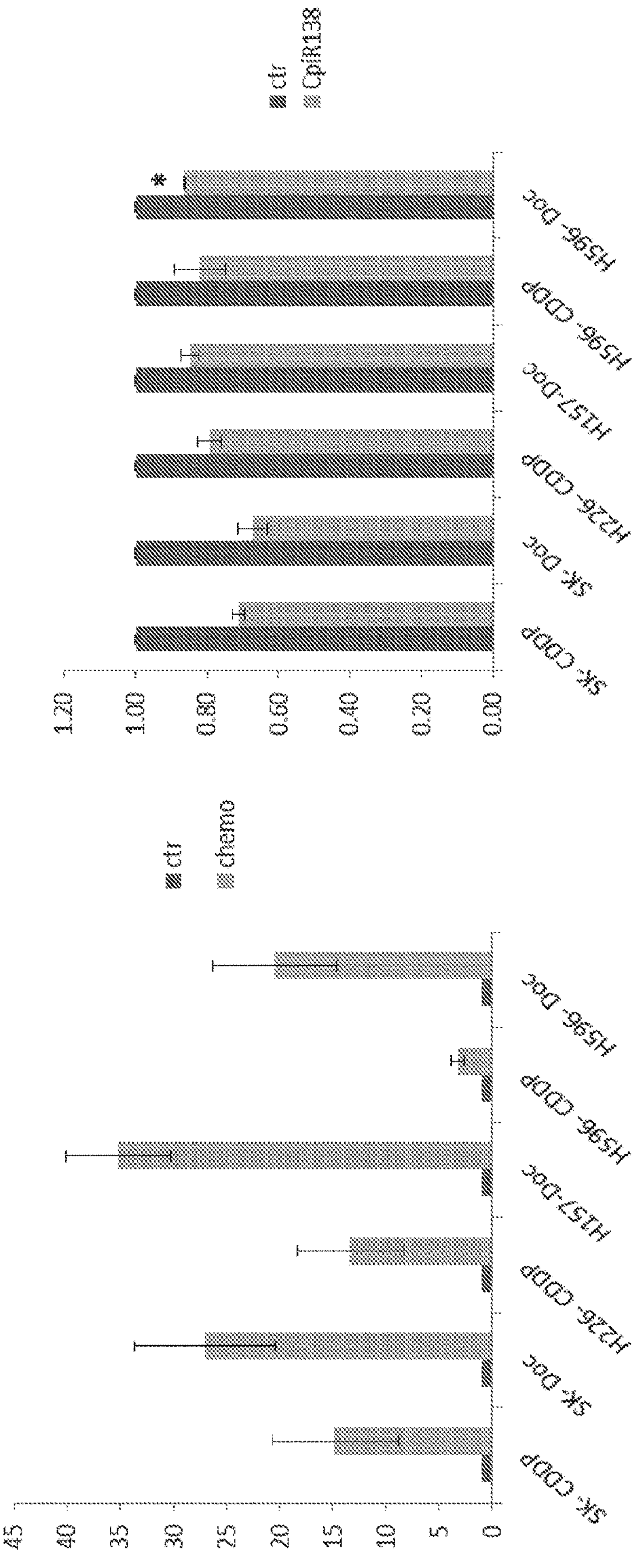

FIG. 26. piRNA Levels are highly Modulated in NSCLC Cells Following Chemotherapy (piRNA138 as an example).

Figure 27:
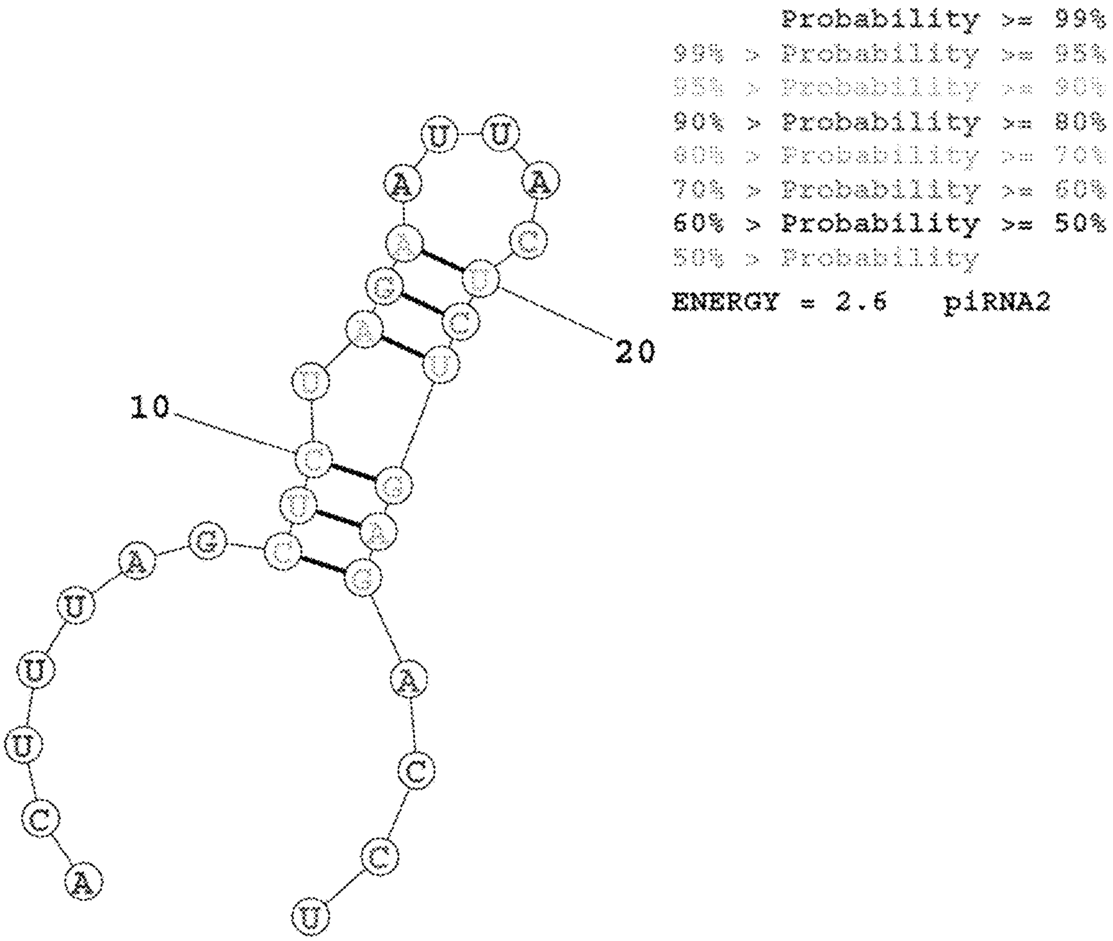

FIG. 27. Secondary structure prediction of piR-L-138.

Figure 28A:
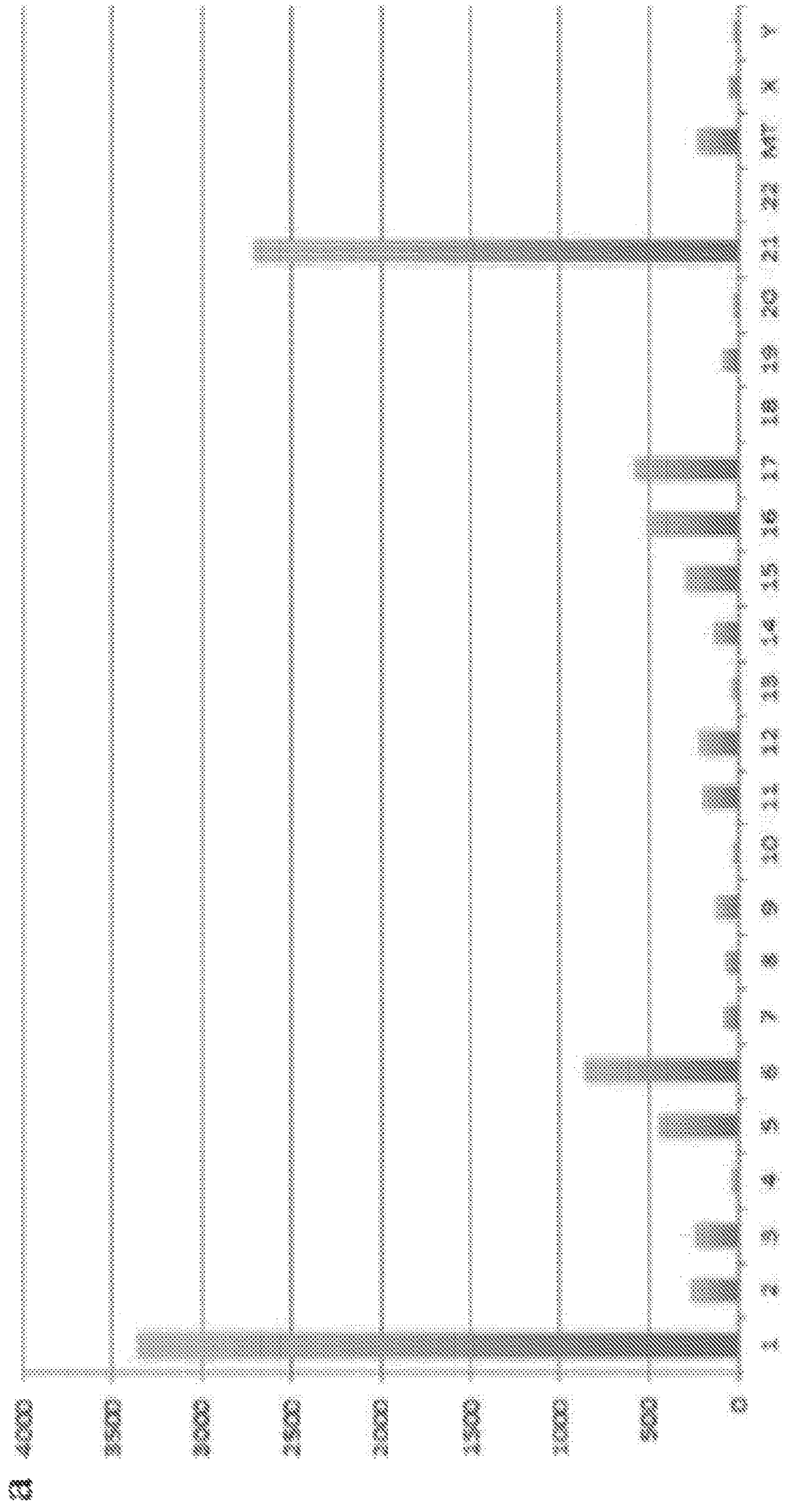

FIG. 28. Profile of phosphorylation related sprRNAs in HBE and SCC. a, Mitochondrial and chromosomal genomes distribution of sprRNAs. b-f, Venn diagrams showing the specific numbers and relative proportions of sprRNAs pulled down by antibodies targeting p-Tyr, -Ser and -Thr in HBE and SCC, respectively.

Figure 29C:
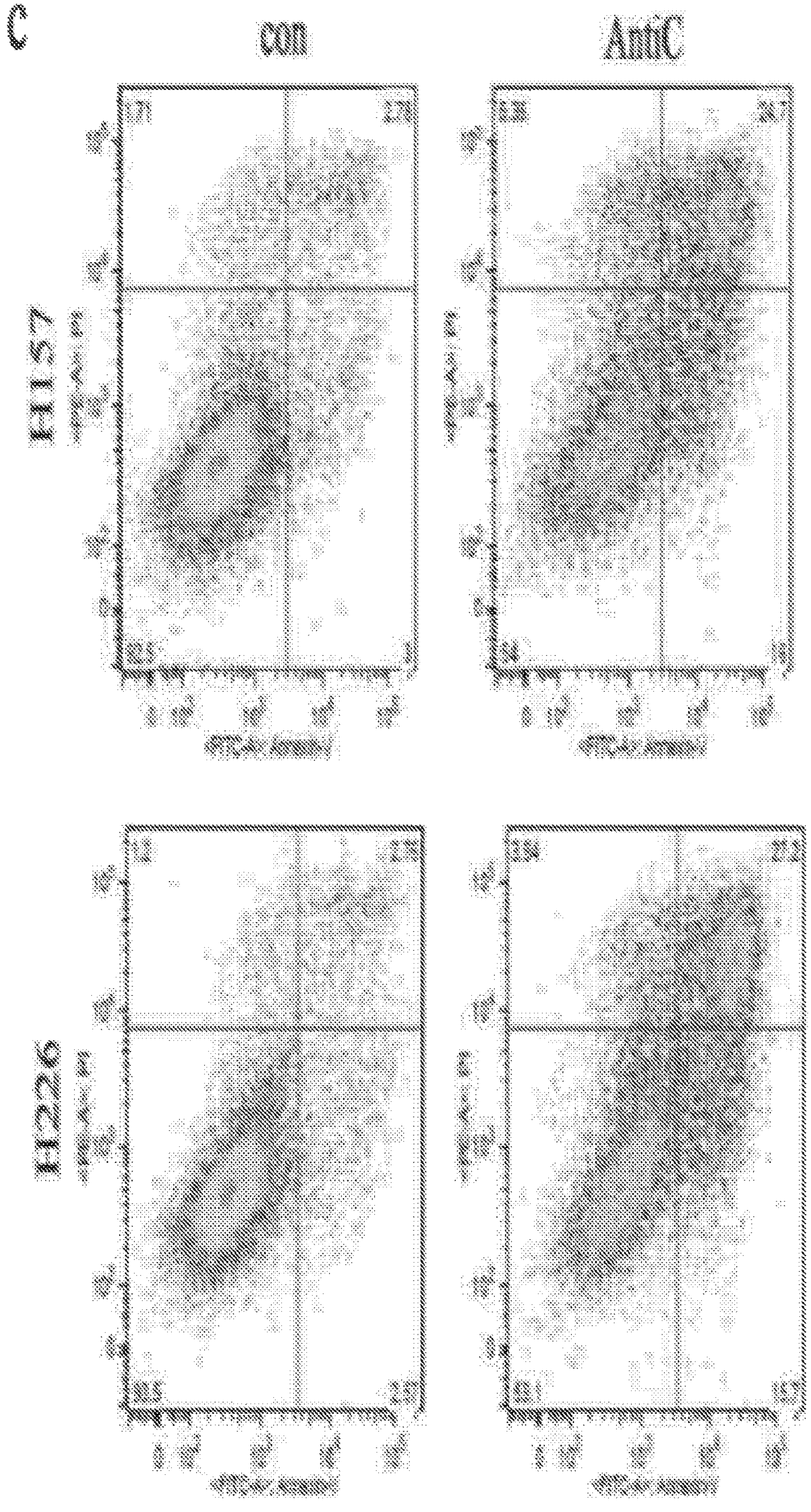

FIG. 29. Function of sprRNAs. a, Clustering on the bases of expression patterns of sprRNAs in HBE and SCC. b, Relative cell viability of SCC cells after treatment with control or AntiC. c, Cells stained with Annexin V and PI were analyzed by Flow Cyto after treatment with control and AntiC. d, Cleaved PARP and Caspase3 were detected by W.B. in cells treated with control and AntiC. e, Relative cell viability of NHBE cells treated with control or ectopic expression of core sequence.

Figure 30:
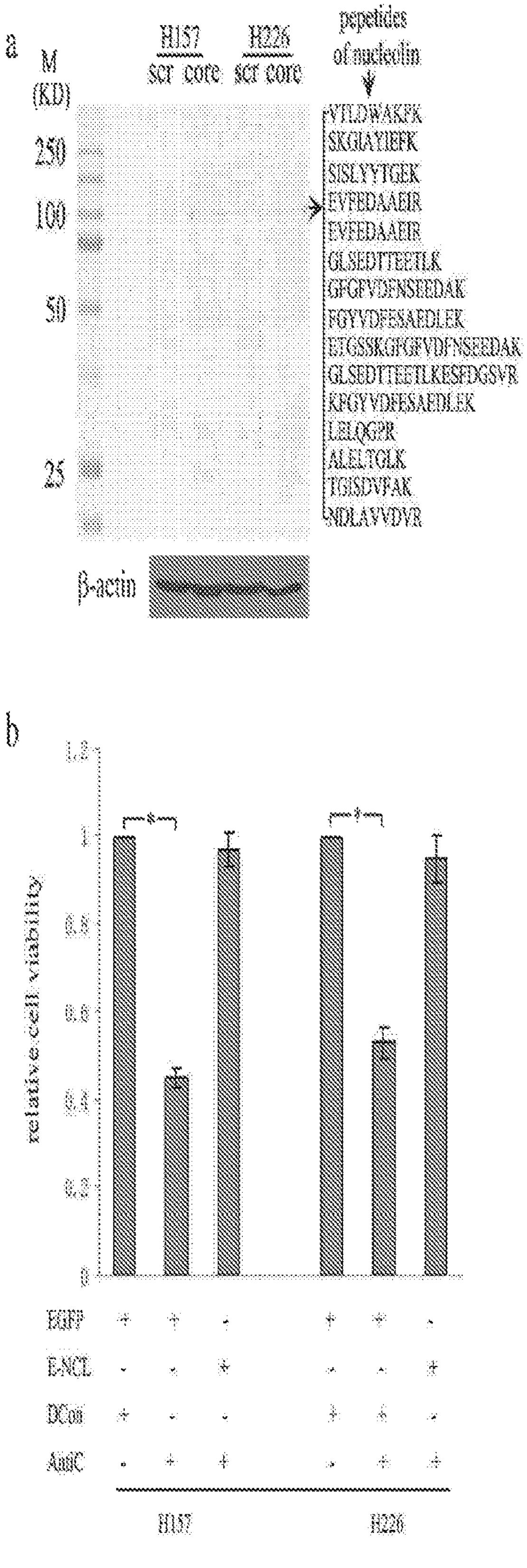

FIG. 30. Interaction of necleolin and core sequence (5'-CUCUCACCGCCGCGGCCCGGGUUCG-3') (SEQ ID NO:489) of sprRNA12600 (5'-CUCUCACCGCCGCGGCCCGGGUUCGAUUCCCGGUCAGGGAACC-3') (SEQ ID NO:490), sprRNA11568 (5'-CUCUCACCGCCGCGGCCCGGGUUCGAUUCCCGGUCAGGGAAC-3') (SEQ ID NO:491), sprRNA7410 (5'-CUCUCACCGCCGCGGCCCGGGUUCGAUUCCCGGUCAGGGAACCA-3') (SEQ ID NO:492), sprRNA9378 (5'-CUCUCACCGCCGCGGCCCGGGUUCGUUUCCCGGUCAGGGAACC-3') (SEQ ID NO:493) and sprRNA10698 (5'-CUCUCACCGCCGCGGCCCGGGUUCGUUUCCCGGUCAGGGAACCA-3') (SEQ ID NO:494). a, Pulled-down proteins from H157 and H226 cell lysates with biotinylated scrambled RNA or core sequence. Arrows indicate differentially presented bands and detected peptides nucleolin. b, Nuleolin could override the effects of AntiC.

Figure 31:
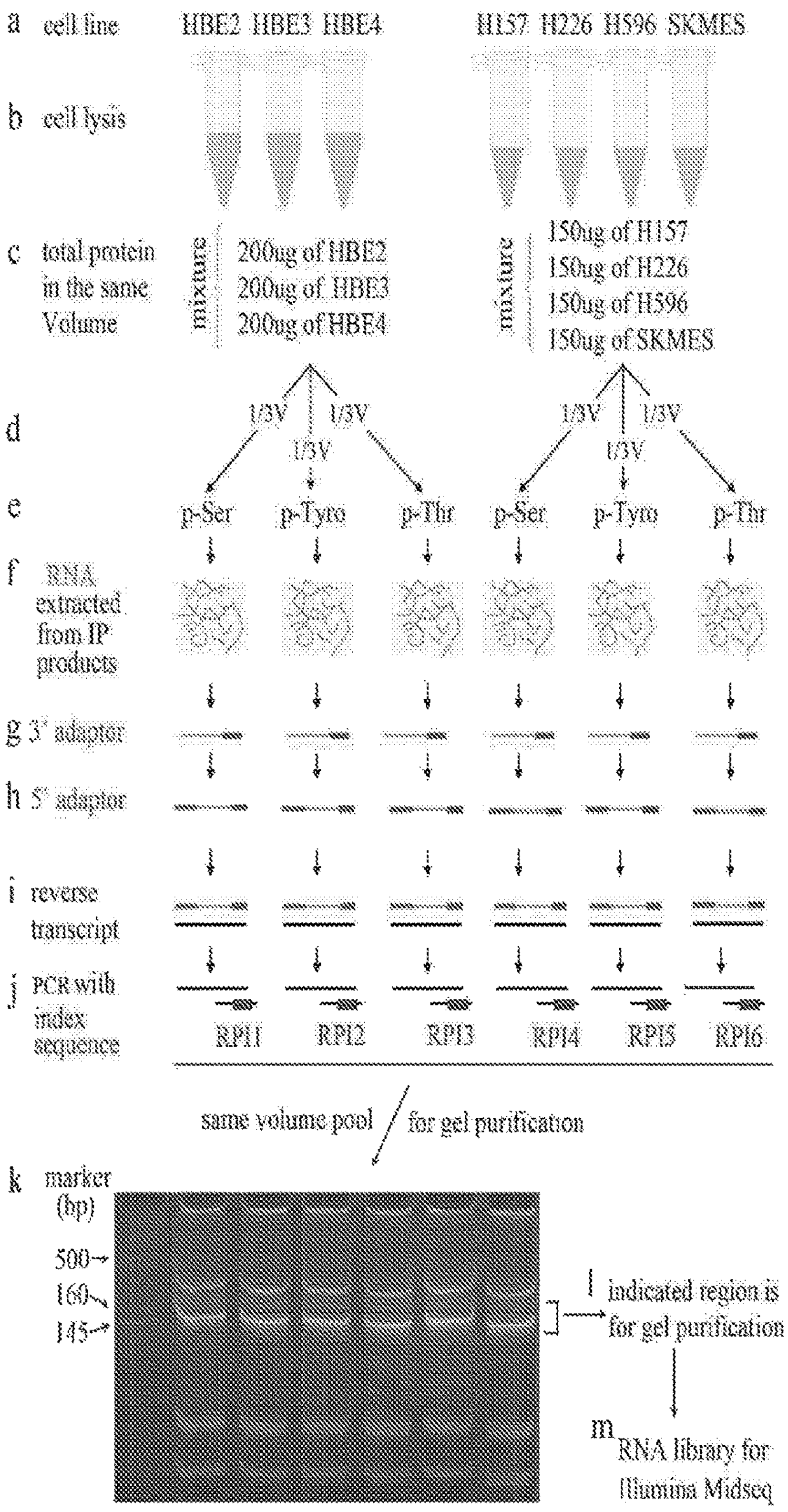

FIG. 31. Flowchart of the protocol used to prepare sncRNAs library from cell lines for RNA sequencing. a, Specific cell lines for sncRNAs library preparation. b-c, Cells were lysed and proteins were quantified. d-e, Lysed buffer was processed for IP using p-Ser, p-Tyr and p-Thr. f, RNAs were extracted from IP products. g-h, Adaptors were ligated. i-j, Extracted RNAs were processed for reverser transcription and polymerase chain reaction (PCR) using unique index sequence. k, PCR products were run in one nucleotide resolution gel. i-m, Targets bands were purified and sent for illumine Midseq.

Figure 32:
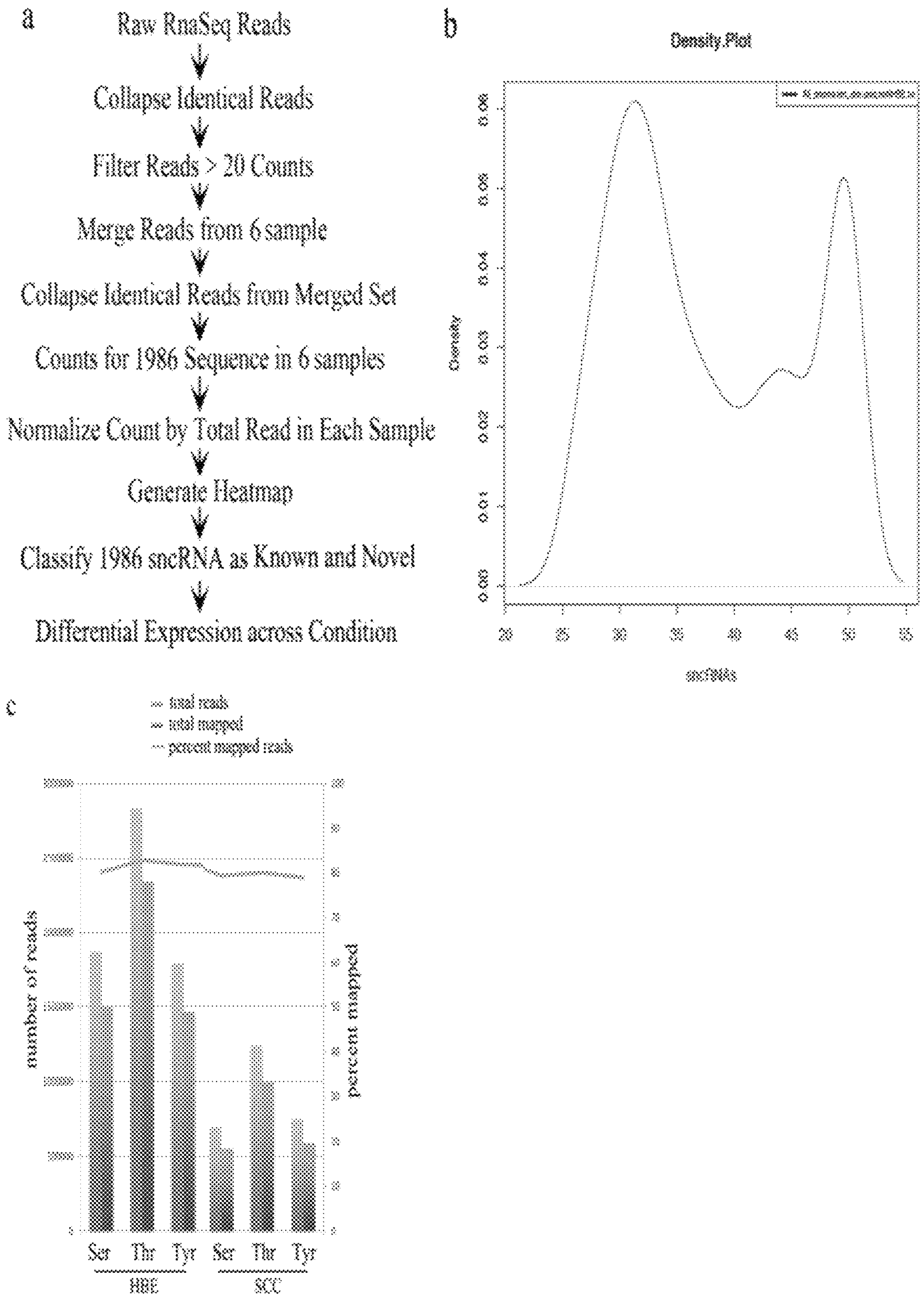

FIG. 32. Pipeline for analyzing reads and reads statistics. a, Pipeline for reads processing. b, Total and aligned reads of p-Ser, p-Thr and p-Tyr in HBE and SCC cell lines. c, Percentage of the mapped reads distributed in different hit (s) of loci in the human genome sequences.

DETAILED DESCRIPTION OF THE INVENTION

The present invention is based at least in part on the surprising discovery of a novel class of short non-coding RNAs (sncRNAs) referred to herein as sprRNAs (short non-coding protein regulatory RNAs) which are proposed to be integral components for the function of certain proteins in regulating cellular processes. It is also provided herein that abnormal expression of sprRNAs can contribute to cancer development and progression. Therefore, sprRNAs essential for maintaining cancer phenotypes are novel therapeutic targets and/or biomarkers for patients with cancers. These findings are based on the following observations: first, it is shown that piwi-interacting RNA-Like sncRNAs (piRNA-Ls) are expressed in somatic epithelial cells (although the total numbers of piRNA-Ls are substantially smaller than piRNAs expressed in germ line cells); second, piRNA-Ls are differentially expressed between normal bronchial epithelial cells (HBEs) and non-small cell lung cancer (NSCLC) cells as well as between different NSCLC histology subtypes; third, sncRNAs can bind directly to proteins and regulate protein functions, a mechanism never before suspected for sncRNAs. Provided herein are three lines of evidence to support the last claim: 1) piRNA-L-163, a novel sprRNA described herein, binds to phosphorylated ERM proteins (p-ERMs), a key cell cortex organizer, and regulates the protein functions; 2) piRNA-L-138, a novel sprRNA described herein, binds and stabilizes MDM2 oncogene upon treatment with chemotherapeutic agents; and 3) a considerable number of sncRNAs can be co-precipitated with phosphor-proteins, including 30-60% of the piRNA-Ls identified in HBE and NSCLC cells, with distinct patterns in the samples from proteins with different phosphorylated residuals as well as proteins from different types of cell lines. The present results are shown on lung cancer cells, the lead cause of cancer-related death in the United States. The present findings are significant paradigm shifting discoveries and pave the way for a new class of cancer therapeutic targets and beyond.

Unless otherwise noted, technical terms are used according to conventional usage. Definitions of common terms in molecular biology may be found, for example, in Benjamin Lewin, *Genes VII*, published by Oxford University Press, 2000 (ISBN 019879276X); Kendrew et al. (eds.); *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar technical references. As used herein, the word "about" means±10% of the numerical value.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

In some aspects, the invention relates to short non-coding protein regulatory RNAs (sprRNAs), variants, fragments and inhibitors thereof including piRNA-like molecules and their uses as markers in certain disease states such as cancer, in particular lung cancer. In some embodiments, the sprRNAs, variants, fragments and inhibitors thereof are useful as therapeutic molecules in the treatment of diseases or conditions in subjects.

As described herein, sprRNAs are short non-coding RNAs. sprRNAs are believed to represent a new class of noncoding RNAs and are not believed to function directly to mediate silencing of gene expression or suppress transposon mobility, unlike many other non-coding RNAs such as piRNAs, siRNAs and miRNAs. sprRNAs also do not include other noncoding tRNAs and ribosomal RNAs, although sprRNAs might compose sequences identical to partial sequences of tRNAs or ribosomal RNAs. In contrast, it has been discovered that sprRNAs interact with proteins, and through these interactions, affect one or more cellular processes mediated by the proteins. In some embodiments, the sprRNA ranges in size from about 24-55 nucleotides in length. In some embodiments, the sprRNA ranges in size from about 25-50 nucleotides in length or about 26-32 nucleotides in length. In some embodiments, the sprRNA comprise modifications of the RNA, including 3' end 2'-O-methylation. In some embodiments, the sprRNAs bind to phosphorylated proteins. RNA-Like sncRNAs (piRNA-Ls) referred to herein are encompassed by sprRNAs.

Nucleic Acids of the Invention

In one aspect, the present invention provides an isolated nucleic acid molecule comprising a short non-coding protein regulatory RNA (sprRNA), variants, fragments, and inhibitors thereof. In some embodiments, the invention provides isolated nucleic acid molecules having the nucleic acid sequence set out in SEQ ID NOS:1-486, 489-494, or 560-2802, variants, fragments, or inhibitors thereof. In some embodiments, the invention further provides nucleic acid molecules that are antisense nucleic acid molecules to the nucleic acid sequences set forth in SEQ ID NOS:1-486, 489-494, or 560-2802. In some embodiments, the present invention provides cDNA of the sprRNAs of the invention. In some embodiments, the sprRNA inhibitor is an antisense nucleic acid molecule. In some embodiments, the inhibitor comprises an antisense nucleic acid molecule comprising SEQ ID NOS:496, 497, or 556-559. In some embodiments the antisense molecules are selected from DNA and RNA molecules.

A particular nucleotide sequence comprising an sprRNA, variant, fragment or inhibitor may be identical over its entire length, for example, of SEQ ID NOS:1-486, 489-494, 496, 497, 556-559 or 560-2802. In some embodiments, the nucleic acids of the invention contain a nucleotide sequence that is highly identical, e.g., at least 90% identical, with a nucleotide sequence of an sprRNA, variant, fragment or inhibitor as set forth in SEQ ID NOS:1-486, 489-494, 496, 497, 556-2802.

In some embodiments the nucleic acid comprises variants of sprRNAs. In some embodiments, variants can include sequences with insertions, deletions, point mutations and modifications of the nucleotide bases. In some embodiments, antisense inhibitors include sequences with insertions, deletions, point mutations, and modifications of the nucleotide bases relative to the native sprRNA sequence.

In some embodiments, the nucleic acids of the invention, e.g., SEQ ID NOS:1-486, 489-494, 496, 497, or 556-2802, variants, fragments or inhibitors thereof, can also include additional or modified sequences of the above mentioned sequences which can aid in their purification or stability, for example. In some embodiments, one or more adaptor sequences can be attached to either the 3' and/or 5' ends of the molecule to facilitate amplification, purification and/or cloning. In some embodiments, the adaptor sequence comprises SEQ ID NO:499. In some embodiments, the sprRNAs, variants, fragments and inhibitors thereof (such as antisense nucleic acids as described herein) can be modified to include a phosphorothioate (PS) backbone. The modification to the backbone can be throughout the molecule or at one or more defined sites. In some embodiments, the sprRNAs, variants, fragments and inhibitors thereof can be modified at one or more sites to include 2'-O-methyl (2OMe) and/or 2'-O-methoxy-ethyl (MOE) groups. In some embodiments, the sprRNAs, variants, fragments and inhibitors thereof can be modified to encompass peptide nucleic acids (PNA). In some embodiments, the sprRNAs, variants, fragments and inhibitors thereof can be modified to encompass phosphorodiamidate morpholino oligomers (PMO).

Embodiments of the invention further include isolated nucleic acid molecules comprising a nucleotide sequence at least 90% identical, and more preferably at least 91%, 92%, 93%, 94%, 95%, 96%, 97%, 98% 99% or 100% identical to (a) SEQ ID NOS:1-486, 489-494, 496, 497, or 556-2802; or (b) a nucleotide sequence complementary to the nucleotide sequences in (a).

Conventional means utilizing known computer programs such as the BestFit program (Wisconsin Sequence Analysis Package, Version 10 for Unix, Genetics Computer Group, University Research Park, 575 Science Drive, Madison, Wis. 53711) may be utilized to determine if a particular nucleic acid molecule is at least 90%, 91%, 92%, 93%, 94%, 95%, 96%, 97%, 98% or 99% identical to any one of the nucleotide sequences shown in SEQ ID NOS:1-486, 489-494, 496, 497, or 556-2802.

In some embodiments, the invention provides a nucleic acid comprising an sprRNA, fragment or inhibitor of SEQ ID NOS:1-486, 489-494, 496, 497, or 556-2802 in which several, 1, 1-2, 1-3, or 1-5, 1-10, or 1-20 nucleotide residues are substituted, deleted or added, in any combination. In some embodiments, the variants maintain the desired activity, have abrogated activity, or enhanced activity.

In some embodiments, the nucleic acid are at least 90% identical over their entire length to a nucleic acid having the sequence set out in SEQ ID NOS:1-486, 489-494, 496, 497, or 556-2802, and nucleic acids which are complementary to such nucleic acids. In some embodiments, the nucleic acids are at least 95% identical over their entire length, at least 97% identical, at least 98% identical, or at least 99% identical.

The present invention is further directed to fragments of SEQ ID NOS:1-486, 489-494, 496, 497, or 556-2802 and sequences complementary thereto. A fragment can be defined to be at least about 10 nt, at least about 15 nt, at least about 20 nt, at least about 25 nt, and at least about 40 nt in length. Such fragments are useful as therapeutic agents, screening agents, diagnostic probes and primers as discussed herein and can be incorporated into detection kits to detect the nucleic acids in biological samples. The fragments can include truncations at the 5' or 3' ends, and can also include internal fragments with both 5' and 3' truncations.

In some embodiments, the invention provides an isolated probe or primer comprising a nucleic acid sequence that hybridizes to an isolated nucleic acid molecule comprising a sprRNA that is at least 90% identical to any one of SEQ ID NOS:1-486, 489-494, or 560-2802. In some embodiments, the probe or primer further comprises a detectable label. Methods of modifying probes or primers with detectable labels are well known in the art, and can include, e.g., fluorescent labels, enzymatic labels, and radiolabels. In some embodiments the probe or primer is DNA. In some embodiments, the probe or primer is RNA. In some embodiments, the invention provides a probe for detecting piR-L-163 (SEQ ID NO:498).

The present invention further relates to nucleic acids that hybridize to the above-described sequences. In this regard, the present invention especially relates to nucleic acids that hybridize under stringent conditions to the above-described nucleic acids. As herein used, the term "stringent conditions" means hybridization will occur only if there is at least 90% and preferably at least 95% identity and more preferably at least 97%, 98%, 99% and 100% identity between the sequences.

Furthermore, a major consideration associated with hybridization analysis of DNA or RNA sequences is the degree of relatedness the probe has with the sequences present in the specimen under study. This is important with a blotting technique (e.g., Southern or Northern Blot), since a moderate degree of sequence homology under nonstringent conditions of hybridization can yield a strong signal even though the probe and sequences in the sample represent non-homologous genes.

The particular hybridization technique is not essential to the invention, any technique commonly used in the art is within the scope of the present invention. Typical probe technology is described in U.S. Pat. No. 4,358,535 to Falkow et al., incorporated by reference herein. For example, hybridization can be carried out in a solution containing 6×SSC (10×SSC: 1.5 M sodium chloride, 0.15 M sodium citrate, pH 7.0), 5×Denhardt's (1.times.Denhardt's: 0.2% bovine serum albumin, 0.2% polyvinylpyrrolidone, 0.02% Ficoll 400), 10 mM EDTA, 0.5% SDS and about $10^7$ cpm of nick-translated DNA for 16 hours at 65° C. Additionally, if hybridization is to an immobilized nucleic acid, a washing step may be utilized wherein probe binding to nucleic acids of low homology, or nonspecific binding of the probe, may be removed. For example, a stringent wash step may involve a buffer of 0.2×SSC and 0.5% SDS at a temperature of 65° C.

Additional information related to hybridization technology and, more particularly, the stringency of hybridization and washing conditions may be found in Sambrook et al., *Molecular Cloning: A Laboratory Manual*, Second Edition, Cold Spring Harbor Laboratory, Cold Spring Harbor, N.Y. (1989), which is incorporated herein by reference.

Nucleic acids of the invention which are sufficiently identical to a nucleotide sequence contained in 1-486, 489-494, 496, 497, or 556-2802 or sequences complementary thereto can be used as hybridization probes, to isolate full-length sequences, interacting proteins or protein complexes, and/or genomic clones comprising the sequences and clones of other nucleic acids that have a high sequence similarity. Such hybridization techniques are known to those of skill in the art. Typically, these nucleotide sequences are at least about 90% identical, preferably at least about 95% identical, more preferably at least about 97%, 98% or 99% identical to that of the reference. In some embodiments, the probes generally will comprise at least 15 nucleotides. In some embodiments, such probes will have at least 20 nucleotides and can have at least 50 nucleotides or greater.

In some embodiments, the invention provides an isolated nucleic acid molecule that is at least 90% identical to any one of SEQ ID NOS:1-486, 489-494, 496, 497, or 556-2802. In some embodiments, the invention provides an isolated nucleic acid comprising a sequence that is at least 95% identical to any one of SEQ ID NOS:1-486, 489-494, 496, 497, or 556-2802. In some embodiments, the nucleic acid molecule comprises a sequence that is at least 99% identical to any one of SEQ ID NOS: 1-486, 489-494, 496, 497, or 556-2802. In another embodiment, the nucleic acid molecule comprises a sequence that is identical to any one of SEQ ID NOS: 1-486, 489-494, 496, 497, or 556-2802.

In some embodiments, the nucleic acid comprises the sprRNA piR-L-163 (SEQ ID NO:282).

In some embodiments, the nucleic acid comprises the sprRNA is piR-L-138 (SEQ ID NO:268).

In some embodiments, the nucleic acid comprises SEQ ID NO:489.

In some embodiments, the nucleic acid comprises an sprRNA selected from the group consisting of:

i) sprRNA12600 (SEQ ID NO:490);
ii) sprRNA11568 (SEQ ID NO:491);
iii) sprRNA7410 (SEQ ID NO:492);

iv) sprRNA9378 (SEQ ID NO:493); and v) sprRNA10698 (SEQ ID NO:494).

In some embodiments, the nucleic acid comprises Ant-138 (SEQ ID NO:556) which is DNA sequence that is antisense to piR-L-138 (SEQ ID NO:268). The RNA antisense sequence is set forth in SEQ ID NO: 557.

In some embodiments, the nucleic acid comprises Ant-163 (SEQ ID NO:496), which is DNA sequence that is antisense to piR-L-163 (SEQ ID NO:282). The RNA antisense sequence is set forth in SEQ ID NO: 497.

In some embodiments, the nucleic acid comprises AntiC (SEQ ID NO:558), which is a DNA sequence that is antisense to SEQ ID NO:489. The RNA antisense sequence is set forth in SEQ ID NO: 559.

Vectors and Host Cells

The present invention also relates to vectors that comprise nucleic acids of the present invention, host cells which are genetically engineered with vectors of the invention and the production of nucleic acids of the invention by recombinant techniques.

Representative examples of appropriate hosts include bacterial cells, such as streptococci, staphylococci, *E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, 293 and Bowes melanoma cells; and plant cells. A great variety of systems can be used, including DNA or RNA vectors and viral vectors.

In some embodiments, the invention provides a vector comprising any one of SEQ ID NOS: 1-486, 489-494, 496, 497, or 556-2802. In another embodiment, the invention comprises a host cell comprising a vector comprising any one of SEQ ID NOS: 1-486, 489-494, 496, 497, or 556-2802.

Methods of Treatment

In another embodiment, the invention provides a method of treating a disease or condition in a subject in need of treatment comprising administering to the subject a composition comprising an effective amount of a nucleic acid comprising an sprRNA, variant, fragment or inhibitor thereof of the invention.

In another embodiment, the invention provides a method of preventing the binding of a sprRNA, variant, or fragment thereof to a protein target, comprising contacting a nucleic acid comprising an sprRNA, variant, or fragment thereof and protein target with an inhibitor whereby the inhibitor prevents binding of the sprRNA, variant, or fragment thereof and protein target.

The sprRNA is not limiting and in some embodiments, the sprRNA is any one of SEQ ID NOS:1-486, 489-494 or 560-2802. In some embodiments, the sprRNA is at least 90% identical to any one of SEQ ID NOS:1-486, 489-494 or 560-2802. In some embodiments, the sprRNA is at least 90% identical to any one of SEQ ID NOS:1-191. In some embodiments, the sprRNA is at least 90% identical to any one of SEQ ID NOS:192-486, 489-494 or 560-2802. In some embodiments, the sprRNA is piR-L-138 (SEQ ID NO:268). In some embodiments, the sprRNA is piR-L-163 (SEQ ID NO:282). In some embodiments the nucleic acid administered comprises SEQ ID NO:489. In some embodiments, the sprRNA selected from the group consisting of:

i) sprRNA12600 (SEQ ID NO:490);

ii) sprRNA11568 (SEQ ID NO:491);

iii) sprRNA7410 (SEQ ID NO:492);

iv) sprRNA9378 (SEQ ID NO:493); and v) sprRNA10698 (SEQ ID NO:494).

In some embodiments, the inhibitor that is administered is an antisense nucleic acid molecule of the nucleic acid comprising the sprRNA, variant or fragment thereof of the invention. Antisense therapy is the administration of exogenous oligonucleotides which bind to a target nucleic acid. In some embodiments the antisense molecules can be antisense over the entire length of the sprRNA (i.e., 100% complementary). In some embodiments the antisense molecules can be complementary over only a portion of the sprRNA. In some embodiments, the antisense RNA is complementary over at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 nucleotides, which can be contiguous and non-contiguous nucleotides. In some embodiments, the antisense nucleic acid molecule is complementary to the sprRNA over contiguous nucleotides, while in other embodiments, one or more mismatches can occur between regions that are fully complementary in sequence. The antisense nucleotides herein in some embodiments are capable of disrupting the sprRNA-protein interaction and/or modulating the function of the sprRNA-protein interaction. In some embodiments, the antisense nucleic acid molecules of the invention can be modified and can include derivatives such as S-oligonucleotides (phosphorothioate derivatives or S-oligos, see, Jack Cohen, supra). S-oligos (nucleoside phosphorothioates) are isoelectronic analogs of an oligonucleotide (0-oligo) in which a nonbridging oxygen atom of the phosphate group is replaced by a sulfur atom. The S-oligos of the present invention may be prepared by treatment of the corresponding 0-oligos with 3H-1,2-benzodithiol-3-one-1,1-dioxide which is a sulfur transfer reagent. See Iyer et al., *J. Org. Chem.* 55:4693-4698 (1990); and Iyer et al., *J. Am. Chem. Soc.* 112:1253-1254 (1990), the disclosures of which are fully incorporated by reference herein. In some embodiments, the antisense nucleic acids can be modified at one or more sites to include 2'-O-methyl (2OMe) and/or 2'-O-methoxy-ethyl (MOE) groups. In some embodiments, the antisense nucleic acids can be modified to encompass peptide nucleic acids (PNA). In some embodiments, the antisense nucleic acids can be modified to encompass phosphorodiamidate morpholino oligomers (PMO).

In some embodiments, the antisense oligonucleotides of the present invention can be RNA or DNA that is complementary to sequences within SEQ ID NOS:1-486, 489-494, or 560-2802 and stably hybridize with such sequences. Use of an oligonucleotide complementary to such regions allows for selective hybridization to the sprRNA. In some embodiments, the antisense oligonucleotides of the present invention are at least 15 to 30-mer fragments of the antisense DNA molecule. Other criteria that are known in the art may be used to select the antisense oligonucleotides, varying the length or the annealing position in the targeted sequence.

The term "subject" as used herein is not limiting and is used interchangeably with patient. In some embodiments, the subject refers to animals, such as mammals. For example, mammals contemplated include humans, primates, dogs, cats, sheep, cattle, goats, pigs, horses, chickens, mice, rats, rabbits, guinea pigs, and the like. The terms "subject" and "patient."

As used herein, "treat" and all its forms and tenses (including, for example, treating, treated, and treatment) can refer to therapeutic or prophylactic treatment. In certain aspects of the invention, those in need thereof of treatment include those already with a pathological condition of the invention (including, for example, a cancer), in which case treating refers to administering to a subject (including, for example, a human or other mammal in need of treatment) a therapeutically effective amount of a composition so that the subject has an improvement in a sign or symptom of a pathological condition of the invention. The improvement may be any observable or measurable improvement. Thus, one of skill in the art realizes that a treatment may improve the patient's condition, but may not be a complete cure of the pathological condition. In other certain aspects of the invention, those in need thereof of treatment include, those in which a pathological condition is to be prevented, in which case treating refers to administering a therapeutically effective amount of a composition to a subject (including, for example, a human or other mammal in need of treatment) at risk of developing a disease or condition such as cancer.

The disease or condition to be treated is not limiting. In some embodiments, the disease or condition to be treated is selected from the group consisting of cancer, abnormal cell proliferation, tissue degeneration and wound healing.

As used herein, cancer includes but is not limited to, carcinomas and sarcomas, such as, for example, acute lymphoblastic leukemia, acute myeloid leukemia, adrenocortical cancer, AIDS-related cancers, AIDS-related lymphoma, anal cancer, astrocytoma (including, for example, cerebellar and cerebral), basal cell carcinoma, bile duct cancer, bladder cancer, bone cancer, brain stem glioma, brain tumor (including, for example, ependymoma, medulloblastoma, supratentorial primitive neuroectodermal, visual pathway and hypothalamic glioma), cerebral astrocytoma/malignant glioma, breast cancer, bronchial adenomas/carcinoids, Burkitt's lymphoma, carcinoid tumor (including, for example, gastrointestinal), carcinoma of unknown primary site, central nervous system lymphoma, cervical cancer, chronic lymphocytic leukemia, chronic myelogenous leukemia, chronic myeloproliferative disorders, colon cancer, colorectal cancer, cutaneous T-Cell lymphoma, endometrial cancer, ependymoma, esophageal cancer, Ewing's Family of tumors, extrahepatic bile duct cancer, eye cancer (including, for example, intraocular melanoma, retinoblastoma, gallbladder cancer, gastric cancer, gastrointestinal carcinoid tumor, gastrointestinal stromal tumor (GIST), germ cell tumor (including, for example, extracranial, extragonadal, ovarian), gestational trophoblastic tumor, glioma, hairy cell leukemia, head and neck cancer, squamous cell head and neck cancer, hepatocellular cancer, Hodgkin's lymphoma, hypopharyngeal cancer, islet cell carcinoma (including, for example, endocrine pancreas), Kaposi's sarcoma, laryngeal cancer, leukemia, lip and oral cavity cancer, liver cancer, lung cancer (including, for example, non-small cell), lymphoma, macroglobulinemia, malignant fibrous histiocytoma of bone/osteosarcoma, medulloblastoma, melanoma, Merkel cell carcinoma, mesothelioma, metastatic squamous neck cancer with occult primary, mouth cancer, multiple endocrine neoplasia syndrome, multiple myeloma/plasma cell neoplasm, mycosis fungoides, myelodysplastic syndromes, myelodysplastic/myeloproliferative diseases, myeloma, nasal cavity and paranasal sinus cancer, nasopharyngeal cancer, neuroblastoma, non-Hodgkin's lymphoma, oral cancer, oral cavity cancer, osteosarcoma, oropharyngeal cancer, ovarian cancer (including, for example, ovarian epithelial cancer, germ cell tumor), ovarian low malignant potential tumor, pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, pregnancy and breast cancer, primary central nervous system lymphoma, prostate cancer, rectal cancer, retinoblastoma, rhabdomyosarcoma, salivary gland cancer, soft tissue sarcoma, uterine sarcoma, Sezary syndrome, skin cancer (including, for example, non-melanoma or melanoma), small intestine cancer, supratentorial primitive neuroectodermal tumors, T-Cell lymphoma, testicular cancer, throat cancer, thymoma, thymoma and thymic carcinoma, thyroid cancer, transitional cell cancer of the renal pelvis and ureter, trophoblastic tumor (including, for example, gestational), unusual cancers of childhood and adulthood, urethral cancer, endometrial uterine cancer, uterine sarcoma, vaginal cancer, viral induced cancers (including, for example, HPV induced cancer), vulvar cancer, Waldenstrom's macroglobulinemia, Wilms' Tumor, and women's cancers.

In some embodiments, the disease is cancer selected from the group consisting of breast cancer, prostate cancer, lung cancer, bladder cancer, pancreatic cancer, brain cancer, liver cancer, testicular cancer, skin cancer, colon cancer, ovarian cancer, cervical cancer, and uterine cancer.

In some embodiments, the sprRNA, variant, fragment or inhibitor thereof is administered in combination with one or more additional therapies. The administration can be together in the same composition or in separate compositions. The sprRNA, variant, fragment or inhibitor thereof can be administered at substantially the same time with one or more additional therapies or at different times, and the spacing of time between the various treatments is not limiting. In some embodiments, the sprRNA, variant, fragment or inhibitor thereof of the invention is administered in combination to a cell or a subject before, during, or after another treatment, such as a chemotherapeutic agent (e.g. alkylating agents, antimetabolites, anthracyclines, alkaloids, topoisomerase inhibitors, select monoclonal antibodies, kinase inhibitors, tyrosine kinase inhibitors, select cytotoxic antibiotics, taxanes, actinomycin, bleomycin, plicamycin, mitomycin, targeted cancer therapies), anthracycline, doxorubicin, an alkylating agent, an antimetabolite, a *vinca* alkaloid, a taxane, a topoisomerase inhibitor, actinomycin, an anthracycline, bleomycin, plicamycin, mitomycin. In some embodiments, the sprRNA, variant, fragment or inhibitor thereof of the invention is administered in combination with radiation therapy, hormonal therapy, an aromatase inhibitor, tamoxifen, gonadotropin-releasing hormone analog, a selective estrogen receptor modulator, an antiandrogen, and a progestin.

In some embodiments, the sprRNA, variant, fragment or inhibitor thereof of the invention is administered in combination with one or more of the following additional therapies: Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Adrucil (Fluorouracil), Afatinib Dimaleate, Afinitor (Everolimus), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Avastin (Bevacizumab), Axitinib, Azacitidine, BEACOPP, Becenum (Carmustine), Beleodaq (Belinostat), Belinostat, Bendamustine Hydrochloride, BEP, Bevacizumab, Bexarotene, Bexxar (Tositumomab and I 131 Iodine Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Busulfan, Busulfex (Busulfan), Cabazitaxel, Cabozantinib-S-Malate, CAF, Campath (Alemtuzumab), Camptosar (Irinotecan Hydrochloride), Capecitabine, CAPDX, Carboplatin, CARBOPLATIN-TAXOL, Carfilzomib, Carmubris (Carmustine), Carmustine, Carmustine Implant, Casodex (Bicalutamide), CeeNU (Lomustine) Ceritinib, Cerubidine (Daunorubicin Hydrochloride), Cervarix (Recombinant HPV Bivalent Vaccine), Cetuximab, Chlorambucil, CHLORAMBUCIL-PREDNISONE, CHOP, Cisplatin, Clafen (Cyclophosphamide), Clofarabine, Clofarex (Clofarabine), Clolar (Clofarabine), CMF, Cometriq (Cabozantinib-S-Malate), COPP, COPP-ABV, Cosmegen (Dactinomycin), Crizotinib, CVP, Cyclophosphamide, Cyfos (Ifosfamide), Cyramza (Ramucirumab), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Ifex (Ifosfamide), Ifosfamide, Ifosfamidum (Ifosfamide), Imatinib Mesylate, Imbruvic a (Ibrutinib), Imiquimod, Inlyta (Axitinib), Intron A (Recombinant Interferon Alfa-2b), Iodine 131 Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Keytruda (Pembrolizumab), Kyprolis (Carfilzomib), Lanreotide Acetate, Lapatinib Ditosylate, Lenalidomide, Lenvatinib Mesylate, Lenvima (Lenvatinib Mesylate), Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Lynparza (Olaparib), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Neupogen (Filgrastim), Nexavar (Sorafenib Tosylate), Nilotinib, Nivolumab, Nolvadex (Tamoxifen Citrate), Nplate (Romiplostim), Obinutuzumab, OEPA, Ofatumumab, OFF, Olaparib, Omacetaxine Mepesuccinate, Oncaspar (Pegaspargase), Ontak (Denileukin Diftitox), Opdivo (Nivolumab), OPPA, Oxaliplatin, Paclitaxel, Paclitaxel Albumin-stabilized Nanoparticle Formulation, PAD, Palbociclib, Palifermin, Palonosetron Hydrochloride, Pamidronate Disodium, Panitumumab, Paraplat (Carboplatin), Paraplatin (Carboplatin), Pazopanib Hydrochloride, Pegaspargase, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Purixan (Mercaptopurine), Radium 223 Dichloride, Raloxifene Hydrochloride, Ramucirumab, Rasburicase, R—CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, R-EPOCH, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Siltuximab, Sipuleucel-T, Somatuline Depot (Lanreotide Acetate), Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synovir (Thalidomide), Synribo (Omacetaxine Mepesuccinate), TAC, Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Thiotepa, Toposar (Etoposide), Topotecan Hydrochloride, Toremifene, Torisel (Temsirolimus), Tositumomab and I 131 Iodine Tositumomab, Totect (Dexrazoxane Hydrochloride), TPF, Trametinib, Trastuzumab, Treanda (Bendamustine Hydrochloride), Trisenox (Arsenic Trioxide), Tykerb (Lapatinib Ditosylate), Vandetanib, VAMP, Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELIRI, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoladex (Goserelin Acetate), Zoledronic Acid, Zolinza (Vorinostat), Zometa (Zoledronic Acid), Zydelig (Idelalisib), Zykadia (Ceritinib), and Zytiga (Abiraterone Acetate). In some embodiments, the drug is selected from the group consisting of Paclitaxel, Curcumin, Docetaxel, Ixabepilone, Vinblastine, Colchicine, Y-27632 Fasudil, SU6656 Dasatinib, HDAC inhibitors, ROCK inhibitors, Parthenolide, Costunolide and ML-7 Jazplakinolide.

In some embodiments, the nucleic acid comprising the sprRNA, variant, fragment or inhibitor thereof prevents resistance to one or more additional therapies, such as the therapies described above. In some embodiments, inhibitor is an inhibitor to piR-L-138 (SEQ ID NO:268), such as Ant-138 (SEQ ID NO:556), and the one or more additional therapies are referred to above. In some embodiments, the one or more additional therapies to which the inhibitor of piR-L-138 prevents resistance is selected from the group consisting of cisplatin, gemcitabine (GEM), docetaxel and combinations thereof.

In one embodiment, the condition to be treated is cancer, such as lung cancer and an inhibitor of any of SEQ ID NOS: 489-494 is administered. In some embodiments, the inhibitor is AntiC (SEQ ID NO:558). In some embodiments, the invention provides a method of treating cancer comprising administering an effective amount of piRNA-L-163 (SEQ ID NO:282), a variant, or fragment thereof.

In some embodiments, the condition to be treated is selected from wound healing and tissue degeneration. In some embodiments, an inhibitor of sprRNA piR-L-163 (SEQ ID NO:282) is administered, such as Ant-163 (SEQ ID NO:496).

The frequency of administration is not limiting. In some embodiments, the the sprRNA, variant, fragment or inhibitor thereof of the invention administered to the subject or cell can vary from about once every 2, 3, 4, 5, or 6 months to about 1, 2, 3, 4, or 5 times a month, to about 1, 2, 3, 4, or 5 times a week, to about once per day, to about 1, 2, 3, 4, 5, 6, 7, 8, 9 or 10 times a day.

In some embodiments, the invention provides a method for treating cancer or tumorigenesis in a patient comprising introducing into the patients cells an inhibitor molecule which prevents binding of piRNA-L-163 to ERM proteins. In some embodiments, the invention provides a method of treating cancer comprising administering an effective amount of piRNA-L-163, a variant, or fragment thereof.

Diagnostic Assays

This invention also relates to the use of nucleic acids, antibodies or other binding reagents reactive specifically against the sprRNAs as diagnostic reagents. Detection of altered sprRNA (or cDNA) can provide a diagnostic tool that can add to or define a diagnosis of a disease or susceptibility to a disease which results from altered expression of the sprRNA. The detection of normal or altered levels of the sprRNA can direct the medical practitioner to set an appropriate course of treatment for the patient.

As a means to detect or diagnose neoplastic disorders, such as lung cancer, differences in the levels of sprRNA (or cDNA generated therefrom) between affected and unaffected individuals, or between normal and cancerous tissues can be determined.

Nucleic acids for diagnosis may be obtained, for example, from a biopsy of cells from the tissue. In some embodiments, bodily fluids, e.g., urine, are obtained from the patient are used to detect elevated or reduced levels. Alterations in levels can be assayed by comparison to a standard or control level of sprRNA. RNA may be used directly for detection or may be converted to cDNA and amplified enzymatically by using PCR or other amplification techniques prior to analysis.

The diagnostic assays offer a process for diagnosing or determining a susceptibility to a disease or condition, such as a neoplastic disorder, through detection of altered levels of one or more sprRNA by the methods described. Decreased or increased levels can be measured at the RNA level using any of the methods well known in the art for the quantitation of nucleic acids; for example, RT-PCR, RNase protection, Northern blotting, array analysis, and other hybridization methods may be utilized.

The sprRNAs can be assayed individually or in combination, e.g., as a panel of biomarkers to indicate the presence or absence of the disease or condition. Other known markers, can also be simultaneously assayed, in accordance with the methods of the present invention.

In some embodiments, the invention provides a method of detecting the presence or absence of one or more sprRNAs in a sample, comprising contacting the sample with a probe comprising a nucleic acid that hybridizes to one or more of the sprRNAs. In some embodiments, the sprRNAs comprise any one of SEQ ID NOS:1-486, 489-494 or 560-2802. In some embodiments, the method comprises contacting a sample from a subject with a probe comprising a nucleic acid that hybridizes to one or more of SEQ ID NOS:1-486, 489-494 or 560-2802.

In another embodiment, the invention provides a method of detecting the presence or absence of one or more sprRNA sequences according to SEQ ID NOS:1-486, 489-494 or 560-2802 in a sample from a patient comprising isolating the sprRNAs from the patient, optionally making cDNA from the sprRNAs, and detecting the sprRNAs or complementary DNA. Methods of making cDNA from RNA templates are well known in the art and is not limiting.

In another embodiment, the invention provides a method of detecting sprRNA, comprising i) contacting a cell lysate with an antibody that binds one or more proteins;
ii) isolating the components from the cell lysate that bind the antibody; and
iii) detecting the sprRNA from the isolated components.

An exemplary approach is described in FIG. 31 and Example 3 herein. For example, immunoprecipitation (IP) assays can be performed using antibodies specifically generated for phosphor-serine, phosphor-threonine and/or phosphor-tyrosine, and total RNA can be extracted from the IP products of the cell lysate mixture followed by attaching adaptors as described herein to one or both 3' and 5' ends of the RNAs. RT-PCR can be performed to amplify the phosphor-protein binding RNAs. In some embodiments, the sprRNAs capable of binding phosphoproteins include any one of SEQ ID NOS:1-486, 489-494 or 560-2802.

In another embodiment, the invention provides a method for diagnosing cancer or tumorigenesis in a subject comprising measuring the levels of one or more sprRNAs according to any one of SEQ ID NOS:1-486, 489-494 or 560-2802 in a subject's sample and comparing it to a control sample. In some embodiments, the cancer is lung cancer.

The levels of sprRNAs can be measured in any number of ways, including using techniques well known to persons skilled in the art. In some embodiments, the levels are measured using intracellular probes to assay cells directly for the presence or absence of the sprRNAs as described herein in the Examples. For example, in some embodiments, the levels of the sprRNA are detected using an fluorescence in situ hybridization (FISH) assay using, e.g., a digoxin (DIG)-labelled DNA or RNA probe complementary to the sprRNA. In some embodiments, the levels of the sprRNA can be measured by the fluorescence intensity using standard techniques and methods. In some embodiments, the sprRNA is isolated from the cell. For example, the sprRNAs can be separated from total RNA using one-nucleotide-resolution PAGE gels and processed using the True® Small RNA kit. In other embodiments, the sprRNA can isolated by co-immunoprecipitation using antibodies to binding proteins. Adaptors can also be ligated to the sprRNA to facilitate purification or amplification. The sprRNA can be subjected to semi-quantitative RT-PCR, quantitative RT-PCR, or real-time qRT-PCR to determine the levels of the sprRNA in the cells and compare the levels to control samples. In some embodiments, the control sample is from a noncancerous patient. In some embodiments, the sample is selected from the group consisting of cells, blood, plasma, serum saliva, sputum or urine.

The cancer to be detected or diagnosed is not limiting, and can include a cancer selected from the group consisting of breast cancer, prostate cancer, lung cancer, bladder cancer, pancreatic cancer, brain cancer, liver cancer, testicular cancer, skin cancer, colon cancer, ovarian cancer, cervical cancer, uterine cancer or any other cancer as described herein.

In one embodiment, the cancer detected or diagnosed is lung cancer. In some embodiments, one or more sprRNAs are measured and compared to control samples. In some embodiments, one or more sprRNAs are assayed from Table 1, below, and compared to control samples. In some embodiments, one or more or a panel of markers shown below can be used to distinguish between normal and cancer tissue, including distinguishing between squamous cell versus adenocarcinoma since there are differences in the markers between such cell types.

TABLE 1

Differentially expressed sprRNAs between normal human bronchial epithelial (HBE) cells and lung cancer adenocarcinoma (ACD) cells and squamous cell carcinoma (SCC) cells

| Between ADC and HBE Cells | Between SCC and HBE cells |
|---|---|
| piRNA-L-163 (SEQ ID NO: 282) | piRNA-L-163 (SEQ ID NO: 282) |
| piRNA-L-132 (SEQ ID NO: 265) | piRNA-L-132 (SEQ ID NO: 265) |
| piRNA-L-133 (SEQ ID NO: 266) | piRNA-L-133 (SEQ ID NO: 266) |
| piRNA-L-184 (SEQ ID NO: 293) | piRNA-L-184 (SEQ ID NO: 293) |
| piRNA-L-208 (SEQ ID NO: 309) | piRNA-L-208 (SEQ ID NO: 309) |
| piRNA-L-216 (SEQ ID NO: 314) | piRNA-L-216 (SEQ ID NO: 314) |
| piRNA-L-261 (SEQ ID NO: 335) | piRNA-L-261 (SEQ ID NO: 335) |
| piRNA-L-232 (SEQ ID NO: 322) | piRNA-L-232 (SEQ ID NO: 322) |
| piRNA-L-409 (SEQ ID NO: 417) | piRNA-L-409 (SEQ ID NO: 417) |
| piRNA-L-37 (SEQ ID NO: 210) | piRNA-L-495 (SEQ ID NO: 475) |
| piRNA-L-101 (SEQ ID NO: 248) | piRNA-L-488 (SEQ ID NO: 470) |

TABLE 1-continued

Differentially expressed sprRNAs between normal human bronchial epithelial (HBE) cells and lung cancer adenocarcinoma (ACD) cells and squamous cell carcinoma (SCC) cells

| Between ADC and HBE Cells | Between SCC and HBE cells |
|---|---|
| piRNA-L-490 (SEQ ID NO: 472) | piRNA-L-138 (SEQ ID NO: 268) |
| piRNA-L-124 (SEQ ID NO: 260) | piRNA-L-276 (SEQ ID NO: 344) |
| piRNA-L-50 (SEQ ID NO: 220) | piRNA-L-334 (SEQ ID NO: 372) |
| piRNA-L-505 (SEQ ID NO: 483) | piRNA-L-408 (SEQ ID NO: 416) |
| piRNA-L-369 (SEQ ID NO: 393) | piRNA-L-127 (SEQ ID NO: 261) |
| piRNA-L-381 (SEQ ID NO: 400) | piRNA-L-450 (SEQ ID NO: 442) |
| piRNA-L-130 (SEQ ID NO: 264) | |
| piRNA-L-87 (SEQ ID NO: 237) | |
| piRNA-L-40 (SEQ ID NO: 211) | |
| piRNA-L-181 (SEQ ID NO: 290) | |
| piRNA-L-212 (SEQ ID NO: 312) | |
| piRNA-L-89 (SEQ ID NO: 239) | |
| piRNA-L-112 (SEQ ID NO: 254) | |
| piRNA-L-246 (SEQ ID NO: 329) | |
| piRNA-L-290 (SEQ ID NO: 352) | |
| piRNA-L-143 (SEQ ID NO: 272) | |
| piRNA-L-420 (SEQ ID NO: 423) | |
| piRNA-L-196 (SEQ ID NO: 301) | |
| piRNA-L-142 (SEQ ID NO: 271) | |
| piRNA-L-2 (SEQ ID NO: 192) | |
| piRNA-L-13 (SEQ ID NO: 197) | |
| piRNA-L-85 (SEQ ID NO: 236) | |
| piRNA-L-146 (SEQ ID NO: 275) | |
| piRNA-L-245 (SEQ ID NO: 328) | |
| piRNA-L-350 (SEQ ID NO: 379) | |
| piRNA-L-9 (SEQ ID NO: 196) | |
| piRNA-L-97 (SEQ ID NO: 244) | |
| piRNA-L-404 (SEQ ID NO: 414) | |
| piRNA-L-257 (SEQ ID NO: 333) | |
| piRNA-L-230 (SEQ ID NO: 321) | |
| piRNA-L-432 (SEQ ID NO: 432) | |
| piRNA-L-18 (SEQ ID NO: 199) | |
| piRNA-L-188 (SEQ ID NO: 294) | |

In some embodiments, the measured sprRNA comprises piRNA-L-163 (SEQ ID NO:282). In some embodiments, the measured sprRNA comprises piRNA-L-138 (SEQ ID NO:268). In some embodiments, the measured sprRNA comprises any one of SEQ ID NOS:490-494.

In some embodiments, following detection and/or diagnosis, the subject is administered an effective amount of one or more therapeutic agents. In some embodiments, the therapeutic agent comprises an sprRNA, variant, fragment, or inhibitor thereof, such as an antisense nucleic acid. In some embodiments, the therapeutic agent comprises a nucleic acid comprising any one of SEQ ID NOS:1-486, 489-494, or 560-2802, variants, fragments, or inhibitors thereof, such as an antisense nucleic acid. In some embodiments, the therapeutic agent comprises a nucleic acid comprising any one of SEQ ID NOS:282, 268 or 489-494, variants, fragments, or inhibitors thereof. In some embodiments, the therapeutic agent comprises SEQ ID NOS:496, 497, or 556-559, variants or fragments thereof.

In another embodiment the present invention relates to a kit for diagnosing cancer in a human subject comprising one or more detection reagents capable of detecting any one or more of the sprRNAs of SEQ ID NOS:1-486, 489-494, or 560-2802. In some embodiments, the sprRNAs are one or more of the sprRNAs of Table 1. In some embodiments, the detection reagent comprises one or more probes comprising a nucleic acid that hybridizes to any one or more of the sprRNAs of Table 1.

Agonist and Antagonist Screening

In some embodiments, the ability of antagonists (inhibitors) and agonists of sprRNAs to interfere or enhance the activity of the sprRNA can be evaluated. In some embodiments, the assay can be conducted in vitro to determine whether the inhibitors or agonist reduces or enhances the interaction between the sprRNA and its protein binding partner. In some embodiments of the invention, an assay for sprRNA activity in cells can be used to determine the functionality of the sprRNA in the presence of an agent which may act as an inhibitor or agonist, and thus, agents that interfere or enhance the activity of sprRNA can be identified. In some embodiments, the sprRNAs include any one of SEQ ID NOS:1-486, 489-494, or 560-2802.

In some embodiments, the sprRNAs of the present invention are employed in a screening process for compounds which bind one of the sprRNAs or one of its binding proteins or both and which enhances or inhibits the biological activity of the sprRNA-protein interaction. Thus, the nucleic acids of the invention may also be used to assess the binding of molecular substrates and ligands in, for example, cells, cell-free preparations, chemical libraries, and natural product mixtures. These substrates and ligands may be natural substrates and ligands or may be structural or functional mimetics. Inhibitors of sprRNAs are particularly advantageous and can be used in methods as therapeutic agents in the treatment of cancer, for example, lung cancer, particularly in instances where the sprRNA is upregulated in the cancer cell. In some embodiments, the inhibitors are antisense nucleic acids to the sprRNA. In some embodiments, the antisense nucleic acids are DNA.

By “agonist” is intended naturally occurring and/or synthetic compounds capable of enhancing the biological activity that results from the sprRNA-protein interaction and/or enhancing the interaction of the sprRNA and protein to which it binds. By “antagonist” or “inhibitor” is intended naturally occurring and/or synthetic compounds capable of inhibiting the sprRNA-protein interaction and/or the biological activity that results from the sprRNA-protein interaction.

In some embodiments, the screening procedures involve producing appropriate cells which harbor the nucleic acids of the present invention. Such cells can include cells from mammals, yeast, *Drosophila* or *E. coli*. In some embodiments, the cells express the nucleic acid endogenously. In other embodiments, the cells have been transfected or engineered to express the nucleic acid. In some embodiments, cells expressing the nucleic acid (or extracts or purified preparations from cells) are contacted with a test compound to observe stimulation or inhibition of a functional response.

In some embodiments, assays can test binding of a candidate compound to the sprRNA or assays can involve competition with a competitor compound, such as a labeled competitor. In some embodiments, inhibitors can be assayed in the presence of a labeled antisense nucleic acid, and displacement of the labeled antisense nucleic acid can be measured.

Potential agonists or antagonists are not limiting and examples include antibodies, peptides, carbohydrates, or small molecules which bind to the sprRNA and/or protein to which it binds. These agents can be selected and screened 1) at random, 2) by a rational selection or 3) by design using for example, ligand modeling techniques (e.g., computer modeling).

For random screening, agents such as antibodies, peptides, carbohydrates, pharmaceutical agents and the like are selected at random and are assayed for their ability to bind to or stimulate/block the interaction of the sprRNA and protein or the biological activity.

Alternatively, agents may be rationally selected or designed. As used herein, an agent is said to be “rationally selected or designed” when the agent is chosen based on the configuration of the sprRNA and/or binding protein.

In one aspect, the invention provides a method of screening for an agent which modulates the activity of an sprRNA, e.g., an agonist or antagonist, comprising: (a) contacting a sprRNA and/or protein to which the sprRNA binds with the agent to be tested; and (b) assaying the agent's effect on the sprRNAs activity. In some embodiments, the activity to be tested is sprRNA-protein binding, and/or biological activity that results from the sprRNA-protein interaction.

In another embodiment the present invention relates to a screening method for identifying inhibitors of cell proliferation in human bronchial epithelial cells comprising identifying molecule(s) which bind piRNA-L-163 and inhibit their function.

In another aspect, the invention provides a method for identifying inhibitors that prevent binding of sprRNA to a protein target, comprising contacting the sprRNA and protein with the inhibitor and detecting whether the inhibitor prevents binding of the sprRNA and protein. In some embodiments, the sprRNA corresponds to one or more of SEQ ID NOS:1-486, or 489-494. In some embodiments, the inhibitor is an antisense nucleic acid to the sprRNA.

Pharmaceutical Compositions

In some embodiments, the invention provides a pharmaceutical composition comprising one or more therapeutic agents and a pharmaceutically acceptable carrier.

The therapeutic agents can include sprRNAs including the specific sprRNAs described herein, as well as variants, fragments and inhibitors thereof. In some embodiments, the sprRNAs include any one of SEQ ID NOS:1-486, 489-494, or 560-2802.

The therapeutic agents affect one or more cellular processes mediated by the protein and sprRNA interaction. The compositions can also include one or more additional therapeutic agents that is useful to treat a disease or condition in combination with the sprRNAs, derivatives, analogs and inhibitors thereof.

Certain embodiments of the present invention relate to pharmaceutical compositions comprising one or more therapeutic agents, and methods of administering a therapeutically effective amount of one or more therapeutic agents, which are capable of prophylactic and/or therapeutic treatment of one or more conditions or diseases, such as cancer. The term “therapeutic agent” refers to any pharmaceutically acceptable acid, salt, ester, derivative, a stereoisomer, prodrug or mixtures of stereoisomers of a therapeutic agent or to the therapeutic agent itself. Pharmaceutically acceptable acids, salts, esters, derivatives, stereoisomers, pro-drugs, and mixtures of therapeutic agents may also be used in the methods and compositions of the present invention.

The pharmaceutical compositions can be formulated according to known methods for preparing pharmaceutically acceptable useful compositions, and can include a pharmaceutically acceptable carrier. The carrier may be liquid, solid, or semi-solid for example. Formulations are described in a number of sources which are well known to those of skill in the art. The physical and/or chemical characteristics of compositions of the inventions may be modified or optimized according to skill in the art, depending on the mode of administration and the particular disease or condition to be treated. The compositions may be in any suitable form, depending on the desired method of administration, and may be provided in unit dosage form, a sealed container, or as part of a kit, which may include instructions for use and/or a plurality of unit dosage forms.

The term "pharmaceutically acceptable" with reference to the therapeutic agent used herein refers to those modifications of the parent compound (acids, salts, ester, etc.) that do not significantly or adversely affect the pharmaceutical properties of the parent therapeutic agent. For example, exemplary pharmaceutically acceptable salts administrable by means of the compositions of this invention include chloride, bromide, iodide, hydrochloride, acetate, nitrate, stearate, palmoate, phosphate, and sulfate salts. Exemplary techniques for producing pharmaceutically acceptable derivatives include for example, methylation, halogenation, acetylation, esterification and hydroxylation.

The term "therapeutically effective amount" means the total amount of each active component of the pharmaceutical composition or method that is sufficient to show meaningful patient benefits, e.g, a decrease in tumor size or metastatic potential of the tumor, an increase in patient survival time, sensitization of patients to other therapeutic agents including but not limited to chemotherapy.

The pharmaceutical composition may be adapted for administration by any appropriate route, for example by the oral, rectal, nasal, topical, vaginal or parenteral routes. Other routes, e.g., intra-articular, may also be used. Such compositions may be prepared by any known method, for example by admixing the active ingredient with the carrier(s) or excipient(s) under sterile conditions.

Pharmaceutical compositions adapted for oral administration may be presented as discrete units such as capsules or tablets; as powders or granules, as solutions, syrups or suspensions. Suitable excipients for tablets or hard gelatin capsules include lactose, maize starch, or derivative thereof, stearic acids or salts thereof. Suitable excipients for use with soft gelatin capsules include for example vegetable oils, waxes, fats, semi-solid, or liquid polyols etc. For the preparation of solutions and syrups, excipients which may be used include for example water, polyols, and sugars. For the preparation of suspension, oils (e.g., vegetable oils) may be used to provide oil-in-water or water-in-oil suspensions. In certain situations, delayed release or enteric-coated preparations may be advantageous, for example to decrease gastric residence time and thereby reduce degradation of the pharmaceutical composition en route to the lower GI tract.

Pharmaceutical compositions adapted for rectal administration may be presented as suppositories or enemas. Pharmaceutical compositions adapted for nasal administration wherein the carrier is a solid can include a coarse powder having a particle size ranging from about 20 to about 500 microns. Suitable compositions wherein the carrier is a liquid for administration as a nasal spray or as nasal drops, include aqueous or oil solution of the active ingredient. Pharmaceutical compositions adapted for administration by inhalation include fine particle dusts or mists which may be generated by means of various types of metered dose pressurized aerosols, nebulizer or insufflators.

Pharmaceutical compositions adapted for topical administration may be formulated as ointments, creams, suspensions, lotions, powders, solutions, pastes, gels, sprays, aerosols, or oils. When formulated in an ointment, the therapeutic agent may be employed with either a parafinninic or a water-miscible ointment base. Pharmaceutical compositions adapted from topical administration to the eye include eye drops wherein the therapeutic agent is dissolved or suspended in a suitable carrier, especially an aqueous solvent. Pharmaceutical compositions adapted for topical administration in the mouth include lozenges, pastilles, and mouth washes. Pharmaceutical compositions adapted for transdermal administration may be presented as discrete patches intended to remain in intimate contact with the epidermis of the recipient for a prolonged period of time. Pharmaceutical compositions adapted for vaginal administration may be presented as pessaries, tampons, creams, gels, pastes, foams, or spray formulations.

Pharmaceutical compositions adapted for parenteral administration include aqueous and non-aqueous sterile injection solutions which may contain anti-oxidants, buffers, bacteriostats, and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerin and vegetable oils, for example. The compositions may be presented in unit-dose or multi-dose containers, for example sealed ampoules and vials, and may be stored in freeze-dried conditions requiring only the addition of a sterile liquid immediately prior to use. Extemporaneous injection solutions and suspensions may be prepared from sterile powders, granules, and tablets. The pharmaceutical compositions may contain preserving agents, solubilizing agents, stabilizing agents, wetting agents, emulsifiers, sweeteners, colorants, salts, buffers, antioxidants, etc.

The administration of the compositions of the present invention may be for a "prophylactic" or "therapeutic" purpose, or alternatively can be used for diagnostic purposes. The compositions of the present invention are said to be administered for a "therapeutic" purpose if the amount administered is physiologically significant to provide a therapy for an actual manifestation of the disease or condition. When provided therapeutically, the therapeutic agent is preferably provided at (or shortly after) the identification of a symptom of actual disease. The therapeutic administration of the agent serves to attenuate the severity of such disease or to reverse its progress. The compositions of the present invention are said to be administered to provide a therapy for a potential disease or condition. When provided prophylactically, the therapeutic agent is preferably provided in advance of any symptom thereof. The prophylactic administration of the therapeutic agent serves to prevent or attenuate any subsequent advance of the disease.

In some embodiments the therapeutic agents of the invention are nucleic acids, such as sprRNAs, analogs, derivatives, and antisense inhibitors thereof. The nucleic acids of the invention can be administered to a subject by any suitable means including parenteral or oral administration. The nucleic acids of the invention may be administered parenterally by intraarterial, intravenous, intraperitoneal, intraocular, subcutaneous or intramuscular injection either continuously or by bolus injection, depending on the route of administration. The administration may also be transmembrane or transmucosal using suppositories and, optionally, agents to aid penetration of membranes or mucosal membranes. Topical administration and direct administration to a target area may also be performed. In some embodiments, the administration is about 0.01-1 mg/kg, 0.0005-5 mg/kg, 0.001-0.35 mg/kg or, for example, 0.25 mg (40 pmol) nucleic acid/kg of the subject may be desirable.

In some embodiments, the nucleic acids of the invention can be administered to a subject or a cell with a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration.

Pharmaceutically acceptable carriers are generally known to those skilled in the art and include saline, sugars, polypeptides, polymers, lipids, creams, gels, micelle materials, and nanoparticles. In some embodiments, the carrier comprises at least one of: a glucose solution, a polycationic binding agent, a cationic lipid, a cationic micelle, a cationic polypeptide, a hydrophilic polymer grafted polymer, a non-natural cationic polymer, a cationic polyacetal, a hydrophilic polymer grafted polyacetal, a ligand functionalized cationic polymer, a ligand functionalized-hydrophilic polymer grafted polymer, and a ligand functionalized liposome. In other embodiments, the polymers comprise a biodegradable histidine-lysine polymer, a biodegradable polyester, such as poly(lactic acid) (PLA), poly(glycolic acid) (PGA), and poly(lactic-co-glycolic acid) (PLGA), a polyamidoamine (PAMAM) dendrimer, a cationic lipid (such as DOTAP), or a PEGylated PEI. A ligand can be adapted to the composition to target the composition to particular cell types. In some embodiments, the ligand is specific for one or more particular cell surface markers. In some embodiments, ligands can include small molecules, proteins, antibodies, and the like. In some embodiments, the ligand binds a cancer cell surface marker.

In some embodiments, the pharmaceutically acceptable carrier is a nanoparticle. In some embodiments, nanoparticles can be formulated to include high concentrations or amounts of the nucleic acids of the invention. For example, in some embodiments, nanoparticles can be formulated to include up to 15 ng, 20 ng, 25 ng, 30 ng, 40 ng, 50 ng, or more nucleic acids of the invention per $1\times10^9$ particles. However, concentration or amounts included can be lowered if needed, e.g., 1-12 μg nucleic acid or less per $1\times10^9$ particles. Exemplary amounts or concentrations of nucleic acids of the invention can include 10-1000 pmol/$5\times10^7$ particles, e.g., 20, 40, 100, 200 of 500 pmol nucleic acid/$5\times10^7$ particles.

In some embodiments, the nanoparticle is a histidine-lysine copolymer that forms a nanoparticle with the nucleic acids of the invention, wherein the diameter of the nanoparticle is about 50 nm to about 500 nm. Some embodiments of the invention, the nanoparticle encapsulates the nucleic acids of the invention for topical transcutaneous or transdermal delivery or targeted epidermal delivery via nanoparticle projectile bombardment or other transcutaneous/transdermal means.

In some embodiments, the nanoparticles comprise at least one positively charged shell substrate and at least one negatively charged core substrate, wherein the core substrate is selected from the group consisting of heparin, heparin analogs, low molecular weight heparin, glycosaminoglycans, and alginate. In one embodiment, the nucleic acids of the invention are conjugated with the core substrate.

In a further embodiment, the nanoparticles can have a mean particle size between about 50 and 500 nanometers, between about 100 and 300 nanometers, or between about 150 and 250 nanometers.

In some embodiments, the pharmaceutically acceptable carrier may be a lipid nanoparticle. The lipid nanoparticle may be engineered to penetrate mucus and may include surface altering agents such as, but not limited to, anionic protein, surfactants, sugars or sugar derivatives, nucleic acids, polymers, mucolytic agents and various DNases including rhDNase.

The mucus penetrating lipid nanoparticles can comprise at least one nucleic acid of the invention. The nucleic acids of the invention can be encapsulated in the lipid nanoparticle and/or disposed on the surface of the particle. The nucleic acid of the invention may be covalently coupled to the lipid nanoparticle. Formulations of mucus penetrating lipid nanoparticles may comprise a plurality of nanoparticles. Further, the formulations may contain particles which may interact with the mucus and alter the structural and/or adhesive properties of the surrounding mucus to decrease mucoadhesion which may increase the delivery of the mucus penetrating lipid nanoparticles to the mucosal tissue.

In one embodiment, a nucleic acid of the invention is formulated as a solid lipid nanoparticle. The solid lipid nanoparticle (SLN) may be spherical with an average diameter between 10 to 1000 nm. SLN possess a solid lipid core matrix that can solubilize lipophilic molecules and may be stabilized with surfactants and/or emulsifiers. The lipid nanoparticle may be a self-assembly lipid-polymer nanoparticle.

In some embodiments, the nucleic acids of the invention can be administered to a subject or a cell via liposomes as a pharmaceutically acceptable composition. In some embodiments, liposomes can be manufactured by sonicating lipids in an aqueous solution. Low shear rates create multilamellar vesicles, which have many lipid layers. Continued high-shear sonication tends to form smaller unilamellar liposomes. In some embodiments, liposomes can be constructed using polyethylene glycol (PEG) as a coating. The liposomes can have a ligand attached to the surface of the liposome for binding to a target cell via a cell surface receptor or other surface molecule.

In some embodiments, the liposome as a pharmaceutically acceptable carrier can include opsonins or ligands in enhance the attachment of liposomes to unhealthy tissue or to activate events such as endocytosis. Liposomes can contain a low or a high pH to enhance the delivery of the nucleic acids of the invention.

In some embodiments, the pharmaceutically acceptable carrier may include liposomes such as those formed from 1,2-dioleyloxy-N,N-dimethylaminopropane (DODMA) liposomes, DiLa2 liposomes from Marina Biotech (Bothell, Wash.), 1,2-dilinoleyloxy-3-dimethylaminopropane (DLin-DMA), 2,2-dilinoleyl-4-(2-dimethylaminoethyl)-[1,3]-dioxolane (DLin-KC2-DMA), and MC3 (US Appl. Pub. No. 2010/0324120).

In some embodiments, the pharmaceutically acceptable carrier can include liposomes such as those formed from the synthesis of stabilized plasmid-lipid particles (SPLP) or stabilized nucleic acid lipid particle (SNALP) that have been previously described for delivery to cells or subjects (see Wheeler et al., *Gene Therapy.* 1999 6:271-281; Zhang et al. *Gene Therapy.* 1999 6:1438-1447; Jeffs et al. *Pharm Res.* 2005 22:362-372; Morrissey et al., *Nat Biotechnol.* 2005 2:1002-1007; Zimmermann et al., *Nature.* 2006 441:111-114; Heyes et al. *J Contr Rel.* 2005 107:276-287; Semple et al. *Nature Biotech.* 2010 28:172-176; Judge et al. *J Clin Invest.* 2009 119:661-673; deFougerolles *Hum Gene Ther.* 2008 19:125-132).

In some embodiments, the nucleic acids of the invention may be formulated in a lipid-polycation complex. The formation of the lipid-polycation complex may be accomplished by methods known in the art and/or as described in U.S. Pub. No. 20120178702. The polycation may include a cationic peptide or a polypeptide such as polylysine, polyornithine and/or polyarginine.

In some embodiments, the cationic lipid pharmaceutically acceptable carrier may be synthesized by methods known in the art and/or as described in International Publication Nos. WO2012040184, WO2011153120, WO2011149733, WO2011090965, WO2011043913, WO2011022460, WO2012061259, WO2012054365, WO2012044638, WO2010080724 and WO201021865.

In some embodiments, the pharmaceutically acceptable carrier may include at least one of the PEGylated lipids described in International Publication No. 2012099755, herein incorporated by reference.

In some embodiments, the concentration of the nucleic acids of the invention in the lipid pharmaceutically acceptable carrier is about 0.2 to 0.4 mg/ml, and the total lipid concentration is about 1.5 to 2.7 mg/ml. In some embodiments, the ratio of lipid:nucleic acid can be about 2:1, at least about 3:1, at least about 4:1, at least about 5:1, at least about 6:1, at least about 7:1, at least about 8:1, at least about 10:1, at least about 15:1.

In some embodiments, the nucleic acids can be formulated with MaxSuppr in vivo RNALancerII as described previously (Wiggins J F, et al. Development of a Lung Cancer Therapeutic Based on the Tumor Suppressor MicroRNA-34. *Cancer Res.* 70, 5923-30(2010)) due to the requirement of very large quantity of formulated reagents needed for systemic delivery.

In some embodiments, the nucleic acids of the invention can be administered to a subject through an implanted, indwelling, intrathecal or intraparenchymal catheter that provide a means for injecting fluid containing the nucleic acids of the invention directly into a desired tissue such as local nerves or local brain tissue. Embodiments of the invention include delivery of the nucleic acids of the invention via implantable delivery devices, such as an implantable pump like that taught in U.S. Pat. Nos. 5,735,814 and 6,042,579, and further using a sensor as part of the infusion system to regulate the amount of nucleic acids of the invention delivered, like that taught in U.S. Pat. No. 5,814,014.

Relative amounts of the active ingredient, the pharmaceutically acceptable excipient, and/or any additional ingredients in a pharmaceutical composition of the nucleic acids of the invention will vary, depending upon the identity, size, and/or condition of the subject treated and further depending upon the route by which the composition is to be administered. By way of example, the composition may comprise between 0.01% and 100%, e.g., between 0.5 and 50%, between 1-30%, between 5-80%, at least 80% (w/w) active ingredient.

While the invention has been described with reference to certain particular examples and embodiments herein, those skilled in the art will appreciate that various examples and embodiments can be combined for the purpose of complying with all relevant patent laws (e.g., methods described in specific examples can be used to describe particular aspects of the invention and its operation even though such are not explicitly set forth in reference thereto).

EXAMPLES

Example 1

A piRNA Like Small RNA Interacts with and Modulates p-ERM Proteins in Human Somatic Cells PIWI-interacting RNAs (piRNAs) are thought to silence transposon and gene expression during development. However, the roles of piRNAs in somatic tissues are largely unknown. Here we report the identification of 555 piRNAs in human lung bronchial epithelial (HBE) and non-small cell lung cancer (NSCLC) cell lines, including 295 that don't exist in databases termed as piRNA-Like sncRNAs or piRNA-Ls. Distinctive piRNA/piRNA-L expression patterns are observed between HBE and NSCLC cells. piRNA-L-163 (piR-L-163) (SEQ ID NO:282), the top down-regulated piRNA-L in NSCLC cells, binds directly to phosphorylated ERM proteins (p-ERM), which is dependent on the central part of UUNNUUUNNUU (SEQ ID NO:495) motif in piR-L-163 (SEQ ID NO:282) and the RRRKPDT (SEQ ID NO:488) element in ERM, and. The piR-L-163/p-ERM interaction is critical for p-ERM's binding capability to filamentous actin (F-actin) and ERM-binding phosphoprotein 50 (EBP50). Thus, piRNA/piRNA-L may play a regulatory role through direct interaction with proteins in physiological and pathophysiological conditions.

Piwi-interacting RNAs (piRNAs) are the largest class of small non-coding RNAs (sncRNAs) expressed primarily in germ line cells and thought to function with PIWI proteins to silence transposon activity and gene expression in a sequence-dependent manner during development (Ross, R. J., Weiner, M. M. & Lin, H. PIWI proteins and PIWI-interacting RNAs in the soma. *Nature* 505, 353-359 (2014). PIWI-piRNA pathway has been implicated in transposon silencing and repression of gene expression through heterochromatin modification in germ line cells (Fang, W., Wang, X., Bracht, J. R., Nowacki, M. & Landweber, L. F. Piwi-interacting RNAs protect DNA against lost during Oxytricha genome arrangement. *Cell* 151, 1243-1255 (2012); Brennecke, J. et al. Discrete small RNA-generating loci as master regulators of transposon activity in *Drosophila. Cell* 128, 1089-1103 (2007); Batista, P. J. et al. PRG-1 and 21U-RNAs interact to form the piRNA complex required for fertility in *C. elegans. Mol. Cell* 31, 67-78 (2008); Das, P. P. et al. Piwi and piRNAs act upstream of an endogenous siRNA pathway to suppress Tc3 transposon mobility in the *Caenorhabditis elegans* germline *Mol. Cell* 31, 79-90 (2008); Rajasethupathy, P. et al. A role for neuronal piRNAs in the epigenetic control of memory-related synaptic plasticity. *Cell* 149: 693-707 (2012); Shirayama, M. et al. piRNAs initiate an epigenetic memory of nonself RNA in the *C. elegans* germline. *Cell* 150, 65-77 (2012); Lee, H. C. et al. *C. elegans* piRNAs mediate the genome-wide surveillance of germline transcripts. *Cell* 150, 78-87 (2012); Ashe, A. et al. piRNAs can trigger a multigenerational epigenetic memory in the germline of *C. elegans. Cell* 150, 88-99 (2012)). Although piRNA expression has been observed in human somatic cells such as cancer cells (Mei, Y., Clark, D. & Mao, L. Novel dimensions of piRNAs in cancer. *Cancer Lett* 336, 46-52 (2013)), the extent of piRNA expression in mammalian somatic tissues remains an outstanding question (Ross, R. J., Weiner, M. M. & Lin, H. PIWI proteins and PIWI-interacting RNAs in the soma. *Nature* 505, 353-359 (2014), as are the functional roles of piRNAs in these tissues.

The ERM proteins (ezrin, radixin and moesin) belong to a family of proteins located at cell cortex (Fehon, R. G., Mclatchey, A. I. & Bretscher, A. Organizing the cell cortex: the role of ERM proteins. *Nat Rev Mol Cell Biol.* 11, 276-287 (2010); Fiévet, B., Louvard, D. & Arpin, M. ERM proteins in epithelial cell organization and functions. *Biochim Biophys Acta.* 1773, 653-560 (2007); McClatchey, A. I. ERM proteins at a glance. *J Cell Sci.* 127:3199-204 (2014); Neisch, A. L & Fehon, R. G. Ezrin, Radixin and Moesin: key regulators of membrane-cortex interactions and signaling. *Curr Opin Cell Biol.* 23, 377-82 (2011)). They are critical in connecting transmembrane proteins, such as EBP50, and the cytoskeleton to play important role in regulating signal transduction pathways (McClatchey, A. I & Fehon, R. G. Merlin and the ERM proteins—regulators of receptor distribution and signaling at the cell cortex. *Trends Cell Biol.* 19, 198-206 (2009); Bretscher, A., Edwards, K. &

Fehon, R. G. ERM proteins and merlin: integrators at the cell cortex. *Nat Rev Mol Cell Biol.* 3, 586-99 (2002); Solinet, S. et al. The actin-binding ERM protein Moesin binds to and stabilizes microtubules at the cell cortex. *J Cell Biol.* 202, 251-60 (2013); Morales, F. C., Takahashi, Y., Kreimann, E. L & Georgescu, M. M. Ezrin-radixin-moesin (ERM)-binding phosphoprotein 50 organizes ERM proteins at the apical membrane of polarized epithelia. *Proc Natl Acad Sci.* 101, 17705-17710 (2004); Fouassier, L., Yun, C. C., Fitz, J. G.& Doctor, R. B. Evidence for ezrin-radixin-moesin-binding phosphoprotein 50 (EBP50) self-association through PDZ-PDZ interactions. *J Biol Chem.* 275, 25039-25045 (2000); Lamb, R. F. et al. The TSC1 tumor suppressor hamartin regulates cell adhesion through ERM proteins and the GTPase Rho. *Nat Cell Biol.* 2, 281-287(2000)). These proteins are highly conserved throughout evolution, particularly at their N-terminus and C-terminus regions (Turunen, O., Wahlstrom, T. & Vaheri, A. Ezrin has a COOH-terminal actin-binding site that is conserved in the ezrin protein family. *J Cell Biol.* 126, 1445-1453 (1994); Matsui, T. et al. Rho-kinase phosphorylates COOH-terminal threonines of ezrin/radixin/moesin (ERM) proteins and regulates their head-to-tail association. *J Cell Biol.* 140, 647-657 (1998); Gary, R. & Bretscher, A. Ezrin self-association involves binding of an N-terminal domain to a normally masked C-terminal domain that includes the F-actin binding site. *Mol Biol Cell.* 6, 1061-75 (1995)) and expressed in a tissue-specific manner (Fehon, R. G., Mclatchey, A. I. & Bretscher, A. Organizing the cell cortex: the role of ERM proteins. *Nat Rev Mol Cell Biol.* 11, 276-287 (2010); Doi, Y. et al. Normal development of mice and unimpaired cell adhesion/cell motility/actin-based cytoskeleton without compensatory up-regulation of ezrin or radixin in moesin gene knockout. *J Biol Chem.* 274, 2315-2321 (1999)). It is believed that ERM function is regulated through changing the folding of the protein (Fiévet, B., Louvard, D. & Arpin, M. ERM proteins in epithelial cell organization and functions. *Biochim Biophys Acta.* 1773, 653-560 (2007); McClatchey, *A. I. ERM proteins at a glance. J Cell Sci.* 127:3199-204 (2014); Neisch, A. L & Fehon, R. G. Ezrin, Radixin and Moesin: key regulators of membrane-cortex interactions and signaling. *Curr Opin Cell Biol.* 23, 377-82 (2011); Matsui, T. et al. Rho-kinase phosphorylates COOH-terminal threonines of ezrin/radixin/moesin (ERM) proteins and regulates their head-to-tail association. *J Cell Biol.* 140, 647-657 (1998). In the inactive form, the proteins are folded and the binding sites to EBP50 and F-actin are masked (Matsui, T. et al. Rho-kinase phosphorylates COOH-terminal threonines of ezrin/radixin/moesin (ERM) proteins and regulates their head-to-tail association. *J Cell Biol.* 140, 647-657 (1998); Gary, R. & Bretscher, A. Ezrin self-association involves binding of an N-terminal domain to a normally masked C-terminal domain that includes the F-actin binding site. *Mol Biol Cell.* 6, 1061-75 (1995)). Upon phosphorylation at a particular C-terminus site (Thr558 for moesin or Thr576 and Thr564 for ezrin and radixin, respectively), ERM proteins become activated by unfolding to expose the masked binding sites and allowing the proteins bind to EBP50 and F-actin (Fiévet, B., Louvard, D. & Arpin, M. ERM proteins in epithelial cell organization and functions. *Biochim Biophys Acta.* 1773, 653-560 (2007); McClatchey, A. I. ERM proteins at a glance. *J Cell Sci.* 127:3199-204 (2014); Neisch, A. L & Fehon, R. G. Ezrin, Radixin and Moesin: key regulators of membrane-cortex interactions and signaling. *Curr Opin Cell Biol.* 23, 377-82 (2011); Solinet, S. et al. The actin-binding ERM protein Moesin binds to and stabilizes microtubules at the cell cortex. *J Cell Biol.* 202, 251-60 (2013); Morales, F. C., Takahashi, Y., Kreimann, E. L & Georgescu, M. M. Ezrin-radixin-moesin (ERM)-binding phosphoprotein 50 organizes ERM proteins at the apical membrane of polarized epithelia. *Proc Natl Acad Sci.* 101, 17705-17710 (2004); Fouassier, L., Yun, C. C., Fitz, J. G. & Doctor, R. B. Evidence for ezrin-radixin-moesin-binding phosphoprotein 50 (EBP50) self-association through PDZ-PDZ interactions. *J Biol Chem.* 275, 25039-25045 (2000)).

Here, we demonstrated that piRNAs are expressed in somatic human bronchial epithelial cells and the expression patterns are distinctive between normal bronchial epithelial cells and lung cancer cells. Importantly, we further demonstrated that piRNA-Like-163 (piR-L-163 (SEQ ID NO:282)), the top down-regulated piRNAs in lung cancer cells, directly binds to phosphorylated ERM (p-ERM) and play a critical role in ERM activation.

Results

Expression of piRNAs/piRNA-Like sncRNAs in Somatic Cells

To explore potential implications of piRNA in lung cancer, we firstly analyzed global piRNA expression profiles in 8 NSCLC and 3 HBE cell lines. Small RNAs ranging approximately from 25 to 33 bases were used for library construction (FIG. 1*a-c* and Table 2) based on previous reports (Aravin, A. et al. A novel class of small RNAs bind to MILI protein in mouse testes. *Nature* 442, 203-207 (2006); Grivna, S. T., Beyret, E., Wang, Z. & Lin, H. A novel class of small RNAs in mouse spermatogenic cells. *Genes Dev* 20, 1709-1714 (2006); Watanabe, T. et al. Identification and characterization of two novel classes of small RNAs in the mouse germline: retrotransposon-derived siRNAs in oocytes and germline small RNAs in testes. *Genes Dev* 20, 1732-1743 (2006); Girard, A., Sachidanandam, R., Hannon, G. J. & Carmell, M. A. A germline-specific class of small RNAs binds mammalian Piwi proteins. *Nature* 442, 199-202 (2006); Samji, T. PIWI, piRNAs, and germline stem cells: what's the link? *Yale J Biol Med.* 82, 121-124 (2009); Peng, H. et al. A novel class of tRNA-derived small RNAs extremely enriched in mature mouse sperm. *Cell Res.* 22, 1609-1612 (2012)). RNA-seq was performed and resulted in approximately 4.5 million reads with >99% of the reads between 26 and 32 bases (FIG. 7*a*), and approximately 50% of the reads mapped to ≥2 loci in the human genome sequences (FIG. 7*b*), indicating that the piRNA reads captured a nontrivial portion of piRNA diversity (Ruby, J. G. et al. Large-scale sequencing reveals 21U-RNAs and additional microRNAs and endogenous siRNAs in *C. elegans. Cell* 127, 1193-1207 (2006)). The original sequence data is deposited in GEO database and accessible through the following link: http://www.ncbi.nlm.nih.gov/geo/query/acc.cgi?token=mfotwauavbsztsr&acc=GSE 57681.

Figure 9:
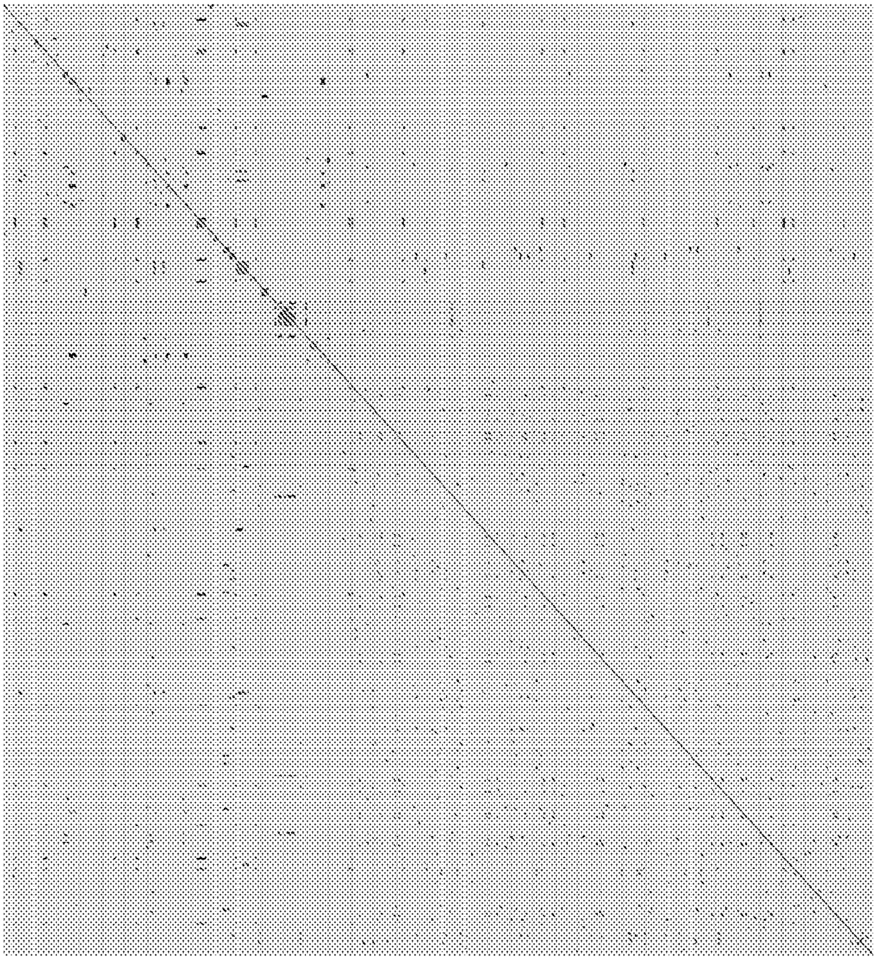
FIG. 9. Heat map of expression of piRNAs and piRNA-Ls identified in the 11 cell lines.
Figure 10:
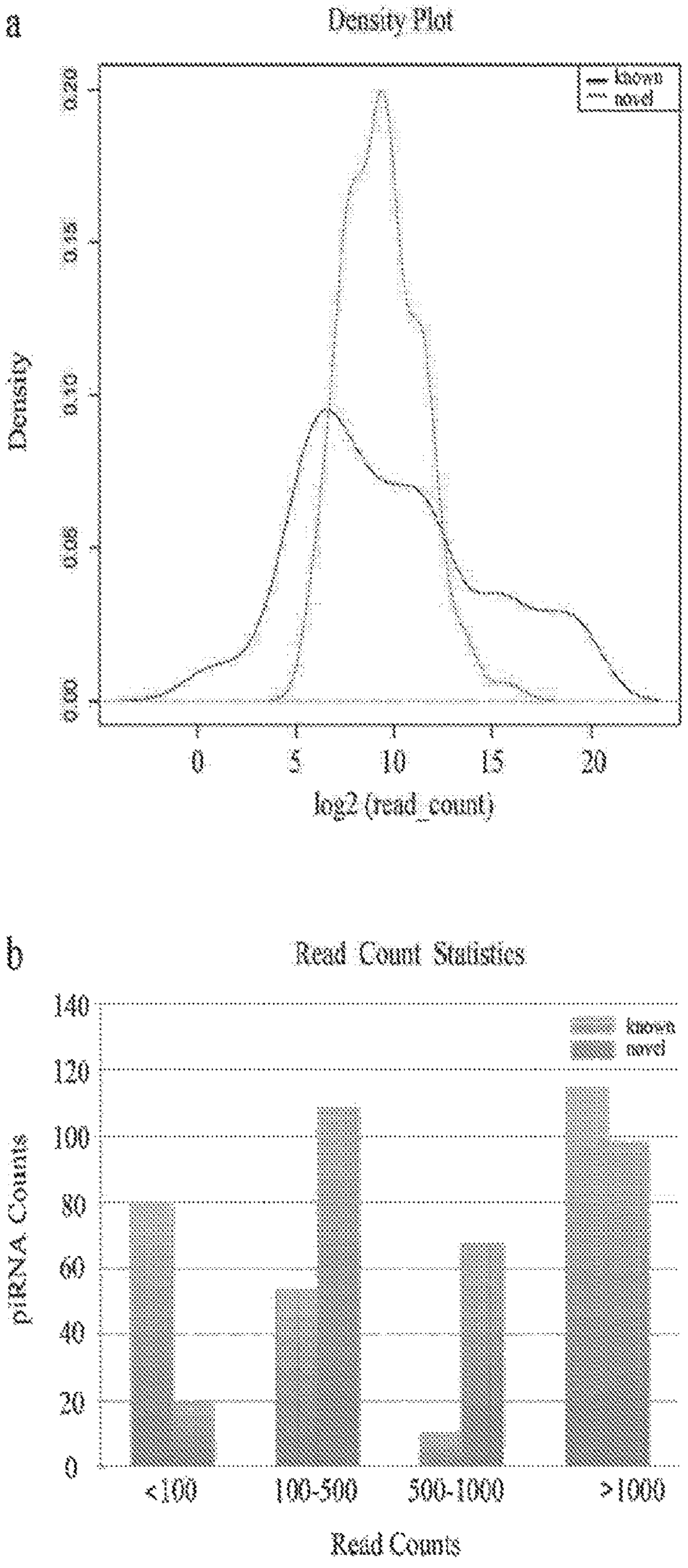
FIG. 10. Expression levels of piRNAs (known) and piRNA-Ls (novel). (a) Density plot of all the reads separated by known and novel. (b) Histogram of average read counts covering the known and novel piRNAs (piRNA/piRNA-L).

A total of 555 piRNAs between 26 and 32 bases were called based on ≥20 reads of individual piRNA in any of the cell lines. These piRNAs are distributed among chromosomal and mitochondrial genomes with bias in chromosomes 1 and 6 (FIGS. 2*a* and 2*b*; FIG. 8*a*). Consistent with previous reports, 99% of the piRNAs are mapped to intergenic regions (64%) or introns (35%) and 1% to exons (Gan, H. et al. piRNA profiling during specific stages of mouse spermatogenesis. *RNA* 17, 1191-1203 (2011); Robine, N. et al. A broadly conserved pathway generates 3'UTR-directed primary piRNAs. *Curr. Biol.* 19, 2066-2076 (2009)). (FIG. 8*b* and Table 2). Of the 555 piRNAs, 191 (47%) are matched in the NCBI (SEQ ID NO:1-191) and 295 (53%) are novel (FIG. 9 (SEQ ID NOS:192-486)). A majority of the novel piRNAs had >100 reads in the samples (FIG. 10). Because many of these piRNAs are new, identified in adult tissues and not yet fully characterized, we refer to these sncRNAs as piRNA-Like sncRNAs or piRNA-Ls in this report.

Expression Patterns of piRNAs and piRNA-Ls

To determine potential biological roles of these sncRNAs, piRNA and piRNA-L expression patterns were firstly used in an unsupervised hierarchy clustering analysis for the 11 cell lines. NSCLC lines and HBE lines can be clearly clustered together based on the expression patterns of the entire piRNAs and piRNA-Ls (FIG. 2*c*) as well as piRNAs or piRNA-Ls individually (FIG. 2*d, e*). Because among the 8 NSCLC cell lines, 4 (H157, H226, H596 and SK-MES-1) derived from patients with lung squamous cell carcinoma (SCC) and 4 (H522, H1437, H1792 and H1944) from patients with adenocarcinoma (ADC), we could also examine the patterns between these two major NSCLC subtypes. The expression patterns were in fact able to separate ADC subtype from SCC subtype of NSCLC (Table 1 and FIG. 1*d, e*). These results suggest that these sncRNAs may play a biological role in lung tumorigenesis and NSCLC differentiation.

Figure 11:
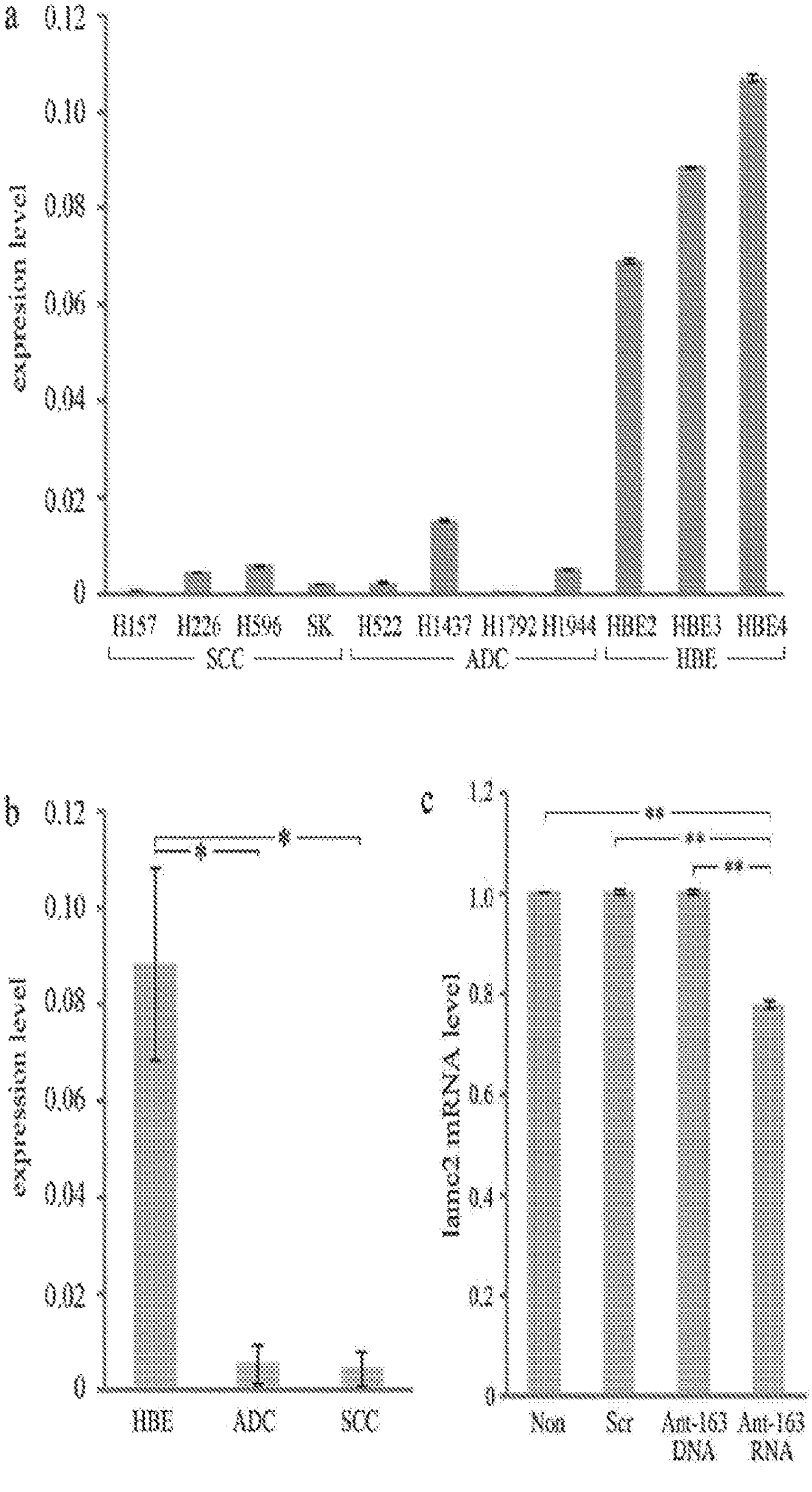
FIG. 11. Expression of piR-L-163 in NSCLC and HBE cell lines measured by real time RT-PCR. (a) piR-L-163 expression levels in individual cell lines. (b) piR-L-163 express ion levels in HBE, ADC and SCC as groups. All the values are averages of four independent replicates, error bars represent mean s.d., and * indicates p<0.01 by Student's t-test. (c) LAMC2 express ion levels in HBE4 cells measured by real time RT-PCR in the conditions as labeled. Values are averages of three independent replicates, error bars represent mean s.d., and ** indicates p<0.05 by Student's t-test.

We then analyzed differentially expressed piRNAs and piRNA-Ls between NSCLC (ADC or SCC) and HBE cell lines. Using filtered log fold change (LFC)=1 and false discovery rate (FDR)<0.05 as criteria, we observed 51 differentially expressed piRNAs or piRNA-Ls between ADC cells and HBE cells, 18 between SCC cells and HBE cells, including 9 differentially expressed piRNA-Ls common for both ADC and SCC (Table 5). Of these, piRNA-L-163_igs (in brief as piR-L-163 (SEQ ID NO:282)) is a piRNA-L aligned to intron 10 of LAMC2 gene on Chromosome 1 and the top commonly down-regulated piRNA-L in NSCLC cell lines (FIG. 3*a*; FIG. 11*a, b*).

piR-L-163 and its Biological Impact in Cell Cycle Regulation

First, we analyzed whether piR-L-163 (SEQ ID NO:282) carries a 3 terminal 2'-O-methylation, a characteristic feature of piRNA (Luteijn, M. J. & Ketting, R. F. PIWI-interacting RNAs: from generation to transgenerational epigenetics. *Nat Rev Genet.* 14, 523-534 (2013); Houwing, S., et al. A Role for Piwi and piRNAs in Germ Cell Maintenance and Transposon Silencing in Zebrafish. *Cell* 129, 69-82 (2007); Kirino, Y. & Mourelatos, Z. Mouse Piwi-interacting RNAs are 2[prime]-O-methylated at their 3[prime] termini. *Nat Struct Mol Biol.* 14, 347-348 (2007); Faehnle, C. R. & Joshua-Tor, L., Argonautes confront new small RNAs. *Curr Opin Chem Biol.* 11, 569-577 (2007)).

We used both synthesized oligo RNA and RNA isolated from HBE4 cells and treated these RNAs with periodate ($IO_4$) followed by beta elimination and analyzed them. As expected, the synthesized oligo RNA without 3 prime 2'-O-methylation was sensitive to the $IO_4$ treatment and resulted in a 2 bases reduction (FIG. 3*b*, left) whereas no reduction was observed for piR-L-163 (SEQ ID NO:282) (FIG. 3*b*, right), indicating that piR-L-163 (SEQ ID NO:282) carried a 3 prime 2'-O-methylation. We then performed RTL-P (Reverse Transcription at Low dNTP concentrations followed by PCR) and showed that the signal intensities of RT-PCR products produced with an unanchored primer was only 20% of the products with an anchored primer when 0.4 μM dNTPs were used (FIG. 3*c*), further supporting that piR-L-163 (SEQ ID NO:282) had RNA 2'-O-methylation consistent with a mature piRNA.

Figure 3:
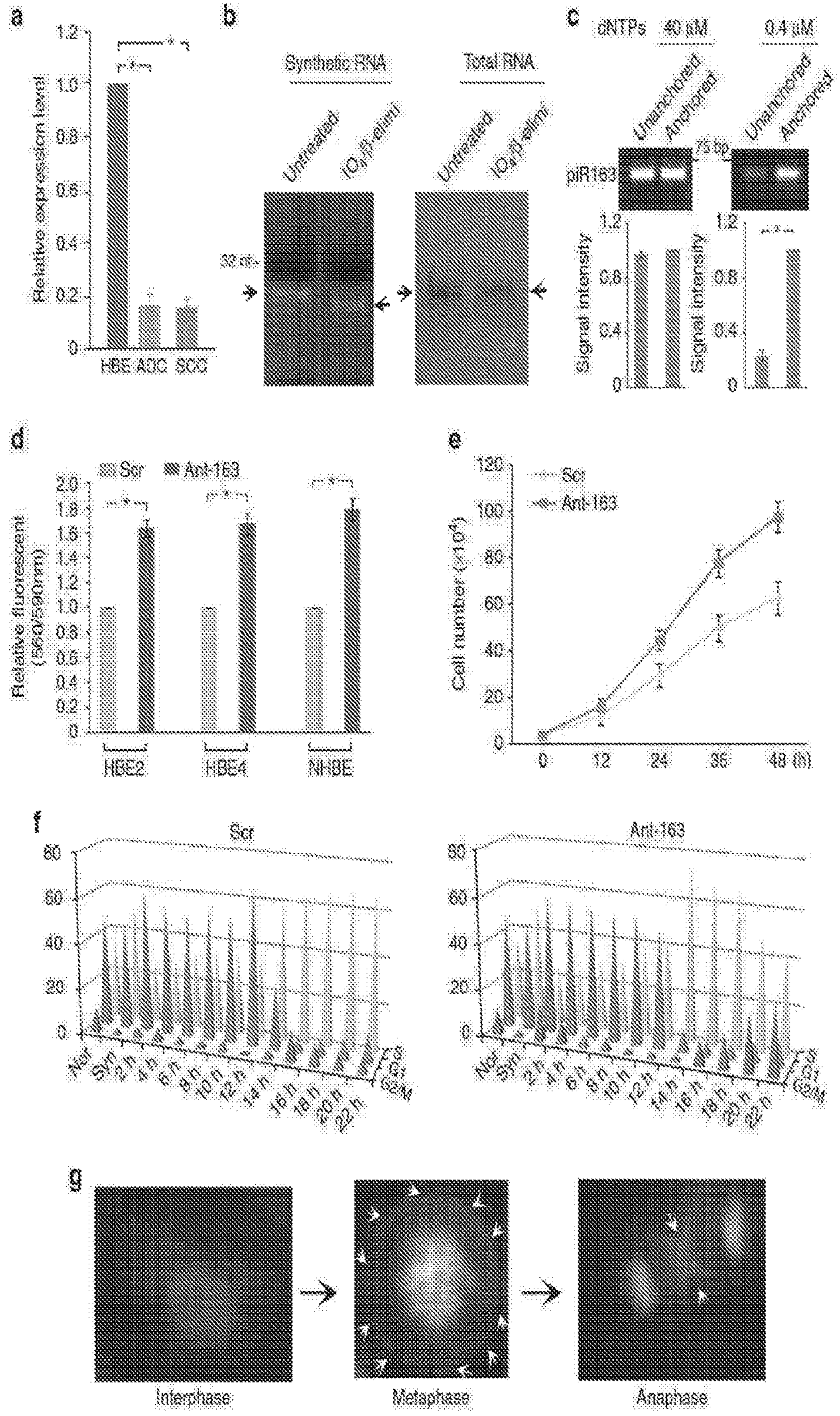
FIG. 3. Characteristics of piR-L-163 and its impact in cell cycle. (a) Expression levels of piR-L-163 in HBE and NSCLC (ADC and SCC) cells based on RNA-seq data. (b) 2'-O-methylation at the 3-terminal of piR-L-163 measured using periodate treatment followed by β-elimination. Synthetic RNAs separated and stained with ethidium bromide (left). Total RNAs separated and detected by Northern blot using a probe specific for piR-L-163 (right). Arrows indicate piR-L-163 bands. (c) The 2'-O-methylation of piR-L-163 determined by RTL-P. (d) Cell survivals after Ant-163 or Scr treatment (48 hrs). (e) Growth of cells treated with Ant-163 or Scr. (f) Cell cycle distributions at different time points for HBE4 cells treated with Ant-163 or Scr. (g) piR-L-163 distribution at cell cycle phases as merged images of FISH and DAPI. All values are averages of three independent replicates, the error bars reflect mean s.d., and * indicate p<0.01 by Student's t-test.

We then wanted to determine whether piR-L-163 (SEQ ID NO:282) plays a functional role in human bronchial epithelial cells. We treated HBE4 cells as well as primary normal human bronchial epithelial (NHBE) cells with piR-L-163 complementary DNA oligonucleotides (Ant-163) (SEQ ID NO:496) or RNA oligonucleotides (Ant-163R) (SEQ ID NO:497) in the experiment. The RNA oligonucleotides triggered a siRNA like response as expected (Fire, A. et al. Potent and specific genetic interference by double-stranded RNA in *Caenorhabditis elegans. Nature* 391, 806-811 (1998) and resulted in reduced expression levels of LAMC2 but not the DNA oligonucleotides (FIG. 11*c*). We, therefore, used the DNA oligonucleotides in all subsequent experiments as the piR-L-163 blocking agent. Compared with HBE or NHBE cells treated with scrambled DNA oligonucleotides (Scr), the cells treated with Ant-163 showed enhanced cell viability and proliferation (FIG. 3*d-e*). We next performed cell cycle analysis using HBE4 cells synchronized at S phase followed by treatment with either Ant-163 or Scr. Cell cycle distributions were measured every 2 hrs. We showed an accelerated DNA synthesis and G2-M accumulation for the cells treated with Ant-163 compared to the cells treated with Scr (FIG. 3*f*), suggesting a functional role of piR-L-163 in the cell cycle regulation.

We next wanted to know the cellular localization of piR-L-163 in HBE cells. Using a fluorescence in situ hybridization (FISH) method with a digoxin (DIG)-labelled probe complimentary to piR-L-163, we surprisingly observed that piR-L-163 was not localized in the nucleus as expected for piRNAs (Siomi, M. C., Sato, K., Pezic, D. & Aravin, A. A. PIWI-interacting RNAs: the vanguard of genome defence. *Nature* 12: 246-258 (2011)), but predominantly located in cytoplasm during interphase, moved into the cell cortex in metaphase, and concentrated on junctions of cell division in anaphase (FIG. 3*g*). The finding is intriguing because piRNAs are believed to function as a PIWI-binding and sequence-dependent epigenetic regulator (Ross, R. J., Weiner, M. M. & Lin, H. PIWI proteins and PIWI-interacting RNAs in the soma. *Nature* 505, 353-359 (2014)).

piR-L-163 Binds to p-ERM and Regulates p-ERM Activity

Figure 4:
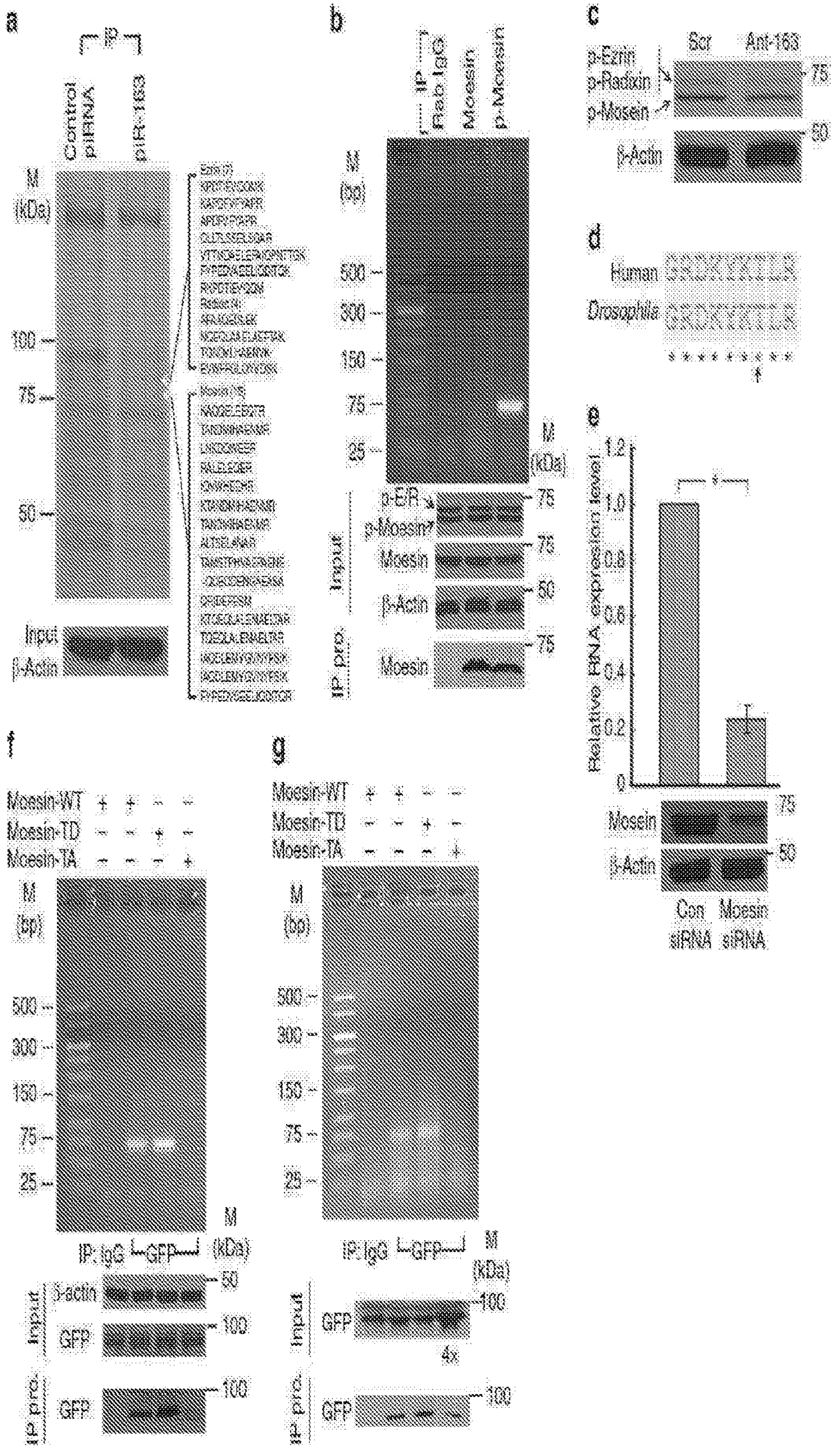
FIG. 4. piR-L-163 binds to p-ERM. (a) Pull downed proteins from HBE4 cell lysates with biotinylated scrambled RNA or piR-L-163. Arrows indicate differentially presented bands and detected peptides of ezrin and moesin. (b) piR-L-163 detected in RNA purified from various IP products. (c) Endogenous p-ERM levels in HBE4 cells. (d) Threonine residue in C-terminal of human ERM and *Drosophila* moesin. (e) Endogenous moesin was effectively down-regulated in HBE4 cells. (f) and (g) piR-L-163 detected in RNAs purified from various IP products in conditions as indicated. All values are averages of three independent replicates, the error bars reflect mean s.d., and * indicate p<0.01 by Student's t-test.

Because of the unexpected cellular localizations of piR-L-163 during cell cycle progression, we suspected that piR-L-163 plays a biological role through interaction with proteins. To identify potential piR-L-163 interacting proteins, biotin-conjugated piR-L-163 RNA oligonucleotides were used as a bait to pull down cellular binding proteins in HBE4 cells. Compared to proteins pulled down using Scr control RNA, we revealed two protein bands predominantly presented in the piR-L-163 pull down product (FIG. 4*a*). Liquid chromatography-tandem mass spectrometry (LC-MS-MS) analysis of the bands revealed ERM proteins as the major protein components, including 7 peptides of ezrin, 5 peptides of radixin and 15 peptides of moesin (FIG. 4*a*), suggesting that piR-L-163 binds to ERM proteins in HBE4 cells.

To confirm the binding between piR-L-163 and ERM proteins, we performed immune-precipitation (IP) assays using anti-Moesin antibodies followed by RT-PCR using primers specific for piR-L-163. While piR-L-163 was not detectable in the IP products using either a control IgG antibody or an antibody for non-phosphorylated moesin (FIG. 4*b*), piR-L-163 was readily detected in the IP product using an antibody specific for ERM proteins with phosphorylated threonine (p-Thr) in the C termini of the proteins (p-ERM), which is the functionally active form of ERM proteins (Roubinet, C. et al. Molecular networks linked by Moesin drive remodeling of the cell cortex during mitosis. *J. Cell Biol.* 195, 99-112 (2011); Kunda, P., Pelling, A. E., Liu, T. & Baum, B. Moesin controls cortical rigidity, cell rounding, and spindle morphogenesis during mitosis. *Curr. Biol.* 18, 91-101 (2008)) (FIG. 4*b*). It should be noted that p-Moesin is the predominant p-ERM protein in HBE4 cells as detected by the phosphorylation specific antibody (FIG. 4c) and the protein levels were not significantly changed following treatment with Ant-163 (FIG. 4c). These results suggest that piR-L-163 only binds to functionally activated p-ERM proteins but not the inactive form of ERM.

To validate that piR-L-163 and ERM binding is p-ERM specific, we replaced with an exogenous *Drosophila* wild type (Moe-WT-GFP) moesin which shares an identical C-terminal motif with human moesin containing the p-Thr site (Polesello, C., Delon, I., Valenti, P., Ferrer, P. & Payer, F. Dmoesin controls actin-based cell shape and polarity during *Drosophila melanogaster* oogenesis. *Nat Cell Biol.* 4, 782-789 (2002)), a constitutively active phosphor mimetic mutant (Moe-TD-GFP), or an inactivated mutant (Moe-TA-GFP) at the p-Thr site (Roubinet, C. et al. Molecular networks linked by Moesin drive remodeling of the cell cortex during mitosis. *J. Cell Biol.* 195, 99-112 (2011); Kunda, P., Pelling, A. E., Liu, T. & Baum, B. Moesin controls cortical rigidity, cell rounding, and spindle morphogenesis during mitosis. *Curr. Biol.* 18, 91-101 (2008)) (FIG. 4d) in HBE4 cells. To be effective, the HBE4 cells expressing these transgenes were treated with dsRNA specifically targeting the 3' untranslated region (UTR) of the endogenous moesin RNA to reduce the endogenous moesin level (FIG. 4e). Because all the proteins generated from transfected *Drosophila* moesins contained GFP, an anti-GFP antibody was used to pull down the fusion proteins and to determine whether the IP products containing piR-L-163, an indication of their binding with piR-L-163.

piR-L-163 was only detected in the IP products from Moe-WT-GFP and Moe-TD-GFP transfected cells but not Moe-TA-GFP transfected cells (FIG. 40, supporting the notion that the threonine phosphorylation is critical for the binding between piR-L-163 and moesin. However, we noticed that the amount of Moe-TA-GFP pull downed in the IP product was much lower than that of Moe-WT-GFP (FIG. 40. It is likely due to difference in the protein conformation of Moe-TA-GFP because the mutation prevented the specific amino acid from phosphorylated, which resulted in a weakened binding affinity between the fusion protein and the anti-GFP antibody. It is also possible that the lack of detectable piR-L-163 in the PI product from Moe-TA-GFP transfected cells was simply due to the lower amount of Moe-TA-GFP in the IP product. To rule out the later possibility, we used 4-fold input of the PI product from Moe-TA-GFP transfected cells and repeated the experiment. With a comparable amount of pull downed Moe-TA-GFP compared to Moe-WT-GFP (FIG. 4g), piR-L-163 remained undetectable in the PI product from Moe-TA-GFP transfected cells (FIG. 4g), confirming that the lack of detectable piR-L-163 was not due to the amount of Moe-TA-GFP in the IP product.

Motif and Element Critical for piR-L-163 and ERM Interaction

We next wanted to determine the site critical for piR-L-163's binding to$_P$-ERM. We first analyzed the piR-L-163 sequence and identified a candidate motif "UUNNUUUNNUU" (SEQ ID NO:495) with potentially critical for the binding (FIG. 5a). We then generated 5 mutant forms of piR-L-163 named as M1-M5 (FIG. 5b and Table 3) to test their potential impact on the p-ERM binding. For this experiment, we used H1792 cells because these cells expressed extremely low level of endogenous piR-L-163 but considerable amount of p-ERM (FIG. 5c and FIG. 11a). H1792 cells were transfected with Scr (control), Ant-163, piR-L-163 (WT), or Mutant 1 (M1) to Mutant 5 (M5) RNA oligonucletides, respectively. An anti-p-ERM antibody was used for IP followed by RT-PCR using primers specific for Scr, Ant-163, piR-L-163, or M1-M5 (Table 6) to detect the corresponding oligonucleotides. As shown in FIG. 5e, while strong RT-PCR band was detected in the cells transfected with piR-L-163, no RT-PCR band could be detected in the IP products from the cells transfected with Scr, Ant-163, M1 or M2, indicating these oligonucleotides do not bind p-ERM. Conversely, RT-PCR bands with expected sizes were detected in the IP products from cells transfected with M3, M4 or M5, although the band from the M3 transfected cells was substantially weaker than those from M4 and M5 transfected cells (FIG. 5e). These results indicate that the central 3 nucleotides of the UUNNUUUNNUU (SEQ ID NO:495) motif (FIG. 5b) are critical for piR-L-163 to bind p-ERM.

To determine potential element of ERM proteins critical for their binding with piR-L-163, we analyzed human and *Drosophila* moesin sequences using BindN (http://bioinfo.ggc.org/bindn/) and identified RRRKPDT (SEQ ID NO:488) at position 293-299 as a candidate RNA binding element (FIG. 12a, b). We then constructed plasmids containing either wild-type human moesin (Moesin-WT) or a mutant form of moesin with RRRKPDT (SEQ ID NO:488) deletion (Moesin-DM). Both plasmids produce high levels of moesin proteins in the transfected cells (FIG. 5d). We used two cell lines (H522 and HBE4) to test if this element contributes to the binding between moesin and piR-L-163. H522 cells expressed extremely low level of endogenous p-ERM (FIG. 5c) and very low level of piR-L-163 (FIG. 11a). H522 cells transfected with piR-L-163 were simultaneously transfected with either Moesin-WT or Moesin-DM to determine the potential binding ability of the introduced moesin proteins with piR-L-163. We also used the non-functional piR-L-163M1 mutant to replace piR-L-163 in the experiment as a negative control. While Moesin-WT bound to piR-L-163 but not piR-L-163M1 as expected (FIG. 5f, left panel), Moesin-DM failed to bind piR-L-163 (FIG. 5f, left panel), indicating that the RRRKPDT (SEQ ID NO:488) element is critical for moesin's interaction with piR-L-163. We next transfected HBE4 cells which expressed both p-ERM and piR-L-163 (FIG. 4e and FIG. 11a) with either Moesin-WT or Moesin-DM after knocked down the endogenous moesin in the cells. We demonstrated again that only Moesin-WT but not Moesin-DM bound piR-L-163 (FIG. 5f, right panel).

piR-L-163 is Critical for ERM's Functional Activities

Because p-ERM functions primarily through binding to F-actin and EBP50 (ERM-binding phosphoprotein 50) through their C-ERMAD and TERM domain (Fouassier, L., Yun, C. C., Fitz, J. G.& Doctor, R. B. Evidence for ezrin-radixin-moesin-binding phosphoprotein 50 (EBP50) self-association through PDZ-PDZ interactions. *J Biol Chem.* 275, 25039-25045 (2000); Turunen, O., Wahlström, T. & Vaheri, A. Ezrin has a COOH-terminal actin-binding site that is conserved in the ezrin protein family. *J Cell Biol.* 126, 1445-1453 (1994); Bretscher, A. et al. ERM-Merlin and EBP50 protein families in plasma membrane organization and function. *Annu Rev Cell Dev Biol.* 16, 113-143 (2000)), we analyzed the binding affinities of p-ERM with both EBP50 and F-actin in IP products from H1792 cells treated with Scr, Ant-163, WT, or M1-M5. As expected, p-ERM's ability to bind F-actin and EBP50 were closely correlated with binding of piR-L-163 and p-ERM (FIG. 5e). In H522 cells, wild-type moesin (Moesin-WT) together with piR-L-163 but not the mutant piR-L-163 (piR-L-163M1) nor a mutant moesin (Moesin-DM) resulted in an enhanced binding with F-actin and EBP50 (FIG. 5*f*). These results indicate that piR-L-163 binds moesin and is critical for moesin's ability to interact with F-actin and EBP50.

Figure 6:
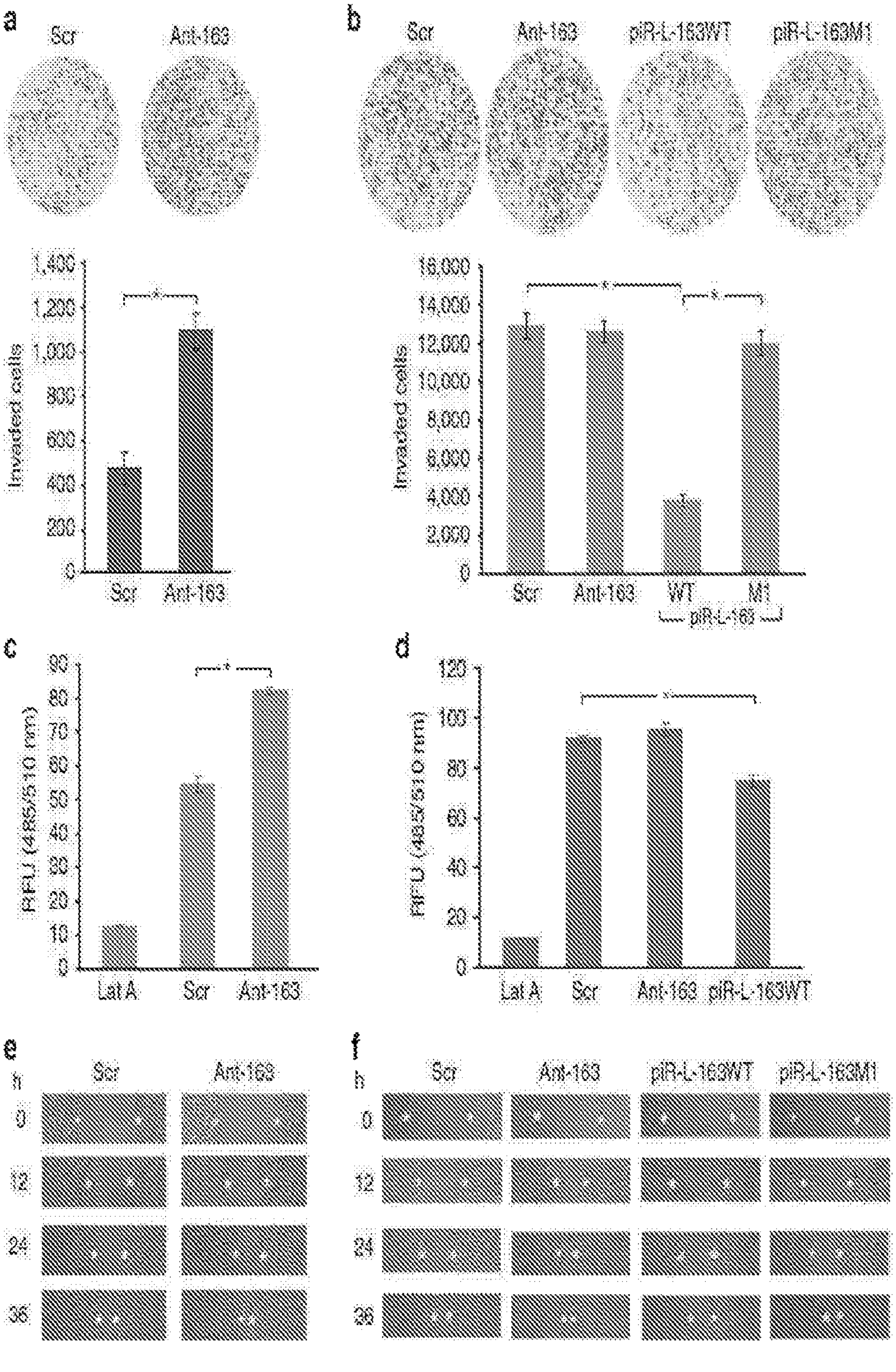
FIG. 6. piR-L-163 impacted migration and invasion. (a) Trans-well assay showed increased invading cells after treating HBE4 cells with Ant-163 compared with cells treated with Ant-163. (b) In H1792 cells (extremely low endogenous piR-L-163 expression), piR-L-163 significantly reduced the number of invading cells but no impact of Ant-163 or piR-L-163M1 treatment. (c) Migration capability of HBE4 cells treated with either Ant-163 or Scr measured by a quantitative assay. (d) Migration capability of H1792 cells treated with piR-L-163, Ant-163 or Scr. Lat A served as an internal control for background. (e) Gap closure of HBE4 cells treated with either Ant-163 or Scr. (f) Gap closure of H1792 cells treated with Ant-163, piR-L-163, piR-L-163M1 and Scr. All values are averages of three independent replicates, the error bars reflect mean s.d., and * indicate p<0.01 by Student's t-test.

We then tested the potential impact of piR-L-163 in cell migration and invasion, two of the properties involving ERM's biological functions (Fehon, R. G., Mclatchey, A. I. & Bretscher, A. Organizing the cell cortex: the role of ERM proteins. *Nat Rev Mol Cell Biol.* 11, 276-287 (2010); Hunter, K. W. Ezrin, a key component in tumor metastasis. *Trends Mol. Med.* 10, 201-204 (2004); Luo, Y. et al. Recognition of CD146 as an ERM-binding protein offers novel mechanisms for melanoma cell migration. *Oncogene* 31, 306-321 (2013); Clucas, J. & Valderrama, F. ERM proteins in cancer progression. *J Cell Sci.* 128, 1253 (2015)). In a trans-well invasion assay, HBE4 cells treated with Ant-163 showed a significantly increased invasion capability compared to cells treated with Scr control, even after 15% downward adjustment for the cells treated with Ant-163 to compensate the possible increase of the cell number after 12 hrs (FIG. 6*a*). Conversely, H1792 cells transfected with piR-L-163 exhibited a significantly decreased invasion capability compared to the cells treated with a control RNA oligonucleotides (FIG. 6*b*). The cells transfected with either Ant-163 or a mutant piR-L-163 showed no impact to the cells' invasion capability (FIG. 6*b*).

For cell migration, we used two complementary assays. In a quantitative cell migration assay, HBE4 cells treated with Ant-163 exhibited significantly increased cell migration compared to the cells treated with Scr control (FIG. 6*c*). Conversely, H1792 cells transfected with piR-L-163 showed significantly decreased cell migration compared with the cells treatment with Scr or Ant-163 (FIG. 6*d*). To compensate potential differences in the cell numbers among different treatment conditions, we seeded 10% less cells for Ant-163 treated HBE4 cells and 10% more cells for piR-L-163 transfected H1792 cells. In the wound healing assays, HBE4 cells treated with Ant-163 showed a faster gap closure than the cells treated with Scr control (FIG. 6*e*). Conversely, H1792 cells transfected with piR-L-163 showed a slower gap closure compared to cells transfected with Scr control, Ant-163 or a mutant piR-L-163 (FIG. 6*f*).

In this study, we systematically profiled the expression of piRNAs in adult human airway cells including both immortalized normal bronchial epithelial cells and lung cancer cells. Because piRNAs are predominantly expressed in germline cells to play a key role in suppressing activities of transposons, the identification of more than 550 piRNAs or piRNA-Ls in these adult cells is important, suggesting that these sncRNAs play biological roles beyond transposon regulation. Because we used a conservative calling (≥20 reads in a cell line) and the relatively low total reads (4.5 million) for the 11 cell lines, the actual number of piRNAs/piRNA-Ls expressed should be higher. Further studies will be needed to determine whether these piRNAs/piRNA-Ls are biologically important in the adult cells, particularly those expressed at very low levels.

Nevertheless, our data suggest that these piRNAs/piRNA-Ls play certain biological roles and are involved in lung tumorigenesis because the expression patterns are distinctive between normal bronchial epithelial cells (HBEs) and lung cancer cells. Furthermore, different expression patterns were also observed between adenocarcinomas and squamous cell carcinomas. Although this study did not focus on potential applications of piRNAs/piRNA-Ls for patients with lung cancer, our data suggest that piRNAs/piRNA-Ls may be a new class of molecules potentially useful as biomarkers for cancer classification as well as therapeutic targets.

The finding that piR-L-163 binds directly to p-ERM and regulates ERM functional activities is unexpected and mechanistically important. Our data demonstrate a dynamic interaction between piR-L-163 and p-ERM in subsequent functional activities reflected to cell proliferation, migration and invasion. It should be noted, however, that other factors might also be involved in addition to ERM for piR-L-163 mediated impact in cell proliferation, migration and invasion. Further studies will be necessary to address these issues. Nevertheless, this is the first time that a sncRNA is revealed to participate in a protein functional regulation through a direct interaction with the protein in mammalian cells, in this case, through piR-L-163 binding to p-ERM. We have narrowed down the critical RNA motif in piR-L-163 to the central 3 nucleotides (UUNNUUUNNUU) (SEQ ID NO:495) and a small peptide element in ERM critical for the interaction. Based on current model, upon ERM proteins bind to ptdIns(4,5)P2 (PIP2), which is required for phosphorylation of the threonine in the C-terminus of ERM (Fehon, R. G., Mclatchey, A. I. & Bretscher, A. Organizing the cell cortex: the role of ERM proteins. *Nat Rev Mol Cell Biol.* 11, 276-287 (2010); Fiévet, B., Louvard, D. & Arpin, M. ERM proteins in epithelial cell organization and functions. *Biochim Biophys Acta.* 1773, 653-560 (2007); Bretscher, A., Edwards, K. & Fehon, R. G. ERM proteins and merlin: integrators at the cell cortex. *Nat Rev Mol Cell Biol.* 3, 586-99 (2002); Hao, J. J. et al. Phospholipase C-mediated hydrolysis of PIP2 releases ERM proteins from lymphocyte membrane. *J Cell Biol.* 184, 451-462 (2009)), the bound between FREM and C-ERMAD domains weakens and the clamp formed by the two domains opens. It is therefore possible that piR-163 binds to p-ERM at this point to stabilize the opening structure and allow the binding sites in FREM and C-ERMAD domains interacting with the cytoplasmic tail of EBP50 and F-actin.

Methods

Cell Culture

Human NSCLC cell lines H157, H226, H596, SK-MES-1, H522, H1437, H1792 and H1944 were obtained from ATCC (Manassas, Va., USA) and cultured in RPMI 1640 with 10% FBS (Sigma-Aldrich). Human HBE cell lines (HBE2, HBE3 and HBE4) were provided by Dr. John D. Minna (University of Texas Southwestern Medical Cancer, Dallas, Tex.) and cultured in Keratinocyte-SFM with L-Glutamine, prequalified human recombinant Epidermal Growth Factor and Bovine Pituitary Extract (BPE) (Life Technology). All the cell lines were genotyped for their authentication (the test was done on Oct. 24, 2014). *Mycoplasma* contaminations were regularly tested and the cells were routinely treated to prevent *mycoplasma* growth.

Total Mature piRNA Purification

To obtain purified mature piRNAs, sncRNAs (<200 nt) were firstly separated from total RNA, and then piRNAs were purified from sncRNA in one nucleotide resolution gel. The entire process consisted of total RNA extraction, sncRNA separation, piRNA separation and piRNA enrichment. For total RNA extraction, mirVana™ miRNA isolation kit (Ambion) was used according to the manufacturer's instructions. For sncRNA separation, extracted total RNAs were separated using Craig C. Mello Lab's sncRNA cloning protocols (Gu W and Conte D. http://www.umassmed.edu/uploadedFiles/nemo/Mello%20lab%20small%20RNA%20cloning%20protocol.pdf) with following minor modifications: Mixed 80 μl (≤1 mg) of total RNA, 400 μl (5× volume of total RNA) of MirVana lysis/binding buffer, and 48 μl (1/10 volume of total RNA and lysis/binding buffer) of MirVana homogenate buffer in a 1.5 mL Eppendorf (EP) tube; Incubated the tube at room temperature (RT) for 5 min to denature RNA followed by adding 1/3 volume (176 μl) of 100% ethanol and mixed well; Span the tube at 2,200×g for 4 min at RT to remove larger (>200 nt) RNA, and then transferred the supernatant to a new EP tube and added isopropanol (~700 μl); Precipitated sncRNAs at −80° C. until it was frozen (~30 min), and pelleted sncRNA at 20,000×g at 4° C. for 40 min; Washed once with 70% cold ethanol (American Bioanalytic), and dissolved the pellet with Nuclease-free water.

Next, piRNAs were separated on 15% denaturing acrylamide gel with following specific steps: Prepared gel by mixing the following reagents in 50 mL tube: 6.3 g Urea (Fish Scientific), 1.5 mL 10×TBE (Life technology), 5.6 mL 40% Acrylamide (Bio-Rad), and 3 mL Nuclease-free water (Quality Biological); Stirred at RT until urea is completely dissolved, then added 75 ul of 10% AP (Sigma-Aldrich) and 15 μl of TEMED (Bio-Rad), mixed well and loaded into the electrophoresis shelf to form gel; Pre-run gel in 1×TBE for 20 min at 300V; Heated samples and markers at 75° C. for 5 min, and put them immediately on ice; Run the samples at 300V for 35 min; Stained the gel with 0.5 ng/mlEthidium Bromide (EB, Sigma-Aldrich) in a clean container for 2-3 min, carefully cut out the target band with a scalpel using UV light for visualizing bands.

piRNAs were pelleted using a modified protocol of True® Small RNA for sequence preparation (Illumina): Punctured the bottom of a sterile, Nuclease-free, 0.5 mL micro centrifuge tube 3-4 times with a 21-gauge needle; Placed the target band into punctured tube, and put the tube into a new 1.5 mL EP tube; Centrifuged the stacked tubes in 20,000×g in a micro centrifuge for 2 min at RT to move the gel through the holes into the 1.5 ml tube, and ensured that the gel was completely moved into the bottom tube; Added 300 nl of Nuclease-free water to the gel debris, and eluted the DNA by shaking the tube overnight at RT followed by transfering to the top of a 5 nm filter, and centrifuged the filter for 10 sec in 600×g; Added the following reagents to the collected fluid: 2 μl Glycogen (Invitrogen), 30 μl 3M NaAc (Invitrogen), and 975 μl Pre-chilled 100% Ethanol; Precipitated at −80° C. until it was frozen, and then pelleted by 20,000×g at 4° C. for 40 min; Washed once with 70% cold ethanol, and dissolved the pellet in Nuclease-free water.

Prepare piRNAs for Sequencing

Figure 1:
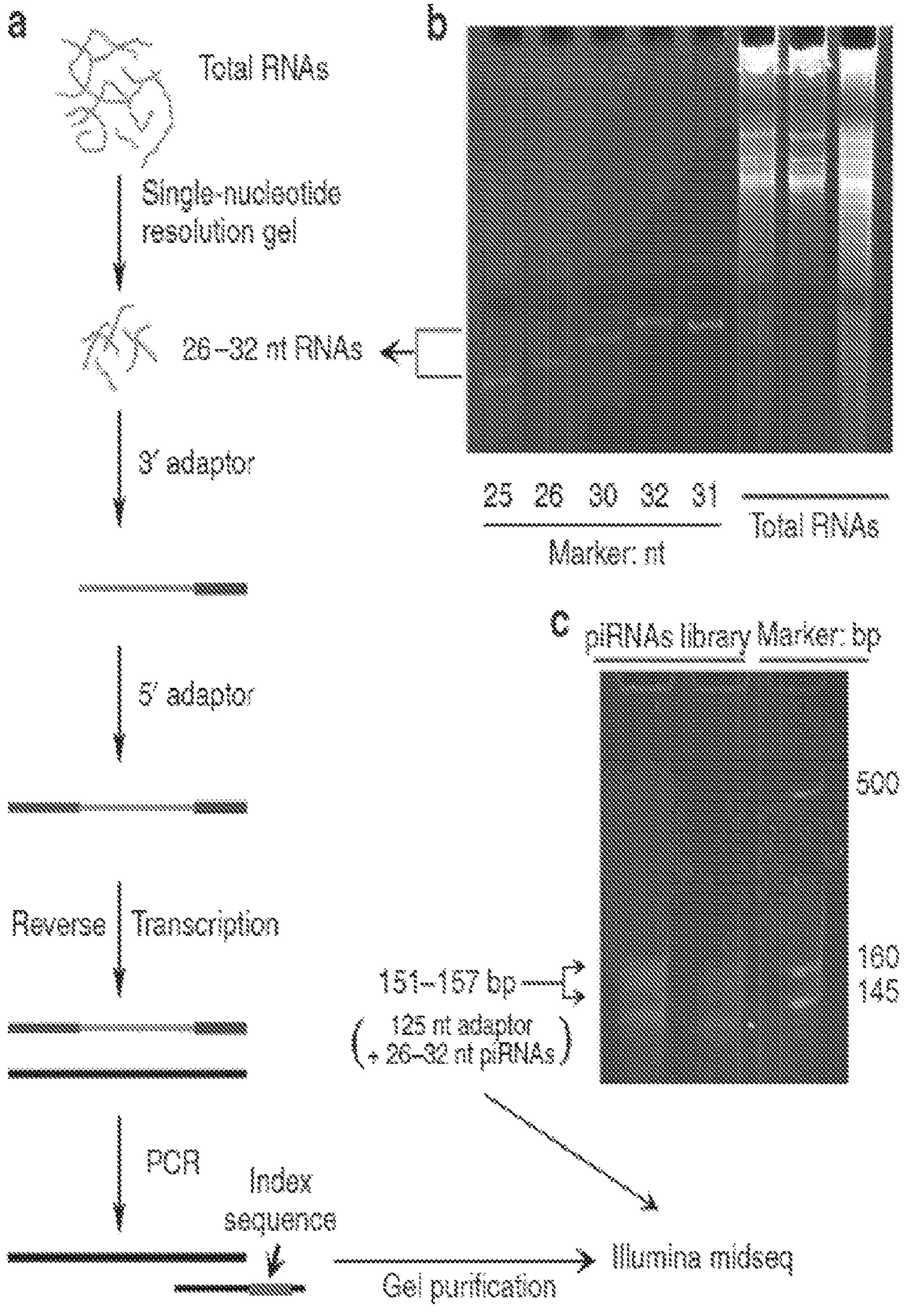
FIG. 1. Flowchart of the protocol used to prepare sncRNAs from the cell lines for RNA-seq. (a) Outlined steps of the preparation. (b) Size-guided sncRNA extraction at one-nucleotide resolution. (c) Secondary sncRNA purification after library construction based on sizes for RNA-seq. The smaller sized products (low band) are likely microRNAs.

As described in FIG. 1, 5'- and 3'-end adaptors containing barcodes were added to extracted sncRNAs. RT-PCR was performed according to the manufacturer's instructions of True® Small RNA kit. RNA-seq was performed using Illumina sequencer in the University of Maryland Institute for Genome Sciences.

Periodate Treatment and Beta Elimination

The method was used to determine 2-O-methylation at the 3' end (Gunawardane, L. S. et al. A slicer-mediated mechanism for repeat-associated siRNA 5' end formation in *Drosophila*. *Science* 315, 1587-1590 (2007); Kirino, Y. & Mourelatos, Z. Mouse Piwi-interacting RNAs are 2'-O-methylated at their 3' termini *Nat Struct Mol Biol.* 14, 347-348 (2007)). Synthetic 30 bases RNA without modification was used as a control. Briefly, sncRNAs from HBE4 cells or synthetic RNA was dissolved in 25 μl of 10 mM NaIO4, kept at 4° C. for 40 min in dark room; RNAs were precipitated and the pellet was dissolved in 60 nl of 1M L-Lysine (PH8.5, Sigma-Alrich), and kept the tube at 45° C. for 90 min; RNAs were precipitated and dissolved in Nuclease-free water; Separated the RNAs on 15% denaturing acrylamide gel; For positive control, stained the gel with EB in a clean container for 2-3 min, then took photos (UVP, BioSpectrum® AC imaging system); For sncRNAs extracted from HBE4 cells, transferred the gel to Zeta-Probe® Membrane (Bio-RAD) in 0.5×TBE for 60 min at 80V for Northern blot after UV cross-linking (UV Stratalinker 2400, Stratagene).

Northern Blot

Probe for detecting piR-L-163 was 5'-GGTCAGAGAATCAAAGTAACATCATGATAT-3' (SEQ ID NO:498) (Synthesized by IDT). Chemically synthesized oligonucleotides were labelled with γ-$^{32}$P-ATP with T4 polynucleotide Kinase (Thermo Scientific). Briefly, separated labeled oligonucleotides from unincorporated label by gel filtration on NucAway™ Spin Columns (Ambion), and 10 k cpm of $^{32}$P labeled oligonucleotides was used for each reaction; Prewash the membrane in 0.1×SSC (Quality Biological) with 0.1% SDS (Bio-Rad) for 1 hr at 65° C.; Removed prewash solution, preheated pre-hybridization buffer (Ambion) to 40° C. and then hybridized the membrane in the buffer for 2 hrs at 40° C.; Removed pre-hybridization buffer, added labeled probe to 10 ml hybridization buffer (Ambion), and hybridized overnight at 37° C.; Washed blot in 6×SSC with 0.1% SDS for 5 min at RT for three times, and pre-erased Phosphorlmager screen simultaneously for 20 min on light table; Repeated wash a fourth time for 20 min at 30° C., laid the damp blot on clean saran wrap after finishing wash, and fold wraps to seal blot; Exposed wrapped blot to Phosphorlmager screen in cassette, and imaged screen after 2 hrs.

Reverse Transcription (RT)-PCR

To amplify sncRNAs, we added an adaptor to the 3' end, a process including adaptor ligation, RT and PCR (de Vanssay, A. et al. Paramutation in *Drosophila* linked to emergence of a piRNA-producing locus. *Nature* 490, 112-115 (2012); Li, Z. et al. Characterization of viral and human RNAs smaller than canonical MicroRNAs. *J Virol.* 83, 12751-12758 (2009)). For adaptor ligation, the adaptor /5'rapp/CTGTAGGCACCATCAAT/3'ddc/ (SEQ ID NO:499) with both 5' and 3' modification was used. Briefly, mixed 1 μl (10 pmol, ~55 ng) of RNA 3' adaptor and 4.4 μl (~100 ng) of purified sncRNAs in a 1.5 ml EP tube; Incubated at 72° C. for 2 min, then placed on ice immediately and kept it on ice for at least 1 min; Added the following reagents (New England Biolabs) to the above tube: 0.8 μl 10×RNA ligase buffer, 1 μl RNase inhibitor, and 1 μl single strand RNA ligase; Mixed it well and incubated at 37° C. for 1 hr, then terminated the reaction at 65° C. for 15 min. For RT, SuperScript™ III First-Strand Synthesis System (Invitrogen) was used according to the manufacturer's instructions with gene specific primer (5'-CAAGCAGAAGACGGCATACGAATTGATGGTGCCTACAG-3') (SEQ ID NO:500). For PCR, a common reverse primer (5'-CAAGCAGAAGACGGCATACGA-3') (SEQ ID NO:501) and primers specific for individual sncRNAs (Table 6). Amplification conditions were denaturation at 95° C. for 30 s (5 min for the first cycle), annealing at 60° C. for 20 s and extension at 72° C. for 20 s (2 min for the last cycle) for 25 cycles.

Immune Precipitation (IP)

For IP using piR-L-163, synthesized biotin labeled RNA oligonucleotides (/5'Biosg/AUAUCAUGAUGUUACUUUGAUUCUCUGACC-3') (SEQ ID NO:502) was used and scrambled RNA (/5'Biosg/GAUACCAAGGACAUACGCUUAUGCAUGCUA-3') (SEQ ID NO:503) used as a control.

Protein extracts from 1×10$^{7}$ cells using HKMG lysis buffer (10 mM HEPES pH 7.9, 100 mM KCL, 5 mM MgCl2, 10% glycerol, 1 mM dithiothreitol, 0.1% NP40) with protease and phosphatase inhibitors (Roche) were incubated with 1 μg biotin-labeled RNA for 16 hr at 4° C. with rotation after pre-clearing with streptavidin beads, then coupled to 10 μl 50% of streptavidin agarose beads (Sigma-Aldrich). After incubation, the biotin-labeled oligonucleotide-coupled streptavidin beads were washed four times with HKMG lysis buffer. Samples were denatured in SDS protein loading buffer before running on a SDS-acrylamide gel.

For IP using anti-human Moesin or p-ERM antibodies, anti-Moesin (Clone Q480, Catalog No. 3150, Cell Signaling) or anti-p-ERM (Clone 41A3, Catalog No. 3149, Cell Signaling) antibodies were used and a rabbit IgG was used as a control. Briefly, Saturated protein G agarose beads (Sigma-Aldrich) with rabbit IgG, anti-Moesin or anti-p-ERM antibodies, respectively (1 μg antibody was used for 4 μl agarose beads) at 4° C. for 3 hrs, centrifuged at 2,200×g for 5 min, and discarded the upper aqueous phase; (2) Protein extracts prepared from cells using lysis buffer (20 mM Tris-cl, pH7.6, 150 mM NaCl, 20 mM KCl, 1.5 mM $MgCl_2$, 0.5% NP-40, 0.5 mM PMSF) were pre-cleared using protein G agarose at 4° C. for 2 hrs, centrifuged at 2,200×g for 5 min, and transferred the upper aqueous phase to above tubes with agarose beads saturated with antibodies, respectively; Kept the tubes rotating overnight at 4° C., centrifuged at 2,200×g for 5 min, and washed the beads with lysis buffer twice; Extracted total RNAs from beads using Trizol Reagent (Life Technologies); Amplification of piR-L-163 or its mutants was performed according to the steps described in the "RT-PCR" section.

For IP using GFP antibody (Clone GSN149, Catalog No. G1546, Sigma-Aldrich), Moesin mutants of *Drosophila* were used to test piR-L-163 binding ability. Protein extracts were prepared from cells at 48 hrs after plasmids transfection. GFP saturated protein G agarose beads were added to the pre-cleared extracts; RNA precipitation, adaptor ligation, reverse transcription and PCR were performed as described above.

Mass Spectrometry

The target band for mass spectrometry was performed. The specific protocol is as follows: Selected gel bands were excised from the one-dimensional SDS-polyacrylamide gel electrophoresis gel, cut into 1×1 mm cubes and destained in 50% acetonitrile in 100 mM NH4HCO3. Gel pieces were reduced with 10 mM tris (2-carboxyethyl) phosphine hydrochloride Q22 (Thermo Scientific) in 100 mM NH4HCO3 for 60 min at 56° C., and were alkylated with 55 mM iodoacetamide (Sigma) in 100 mM NH4HCO3 for 1 h at room temperature in the dark. After washing, the gel pieces were dehydrated with 100% acetonitrile and dried using a speed vacuum of Q23 1.5 mg of trypsin (Promega), and a volume of 50 mM NH4HCO3 was added to each gel piece and the gel pieces were allowed to swell for 30 min on ice. Excess trypsin was removed and replaced with 50 mM NH4HCO3 and samples were incubated at 37 1 C overnight. The resulting peptides were extracted using 2.5% formic acid, 50% acetonitrile in 50 mM NH4HCO3.

The processed samples were analyzed using a nanoscale reverse-phase liquid chromatography using an Xtreme Simple nanoLC system (CVC/Q24 MicroTech). The analytical column was prepared by packing into a laser-pulled fused silica capillary, and peptides were injected into the sample loop using an Endurance auto sampler. A 120-min liquid chromatography-gradient method with a post-split flow rate of 0.6 ml/min was used to elute Q25 the peptides into the LTQ mass spectrometer with a nanospray ionization source. Dynamic exclusion was enabled with repeat count 2, repeat duration 30 s and exclusion duration 120 s. Mass spectrometry and tandem Q26 mass spectrometry data were searched against the UniProtKB human protein database using Bioworks 3.3.1 SP1 with the SEQUEST algorithm. Search parameters included 1.5 Da peptide mass tolerance, 1.0 Da fragment tolerance, static Cys+57.02510 (carbamidomethylation) modification and differential modification Met+15.99492. Fully tryptic peptides with up to two missed cleavages and charge-state-dependent cross-correlation scores ≥2.5, 3.0 and 3.5 for 2+, 3+ and 4+ peptides, respectively.

RNA Interference

The small interference RNA targeting untranslated region (UTR) of human Moesin (5'-CCGUUAGCAGGAAGCC-UAA-3') (SEQ ID NO:504) with scrambled sequence as a control (5-GAUACCAAGGGACAUACGCUU-3') (SEQ ID NO:505). Sense and anti-sense oligo RNAs of Moesin and scrambled control were annealed, respectively. Transfection is performed using Lipofectamine™ RNAiMAX (Invitrogen) according to its manual, and the final concentration of annealed oligo RNAs is 400 nM. Transfection and knockdown efficiency were tested at both RNA and protein levels.

Blocking piR-L-163 Expression

To avoid triggering uncertain siRNA (Lamb, R. F. et al. The TSC1 tumour suppressor hamartin regulates cell adhesion through ERM proteins and the GTPase Rho. *Nat Cell Biol.* 2, 281-287(2000)), complementary DNA was used as antagonism targeting piR-163 (5'-GGTCAGAGAAT-CAAAGTAACATCATGATAT-3') (SEQ ID NO:496) with scrambled DNA (5'-GATACCAGGGACATACGCTT-GATCCTAGC-3') (SEQ ID NO: 506) as a control.

Western Blot and Antibodies

Figure 5:
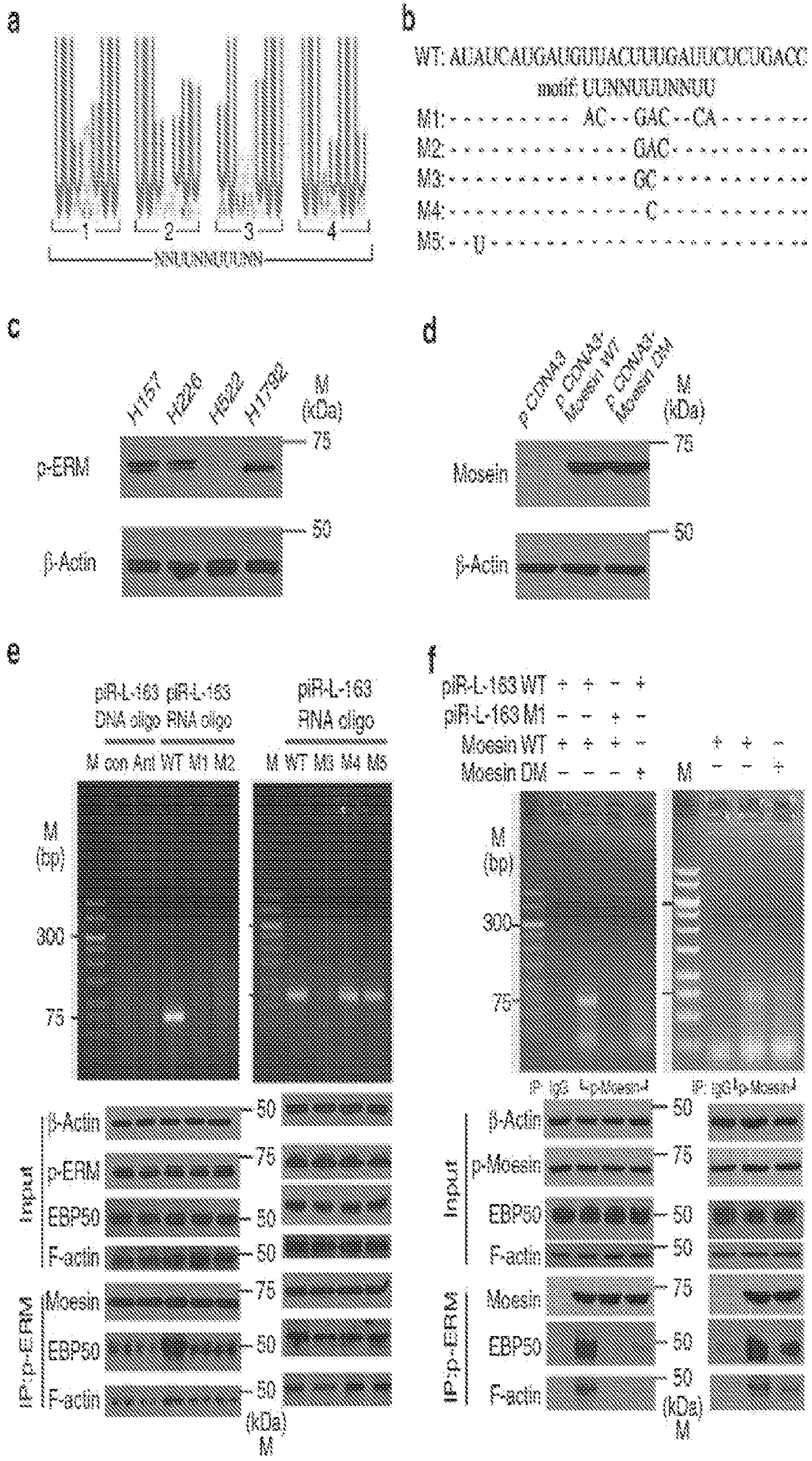
FIG. 5. piR-L-163 motif and ERM element critical for binding and p-ERM's interaction with EBP50 and F-actin. (a) Predicted protein binding motif NNUUNNUUUNN (SEQ ID NO:487) in piR-L-163. (b) Sequences of the mutant piR-L-163s. (c) Endogenous p-ERM levels in 4 NSCLC cell lines. (d) Moesin levels in H522 cells transfected with pCDNA3 (empty vector), pCDNA3-Moesin WT (wild type moesin) and pCDNA3-Moesin DM (RRRKPDT (SEQ ID NO:488) element deleted). (e) piR-L-163 and its mutant forms detected in RNAs purified from the IP products and the correlated binding capabilities between p-ERM and EBP50 or F-actin in H1792 cells. (f) piR-L-163 or piR-L-163M1 detected in RNAs purified from IP products of H522 cells (left) or HBE4 cells (right) transfected with p-Moesin in conditions as indicated and the correlated binding capabilities between p-ERM and EBP50 or F-actin.

Primary antibodies used were: anti-Moesin (1:1,000, Clone Q480, Catalog No. 3150, Cell Signaling), anti-p-ERM (Clone 41A3, Catalog No. 3149, Cell Signaling), anti-Moesin (Clone 38/Moesin, Catalog No. 610401, BD Transduction Laboratories), anti-p-Moesin (Thr558, Catalog No. 12895, Sanra Cruz), anti-β-actin (1:5,000, Catalog No. A228, Sigma-Aldrich), anti-EBP50 (1:100, Clone 6/EBP50, Catalog No. 61160, BD Transduction Laboratories), anti-F-actin (1:100, Clone NH3, Catalog No. MA1-80729, Thermor Fisher), anti-p-Wee 1 (Se53, 1:1000, Catalog No. sc-130223, Sanra Cruz), anti-Wee 1 (C-20, 1:1000, Catalog No. sc-325, Sanra Cruz), anti-p-Cdc2 (Tyr15, 1:1000, Catalog No. 9111, Cell Signaling), anti-p-Cdk (Thr14/Tyr15-R, 1:1000, Catalog No. sc-28435-R, Sanra Cruz), anti-Cdc2 p34 (H-297, 1:1000, Catalog No. sc-747, Sanra Cruz), anti-p-Cdc25C (Ser198, 1:1000, Catalog No. 9529, Cell Signaling), anti-CDK2 (78B2, 1:1000, Catalog No. 2546, Cell Signaling), anti-p-Histone H2AX (Ser139, 20E3, :1000, Catalog No. 9718, Cell Signaling), and anti-GFP (N-terminal, 1:4000, Catalog No. G1544, Sigma). Secondary antibodies used were: Goat anti-Mouse (1:2,500, Catalog No. 31160, Pierce), and Goat anti-Rabbit (1:2,500, Catalog No. 31460, Pierce). Cells were lysed in RIPA buffer (Sigma) on ice after washed in PBS twice, centrifuge at 160,000×g for 10 min at 4° C. Protein in supernatant was qualified using BCA™ protein assay kit (Thermo Scitific) and denatured in SDS loading buffer in boiling water, run 10% SDS-PAGE gel and transferred to nitrocellulose membrane (Thermo Scitific). Membrane was incubated with primary antibody overnight at 4° C. after blocking, washed in PBST and incubated corresponding secondary antibody for 1 h at RT, finally was developed using SuperSignal® west pico chemiluminescent substrate (Thermo Scitific). The full gels of the Western blots presented in FIG. 5 are shown in FIG. 13.

Cell Cycle Analysis

Cell cycle distribution was analyzed by Flow Cytometry (Becton-Dickinson). Cells were synchronized in growth factor-free Keratinocyte-SFM with 2 mM Thymidine (Catalog No. T1895, Sigma-Aldrich) for 24 hrs. Transfection is performed using Lipofectamine™ RNAiMAX (Invitrogen) according to its manual, and the final concentration of annealed oligo RNAs is 400 nM. Four hour after transfection, culture medium was replaced by complete Keratinocyte-SFM supplemented with L-Glutamine, prequalified human recombinant EGF 1-53 and BPE. Cells were harvested at different time points, washed in phosphate-buffer saline (PBS), fixed with ice-cold 70% ethanol, and strained in PI/RNase solution (BD Pharmigen). The samples were analyzed on a FACScan flow cytometer in combination with BD lysis software (Becton-Dickinson).

Cell Viability and Cell Growth Curve Assay

Cell viability and cell growth curve assay were determined by MTT assay and trypan blue exclusion assay, respectively as described previously (Kirino, Y. & Mourelatos, Z. Mouse Piwi-interacting RNAs are 2'-O-methylated at their 3' termini *Nat Struct Mol Biol.* 14, 347-348 (2007)). BrieflySpecifically, MTT (5 mg/ml) was added into cells and incubated at culture condition for 3 hours, removed the medium carefully and dissolved formazan in DMSO, assay was used to assess the surviving cells and OD values were measured using Microplate Reader Manager (Bio Rad) at wavelengths of 570/690 nm. For trypan blue exclusion assay, cells were washed in PBS for three times, and dyed in 0.4% tyrpan blue solution. Unstained viable cells were counted in hemocytometer chamber under microscope. Each experiment was performed three times independently.

Invasion Assay

Briefly, 24 hrs after transfection, $6\times10^4$ cells were placed in the upper chamber of Matrigel Invasion Chambers (BD Bioscience) with growth factor-free Keratinocyte-SFM and the bottom chamber were exposed to Keratinocyte-SFM medium supplemented with L-Glutamine, prequalified human recombinant EGF 1-53 and BPE. Invading cells were evaluated after 12 hrs according to the manufacturer's instruction. The numbers of invading cells were adjusted 15% downwards for Ant-163 treated cells or 15% upwards for piR-L-163 treated cells to compensate the differences for the proliferation rates.

Migration Assays

Two complimentary methods were used. For quantitative fluorescent dye assay, Innocyto™ Cell migration Assay kit (EMD Millipore) was used. Briefly, 24 hrs after treatment, $1\times10^5$ cells (10% less for Ant-163 treated cells or 10% more for piR-L-163 treated cells) were loaded to the upper chamber with growth factor-free Keratinocyte-SFM for (HBE4 cells) or serum-free DMEM (for H1792 cells) with the bottom chamber exposed to completed culture medium. Negative controls were used with 3 μM Latrunculin A. After 12 hrs incubation, fluorescence was measured using a fluorescence plate reader 485 nm (excitation) and 520 nm (emission) according to the manufacturer's instruction. For wound-healing assay, cells (24 hrs after treatment with different DNA or RNA oligonucleotides) were grown to confluence followed by scratching with a pipette tip to create a gap. The floating cells were removed and the gaps were monitored/photographed every 12 hrs.

Statistical Analysis

The results reported as mean±s.d. indicated in the data sets were analyzed using student's t-test under the assumption of equal variance for comparisons. All tests were determined by unpaired two-sided tests, and P-values $<0.05$ were considered statistically significant.

Bioinformatics Analysis

The sequencing reads from each of the 11 samples were individually processed and aligned to the human reference (build hg19) using Bowtie 0.12.9 (Langmead, B., Trapnell, C., Pop, M. & Salzberg, S. L. Ultrafast and memory-efficient alignment of short DNA sequences to the human genome. *Genome Biol.* 10, R25 (2009)). In-house Perl scripts were used to detect piRNAs expression based on genomic coverage after using a cut-off of 30× across a minimum length of 26 bp regions. A piRNA prediction tool (Zhang, Y., Wang, X. & Kang, L. A k-mer scheme to predict piRNAs and characterize locust piRNAs. *Bioinformatics* 27, 771-776 (2011)) was used to filter the detected piRNAs loci from individual samples utilizing the piRNAs sequence. The piRNAs loci from all 11 samples were collated using custom Perl scripts. This merged set of piRNAs loci was further filtered to exclude piRNAs loci that overlapped known protein coding genes and other sncRNAs. Only those piRNAs loci with lengths between 26 nucleotides to 32 nucleotides were retained as the final set of novel piRNAs loci.

Simultaneously, 32,046 piRNAs nucleotide sequences were queried and downloaded from NCBI. The Blat program (Kent, W. J. BLAT—The BLAST-Like Alignment Tool. *Genome Res.* 12, 656-664 (2002)) was used to align these nucleotide sequences against human reference (build hg19) to infer the genomic coordinates for the known piRNA sequences. Blat hits showing 100% alignment against the human reference were retained as the coordinates of the known piRNAs sequences. Known piRNAs sequences that aligned to multiple locations were given separate unique IDs. The read coverage across these known piRNAs loci was calculated using custom Perl scripts. The final set of known piRNAs loci was determined by filtering out piRNAs loci with Reads per Kilobase per Million mapped reads (RPKM)≤15. Known piRNAs loci that showed partial read support across the entire length were also filtered out.

HTSeq (Anders, S., Pyl, P. T. & Huber, W. HTSeq—A Python framework to work with high-throughput sequencing data. *Bioinformatics* 31, 166-169 (2015)) was used to compute read counts across each piRNA in each of the 11 samples which in turn were used as input to the R package DESeq (Anders, S. & Huber, W. Differential expression analysis for sequence count data. *Genome Biol.* 11, R106 (2010)). DESeq was used to normalize the read counts for library size and dispersion followed by tests for differential piRNA expression between the Immortalized and Adenocarcinoma cell line and the Immortalized and Squamous cell line. The significant differentially expressed piRNA (the unknown piRNAs are referred as piRNA-Ls in the text) were determined using an FDR cut-off ≤0.05 and at least two-fold change between conditions.

Constructing Wild Type and Mutant Moesin Plasmids

We used pcDNA3.1 (+) vector for cloning moesin wild type and mutant plasmids. All plasmids were sequenced for verification.

Interaction Between piR163 and Moesin

To determine specific piR-L-163 site critical for its binding to moesin, a series of piR-L-163 mutants in the NNUUNNUUUNNUU motif predicted with protein binding capability (Ray, D. et al. A compendium of RNA-binding motifs for decoding gene regulation. *Nature* 499, 172-177

(2013)) were generated. To determine moesin domain critical for its interaction with piR-L-163, a construct was generated with deletion of a candidate RNA binding element (RRRKPDT) (SEQ ID NO:488) based on structures of Human and *Drosophila* moesin predicted using software BindN (http://bioinfo.ggc.org/bindn/).

TABLE 2

Index sequences for individual cell lines.

| Cell Line Name | Index Sequence |
|---|---|
| H157 | ATCACG (SEQ ID NO: 507) |
| H226 | CGATGT (SEQ ID NO: 508) |
| H596 | TTAGGC (SEQ ID NO: 509) |
| SKMES1 | TGACCA (SEQ ID NO: 510) |
| H522 | ACAGTG (SEQ ID NO: 511) |

TABLE 2-continued

Index sequences for individual cell lines.

| Cell Line Name | Index Sequence |
|---|---|
| H1437 | GCCAAT (SEQ ID NO: 512) |
| H1792 | CAGATC (SEQ ID NO: 513) |
| H1944 | ACTTGA (SEQ ID NO: 514) |
| HBE2 | TAGCTT (SEQ ID NO: 515) |
| HBE3 | GGCTAC (SEQ ID NO: 516) |
| HBE4 | CTTGTA (SEQ ID NO: 517) |

Specific sequence tag was added to RNAs of individual cell lines to allow identify the origins of the RNAs for RNA-seq analysis.

TABLE 3

Synthesized DNA and RNA oligonucleotides

| name | sequence (5' to 3') | application | |
|---|---|---|---|
| 3' Adaptor | /5rapp/CTGTAGGCACCATCAAT/3ddc/ (SEQ ID NO: 499) | adaptor for snRNAs PCR or QPCR | Adenylation-5 and dideoxy C-3' |
| Cmop7modban | CAAGCAGAAGACGGCATACGAATTGATGGTGCCTACAG (SEQ ID NO: 500) | for sncRNAs reverse transcription | |
| Cmo RP | CAAGCAGAAGACGGCATACGA (SEQ ID NO: 501) | reverse primer | |
| piR163-L-Bio | /5Biosg/rArUrArUrCrArUrGrArUrGrUrUrArCrUrUrUrGrAr UrUrCrUrCrUrGrArCmC (SEQ ID NO: 502) | for IP | m is 2-O-methylation |
| ControlBio | /5Biosg/rGrArUrArCrCrArArGrGrArCrArUrArCrGrCrUrUr ArUrGrCrArUrGrCrUrA (SEQ ID NO: 503) | IP control | Bio is Biotin |
| Ant163 | GGTCAGAGAATCAAAGTAACATCATGATAT (SEQ ID NO: 496) | for blocking piR-L-163 control for blocking | |
| piRcon | GATACCAGGGACATACGCTTGATCCTAGC (SEQ ID NO: 506) | piR163 | |
| piR163-L-WT | rArUrArUrCrArUrGrArUrGrUrUrArCrUrUrUrGrArUrUrCrUr CrUrGrArCmC (SEQ ID NO: 518) | interaction study | m is 2-O-methylation |
| piR163-L-M1 | rArUrArUrCrArUrGrArUrGrArCrArCrGrArCrGrArCrArCrUr CrUrGrArCmC (SEQ D NO: 519) | interaction study | m is 2-O-methylation |
| piR163-L-M2 | rArUrArUrCrArUrGrArUrGrUrUrArCrGrArCrGrArUrUrCrUr CrUrGrArCmC (SEQ ID NO: 520) | interaction study | m is 2-O-methylation |
| piR163-L-M3 | rArUrArUrCrArUrGrArUrGrUrUrArCrGrCrUrGrArUrUrCrUr CrUrGrArCmC (SEQ ID NO: 521) | interaction study | m is 2-O-methylation |
| piR163-L-M4 | rArUrArUrCrArUrGrArUrGrUrUrArCrUrCrUrGrArUrUrCrUr CrUrGrArCmC (SEQ ID NO: 522) | interaction study | m is 2-O-methylation |
| piR163-L-M5 | rArUrUrUrCrArUrGrArUrGrUrUrArCrUrUrUrGrArUrUrCrUr CrUrGrArCmC (SEQ ID NO: 523) | interaction study | m is 2-O-methylation |
| AntipiR163-L-RNA | rGrGrUrCrArGrArGrArArUrCrArArArGrUrArArCrArUrCrAr UrGrArUrArU (SEQ ID NO: 497) | blocking piR-L-163 | |
| Control RNA oligos | rGrArUrArCrCrArArGrGrArCrArUrArCrGrCrUrUrArUrGrCr ArUrGrCrUrA (SEQ ID NO: 524) | sncRNAs control | |
| CpiR163-L-DigN | /5DigN/GGTCAGAGAATCAAAGTAACATCATGATAT (SEQ ID NO: 525) | for FISH DigN is Digoxin | |
| piR163-L-F | ATATCATGATGTTACTTTGATTCTCT (SEQ ID NO: 526) | for PCR or QPCR | |
| U6F | ATGACACGCAAATTCGTGAA (SEQ ID NO: 527) | QPCR inner control for snRNAs | |

TABLE 3-continued

| Synthesized DNA and RNA oligonucleotides | | |
|---|---|---|
| name | sequence (5' to 3') | application |
| Con F | GATACCAGGGACATACGCTTGA (SEQ ID NO: 506) | for control amplification |
| Ant163-L-F | GGTCAGAGAATCAAAGTAACATCATGA (SEQ ID NO: 528) | for Ant-163 amplification |
| piR163-L-M1F | ATATCATGATGACACGACGACA (SEQ ID NO: 529) | for piR-L-163M1 amplification |
| piR163-L-M2F | ATATCATGATGTTACGAC (SEQ ID NO: 530) | for piR-L-163M2 amplification |
| piR163-L-M3F | ATATCATGATGTTACGC (SEQ ID NO: 531) | for piR-L-163M3 amplification |
| piR163-L-M4F | ATATCATGATGTTACTC (SEQ ID NO: 532) | for piR-L-163M4 amplification |
| piR163-L-M5F | ATTTCATGATGTTACTTTGATT (SEQ ID NO: 533) | for piR-L-163M5 amplification |
| MoesinVF1 | AGCAAGCTTATGCAAAACAACCAAAT (SEQ ID NO: 534) | for human Moesin plasmid constraction |
| MoesinVR1 | ATCTCGAGTTACATAGACTCAAATTCGTCA (SEQ ID NO: 535) | for human Moesin plasmid constraction |
| MoesinVF2 | AACTATACATGATTGAGGTGCAGCAGATGAAGG (SEQ ID NO: 536) | for human Moesin plasmid constraction |
| MoesinVR2 | GCACCTCAATCATGTATAGTTCATGGTTCCCCATG (SEQ ID NO: 537) | for human Moesin plasmid constraction |
| GAPDHF | TGCACCACCAACTGCTTAGC (SEQ ID NO: 538) | inner control for coding gene QPCR |
| GAPDHR | GGCATGGACTGTGGTCATGAG (SEQ ID NO: 539) | inner control for coding gene QPCR |
| moesinF1 | GGGAAGCAGCTATTTGACCA (SEQ ID NO: 540) | for QPCR |
| moesinR1 | CTTAAAGAGCAGGGGGCTTT (SEQ ID NO: 541) | for QPCR |
| Moe3UTRsiF | rCrCrGrUrUrArGrCrArGrGrArArGrCrCrUrArArUrU (SEQ ID NO: 542) | for Moesin knockdown |
| Moe3UTRsiR | rUrUrArGrGrCrUrUrCrCrUrGrCrUrArArCrGrGrUrU (SEQ ID NO: 543) | for Moesin knockdown |
| Neg S | rGrArUrA rCrCrArA rGrGrGrA rCrArUrA rCrGrC rUrU (SEQ ID NO: 544) | knockdown control |
| Neg AS | rGrCrG rUrArUrG rUrCrCrC rUrUrGrG rUrArUrC rUrU (SEQ ID NO: 545) | knockdown control |
| PIWIL1F | GAGCCAGAGCCAGAGGAAG (SEQ ID NO: 546) | for QPCR |
| PIWIL1R | ATAATTCCCCCTCTGCTGGT (SEQ ID NO: 547) | for QPCR |
| PIWIL2F | GTGGGTTTGGTCTCCATGTT (SEQ ID NO: 548) | for QPCR |
| PIWIL2R | CCTGTCCTTGCGTACCAGAT (SEQ ID NO: 549) | for QPCR |
| PIWIL3F | GCAGGGAGAGCTACCAACAA (SEQ ID NO: 550) | for QPCR |
| PIWIL3R | AACCACTGGGACTTCCTCCT (SEQ ID NO: 551) | for QPCR |
| PIWIL4F | ACCAGAGAAAAATTGGCACA (SEQ ID NO: 552) | for QPCR |
| PIWIL4R | GCCAGTCTTGGGGAAAATCT (SEQ ID NO: 553) | for QPCR |
| LAMC2F1 | CTACTTCGGGGACCCATTG (SEQ ID NO: 554) | for QPCR |
| LAMC2R1 | CAAACACAGGTGCCATCACT (SEQ ID NO: 555) | for QPCR |

Example 2

Cisplatin Upregulates piRNA-L-138 which Confers Cisplatin-Resistance by Inhibiting Apoptosis in Lung Squamous Cell Carcinoma PIWI-interacting RNAs (piRNAs) is the largest family of short non-coding RNAs (sncRNAs) and plays an important role in suppressing transposon activities during development (Ross, R. J., Weiner, M. M. & Lin, H. PIWI proteins and PIWI-interacting RNAs in the soma. *Nature* 505, 353-359 (2014)). We recently showed that piRNA-Like sncRNAs (piRNA-Ls) are aberrantly expressed and biologically functional in non-small cell lung cancer (NSCLC) cells (Mei Y, Wang Y, Kumari P, et al. A piRNA-like small RNA interacts with and modulates p-ERM proteins in human somatic cells. *Nat Commun* 6, 7316. doi: 10.1038/ncomms8316 (2015)). Here, we show that piRNA-L-138 (piR-L-138), a piRNA-L down-regulated in NSCLC cells, is up-regulated upon cisplatin (CDDP) treatment particularly in lung squamous cell carcinoma (SCC) cells. Blocking piR-L-138 by an antisense oligo (Ant-138) (SEQ ID NO:556) resulted in an increased apoptosis and a reduced cleavage of MDM2 in CDDP-treated SCC cells. Conversely, exogenously transfecting piR-L-138 into SCC cells accelerated MDM2 cleavage. Interestingly, piR-L-138 was found in the same complex with cleaved 60 kD MDM2 isoform in CDDP-treated SCC cells. The interaction between piR-L-138 and the MDM2 isoform was further confirmed visually by co-localization of the two molecules within individual cells. In patient-derived xenograft (PDX) lung SCC models, CDDP-based chemotherapy resulted in an increased piR-L-138 expression. In a SCC xenograft model treated with CDDP, a significantly increased apoptosis was observed in tumor regions locally delivered Ant-138. Thus, we revealed upregulating piR-L-138 as a novel mechanism of CDDP resistance in lung SCC and potentially targetable to overcome the resistance.

piRNAs are primarily investigated for their functions in renewal of germ line cells and development (Lin, H. & Spradling, A. C. A novel group of *pumilio* mutations affects the asymmetric division of germline stem cells in the *Drosophila* ovary. *Development* 124, 2463-2476 (1997); Cox D N, et al. A novel class of evolutionarily conserved genes defined by piwi are essential for stem cell self-renewal. *Genes Dev.* 12, 3715-3727 (1998); Girard, A., et al. A germline-specific class of small RNAs binds mammalian Piwi proteins. *Nature* 442, 199-202 (2006); Brennecke J, et al. Discrete small RNA-generating loci as master regulators of transposon activity in *Drosophila. Cell* 128, 1089-1103 (2007); Shirayama M. et al. piRNAs initiate an epigenetic memory of nonself RNA in the *C. elegans* germline. *Cell* 150, 65-77 (2012); Lee H. C. et al. *C. elegans* piRNAs mediate the genome-wide surveillance of germline transcripts. *Cell* 150, 78-87 (2012); Ashe A. et al. piRNAs can trigger a multigenerational epigenetic memory in the germline of *C. elegans. Cell* 150, 88-99 (2012)). Their potential roles in somatic tissues, while poorly studied, have recently been recognized (Ross, R. J., Weiner, M. M. & Lin, H. PIWI proteins and PIWI-interacting RNAs in the soma. *Nature* 505, 353-359 (2014); Mei Y, Wang Y, Kumari P, et al. A piRNA-like small RNA interacts with and modulates p-ERM proteins in human somatic cells. *Nat Commun* 6, 7316. doi: 10.1038/ncomms8316 (2015); Brower-Toland B, et al. *Drosophila* Piwi associates with chromatin and interacts directly with HP 1a. *Genes Dev.* 21, 2300-2311 (2007); Yan Z, et al. Widespread expression of piRNA-like molecules in somatic tissues. *Nucleic Acids Res.* 39, 6596-6607 (2011); Qiao, D., et al. Molecular characterization of hiwi, a human member of the piwi gene family whose overexpression is correlated to seminomas. *Oncogene.* 21, 3988-3999 (2002)). A number of studies have shown an abnormal expression of piRNAs in various cancer types, suggesting biological roles of piRNAs in cancer development and progression (Mei, Y., Clark, D. & Mao L. Novel dimensions of piRNAs in cancer. *Cancer Lett* 336, 46-52 (2013); Lee J H, et al. Stem-cell protein Piwil2 is widely expressed in tumors and inhibits apoptosis through activation of Stat3/Bcl-XL pathway. *Hum. Mol. Genet.* 15, 201-211 (2006); Taubert H, et al. Expression of the stem cell self-renewal gene Hiwi and risk of tumour-related death in patients with soft-tissue sarcoma. *Oncogene* 26, 1098-1100 (2007); Grochola L F, et al. The stem cell-associated Hiwi gene in human adenocarcinoma of the pancreas: expression and risk of tumour-related death. *Br. J. Cancer* 99, 1083-1088 (2008); Lee J H, et al. Pathways of proliferation and antiapoptosis driven in breast cancer stem cells by stem cell protein Piwil2. *Cancer Res.* 70, 4569-4579 (2010); Janic, A., et al. Ectopic expression of germline genes drives malignant brain tumor growth in *Drosophila. Science* 330, 1824-1827 (2010); Zhao Y M, et al. HIWI is associated with prognosis in patients with hepatocellular carcinoma after curative resection. *Cancer* 118, 2708-2717 (2012); Lee E, et al. Landscape of somatic retrotransposition in human cancers. *Science* 337, 967-971 (2012)). We recent identified 555 piRNAs expressed in immortalized normal human lung bronchial epithelial (HBE) and NSCLC cell lines. Because more than half of the piRNAs are not presented in any of the existing databases and also lack of certain characteristic features, we termed these sncRNAs as piRNA-Ls (Mei Y, Wang Y, Kumari P, et al. A piRNA-like small RNA interacts with and modulates p-ERM proteins in human somatic cells. *Nat Commun* 6, 7316. doi: 10.1038/ncomms8316 (2015)). Many of these piRNA-Ls were differentially expressed between HBE and NSCLC cell lines as well as between adenocarcinoma (ADC) and SCC cell types including piR-L-138. We uncovered a novel mechanism of sncRNAs where a sncRNA, piR-L-163 in this case, can directly bind to proteins and regulate functional activities of the proteins (Mei Y, Wang Y, Kumari P, et al. A piRNA-like small RNA interacts with and modulates p-ERM proteins in human somatic cells. *Nat Commun* 6, 7316. doi: 10.1038/ncomms8316 (2015)).

Figure 14A:
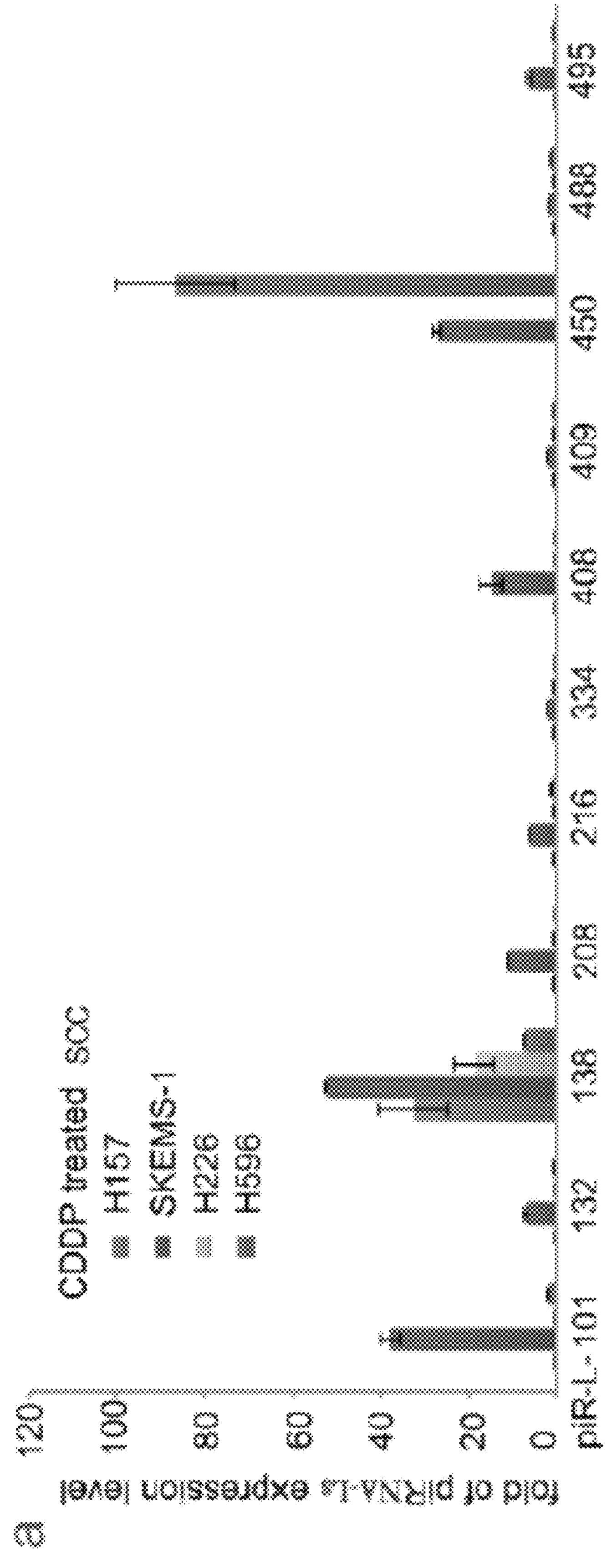
FIG. 14. piR-L-138 3'-end 2'-O-methylation and expression patterns in NSCLC cell lines. (a) Expression levels of selected piRNA-Ls in SCC cell lines 24 h after treated with cisplatin treatment. (b) Average levels of piR-L-138 in ADC and SCC cell lines in comparison with the levels in HBE lines based analyzed using RNA-seq (left) and quantitative RT-PCR (right). (c) 2'-O-methylation at the 3'-end of piR-L-138 is indicated by periodate treatment followed by β-elimination. The untreated and treated synthetic oligo RNAs separated in PAGE and stained with ethidium bromide (left). The untreated or treated total RNAs were detected using northern blot (right). Red arrows indicate piR-L-138. (d) Relative piR-L-138 levels detected in tumors from 4 PDX NSCLC models treated with cisplatin-based chemotherapy. Values are averages of three independent replicates; error bars represent mean s.d.; * p<0.05,  p<0.01, * p<0.001.

To determine if piRNA-Ls play a role in chemo-sensitivity, we first selected 11 piRNA-Ls differentially expressed between NSCLC and HBE cells (Mei Y, Wang Y, Kumari P, et al. A piRNA-like small RNA interacts with and modulates p-ERM proteins in human somatic cells. *Nat Commun* 6, 7316. doi: 10.1038/ncomms8316 (2015)) and analyzed the relationship between the expression levels and the sensitivities to chemotherapeutic agents commonly used clinically for patients with NSCLC. We established doses of 50% inhibitory concentration (IC50) for CDDP, gemcitabine, and docetaxel in 4 SCC and 4 ADC cell lines based on 3-(4,5-dimethylthiazol-2-yl)-2,5-diphenyltetrazolium bromide (MTT) assay (Table 4). Examples of the inhibitory curves and morphological changes by these agents were presented in FIG. 18 (18*a*-18*c*). We then measured expression levels of the 11 selected piRNA-Ls using real-time RT-PCR before and 24 h after treatment with both IC50 (H) and IC25 (L) doses for each of the agents. Among these piRNA-Ls, we observed a consistent and substantial increase of piR-L-138 levels in all SCC cell lines after CDDP treatment (FIG. 14*a*) but no or much smaller increase of piR-L-138 expression was observed in the ADC cell lines (FIG. 18*d*). Impact of gemcitabine and docetaxel in piR-L-138 expression was also determined in these NSCLC cell lines (FIG. 19). As CDDP is the backbone agent to treat patients with NSCLC, we selected CDDP as the representative agent to further determine the role of piR-L-138 in SCC cells' response to chemotherapy.

Consistent with the data obtained by using RNA-seq (FIG. 14*b*, left) as we reported previously (Mei Y, Wang Y, Kumari P, et al. A piRNA-like small RNA interacts with and modulates p-ERM proteins in human somatic cells. *Nat Commun* 6, 7316. doi: 10.1038/ncomms8316 (2015)), expression level of piR-L-138 was down regulated in both ADC and SCC cell lines compared to that observed in HBE cell lines by RT-PCR (FIG. 14*b*, right). Similar to piR-NAs21, piR-L138 also contains a 3 prime nucleotide 2'-O-methylation (FIG. 14*c*).

To determine if the CDDP-induced piR-L-138 up-regulation is a cell culture artifact, we analyzed 10 NSCLC tissues from 4 patient-derived xenograft (PDX) models (2 SCC and 2 ADC) used in our previously published study (Jun Zhao, et al. Anti-HDGF Targets Cancer and Cancer Stromal Stem Cells Resistant to Chemotherapy. *Clin Cancer Res.* 19, 3567-76 (2013)), including 4 tumors of unrelated patients from untreated animals, 2 tumors obtained at 8 days after treatment (CDDP plus gemcitabine) and 4 tumors obtained 28 days after the treatment. We found that piR-L-138 levels were significantly increased in the two SCC models (UMB410 and MDA2131-11) with tumors collected at both 8 or 28 days after the treatment compared with tumors from untreated controls (FIG. 14*d*). While one tumor (28 days after treatment) from one of two ADC models (MDA274-2) also showed an increase of piR-L-138 level, both tumors (8 and 28 days after treatment) from the other ADC model (MDA2131-1) exhibited a decrease of piR-L-138 expression (FIG. 14*d*). The data support the impact of CDDP on piR-L-138 expression also occurs in vivo of lung PDX SCCs.

Figure 15C:
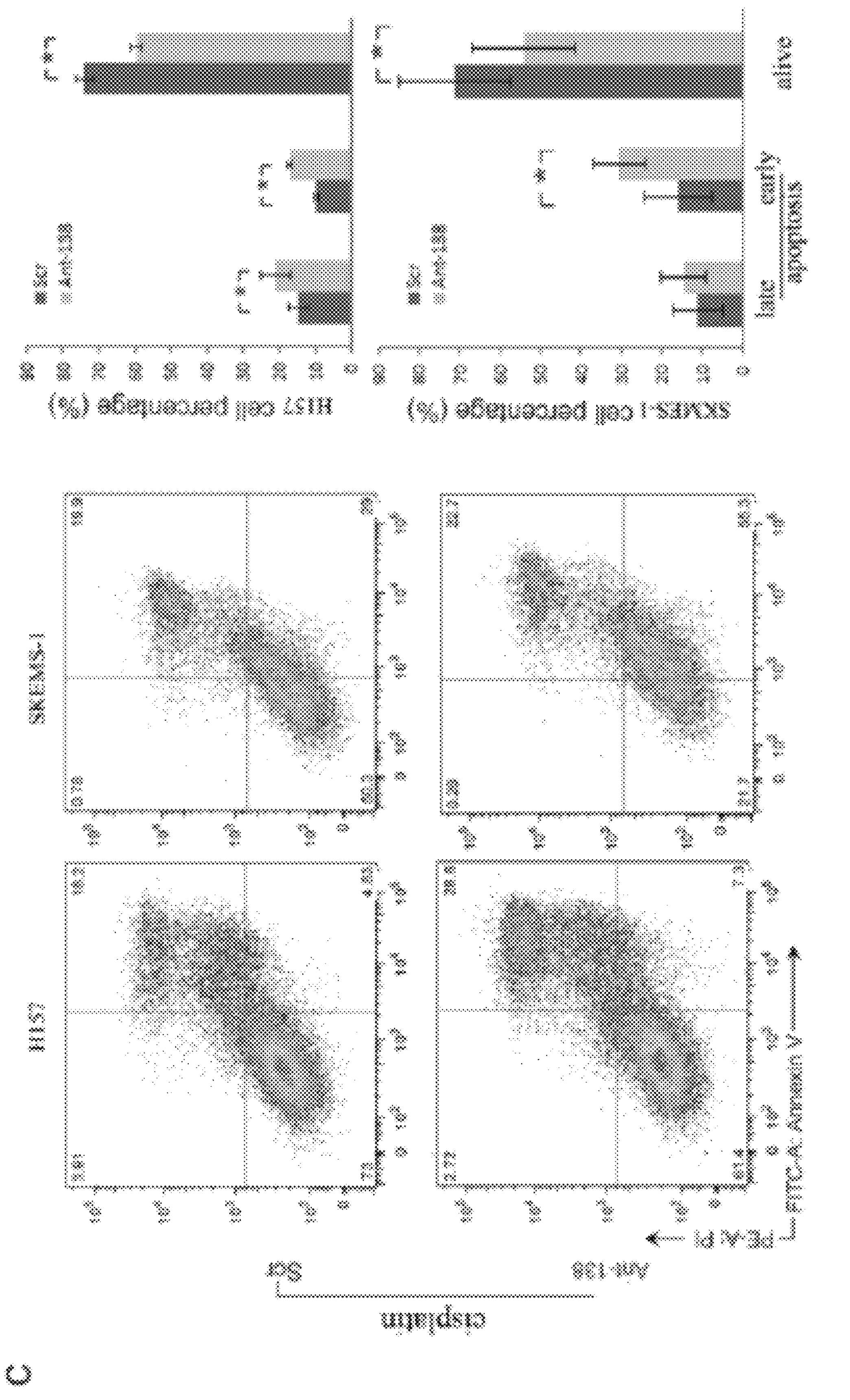
FIG. 15. piR-L-138 impacts MDM2 cleavage and apoptosis in SCC cells. (a) Numbers of SCC cells 24 h after CDDP treatment with either Scr or Ant-138 transfection measured by MTT assay. (b) Cell cycle distributions of H157 cells collected 24 h after CDDP treatment, with no treatment or treated with Scr or Ant-138 6 h after CDDP. Red arrows indicate the sub-G1 fraction. (c) Apoptotic and pre-apoptotic SCC cells transfected with either Scr or Ant-138 after CDDP treatment measured by FITC annexin V assay. (d) Western blot analysis of levels of full length MDM2, cleaved 60 kD MDM2 (total and phosphorylated form) and cleaved PARP in SCC cells transfected with either Scr or Ant-138 after CDDP treatment. (e) Western blot analysis of levels of full length and cleaved 60 kD MDM2 (total and phosphorylated form) in SCC cells transfected with either Scr RNA or piR-L-138. Values are averages of three independent replicates; error bars represent mean s.d.; * p<0.05,  p<0.01, * p<0.001.

To determine if the increased piR-L-138 plays a functional role in CDDP treated SCC cells, we used DNA antisense oligos of piR-L-138 (Ant-138) to block piR-L-138 in H157 and SKMES-1 cells. Six hours after Ant-138 treatment, we treated the cells with CDDP (IC25 dose). We observed a significantly increased cell killing compared with control cells pre-treated with scrambled oligonucleotides (Scr) measured by MTT assay (FIG. 15*a*). Using flow cytometry, we further observed a substantially increased proportion of the sub-G1 phase in cells treated with Ant-138 compared with cells treated with Scr before CDDP treatment (FIG. 15*b*; FIGS. 19*c* and 20*a*), suggesting the increased cell killing was due to an enhancement of en apoptosis. To validate the increased sub-G1 fragment represents apoptotic cells, we performed annexin V staining assay and indeed observed Ant-138 pre-treated SCC cells were more sensitive to CDDP-induced apoptosis compared to Scr pre-treated cells (FIG. 15*c*; FIG. 20*b*). These results indicate the involvement of piR-L-138 in inhibiting CDDP-induced apoptosis in lung SCC cells.

Next, we wanted to explore potential mechanism of piR-L-138-mediated apoptosis inhibition in CDDP treated lung SCC cells. We first analyzed cleaved PARP, a protein marker indicative of apoptosis, and found it was increased in the SCC cells pre-treated with Ant-138 compared with Scr pre-treated cells (FIG. 15*d*). As both of the SCC cell lines harbor p53 mutations, we analyzed mouse double minute 2 homolog (MDM2) which has been implicated in apoptosis including p53-independent pathway (Bohlman S, Manfredi J J. p53-independent effects of Mdm2. Subcell *Biochem.* 85,235-46 (2014); Bouska A, Eischen C M. Mdm2 affects genome stability independent of p53. *Cancer Res.* 69, 1697-701 (2009); Zhang, Z., Li, M., Wang, H., Agrawal, S., and Zhang, R. Antisense therapy targeting MDM2 oncogene in prostate cancer: Effects on proliferation, apoptosis, multiple gene expression, and chemotherapy. *Proc. Natl. Acad. Sci.* 100, 11636-11641 (2003); Zhang Z, Wang H, Li M, Agrawal S, Chen X, Zhang R. MDM2 Is a Negative Regulator of p21WAF1/CIP1, Independent of p53. *J. Biol. Chem.* 279: 16000-16006 (2004); Zhu Y, et al. Cisplatin causes cell death via TAB1 regulation of p53/MDM2/MDMX circuitry. *Genes Dev.* 27, 1739-51 (2013); Yang J Y, et al. ERK promotes tumorigenesis by inhibiting FOXO3a via MDM2-mediated degradation. *Nat Cell Biol.* 10, 138-48 (2008); Yang W, Dolloff N G, El-Deiry W S. ERK and MDM2 prey on FOXO3a. *Nat Cell Biol.* 10,125-6 (2008)). In the SCC cells pre-treated with Ant-138, we observed a substantially reduced MDM2 cleavage upon CDDP treatment (FIG. 15*d*). Conversely, the SCC cells transfected with piR-L-138 enhanced MDM2 cleavage with an increased 60 kD cleaved fragment (FIG. 15*d*). Interestingly, a reduced MDM2 cleavage is accompanied with an increase of serine-166 phosphorylation in the cleaved MDM2, which has been shown to stimulate p53 degradation and to block MDM2's inhibitory effects (Cheng Q, et al. Autoactivation of the MDM2 E3 ligase by intramolecular interaction. *Mol Cell Biol.* 34, 2800-10(2014); Meek DW1, Knippschild U. Posttranslational modification of MDM2. *Mol Cancer Res.* 1,1017-26 (2003); Mayo L. D. & Donner D. B. Aphosphatidylinositol3-kinase/Aktpathway promotes translocation of Mdm2 from the cytoplasm to the nucleus. *Proc. Natl. Acad. Sci.* 98,11598-11603(2001); Ogawara, Y., et al. Akt enhances Mdm2-mediated ubiquitination and degradation of p53. *J. Biol. Chem.* 277,21843-21850(2002); Zhou, B. P., et al. HER-2/neu induces p53 ubiquitination via Akt-mediated MDM2 phosphorylation. *Nat. Cell Biol.* 3, 973-982(2001)). Conversely, exogenous piR-L-138 transfection into the SCC cells enhanced MDM2 cleavage and reduced Serine-166 phosphorylation in cleaved MDM2 (FIG. 15*e*).

Figure 16:
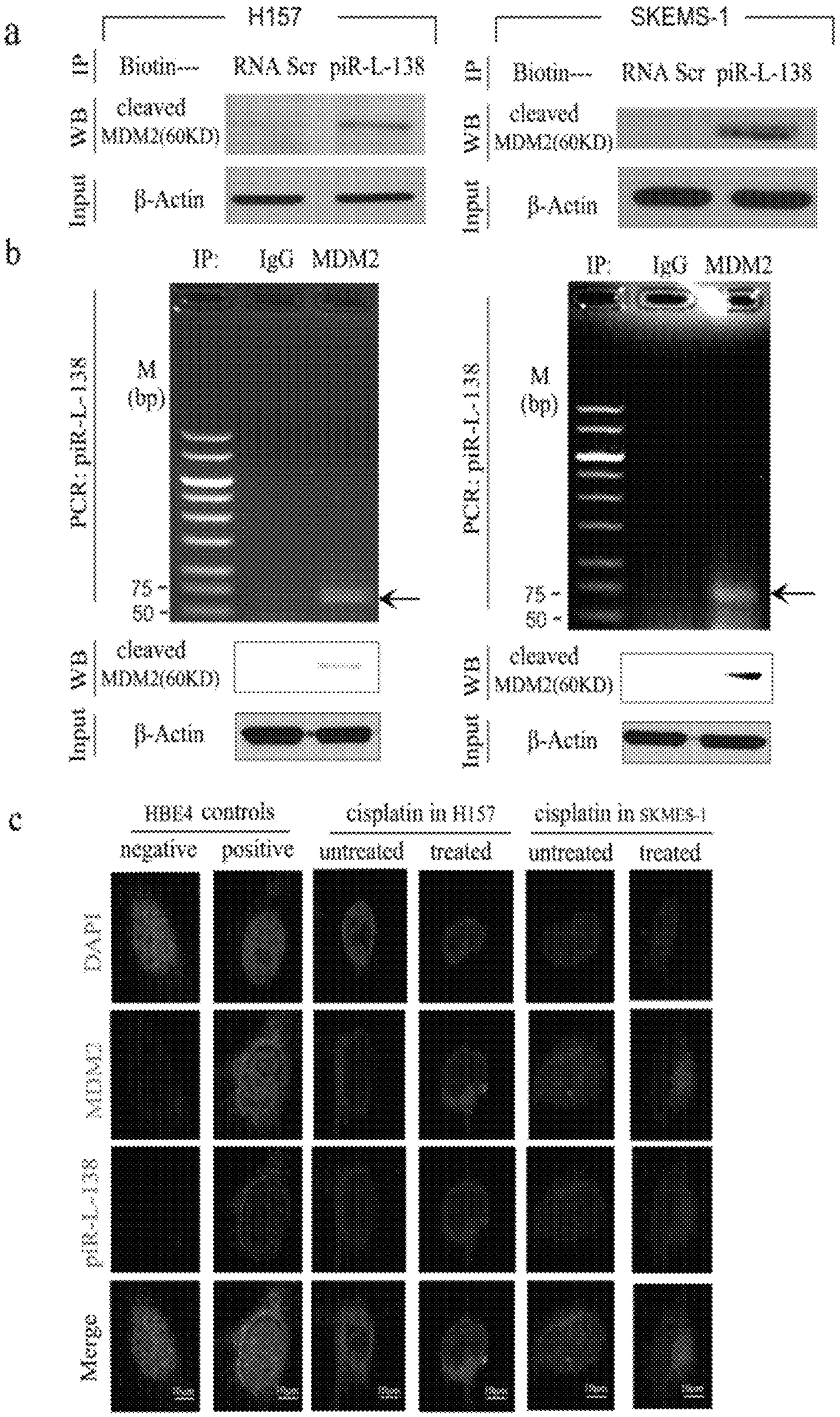
FIG. 16. piR-L-138 interacts with MDM2. (a) Pull-down experiment using immobilized Scr RNA or piR-L-138 followed by Western blot to detect cleaved 60 kD MDM2 in CDDP treated SCC cells. (b) Immunoprecipitation experiment using either IgG or an anti-MDM2 antibody followed by RT-PCR using piR-L-138 specific primers in CDDP treated SCC cells. (c) piR-L-138 and MDM2 co-localization analyzed in HBE4 cells with or without the antibody or oligos probe, H157 and SKMES-1 cells untreated or treated with CDDP as indicated by fluorescence in situ hybridization (FISH) analysis.

To determine if piR-L-138 is functioning through direct interaction with MDM2, biotin-conjugated piR-L-138 was used as a bait to pull down its potential binding proteins in CDDP treated H157 and SKEMS-1 cells followed by Western blot analysis. The cleaved 60 kD MDM2 was detectable in the pulled down products using piR-L-138 but not in the products using Scr RNA control (FIG. 16*a*), indicating piR-L-138 binds to the MDM2 fragment. To confirm the binding between piR-L-138 to the MDM2 fragment, we performed immuno-precipitation (IP) assay using an anti-MDM2 antibody followed by RT-PCR using primers specific for piR-L-138. While piR-L-138 was not detectable in the IP products by using a control Rabbit IgG antibody, it was readily detected in the products pulled down by using the anti-MDM2 antibody (FIG. 16*b*).

To further validate the interaction between piR-L-138 and MDM2 at the individual cell level, we performed fluorescence in situ hybridization (FISH) assay using a digoxin (DIG)-labelled RNA probe complimentary to piR-L-138 and an anti-MDM2 antibody. We first tested the probes in HBE4 cells which express high levels of piR-L-138 to ensure the sensitivity and specificity of the piR-L-138 probe and MDM2 antibody (FIG. 16*c*). We found that both MDM2 and piR-L-138 were predominantly co-localized at a perinuclear area in SCC cells when unchallenged and showed an enhanced and polarized perinuclear pattern following CDDP treatment (FIG. 16*c*). This is consistent with the observed up-regulation of piR-L-138 in SCC cells upon CDDP treatment and the interaction between piR-L-138 and MDM2.

Figure 17:
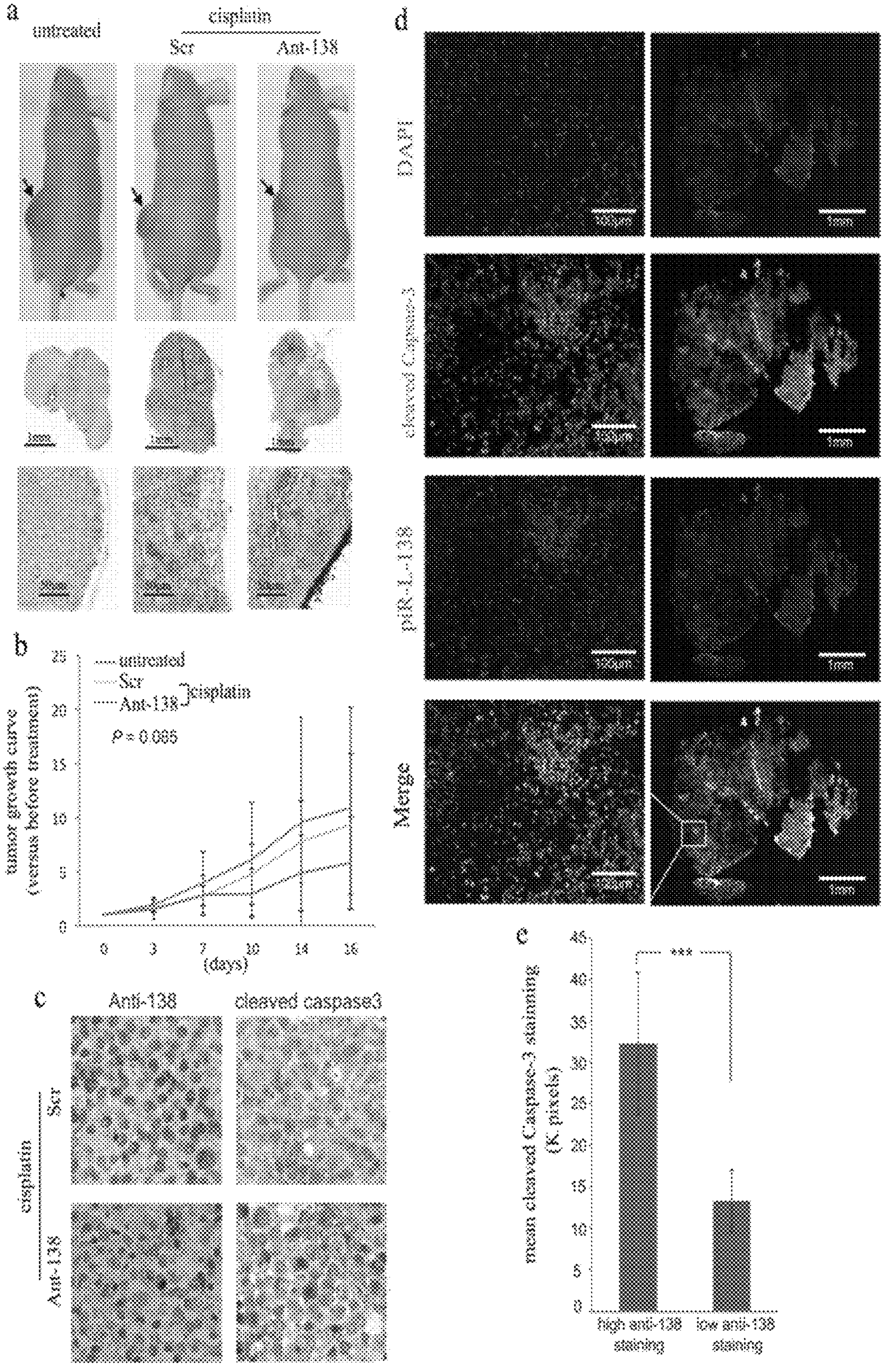
FIG. 17. Ant-138 enhances CDDP-mediated apoptosis in xenograft tumor model. (a) Representative animals and hematoxylin and eosin (H&E) stained tumor sections 16 days after treatment as indicated HE staining morphology were presented. (b) Tumor growth curves in animals of each treatment group as indicated (relative tumor volumes compared to volumes before treatment). (c) The presence of Ant-138 and cleaved caspase 3 in tumor sections from treatment groups as indicated. (d) Immunofluorescence stained cleaved caspase 3 (Red) and Ant-138 (Green) in tumor sections of animals treated with CDDP and plus Ant-138 (left panel is the 10 times magnified images of right panel). (e) Intensities of cleaved caspase 3 signal in tumor regions with high (>20,000 pixels) and low (≤20,000 pixels) Ant-138 signals (20 regions for each category). Error bars represent mean s.d., *** $p<0.001$.

Next, we used H157 tumor xenograft model to determine if targeting piR-L-138 can enhance CDDP-mediated tumor cell apoptosis in SCC in vivo. In this proof of principle experiment, we used intra-tumor injection of Ant-138 (SEQ ID NO:556) which was formulated with MaxSuppr in vivo RNALancerll as described previously (Wiggins J F, et al. Development of a Lung Cancer Therapeutic Based on the Tumor Suppressor MicroRNA-34. *Cancer Res.* 70, 5923-30 (2010)) due to the requirement of very large quantity of formulated reagents needed for systemic delivery. Compared to tumors formed in untreated mice and mice treated with CDDP plus Scr control, tumors in mice treated with CDDP plus Anti-138 were smaller but the difference was only border line statistically (FIGS. 17*a* and 17*b*). Since we were using local injection with sub-optimal dose, such modest anti-tumor activity was expected. We were focusing on determining if Ant-138 increased apoptosis at the sites of injection by analyzing tumor tissue sections for cleaved caspase 3 as an indicator of apoptosis and Ant-138. Compared with tumors treated with CDDP and Scr control, tumors treated with CDDP and Ant-138 exhibited higher expression of cleaved caspase 3 (FIG. 17*c*), an indication of enhanced apoptotic process by inhibiting piR-L-138 induced by CDDP treatment. Further analysis using due-immunofluorescence staining (for cleaved caspase 3 and Ant-138) showed a significantly concentrated caspase 3 positive tumor cells in areas with high levels of Ant-138 (FIGS. 17*d* and 17*e*). These results support the role of piR-L-138 in protecting SCC cells from CDDP induced apoptosis and piR-L-138 targeting as a potential strategy to enhance CDDP efficacy in treating patients with lung SCC.

In summary, we identified a novel mechanism of CDDP treatment resistance for Lung SCC, where a short non-coding RNA, piR-L-138, up-regulated upon CDDP administration interacts with MDM2 onco-protein to increase its degradation and contributes to inhibition of apoptosis. Targeting piR-L-138 can improve the sensitivity of lung SCC to CDDP treatment in both in vitro and in vivo, which warrants further testing to determine its clinical utility for patients with lung SCC.

Method Summary sncRNAs were separated from total RNA using one-nucleotide-resolution PAGE gels and processed using the True® Small RNA kit. sncRNAs purification, adaptor ligation and reverse transcription for PCR or RT-PCR are described in the Methods. Mass spectrometry, oligonucleotide precipitation assay, IP, FISH, Western blot, apoptosis and cell cycle distribution assay, DNA or RNA transfection, animal model establishment etc., were performed as described in the Methods.

TABLE 4

$IC_{50}$ of CDDP in NSCLC cell lines

| cell line | $IC_{50}$ (μM/L) |
|---|---|
| H157 | 80 |
| SKMES-1 | 10 |
| H596 | 30 |
| H226 | 40 |
| H1944 | 100 |
| H1792 | 50 |
| H1437 | 50 |
| H522 | 45 |

Example 3

Co-Precipitation of Large Numbers of sncRNAs with Phosphor-Proteins

To determine the potential scale of sncRNAs with capability to bind with cellular proteins, we performed IP assays using antibodies specifically generated for phosphor-Serine, phosphor-Threonine or phosphor-tyrosine, respectively and cell lysates from pooled HBE or lung SCC cell lines (200 μg from each of the 3 HBE lines and 150 μg from each of the 4 lung SCC lines). Total RNA was extracted from the IP products of each lysate mixture followed by attaching adaptors to both 3' and 5' ends of the RNAs. RT-PCR was performed to amplify the phosphor-protein binding RNAs. RT-PCR of the IP products showed two clusters of bands with approximately 300 and 150 nt respectively (FIG. 21), representing 150-200 nt and 25-50 nt original single strand RNAs considering the sizes of adaptors. We focused on the cluster of sncRNAs with 150 bases bands. We purified RT-PCR products in the gels sized approximately 140-180 nt for generating individual DNA library followed by RNA-seq analysis using Illumila MiSeq (each library was uniquely barcoded). Total reads from individual library were between 700,000 and 2,830,000. A total of 2,647 unique reads (sncRNAs) were identified from these libraries ranging from 1,669 to 1,912 in individual libraries based on cutoff of ≥20 copies (including SEQ ID NOS:560-2802). The average copy numbers were 400-600 per unique sncRNA but 83 sncRNAs ≥5,000 copies for individual libraries. While the same amount of cellular proteins were used for each IP experiment, the total reads were twice as much in the libraries from HBE cells compared with those detected in libraries from lung SCC cells in all three IP pull-downs with antibodies against different phosphor amino acids, suggesting the presence of more and abundant sprRNAs in HBE cells than the cancerous SCC cells. After normalization using equal number of reads for each library, 1,825 unique sncRNAs were found in the library of HBE cells when an anti-phosphor-Tyr antibody was used for IP compared to 1,669 unique sncRNAs detected in the library of lung SCC cells. In an unsupervised clustering analysis based on the abundancies of the unique sncRNAs detected in each library, HBE libraries and lung SCC libraries clustered together, although the differences of the sncRNA abundancies existed among different libraries from the same cell type, suggesting the cell types are more important for the sprRNA patterns or the phosphor-proteins' capable to interact with these sprRNAs due to the fundamental biological features of the cell types. Additionally, approximately one third of the piRNA-Ls (Mei Y, Wang Y, Kumari P, Shetty A C, Clark D, Gable T, MacKerell A D, Ma M Z, Weber D J, Yang A J, Edelman M J, Mao L. A piRNA-like small RNA interacts with and modulates p-ERM proteins in human somatic cells. *Nat Commun.* 6:7316, 2015) were among the unique sncRNAs identified in HBE cells and 50% of the piRNA-Ls identified in lung SCC cells. The higher number of sncRNAs identified in the later experiment is probably due to the enrichment by the protein binding and the expanded range of size beyond 35 nt. In a distribution analysis, the unique sncRNAs (candidate sprRNAs) were peaked around 32 nt and 50 nt (FIG. 22). Another interesting finding is that about 70% of the unique sncRNAs were mapped to exons (30%) or introns (40%) with less than one third mapped to intergenic regions.

To test the potential impact of the candidate sprRNAs identified by phosphor-protein binding in the phosphorylation status of the proteins, we selected a panel of 5 sprRNAs with sizes ranging from 25-50 nt but sharing a common 25 nt sequence and used DNA oligo complementary to the common sequence (5'-CTCTCACCGCCGCGGCCCGGGTTCG-3') (SEQ ID NO:489) to block these sprRNAs. Twenty-four hours after the DNA oligo treatment, we measured the cell viability using MTT assay and observed a significant growth inhibition in all 4 lung SCC cell lines (FIG. 23*a*), suggesting these sprRNAs play biological roles in these cells. We further measured levels of phosphorylated proteins using antibodies against p-Tyrosine and p-Theronin/Serine respectively on Western blots and observed changes of levels in certain phosphor-proteins in lung SCC cells treated with the DNA oligo (FIG. 23*b*).

Lack of Expression of Human Piwi Genes in Some of the HBE Cell Lines

Using RT-PCR, we measured the expression levels of PiwiL1-4 in the 3 HBE cell lines (HBE2, HBE3 and HBE4) and observed either undetectable or extremely low level of expression of these genes in HBE3 and HBE4 cells except moderate expression levels of PiwiL2 and PiwiL4 in HBE2 cells, suggesting these PiwiLs are not the primary contributors for sprRNA biogenesis in these airway epithelial cells.

Nucleus Localization of sprRNA Precursors

Figure 24A:
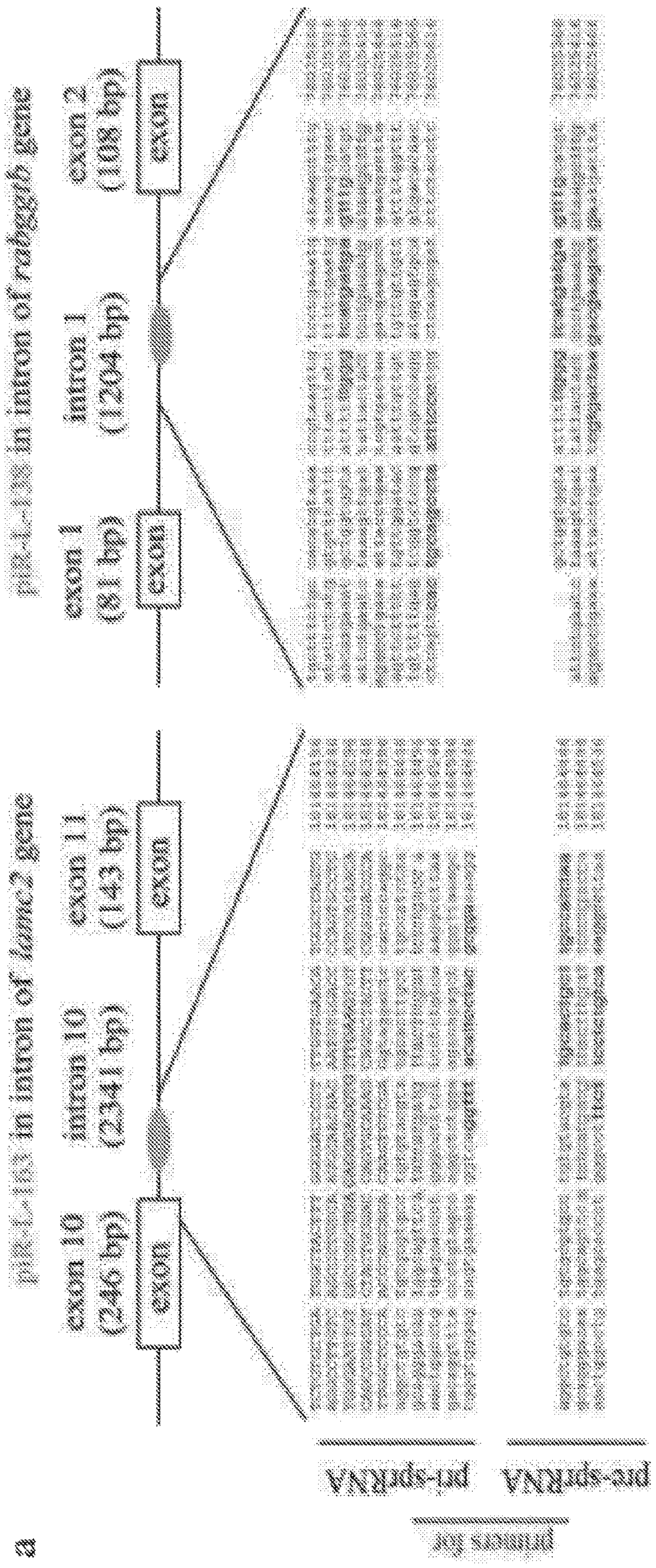

To assess the possible location of sprRNA processing, we analyzed cellular localizations of the precursors of piR-L-163 and piR-L-138 which have been shown as sprRNAs based on our preliminary studies. We designed primer sets for presumable pri- and pre-sprRNAs of the 2 candidates (FIG. 24*a*). RNAs were extracted from cytoplasm and nucleus of HBE2 and HBE4 cells respectively (FIG. 24*b*) and used for cDNA synthesis. The primer sets were used to amplify the pri- and pre-sprRNAs in each of the samples. The pri- and pre-sprRNAs could only be detected in RNAs extracted from nucleus (FIG. 24*c*), suggesting the early biogenesis likely occurs in nucleus.

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein. All patents and publications mentioned and/or cited herein are incorporated by reference to the same extent as if each individual publication was specifically and individually indicated as having been incorporated by reference in its entirety.

What is claimed is:

1. An isolated nucleic acid molecule comprising:
   (i) a short non-coding protein regulatory RNA (sprRNA) that is at least 90% identical to any one of SEQ ID NOS:193-196, 198-267, 269-413, 415-445, 447-462, 464-469, 471-474, 476-486, or 560-2802; and
   (ii) at least one adaptor sequence, wherein the adaptor sequence has been added to one or both of a 3' end and a 5' end of the sprRNA.

2. The nucleic acid molecule of claim 1, wherein the sprRNA is at least 95% identical to SEQ ID NOS:193-196, 198-267, 269-413, 415-445, 447-462, 464-469, 471-474, 476-486, or 560-2802.

3. The nucleic acid molecule of claim 1, wherein the sprRNA is at least 99% identical to SEQ ID NOS:193-196, 198-267, 269-413, 415-445, 447-462, 464-469, 471-474, 476-486, or 560-2802.

4. The nucleic acid molecule of claim 1, wherein the sprRNA comprises SEQ ID NOS:193-196, 198-267, 269-413, 415-445, 447-462, 464-469, 471-474, 476-486, or 560-2802.

5. The nucleic acid molecule of claim 4, wherein the sprRNA is piR-L-163 (SEQ ID NO:282).

6. The isolated nucleic acid molecule of claim 1, wherein the sprRNA is selected from the group consisting of:
   i) sprRNA12600 (SEQ ID NO:490);
   ii) sprRNA11568 (SEQ ID NO:491);
   iii) sprRNA7410 (SEQ ID NO:492);
   iv) sprRNA9378 (SEQ ID NO:493); and
   v) sprRNA10698 (SEQ ID NO:494).

7. An isolated nucleic acid molecule comprising:
   i) cDNA of sprRNA that is at least 90% identical to any one of SEQ ID NOS:193-196, 198-267, 269-413, 415-445, 447-462, 464-469, 471-474, 476-486, 490-494, or 560-2802; and
   ii) at least one adaptor sequence, wherein the adaptor sequence has been added to one or both of a 3' end and a 5' end of the cDNA.

8. The nucleic acid molecule of claim 7, wherein the sprRNA comprises an sprRNA selected from the group consisting of:

i) sprRNA12600 (SEQ ID NO:490);
ii) sprRNA11568 (SEQ ID NO:491);
iii) sprRNA7410 (SEQ ID NO:492);
iv) sprRNA9378 (SEQ ID NO:493); and
v) sprRNA10698 (SEQ ID NO:494).

9. A nucleic acid molecule comprising:
a sequence that is antisense to the sprRNA of claim 1; and
(ii) at least one adaptor sequence, wherein the adaptor sequence has been added to one or both of a 3' end and a 5' end of the antisense sequence.

10. The isolated nucleic acid molecule of claim 1, wherein the at least one adaptor sequence comprises SEQ ID NO:499.

* * * * *